(12) United States Patent
Mazitschek et al.

(10) Patent No.: US 10,662,218 B2
(45) Date of Patent: May 26, 2020

(54) ANALOGS OF CELASTROL

(71) Applicant: ERX Pharmaceuticals, Inc., Cambridge, MA (US)

(72) Inventors: Ralph Mazitschek, Belmont, MA (US); Yanbing Ding, Richmond (CA); Kaisheng Shen, Shanghai (CN)

( * ) Notice: Subject to any disclaimer, the term of this patent is extended or adjusted under 35 U.S.C. 154(b) by 0 days.

(21) Appl. No.: 15/771,077

(22) PCT Filed: Oct. 21, 2016

(86) PCT No.: PCT/US2016/058313
§ 371 (c)(1),
(2) Date: Apr. 25, 2018

(87) PCT Pub. No.: WO2017/070615
PCT Pub. Date: Apr. 27, 2017

(65) Prior Publication Data
US 2018/0362575 A1 Dec. 20, 2018

Related U.S. Application Data

(60) Provisional application No. 62/245,356, filed on Oct. 23, 2015.

(51) Int. Cl.
*A61K 31/56* (2006.01)
*A61K 31/58* (2006.01)
*C07C 13/62* (2006.01)
*A61P 3/04* (2006.01)
*C07J 63/00* (2006.01)

(52) U.S. Cl.
CPC .......... *C07J 63/008* (2013.01); *A61K 31/56* (2013.01); *A61K 31/58* (2013.01); *A61P 3/04* (2018.01)

(58) Field of Classification Search
CPC .... A61K 31/56; A61K 31/58; C07C 2603/52; C07C 13/62; A61P 3/04
USPC ....... 514/765, 766, 176, 172, 180, 181, 179; 564/426, 222, 196, 194; 540/47
See application file for complete search history.

(56) References Cited

U.S. PATENT DOCUMENTS

| | | | |
|---|---|---|---|
| 4,861,760 A | 8/1989 | Mazuel et al. | |
| 4,911,920 A | 3/1990 | Jani et al. | |
| 5,212,162 A | 5/1993 | Missel et al. | |
| 5,403,841 A | 4/1995 | Lang et al. | |
| 9,925,161 B2 * | 3/2018 | Ozcan | A61K 45/06 |
| 9,968,575 B2 * | 5/2018 | Ozcan | A61K 45/06 |
| 2010/0240581 A1 | 9/2010 | Tortoriello et al. | |
| 2011/0166216 A1 | 7/2011 | Ronai et al. | |
| 2015/0274634 A1 | 10/2015 | Mazitschek et al. | |
| 2018/0185314 A1* | 7/2018 | Ozcan | A61K 45/06 |
| 2019/0062254 A1* | 2/2019 | Mazitschek | C07C 62/38 |

FOREIGN PATENT DOCUMENTS

| | | | | |
|---|---|---|---|---|
| RU | 2008131311 A | 2/2010 | | |
| WO | 96/05309 A2 | 2/1996 | | |
| WO | 2007/077203 A2 | 7/2007 | | |
| WO | 2007/117466 A2 | 10/2007 | | |
| WO | 2009/026163 A1 | 2/2009 | | |
| WO | WO-2012024893 A1 * | 3/2012 | ........... | C07J 63/008 |
| WO | 2013/177353 A2 | 11/2013 | | |
| WO | 2014/052583 A1 | 4/2014 | | |
| WO | 2015/148802 A1 | 10/2015 | | |

OTHER PUBLICATIONS

Ryu, Y., S. Park, Y. Kim, J. Lee, W. Seo, J. Chang, K. Park, M. Rho and W. Lee, "SARS-CoV 3CLpro inhibitory effects of quinone-methide triterpenes from Tripterygium regelii", Bioorg. & Med. Chem. Lett. (2010), 20: pp. 1873-1876. (Year: 2010).*
International Search Report, International Application No. PCT/US2016/058313, dated Mar. 17, 2017, 3 pages.
Sweeting (Oct. 26, 2007) "Measurement and Definitions of Obesity in Childhood and Adolescence: A field guide for the uninitiated", Nutrition Journal, 6(32):8 pages.
Van Meir et al. (2010) "Exciting New Advances in Neuro-Oncology :The Avenue to a Cure for Malignant Glioma", CA: A Cancer Journal for Clinicians, 60(3):166-193.
Wang et al. (2004) "Plasma Natriuretic Peptide Levels and the Risk of Cardiovascular Events and Death", The New England Journal of Medicine, 350(7):655-663.
Adams et al. (2006) "Treatment of Non-Alcoholic Fatty Liver Disease", Postgraduate Medical Journal, 82 (967):315-322.
Alberti et al. (2009) "A Joint Interim Statement of the International Diabetes Federation Task Force on Epidemiology and Prevention; National Heart, Lung, and Blood Institute; American Heart Association; World Heart Federation; International Atherosclerosis Society; and Internat", Circulation, 120(16):1640-1645.
Al-Muhammed et al. (1996) "In-Vivo Studies on Dexamethasone Sodium Phosphate Liposomes", Journal of Microencapsulation, 13(3):293-306.
Aronow (Jul.-Aug. 2011) "ACCF/AHA 2011 Expert Consensus Document on Hypertension in the Elderly", Journal of The American Society of Hypertension, 5(4):259-352.
Bartoli et al. (2011) "The Oral Glucose Tolerance Test (OGTT) Revisited", European Journal of Internal Medicine, 22(1):8-12.
Baylin et al. (Feb. 2006) "Epigenetic Gene Silencing in Cancer—A Mechanism for Early Oncogenic Pathway Addiction?", Nature Reviews Cancer, 6(2):107-116.
Beales et al. (Jun. 1999) "New Criteria for Improved Diagnosis of Bardet-Biedl Syndrome: Results of a Population Survey", Journal of Medical Genetics, 36(6):437-446.
Bertazzo et al. (Jun. 2013) "Nano-Analytical Electron Microscopy Reveals Fundamental Insights into Human Cardiovascular Tissue Calcification", Nature Materials, 12(6):576-583.
Bleeker (May 2012) "Recent Advances in the Molecular Understanding of Glioblastoma", Journal of Neuro-oncology, 108(1):11-27.
Buiting et al. (Apr. 1995) "Inherited Microdeletions in the Angelman and Prader—Willi Syndromes Define an Imprinting Centre on Human Chromosome 15", Nature Genetics, 9(4):395-400.

(Continued)

*Primary Examiner* — Matthew P Coughlin
*Assistant Examiner* — Sagar Patel
(74) *Attorney, Agent, or Firm* — Mintz Levin Cohn Ferris Glovsky and Popeo, P.C.; Ingrid A. Beattie; Joohee Lee

(57) ABSTRACT

Described herein, inter alia, are compositions and methods for treating or preventing obesity and using the same.

48 Claims, 30 Drawing Sheets

(56) References Cited

OTHER PUBLICATIONS

Chonn et al. (1995) "Recent Advances in Liposomal Drug-Delivery Systems", Current Opinion in Biotechnology, 6(6):698-708.
Clark et al. (2003) "Nonalcoholic Fatty Liver Disease an Under-recognized Cause of Cryptogenic Cirrhosis", JAMA, 289(22):3000-3004.
Croce (Jan. 31, 2008) "Oncogenes and Cancer", The New England Journal of Medicine, 358(5):502-511.
Cromwell (Dec. 2007) "LDL Particle Number and Risk of Future Cardiovascular Disease in the Framingham Offspring Study—Implications for LDL Management", Journal of Clinical Lipidology, 1(6):583-592.
Donnan et al. (May 10-16, 2008) "Stroke", The Lancet, 371(9624):1612-1623.
Eyles et al. (Jul. 1997) "Oral Delivery and Fate of Poly(Lactic Acid) Microsphere-Encapsulated Interferon in Rats", Journal of Pharmacy and Pharmacology, 49(7):669-674.
Feigin et al. (Dec. 2005) "Risk Factors for Subarachnoid Hemorrhage: An Updated Systematic Review of Epidemiological Studies", Stroke, 36(12):2773-2780.
Felizola (2015) "Ursolic Acid in Experimental Models and Human Subjects: Potential as an Antiobesity/ Overweight Treatment?", ResearchGate, 10 pages.
Franklin et al. (Feb. 2012) "Unusual Hypertensive Phenotypes: What Is Their Significance?", Hypertension, 59(2):173-178.
Gao et al. (Jun. 1995) "Controlled Release of a Contraceptive Steroid from Biodegradable and Injectable Gel Formulations: In Vitro Evaluation", Pharmaceutical Research, 12(6):857-863.
Gray et al. (1991) "Use of Relative Weight and Body Mass Index for the Determination of Adiposity", Journal of Clinical Epidemiology, 44(6):545-550.
Hanahan et al. (Mar. 4, 2011) "Hallmarks of Cancer: The Next Generation", Cell, 144(5):646-674.
Hanahan et al. (Jan. 7, 2000) "The Hallmarks of Cancer", Cell, 100(1):57-70.
Haslam et al. (Oct. 1, 2005) "Obesity", The Lancet, 366(9492):1197-1209.
Hill (Nov. 2005) "Diagnostic Biomarkers for Stroke: A Stroke Neurologist's Perspective", Clinical Chemistry, 51(11):2001-2002.
Inaba et al. (Jan. 2012) "Carotid Plaque, Compared with Carotid Intima-Media Thickness, More Accurately Predicts Coronary Artery Disease Events: A Meta-Analysis", Atherosclerosis, 220(1):128-133.
Johnson et al. (Apr. 2012) "Glioblastoma Survival in the United States Before and During the Temozolomide Era", Journal of Neuro-Oncology, 107(2):359-364.
Kaur et al. (2014) "A Comprehensive Review on Metabolic Syndrome", Cardiology Research and Practice, 21 pages.
Kitabchi et al. (Jul. 7, 2009) "Hyperglycemic Crises in Adult Patients With Diabetes", Diabetes Care, 32(7):1335-1343.
Kivitie-Kallio et al. (Aug. 1, 2001) "Cohen Syndrome: Essential Features, Natural History, and Heterogeneity", American Journal of Medical Genetics, 102(2):125-135.
Klaic et al. (Mar. 14, 2012) "Celastrol Analogues as Inducers of the Heat Shock Response, Design and Synthesis of Affinity Probes for the Identification of Protein Targets", ACS Chemical Biology, 7(5):928-937.
Knudson (Nov. 2001) "Two Genetic Hits (more or less) to Cancer", Nature Reviews Cancer, 1(2):157-162.
Kolehmainen et al. (Jun. 2003) "Cohen Syndrome Is Caused by Mutations in a Novel Gene, COH1, Encoding a Transmembrane Protein with a Presumed Role in Vesicle-Mediated Sorting and Intracellular Protein Transport", American Journal of Human Genetics, 72(6):1359-1369.
Kutney et al. (1981) "Cytotoxic Diterpenes Triptolide, Tripdiolide, and Cytotoxic Triterpenes from Tissue Cultures of Tripterygium Wilfordii", Canadian Journal of Chemistry, 59:2677-2683.
Lee et al. (2011) "The Effect of Celastrol on Metabolic Disturbances and Renal Injury in High Fat Diet-induced Obesity Mice", The Korean Journal of Nephrology, 1 page.
Liangpunsakul et al. (Oct. 2003) "Is Hypothyroidism a Risk Factor for Non-Alcoholic Steatohepatitis?", Journal of Clinical Gastroenterology, 37(4):340-343.
Lieberman et al. (1990) "Pharmaceutical Dosage Forms—Tablets", Second Edition, 3:114-116.
Minto et al. (Apr. 1, 1997) "Pharmacokinetics and Pharmacodynamics of Nandrolone Esters in Oil Vehicle: Effects of Ester, Injection Site and Injection Volume", The Journal of Pharmacology and Experimental Therapeutics, 281(1):93-102.
Molenaar et al. (Dec. 2014) "The Driver and Passenger Effects of Isocitrate Dehydrogenase 1 and 2 Mutations in Oncogenesis and Survival Prolongation", Biochimica et Biophysica Acta, 1846(2):326-341.
Moretti-Ferrerira et al. (Jun. 15, 1993) "Macrosomia, Obesity, Macrocephaly and Ocular Abnormalities (MOMO Syndrome) in Two Unrelated Patients: Delineation of a Newly Recognized Overgrowth Syndrome", American Journal of Medical Genetics, 46(5):555-558.
Ostro et al. (1989) "Use of Liposomes as Injectable-Drug Delivery Systems", American Journal of Health-System Pharmacy, 46(8):1576-1587.
Rao (1995) "Recent Developments of Collagen-Based Materials for Medical Applications and Drug Delivery Systems", Journal of Biomaterials Science, Polymer Edition, 7(7):623-645.
Rautio et al. (Mar. 2008) "Prodrugs: Design and Clinical Applications", Nature Reviews Drug Discovery, 7:255-270.
Remington et al. (2003) "The Science and Practice of Pharmacy", Published by Lippincott,Williams and Wilkins, 20th Edition, p. 704.
Ross et al. (Oct. 2012) "The Clinical, Molecular, and Functional Genetics of Bardet-Biedl Syndrome", Genetics of Obesity Syndromes, 2 pages.
Saydah et al. (Aug. 2001) "Postchallenge Hyperglycemia and Mortality in a National Sample of U.S. Adults", Diabetes Care, 24(8):1397-1402.
Selvin et al. (Mar. 4, 2010) "Glycated Hemoglobin, Diabetes, and Cardiovascular Risk in Nondiabetic Adults", The New England Journal of Medicine, 362(9):800-811.
Shanthi et al. (2011) "Cardiovascular Diseases (CVDS) Due to Atherosclerosis", Global Atlas on Cardiovascular Disease Prevention and Control, 3-18.
Smirniotopoulos (Mar.-Apr. 2007) "From the Archives of the AFIP : Patterns of Contrast Enhancement in the Brain and Meninges", RadioGraphics, 27(2):525-551.
Sturm et al. (Jul. 2007) "Increases in Morbid Obesity in the USA: 2000-2005", Public Health, 121(7):492-496.
Sun et al. (Jul. 1, 2010) "Synthesis and Preliminary Evaluation of Neuroprotection of Celastrol Analogues in PC12 Cells", Bioorganic & Medicinal Chemistry Letters, 20(13):3844-3847.
Tang et al. (2014) "Design, Synthesis and Biological Evaluation of C(6)-Modified Celastrol Derivatives as Potential Antitumor Agents", Molecules, 19:10177-10188.

* cited by examiner

Daily BW

| Animal # | Group | 1 BW | 2 BW | 3 BW | 4 BW | 5 BW | 6 BW | 7 BW | 8 BW | 9 BW | 10 BW | 11 |
|---|---|---|---|---|---|---|---|---|---|---|---|---|
| 1 | Vehicle | 33 | 32.1 | 32.1 | 31.5 | 31 | 30.3 | 30.9 | 30.6 | 29.8 | 29.7 | 30.7 |
| 2 | Vehicle | 35.2 | 34.8 | 34.3 | 34 | 34.5 | 34.8 | 35 | 35.5 | 35.4 | 35.8 | 35.5 |
| 3 | Vehicle | 34.4 | 35.7 | 35.6 | 36 | 36.1 | 35.3 | 35.7 | 36.2 | 35.6 | 35.8 | 36.7 |
| 4 | Vehicle | 37.5 | 37.9 | 36.5 | 36.2 | 36.3 | 36.1 | 35.7 | 35.2 | 35.4 | 35.9 | 36 |
| 5 | Vehicle | 31.3 | 32.1 | 31.1 | 29.2 | 31.2 | 30.9 | 30.7 | 31.2 | 30 | 30.5 | 31.5 |
| AVG | | 34.28 | 34.52 | 33.92 | 33.38 | 33.62 | 33.48 | 33.54 | 33.76 | 33.24 | 33.54 | 34.08 |
| SEM | | 1.04 | 1.11 | 1.02 | 1.35 | 1.16 | 1.20 | 1.12 | 1.18 | 1.36 | 1.41 | 1.24 |
| 6 | ERX1000-4 | 30.8 | 30.8 | 30.3 | 29.2 | 30.1 | 29.6 | 28.4 | 27.8 | 27.4 | 27.5 | 26.9 |
| 7 | ERX1000-4 | 37 | 36.4 | 36 | 36.3 | 37 | 35.4 | 34.6 | 34.2 | 33.9 | 33.7 | 32.9 |
| 8 | ERX1000-4 | 33.5 | 33.5 | 32.2 | 31.4 | 30.7 | 29.5 | 28.9 | 29.4 | 29 | 27.7 | 27.3 |
| 9 | ERX1000-4 | 34.9 | 35 | 33.5 | 33.1 | 31.7 | 31.8 | 31.4 | 30.3 | 30.4 | 31.1 | 29.8 |
| 10 | ERX1000-4 | 34.6 | 34.4 | 33.3 | 32.7 | 31.1 | 30.6 | 29.8 | 30.2 | 30.8 | 30.1 | 28.7 |
| AVG | | 34.16 | 34.02 | 33.06 | 32.54 | 32.12 | 31.38 | 30.62 | 30.38 | 30.30 | 30.02 | 29.12 |
| SEM | | 1.01 | 0.93 | 0.93 | 1.16 | 1.25 | 1.09 | 1.12 | 1.06 | 1.08 | 1.15 | 1.08 |
| 11 | ERX1006 | 35.7 | 35 | 33.4 | 31.9 | 32.1 | 31.5 | 30.4 | 29.2 | 28.9 | 28.2 | 27.6 |
| 12 | ERX1006 | 35 | 35.6 | 35.1 | 35.7 | 35.6 | 34.8 | 34.3 | 34.2 | 33.7 | 34.4 | 33.9 |
| 13 | ERX1006 | 32.7 | 31.8 | 32.1 | 32 | 31.7 | 31.8 | 31.1 | 31.5 | 31.2 | 31.9 | 31.4 |
| 14 | ERX1006 | 32.4 | 31.8 | 31.2 | 30 | 30 | 30.3 | 30 | 30.1 | 30.1 | 29.6 | 29.8 |
| 15 | ERX1006 | 34.9 | 35.2 | 35.4 | 34.4 | 33.6 | 34.2 | 34 | 33.7 | 33.3 | 31.9 | 31.6 |
| AVG | | 34.14 | 33.88 | 33.44 | 32.80 | 32.60 | 32.52 | 31.95 | 31.74 | 31.44 | 31.20 | 30.86 |
| SEM | | 0.67 | 0.85 | 0.82 | 1.01 | 0.94 | 0.85 | 0.91 | 0.98 | 0.92 | 1.07 | 1.04 |
| 16 | ERX1007 | 33.8 | 33.2 | 32.4 | 32.9 | 32.1 | 31.9 | 32 | 31.8 | 31.2 | 30.9 | 30.8 |
| 17 | ERX1007 | 36.3 | 36.4 | 35.7 | 35.1 | 35.4 | 34.8 | 34.7 | 34.8 | 34.6 | 34.7 | 35.3 |
| 18 | ERX1007 | 34.7 | 34.2 | 33.1 | 32.8 | 32.4 | 31.7 | 31.6 | 32 | 31.3 | 30.7 | 31.3 |
| 19 | ERX1007 | 31.4 | 30.3 | 30.2 | 30.4 | 30.4 | 29 | 29.4 | 29.6 | 29.1 | 28.9 | 28.7 |
| 20 | ERX1007 | 36.2 | 36.2 | 35.3 | 35.4 | 35.1 | 34.6 | 34.5 | 35.3 | 35.2 | 35.5 | 35.5 |
| AVG | | 34.48 | 34.06 | 33.34 | 33.32 | 33.08 | 32.40 | 32.44 | 32.70 | 32.28 | 32.14 | 30.86 |
| SEM | | 0.90 | 1.12 | 1.01 | 0.91 | 0.95 | 1.07 | 0.99 | 1.05 | 1.14 | 1.26 | 1.04 |
| 21 | ERX1037 | 35.1 | 36.4 | 35.5 | 34.6 | 34.9 | 35.8 | 36.1 | 36.2 | 36.2 | 36.1 | 36.5 |
| 22 | ERX1037 | 39.1 | 38.4 | 39 | 38.9 | 38.8 | 38.6 | 38.8 | 39 | 39 | 39.6 | 39.7 |
| 23 | ERX1037 | 32 | 32.4 | 32.4 | 31.3 | 31.5 | 31.7 | 32.7 | 31.3 | 31 | 30.8 | 31.2 |
| 24 | ERX1037 | 35.7 | 34.1 | 33.3 | 33.5 | 34.7 | 34.4 | 35.1 | 34.9 | 34.5 | 35.2 | 35 |
| 25 | ERX1037 | 33.1 | 32.7 | 32.6 | 32.5 | 32 | 32.2 | 32.3 | 32.5 | 31 | 32.3 | 32.1 |
| AVG | | 34.48 | 34.06 | 33.34 | 33.32 | 33.08 | 32.40 | 32.44 | 32.70 | 32.28 | 32.14 | 32.32 |
| SEM | | 0.90 | 1.12 | 1.01 | 0.91 | 0.95 | 1.07 | 0.99 | 1.05 | 1.14 | 1.26 | 1.33 |

FIG. 10

| | | | | | | | | | | |
|---|---|---|---|---|---|---|---|---|---|---|
| AVG | 35.00 | 34.80 | 34.66 | 34.16 | 34.34 | 34.64 | 35.00 | 34.78 | 34.34 | 34.80 | 34.90 |
| SEM | 1.22 | 1.14 | 1.24 | 1.30 | 1.27 | 1.26 | 1.19 | 1.36 | 1.54 | 1.54 | 1.54 |
| 26 ERX1060 | 32.9 | 33.2 | 32.7 | 33.4 | 33.3 | 33.6 | 32.2 | 32 | 31.1 | 30.6 | 31.5 |
| 27 ERX1060 | 34.3 | 34.1 | 34.6 | 33.1 | 33.5 | 32.5 | 32.2 | 31.9 | 31.6 | 32.4 | 32.7 |
| 28 ERX1060 | 31.3 | 29.8 | 31.3 | 30.9 | 31.2 | 31.5 | 30.7 | 30.2 | 29.8 | 30.8 | 32 |
| 29 ERX1060 | 38.7 | 38.2 | 37.8 | 38 | 37.8 | 38.1 | 37.3 | 36.5 | 37.5 | 38 | 38.9 |
| 30 ERX1060 | 35.6 | 35.2 | 35.7 | 35 | 35.4 | 36.4 | 36.4 | 35.8 | 35.7 | 35.8 | 36.8 |
| AVG | 34.56 | 34.10 | 34.42 | 34.08 | 34.24 | 34.42 | 33.76 | 33.28 | 33.14 | 33.62 | 34.38 |
| SEM | 1.26 | 1.37 | 1.14 | 1.18 | 1.11 | 1.23 | 1.30 | 1.22 | 1.47 | 1.46 | 1.47 |
| 31 ERX1077 | 31.5 | 31.2 | 31.3 | 31.3 | 31.1 | 31.9 | 31.1 | 32 | 32.1 | 31.9 | 31.9 |
| 32 ERX1077 | 32.8 | 32.5 | 32.4 | 31.5 | 31.7 | 32.3 | 31.3 | 32.1 | 31.5 | 31.7 | 31.3 |
| 33 ERX1077 | 34.5 | 34.1 | 34.3 | 33.6 | 33.4 | 33.1 | 33 | 33.1 | 33.4 | 33.4 | 33.3 |
| 34 ERX1077 | 38.3 | 38.4 | 37.7 | 37.6 | 37.6 | 38.4 | 37.3 | 37.6 | 37 | 37.7 | 38.1 |
| 35 ERX1077 | 34.9 | 34.4 | 34.4 | 34.7 | 34.7 | 34.1 | 34 | 33.7 | 33.4 | 34.1 | 34.7 |
| AVG | 34.40 | 34.12 | 34.02 | 33.74 | 33.70 | 33.96 | 33.34 | 33.70 | 33.48 | 33.76 | 33.86 |
| SEM | 1.15 | 1.22 | 1.09 | 1.16 | 1.16 | 1.17 | 1.13 | 1.03 | 0.95 | 1.08 | 1.21 |
| 36 ERX1107 | 33.6 | 33.5 | 31.9 | 32 | 32 | 31.4 | 31.2 | 30.8 | 30 | 30 | 30.1 |
| 37 ERX1107 | 35.8 | 36.5 | 35.6 | 35.4 | 35.2 | 34.7 | 34.6 | 34.9 | 34.6 | 35.2 | 35.4 |
| 38 ERX1107 | 36.3 | 36.5 | 35 | 34.5 | 34.7 | 34.7 | 34.7 | 33.9 | 34.3 | 34.5 | 34.7 |
| 39 ERX1107 | 31.2 | 31 | 31 | 30.3 | 29.6 | 29.5 | 28.7 | 29 | 29.6 | 28.8 | 30.5 |
| 40 ERX1107 | 34.1 | 33.9 | 33.7 | 33.9 | 33.9 | 33.3 | 33 | 32.8 | 32.7 | 33.6 | 33 |
| AVG | 34.20 | 34.28 | 33.44 | 33.22 | 33.08 | 32.72 | 32.44 | 32.28 | 32.24 | 32.42 | 32.74 |
| SEM | 0.90 | 1.03 | 0.88 | 0.92 | 1.03 | 1.01 | 1.13 | 1.07 | 1.05 | 1.27 | 1.07 |
| 41 ERX1149 | 33.3 | 32.2 | 31.2 | 31 | 30.8 | 30.6 | 30.3 | 30.5 | 31.1 | 31.8 | 30.7 |
| 42 ERX1149 | 35.8 | 34.8 | 35 | 35.5 | 35.1 | 34.3 | 34.4 | 34.5 | 34.4 | 34.3 | 36.1 |
| 43 ERX1149 | 39.7 | 39.9 | 39.5 | 39.6 | 39 | 38.9 | 38.8 | 38.9 | 38.9 | 38.6 | 39.1 |
| 44 ERX1149 | 31.5 | 31.7 | 31.1 | 31.1 | 30.1 | 29.4 | 29 | 29.6 | 28.9 | 29.9 | 29.3 |
| 45 ERX1149 | 34.3 | 34.1 | 33.8 | 32.7 | 32.5 | 32.2 | 31.5 | 32.8 | 32 | 32.8 | 32.6 |
| AVG | 34.92 | 34.54 | 34.12 | 33.98 | 33.60 | 33.08 | 32.80 | 33.26 | 33.06 | 33.48 | 33.56 |
| SEM | 1.38 | 1.46 | 1.54 | 1.62 | 1.62 | 1.67 | 1.75 | 1.65 | 1.71 | 1.47 | 1.79 |
| 46 ERX1168 | 33.1 | 32.5 | 30.7 | 30 | 29.2 | 28.4 | 28.9 | 28.7 | 29.5 | 28.3 | 28.9 |
| 47 ERX1168 | 39.5 | 40.4 | 37.3 | 37.5 | 36.1 | 33.9 | 32.3 | 32.7 | 34.1 | 34.6 | 34 |
| 48 ERX1168 | 36.9 | 36.2 | 34.4 | 34.2 | 33.2 | 31.6 | 30.7 | 29.5 | 30.4 | 30.7 | 30.9 |
| 49 ERX1168 | 31.9 | 31.2 | 30.5 | 29.1 | 28.8 | 27 | 27 | 27.7 | 27.8 | 27.2 | 26 |
| 50 ERX1168 | 31.1 | 29.9 | 28.3 | 28.8 | 28 | 26.7 | 27.3 | 26.9 | 28.3 | 25.4 | 26.3 |

| | | | | | | | | | | | |
|---|---|---|---|---|---|---|---|---|---|---|---|
| 51 ERX1177 | 32 | 32.2 | 31.8 | 31.2 | 31.3 | 31.4 | 31.4 | 31 | 31 | 31.2 | 31.3 |
| 52 ERX1177 | 32.1 | 31.9 | 31.8 | 30.8 | 30.9 | 30.1 | 29.9 | 29.8 | 29.4 | 29.5 | 28.8 |
| 53 ERX1177 | 35.5 | 34.5 | 34.8 | 34.8 | 34.2 | 33.7 | 33.7 | 33.4 | 33.3 | 33.8 | 34 |
| 54 ERX1177 | 40.1 | 38.4 | 38.2 | 37.7 | 38 | 38.1 | 38 | 37.8 | 38.1 | 37.9 | 38.2 |
| 55 ERX1177 | 35 | 34.9 | 34.6 | 34.2 | 34.4 | 34.4 | 34.1 | 33.7 | 33.4 | 33 | 32.6 |
| AVG | 34.50 | 34.04 | 32.24 | 31.94 | 31.06 | 29.52 | 29.24 | 29.10 | 30.02 | 29.24 | 29.22 |
| SEM | 1.60 | 1.91 | 1.60 | 1.69 | 1.55 | 1.40 | 1.01 | 1.00 | 1.12 | 1.59 | 1.49 |
| 56 Pristimerin | 40 | 39.4 | 40.1 | 40.3 | 40.3 | 40.9 | 40.7 | 40.3 | 40.6 | 40.2 | 41.4 |
| 57 Pristimerin | 33.3 | 33.1 | 32.6 | 32.4 | 32.3 | 32.2 | 31.6 | 31.2 | 31.4 | 31.3 | 32.3 |
| 58 Pristimerin | 29.8 | 30.2 | 29.2 | 29 | 28.6 | 28.7 | 29.1 | 28.2 | 28.2 | 28.6 | 29.6 |
| 59 Pristimerin | 35.5 | 35.4 | 35.3 | 34.7 | 35.1 | 35.1 | 35.8 | 35.8 | 35.2 | 35.9 | 36.4 |
| 60 Pristimerin | 32.3 | 32.4 | 31.2 | 30.3 | 30.1 | 29.9 | 30.2 | 30 | 29.3 | 29.8 | 29.8 |
| AVG | 34.94 | 34.38 | 34.20 | 33.74 | 33.76 | 33.54 | 33.42 | 33.14 | 33.04 | 33.08 | 32.98 |
| SEM | 1.48 | 1.17 | 1.18 | 1.27 | 1.28 | 1.38 | 1.38 | 1.38 | 1.47 | 1.42 | 1.56 |
| AVG | 34.18 | 34.04 | 33.68 | 33.34 | 33.28 | 33.36 | 33.48 | 33.10 | 32.94 | 33.16 | 33.90 |
| SEM | 1.72 | 1.58 | 1.89 | 1.99 | 2.07 | 2.18 | 2.13 | 2.19 | 2.26 | 2.15 | 2.24 |

Daily BW Change

| Animal # | Group | BW | BW | BW | BW | BW | BW | BW | BW | BW | BW | BW | AUC (Daily BW Δ) |
|---|---|---|---|---|---|---|---|---|---|---|---|---|---|
| 1 | Vehicle | -0.9 | 0 | -0.6 | -0.5 | -0.7 | 0.6 | -0.3 | -0.8 | -0.1 | 1 | | -2.8 |
| 2 | Vehicle | -0.4 | -0.5 | -0.3 | -0.5 | -0.3 | 0.2 | 0.8 | -0.2 | 0.4 | | | 0.6 |
| 3 | Vehicle | 1.3 | -0.1 | 0.4 | 0.1 | -0.8 | 0.1 | 0.8 | -0.6 | 0.2 | -0.3 | | 0.65 |
| 4 | Vehicle | 0.4 | -1.4 | -0.3 | 0.1 | -0.2 | -0.4 | -0.5 | 0.2 | 0.5 | 0.9 | | -2.05 |
| 5 | Vehicle | 0.8 | -1 | -1.9 | 2 | -0.3 | -0.2 | 0.5 | -1.2 | 0.5 | 0.1 | | -1.45 |
| AVG | | 0.24 | -0.60 | -0.54 | 0.44 | -0.34 | 0.06 | 0.22 | -0.52 | 0.30 | 0.54 | | -1.01 |
| SEM | | 0.40 | 0.27 | 0.38 | 0.42 | 0.20 | 0.17 | 0.26 | 0.24 | 0.11 | 0.27 | | 0.70 |
| 6 | ERX1000-4 | 0 | -0.5 | -1.1 | 0.9 | -0.5 | -1.2 | -0.6 | -0.4 | 0.1 | -0.6 | | -3.35 |
| 7 | ERX1000-4 | -0.6 | -0.4 | 0.3 | 0.7 | -1.6 | -0.8 | -0.4 | -0.3 | -0.2 | -0.8 | | -2.9 |
| 8 | ERX1000-4 | 0 | -1.3 | -0.8 | -0.7 | -1.2 | -0.6 | 0.5 | -0.4 | -1.3 | -0.4 | | -5.15 |
| 9 | ERX1000-4 | 0.1 | -1.5 | -0.4 | -1.4 | 0.1 | -0.4 | -1.1 | 0.1 | 0.7 | -1.3 | | -4.2 |
| 10 | ERX1000-4 | -0.2 | -1.1 | -0.6 | -1.6 | -0.5 | -0.8 | 0.4 | 0.6 | -0.7 | -1.4 | | -4.05 |
| AVG | | -0.14 | -0.96 | -0.52 | -0.42 | -0.74 | -0.76 | -0.24 | -0.08 | -0.28 | -0.90 | | -3.93 |
| SEM | | 0.12 | 0.22 | 0.24 | 0.52 | 0.30 | 0.13 | 0.30 | 0.19 | 0.34 | 0.19 | | 0.39 |
| 11 | ERX1006 | -0.7 | -1.6 | -1.5 | 0.2 | -0.6 | -1.1 | -1.2 | -0.3 | -0.7 | -0.6 | | -6.8 |
| 12 | ERX1006 | 0.6 | -0.5 | 0.6 | -0.1 | -0.8 | -0.5 | -0.6 | -0.5 | 0.7 | -0.6 | | -1.25 |
| 13 | ERX1006 | -0.9 | 0.3 | -0.1 | -0.3 | 0.1 | -0.7 | -0.4 | -0.3 | 0.7 | -0.5 | | -0.7 |
| 14 | ERX1006 | -0.6 | -0.6 | -1.2 | 0 | 0.3 | -0.3 | 0.1 | 0 | -0.5 | 0.2 | | -2.25 |
| 15 | ERX1006 | 0.3 | 0.2 | -1 | -0.8 | 0.6 | -0.2 | -0.3 | -0.4 | -1.4 | -0.3 | | -2.45 |
| AVG | | -0.26 | -0.44 | -0.64 | -0.20 | -0.08 | -0.56 | -0.22 | -0.30 | -0.24 | -0.34 | | -2.69 |
| SEM | | 0.30 | 0.34 | 0.39 | 0.17 | 0.27 | 0.16 | 0.27 | 0.08 | 0.41 | 0.14 | | 1.08 |
| 16 | ERX1007 | -0.6 | -0.8 | 0.5 | -0.8 | -0.2 | 0.1 | -0.2 | -0.6 | -0.3 | -0.1 | | -2.45 |
| 17 | ERX1007 | 0.1 | -0.7 | -0.6 | 0.3 | -0.6 | -0.1 | 0.2 | -0.7 | -0.7 | 0.6 | | -1.7 |
| 18 | ERX1007 | -0.5 | -1.1 | -0.3 | -0.4 | -0.7 | -0.1 | -1.4 | -0.7 | -0.6 | 0.6 | | -3.45 |
| 19 | ERX1007 | -1.1 | -0.1 | 0.2 | 0 | -1.4 | 0.4 | -0.2 | -0.5 | -0.2 | -0.2 | | -1.85 |
| 20 | ERX1007 | 0 | -0.9 | 0.1 | -0.3 | -0.5 | -0.1 | 0.8 | -0.1 | 0.3 | 0 | | -0.85 |
| AVG | | -0.42 | -0.72 | -0.02 | -0.24 | -0.68 | 0.04 | 0.26 | -0.42 | -0.14 | 0.18 | | -2.06 |
| SEM | | 0.22 | 0.17 | 0.19 | 0.19 | 0.20 | 0.10 | 0.17 | 0.12 | 0.16 | 0.17 | | 0.43 |
| 21 | ERX1037 | 1.3 | -0.9 | -0.9 | 0.3 | 0.9 | 0.3 | 0.1 | 0 | -0.1 | 0.4 | | 0.4 |
| 22 | ERX1037 | -0.7 | 0.6 | -0.1 | -0.3 | 0.2 | 0.2 | 0.2 | -0.3 | 0.6 | 0.1 | | 0.55 |
| 23 | ERX1037 | 0.4 | 0 | -1.1 | -0.2 | 0.2 | -1 | -1.4 | -0.4 | -0.2 | 0.4 | | -1.3 |
| 24 | ERX1037 | -1.6 | -0.8 | 0.2 | 1.2 | -0.3 | 0.7 | -0.2 | -0.7 | 0.7 | -0.2 | | -0.05 |
| 25 | ERX1037 | -0.4 | -0.1 | -0.1 | -0.5 | 0.2 | 0.1 | 0.2 | -1.5 | 1.3 | -0.2 | | -1.25 |

FIG. 11

| | | | | | | | | | | | |
|---|---|---|---|---|---|---|---|---|---|---|---|
| AVG<br>SEM | | -0.20<br>0.49 | -0.24<br>0.28 | -0.40<br>0.25 | 0.18<br>0.30 | 0.20<br>0.20 | 0.46<br>0.17 | -0.22<br>0.30 | -0.44<br>0.28 | 0.46<br>0.28 | 0.10<br>0.13 | -0.33<br>0.40 |
| 26 | ERX1060 | 0.3 | -0.5 | 0.7 | -0.1 | 0.3 | -1.4 | -0.2 | -0.9 | -0.5 | 0.9 | -2.2 |
| 27 | ERX1060 | -0.2 | 0.5 | -1.5 | 0.4 | -1 | -0.3 | -0.3 | -0.3 | 0.8 | 0.3 | -2.2 |
| 28 | ERX1060 | -1.5 | 1.5 | -0.4 | 0.3 | 0.3 | -0.8 | -0.5 | -0.4 | -1 | 1.2 | -0.25 |
| 29 | ERX1060 | -0.5 | -0.4 | 0.2 | -0.2 | 0.3 | -0.8 | -0.8 | -1 | 0.5 | 0.9 | -0.7 |
| 30 | ERX1060 | -0.4 | 0.5 | -0.7 | 0.4 | -1 | 0 | -0.6 | -0.1 | 0.1 | -1 | 0.35 |
| AVG<br>SEM | | -0.46<br>0.29 | 0.32<br>0.36 | -0.34<br>0.38 | 0.16<br>0.13 | 0.18<br>0.32 | -0.66<br>0.24 | -0.48<br>0.11 | -0.14<br>0.31 | 0.38<br>0.27 | 0.86<br>0.15 | -1.00<br>0.52 |
| 31 | ERX1077 | -0.3 | 0.1 | 0 | -0.2 | 0.8 | -0.8 | 0.9 | 0.1 | -0.2 | 0 | 0.65 |
| 32 | ERX1077 | -0.3 | -0.1 | -0.9 | -0.2 | 0.6 | -1 | 0.8 | -0.6 | 0.2 | -0.4 | -1.05 |
| 33 | ERX1077 | -0.4 | 0.2 | -0.7 | 0 | -0.3 | -0.1 | 0.1 | 0.3 | 0 | -0.1 | -0.9 |
| 34 | ERX1077 | 0.1 | -0.7 | -0.1 | 0 | 0.8 | -1.1 | 0.3 | -0.6 | 0.7 | 0.4 | -1 |
| 35 | ERX1077 | -0.5 | 0 | 0.3 | -0.2 | -0.6 | -0.1 | -0.3 | -0.3 | 0.7 | 0.6 | -0.9 |
| AVG<br>SEM | | -0.28<br>0.10 | -0.10<br>0.16 | -0.28<br>0.22 | -0.04<br>0.07 | 0.26<br>0.30 | -0.62<br>0.22 | 0.36<br>0.22 | -0.22<br>0.18 | 0.28<br>0.18 | 0.10<br>0.18 | -0.64<br>0.32 |
| 36 | ERX1107 | -0.1 | -1.6 | 0.1 | 0 | -0.6 | -0.2 | -0.4 | -0.8 | 0 | 0.1 | -3.55 |
| 37 | ERX1107 | 0.7 | -0.9 | -0.2 | -0.2 | -0.5 | -0.1 | -0.3 | -0.3 | 0.6 | 0.2 | -1.25 |
| 38 | ERX1107 | 0.2 | 0.2 | -0.5 | -0.4 | 0 | 0 | -0.8 | 0.4 | 0.2 | 0.2 | -2 |
| 39 | ERX1107 | -0.2 | 0 | -0.7 | -0.6 | -0.1 | -0.8 | 0.3 | 0.6 | -0.8 | 1.7 | -1.9 |
| 40 | ERX1107 | -0.2 | -0.2 | 0.3 | 0 | -0.6 | -0.3 | -0.2 | -0.1 | 0.9 | -0.6 | -0.85 |
| AVG<br>SEM | | 0.08<br>0.17 | -0.84<br>0.33 | -0.22<br>0.17 | -0.14<br>0.15 | -0.36<br>0.13 | -0.28<br>0.14 | -0.16<br>0.21 | -0.04<br>0.25 | 0.18<br>0.29 | 0.32<br>0.38 | -1.91<br>0.46 |
| 41 | ERX1149 | -1.1 | -1 | -0.2 | -0.2 | -0.8 | 0.5 | 0.2 | 0.6 | 0.7 | -1.1 | -1.3 |
| 42 | ERX1149 | -1 | 0.2 | 0.5 | -0.4 | -2.2 | -1.6 | 0.1 | -0.1 | -0.1 | -1.8 | -0.95 |
| 43 | ERX1149 | 0.2 | -0.4 | 0.1 | -0.6 | -1.6 | -0.9 | 0.1 | 0 | -0.3 | 0.5 | -1.05 |
| 44 | ERX1149 | 0.2 | -0.6 | 0 | -1 | -1.8 | -0.4 | 0.6 | -0.7 | 1 | -0.6 | -2.2 |
| 45 | ERX1149 | -0.2 | -0.3 | -1.1 | -0.2 | -1.3 | -0.7 | 1.3 | -0.8 | 0.8 | -0.2 | -1.8 |
| AVG<br>SEM | | -0.38<br>0.28 | -0.42<br>0.20 | -0.14<br>0.27 | -0.48<br>0.15 | -0.42<br>0.14 | -0.28<br>0.14 | 0.46<br>0.23 | -0.20<br>0.25 | 0.42<br>0.26 | 0.08<br>0.50 | -1.46<br>0.24 |
| 46 | ERX1168 | -0.6 | -1.8 | -0.7 | -0.8 | -0.8 | 0.5 | -0.4 | 0.8 | -1.2 | 0.6 | -3.9 |
| 47 | ERX1168 | 0.9 | -3.1 | -0.2 | -1.4 | -2.2 | -1.6 | -0.4 | 1.4 | 0.5 | 0.6 | -5.6 |
| 48 | ERX1168 | -0.7 | -1.8 | -0.2 | -1 | -1.6 | -0.9 | -1.2 | 0.9 | 0.3 | 0.2 | -6 |
| 49 | ERX1168 | -0.7 | -0.7 | -1.4 | -0.3 | -1.8 | -0.4 | 0.7 | 0.1 | -0.6 | -1.2 | -4.05 |
| 50 | ERX1168 | -1.2 | -1.6 | 0.6 | -0.9 | -1.3 | 0.6 | -0.4 | 1.4 | -2.9 | 0.9 | -3.65 |

FIG. 11 (Continued)

| | | | | | | | | | | | |
|---|---|---|---|---|---|---|---|---|---|---|---|
| 51 ERX1177 | 0.2 | -0.4 | -0.6 | 0.1 | 0.1 | 0 | -0.2 | -0.4 | 0 | 0.2 | 0.1 | -1 |
| 52 ERX1177 | -0.2 | -0.1 | -1 | 0.1 | -0.8 | -0.2 | -0.1 | -0.1 | -0.4 | 0.2 | -0.7 | -2.55 |
| 53 ERX1177 | -1 | 0.1 | 0.2 | -0.6 | -0.5 | | -0.3 | 0.3 | -0.1 | 0.1 | -0.2 | -1.45 |
| 54 ERX1177 | -1.7 | -0.2 | -0.5 | 0.3 | 0.1 | -0.1 | -0.2 | -0.3 | 0.3 | 0.5 | 0.3 | -1.25 |
| 55 ERX1177 | -0.1 | -0.3 | -0.4 | 0.2 | 0 | -0.3 | -0.4 | -0.4 | -0.3 | -0.2 | -0.4 | -1.75 |
| AVG | -0.46 | -1.80 | -0.30 | -0.88 | -1.54 | -0.28 | -0.14 | 0.92 | -0.78 | -0.02 | -4.64 |
| SEM | 0.36 | 0.38 | 0.35 | 0.18 | 0.24 | 0.42 | 0.33 | 0.24 | 0.61 | 0.39 | 0.48 |
| 56 Pristimerin | -0.6 | 0.7 | 0.2 | 0.1 | 0.6 | -0.2 | -0.4 | 0.3 | 0.2 | 0.1 | 0.7 |
| 57 Pristimerin | -0.2 | -0.5 | -0.2 | 0 | -0.1 | -0.6 | -0.4 | 0.2 | -0.4 | -0.7 | -1.85 |
| 58 Pristimerin | 0.4 | -1 | -0.2 | -0.1 | 0.1 | 0.4 | -0.9 | 0 | -0.1 | 1 | -1.6 |
| 59 Pristimerin | -0.1 | -0.1 | -0.6 | -0.4 | 0 | 0.7 | 0 | -0.6 | 0.4 | | 0.1 |
| 60 Pristimerin | -0.2 | -0.9 | -0.9 | -0.2 | -0.2 | 0.3 | -0.2 | -0.7 | 0.7 | 0.5 | -2.65 |
| AVG | -0.56 | -0.18 | -0.46 | 0.02 | -0.22 | -0.12 | -0.28 | -0.10 | 0.04 | -0.10 | -0.60 |
| SEM | 0.35 | 0.09 | 0.19 | 0.16 | 0.18 | 0.06 | 0.06 | 0.12 | 0.16 | 0.19 | 0.27 |
| AVG | -0.14 | -0.36 | -0.34 | -0.06 | 0.08 | 0.12 | -0.38 | -0.16 | 0.22 | 0.74 | -1.06 |
| SEM | 0.16 | 0.31 | 0.19 | 0.13 | 0.14 | 0.23 | 0.15 | 0.21 | 0.20 | 0.22 | 0.63 |

FIG. 11 (Continued)

Cumulative BW Change

| Animal # | Group | BW | BW | BW | BW | BW | BW | BW | BW | BW | BW | AUC (CUM BW Δ) |
|---|---|---|---|---|---|---|---|---|---|---|---|---|
| 1 | Vehicle | -0.9 | -0.9 | -1.5 | -.2 | -2.7 | -2.1 | -2.4 | -3.2 | -3.3 | -2.3 | -19.7 |
| 2 | Vehicle | -0.4 | -0.9 | -1.2 | -0.7 | -0.4 | -0.2 | 0.4 | 0.2 | 0.6 | 0.3 | -2.25 |
| 3 | Vehicle | 1.3 | 1.2 | 1.6 | 1.7 | 0.9 | -1 | 1.8 | 1.2 | 1.4 | 2.3 | 12.6 |
| 4 | Vehicle | 0.4 | -1 | -1.3 | -1.2 | -1.4 | -1.8 | -2.3 | -2.1 | -1.6 | -1.5 | -13.25 |
| 5 | Vehicle | 0.8 | -0.2 | -2.1 | -0.1 | -0.4 | -0.6 | -0.1 | -1.3 | -0.8 | 0.2 | -5.1 |
| AVG |  | 0.24 | -0.36 | -0.90 | -0.46 | -0.80 | -0.74 | -0.52 | -1.04 | -0.74 | -0.20 | -5.54 |
| SEM |  | 0.40 | 0.42 | 0.64 | 0.62 | 0.60 | 0.56 | 0.81 | 0.79 | 0.83 | 0.80 | 5.48 |
| 6 | ERX1000-4 | 0 | -0.5 | -1.6 | -0.7 | -1.2 | -2.4 | -3 | -3.4 | -3.3 | -3.9 | -18.05 |
| 7 | ERX1000-4 | -0.6 | -1 | -0.7 | 0 | -1.6 | -2.4 | -2.8 | -3.1 | -3.3 | -4.1 | -17.25 |
| 8 | ERX1000-4 | 0 | -1.3 | -2.1 | -2.8 | -4 | -4.6 | -4.1 | -4.5 | -5.8 | -6.2 | -32.3 |
| 9 | ERX1000-4 | 0.1 | -1.4 | -1.8 | -3.2 | -3.1 | -3.5 | -4.6 | -4.5 | -3.8 | -5.1 | -28.4 |
| 10 | ERX1000-4 | -0.2 | -1.3 | -1.9 | -3.5 | -4 | -4.8 | -4.4 | -3.8 | -4.5 | -5.9 | -31.25 |
| AVG |  | -0.14 | -1.10 | -1.62 | -2.04 | -2.78 | -3.54 | -3.78 | -3.86 | -4.14 | -5.04 | -25.45 |
| SEM |  | 0.12 | 0.16 | 0.24 | 0.71 | 0.59 | 0.52 | 0.37 | 0.28 | 0.47 | 0.46 | 3.25 |
| 11 | ERX1006 | -0.7 | -2.3 | -3.8 | -3.6 | -4.2 | -5.3 | -6.5 | -6.8 | -7.5 | -8.1 | -44.4 |
| 12 | ERX1006 | 0.6 | 0.1 | 0.7 | 0.6 | -0.2 | -0.7 | -0.8 | -1.3 | -0.6 | -1.1 | -2.45 |
| 13 | ERX1006 | -0.9 | -0.6 | -0.7 | -1 | -0.9 | -1.6 | -1.5 | -1.5 | -0.8 | -1.3 | -9.4 |
| 14 | ERX1006 | -0.6 | -1.2 | -2.4 | -2.4 | -2.1 | -2.4 | -2.3 | -2.3 | -2.8 | -2.6 | -19.5 |
| 15 | ERX1006 | 0.3 | 0.5 | -0.5 | -1.3 | -0.7 | -0.9 | -1.2 | -1.6 | -.3 | -3.3 | -10.2 |
| AVG |  | -0.26 | -0.70 | -1.34 | -1.54 | -1.62 | -2.18 | -2.40 | -2.70 | -2.94 | -3.28 | -17.19 |
| SEM |  | 0.30 | 0.49 | 0.79 | 0.70 | 0.72 | 0.84 | 1.05 | 1.04 | 1.24 | 1.27 | 7.32 |
| 16 | ERX1007 | -0.6 | -1.4 | -0.9 | -1.7 | -1.9 | -1.8 | -.2 | -2.6 | -2.9 | -.3 | -.17 |
| 17 | ERX1007 | 0.1 | -0.6 | -1.2 | -0.9 | -1.5 | -1.6 | -1.5 | -1.7 | -1.6 |  | -11.05 |
| 18 | ERX1007 | -0.5 | -1.6 | -1.9 | -2.3 | -.3 | -3.1 | -2.7 | -3.4 | -.4 | -3.4 | -23.95 |
| 19 | ERX1007 | -1.1 | -1.2 | -1 | -1 | -2.4 | -.2 | -1.8 | -2.3 | -2.5 | -2.7 | -16.1 |
| 20 | ERX1007 | 0 | -0.9 | -0.8 | -1.1 | -1.6 | -1.7 | -0.9 | -1 | -0.7 | -0.7 | -9.05 |

FIG. 12

| | | | | | | | | | | | |
|---|---|---|---|---|---|---|---|---|---|---|---|
| 21 ERX1037 | 1.3 | 0.4 | -0.5 | -0.2 | 0.7 | -0.3 | 1.1 | 1.1 | 1 | 1.4 | 5.95 |
| 22 ERX1037 | -0.7 | -0.1 | -0.2 | -0.5 | -0.5 | 0.7 | -0.1 | -0.1 | 0.5 | 0.6 | -1.35 |
| 23 ERX1037 | 0.4 | 0.4 | -0.7 | -0.5 | -0.3 | -0.6 | -0.7 | -1 | -1.2 | -0.8 | -3.5 |
| 24 ERX1037 | -1.6 | -2.4 | -2.2 | -1 | -1.3 | -0.6 | -0.8 | -1.2 | -0.5 | -0.7 | -11.15 |
| 25 ERX1037 | -0.4 | -0.5 | -0.6 | -1.1 | -0.9 | -0.8 | -0.6 | -2.1 | -0.8 | -1 | -8.1 |
| AVG | -0.42 | -1.14 | -1.16 | -1.40 | -2.08 | -2.04 | -1.78 | -2.20 | -2.34 | -2.16 | -15.43 |
| SEM | 0.22 | 0.18 | 0.20 | 0.26 | 0.28 | 0.27 | 0.30 | 0.41 | 0.56 | 0.55 | 2.60 |
| 26 ERX1060 | 0.3 | -0.2 | 0.5 | 0.4 | 0.7 | -0.7 | -0.9 | -1.8 | -2.3 | -1.4 | -4.85 |
| 27 ERX1060 | -0.2 | -0.3 | -1.2 | -0.8 | -1.8 | -2.1 | -2.4 | -2.7 | -1.9 | -1.6 | -13.5 |
| 28 ERX1060 | 0.3 | 0 | -0.4 | -0.1 | 0.2 | -0.6 | -1 | -1.5 | -0.5 | 0.7 | -4.4 |
| 29 ERX1060 | -1.5 | -0.9 | -0.7 | -0.9 | -0.6 | -1.4 | -2.2 | -1.2 | -0.7 | 0.2 | -8.75 |
| 30 ERX1060 | -0.5 | 0.1 | -0.6 | -0.2 | -0.8 | 0.8 | 0.2 | 0 | 0.2 | 1.2 | 1.8 |
| AVG | -0.20 | -0.44 | -0.84 | -0.66 | -0.46 | 0.00 | -0.22 | -0.66 | -0.20 | -0.10 | -3.63 |
| SEM | 0.49 | 0.52 | 0.35 | 0.17 | 0.34 | 0.36 | 0.35 | 0.54 | 0.41 | 0.47 | 2.95 |
| 31 ERX1077 | -0.3 | -0.2 | -0.2 | -0.4 | 0.4 | -0.4 | 0.5 | 0.6 | 0.4 | 0.4 | 0.75 |
| 32 ERX1077 | -0.3 | -0.4 | -1.3 | -1.1 | -0.5 | -1.5 | -0.7 | -1.3 | -1.1 | -1.5 | -8.8 |
| 33 ERX1077 | -0.4 | -0.2 | -0.9 | -1.6 | -1.4 | -1.5 | -1.4 | -1.1 | -1.1 | -1.2 | -9.5 |
| 34 ERX1077 | 0.1 | -0.6 | -0.7 | -0.7 | 0.1 | -1 | -0.7 | -1.3 | -0.6 | -0.2 | -5.55 |
| 35 ERX1077 | -0.5 | -0.5 | -0.2 | -0.2 | -0.8 | -0.9 | -1.2 | -1.5 | -0.8 | -0.2 | -6.45 |
| AVG | -0.46 | -0.14 | -0.48 | -0.32 | -0.14 | -0.80 | -1.28 | -1.42 | -1.04 | -0.18 | -5.94 |
| SEM | 0.29 | 0.21 | 0.28 | 0.24 | 0.48 | 0.48 | 0.47 | 0.46 | 0.46 | 0.56 | 2.53 |
| 36 ERX1107 | -0.1 | -1.7 | -1.6 | -1.6 | -2.2 | -2.4 | -2.8 | -3.6 | -3.6 | -3.5 | -21.3 |
| 37 ERX1107 | 0.7 | -0.2 | -0.4 | -0.6 | -1.5 | -1.2 | -0.9 | -0.6 | -0.6 | -0.4 | -6.05 |
| 38 ERX1107 | 0.2 | -1.3 | -1.8 | -1.6 | -1.6 | -1.6 | -2.4 | -2 | -1.8 | -1.6 | -14.8 |
| 39 ERX1107 | -0.2 | -0.4 | -0.9 | -1 | -0.8 | -2.5 | -2.2 | -1.6 | -2.4 | -0.7 | -13.55 |
| 40 ERX1107 | -0.2 | -0.4 | -0.2 | -0.2 | -0.8 | -1.1 | -1.3 | -1.4 | -0.5 | -1.1 | -6.55 |
| AVG | -0.28 | -0.38 | -0.66 | -0.70 | -0.44 | -1.06 | -0.70 | -0.92 | -0.64 | -0.54 | -5.91 |
| SEM | 0.10 | 0.08 | 0.21 | 0.18 | 0.32 | 0.21 | 0.33 | 0.39 | 0.28 | 0.35 | 1.82 |
| 41 ERX1149 | -1.1 | -2.1 | -2.3 | -2.5 | -2.7 | -3 | -2.8 | -2.2 | -1.5 | -2.6 | -20.95 |
| 42 ERX1149 | -1 | -0.8 | -0.3 | -0.7 | -1.5 | -1.4 | -1.3 | -1.4 | -1.5 | -0.3 | -9.25 |
| 43 ERX1149 | 0.2 | -0.2 | -0.1 | -0.7 | -0.8 | -0.9 | -0.8 | -0.8 | -1.1 | -0.6 | -5.6 |
| 44 ERX1149 | -0.2 | -0.4 | -0.4 | -1.4 | -2.1 | -2.5 | -1.9 | -2.6 | -1.6 | -2.2 | -13.9 |
| 45 ERX1149 | -0.2 | -0.5 | -1.6 | -1.8 | -2.1 | -2.8 | -1.5 | -2.3 | -1.5 | -1.7 | -15.05 |
| AVG | -0.08 | -0.76 | -0.98 | -1.12 | -1.48 | -1.76 | -1.92 | -1.96 | -1.78 | -1.46 | -12.45 |
| SEM | 0.17 | 0.31 | 0.32 | 0.30 | 0.24 | 0.29 | 0.35 | 0.43 | 0.58 | 0.55 | 2.84 |

FIG. 12 (Continued)

| | | | | | | | | | | | |
|---|---|---|---|---|---|---|---|---|---|---|---|
| 46 ERX1168 | -0.6 | -2.4 | -3.1 | -3.9 | -4.7 | -4.2 | -4.4 | -3.6 | -4.8 | -4.2 | -33.5 |
| 47 ERX1168 | 0.9 | -2.2 | -2 | -3.4 | -5.6 | -7.2 | -6.8 | -5.4 | -4.9 | -5.5 | -39.8 |
| 48 ERX1168 | -0.7 | -2.5 | -2.7 | -3.7 | -5.3 | -6.2 | -7.4 | -6.5 | -6.2 | -6 | -43.85 |
| 49 ERX1168 | -0.7 | -1.4 | -2.8 | -3.1 | -4.9 | -4.9 | -4.2 | -4.1 | -4.7 | -5.9 | -33.4 |
| 50 ERX1168 | -1.2 | -2.8 | -2.2 | -3.1 | -4.4 | -3.8 | -4.2 | -2.8 | -5.7 | -4.8 | -3.2 |
| AVG | -0.38 | -0.80 | -0.94 | -1.42 | -1.84 | -2.12 | -1.66 | -1.86 | -1.44 | -1.36 | -12.95 |
| SEM | 0.28 | 0.34 | 0.43 | 0.34 | 0.32 | 0.41 | 0.34 | 0.33 | 0.09 | 0.53 | 2.62 |
| 51 ERX1177 | 0.2 | -0.2 | -0.8 | -0.7 | -0.6 | -0.6 | -1 | -1 | -0.8 | -0.7 | -5.95 |
| 52 ERX1177 | -0.2 | -0.3 | -1.3 | -1.2 | -2 | -2.2 | -2.3 | -2.7 | -2.6 | -3.3 | -16.35 |
| 53 ERX1177 | -1 | -0.9 | -0.7 | -1.3 | -1.8 | -1.8 | -2.1 | -2.2 | -1.7 | -1.5 | -13.75 |
| 54 ERX1177 | -1.7 | -1.9 | -2.4 | -2.1 | -2 | -2.1 | -2.3 | -2 | -2.2 | -1.9 | -18.8 |
| 55 ERX1177 | -0.1 | -0.4 | -0.8 | -0.6 | -0.6 | -0.9 | -1.3 | -1.6 | -2 | -2.4 | -9.45 |
| AVG | -0.46 | -2.26 | -2.56 | -3.44 | -4.98 | -5.26 | -5.40 | -4.48 | -5.26 | -5.28 | -36.51 |
| SEM | 0.36 | 0.24 | 0.20 | 0.16 | 0.21 | 0.63 | 0.70 | 0.66 | 0.29 | 0.34 | 2.28 |
| 56 Pristimerin | -0.6 | -0.1 | 0.3 | 0.3 | 0.9 | 0.7 | 0.3 | 0.6 | 0.2 | 0.7 | 3.8 |
| 57 Pristimerin | -0.2 | -0.7 | -0.9 | -1 | -1.1 | -1.7 | -2.1 | -1.9 | -2 | 1.4 | -.12 |
| 58 Pristimerin | 0.4 | -0.6 | -0.8 | -1.2 | -1.1 | -0.7 | -1.6 | -1.6 | -1.2 | -1 | -8.7 |
| 59 Pristimerin | -0.1 | -0.2 | -0.8 | -0.4 | -0.4 | 0.3 | -0.3 | -0.3 | 0.4 | 0.9 | 0.7 |
| 60 Pristimerin | -0.2 | -1.1 | -2 | -2.2 | -2.4 | -2.1 | -2.3 | -3 | -2.5 | -2.5 | -18.95 |
| AVG | -0.56 | -0.74 | -1.20 | -1.18 | -1.40 | -1.52 | -1.80 | -1.90 | -1.86 | -1.96 | -12.86 |
| SEM | 0.35 | 0.31 | 0.32 | 0.27 | 0.33 | 0.32 | 0.27 | 0.29 | 0.30 | 0.44 | 2.32 |
| AVG | -0.14 | -0.50 | -0.84 | -0.90 | -0.82 | -0.70 | -1.08 | -1.24 | -1.02 | -0.28 | -7.31 |
| SEM | 0.16 | 0.21 | 0.36 | 0.42 | 0.54 | 0.54 | 0.57 | 0.63 | 0.58 | 0.70 | 4.04 |

FIG. 12 (Continued)

Daily Food Intake

| Animal # Group | FI | FI | FI | FI | FI | FI | FI | FI | FI | FI |
|---|---|---|---|---|---|---|---|---|---|---|
| 1 Vehicle | 1.2 | 2.4 | 1.9 | 1.5 | 1.7 | 2.2 | 2.1 | 1.8 | 2.1 | 2.4 |
| 2 Vehicle | 1.9 | 2.2 | 2.4 | 1.8 | 4.2 | 1.3 | 3.7 | 2.3 | 2.2 | 3 |
| 3 Vehicle | 1.3 | 2.8 | 3.1 | 1.8 | 3.7 | 2.6 | 3.4 | 2.3 | 2.8 | 2.8 |
| 4 Vehicle | 0.9 | 2.1 | 1.9 | 0.8 | 3.3 | 1.8 | 2 | 2.4 | 2.3 | 2.3 |
| 5 Vehicle | 2.7 | 1.5 | 1.7 | 1.4 | 3.3 | 2.8 | 2.2 | 2.1 | 2.1 | 2.7 |
| AVG | 1.60 | 2.20 | 2.20 | 1.46 | 3.24 | 2.14 | 2.68 | 2.18 | 2.30 | 2.64 |
| SEM | 0.32 | 0.21 | 0.25 | 0.18 | 0.42 | 0.27 | 0.36 | 0.11 | 0.13 | 0.13 |
| 6 ERX1000-4 | 1.7 | 1.5 | 1 | 0.9 | 2.1 | 2.1 | 1.6 | 1.2 | 1.6 | 1.6 |
| 7 ERX1000-4 | 2 | 2.8 | 3 | 0.3 | 4.3 | 2 | 2.2 | 1.9 | 1.3 | 2.4 |
| 8 ERX1000-4 | 2 | 1.9 | 1.6 | 1.2 | 1.3 | 0.9 | 0.8 | 2 | 0.7 | 0.9 |
| 9 ERX1000-4 | 1.2 | 1.6 | 1.8 | 1.5 | 1.6 | 1.7 | 1.9 | 2.2 | 2.1 | 1.4 |
| 10 ERX1000-4 | 1.2 | 1.4 | 1.2 | 0.6 | 0.4 | 1.4 | 1.6 | 2.1 | 1.6 | 0.8 |
| AVG | 1.62 | 1.84 | 1.72 | 0.90 | 1.94 | 1.62 | 1.62 | 1.88 | 1.46 | 1.42 |
| SEM | 0.18 | 0.25 | 0.35 | 0.21 | 0.65 | 0.22 | 0.23 | 0.18 | 0.23 | 0.29 |
| 11 ERX1006 | 0.5 | 1.1 | 0.6 | 1.1 | 1 | 1.5 | 0.9 | 1 | 0.7 | 1.4 |
| 12 ERX1006 | 1.8 | 2 | 3.2 | 2.3 | 2.4 | 1.6 | 2.2 | 1.6 | 1.7 | 2.4 |
| 13 ERX1006 | 1.6 | 1.5 | 2.9 | 2 | 2.8 | 1.5 | 2 | 2.1 | 1.6 | 2.3 |
| 14 ERX1006 | 1.5 | 1.3 | 2.3 | 2.2 | 2.8 | 2.2 | 2.7 | 2.3 | 2.1 | 2.1 |
| 15 ERX1006 | 2.1 | 1.8 | 2.2 | 1.9 | 2.4 | 2.2 | 2.2 | 1.3 | 1.5 | 1.3 |
| AVG | 1.50 | 1.54 | 2.24 | 1.90 | 2.28 | 1.80 | 2.00 | 1.66 | 1.52 | 1.90 |
| SEM | 0.27 | 0.16 | 0.45 | 0.21 | 0.33 | 0.16 | 0.30 | 0.24 | 0.23 | 0.23 |
| 16 ERX1007 | 2 | 1.6 | 2.2 | 1.9 | 2 | 1.1 | 2.1 | 1.4 | 1.8 | 1.5 |
| 17 ERX1007 | 2.1 | 1.3 | 2.3 | 2.4 | 1.9 | 2.3 | 1 | 2.9 | 2 | 3.2 |
| 18 ERX1007 | 1.6 | 1.5 | 2.2 | 1.2 | 0.9 | 2.7 | 1.7 | 3.3 | 1.7 | 3 |
| 19 ERX1007 | 1.6 | 2.5 | 2 | 2.5 | 0.8 | 2.2 | 2.3 | 2.6 | 1.7 | 2.2 |
| 20 ERX1007 | 2.2 | 2 | 2.3 | 2.1 | 1 | 2.3 | 3.1 | 3 | 2.5 | 2.3 |
| AVG | 1.90 | 1.78 | 2.20 | 2.02 | 1.32 | 1.92 | 2.04 | 2.64 | 1.94 | 2.58 |
| SEM | 0.13 | 0.21 | 0.08 | 0.23 | 0.26 | 0.23 | 0.35 | 0.33 | 0.15 | 0.32 |
| 21 ERX1037 | 3.5 | 2.3 | 1.6 | 2.8 | 2.7 | 3 | 3.7 | 2.6 | 3 | 2.5 |
| 22 ERX1037 | 1.9 | 2.5 | 2.8 | 1.7 | 2.2 | 2.2 | 2.6 | 3 | 2.6 | 2.4 |
| 23 ERX1037 | 2.8 | 2.3 | 2.2 | 2.4 | 3 | 2.7 | 2.1 | 2.4 | 2.1 | 2.7 |
| 24 ERX1037 | 3 | 0.4 | 2 | 2.9 | 2.7 | 3 | 2.6 | 2.7 | 2.5 | 2.6 |
| 25 ERX1037 | 1.8 | 2.6 | 2.3 | 2.3 | 2.2 | 2.2 | 2.5 | 2.7 | 2.4 | 2.2 |

| | | | | | | | | | | |
|---|---|---|---|---|---|---|---|---|---|---|
| AVG | 2.60 | 2.02 | 2.18 | 2.42 | 2.56 | 2.62 | 2.70 | 2.68 | 2.52 | 2.48 |
| SEM | 0.33 | 0.41 | 0.20 | 0.21 | 0.16 | 0.18 | 0.27 | 0.10 | 0.15 | 0.09 |
| 26 ERX1060 | 2.2 | 2.5 | 3 | 2.2 | 2.3 | .2 | .2 | 1.3 | 0.6 | 1.6 |
| 27 ERX1060 | 1.2 | 3.1 | 2.5 | 3.2 | 0.8 | 0.9 | 2.5 | 1.9 | .2 | 2.1 |
| 28 ERX1060 | 1.1 | 0.9 | 2.9 | 2.4 | 1.4 | 2.2 | 2.2 | 1.9 | 1.9 | 2.9 |
| 29 ERX1060 | 1.5 | 1.1 | 2.9 | 2.1 | 1.4 | 2.1 | 2.3 | .3 | 2.5 | 2.1 |
| 30 ERX1060 | 1.6 | 2.5 | 1.9 | 2.6 | 1.7 | 3.6 | 3.1 | 2.6 | 1.9 | 3 |
| AVG | 1.52 | 2.02 | 2.64 | 2.50 | 1.52 | 2.16 | 2.42 | 2.14 | 1.78 | 2.34 |
| SEM | 0.19 | 0.43 | 0.20 | 0.19 | 0.24 | 0.43 | 0.19 | 0.30 | 0.32 | 0.27 |
| 31 ERX1077 | 1.5 | 1.8 | 2.5 | 2.3 | 1.9 | 2.7 | 3.1 | 2.8 | 1.7 | 2.4 |
| 32 ERX1077 | .2 | 2.2 | 2.2 | 2.3 | 1.9 | | 3.2 | 2.1 | 1.9 | 2.4 |
| 33 ERX1077 | 1.8 | 1.9 | 2.2 | 1.9 | 1.5 | 3 | 2.6 | 2.7 | 1.7 | 2.6 |
| 34 ERX1077 | .2 | 1.5 | 2.5 | 2.4 | 2.8 | 2.5 | 2.5 | 2.5 | 2.3 | 3.2 |
| 35 ERX1077 | 1.6 | 1.8 | 2.8 | 2.4 | 2.1 | 2.2 | 2.4 | 2.3 | 2.1 | 2.9 |
| AVG | 1.78 | 1.84 | 2.44 | 2.26 | 2.04 | 2.68 | 2.76 | 2.48 | 1.94 | 2.70 |
| SEM | 0.10 | 0.11 | 0.11 | 0.09 | 0.21 | 0.15 | 0.16 | 0.13 | 0.12 | 0.15 |
| 36 ERX1107 | 1.4 | 1.7 | 1.8 | .2 | 1.8 | 2.2 | 2.5 | 1.5 | 1.9 | 2.1 |
| 37 ERX1107 | 2.3 | 1.6 | 2.1 | 1.8 | 1.9 | 2.1 | 2.8 | 2.2 | 1.8 | 3.2 |
| 38 ERX1107 | 2.3 | 0.9 | 1.6 | 1.9 | 2.8 | 2.4 | 1.9 | 2.6 | 2.2 | 2.7 |
| 39 ERX1107 | 1.4 | 2.6 | 2.3 | 1.2 | 2.2 | 1.6 | 2.6 | 2.6 | 1.9 | 3.3 |
| 40 ERX1107 | 2.1 | 2.4 | 3.1 | 2.2 | 2.7 | 2.5 | 2.4 | 2.6 | 2.7 | 2.4 |
| AVG | 1.90 | 1.84 | 2.18 | 1.82 | 2.28 | 2.16 | 2.44 | 2.30 | 2.10 | 2.74 |
| SEM | 0.21 | 0.30 | 0.26 | 0.17 | 0.20 | 0.16 | 0.15 | 0.21 | 0.16 | 0.23 |
| 41 ERX1149 | 1.9 | 1.4 | 2.1 | 1.4 | 2.2 | 2.2 | 2.3 | 3.2 | 1.9 | .2 |
| 42 ERX1149 | 1.6 | 2.2 | 3.3 | 2.3 | 2.1 | 2.5 | 2.1 | 2.8 | 2.5 | 3.2 |
| 43 ERX1149 | | 2.1 | 2.5 | 2.1 | 2.6 | 2.3 | 2.2 | 2.4 | .2 | 2.6 |
| 44 ERX1149 | 2.1 | 1.7 | 2.8 | 1.7 | 1.6 | 1.4 | 2.2 | 2.1 | 2.4 | .2 |
| 45 ERX1149 | 1.7 | 1 | 2.3 | 1.7 | 1.9 | 1.4 | 2.8 | 2.5 | 1.9 | 2.2 |
| AVG | 1.66 | 1.68 | 2.60 | 1.84 | 2.08 | 1.96 | 2.32 | 2.60 | 2.14 | 2.40 |
| SEM | 0.19 | 0.22 | 0.21 | 0.16 | 0.17 | 0.23 | 0.12 | 0.19 | 0.13 | 0.23 |
| 46 ERX1168 | 1.1 | 0.6 | | 1.1 | 1.2 | 1.3 | 1.9 | 2.2 | 1.4 | 1.2 |
| 47 ERX1168 | 3.4 | | 1.4 | 1.1 | 1.8 | 0.4 | 1.7 | 2.8 | 3.2 | 2.6 |
| 48 ERX1168 | 1.8 | 0.5 | 1.3 | 0.7 | 1.7 | 0.1 | 0.3 | 1.6 | 2.3 | .2 |
| 49 ERX1168 | 1.9 | 0.8 | 1.5 | 0.7 | 1.5 | 0.6 | 2.1 | 1.9 | 2.3 | 0.9 |
| 50 ERX1168 | 1.6 | 0.9 | 2.2 | 1.8 | 1.5 | 1 | 2.2 | 3 | 0.9 | 1.9 |

|  | | | | | | | | | | | |
|---|---|---|---|---|---|---|---|---|---|---|---|
| 51 ERX1177 | 1.96 | 0.76 | 1.48 | 1.06 | 1.54 | 0.68 | 1.64 | 2.30 | 2.02 | 1.72 | |
| 52 ERX1177 | 3 | 2.3 | 2.5 | 2.5 | 3.4 | 2.9 | 2.4 | 2.6 | 2.8 | 2.5 | |
| 53 ERX1177 | 1.9 | 1.3 | 1.6 | 1.8 | 1.8 | 1.5 | 1.7 | 1.9 | 1.6 | 1.2 | |
| 54 ERX1177 | 1.4 | 1.5 | 2.3 | 1.9 | 2.2 | 2.2 | 1.9 | 2 | 2.1 | 2.3 | |
| 55 ERX1177 | 1.3 | 1.1 | 2.3 | 2.5 | 2.9 | 2.8 | 2.3 | 2.6 | 1.7 | 2.6 | |
|  | 2.1 | 0.7 | 2.6 | 2.1 | 2.3 | 2.2 | 2.1 | 1.8 | 0.9 | 1.2 | |
| AVG | 1.96 | 0.76 | 1.48 | 1.06 | 1.54 | 0.68 | 1.64 | 2.30 | 2.02 | 1.72 | |
| SEM | 0.39 | 0.09 | 0.20 | 0.20 | 0.10 | 0.21 | 0.35 | 0.26 | 0.40 | 0.30 | |
| 56 Pristimerin | 1.94 | 1.38 | 2.26 | 2.16 | 2.52 | 2.32 | 2.08 | 2.18 | 1.82 | 1.96 | |
| 57 Pristimerin | 1.8 | 2.9 | 3 | 2.9 | 3.1 | 2.9 | 2.3 | 3 | 2.3 | 2.9 | |
| 58 Pristimerin | 2.2 | 2 | 2.5 | 2.3 | 3.2 | 1.8 | 1.7 | 3 | 2.7 | 2.3 | |
| 59 Pristimerin | 1.4 | 1.4 | 2.1 | 1.5 | 1.9 | 2.6 | 1.2 | 2.2 | 3 | 1.7 | |
| 60 Pristimerin | 1.4 | 1.9 | 2.5 | 2.7 | 2.5 | 2.7 | 2.7 | 2.4 | 2.9 | 2.1 | |
|  | 1.4 | 1.5 | 2.1 | 1.8 | 1.4 | 2 | 2.2 | 2.2 | 2.6 | 1.7 | |
| AVG | 1.94 | 1.38 | 2.26 | 2.16 | 2.52 | 2.32 | 2.08 | 2.18 | 1.82 | 1.96 | |
| SEM | 0.30 | 0.27 | 0.17 | 0.15 | 0.28 | 0.25 | 0.13 | 0.17 | 0.31 | 0.31 | |
| AVG | 1.64 | 1.94 | 2.44 | 2.24 | 2.42 | 2.40 | 2.02 | 2.56 | 2.70 | 2.14 | |
| SEM | 0.16 | 0.27 | 0.17 | 0.26 | 0.35 | 0.21 | 0.26 | 0.18 | 0.12 | 0.22 | |

FIG. 13 (Continued)

Cumulative Food Intake

| Animal # | Group | FI | FI | FI | FI | FI | FI | FI | FI | FI | CUM FI AUC |
|---|---|---|---|---|---|---|---|---|---|---|---|
| 1 | Vehicle | 1.2 | 3.6 | 5.5 | 7.0 | 8.7 | 10.9 | 13.0 | 14.8 | 16.9 | 19.3 | 90.65 |
| 2 | Vehicle | 1.9 | 4.1 | 6.5 | 8.3 | 12.5 | 13.8 | 17.5 | 19.8 | 22.0 | 25.0 | 117.95 |
| 3 | Vehicle | 1.3 | 4.1 | 7.2 | 9.0 | 12.7 | 15.3 | 18.7 | 21.0 | 23.8 | 26.6 | 125.75 |
| 4 | Vehicle | 0.9 | 3.0 | 4.9 | 5.7 | 9.0 | 10.8 | 12.8 | 15.2 | 17.5 | 19.8 | 89.25 |
| 5 | Vehicle | 2.7 | 4.2 | 5.9 | 7.3 | 10.6 | 13.4 | 15.6 | 17.7 | 19.8 | 22.5 | 107.1 |
| AVG |  | 1.60 | 3.80 | 6.00 | 7.46 | 10.70 | 12.84 | 15.52 | 17.70 | 20.00 | 22.64 | 106.14 |
| SEM |  | 0.32 | 0.23 | 0.40 | 0.57 | 0.84 | 0.87 | 1.18 | 1.22 | 1.31 | 1.42 | 7.25 |
| 6 | ERX1000-4 | 1.7 | 3.2 | 4.2 | 5.1 | 7.2 | 9.3 | 10.9 | 12.1 | 13.7 | 15.3 | 74.2 |
| 7 | ERX1000-4 | 2.0 | 4.8 | 7.8 | 8.1 | 12.4 | 14.4 | 16.6 | 18.5 | 19.8 | 22.2 | 114.5 |
| 8 | ERX1000-4 | 2.0 | 3.9 | 5.5 | 6.7 | 8.0 | 8.9 | 9.7 | 11.7 | 12.4 | 13.3 | 74.45 |
| 9 | ERX1000-4 | 1.2 | 2.8 | 4.6 | 6.1 | 7.7 | 9.4 | 11.3 | 13.5 | 15.6 | 17.0 | 80.1 |
| 10 | ERX1000-4 | 1.2 | 2.6 | 3.8 | 4.4 | 4.8 | 6.2 | 7.8 | 9.9 | 11.5 | 12.3 | 57.75 |
| AVG |  | 1.62 | 3.46 | 5.18 | 6.08 | 8.02 | 9.64 | 11.26 | 13.14 | 14.60 | 16.02 | 80.20 |
| SEM |  | 0.18 | 0.40 | 0.71 | 0.64 | 1.23 | 1.33 | 1.47 | 1.46 | 1.47 | 1.75 | 9.35 |
| 11 | ERX1006 | 0.5 | 1.6 | 2.2 | 3.3 | 4.3 | 5.8 | 6.7 | 7.7 | 8.4 | 9.8 | 45.15 |
| 12 | ERX1006 | 1.8 | 3.8 | 7.0 | 9.3 | 11.7 | 13.3 | 15.5 | 17.1 | 18.8 | 21.2 | 108 |
| 13 | ERX1006 | 1.6 | 3.1 | 6.0 | 8.0 | 10.8 | 12.3 | 14.3 | 16.4 | 18.0 | 20.3 | 99.85 |
| 14 | ERX1006 |  | 1.3 | 3.6 | 5.8 | 8.6 | 10.8 | 13.5 | 15.8 | 17.9 | 20.0 | 87.95 |
| 15 | ERX1006 | 2.1 | 3.9 | 6.1 | 8.0 | 10.4 | 12.6 | 14.8 | 16.1 | 17.6 | 18.9 | 100 |
| AVG |  | 1.50 | 2.74 | 4.98 | 6.88 | 9.16 | 10.96 | 12.96 | 14.62 | 16.14 | 18.04 | 88.19 |
| SEM |  | 0.35 | 0.55 | 0.89 | 1.06 | 1.32 | 1.35 | 1.60 | 1.74 | 1.95 | 2.09 | 11.23 |
| 16 | ERX1007 | 2.0 | 3.6 | 5.8 | 7.7 | 9.7 | 10.8 | 12.9 | 14.3 | 16.1 | 17.6 | 90.7 |
| 17 | ERX1007 | 2.1 | 3.4 | 5.7 | 8.1 | 10.0 | 12.3 | 13.3 | 16.2 | 18.2 | 21.4 | 98.95 |
| 18 | ERX1007 | 1.6 | 3.1 | 5.0 | 6.2 | 7.1 | 8.8 | 10.5 | 13.8 | 15.5 | 18.5 | 80.05 |
| 19 | ERX1007 | 1.6 | 4.1 | 6.5 | 9.0 | 9.8 | 12.0 | 14.3 | 16.9 | 18.6 | 20.8 | 102.4 |
| 20 | ERX1007 | 2.2 | 4.2 | 6.4 | 8.5 | 9.5 | 11.8 | 14.9 | 17.9 | 20.4 | 23.4 | 106.4 |
| AVG |  | 1.90 | 3.68 | 5.88 | 7.90 | 9.22 | 11.14 | 13.18 | 15.82 | 17.76 | 20.34 | 95.70 |
| SEM |  | 0.13 | 0.21 | 0.27 | 0.48 | 0.54 | 0.64 | 0.76 | 0.78 | 0.89 | 1.04 | 4.69 |
| 21 | ERX1037 | 3.5 | 5.8 | 7.4 | 10.2 | 12.9 | 15.9 | 19.6 | 22.2 | 25.2 | 27.7 | 134.8 |
| 22 | ERX1037 | 1.9 | 4.4 | 7.2 | 8.9 | 11.1 | 13.3 | 15.9 | 18.9 | 21.5 | 23.9 | 114.1 |
| 23 | ERX1037 | 2.8 | 5.1 | 7.3 | 9.7 | 12.7 | 15.4 | 17.5 | 19.9 | 22.0 | 24.7 | 123.35 |
| 24 | ERX1037 | 3.0 | 3.4 | 5.4 | 8.3 | 11.0 | 14.0 | 16.6 | 19.3 | 21.8 | 24.4 | 113.5 |
| 25 | ERX1037 | 1.8 | 4.4 | 6.7 | 9.0 | 11.2 | 13.4 | 15.9 | 18.6 | 21.0 | 23.2 | 112.7 |

FIG. 14

| | | | | | | | | | | | |
|---|---|---|---|---|---|---|---|---|---|---|---|
| AVG | | 2.60 | 4.62 | 6.80 | 9.22 | 11.78 | 14.40 | 17.10 | 19.78 | 22.30 | 24.78 | 119.69 |
| SEM | | 0.33 | 0.40 | 0.37 | 0.33 | 0.42 | 0.53 | 0.69 | 0.64 | 0.74 | 0.77 | 4.24 |
| 26 | ERX1060 | 2.2 | 4.7 | 7.7 | 9.9 | 12.2 | 14.2 | 16.2 | 17.5 | 18.1 | 19.7 | 111.45 |
| 27 | ERX1060 | 1.2 | 4.3 | 6.8 | 10.0 | 10.8 | 11.7 | 14.2 | 16.1 | 18.1 | 20.2 | 102.7 |
| 28 | ERX1060 | 1.1 | 2.0 | 4.9 | 7.3 | 8.7 | 10.9 | 13.1 | 15.0 | 16.9 | 19.8 | 89.25 |
| 29 | ERX1060 | 1.5 | 2.6 | 5.5 | 7.6 | 9.0 | 11.1 | 13.4 | 16.4 | 18.9 | 21.0 | 95.75 |
| 30 | ERX1060 | 1.6 | 4.1 | 6.0 | 8.6 | 10.3 | 13.9 | 17.0 | 19.6 | 21.5 | 24.5 | 114.05 |
| AVG | | 1.52 | 3.54 | 6.18 | 8.68 | 10.20 | 12.36 | 14.78 | 16.92 | 18.70 | 21.04 | 102.64 |
| SEM | | 0.19 | 0.52 | 0.49 | 0.56 | 0.63 | 0.70 | 0.77 | 0.78 | 0.77 | 0.89 | 4.66 |
| 31 | ERX1077 | 1.5 | 3.3 | 5.8 | 8.1 | 10.0 | 12.7 | 15.8 | 18.6 | 20.3 | 22.7 | 106.7 |
| 32 | ERX1077 | 2.0 | 4.2 | 6.4 | 8.7 | 10.6 | 13.6 | 16.8 | 18.9 | 20.8 | 23.2 | 112.6 |
| 33 | ERX1077 | 1.8 | 3.7 | 5.9 | 7.8 | 9.3 | 12.3 | 14.9 | 17.6 | 19.3 | 21.9 | 102.65 |
| 34 | ERX1077 | 2.0 | 3.5 | 6.0 | 8.4 | 11.2 | 13.7 | 16.2 | 18.7 | 21.0 | 24.2 | 111.8 |
| 35 | ERX1077 | 1.6 | 3.4 | 6.2 | 8.6 | 10.7 | 12.9 | 15.3 | 17.6 | 19.7 | 22.6 | 106.5 |
| AVG | | 1.78 | 3.62 | 6.06 | 8.32 | 10.36 | 13.04 | 15.80 | 18.28 | 20.22 | 22.92 | 108.05 |
| SEM | | 0.10 | 0.16 | 0.11 | 0.17 | 0.33 | 0.27 | 0.33 | 0.28 | 0.32 | 0.38 | 1.85 |
| 36 | ERX1107 | 1.4 | 3.1 | 4.9 | 6.9 | 8.7 | 10.9 | 13.4 | 14.9 | 16.8 | 18.9 | 89.75 |
| 37 | ERX1107 | 2.3 | 3.9 | 6.0 | 7.8 | 9.7 | 11.8 | 14.6 | 16.8 | 18.6 | 21.8 | 101.25 |
| 38 | ERX1107 | 2.3 | 3.2 | 4.8 | 6.7 | 9.5 | 11.8 | 13.8 | 16.4 | 18.6 | 21.3 | 96.7 |
| 39 | ERX1107 | 1.4 | 4.0 | 6.3 | 7.5 | 9.7 | 11.3 | 13.9 | 16.5 | 18.4 | 21.7 | 99.15 |
| 40 | ERX1107 | 2.1 | 4.5 | 7.6 | 9.8 | 12.5 | 15.0 | 17.4 | 20.0 | 22.7 | 25.1 | 123.1 |
| AVG | | 1.90 | 3.74 | 5.92 | 7.74 | 10.02 | 12.18 | 14.62 | 16.92 | 19.02 | 21.76 | 101.99 |
| SEM | | 0.21 | 0.26 | 0.51 | 0.55 | 0.65 | 0.73 | 0.72 | 0.84 | 0.98 | 0.99 | 5.62 |
| 41 | ERX1149 | 1.9 | 3.3 | 5.4 | 6.8 | 9.0 | 11.2 | 13.5 | 16.7 | 18.6 | 20.6 | 95.75 |
| 42 | ERX1149 | 1.6 | 3.8 | 7.1 | 9.4 | 11.5 | 14.0 | 16.1 | 18.9 | 21.4 | 24.6 | 115.3 |
| 43 | ERX1149 | 2.1 | 4.2 | 6.7 | 8.8 | 11.4 | 13.7 | 15.9 | 18.3 | 20.3 | 22.9 | 111.8 |
| 44 | ERX1149 | 1.7 | 3.4 | 6.2 | 7.9 | 9.5 | 10.9 | 13.1 | 15.2 | 17.6 | 19.6 | 94.45 |
| 45 | ERX1149 | 1.0 | 2.0 | 4.3 | 6.0 | 7.9 | 9.3 | 12.1 | 14.6 | 16.5 | 18.7 | 82.55 |
| AVG | | 1.66 | 3.34 | 5.94 | 7.78 | 9.86 | 11.82 | 14.14 | 16.74 | 18.88 | 21.28 | 99.97 |
| SEM | | 0.19 | 0.37 | 0.50 | 0.62 | 0.70 | 0.89 | 0.79 | 0.84 | 0.89 | 1.09 | 6.03 |
| 46 | ERX1168 | 1.1 | 1.7 | 2.7 | 3.7 | 4.9 | 6.2 | 8.1 | 10.3 | 11.7 | 12.9 | 56.3 |
| 47 | ERX1168 | 3.4 | 4.4 | 5.8 | 6.9 | 8.7 | 9.1 | 10.8 | 13.6 | 16.8 | 19.4 | 87.5 |
| 48 | ERX1168 | 1.8 | 2.3 | 3.6 | 4.3 | 6.0 | 6.1 | 6.4 | 8.0 | 10.3 | 12.3 | 54.05 |
| 49 | ERX1168 | 1.9 | 2.7 | 4.2 | 4.9 | 6.4 | 7.0 | 9.1 | 11.0 | 13.3 | 14.2 | 66.65 |
| 50 | ERX1168 | 1.6 | 2.5 | 4.7 | 6.5 | 8.0 | 9.0 | 11.2 | 14.2 | 15.1 | 17.0 | 80.5 |

FIG. 14 (Continued)

|     |              |      |      |      |      |      |      |      |      |      |      |      |
|-----|--------------|------|------|------|------|------|------|------|------|------|------|------|
|     |              | 1.96 | 2.72 | 4.20 | 5.26 | 6.80 | 7.48 | 9.12 | 11.42| 13.44| 15.16| 69.00|
|     |              | 0.39 | 0.45 | 0.52 | 0.62 | 0.69 | 0.66 | 0.88 | 1.13 | 1.16 | 1.33 | 6.58 |
| 51  | ERX1177      | 3.0  | 5.3  | 7.8  | 10.3 | 13.7 | 16.6 | 19.0 | 21.6 | 24.4 | 26.9 | 133.65|
| 52  | ERX1177      | 1.9  | 3.2  | 4.8  | 6.6  | 8.4  | 9.9  | 11.6 | 13.5 | 15.1 | 16.3 | 82.2 |
| 53  | ERX1177      | 1.4  | 2.9  | 5.2  | 7.1  | 9.3  | 11.5 | 13.4 | 15.4 | 17.5 | 19.8 | 92.9 |
| 54  | ERX1177      | 1.3  | 2.4  | 4.7  | 7.2  | 10.1 | 12.9 | 15.2 | 17.8 | 19.5 | 22.1 | 101.5|
| 55  | ERX1177      | 2.1  | 2.8  | 5.4  | 7.5  | 9.8  | 12.0 | 14.1 | 15.9 | 16.8 | 18.0 | 94.35|
| AVG |              | 1.94 | 3.32 | 5.58 | 7.74 | 10.26| 12.58| 14.66| 16.84| 18.66| 20.62| 100.92|
| SEM |              | 0.30 | 0.51 | 0.57 | 0.66 | 0.91 | 1.12 | 1.23 | 1.37 | 1.60 | 1.84 | 8.75 |
| 56  | Pristimerin  | 1.8  | 4.7  | 7.7  | 10.6 | 13.7 | 16.6 | 18.9 | 21.9 | 24.2 | 27.1 | 132.75|
| 57  | Pristimerin  | 2.2  | 4.2  | 6.7  | 9.0  | 12.2 | 14.0 | 15.7 | 18.7 | 21.4 | 23.7 | 114.85|
| 58  | Pristimerin  | 1.4  | 2.8  | 4.9  | 6.4  | 8.3  | 10.9 | 12.1 | 14.3 | 17.3 | 19.0 | 87.2 |
| 59  | Pristimerin  | 1.4  | 3.3  | 5.8  | 8.5  | 11.0 | 13.7 | 16.4 | 18.8 | 21.7 | 23.8 | 111.8|
| 60  | Pristimerin  | 1.4  | 2.9  | 5.0  | 6.8  | 8.2  | 10.2 | 12.4 | 14.6 | 17.2 | 18.9 | 87.45|
| AVG |              | 1.64 | 3.58 | 6.02 | 8.26 | 10.68| 13.08| 15.10| 17.66| 20.36| 22.50| 106.81|
| SEM |              | 0.16 | 0.37 | 0.53 | 0.76 | 1.08 | 1.15 | 1.28 | 1.43 | 1.36 | 1.57 | 8.72 |

| # | Group | Glucose 1 (mg/dl) | Glucose 2 (mg/dl) | Day -1 AVG (mg/dl) | Group Avg (mg/dl) | Group SE |
|---|---|---|---|---|---|---|
| 1 | Vehicle | 156 | 154 | 155 | | |
| 2 | Vehicle | 147 | 166 | 156.5 | | |
| 3 | Vehicle | 168 | 165 | 166.5 | | |
| 4 | Vehicle | 163 | 165 | 164 | | |
| 5 | Vehicle | 134 | 139 | 136.5 | 155.7 | 5.27 |
| 6 | ERX1000-4 | 172 | 161 | 166.5 | | |
| 7 | ERX1000-4 | 166 | 178 | 172 | | |
| 8 | ERX1000-4 | 155 | 162 | 158.5 | | |
| 9 | ERX1000-4 | 169 | 161 | 165 | | |
| 10 | ERX1000-4 | 146 | 151 | 148.5 | 162.1 | 4.02 |
| 11 | ERX1006 | 168 | 176 | 172 | | |
| 12 | ERX1006 | 152 | 158 | 155 | | |
| 13 | ERX1006 | 165 | 165 | 165 | | |
| 14 | ERX1006 | 161 | 166 | 163.5 | | |
| 15 | ERX1006 | 175 | 190 | 182.5 | 167.6 | 4.60 |
| 16 | ERX1007 | 183 | 170 | 176.5 | | |
| 17 | ERX1007 | 184 | 171 | 177.5 | | |
| 18 | ERX1007 | 180 | 178 | 179 | | |
| 19 | ERX1007 | 142 | 156 | 149 | | |
| 20 | ERX1007 | 183 | 170 | 176.5 | 171.7 | 5.69 |
| 21 | ERX1037 | 195 | 187 | 191 | | |
| 22 | ERX1037 | 162 | 166 | 164 | | |
| 23 | ERX1037 | 155 | 157 | 156 | | |
| 24 | ERX1037 | 207 | 203 | 205 | | |
| 25 | ERX1037 | 201 | 197 | 199 | 183 | 9.73 |
| 26 | ERX1060 | 174 | 195 | 184.5 | | |
| 27 | ERX1060 | 136 | 154 | 145 | | |
| 28 | ERX1060 | 172 | 170 | 171 | | |
| 29 | ERX1060 | 188 | 195 | 191.5 | | |
| 30 | ERX1060 | 144 | 139 | 141.5 | 166.7 | 10.14 |

FIG. 15 (Continued)

| | | | | |
|---|---|---|---|---|
| 31 ERX1077 | 176 | 173 | 174.5 | |
| 32 ERX1077 | 166 | 161 | 163.5 | |
| 33 ERX1077 | 159 | 162 | 160.5 | |
| 34 ERX1077 | 238 | 220 | 229 | |
| 35 ERX1077 | 136 | 156 | 146 | 174.7 14.32 |
| 36 ERX1107 | 187 | 198 | 192.5 | |
| 37 ERX1107 | 169 | 156 | 162.5 | |
| 38 ERX1107 | 182 | 186 | 184 | |
| 39 ERX1107 | 179 | 160 | 169.5 | 177.7 5.30 |
| 40 ERX1107 | 170 | 190 | 180 | |
| 41 ERX1149 | 150 | 151 | 150.5 | |
| 42 ERX1149 | 177 | 177 | 177 | |
| 43 ERX1149 | 221 | 223 | 222 | |
| 44 ERX1149 | 154 | 141 | 147.5 | 172 13.54 |
| 45 ERX1149 | 162 | 164 | 163 | |
| 46 ERX1168 | 157 | 157 | 157 | |
| 47 ERX1168 | 214 | 219 | 216.5 | |
| 48 ERX1168 | 181 | 179 | 180 | |
| 49 ERX1168 | 159 | 154 | 156.5 | 169.5 13.54 |
| 50 ERX1168 | 144 | 131 | 137.5 | |
| 51 ERX1168 | 154 | 160 | 157 | |
| 52 ERX1177 | 179 | 179 | 179 | |
| 53 ERX1177 | 181 | 183 | 182 | |
| 54 ERX1177 | 188 | 196 | 192 | |
| 55 ERX1177 | 183 | 188 | 185.5 | 179.1 5.93 |
| 56 Pristimerin | 228 | 208 | 218 | |
| 57 Pristimerin | 179 | 180 | 179.5 | |
| 58 Pristimerin | 152 | 143 | 147.5 | |
| 59 Pristimerin | 145 | 166 | 155.5 | |
| 60 Pristimerin | 187 | 182 | 184.5 | 177 12.40 |

FIG. 16

| Study # | Group | Glucose 1 (mg/dl) | Glucose 2 (mg/dl) | Day 11 AVG (mg/dl) | Group Avg (mg/dl) | Group SE |
|---|---|---|---|---|---|---|
| 1 | Vehicle | 157 | 170 | 163.5 | | |
| 2 | Vehicle | 149 | 154 | 151.5 | | |
| 3 | Vehicle | 158 | 192 | 175 | | |
| 4 | Vehicle | 149 | 150 | 149.5 | | |
| 5 | Vehicle | 167 | 169 | 168 | 161.5 | 4.86 |
| 6 | ERX1000-4 | 125 | 122 | 123.5 | | |
| 7 | ERX1000-4 | 113 | 106 | 109.5 | | |
| 8 | ERX1000-4 | 99 | 99 | 99 | | |
| 9 | ERX1000-4 | 126 | 125 | 125.5 | | |
| 10 | ERX1000-4 | 104 | 109 | 106.5 | 112.8 | 5.08 |
| 11 | ERX1006 | 98 | 98 | 98 | | |
| 12 | ERX1006 | 137 | 140 | 138.5 | | |
| 13 | ERX1006 | 161 | 169 | 165 | | |
| 14 | ERX1006 | 143 | 141 | 142 | | |
| 15 | ERX1006 | 129 | 143 | 136 | 135.9 | 10.79 |
| 16 | ERX1007 | 130 | 136 | 133 | | |
| 17 | ERX1007 | 163 | 165 | 164 | | |
| 18 | ERX1007 | 131 | 120 | 125.5 | | |
| 19 | ERX1007 | 175 | 193 | 184 | | |
| 20 | ERX1007 | 182 | 171 | 176.5 | 156.6 | 11.67 |
| 21 | ERX1037 | 191 | 175 | 183 | | |
| 22 | ERX1037 | 163 | 159 | 161 | | |
| 23 | ERX1037 | 148 | 146 | 147 | | |
| 24 | ERX1037 | 196 | 194 | 195 | | |
| 25 | ERX1037 | 155 | 160 | 157.5 | 168.7 | 8.81 |
| 26 | ERX1060 | 137 | 183 | 160 | | |
| 27 | ERX1060 | 155 | 151 | 153 | | |
| 28 | ERX1060 | 134 | 143 | 138.5 | | |
| 29 | ERX1060 | 150 | 128 | 139 | | |
| 30 | ERX1060 | 163 | 144 | 153.5 | 149.8 | 4.29 |

FIG. 16 (Continued)

| | | | | | |
|---|---|---|---|---|---|
| 31 ERX1077 | 153 | 157 | 155 | | |
| 32 ERX1077 | 151 | 170 | 160.5 | | |
| 33 ERX1077 | 156 | 165 | 160.5 | | |
| 34 ERX1077 | 169 | 177 | 173 | | |
| 35 ERX1077 | 142 | 160 | 151 | 160 | 3.71 |
| 36 ERX1107 | 143 | 140 | 141.5 | | |
| 37 ERX1107 | 171 | 180 | 175.5 | | |
| 38 ERX1107 | 154 | 152 | 153 | | |
| 39 ERX1107 | 130 | 139 | 134.5 | | |
| 40 ERX1107 | 205 | 213 | 209 | 162.7 | 13.50 |
| 41 ERX1149 | 160 | 152 | 156 | | |
| 42 ERX1149 | 170 | 180 | 175 | | |
| 43 ERX1149 | 173 | 168 | 170.5 | | |
| 44 ERX1149 | 153 | 160 | 156.5 | | |
| 45 ERX1149 | 164 | 165 | 164.5 | 164.5 | 3.76 |
| 46 ERX1168 | 135 | 130 | 132.5 | | |
| 47 ERX1168 | 130 | 140 | 135 | | |
| 48 ERX1168 | 121 | 112 | 116.5 | | |
| 49 ERX1168 | 100 | 99 | 99.5 | | |
| 50 ERX1168 | 92 | 99 | 95.5 | 115.8 | 8.14 |
| 51 ERX1177 | 141 | 142 | 141.5 | | |
| 52 ERX1177 | 137 | 130 | 133.5 | | |
| 53 ERX1177 | 173 | 177 | 175 | | |
| 54 ERX1177 | 172 | 168 | 170 | | |
| 55 ERX1177 | 126 | 133 | 129.5 | 149.9 | 9.46 |
| 56 Pnstimenn | 185 | 188 | 186.5 | | |
| 57 Pnstimenn | 158 | 177 | 167.5 | | |
| 58 Pnstimenn | 160 | 158 | 159 | | |
| 59 Pnstimenn | 171 | 189 | 180 | | |
| 60 Pnstimenn | 175 | 180 | 177.5 | 174.1 | 4.86 |

FIG. 17

| Study # | Group | Glucose % Change (Day -1 to 11) | Group Avg (mg/dl) | Group SE |
|---|---|---|---|---|
| 1 | Vehicle | 5.48 | | |
| 2 | Vehicle | -3.19 | | |
| 3 | Vehicle | 5.11 | | |
| 4 | Vehicle | -8.84 | | |
| 5 | Vehicle | 23.08 | 4.325909511 | 5.401345378 |
| 6 | ERX1000-4 | -25.83 | | |
| 7 | ERX1000-4 | -36.34 | | |
| 8 | ERX1000-4 | -37.54 | | |
| 9 | ERX1000-4 | -23.94 | | |
| 10 | ERX1000-4 | -28.28 | -30.38493791 | 2.769167094 |
| 11 | ERX1006 | -43.02 | | |
| 12 | ERX1006 | -10.65 | | |
| 13 | ERX1006 | 0.00 | | |
| 14 | ERX1006 | -13.15 | | |
| 15 | ERX1006 | -25.48 | -18.45954325 | 7.35753787 |
| 16 | ERX1007 | -24.65 | | |
| 17 | ERX1007 | -7.61 | | |
| 18 | ERX1007 | -29.89 | | |
| 19 | ERX1007 | 23.49 | | |
| 20 | ERX1007 | 0.00 | -7.729972285 | 9.517323253 |
| 21 | ERX1037 | -4.19 | | |
| 22 | ERX1037 | -1.83 | | |
| 23 | ERX1037 | -5.77 | | |
| 24 | ERX1037 | -4.88 | | |
| 25 | ERX1037 | -20.85 | -7.503860175 | 3.400955976 |
| 26 | ERX1060 | -13.28 | | |
| 27 | ERX1060 | 5.52 | | |
| 28 | ERX1060 | -19.01 | | |
| 29 | ERX1060 | -27.42 | | |
| 30 | ERX1060 | 8.48 | -9.140463519 | 6.977704843 |

FIG. 17 (Continued)

| # | Compound | Value 1 | Value 2 | Value 3 |
|---|---|---|---|---|
| 31 | ERX1077 | -11.17 | | |
| 32 | ERX1077 | -1.83 | | |
| 33 | ERX1077 | 0.00 | | |
| 34 | ERX1077 | -24.45 | | |
| 35 | ERX1077 | 3.42 | -6.807827685 | 5.031121196 |
| 36 | ERX1107 | -26.49 | | |
| 37 | ERX1107 | 8.00 | | |
| 38 | ERX1107 | -16.85 | | |
| 39 | ERX1107 | -20.65 | | |
| 40 | ERX1107 | 16.11 | -7.975837804 | 8.419123912 |
| 41 | ERX1149 | 3.65 | | |
| 42 | ERX1149 | -1.13 | | |
| 43 | ERX1149 | -23.20 | | |
| 44 | ERX1149 | 6.10 | | |
| 45 | ERX1149 | 0.92 | -2.730343267 | 5.261141005 |
| 46 | ERX1168 | -15.61 | | |
| 47 | ERX1168 | -37.64 | | |
| 48 | ERX1168 | -35.28 | | |
| 49 | ERX1168 | -36.42 | | |
| 50 | ERX1168 | -30.55 | -31.09887898 | 4.055875829 |
| 51 | ERX1168 | -9.87 | | |
| 52 | ERX1177 | -25.42 | | |
| 53 | ERX1177 | -3.85 | | |
| 54 | ERX1177 | -11.46 | | |
| 55 | ERX1177 | -30.19 | -16.15695446 | 4.978958243 |
| 56 | Pristimerin | -14.45 | | |
| 57 | Pristimerin | -6.69 | | |
| 58 | Pristimerin | 7.80 | | |
| 59 | Pristimerin | 15.76 | | |
| 60 | Pristimerin | -3.79 | -0.275315763 | 5.36900492 |

ANALOGS OF CELASTROL

CROSS-REFERENCE TO RELATED APPLICATIONS

This application is a national stage application, filed under 35 U.S.C. § 371, of International Application No. PCT/US2016/058313, filed Oct. 21, 2016, which claims priority to, and the benefit of, U.S. provisional application No. 62/245,356, filed Oct. 23, 2015, the entire contents of which are incorporated herein by reference in their entirety.

BACKGROUND OF THE INVENTION

In 2008, the World Health Organization (WHO) estimated that 1.4 billion adults worldwide were overweight; of these, 200 million men and 300 million women were obese. It is predicted that more than one billion people in the world will be obese by 2030. Obesity is a major cause for the development of debilitating conditions such as type 2 diabetes, cardiovascular disease, osteoarthritis (a health problem causing pain, swelling, and stiffness in one or more joints), stroke, hypertension, cancer (breast, colon, endometrial (related to the uterine lining), and kidney), and non-alcoholic steatohepatitis, all of which reduce life quality as well as lifespan.

Amongst healthcare experts around the world, there is now agreement that the global epidemic of obesity will be one of the leading causes of morbidity and mortality for current and future generations, unless the inexorable rise in the prevalence of this disorder is reversed. Once considered to be a problem mainly in Western cultures, developing nations have now joined the ranks of countries burdened by obesity. A 1999 United Nations study found obesity to be present in all developing regions and growing rapidly, even in countries where hunger also existed. Obesity is defined by the World Health Organization (WHO) as a subject who has a body mass index (BMI=weight in kg/height in $m^2$) value of >30 kg $m^{-2}$ (normal BMI=20-25 kg $m^{-2}$).

Overweight and obesity result from an energy imbalance. The body needs a certain amount of energy (calories) from food to keep up basic life functions. Body weight tends to remain the same when the number of calories eaten equals the number of calories the body uses or "burns." Over time, when people eat and drink more calories than they burn, the energy balance tips toward weight gain, overweight, and obesity.

A possible explanation for the rapid increase in obesity is that it is being driven by a combination of genetic, social and environmental factors. Although a significant proportion of people manage very successfully to maintain a healthy bodyweight by following a careful diet and having a reasonable level of physical exercise, for many others this plan has not resulted in the desired healthy outcome. For some of the obese population, pharmacotherapy will be required to provide the requisite adjunctive support to diet, exercise and lifestyle modification that will deliver a clinically beneficial bodyweight reduction of >5%.

There is no single cause of all overweight and obesity. There is no single approach that can help prevent or treat overweight and obesity. Treatment may include a mix of behavioral treatment, diet, exercise, and sometimes weight-loss drugs. In some cases of extreme obesity, weight-loss surgery may be an option. Over the last 15 years, only four new drugs, i.e. dexfenfluramine (Redux®), sibutramine (Meridia®, Reductil®), orlistat (Xenical®) and rimonabant (Acomplia®), have been registered for the treatment of obesity. Of these drugs, only three, dexfenfluramine, sibutramine and orlistat, have achieved global (with the exception of Japan) registration. There is a great need to develop additional anti-obesity drugs, which are safe and effective.

SUMMARY OF THE INVENTION

Provided herein, inter alia, are compositions comprising compounds disclosed herein and methods of using the same.

In various embodiments, the compounds provided herein comprises structural modifications compared to celastrol.

In one aspect, the compositions may promote weight loss, reduce body fat, reduce food intake, improve homeostasis, or combinations thereof. The compounds have a structure of Formula (I):

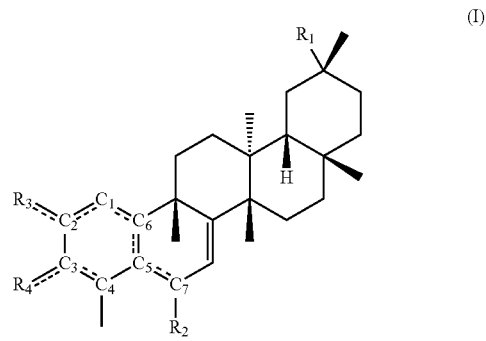

(I)

wherein
the dotted lines between $C_1$ and $C_2$, $C_2$ and $R_3$, $C_3$ and $R_4$, $C_5$ and $C_6$, $C_5$ and $C_7$, $C_1$ and $C_6$, and $C_3$ and $C_4$ indicate that a single or double bond may be present, as valence permits;
$R_1$ is —CN, —COOH, —COOCH$_2$CH$_3$, —CONHR$_5$, —CONR$_5$R$_5$, —COOR$_5$, —COOCH$_3$, —CH$_2$NR$_5$R$_5$, —CH$_2$OCONR$_5$R$_5$, —CH$_2$NR$_5$COOR$_5$, —CH$_2$R$_5$, —CH$_2$NR$_5$CONR$_5$R$_5$, —CH$_2$OH, —CH$_2$OR$_5$, alkylsulfate, alkylsulfonate, alkylphosphate, —CH$_2$OSO$_3$R$_5$, —CH$_2$OSO$_2$R$_5$, —CH$_2$OPO$_3$R$_5$R$_5$, —CH$_2$OPO$_3$HR$_5$, —CH$_2$OPO$_3$H$_2$, —C(=NR$_5$)NR$_5$R$_5$, —NR$_5$C(=NR$_5$)NR$_5$R$_5$, —CONH$_2$, —CH$_2$CONR$_5$R$_5$, —SR$_5$, —SO$_3$R$_5$, —SO$_2$R$_5$, —CH$_2$NHCOR$_5$, —CH$_2$NHCNR$_5$NR$_5$R$_5$, —CH$_2$COSR$_5$, CH$_2$NR$_5$COR$_5$, —CH$_2$NR$_5$CNR$_5$NR$_5$R$_5$, —CH$_2$NR$_5$COSR$_5$, —CH$_2$NHSO$_2$R$_5$, —CH$_2$N R$_5$SO$_2$R$_5$, —CHNR$_5$, —CHNOR$_5$, —H, —NH$_2$, —NHR$_5$, —NR$_5$R$_5$, —OH, —OR$_5$, phosphate, —OPO$_3$R$_5$R$_5$, —OPO$_3$HR$_5$, —OPO$_3$H$_2$, —NCO, —NCS, —N$_3$, —R$_5$, —C≡CR$_5$, —(CH=CH)R$_5$, —SH, —SR$_5$, —SO$_2$H, —SO$_3$H, —SO$_2$NR$_5$R$_5$, —SO$_3$R$_5$, —NHCOR$_5$, —NHCNR$_5$NR$_5$R$_5$, —NHCOSR$_5$, secondary amide, tertiary amide, —NR$_5$COR$_5$, —NR$_5$C(=NH)NR$_5$R$_5$, —NR$_5$COSR$_5$, —NHC(=NR$_5$)R$_5$, —NR$_5$C(=NR$_5$)R$_5$, —NHSO$_2$(NH$_2$), —NHSO$_2$R$_5$, —NR$_5$SO$_2$R$_5$, —NR$_5$SO$_2$NR$_5$R$_5$, —OCOR$_5$, —OCONR$_5$R$_5$, —O(C=O)OR$_5$, —SCOR$_5$, —O(C=NH)NR$_5$R$_5$, —OCSNHR$_5$, —OS(=O$_2$)R$_5$, —OS(=O$_2$)NR$_5$R$_5$, —SCONR$_5$R$_5$, —CH$_2$-aryl, —CH$_2$-heteroaryl,

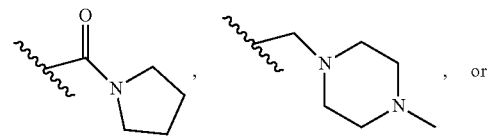

, or

-continued

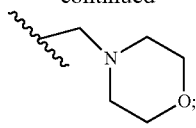

R$_2$ is —H, —CH$_3$, —SCH(CH$_3$)$_2$, —SC(=O)CH$_3$, —SC(=O)R$_5$, —SCH$_2$CH$_2$OCOCH$_3$, —SR$_5$, —SO R$_5$, —SOOR$_5$, —SCONR$_5$R$_5$,

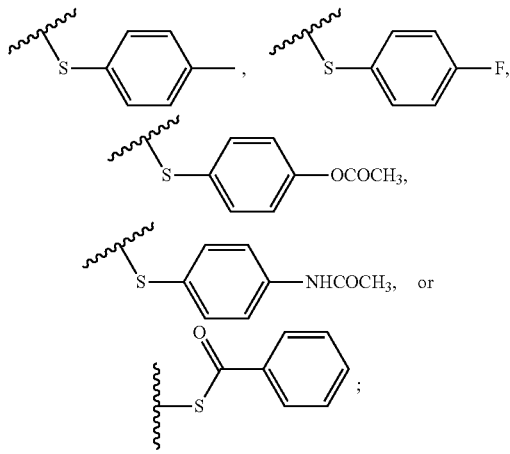

R$_3$ is —OCOCH$_3$, —OCOOCH$_2$CH$_3$, —OR$_7$, —R$_7$, or —NR$_5$R$_5$ when a double bond is present between C$_1$ and C$_2$, C$_3$ and C$_4$, and C$_5$ and C$_6$;

R$_4$ is —OCOCH$_3$, —OCOOCH$_2$CH$_3$, —OR$_7$, —R$_7$, or —NR$_5$R$_5$ when a double bond is present between C$_1$ and C$_2$, C$_3$ and C$_4$, and C$_5$ and C$_6$;

R$_3$ is O when R$_4$ is O and a double bond is present between C$_2$ and R$_3$ and C$_3$ and R$_4$;

R$_4$ is —OCH$_3$, —OP(=O)(OCH$_3$)$_2$, —OH, —OCOOCH$_2$CH$_3$, —OCONHCH$_2$CH$_3$, —OCOOCH(CH$_3$)$_2$, —OR$_7$, —R$_7$, or —NR$_5$R$_5$ when R$_3$ is O and a double bond is present between C$_2$ and R$_3$; R$_3$ and R$_4$ may also be combined to form a heterocylic or carbocyclic ring;

R$_5$ is independently selected for each occurrence hydrogen, an alkyl, cycloalkyl, alkoxy, heterocycloalkyl, alkylaryl, alkenyl, alkynyl, aryl, amine, or heteroaryl, optionally substituted with substituents individually selected from alkyl, alkoxy, cycloalkyl, ether, amine optionally substituted with one or more alkyl, halogen, hydroxyl, ether, cyano, nitrile, CF$_3$, ester, amide, cycloalkyl amide, sugar, heteroarylamide optionally substituted with alkyl and/or alkoxy, urea, carbamate, thioether, sulfate, sulfonyl, sulfonic acid carboxylic acid, and aryl or two R$_5$ groups taken together to form a cycloalkyl, heterocycloalkyl, aryl or heteraryl group, optionally substituted with substituents individually selected from alkyl, cycloalkyl, alkoxy, heterocycloalkyl, alkylaryl, alkenyl, alkynyl, aryl, heteroaryl, amine, halogen, hydroxyl, ether, nitrile, cyano, nitro, CF$_3$, ester amide, urea, carbamate, thioether, or carboxylic acid group; and R$_7$ is hydrogen, an alkyl, cycloalkyl, heterocycloalkyl, alkylaryl, alkenyl, alkynyl, aryl, or heteroaryl, optionally substituted with substituents individually selected from alkyl, cycloalkyl, ether, amine, halogen, hydroxyl, ether, nitrile, cyano, nitrile, CF$_3$, ester, amide, urea, carbamate, thioether, or carboxylic acid, or a pharmaceutically acceptable salt or prodrug thereof. In some embodiments, R$_1$ is —NR$_5$C(=NR$_5$)NR$_5$R$_5$, —SR$_5$, —SO$_3$R$_5$, —SO$_2$R$_5$, —NH$_2$, —NHR$_5$, —NR$_5$R$_5$, —OH, —OR$_5$, —NCO, —NCS, —N$_3$, —SH, —SR$_5$, —SO$_2$H, —SO$_3$H, —SO$_2$NR$_5$R$_5$, —SO$_3$R$_5$, —NHCOR$_5$, —NHCNR$_5$NR$_5$R$_5$, —NHCOSR$_5$, —NR$_5$COR$_5$, —N R$_5$C(=NH)NR$_5$R$_5$, —NR$_5$COSR$_5$, —NHC(=NR$_5$)R$_5$, —NR$_5$C(=NR$_5$)R$_5$, —NHSO$_2$(NH$_2$), —NHSO$_2$R$_5$, —NR$_5$SO$_2$R$_5$, —NR$_5$SO$_2$NR$_5$R$_5$, —OCOR$_5$, —OCONR$_5$R$_5$, —O(C=O)OR$_5$, —SCOR$_5$, —O(C=NH)NR$_5$R$_5$, —OCSNHR$_5$, —OS(=O$_2$)R$_5$, —OS(=O$_2$)NR$_5$R$_5$, or —SCONR$_5$R$_5$.

In some embodiments, R$_2$ is H.

In some embodiments, R$_4$ is —OH, —OR$_7$, or —R$_7$ when R$_3$ is O and a double bond is present between C$_2$ and R$_3$.

In one aspect, the compositions comprise compounds of the structure of Formula (II):

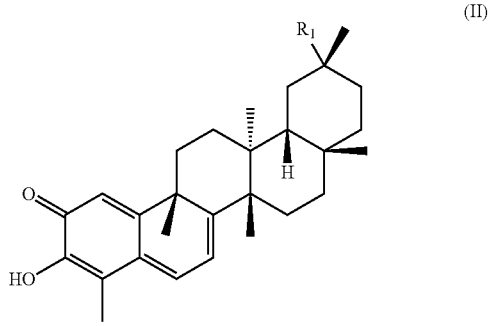

where R$_1$ is OR$_a$ or NR$_a$R$_b$ where each R$_a$ and R$_b$ is independently hydrogen, R$_5$, C(=NR$_5$)NR$_5$R$_5$, —CO, —CS, —COR$_5$, —CNR$_5$NR$_5$R$_5$, —COSR$_5$, —C(=NH)NR$_5$R$_5$, —C(=NR$_5$)R$_5$, —SO$_2$(NH$_2$), —SO$_2$R$_5$, —SO$_2$R$_5$, —SO$_2$NR$_5$R$_5$, —COR$_5$, —CONR$_5$R$_5$, —(C=O)OR$_5$, —(C=NH)NR$_5$R$_5$, —CSNHR$_5$, —S(=O$_2$)R$_5$, or —S(=O$_2$)NR$_5$R$_5$, and R$_5$ is each described in Formula (I), or a pharmaceutically acceptable salt or prodrug thereof.

In some embodiments, R$_1$ is NR$_a$R$_b$, which can be presented in Formula (II)-a:

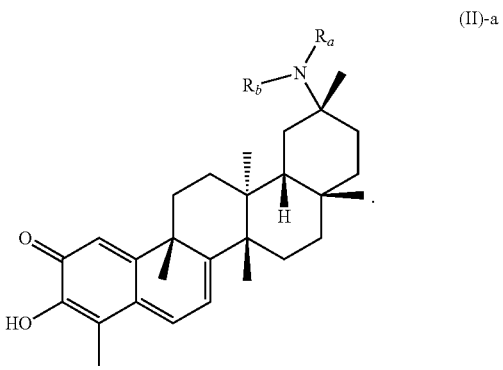

In certain embodiments, R$_1$ is NH(CO)R$_5$ where R$_5$ is preferably alkyl, cycloalkyl, or aryl.

In certain embodiments, R$_1$ is NHAc.

Exemplary compounds, but not limited to, include the following compounds:
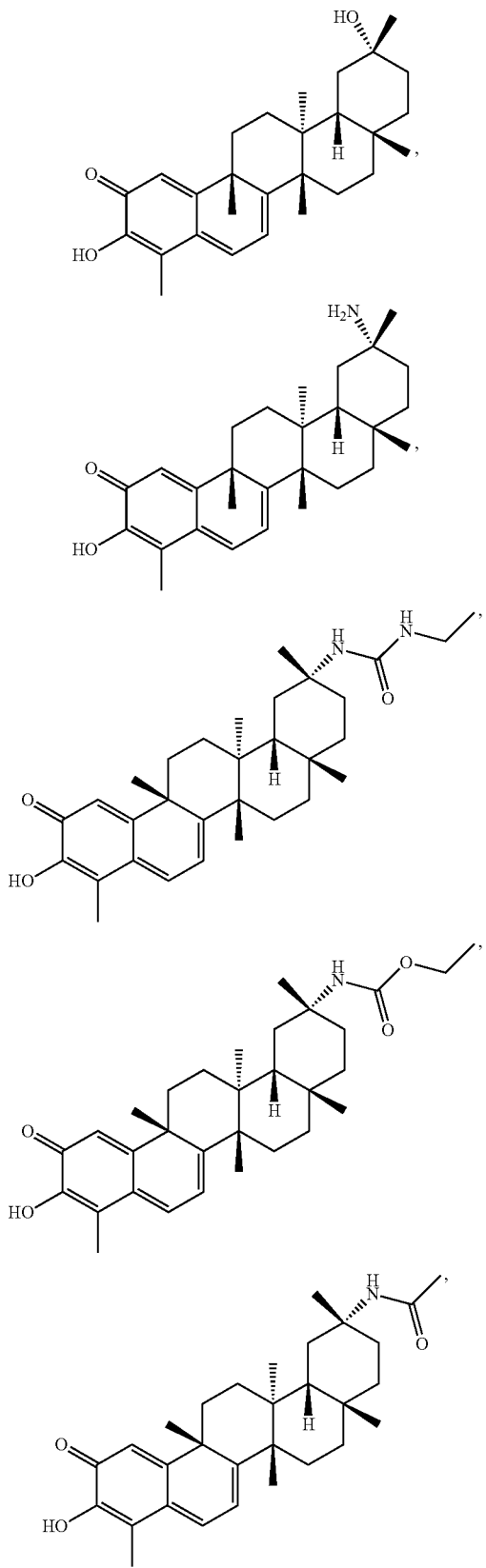
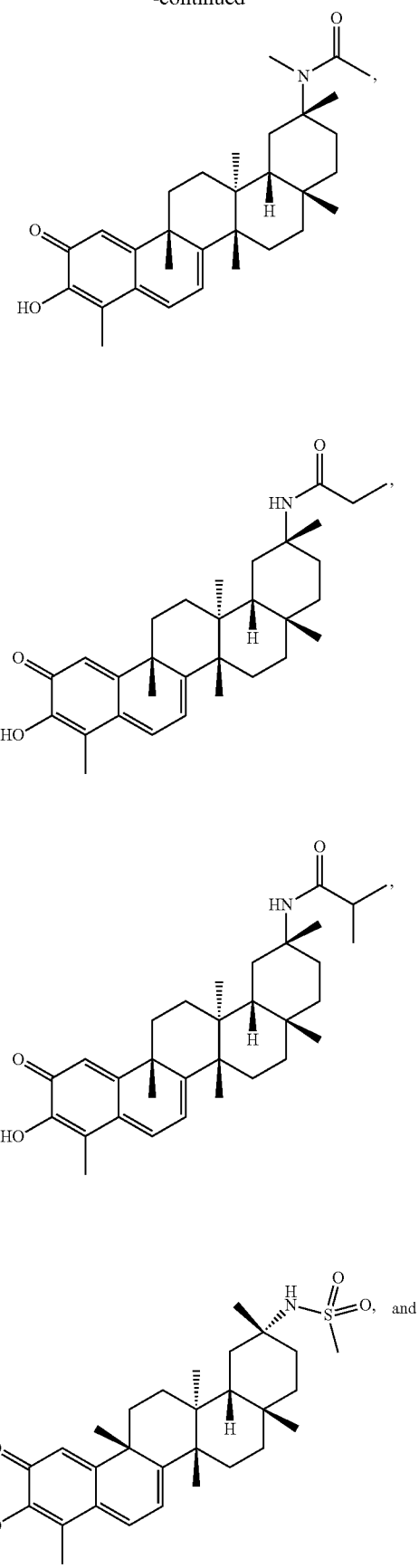

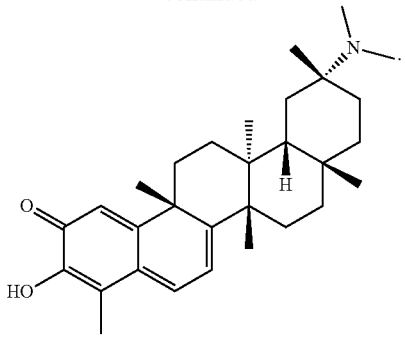

In an aspect, a pharmaceutical composition is provided including the compounds disclosed herein, e.g. compounds of Formula (I) and Formula (II) including embodiments thereof, and a pharmaceutically acceptable excipient.

In an aspect, a method of treating obesity in a subject in need thereof is provided. The method includes administering to the subject a composition that comprises an effective amount of the compounds of Formula (I), including embodiments thereof. Alternatively, the method of treating obesity in a subject in need thereof includes administering to the subject a composition that comprises an effective amount of the compounds of Formula (II), including embodiments thereof. Additionally, the method of treating obesity in a subject in need thereof includes administering to the subject a composition that comprises an effective amount of the compounds of Formula (I), Formula (II) or combinations thereof, including embodiments thereof.

In some embodiments, a subject comprises leptin resistance. In some embodiments, the subject has an increased level of leptin in, e.g., the blood. In certain embodiments, the subject has not responded well (e.g., experienced reduced appetite, improved BMI, and/or a reduction in weight of at least about 5%, 4%, 3%, 2%, or 1%) to leptin administration, and/or the efficacy of leptin administration is diminishing over time (e.g., as determined in a reversal of weight loss or the subject feeling hungry more often). In some embodiments, the subject comprises a blood or serum leptin concentration of about 10, 11, 12, 13, 14, 15, 20, 25, 30, 35, 40, 45, 50, 75, 100 ng/mL or more. In some embodiments, the subject is a male and has a blood or serum leptin concentration of about 10, 11, 12, 13, 14, 15, 20, 25, 30, 35, 40, 45, 50 ng/mL or more. In some embodiments, the subject is a female and has a blood or serum leptin concentration of about 30, 35, 40, 45, 50, 75, 100 ng/mL or more.

In one aspect, the administering the composition comprises oral administration, intravenous administration, topical administration, parenteral administration, intraperitoneal administration, intramuscular administration, intrathecal administration, intralesional administration, intracranial administration, intranasal administration, intraocular administration, intracardiac administration, intravitreal administration, intraosseous administration, intracerebral administration, intraarterial administration, intraarticular administration, intradermal administration, transdermal administration, transmucosal administration, sublingual administration, enteral administration, sublabial administration, insufflation administration, suppository administration, inhaled administration, or subcutaneous administration.

In some embodiments, the method of treating obesity in a subject in need thereof comprises orally administering the composition comprising an effective amount of one or more of the compounds disclosed herein.

In some embodiments, the method of treating obesity in a subject in need thereof comprises intraperitoneally administering the composition comprising an effective amount of one or more of the compounds disclosed herein.

In some embodiments, the method of treating obesity in a subject in need thereof comprises intraperitoneally administering the composition comprising an effective amount of one or more of the compounds disclosed herein.

In one aspect, provided herein is a composition, wherein the composition is used to treat an obesity-related disease or disorder. The obesity-related disease or disorder is selected from a group comprising obesity, pre-obesity, morbid obesity, Prader-Willi Syndrome, Hypothalamic Injury Associated Obesity, Non-alcoholic steatohepatitis, hyperlipidemia, hypertension, diabetes, lipodystrophy, fatty liver, Bardet-Biedl Syndrome, Cohen Syndrome, cardiovascular disease, arthritis, stroke, metabolic syndrome and MOMO (Macrosomia Obesity Macrocephaly Ocular abnormalities) Syndrome.

In an aspect, provided herein is a method of treating an obesity-related disease or disorder comprising administering to a subject suffering from or at risk of suffering from an obesity-related disease or disorder one or more compositions of Formula (I), Formula (II) or combinations thereof. The obesity-related disease or disorder is selected from the group comprising obesity, pre-obesity, morbid obesity, Prader-Willi Syndrome, Hypothalamic Injury Associated Obesity, Non-alcoholic steatohepatitis, hyperlipidemia, hypertension, diabetes, lipodystrophy, fatty liver, Bardet-Biedl Syndrome, Cohen Syndrome, cardiovascular disease, arthritis, stroke, metabolic syndrome and MOMO Syndrome.

In an aspect, the composition is administered in combination with another therapy.

In some aspects, administering further comprises oral administration, intravenous administration, topical administration, parenteral administration, intraperitoneal administration, intramuscular administration, intrathecal administration, intralesional administration, intracranial administration, intranasal administration, intraocular administration, intracardiac administration, intravitreal administration, intraosseous administration, intracerebral administration, intraarterial administration, intraarticular administration, intradermal administration, transdermal administration, transmucosal administration, sublingual administration, enteral administration, sublabial administration, insufflation administration, suppository administration, inhaled administration, or subcutaneous administration.

In an aspect, the composition of is administered in a form selected from the group comprising pills, capsules, tablets, granules, powders, salts, crystals, liquid, serums, syrups, suspensions, gels, creams, pastes, films, patches, and vapors.

In an aspect, the subject is a mammal. Furthermore, the subject is a human. In still another aspect, the subject is a human with a body mass index (BMI) greater than 30 kg/m$^2$.

In an aspect, a method of treating a malignancy in a subject in need thereof is provided. The method includes administering to the subject an effective amount of one or more compounds disclosed herein.

In one aspect, provided is a composition, wherein the composition is used to treat a malignancy-related disease or disorder. The malignancy-related disease or disorder is selected from the group comprising gastric cancer, multiple myeloma, melanoma, leukemia, lymphoma, renal cell carcinoma, hepatocellular carcinoma, breast cancer, prostate cancer, head and neck cancer, non-small cell lung carcinoma, brain cancer, and glioblastoma multiforme (GBM).

In an aspect, included herein is a method of treating a malignancy-related disease or disorder comprising administering to a subject suffering from or at risk of suffering from a malignancy-related disease or disorder one or more compositions of formula (I). The malignancy-related disease or disorder is selected from the group comprising gastric cancer, multiple myeloma, melanoma, leukemia, lymphoma, renal cell carcinoma, hepatocellular carcinoma, breast cancer, prostate cancer, head and neck cancer, non-small cell lung carcinoma, brain cancer, and glioblastoma multiforme (GBM).

In an aspect, provided herein is a kit comprising the compositions used for treating obesity as described herein, and instructions for use in treating obesity. In some embodiments, the kit may be used for an oral administration or intraperitoneal administration of the compositions of treating obesity.

Each embodiment disclosed herein is contemplated as being applicable to each of the other disclosed embodiments. Thus, all combinations of the various elements described herein are within the scope of the invention. Other aspects are disclosed infra.

BRIEF DESCRIPTION OF THE DRAWINGS

FIG. 10 shows data of daily body weight of the diet induced obese (DIO) mice during treatments by oral administration of the compounds at a dose of 2,000 μg/kg as listed in Table 13 for 11 days.

FIG. 11 shows data of daily body weight change of the diet induced obese (DIO) mice during treatments by oral administration of the compounds at a dose of 2,000 μg/kg as listed in Table 13 for 11 days.

FIG. 12 shows data of cumulative body weight change of the diet induced obese (DIO) mice during treatments by oral administration of the compounds at a dose of 2,000 μg/kg as listed in Table 13 for 11 days.

FIG. 13 shows data of daily food intake of the diet induced obese (DIO) mice after treatments by during administration of the compounds at a dose of 2,000 μg/kg as listed in Table 13 for 11 days.

FIG. 14 shows data of cumulative daily food intake of the diet induced obese (DIO) mice during treatments by oral administration of the compounds at a dose of 2,000 μg/kg as listed in Table 13 for 11 days.

FIG. 15 shows glucose data on day 1 of the diet induced obese (DIO) mice during treatments by oral administration of the compounds at a dose of 2,000 μg/kg as listed in Table 13 for 11 days.

FIG. 16 shows glucose data on day 11 of the diet induced obese (DIO) mice during treatments by oral administration of the compounds at a dose of 2,000 μg/kg as listed in Table 13 for 11 days.

FIG. 17 shows data of glucose change of the diet induced obese (DIO) mice during treatments by oral administration of the compounds at a dose of 2,000 μg/kg as listed in Table 13 for 11 days.

DETAILED DESCRIPTION OF THE INVENTION

I. Definitions

Figure 1:
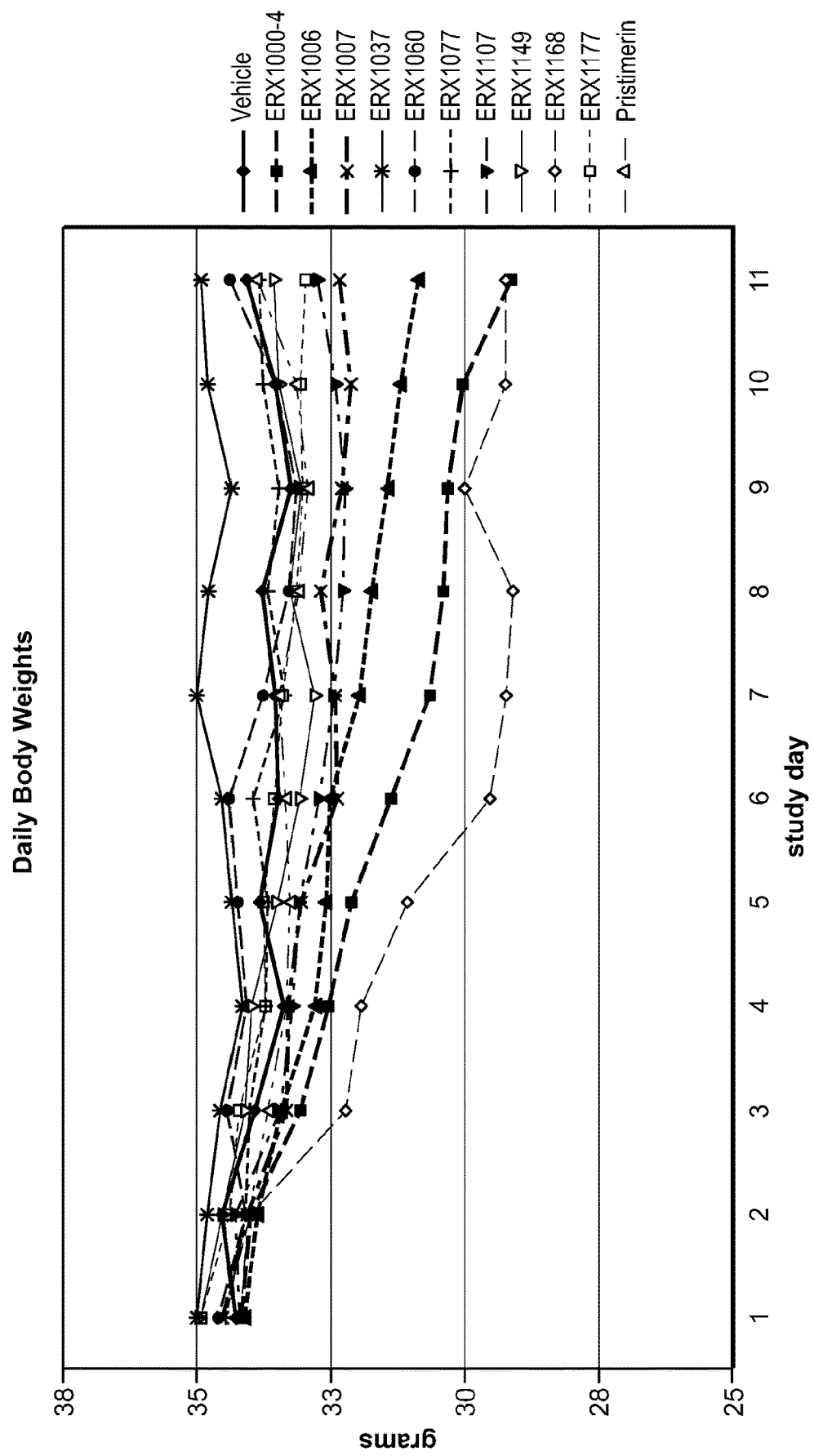
FIG. 1 is a graph of daily body weights of diet induced obese (DIO) mice during treatments by oral administration of the compounds at a dose of 2,000 μg/kg as listed in Table 13 for 11 days.
Figure 2:
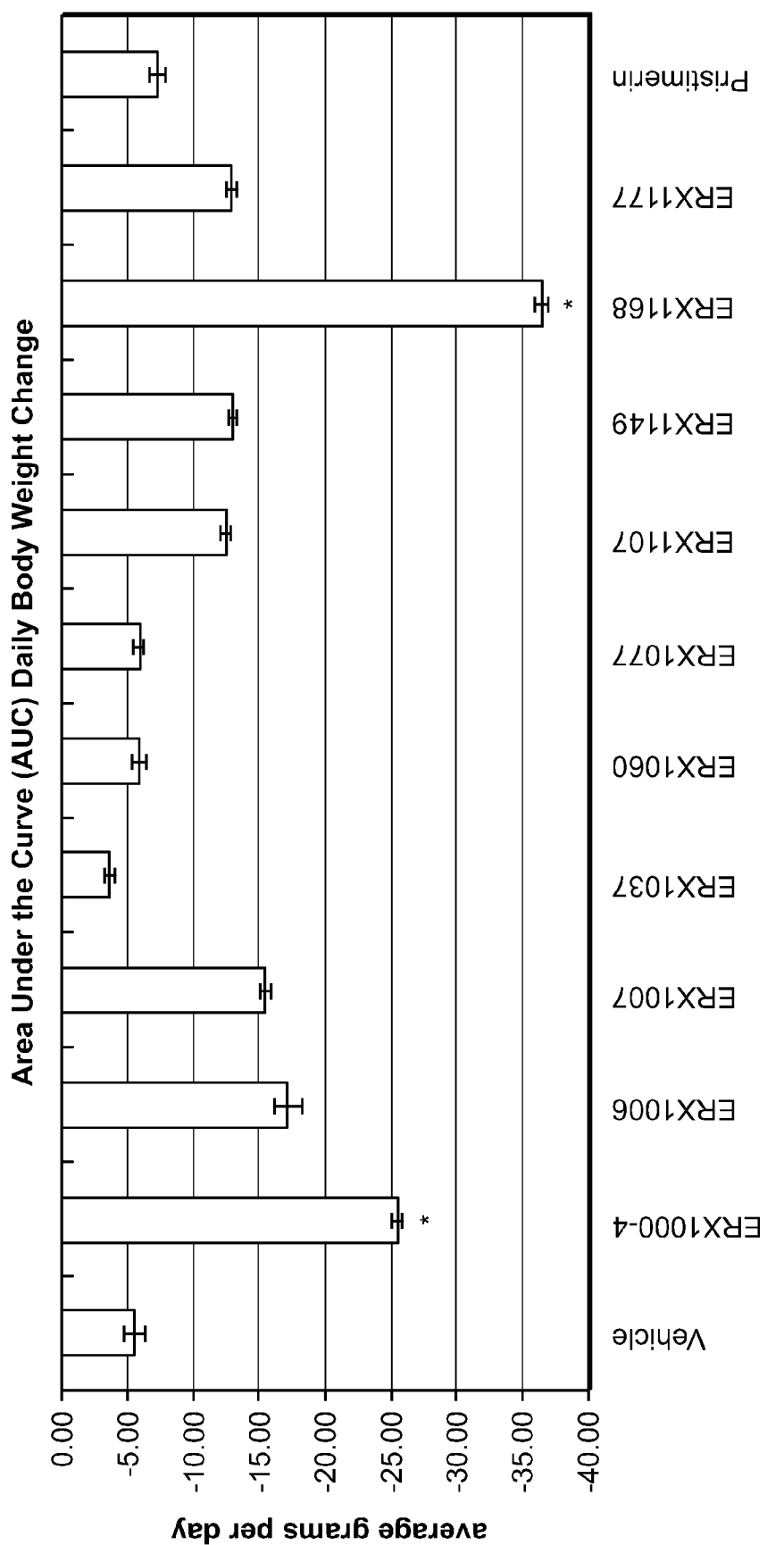
FIG. 2 is a graph of area under the curve (AUC) daily body weight change of the diet induced obese (DIO) mice during treatments by oral administration of the compounds at a dose of 2,000 μg/kg as listed in Table 13 for 11 days.
Figure 3:
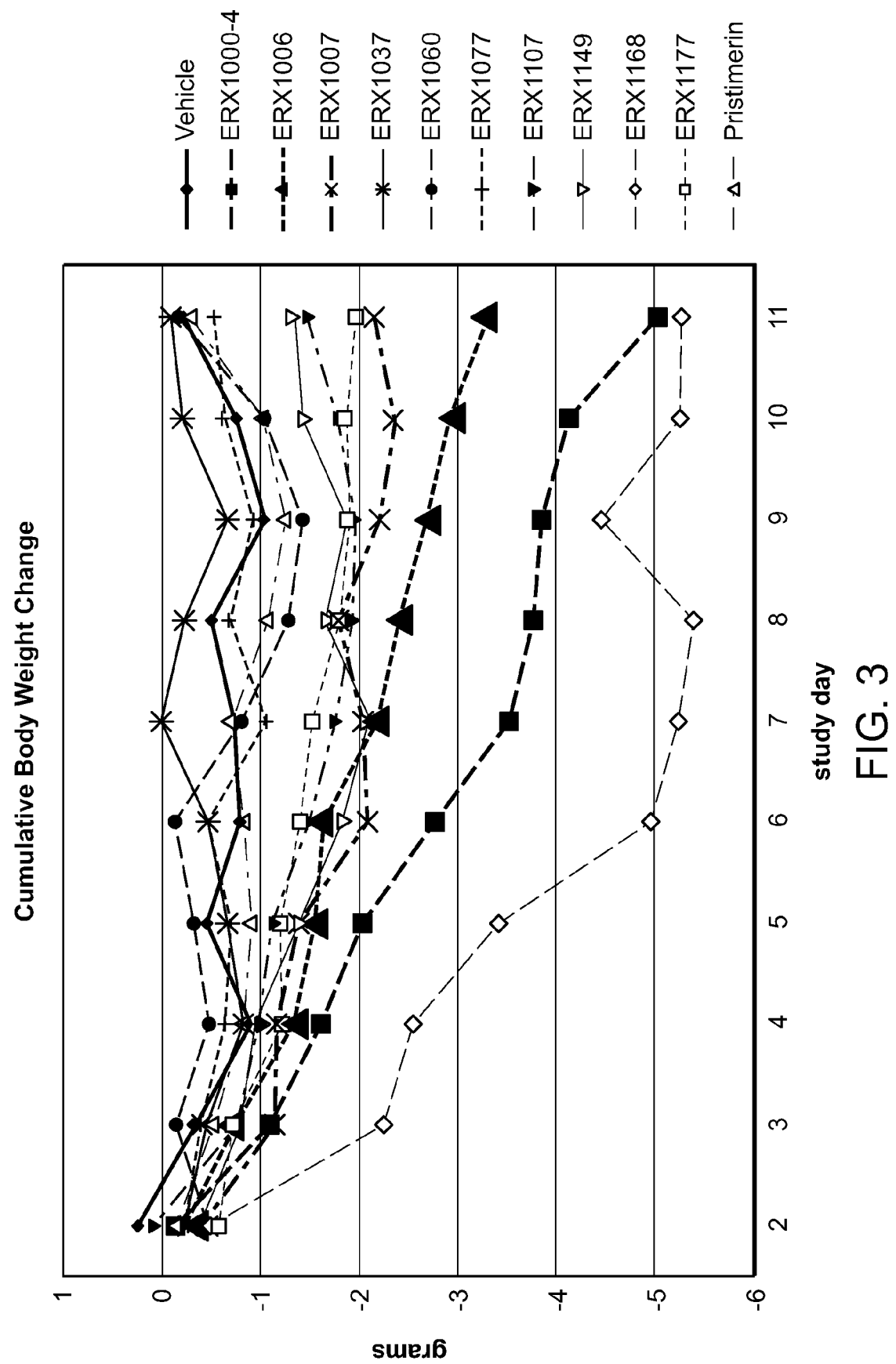
FIG. 3 is a graph of cumulative body weight change of the diet induced obese (DIO) mice during treatments by oral administration of the compounds at a dose of 2,000 μg/kg as listed in Table 13 for 11 days.
Figure 4:
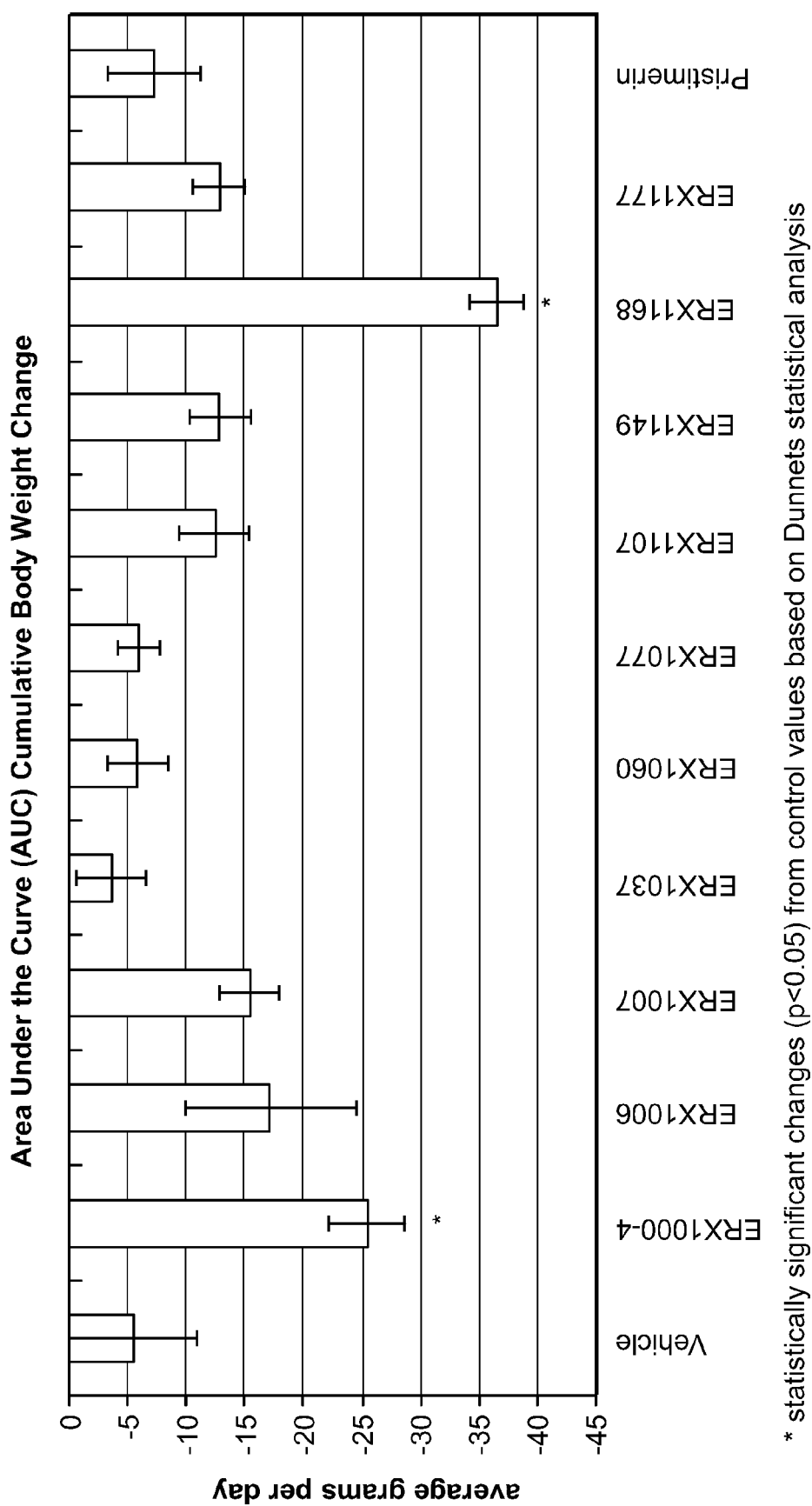
FIG. 4 is a graph of area under the curve (AUC) cumulative body weight change of the diet induced obese (DIO) mice during treatments by oral administration of the compounds at a dose of 2,000 μg/kg as listed in Table 13 for 11 days.
Figure 5:
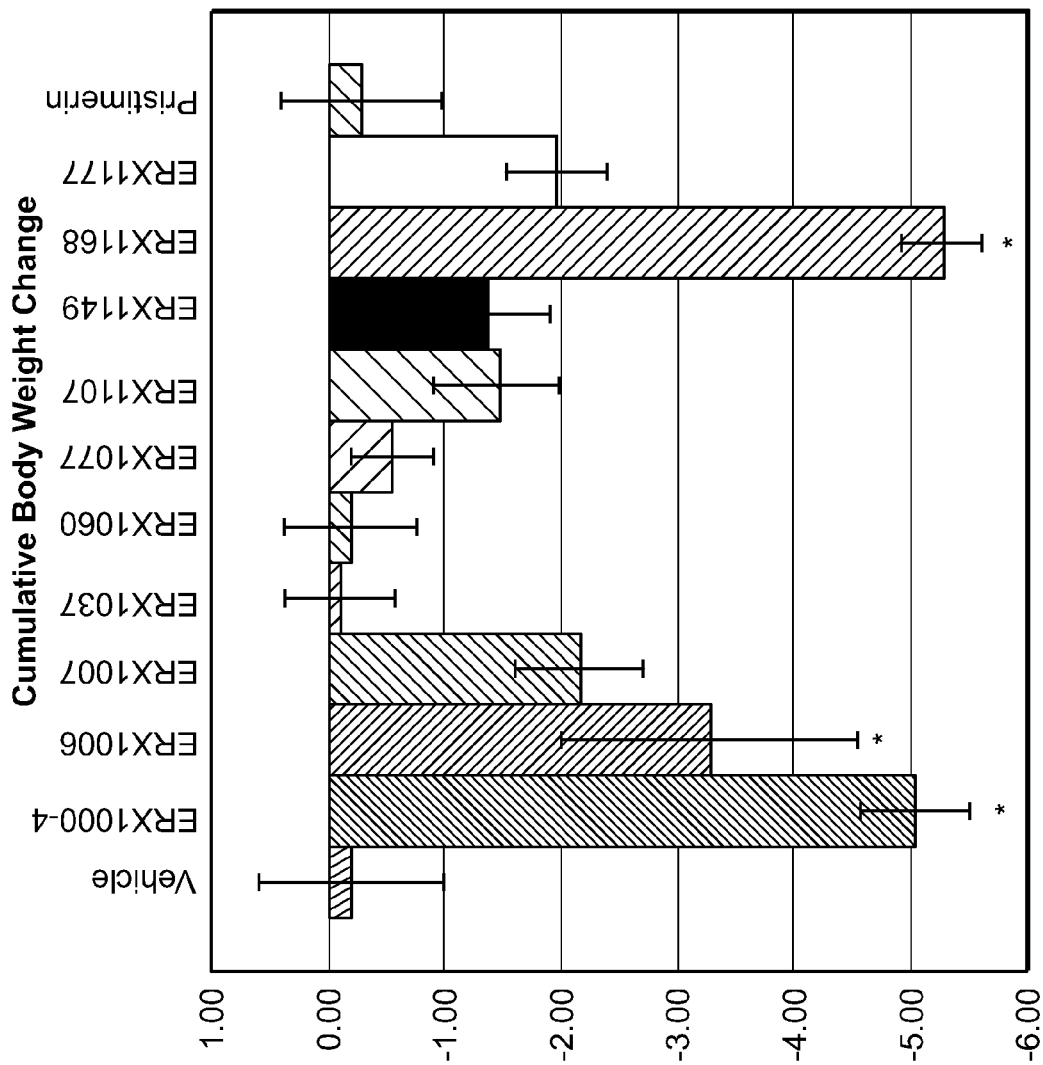
FIG. 5 is a graph of cumulative body weight change of the diet induced obese (DIO) mice during treatments by oral administration of the compounds at a dose of 2,000 μg/kg as listed in Table 13 for 11 days.

The abbreviations used herein have their conventional meaning within the chemical and biological arts. The chemical structures and formulae set forth herein are constructed according to the standard rules of chemical valency known in the chemical arts.

As used herein, the term "about" in the context of a numerical value or range means±10% of the numerical value or range recited or claimed, unless the context requires a more limited range.

It is understood that where a parameter range is provided, all integers within that range, and tenths thereof, are also provided by the invention. For example, "0.2-5 mg" is a disclosure of 0.2 mg, 0.3 mg, 0.4 mg, 0.5 mg, 0.6 mg etc. up to and including 5.0 mg.

Where substituent groups are specified by their conventional chemical formulae, written from left to right, they equally encompass the chemically identical substituents that would result from writing the structure from right to left, e.g., —CH$_2$O— is equivalent to —OCH$_2$—.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to ionic compounds that result from the neutralization reaction of an acid and a base. They are composed of related numbers of cations (positively charged ions) and anions (negative ions) so that the product is electrically neutral (without a net charge). These component ions can be inorganic, such as chloride (Cl$^-$), or organic, such as acetate ($C_2H_3O_2^-$); and can be monatomic, such as fluoride (F$^-$), or polyatomic, such as sulfate ($SO_4^{2-}$).

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present invention, whether radioactive or not, are encompassed within the scope of the present invention.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

The terms "a" or "an," as used in herein means one or more. In addition, the phrase "substituted with a(n)," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated.

The term "alkylsulfate" by itself or as part of another substitutent, means, unless otherwise stated, an alkyl substituted with a sulfate $O(SO_2)O^-$ or salt thereof.

The term "alkylsulfonate" by itself or as part of another substitutent, means, unless otherwise stated, an alkyl substituted with a sulfonate $(SO_2)O^-$ or salt thereof.

The term "alkylphosphate" by itself or as part of another substitutent, means, unless otherwise stated, an alkyl substituted with a phosphate $PO_4^-$ or salt thereof.

The term "cycloalkyl", by itself or as part of another substituent, means, unless otherwise stated, a monocyclic or polycyclic (e.g. bicyclic or tricyclic) saturated hydrocarbon that consists of hydrogen and carbon atoms arranged in a structure containing a single ring or a multiple rings where all of the carbon-carbon bonds are single bonds. Examples of monocyclic alkyl includes cyclopropyl, cyclobutyl, cyclopentyl, cyclohexyl, and the like, and examples of polycyclic alkyl include norbornyl, adamantyl, and the like.

The term "carbocyclic," by itself or as part of another substituent, means, unless otherwise stated, a cyclic carbon chain (or carbon), which may be fully saturated, mono- or polyunsaturated and can include di- and multivalent radicals, having the number of carbon atoms designated (i.e., $C_1$-$C_{10}$ means one to ten carbons). The carbocycle may have a structure containing a single ring or a multiple rings without limitation. Examples of saturated cyclic alkyl groups include cyclopropyl, cyclobutyl, cyclopentyl, cyclohexyl and the like, and examples of unsaturated carbocyclic groups include cyclopropenyl, cyclobutenyl, cyclopentenyl, cyclohexenyl and the like.

The term "heteroalkyl," by itself or in combination with another term, means, unless otherwise stated, a stable straight or branched non-cyclic chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si, but not limited thereto, may be placed at any interior position of the heteroalkyl group or at the position at which the alkyl group is attached to the remainder of the molecule. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

The term "heterocyclic," by itself or in combination with another term, means, unless otherwise stated, a cyclic chain, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the cyclic heteroalkyl group or at the position at which the heterocyclic group is attached to the remainder of the molecule. Examples include, but are not limited to: —CO—, —OCOO—, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N ($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

The term "secondary amide" by itself or as part of another substitutent, means, unless otherwise stated, an amide in which the nitrogen atom is directly bonded to two carbon atoms.

The term "tertiary amide" by itself or as part of another substitutent, means, unless otherwise stated, an amide in which the nitrogen atom is directly bonded to three carbon atoms.

Description of compounds of the present invention is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, certain methods herein treat diseases associated with weight gain such as obesity.

An "effective amount" is an amount sufficient for a compound to accomplish a stated purpose relative to the absence of the compound (e.g. achieve the effect for which it is administered, treat a disease, reduce enzyme activity, increase enzyme activity, reduce signaling pathway, reduce one or more symptoms of a disease or condition. An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. The exact amounts will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

The term "associated" or "associated with" in the context of a substance or substance activity or function associated with a disease (e.g. obesity) means that the disease is caused by (in whole or in part), or a symptom of the disease is caused by (in whole or in part) the substance or substance activity or function. As used herein, what is described as being associated with a disease, if a causative agent, could be a target for treatment of the disease. For example, a disease associated with weight gain such as obesity may be treated with an agent (e.g. compound as described herein) effective for decreasing weight gain.

"Control" or "control experiment" or "standard control" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

As defined herein, the term "inhibition", "inhibit", "inhibiting" and the like in reference to a protein-inhibitor (e.g. antagonist) interaction means negatively affecting (e.g. decreasing) the level of activity or function of the protein relative to the level of activity or function of the protein in the absence of the inhibitor. In some embodiments inhibition refers to reduction of a disease or symptoms of disease. Thus, inhibition may include, at least in part, partially or totally blocking stimulation, decreasing, preventing, or delaying activation, or inactivating, desensitizing, or down-regulating signal transduction or enzymatic activity or the amount of a protein.

As defined herein, the term "activation", "activate", "activating" and the like in reference to a protein-activator (e.g. agonist) interaction means positively affecting (e.g. increasing) the activity or function of the protein relative to the activity or function of the protein in the absence of the activator (e.g. compound described herein). Thus, activation may include, at least in part, partially or totally increasing stimulation, increasing or enabling activation, or activating, sensitizing, or up-regulating signal transduction or enzymatic activity or the amount of a harmful mediator/substance decreased in a disease. Activation may include, at least in part, partially or totally increasing stimulation, increasing or enabling activation, or activating, sensitizing, or up-regulating signal transduction or enzymatic activity or the amount of a harmful mediator/substance.

The term "modulator" refers to a composition that increases or decreases the level of a target molecule or the function of a target molecule. In embodiments, a modulator is an anti-inflammatory agent. In embodiments, a modulator is an inhibitor of leptin. In embodiments, a modulator is a leptin ligand.

"Anti-obesity agent" refers to the property of a substance or treatment that reduces weight gain and promotes weight loss. Examples of anti-obesity agents would be Sibutramine, Phentermine, Mazindol, Diethylpropion, Leptin, Orlistat, Beta-3 agonists, and Rimonabant.

The term "obese" is used therein, refers to a patient having a body mass index of greater than 30 kg/m$^2$. "Overweight" and "pre-obese", as used herein, refer to patients having a body mass index of greater than 25 kg/m$^2$. "Morbidly obese", as used herein, refers to a patient having a BMI of greater than 40 mg/m$^2$, a BMI of greater than 35 kg/m$^2$ in combination with one ore more co-morbidities, a BMI of greater than 30 kg/m$^2$ in combination with uncontrollable diabetes, or combinations thereof.

The term "prodrug" refers to a pharmacological substance such as a drug that is administered to a subject in an inactive (or significantly less active) form. Once administered, the prodrug is metabolized in the body (in vivo) into a compound having the desired pharmacological activity.

The terms "patient" "subject" "individual" and the like refer to a living organism who suffers from or is susceptible to a disease or condition that can be treated by administration of a compound or pharmaceutical composition as provided herein. Non-limiting examples include humans, other mammals, bovines, rats, mice, dogs, cats, apes, monkeys, goat, sheep, cows, deer, and other non-mammalian animals. In some embodiments, the subject is a companion animal, such as a dog or a cat. In some embodiments, a patient is human. In some embodiments, the patient pre-obese, obese or morbidly obese. In certain embodiments, the patient is not pre-obese, obese, or morbidly obese, but was formerly pre-obese, obese, or morbidly obese. In some embodiments, the patient wishes to lose weight or have a decreased appetite. Alternatively or in addition, a patient has an obesity-related disease or disorder. These examples are not limiting. The terms "subject," "patient," "individual," and the like as used herein are not intended to be limiting and can be generally interchanged. That is, an individual described as a "patient" does not necessarily have a given disease or be under the care of a medical professional, but may be merely seeking or wish to have treatment in the absence of medical advice (such as self-treatment). "Disease" or "condition" refer to a state of being or health status of a patient or subject capable of being treated with a compound, pharmaceutical composition, or method provided herein. In some embodiments, the disease is a disease having an increase in body weight. In some embodiments, the disease is obesity. Obesity may be the primary cause of the disease and/or disorder to be treated or may also by a result of the primary disease and/or disorder.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g. anti-obesity agent). The compound can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation, to increase degradation of a prodrug and release of the drug, detectable agent). The compositions can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions can also be delivered as microspheres for slow release in the body. For example, microspheres can be administered via intradermal injection of drug-containing microspheres, which slowly release subcutaneously (see Rao, J. Biomater Sci. Polym. Ed. 7:623-645, 1995; as biodegradable and injectable gel formulations (see, e.g., Gao Pharm. Res. 12:857-863, 1995); or, as microspheres for oral administration (see, e.g., Eyles, J. Pharm. Pharmacol. 49:669-674, 1997). In another embodiment, the formulations of the compositions can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions into the target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989). The compositions can also be delivered as nanoparticles.

II. Compounds

Provided herein, inter alia, are compositions to promote weight loss, reduce body fat, reduce food intake, improve homeostasis, or combinations thereof.

In one preferred aspect, the composition may include a compound having the structure of Formula (I):

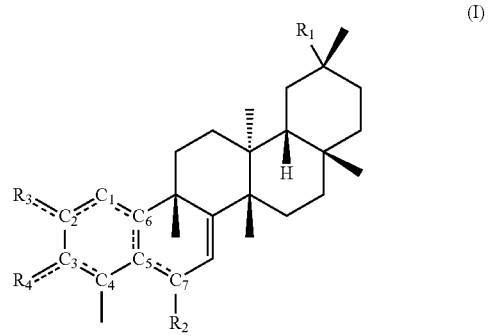

wherein
the dotted lines between $C_1$ and $C_2$, $C_2$ and $R_3$, $C_3$ and $R_4$, $C_5$ and $C_6$, $C_5$ and $C_7$, $C_1$ and $C_6$, and $C_3$ and $C_4$ indicate that a single or double bond may be present, as valence permits;
$R_1$ is —CN, —COOH, —COOCH$_2$CH$_3$, —CONHR$_5$, —CONR$_5$R$_5$, —COOR$_5$, —COOCH$_3$, —CH$_2$NR$_5$R$_5$, —CH$_2$OCONR$_5$R$_5$, —CH$_2$NR$_5$COOR$_5$, —CH$_2$R$_5$, —CH$_2$NR$_5$CONR$_5$R$_5$, —CH$_2$OH, —CH$_2$OR$_5$, alkylsulfate, alkylsulfonate, alkylphosphate, —CH$_2$OSO$_3$R$_5$, —CH$_2$OSO$_2$R$_5$, —CH$_2$OPO$_3$R$_5$R$_5$, —CH$_2$OPO$_3$HR$_5$, —CH$_2$OPO$_3$H$_2$—C(=NR$_5$)NR$_5$R$_5$, —NR$_5$C(=NR$_5$)NR$_5$R$_5$, —CONH$_2$, —CH$_2$CONR$_5$R$_5$, —SR$_5$, —SO$_3$R$_5$, —SO$_2$R$_5$, —CH$_2$NHCOR$_5$, —CH$_2$NHCNR$_5$NR$_5$R$_5$, —CH$_2$COSR$_5$, CH$_2$NR$_5$COR$_5$, —CH$_2$NR$_5$CNR$_5$NR$_5$R$_5$, —CH$_2$NR$_5$COSR$_5$, —CH$_2$NHSO$_2$R$_5$, —CH$_2$N R$_5$SO$_2$R$_5$, —CHNR$_5$, —CHNOR$_5$, —H, —NH$_2$, —NHR$_5$, —NR$_5$R$_5$, —OH, —OR$_5$, phosphate, —OPO$_3$R$_5$R$_5$, —OPO$_3$HR$_5$, —OPO$_3$H$_2$, —NCO, —NCS, —N$_3$, —R$_5$, —C≡CR$_5$, —(CH=CH)R$_5$, —SH, —SR$_5$, —SO$_2$H, —SO$_3$H, —SO$_2$NR$_5$R$_5$, —SO$_3$R$_5$, —NHCOR$_5$, -, NHCNR$_5$NR$_5$R$_5$, —NHCOSR$_5$, secondary amide, tertiary amide, —NR$_5$COR$_5$, —NR$_5$C(=NH)NR$_5$R$_5$, —NR$_5$COSR$_5$, —NHC(=NR$_5$)R$_5$, —NR$_5$C(=NR$_5$)R$_5$, —NHSO$_2$(NH$_2$), —NHSO$_2$R$_5$, —NR$_5$SO$_2$R$_5$, —NR$_5$SO$_2$NR$_5$R$_5$, —OCOR$_5$, —OCONR$_5$R$_5$, —O(C=O)OR$_5$, —SCOR$_5$, —O(C=NH)NR$_5$R$_5$, —OCSNHR$_5$, —OS(=O$_2$)R$_5$, —OS(=O$_2$)NR$_5$R$_5$, —SCONR$_5$R$_5$, —CH$_2$-aryl, —CH$_2$— heteroaryl,

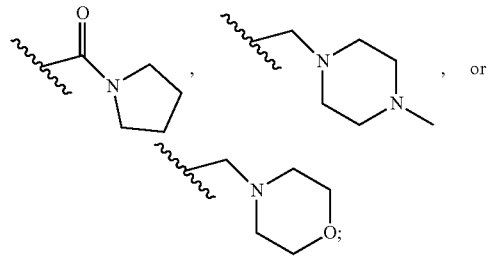

$R_2$ is —H, —CH$_3$, —SCH(CH$_3$)$_2$, —SC(=O)CH$_3$, —SC(=O)R$_5$, —SCH$_2$CH$_2$OCOCH$_3$, —SR$_5$, —SOR$_5$, —SOOR$_5$, —SCONR$_2$,

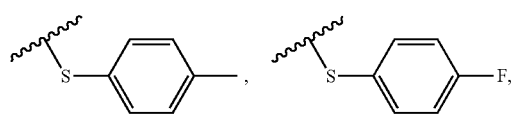

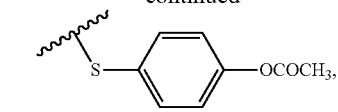

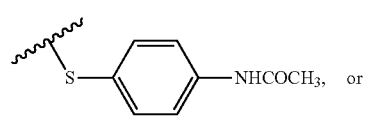

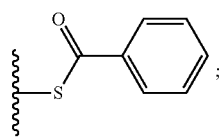

$R_3$ is —OCOCH$_3$, —OCOOCH$_2$CH$_3$, —OR$_7$, —R$_7$, or —NR$_5$R$_5$ when a double bond is present between C$_1$ and C$_2$, C$_3$ and C$_4$, and C$_5$ and C$_6$ $R_4$ is —OCOCH$_3$, —OCOOCH$_2$CH$_3$, —OR$_7$, —R$_7$, or —NR$_5$R$_5$ when a double bond is present between C$_1$ and C$_2$, C$_3$ and C$_4$, and C$_5$ and C$_6$;

$R_3$ is O when $R_4$ is O and a double bond is present between C$_2$ and R$_3$ and C$_3$ and R$_4$;

$R_4$ is —OCH$_3$, —OP(=O)(OCH$_3$)$_2$, —OH, —OCOOCH$_2$CH$_3$, —OCONHCH$_2$CH$_3$, —OCOOCH(CH$_3$)$_2$, —OR$_7$, —R$_7$, or —NR$_5$R$_5$ when R$_3$ is O and a double bond is present between C$_2$ and R$_3$; R$_3$ and R$_4$ may also be combined to form a heterocylic or carbocyclic ring;

$R_5$ is independently selected for each occurrence hydrogen, an alkyl, cycloalkyl, alkoxy, heterocycloalkyl, alkylaryl, alkenyl, alkynyl, aryl, amine, or heteroaryl, optionally substituted with substituents individually selected from alkyl, alkoxy, cycloalkyl, ether, amine optionally substituted with one or more alkyl, halogen, hydroxyl, ether, cyano, nitrile, CF$_3$, ester, amide, cycloalkyl amide, sugar, heteroarylamide optionally substituted with alkyl and/or alkoxy, urea, carbamate, thioether, sulfate, sulfonyl, sulfonic acid carboxylic acid, and aryl or two R$_5$ groups taken together to form a cycloalkyl, heterocycloalkyl, aryl or heteraryl group, optionally substituted with substituents individually selected from alkyl, cycloalkyl, alkoxy, heterocycloalkyl, alkylaryl, alkenyl, alkynyl, aryl, heteroaryl, amine, halogen, hydroxyl, ether, nitrile, cyano, nitro, CF$_3$, ester amide, urea, carbamate, thioether, or carboxylic acid group;

and $R_7$ is hydrogen, an alkyl, cycloalkyl, heterocycloalkyl, alkylaryl, alkenyl, alkynyl, aryl, or heteroaryl, optionally substituted with substituents individually selected from alkyl, cycloalkyl, ether, amine, halogen, hydroxyl, ether, nitrile, cyano, nitrile, CF$_3$, ester, amide, urea, carbamate, thioether, or carboxylic acid, or a pharmaceutically acceptable salt or prodrug thereof.

In some embodiments, the compounds of formula (I) include those which are prodrugs.

In some embodiments, the compounds of formula (I) include those in which R$_1$ is —CONH$_2$, which can be represented in Formula (I)-a:

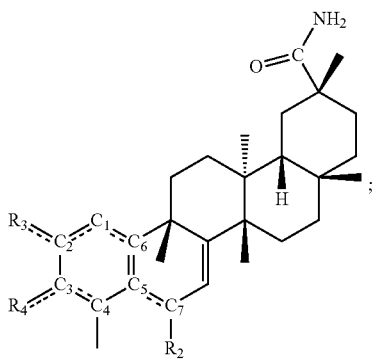

wherein each R$_2$, R$_3$, and R$_4$ is defined in Formula (I).

In some embodiments, R$_2$ is —H, —SCH(CH$_3$)$_2$, —SC(=O)CH$_3$,

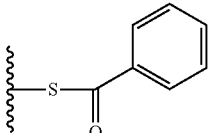 , 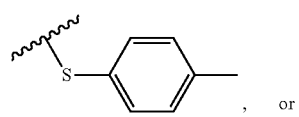 , or

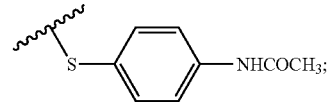

In some embodiments, R$_3$ is —OC(=O)CH$_3$ or —OC(=O)OCH$_2$CH$_3$.

In some embodiments, R$_4$ is —OC(=O)CH$_3$ or —OC(=O)OCH$_2$CH$_3$.

One subset of the compounds of formula (I) includes the compounds shown below:

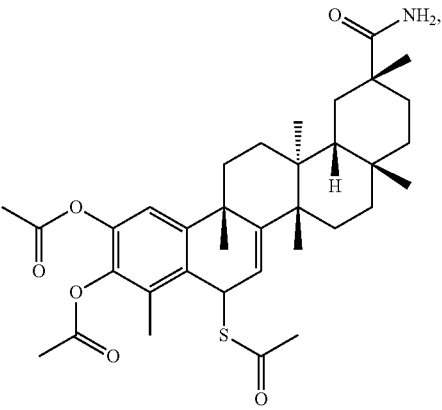

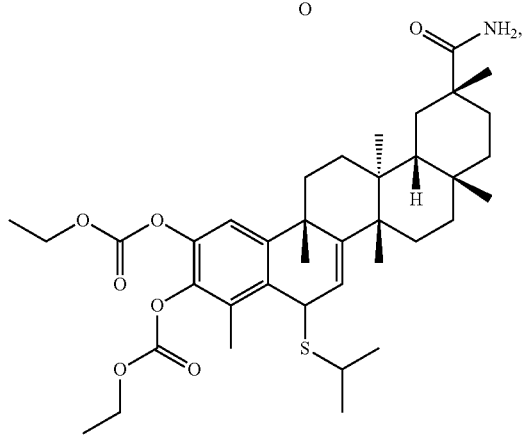

-continued
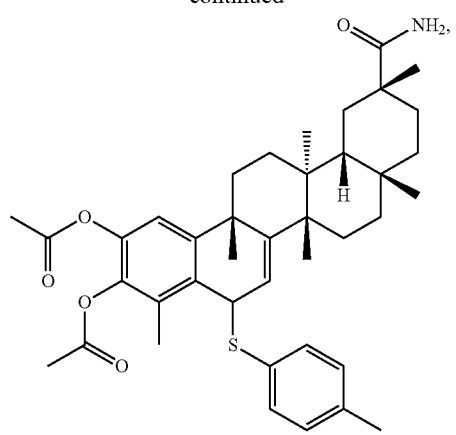
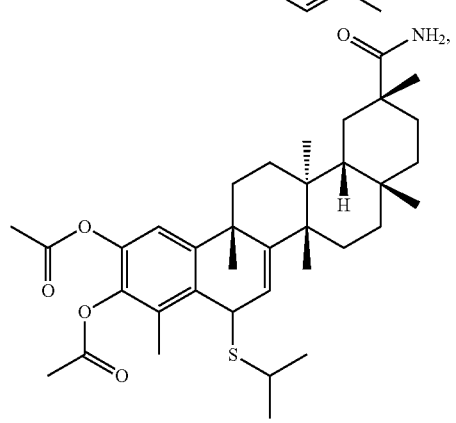
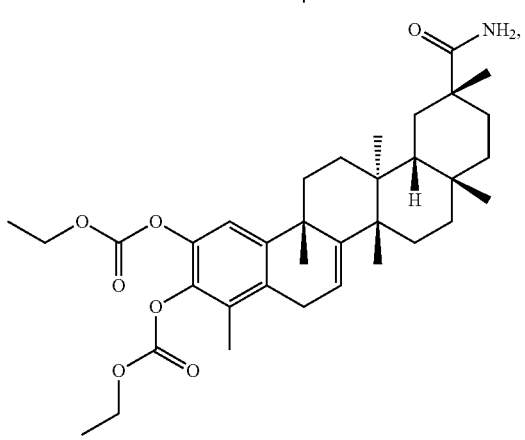
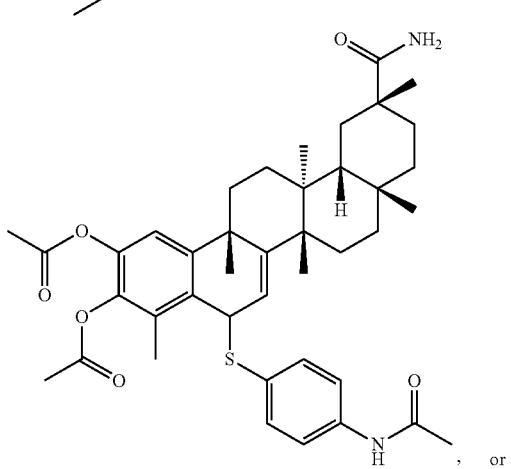
-continued
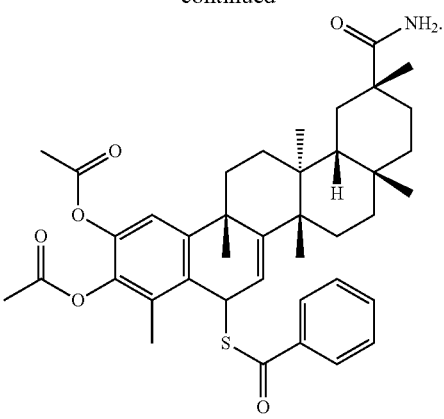
In yet other embodiment, the compounds of formula (I) include those in which $R_1$ is —COOH or —COOCH$_3$.
In some embodiments, $R_2$ is —CH$_3$, —SC(=O)CH$_3$, —SCH(CH$_3$)$_2$, or —SCH$_2$CH$_2$OCOCH$_3$.
In some embodiments, $R_3$ is —OCOCH$_3$ or —OH.
In some embodiments, $R_4$ is —OCOCH$_3$ or —OH.
One subset of the compounds of formula (I) includes the compounds shown below:
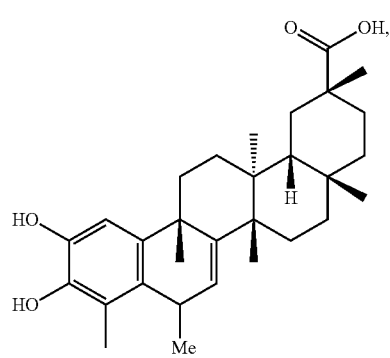
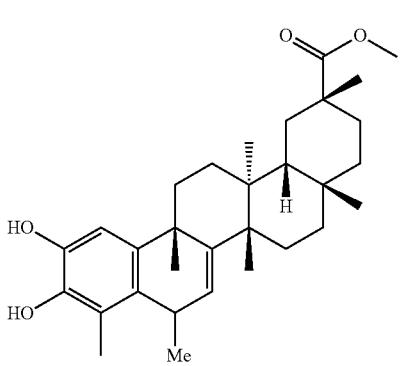

-continued

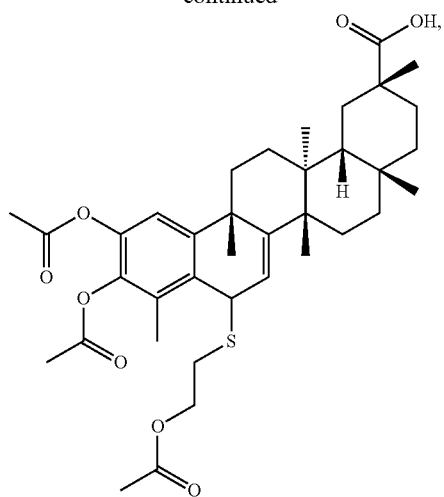

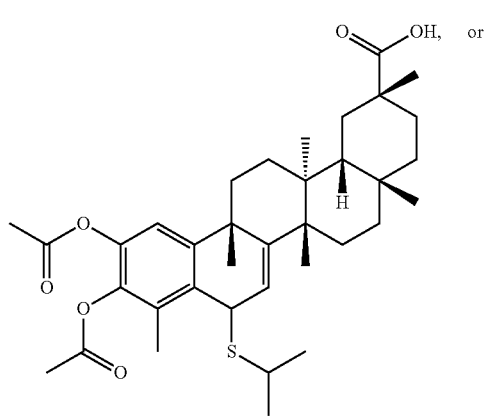, or

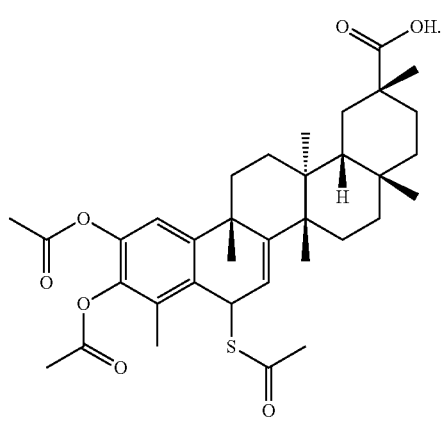

In some embodiments, the compounds of formula (I) include those in which $R_1$ is —CN or —CH$_2$NR$_5$R$_5$ such as —CH$_2$N(CH$_3$)$_2$, which can be represented as Formula (I)-b or Formula (I)-c, respectively:

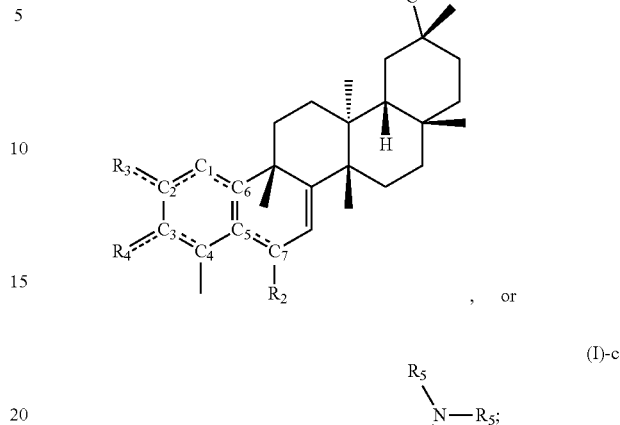

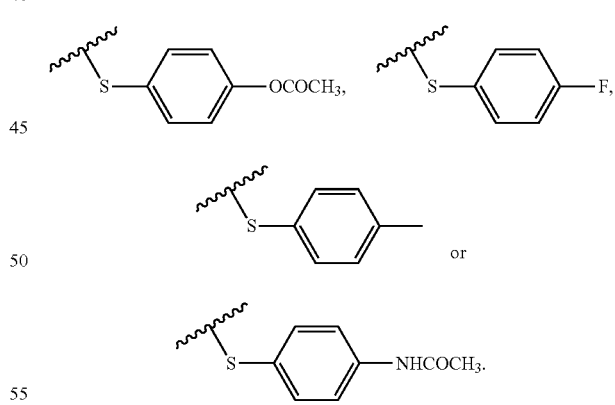

wherein each $R_2$, $R_3$, $R_4$ and $R_5$ is defined in Formula (I)

In some embodiments, $R_2$ is —SCH(CH$_3$)$_2$, —SC(=O)CH$_3$, —H,

[structures shown]

In some embodiments, $R_3$ is —OCOCH$_3$.

In some embodiments, $R_4$ is —OCOCH$_3$.

In some embodiments $R_3$ and $R_4$ form a five membered-heterocycle comprising —OCOO—.

In some embodiments, $R_5$ is alkyl, preferably CH$_3$.

One subset of the compounds of formula (I) includes the compounds shown below:

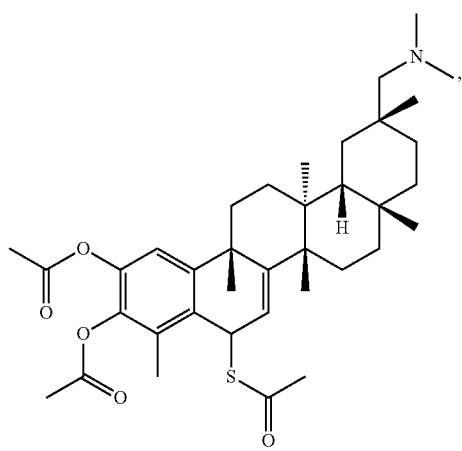
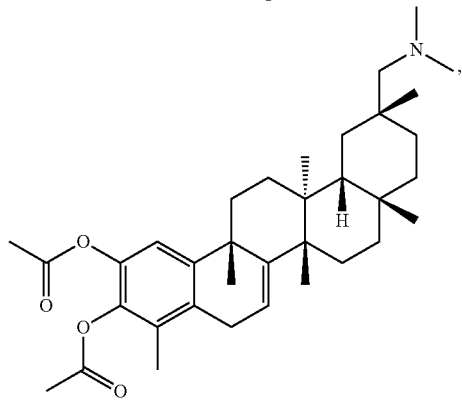
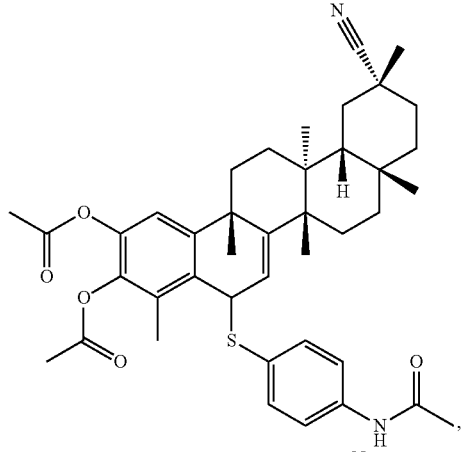
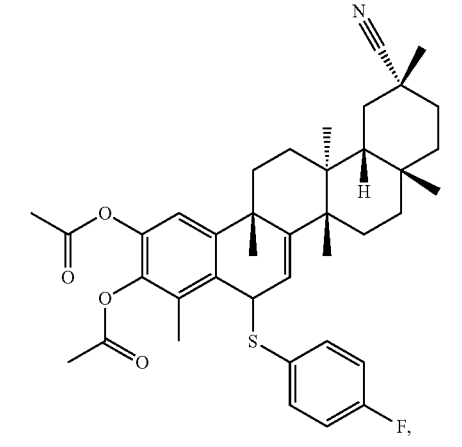
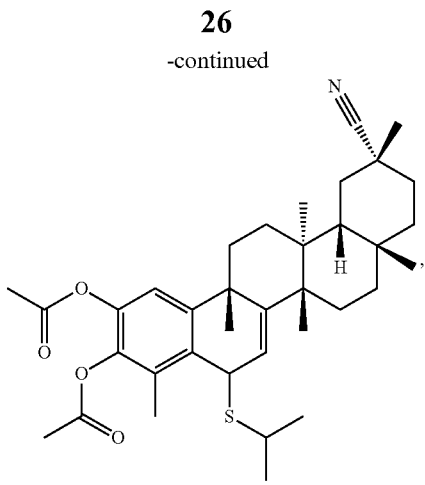
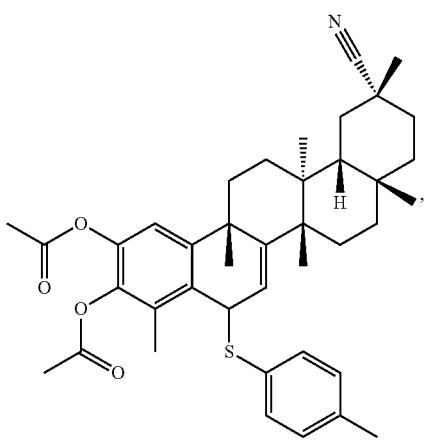
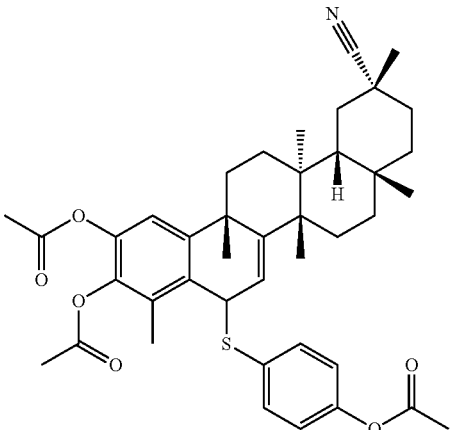
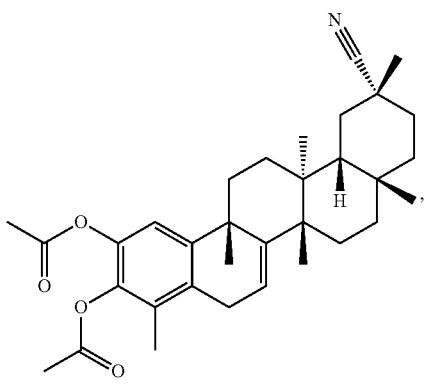

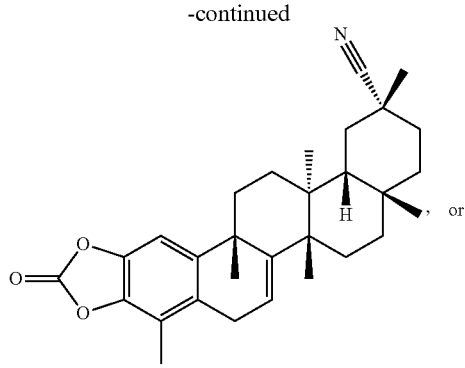

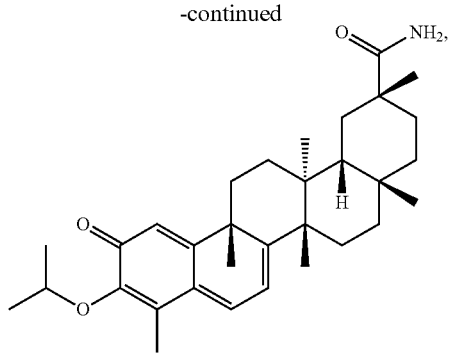

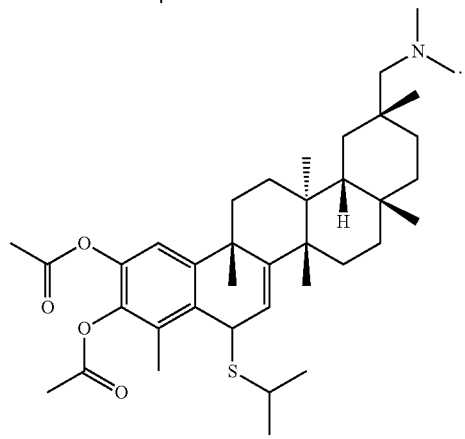

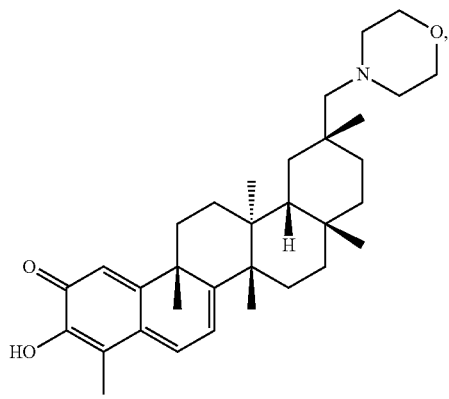

In some embodiments, the compounds of formula (I) include those in which $R_3$ is O and a double bond is present between $C_2$ and $R_3$ and $C_3$ and $C_4$.

In some embodiments, $R_1$ is —C(=O)OCH$_2$CH$_3$, —CN, —CONH$_2$, —CH$_2$N(CH$_3$)$_2$,

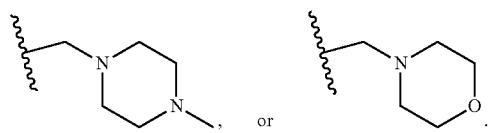

In some embodiments $R_2$ is —H.

In some embodiments, $R_4$ is —OCH$_3$, —OP(=O)(OCH$_3$)$_2$, —OCH$_2$CH$_3$, —OH, —OCONHCH$_2$CH$_3$, —OCH$_2$COOCH$_3$, —OCOOCH$_2$CH$_3$, —OCH$_2$CH$_2$OH, —OCOOCH(CH$_3$)$_2$, or —OCH(CH$_3$)$_2$.

One subset of the compounds of formula (I) includes the compounds shown below:

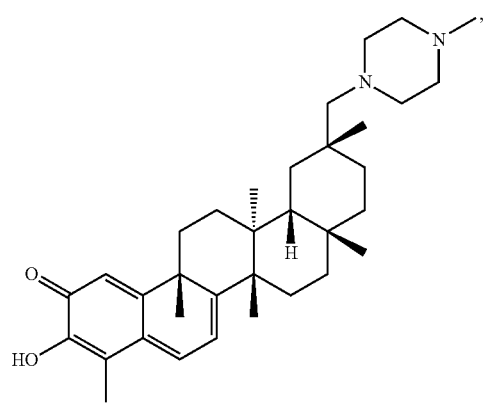

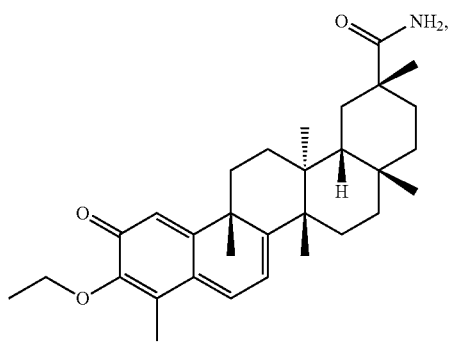

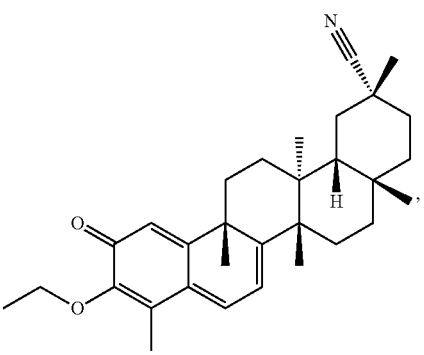

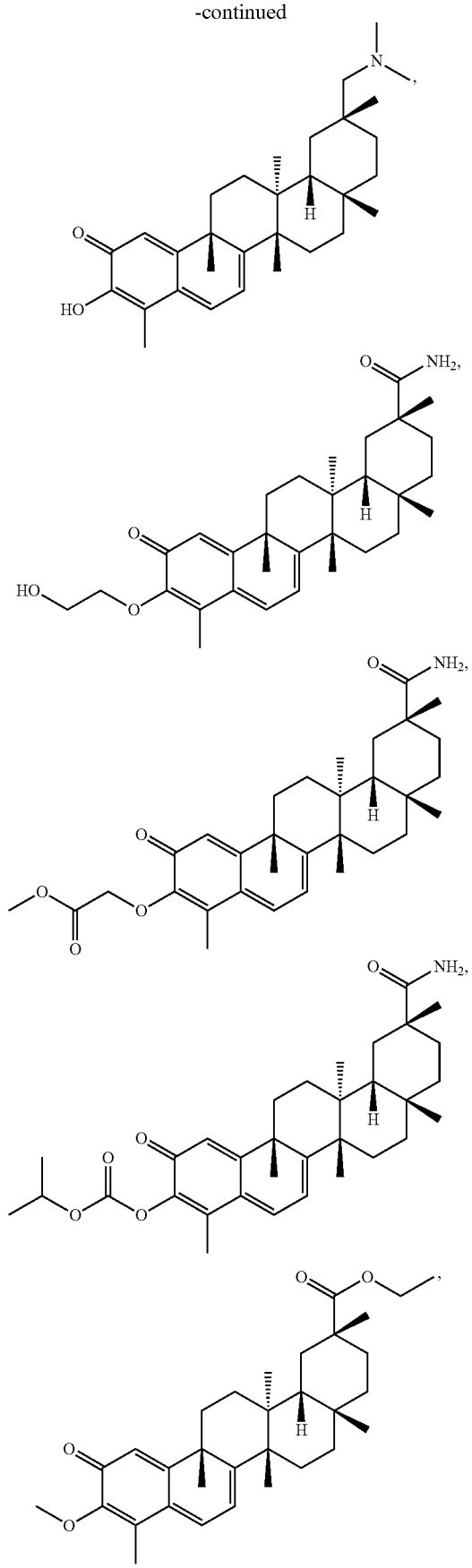
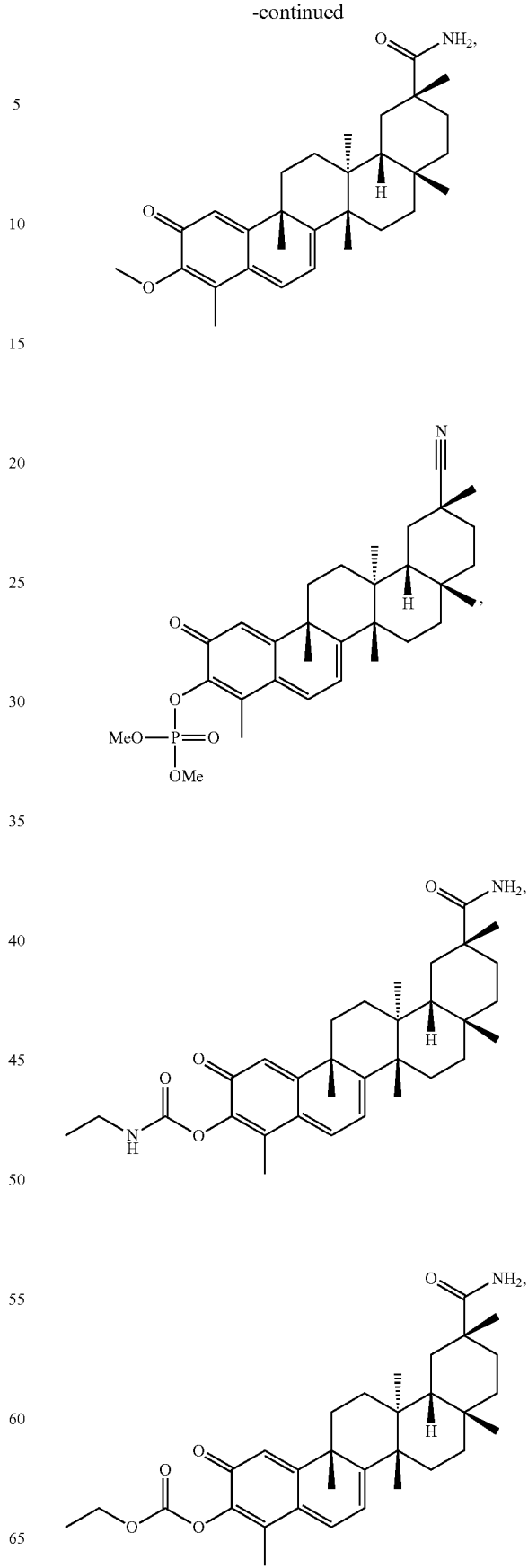

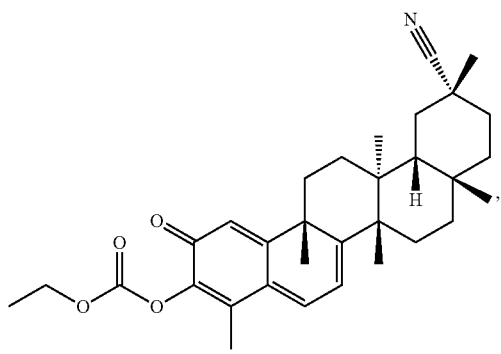

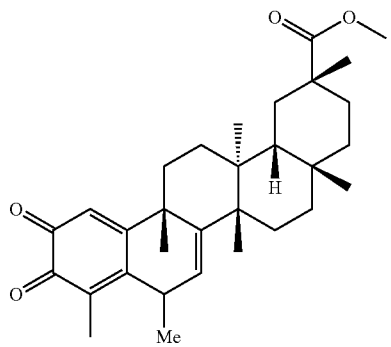

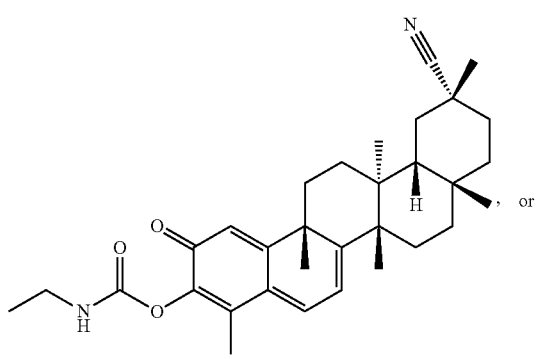

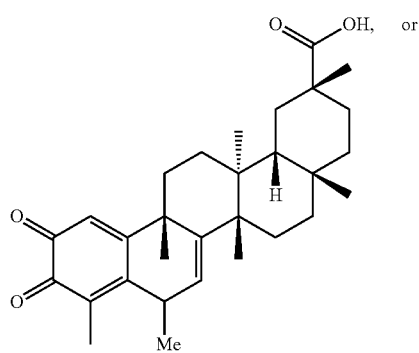

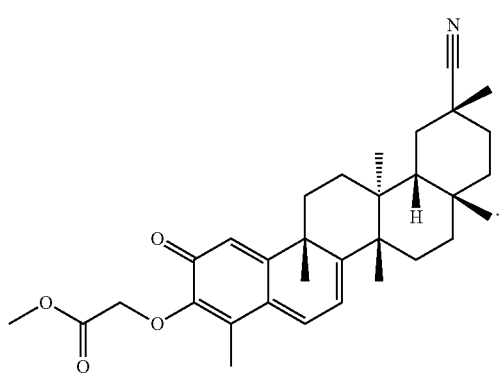

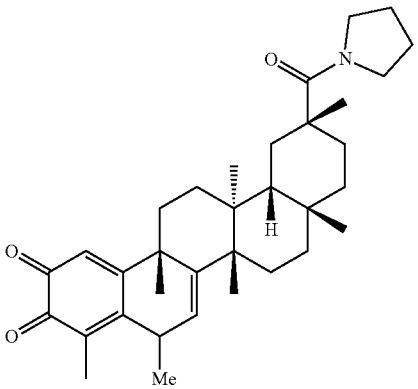

In some embodiments, the compounds of formula (I) include those in which $R_3$ and $R_4$ are O and a double bond is present between $C_2$ and $R_3$ and $C_3$ and $R_4$.

In some embodiments, $R_1$ is COOH, COOCH$_3$, or

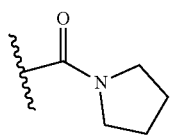 [SMILES: *C(=O)N1CCCC1]

In some embodiments, $R_2$ is CH$_3$.

One subset of the compounds of formula (I) includes the compounds shown below:

In some embodiments, $R_1$ is —NR$_5$C(=NR$_5$)NR$_5$R$_5$, —SR$_5$, —SO$_3$R$_5$, —SO$_2$R$_5$, —NH$_2$, —NHR$_5$, —NR$_5$R$_5$, —OH, —OR$_5$, —NCO, —NCS, —N$_3$, —SH, —SR$_5$, —SO$_2$H, —SO$_3$H, —SO$_2$NR$_5$R$_3$, —SO$_3$R, —NHCOR$_3$, —NHCNR$_5$NR$_5$R$_5$, —NHCOSR$_5$, —NR$_5$COR$_5$, —N R$_5$C(=NH)NR$_5$R$_5$, —NR$_5$COSR$_5$, —NHC(=NR$_5$)R$_5$, —NR$_5$C(=NR$_5$)R$_5$, —NHSO$_2$(NH$_2$), —NHSO$_2$R$_5$, —NR$_5$SO$_2$R$_5$, —NR$_5$SO$_2$NR$_5$R$_5$, —OCOR$_5$, —OCONR$_5$R$_5$, —O(C=O)OR$_5$, —SCOR$_5$, —O(C=NH)NR$_5$R$_5$, —OCSNHR$_5$, —OS(=O$_2$)R$_5$, —OS(=O$_2$)NR$_5$R$_5$, —SCONR$_5$R$_5$.

In some embodiments, $R_2$ is H.

In some embodiments, $R_4$ is OH, —OR$_7$, or —R$_7$ when $R_3$ is O and a double bond is present between $C_2$ and $R_3$.

One subset of the compounds of formula (I) includes the compounds shown below:

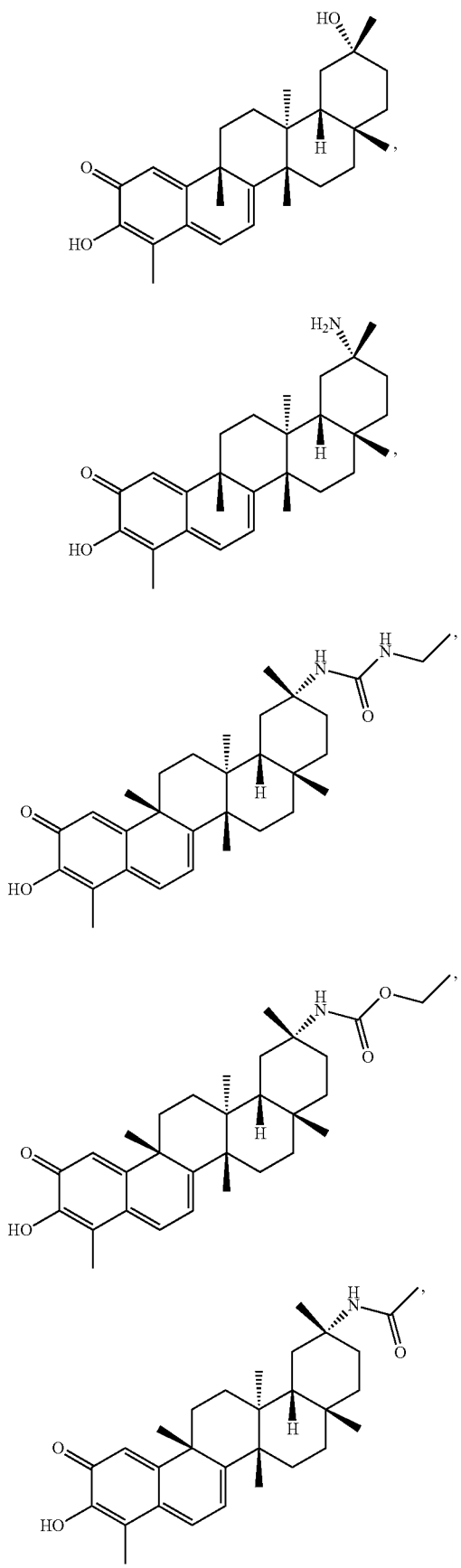

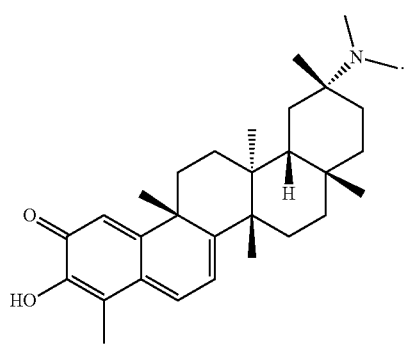

In some embodiments, the compounds may include:

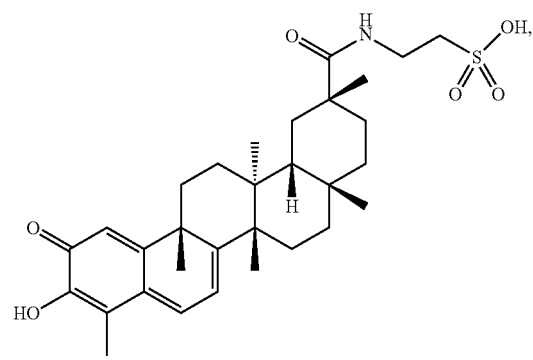

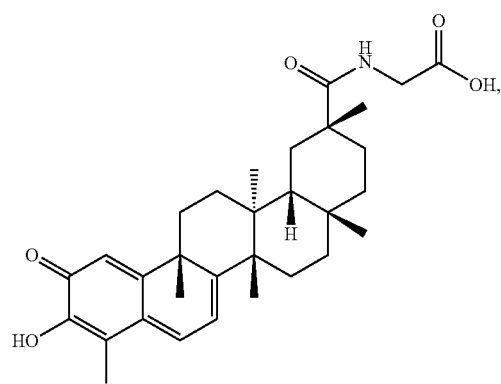

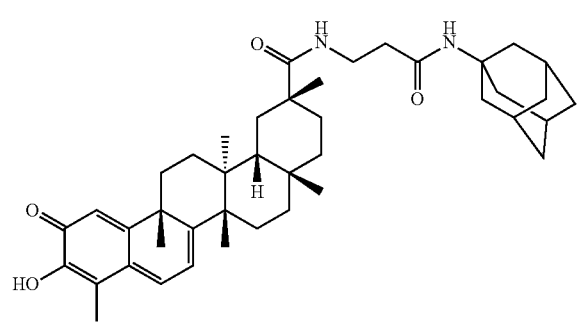

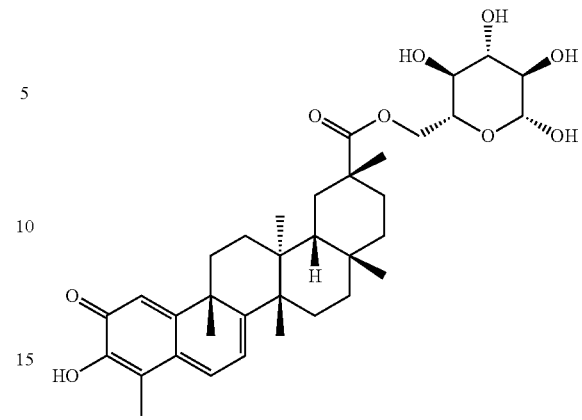

or

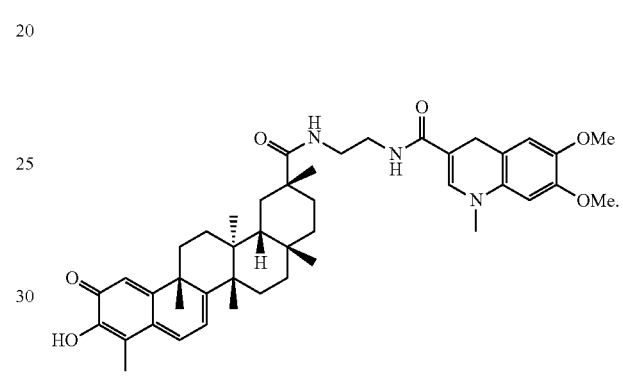

In another preferred aspect, the composition may include a compound having the structure of Formula (II):

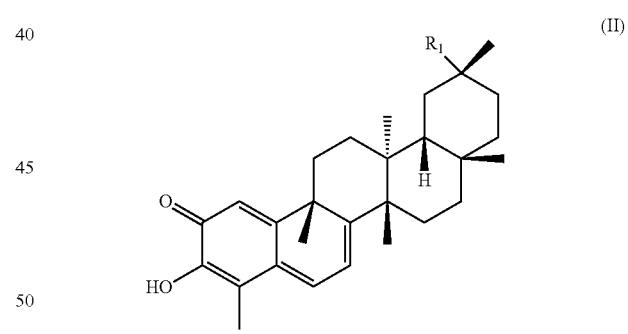

(II)

where $R_1$ is $OR_a$ or $NR_aR_b$ where each $R_a$ and $R_b$ is independently hydrogen, $R_5$, $C(=NR_5)NR_5R_5$, —CO, —CS, —COR_5, —CNR_5NR_5R_5, —COSR_5, —C(=NH)NR_5R_5, —C(=NR_5)R_5, —SO_2(NH_2), —SO_2R_5, —SO_2R_5, —SO_2NR_5R_5, —COR_5, —CONR_5R_5, —(C=O)OR_5, —(C=NH)NR_5R_5, —CSNHR_5, —S(=O_2)R_5, or —S(=O_2)NR_5R_5, $R_5$ is described in Formula (I), or a pharmaceutically acceptable salt or prodrug thereof.

In some embodiments, $R_1$ is $NR_aR_b$, which can be presented in Formula (II)-a:

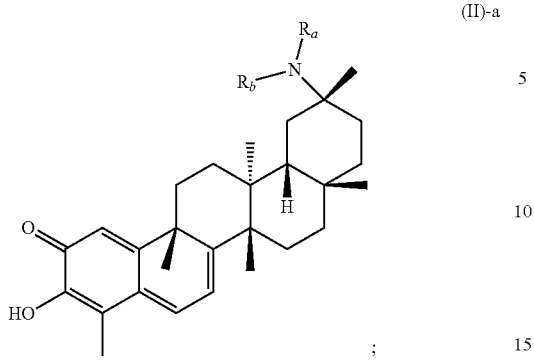
wherein each $R_a$, or $R_b$ is defined in Formula (II).
In certain embodiments, $R_1$ is NH(CO)$R_5$ where $R_5$ is preferably alkyl, cycloalkyl, or aryl, which can be presented in Formula (II)-b:
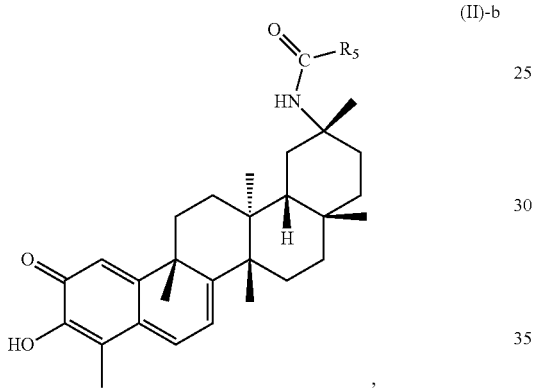
wherein each $R_a$, or $R_b$ is defined in Formula (II).
Exemplary of the compounds of formula (II) include the compounds shown below:
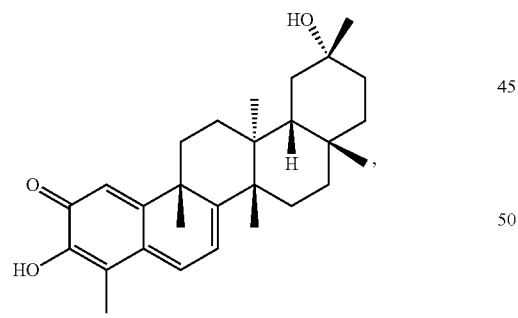
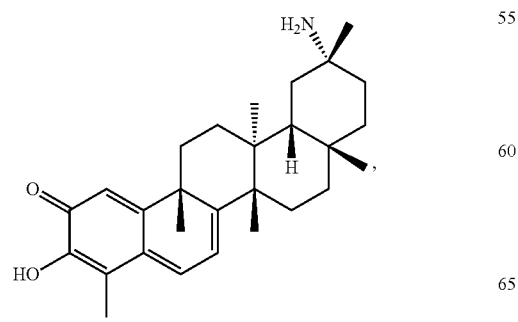
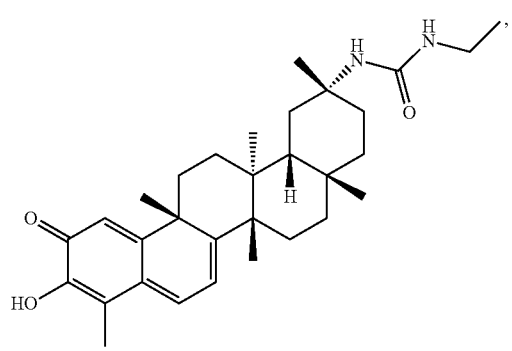
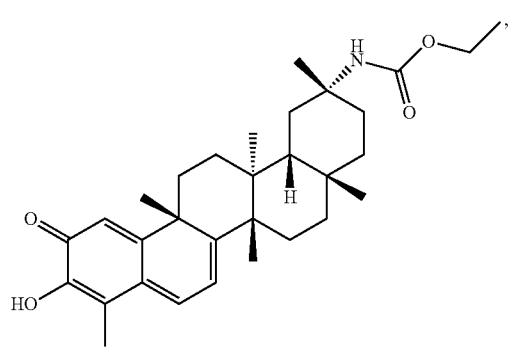
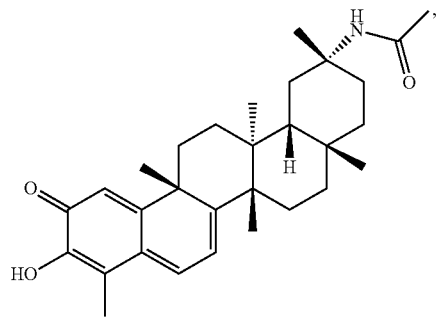
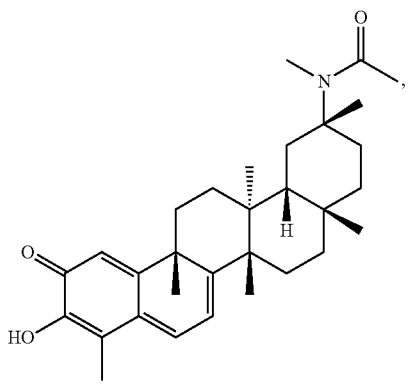

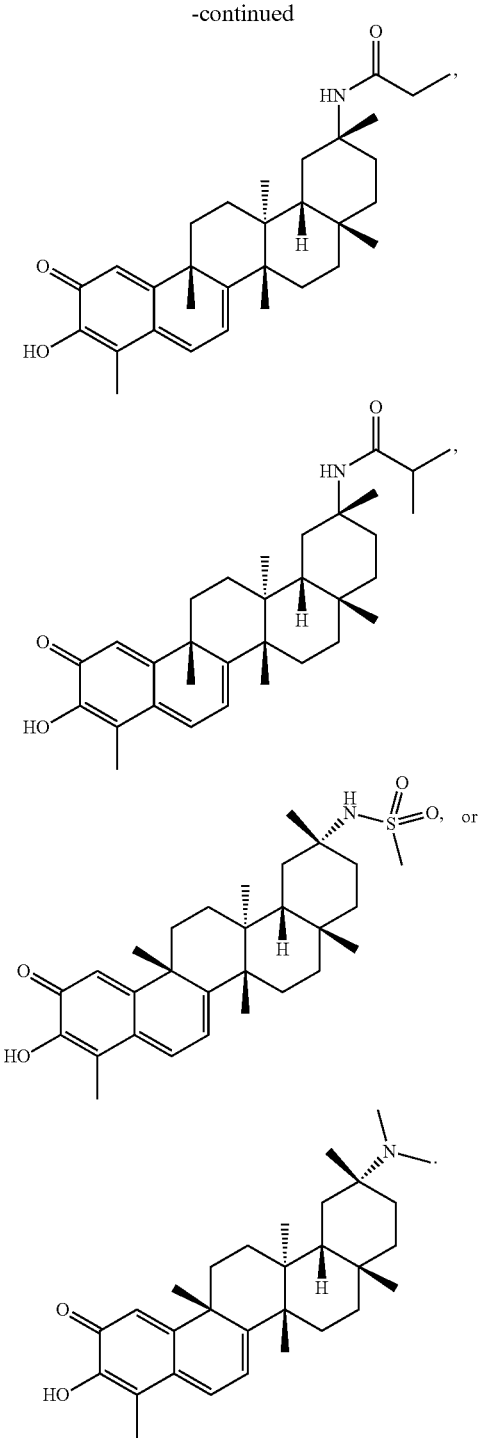

The compounds described by Formula (I) and Formula (II) can be prepared using methods known in the art and described herein. For example, Celastrol can be obtained from commercial sources, or isolated from plants, e.g. Tripterygium, by methods known in the art (Kutney et al, *Can. J. Chem.* 59:2677, 1981) and Zhang et al, *Acta Pharm. Sin.* 212: 592, 1986). Celastrol can be modified to render compounds of Formula (I) or Formula (II). Prepared compounds are purified using conventional methods to obtain compounds free of impurities. Prepared compounds are >75, >80, >85, >90, >95, >96, >97, >98, >99, >99.5% pure. Optionally, preferred compounds are >99% pure.

Further provided are the compounds of Formula (I) and Formula (II) that impart properties for increased or substantially increased oral bioavailability.

In some embodiments, the compounds of Formula (I) and Formula (II) that may have greater or less solubility in water, an aqueous solution and/or a physiological solution than the Celastrol obtainable from commercial sources or isolated from plants. For example, the compounds may have a solubility within ranges from about 0.001 µM to about 150 µM, from 0.01 µM to about 100 µM, from 0.1 µM to about 100 µM, from 1 µM to about 100 µM, from 10 µM to about 100 µM, from 1 µM to about 50 µM, from 10 µM to about 50 µM, from 10 µM to about 80 µM, from 10 µM to about 25 µM, from 25 µM to about 50 µM, from 50 µM to about 100 µM, from 50 µM to about 75 µM, from 25 µM to about 75 µM, or a solubility that is at least about 0.1, 1, 5, 10, 20, 30, 40, 50, 60, 70, 80, 90, or 100 µM, or a solubility that is less than about at least about 0.1, 1, 5, 10, 20, 30, 40, 50, 60, 70, 80, 90, or 100 µM in an aqueous solution (such as phosphate buffered saline (PBS), e.g., at a pH of about 7, 7.1, 7.2, 7.3, 7.4, 7.5, or 7-8).

In some embodiments, the compounds of Formula (I) and Formula (II) have increased or substantially increased stability or half-life in water, aqueous solution or physiological solution. For instance, the compounds may have substantially increased stability or resistance in various pH conditions ranging from 2 to 8 in upper or middle gastroinstestinal (GI), or digestive tracts.

In some embodiments, the compounds of Formula (I) and Formula (II) impart increased or substantially increased uptake when administered to a subject. For instance, the compounds may have substantially improved permeability across biological membranes. The compounds may exhibit suitable balance between hydrophobicity (lipophilicity) and hydrophilicity by local ionic charges.

In one aspect, the composition of the invention comprises at least one compounds having oral efficacy for treating obesity.

Exemplary compounds having oral efficacy for treating obesity may include the following compounds:

-continued
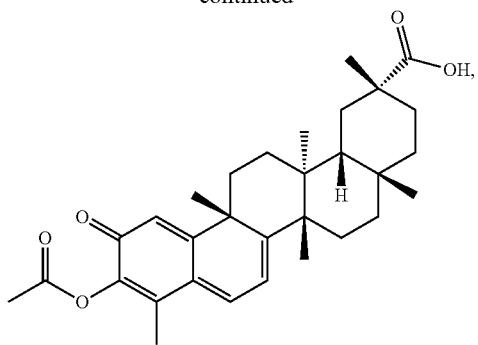
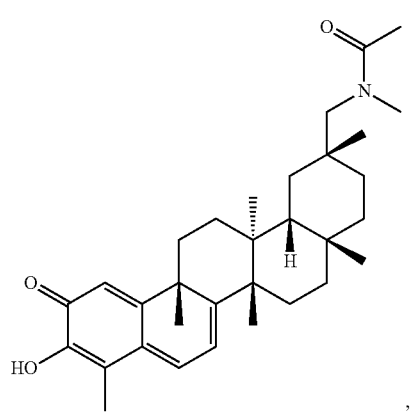
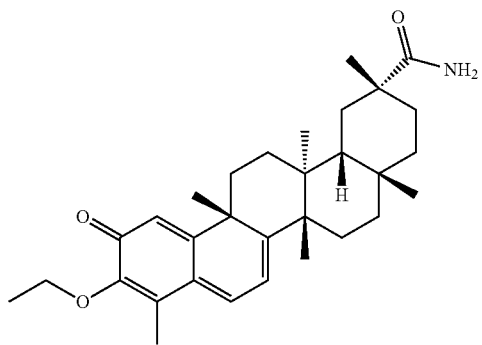
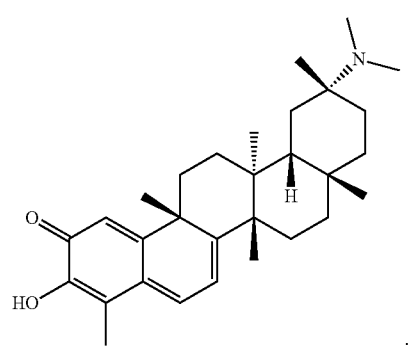
In another aspect, the composition comprises at compounds having intraperitoneal efficacy for treating obesity.
Examples of these compounds having intraperitoneal efficacy for treating obesity may include the following compounds:
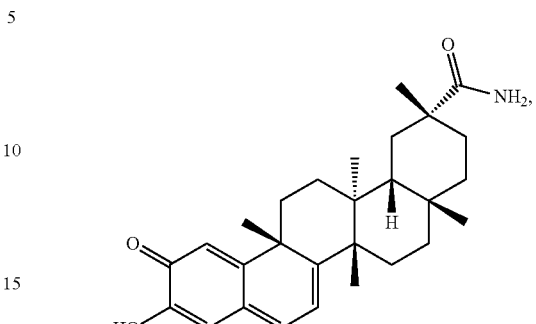
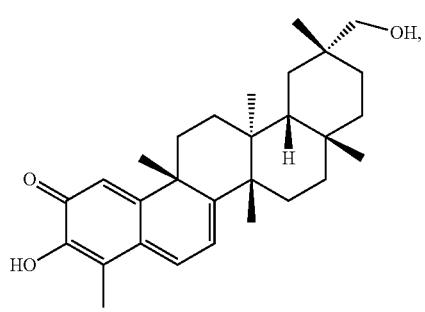
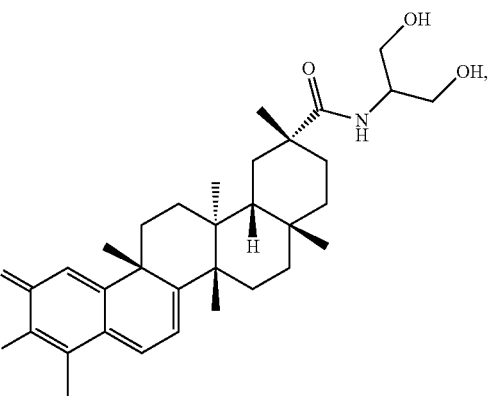
and
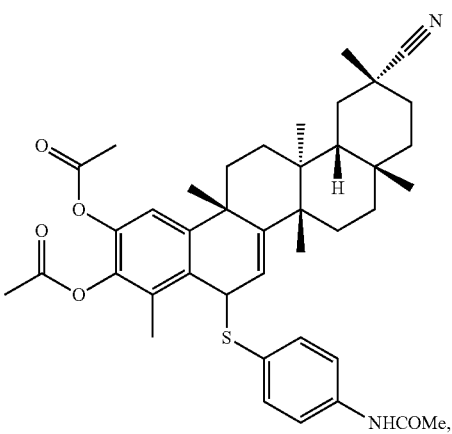

43
-continued
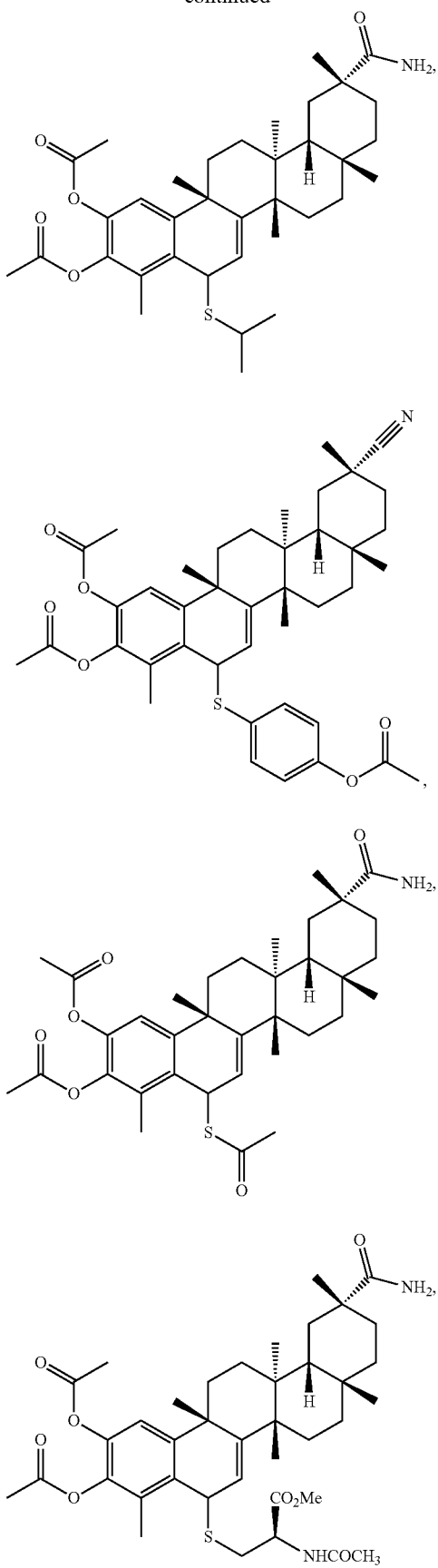
44
-continued
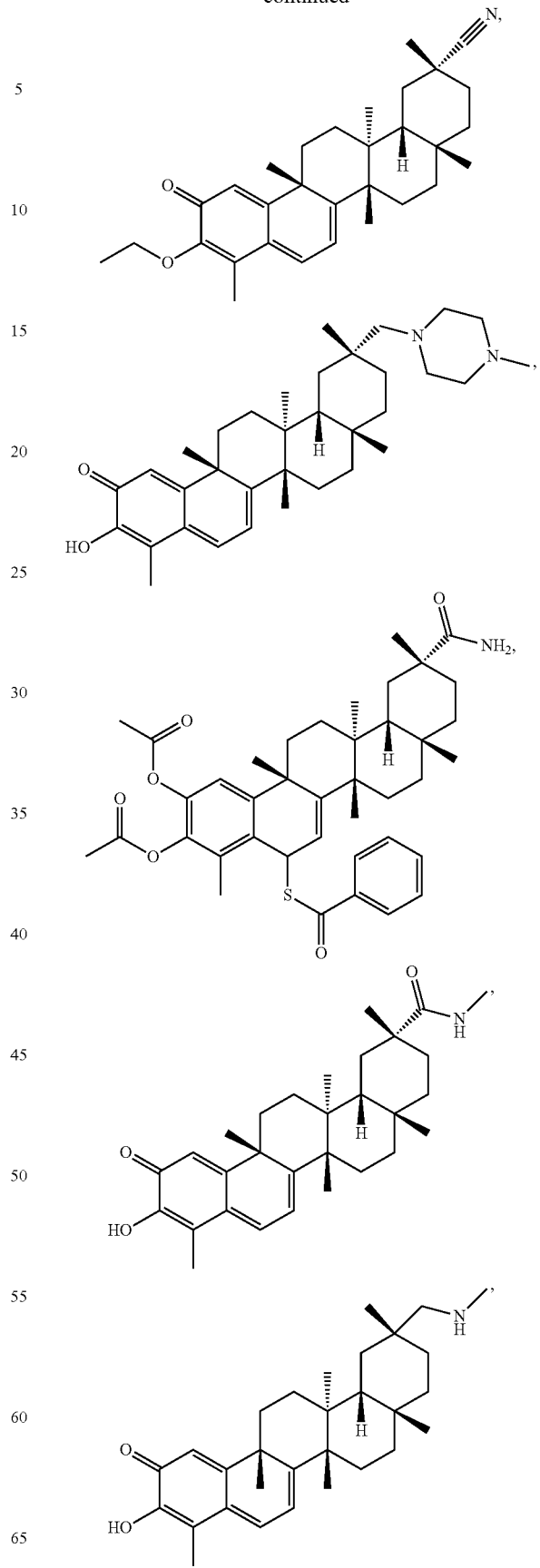

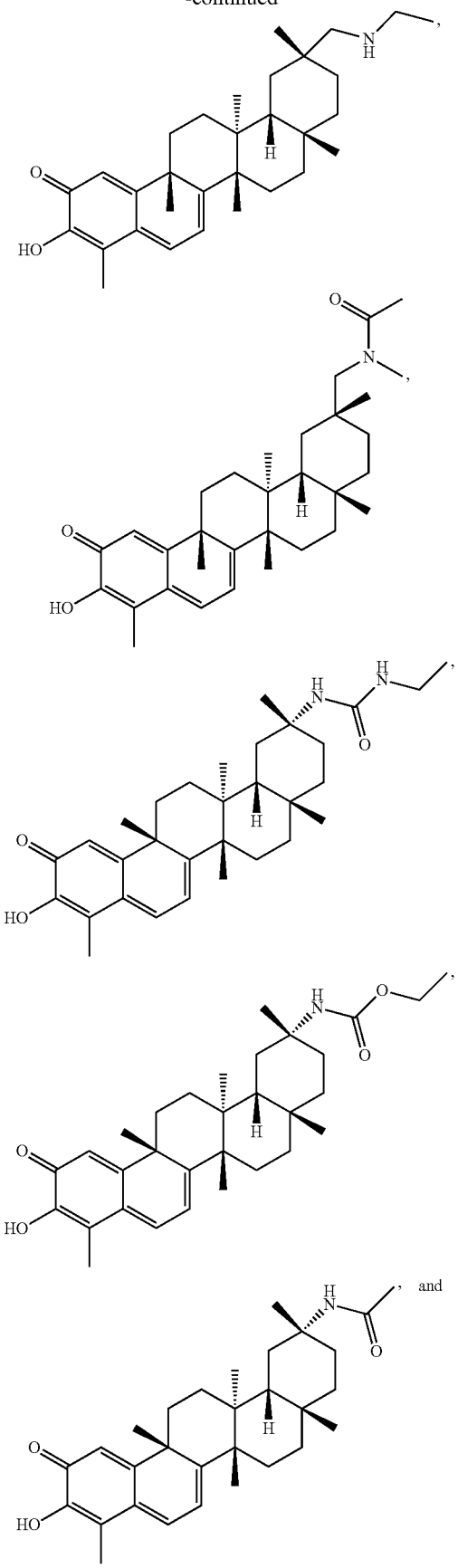

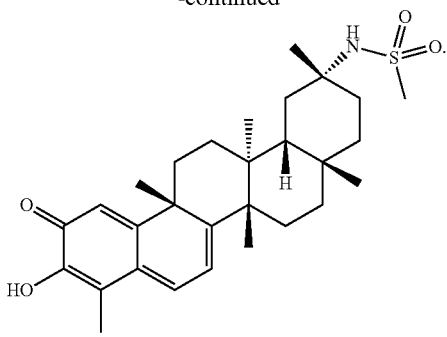

III. Methods of Treatment and Diagnosis

The compounds described above, can be used in the treatment of obesity in a subject in need thereof includes administering to the subject an effective amount of the compounds of formula (I). Obesity may be the primary cause of a disease and/or disorder or may be caused as a result of a disease and/or disorder.

In some cases, an effective amount of a compound of formula (I) may be administered as a method of treating weight gain in pre-obese, obese or morbidly obese patients.

In some cases, a method of reducing body fat in pre-obese, obese or morbidly obese patients includes administering an effective amount of a compound of formula (I). Body mass or body fat may be decreased by about 5%, 10%, 15%, 20%, 25%, 30%, 35%, 40%, 45%, or 50%, about 5-10%, 5-25%, 10-25%, 10-50%, 25-50%, or at least about 5%, 10%, 15%, 20%, 25%, 30%, 35%, 40%, 45%, or 50%.

In some cases, a method of reducing food intake in pre-obese, obese or morbidly obese patients is accomplished by administering an effective amount of a compound of formula (I). The average daily food intake (in terms of calories) may be reduced by at least 5%, 10%, 15%, 20%, 25%, 30%, 35%, 40%, 45%, 50% or higher, or about 5-10%, 5-25%, 10-25%, 10-50%, 25-50%.

In some cases, an effective amount of a compound of formula (I) may be administered to reduced the body mass index (BMI) of a patient suffering from obesity. The BMI of a patient may be reduced to a value of <30 kg m$^{-2}$ (normal BMI=20-25 kg m$^{-2}$).

Lastly, a method of improving glucose homeostatis in pre-obese, obese, or morbidly obese patients may be accomplished by administering a compound of formula (I). The average fasting plasma blood glucose levels may be reduced by at least 10%, 12%, 15%, 18%, 20%, 25%, 30%, 35%, 40%, 45%, or 50% or higher or about 5-10%, 5-25%, 10-25%, 10-50%, 25-50%.

Obesity

Obesity is a medical condition in which excess body fat has accumulated to the extent that it may have a negative effect on health, leading to reduced life expectancy and/or increased health problems (Haslam et al., *Lancet* (*Review*) 366 (9492): 1197-209, 2005). In Western countries, people are considered obese when their BMI, a measurement obtained by dividing a person's weight by the square of the person's height, exceeds 30 kg/m$^2$, with the range 25-30 kg/m$^2$ defined as overweight. Obesity increases the likelihood of various diseases, particularly heart disease, type 2 diabetes, obstructive sleep apnea, certain types of cancer, and osteoarthritis (Haslam et al., *Lancet* (*Review*) 366 (9492): 1197-209, 2005). Obesity is most commonly caused by a combination of excessive food energy intake, lack of physical activity, and genetic susceptibility, although a few cases are caused primarily by genes, endocrine disorders, medications, or psychiatric illness. Evidence to support the view that some obese people eat little yet gain weight due to a slow metabolism is limited. On average, obese people have a greater energy expenditure than their thin counterparts due to the energy required to maintain an increased body mass (Kushner, *Treatment of the Obese Patient*, 2007).

Obesity is a medical condition in which excess body fat has accumulated to the extent that it may have an adverse effect on health. It is defined by BMI and further evaluated in terms of fat distribution via the waist-hip ratio and total cardiovascular risk factors (Sweeting et al., *Nutr. J.* 6 (1): 32, 2007). BMI is closely related to both percentage body fat and total body fat (Gray et al., *J. Clin. Epidemiol.* 44 (6): 545-50, 1991).

BMI is defined as the subject's weight divided by the square of their height. BMI is usually expressed in kilograms per square meter, resulting when weight is measured in kilograms and height in meters. Some modifications to the definitions have been made where the surgical literature breaks down obesity into further categories whose exact values are still disputed (Sturm et al., *Public Health* 121 (7): 492-6, 2007). Any BMI ≥35 or 40 kg/m$^2$ is severe obesity. A BMI of ≥35 kg/m$^2$ and experiencing obesity-related health conditions or ≥40-44.9 kg/m$^2$ is morbid obesity. A BMI of ≥45 or 50 kg/m$^2$ is super obesity. The World Health Organization (WHO) regards a BMI of less than 18.5 as underweight and may indicate malnutrition, an eating disorder, or other health problems, while a BMI equal to or greater than 25 is considered overweight and above 30 is considered obese (World Health Organization, Global Database on Body Mass Index (2006)). A summary of the WHO BMI classification scheme is outlined in the Table 1 below.

TABLE 1

Body Mass Index Classification Scheme

| CATEGORY | BMI range - kg/m$^2$ |
| --- | --- |
| Very severely underweight | less than 15 |
| Severely underweight | from 15.0 to 16.0 |
| Underweight | from 16.0 to 18.5 |
| Normal (healthy weight) | from 18.5 to 25 |
| Overweight | from 25 to 30 |
| Obese Class I (Moderately obese) | from 30 to 35 |
| Obese Class II (Severely obese) | from 35 to 40 |
| Obese Class III (Very severely obese) | over 40 |

Hypothalamic Injury Associated Obesity

Hypothalamic obesity is a complicated medical condition that can occur from the growth of rare brain tumors and from other types of injury to the hypothalamus. Craniopharyngioma is one of the tumors that can cause hypothalamic injury associated obesity. Damage to the hypothalamus disrupts the communication between the gut and the brain, causing a constant feeling of hunger.

The hypothalamus and pituitary gland are tightly integrated. Damage to the hypothalamus will impact the responsiveness and normal functioning of the pituitary. Hypothalamic disease may cause insufficient or inhibited signaling to the pituitary leading to deficiencies of one or more of the following hormones: thyroid-stimulating hormone, adrenocorticotropic hormone, beta-endorphin, luteinizing hormone, follicle-stimulating hormone, and melanocyte-stimulating hormones. Treatment for hypopituitarism involves hormone replacement therapy (Pinkney, *Pituitary News* 17, 2000).

Thyroid hormones are responsible for metabolic activity. Insufficient production of thyroid hormones result in suppressed metabolic activity and weight gain. Hypothalamic disease may therefore have implications for obesity (Pinkney, *Pituitary News* 17, 2000); (Ling, *Trends in Obesity Research*, 2004).

Fatty Liver/NASH

Non-alcoholic fatty liver disease (NAFLD) is one of the causes of fatty liver, occurring when fat is deposited (steatosis) in the liver due to causes other than excessive alcohol use. NAFLD is related to insulin resistance and the metabolic syndrome and may respond to treatments originally developed for other insulin-resistant states (e.g. diabetes mellitus type 2) such as weight loss, metformin and thiazolidinediones (Adams et al. *Postgrad. Med. J.* 82 (967): 315-22, 2006). Non-alcoholic steatohepatitis (NASH) is the most extreme form of NAFLD, and is regarded as a major cause of cirrhosis of the liver of unknown cause (Clark et al. *JAMA* 289 (22):3000-4, 2003).

Most people with NAFLD have few or no symptoms. Patients may complain of fatigue, malaise, and dull right-upper-quadrant abdominal discomfort. Mild jaundice may be noticed although this is rare. More commonly NAFLD is diagnosed following abnormal liver function tests during routine blood tests. NAFLD is associated with insulin resistance and metabolic syndrome (obesity, combined hyperlipidemia, diabetes mellitus (type II) and high blood pressure) (Adams et al. *Postgrad. Med. J.* 82 (967): 315-22, 2006).

Common findings are elevated liver enzymes and a liver ultrasound showing steatosis. An ultrasound may also be used to exclude gallstone problems (cholelithiasis). A liver biopsy (tissue examination) is the only test widely accepted as definitively distinguishing NASH from other forms of liver disease and can be used to assess the severity of the inflammation and resultant fibrosis (Adams et al. *Postgrad. Med. J.* 82 (967): 315-22, 2006).

Other diagnostic tests are available. Relevant blood tests include erythrocyte sedimentation rate, glucose, albumin, and renal function. Because the liver is important for making proteins used in coagulation some coagulation related studies are often carried out especially the INR (international normalized ratio). Blood tests (serology) are usually used to rule out viral hepatitis (hepatitis A, B, C and herpes viruses like EBV or CMV), rubella, and autoimmune related diseases. Hypothyroidism is more prevalent in NASH patients which would be detected by determining the TSH (Liangpunsakul et al. *J. Clin. Gastroenterol.* 37(4):340-3, 2003).

Metabolic Syndrome

Metabolic syndrome is a disorder of energy utilization and storage, diagnosed by a co-occurrence of three out of five of the following medical conditions: abdominal (central) obesity, elevated blood pressure, elevated fasting plasma glucose, high serum triglycerides, and low high-density lipoprotein (HDL) levels. Metabolic syndrome increases the risk of developing cardiovascular disease and diabetes (Kaur, *Cardiology Research and Practice*, 2014) (Felizola, "Ursolic acid in experimental models and human subjects: potential as an anti-obesity/overweight treatment?" ResearchGate, 2015).

The main sign of metabolic syndrome is central obesity (also known as visceral, male-pattern or apple-shaped adiposity), overweight with adipose tissue accumulation particularly around the waist and trunk. Other signs of metabolic syndrome include high blood pressure, decreased fasting serum HDL cholesterol, elevated fasting serum triglyceride level (VLDL triglyceride), impaired fasting glucose, insulin resistance, or prediabetes. Associated conditions include hyperuricemia, fatty liver (especially in concurrent obesity) progressing to nonalcoholic fatty liver disease, polycystic ovarian syndrome (in women), erectile dysfunction (in men), and acanthosis nigricans.

A joint interim statement of the International Diabetes Federation Task Force on Epidemiology and Prevention; National Heart, Lung, and Blood Institute; American Heart Association; World Heart Federation; International Atherosclerosis Society; and International Association for the Study of Obesity published a guideline to harmonize the definition of the metabolic syndrome (Alberti et al., Circulation 120 (16): 1640-5, 2009). This definition recognizes that the risk associated with a particular waist measurement will differ in different populations.

Stroke

Stroke, also known as cerebrovascular accident (CVA), cerebrovascular insult (CVI), or brain attack, is when poor blood flow to the brain results in cell death. There are two main types of stroke: ischemic due to lack of blood flow and hemorrhagic due to bleeding. They result in part of the brain not functioning properly. Signs and symptoms of a stroke may include an inability to move or feel on one side of the body, problems understanding or speaking, feeling like the world is spinning, or loss of vision to one side among others (Donnan et al., Lancet 371 (9624): 1612-23, 2008). Signs and symptoms often appear soon after the stroke has occurred. If symptoms last less than one or two hours it is known as a transient ischemic attack (TIA). Hemorrhagic strokes may also be associated with a severe headache.

The main risk factor for stroke is high blood pressure. Other risk factors include tobacco smoking, obesity, high blood cholesterol, diabetes mellitus, previous TIA, and atrial fibrillation among others (Donnan et al., Lancet 371 (9624): 1612-23, 2008). An ischemic stroke is typically caused by blockage of a blood vessel. A hemorrhagic stroke is caused by bleeding either directly into the brain or into the space surrounding the brain. (Feigin et al., Stroke 36 (12): 2773-80, 2005). Bleeding may occur due to a brain aneurysm. Diagnosis is typically with medical imaging such as a CT scan or MRI scan along with a physical exam. Other tests such as an electrocardiogram (ECG) and blood tests are done to determine risk factors and rule out other possible causes.

Stroke is diagnosed through several techniques: a neurological examination (such as the NIHSS), CT scans (most often without contrast enhancements) or MRI scans, Doppler ultrasound, and arteriography. The diagnosis of stroke itself is clinical, with assistance from the imaging techniques. Imaging techniques also assist in determining the subtypes and cause of stroke. There is yet no commonly used blood test for the stroke diagnosis itself, though blood tests may be of help in finding out the likely cause of stroke (Hill et al., Clin. Chem. 51 (11): 2001-2, 2005).

Cardiovascular Disease

Cardiovascular disease (CVD) is a class of diseases that involve the heart or blood vessels. Cardiovascular disease includes coronary artery diseases (CAD) such as angina and myocardial infarction (commonly known as a heart attack) (Shanthi et al., Global Atlas on Cardiovascular Disease Prevention and Control 3-18, 2011). Other CVDs are stroke, hypertensive heart disease, rheumatic heart disease, cardiomyopathy, atrial fibrillation, congenital heart disease, endocarditis, aortic aneurysms, and peripheral artery disease The underlying mechanisms vary depending on the disease in question. Coronary artery disease, stroke, and peripheral artery disease involve atherosclerosis. This may be caused by high blood pressure, smoking, diabetes, lack of exercise, obesity, high blood cholesterol, poor diet, and excessive alcohol consumption, among others. High blood pressure results in 13% of CVD deaths, while tobacco results in 9%, diabetes 6%, lack of exercise 6% and obesity 5%. Rheumatic heart disease may follow untreated strep throat (Shanthi et al., Global Atlas on Cardiovascular Disease Prevention and Control 3-18, 2011).

Standard tests for cardiovascular disease include: coronary artery calcification, carotid total plaque area, elevated low-density lipoprotein-p, and elevated blood levels of brain natriuretic peptide (also known as B-type) (BNP) (Bertazzo et al., Nat. Mat. 12, 576-583, 2013) (Inaba et al., Atherosclerosis 220 (1): 128-33, 2012) (J. Clin. Lipidol. December; 1(6) 583-92, 2007) (Wang et al., N. Engl. J. Med. 350(7): 655-63, 2004).

Diabetes

Diabetes mellitus (DM), commonly referred to as diabetes, is a group of metabolic diseases in which there are high blood sugar levels over a prolonged period. Symptoms of high blood sugar include frequent urination, increased thirst, and increased hunger. If left untreated, diabetes can cause many complications (Diabetes Fact sheet N° 312". WHO, 2013). Acute complications include diabetic ketoacidosis and nonketotic hyperosmolar coma (Kitabchi, et al., Diabetes Care 32 (7): 1335-43, 2009). Serious long-term complications include cardiovascular disease, stroke, chronic kidney failure, foot ulcers, and damage to the eyes.

Diabetes is due to either the pancreas not producing enough insulin or the cells of the body not responding properly to the insulin produced (Shoback, Greenspan's Basic & Clinical Endocrinology (9th ed.) (2011)).

Diabetes mellitus is characterized by recurrent or persistent high blood sugar, and is diagnosed by demonstrating any one of the following: Fasting plasma glucose level ≥7.0 mmol/l (126 mg/dl); Plasma glucose≥11.1 mmol/l (200 mg/dl) two hours after a 75 g oral glucose load as in a glucose tolerance test; Symptoms of high blood sugar and casual plasma glucose≥11.1 mmol/l (200 mg/dl); and Glycated hemoglobin (HbAlC)≥48 mmol/mol (≥6.5 DCCT %) (National Diabetes Clearinghouse (NDIC): National Diabetes Statistics 2011" U.S. Department of Health and Human Services, 2011) ("Diabetes Care" American Diabetes Association, 2010).

A positive result, in the absence of unequivocal high blood sugar, should be confirmed by a repeat of any of the above methods on a different day. It is preferable to measure a fasting glucose level because of the ease of measurement and the considerable time commitment of formal glucose tolerance testing, which takes two hours to complete and offers no prognostic advantage over the fasting test (Saydah et al., Diabetes Care 24 (8): 1397-402, 2001). According to the current definition, two fasting glucose measurements above 126 mg/dl (7.0 mmol/1) is considered diagnostic for diabetes mellitus.

Per the World Health Organization, people with fasting glucose levels from 6.1 to 6.9 mmol/l (110 to 125 mg/dl) are considered to have impaired fasting glucose; people with plasma glucose at or above 7.8 mmol/1 (140 mg/dl), but not over 11.1 mmol/1 (200 mg/dl), two hours after a 75 g oral glucose load are considered to have impaired glucose tolerance (Definition and diagnosis of diabetes mellitus and intermediate hyperglycemia: report of a WHO/IDF consultation. World Health Organization p. 21, 2006). Of these two prediabetic states, the latter in particular is a major risk factor for progression to full-blown diabetes mellitus, as well as cardiovascular disease. The American Diabetes Association since 2003 uses a slightly different range for impaired fasting glucose of 5.6 to 6.9 mmol/l (100 to 125 mg/dl) (Bartoli et al., Eur. J. Int. Med. 22 (1): 8-12, 2011). Glycated hemoglobin is better than fasting glucose for determining risks of cardiovascular disease and death from any cause (Selvin et al., N. Engl. J. Med. 362 (9): 800-11, 2010).

The rare disease diabetes insipidus has similar symptoms to diabetes mellitus, but without disturbances in the sugar metabolism (insipidus means "without taste" in Latin) and does not involve the same disease mechanisms. Diabetes is a part of the wider condition known as metabolic syndrome.

Hypertension

Hypertension is diagnosed on the basis of a persistently high blood pressure. Traditionally, the National Institute of Clinical Excellence recommends three separate sphygmomanometer measurements at one monthly intervals. The American Heart Association recommends at least three measurements on at least two separate health care visits (Aronow et al., *J. Am. Soc. Hypertension*: JASH 5 (4): 259-352, 2011). An exception to this is those with very high blood pressure readings especially when there is poor organ function. Initial assessment of the hypertensive people should include a complete history and physical examination. With the availability of 24-hour ambulatory blood pressure monitors and home blood pressure machines, the importance of not wrongly diagnosing those who have white coat hypertension has led to a change in protocols. In the United Kingdom, current best practice is to follow up a single raised clinic reading with ambulatory measurement, or less ideally with home blood pressure monitoring over the course of 7 days. Pseudohypertension in the elderly or non-compressibility artery syndrome may also require consideration. This condition is believed to be due to calcification of the arteries resulting in abnormally high blood pressure readings with a blood pressure cuff while intra-arterial measurements of blood pressure are normal (Franklin et al., *Hypertension* 59 (2): 173-8, 2012). Orthostatic hypertension is when blood pressure increases upon standing.

Hyperlipidemia

Hyperlipidemia involves abnormally elevated levels of any or all lipids and/or lipoproteins in the blood (Dorland's Medical Dictionary for Health Consumers, 2007). It is the most common form of dyslipidemia (which includes any abnormal lipid levels). Lipids (fat-soluble molecules) are transported in a protein capsule. The size of that capsule, or lipoprotein, determines its density. The lipoprotein density and type of apolipoproteins it contains determines the fate of the particle and its influence on metabolism.

Hyperlipidemias are divided into primary and secondary subtypes. Primary hyperlipidemia is usually due to genetic causes (such as a mutation in a receptor protein), while secondary hyperlipidemia arises due to other underlying causes such as diabetes. Lipid and lipoprotein abnormalities are common in the general population, and are regarded as a modifiable risk factor for cardiovascular disease due to their influence on atherosclerosis. In addition, some forms may predispose to acute pancreatitis.

Hyperlipidemia is a group of disorders characterized by an excess of serum cholesterol, especially excess LDL-C and/or excess triglycerides. Hypercholesterolemia is generally asymptomatic. Hypertriglyceridemia is generally asymptomatic until triglyceride levels are sustained above 1000 mg/dL—symptoms then include dermatologic manifestations, such as eruptive xanthomas, and gastrointestinal manifestations, such as pancreatitis. Hyperlipidemias are most often genetically determined, but can be caused or amplified by abnormal diet, drugs, and certain disease conditions. Drugs associated with hyperlipidemias include: immunosuppressive therapy, thiazide diuretics, progestins, retinoids, anabolic steroids, glucocorticoids, HIV protease inhibitors, alcohol, retinoic acid, and beta-blockers. Diseases associated with secondary hyperlipidemias include: diabetes mellitus (type I and type II), hypothyroidism, Cushing's syndrome, chronic kidney disease, nephrotic syndrome, and cholestatic disorders. Hyperlipidemia is a major modifiable risk factor for atherosclerosis and cardiovascular disease, including coronary heart disease (Dorland's Medical Dictionary for Health Consumers, 2007).

Prader-Willi Syndrome

Prader-Willi Syndrome affects approximately 1 in 10,000 to 1 in 25,000 newborns (Killeen, Principles of Molecular Pathology 2004). There are more than 400,000 people who live with Prader-Willi Syndrome around the world (Tweed, AOL Health, September 2009). It is traditionally characterized by hypotonia, short stature, hyperphagia, obesity, behavioral issues (specifically OCD-like behaviors), small hands and feet, hypogonadism, and mild intellectual disability (Killeen, Principles of Molecular Pathology 2004). Like autism, Prader-Willi Syndrome is a spectrum disorder and symptoms can range from mild to severe and may change throughout the person's lifetime.

Traditionally, Prader-Willi syndrome was diagnosed by clinical presentation. Currently, the syndrome is diagnosed through genetic testing; testing is recommended for newborns with pronounced hypotonia. Early diagnosis of Prader-Willi Syndrome allows for early intervention. The mainstay of diagnosis is genetic testing, specifically DNA-based methylation testing to detect the absence of the paternally contributed Prader-Willi syndrome/Angelman syndrome (PWS/AS) region on chromosome 15q11-q13. Such testing detects over 97% of cases. Methylation-specific testing is important to confirm the diagnosis of PWS in all individuals, but especially those who are too young to manifest sufficient features to make the diagnosis on clinical grounds or in those individuals who have atypical findings (Buiting et al., Nat. Genet. 9(4):395-400, 1995).

Bardet-Biedl Syndrome

The Bardet-Biedl syndrome (BBS) is a ciliopathic human genetic disorder that produces many effects and affects many body systems. It is characterized principally by obesity, retinitis pigmentosa, polydactyly, hypogonadism, and renal failure in some cases (Beales et al., J. Med. Genet. 36(6): 437-46, 1999).

Bardet-Biedl syndrome is a pleiotropic disorder with variable expressivity and a wide range of clinical variability observed both within and between families. The main clinical features are rod-cone dystrophy, with childhood-onset visual loss preceded by night blindness; postaxial polydactyly; truncal obesity that manifests during infancy and remains problematic throughout adulthood; specific learning difficulties in some but not all individuals; male hypogenitalism and complex female genitourinary malformations; and renal dysfunction, a major cause of morbidity and mortality. There is a wide range of secondary features that are sometimes associated with BBS including: speech disorder/delay, strabismus/cataracts/astigmatism, brachydactyly/syndactyly of both the hands and feet, partial syndactyl (most usually between the second and third toes), developmental delay, polyuria/polydipsia (nephrogenic diabetes insipidus), ataxia/poor coordination/imbalance, mild hypertonia (especially lower limbs), diabetes mellitus, dental crowding/hypodontia/small dental roots; high-arched palate, cardiovascular anomalies, hepatic involvement, anosmia, auditory deficiencies, and Hirschsprung disease (Ross et al. The Clinical, Molecular, and Functional Genetics of Bardet-Biedl Syndrome, in Genetics of Obesity Syndromes, 2008).

Cohen Syndrome

This syndrome is believed to be a gene mutation in chromosome 8 at locus 8q22 gene COH1 (Kolehmainen et al, *Am. J. Hum. Genet.* 72(6):1359-69, 2003). Cohen syndrome has several characteristics such as obesity, mental retardation and craniofacial dysmorphism. It has an autosomal recessive transmission with variable expression (Kivitie-Kallio et al. *Am. J. Med. Genet.* 102(2):125-35, 2001).

Cohen syndrome is diagnosed by clinical examination, but often difficult due to variation in expression. Ocular complications, though rare, are listed as optic atrophy, microphthalmia, pigmentary chorioretinitis, hemeralopia (decreased vision in bright light), myopia, strabismus, nystagmus and iris/retinal coloboma. General appearance is obesity with thin/elongated arms and legs. Micrognathia, short philtrum, and high vaulted palate are common. Variable mental retardation with occasional seizure and deafness also is characteristic of Cohen syndrome.

MOMO Syndrome

MOMO syndrome is an extremely rare genetic disorder which belongs to the overgrowth syndromes and has been diagnosed in only six cases around the world, and occurs in 1 in 100 million births. The name is an acronym of the four primary aspects of the disorder: Macrosomia (excessive birth weight), Obesity, Macrocephaly (excessive head size) and Ocular abnormalities (Moretti-Ferreira et al. Am. J. Med. Genet. 46(5):555-8, 1993). There are also other common symptoms: a downward slant of the forehead, delayed bone maturation, mental retardation. The ocular abnormalities are generally retinal coloboma and nystagmus.

Cancer

Cancer, also known as a malignancy, malignant neoplasm, or malignant tumor, is a group of diseases involving abnormal cell growth with the potential to invade or spread to other parts of the body (Cancer Fact sheet N° 297. World Health Organization. February 2014; Defining Cancer. National Cancer Institute. 2014). Not all tumors are cancerous as benign tumors do not spread (Defining Cancer. National Cancer Institute. 2014). Possible signs and symptoms include: a new lump, abnormal bleeding, a prolonged cough, unexplained weight loss, and a change in bowel movements among others (Cancer—Signs and symptoms. NHS Choices. 2014). While these symptoms may indicate cancer, they may also occur due to other issues (Cancer—Signs and symptoms. NHS Choices. 2014). There are over 100 different known cancers that affect humans (Defining Cancer. National Cancer Institute. 2014). Cancers are a large family of diseases that involve abnormal cell growth with the potential to invade or spread to other parts of the body (Cancer Fact sheet N° 297. World Health Organization. February 2014; Defining Cancer. National Cancer Institute. 2014). A neoplasm or tumor is a group of cells that have undergone unregulated growth, and will often form a mass or lump, but may be distributed diffusely (Cancer Glossary. cancer.org. American Cancer Society. 2013; What is cancer?cancer.gov.National Cancer Institute. 2013). Proposed characteristics of cancer include: 1) insensitivity to anti-growth signals; 2) self-sufficiency in growth signaling; 3) induction and sustainment of angiogenesis; 4) evasion of apoptosis; 5) enabling of a limitless replicative potential; and 6) activation of metastasis and invasion of tissue (Hanahan, Douglas; Weinberg, Robert A. (Jan. 7, 2000). "The hallmarks of cancer". Cell 100 (1): 57-70). Malignant progression is the multi-step process that takes normal cells to cells that can form a discernible mass to cancer (Hanahan, Douglas; Weinberg, Robert A. (Jan. 7, 2000). "The hallmarks of cancer". Cell 100 (1): 57-70; Hanahan, Douglas; Weinberg, Robert A. (2011). "Hallmarks of Cancer: The Next Generation". Cell 144 (5): 646-74).

Cancer is a disease of tissue growth regulation failure. Genes that regulate cell growth and differentiation must be altered for a normal cell to become cancerous (Croce C M (January 2008). "Oncogenes and cancer". N. Engl. J. Med. 358 (5): 502-11). The affected genes are divided into two broad categories—tumor suppressor genes and oncogenes. Tumor suppressor genes inhibit cell division and survival. Oncogenes promote cell growth and reproduction. Tumor suppressor genes are genes that inhibit cell division and survival. Malignant transformation can occur through: the under-expression or disabling of tumor suppressor genes, the inappropriate over-expression of normal oncogenes, or formation of novel oncogenes (Knudson A G (November 2001). "Two genetic hits (more or less) to cancer". Nature Reviews Cancer 1 (2): 157-62). Cancer is driven by progressive genetic abnormalities that include mutations in oncogenes, tumor-suppressor genes chromosomal abnormalities and epigenetic alterations (Baylin S B, Ohm J E (February 2006). "Epigenetic gene silencing in cancer—a mechanism for early oncogenic pathway addiction?". Nature Reviews Cancer 6 (2): 107-16).

Most cancers are initially recognized either because of the appearance of signs or symptoms or through screening. A definitive diagnosis requires the examination of a tissue sample by a pathologist. Patients with suspected cancer are subjected to diagnostic tests which include CT scans, blood tests, endoscopy and X-rays.

Malignant cancers treated by the methods and compositions described herein include gastric cancer, multiple myeloma, leukemia, lymphoma, hepatocellular carcinoma, renal cell carcinoma, prostate cancer, brain cancer, glioblastoma, melanoma, breast cancer, head and neck cancer, and non-small cell lung carcinoma.

Glioblastoma, also known as glioblastoma multiforme (GBM) and grade IV astrocytoma, is the most common and most aggressive malignant primary brain tumor. It involves glial cells and accounting for 52% of all brain tissue tumor cases and 20% of all tumors inside the skull ("Glioblastoma and Malignant Astrocytoma". American Brain Tumour Association (ABTA) 2014). About 50% of the people diagnosed with GBM die within one year, while 90% within three years. Treatment can involve chemotherapy, radiation and surgery. Median survival with standard-of-care radiation and chemotherapy with temozolomide is 15 months (Johnson, Derek R.; O'Neill, Brian Patrick (2011). "Glioblastoma survival in the United States before and during the temozolomide era". Journal of Neuro-Oncology 107 (2): 359-64). Median survival without treatment is 4 months. Although no randomized controlled trials have been done, surgery remains the standard of care (Van Meir, E. G.; Hadjipanayis, C. G.; Norden, A. D.; Shu, H. K.; Wen, P. Y.; Olson, J. J. (2010). "Exciting New Advances in Neuro-Oncology: The Avenue to a Cure for Malignant Glioma". CA: A Cancer Journal for Clinicians 60 (3): 166-93).

Although common symptoms of the disease include seizure, nausea and vomiting, headache, memory loss, and hemiparesis, the single most prevalent symptom is a progressive memory, personality, or neurological deficit due to temporal and frontal lobe involvement. The kind of symptoms produced depends highly on the location of the tumor, more so than on its pathological properties. The tumor can start producing symptoms quickly, but occasionally is an asymptomatic condition until it reaches an enormous size.

When viewed with MRI, glioblastomas often appear as ring-enhancing lesions. The appearance is not specific, however, as other lesions such as abscess, metastasis, tumefactive multiple sclerosis, and other entities may have a similar appearance (Smirniotopoulos, J. G.; Murphy, F. M.; Rushing, E. J.; Rees, J. H.; Schroeder, J. W. (2007). "From the Archives of the AFIP: Patterns of Contrast Enhancement in the Brain and Meninges". Radiographics 27 (2): 525-51). Definitive diagnosis of a suspected GBM on CT or MRI requires a stereotactic biopsy or a craniotomy with tumor resection and pathologic confirmation. Because the tumor grade is based upon the most malignant portion of the tumor, biopsy or subtotal tumor resection can result in undergrading of the lesion. Imaging of tumor blood flow using perfusion MRI and measuring tumor metabolite concentration with MR spectroscopy will add value to standard MRI in the diagnosis of glioblastoma by showing increased relative cerebral blood volume and increased choline peak respectively, but pathology remains the gold standard (Weerakkody, Yuranga; Gaillard, Frank. "Glioblastoma". Radiopaedia.org. 2014).

The diagnosis of glioblastoma depends on distinguishing primary glioblastoma from secondary glioblastoma. These tumors occur spontaneously (de novo) or have progressed from a lower-grade glioma, respectively (Bleeker, F E; Molenaar, R J; Leenstra, S (May 2012). "Recent advances in the molecular understanding of glioblastoma.". Journal of neuro-oncology 108 (1): 11-27). Primary glioblastomas have a worse prognosis, different tumor biology may have a different response to therapy, which makes this a critical evaluation to determine patient prognosis and therapy (Weerakkody, Yuranga; Gaillard, Frank. "Glioblastoma". Radiopaedia.org 2014). Over 80% of secondary glioblastoma carries a mutation in IDH1, whereas this mutation is rare in primary glioblastoma (5-10%). Thus, IDH1 mutations may become a useful tool to distinguish primary and secondary glioblastomas in the future, since histopathologically they are very similar and the distinction without molecular biomarkers is unreliable (The driver and passenger effects of isocitrate dehydrogenase 1 and 2 mutations in oncogenesis and survival prolongation.". Biochim Biophys Acta 1846 (2): 326-41. December 2014).

IV. Pharmaceutical Compositions

The weight loss agents described above, can be formulated into pharmaceutical compositions suitable for use in the present methods. Such compositions include the active agent (compounds of Formula (I)) together with a pharmaceutically acceptable carrier, excipient or diluent.

In some cases, a pharmaceutical composition includes the compounds of formula (I), a pharmaceutically acceptable salt or prodrug thereof and a combination with one or more pharmaceutically acceptable excipients.

In some cases the pharmaceutical composition containing compounds of formula (I) are administered orally and exhibit a higher bioavailability compared to Celastrol. The oral bioavailability may be at least 1%, 2%, 3%, 4%, 5%, 10%, 15%, 20%, 30%, 40%, 50%, 60%, 80%, 90%, or 95% or higher compared to Celastrol. Furthermore, the oral bioavailability may be at least 1%, 2%, 3%, 4%, 5%, 7%, 10%, 15%, 20%, 25%, 30%, 35%, 40%, 45%, 50%, 60%, 70%, 80%, 90%, or 95% higher compared to intravenous bioavailability for a compound of formula (I), and/or at least 1%, 2%, 3%, 4%, 5%, 7%, 10%, 15%, 20%, 25%, 30%, 35%, 40%, 45%, 50%, 60%, 70%, 80%, 90%, or 95% the level of bioavailability when the compound is administered intravenously.

Pharmaceutical compositions provided herein include compositions wherein the active ingredient is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., induce weight loss. Determination of a therapeutically effective amount of compounds is well within the capabilities of those skilled in the art, especially in light of the detailed disclosure herein.

Pharmaceutically acceptable salts can be prepared by reaction of a free acid or base forms of a compound describes above with a stoichiometric amount of the appropriate be or acid in water, in an organic solvent, or mixture of the two. Lists of suitable salts are found in Remington's Pharmaceutical Sciences, 20th ed., Lippincott Williams & Wilkins, Baltimore, Md., 2000, p. 704; and Handbook of Pharmaceutical salts; Properties, Selection, and Use, P. Heinrich Stahl and Camille G. Wermuth, Eds., Wiley-VCH, Weinheim, 2002.

The weight loss agent can also be a pharmaceutically acceptable prodrug of any of the compounds describes above. Prodrugs are compounds that, when metabolized in vivo, undergo conversion to compounds having the desired pharmacological activity. Prodrugs can be prepared by replacing appropriate functionalities present in the compounds describes above with "pro-moieties" as described, for examples, in H. Bundgaar, Design of Prodrugs (1985). Examples of prodrugs include ester, ether or amide derivatives of the compound described above. For further discussion of prodrugs see Rautio, J. et al. Nat. Rev. Drug Disc. 7:255-270, 2008.

For preparing pharmaceutical compositions from comprising compounds disclosed herein, pharmaceutically acceptable carriers can be either solid or liquid. Solid form preparations include powders, tablets, pills, capsules, cachets, suppositories, and dispersible granules. A solid carrier can be one or more substances, that may also act as diluents, flavoring agents, binders, preservatives, tablet disintegrating agents, or an encapsulating material.

In powders, the carrier is a finely divided solid in a mixture with the finely divided active component (e.g. a compound provided herein). In tablets, the active component is mixed with the carrier having the necessary binding properties in suitable proportions and compacted in the shape and size desired. The powders and tablets preferably contain from 5% to 70% of the active compound.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethyl-cellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragees cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations can also be used orally using, for example, push-fit capsules made of gelatin, as well as soft, sealed capsules made of gelatin and a coating such as glycerol or sorbitol.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for salts disclosed herein are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampules are convenient unit dosages. The salts of can also be incorporated into liposomes or administered via transdermal pumps or patches. Pharmaceutical admixtures suitable for use in various embodiments disclosed herein are well-known to those of skill in the art and are described, for example, in Pharmaceutical Sciences (17th Ed., Mack Pub. Co., Easton, Pa.) and WO 96/05309, the teachings of both of which are hereby incorporated by reference.

Aqueous solutions suitable for oral use can be prepared by dissolving the active salt (e.g. compounds described herein, including embodiments, and examples) in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, cyclodextrin, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93-102, 1997. The pharmaceutical formulations can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compounds disclosed herein can be administered alone or can be co-administered to the patient. Co-administration is meant to include simultaneous or sequential administration of the compounds individually or in combination (more than one compound). Thus, the preparations can also be combined, when desired, with other active substances (e.g. to induce weight loss).

The compounds can be administered via a variety of routes and approaches, including but not limited to: oral administration, intravenous administration, topical administration, parenteral administration, intraperitoneal administration, intramuscular administration, intrathecal administration, intralesional administration, intracranial administration, intranasal administration, intraocular administration, intracardiac administration, intravitreal administration, intraosseous administration, intracerebral administration, intraarterial administration, intraarticular administration, intradermal administration, transdermal administration, transmucosal administration, sublingual administration, enteral administration, sublabial administration, insufflation administration, suppository administration, inhaled administration, or subcutaneous administration.

The compounds can be prepared and administered in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. The salts of compounds disclosed herein can also be administered by injection, that is, intravenously, intramuscularly, intracutaneously, subcutaneously, intraduodenally, or intraperitoneally. Also, the salts described herein can be administered by inhalation, for example, intranasally. Additionally, the salts can be administered transdermally. It is also envisioned that multiple routes of administration (e.g., intramuscular, oral, transdermal) can be used to administer the salts of compounds disclosed herein. Accordingly, also provided are pharmaceutical compositions comprising a pharmaceutically acceptable excipient and one or more salts of a compound or compounds disclosed herein.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted, based on per kg of body weight, from about 0.1 µg/kg to about 100,000 µg/kg, from 1.0 µg/kg to 10,000 µg/kg, or from 1 µg/kg to 5,000 µg/kg, according to the particular application and the potency of the active component. Example of single unit doses may be 1, 10, 50, 100, 200, 300, 400, 500, 600, 700, 800, 900, 1000, 2000, or 5000 µg/kg. The composition can, if desired, also contain other compatible therapeutic agents. Multiple unit doses may be administered within a 24 hour time period. Doses may be administered orally but other routes of administration may also be used depending on the severity of the disease/disorder of the patient.

In some embodiments, the quantity of the compounds of Formula (I) or Formula (II) may be varied or adjusted from about 1.0 µg to 10,000 µg, for example, 50, 100, 200, 300, 400, 500, 600, 700, 800, 900, 1000, 2000, or 5000 µg/kg body weight, for treating obesity by oral administration. In some embodiments, the quantity of the compounds of Formula (I) or Formula (II) may be varies or adjusted from about 1.0 µg to 10,000 µg, for example, for example, 50, 100, 200, 300, 400, 500, 600, 700, 800, 900, 1000, 2000, or 5000 µg/kg body weight, for treating obesity by intraperitoneal administration.

Various implementations include the oral administration of a compound that is disclosed herein. In some embodiments, the compound is administered at a dose of about 0.05 to about 100 mg/kg, about 0.1 to about 0.5 mg/kg, about 0.1 to about 1 mg/kg, about 0.1 to about 5 mg/kg, about 0.1 to about 10 mg/kg, about 0.1 to about 25 mg/kg, about 1 to about 5 mg/kg, about 1 to about 25 mg/kg, about 5 to about 25 mg/kg, about 10 to about 25 mg/kg, about 10 to about 50 mg/kg, about 25 to about 50 mg/kg, about 25 to about 75 mg/kg, or about 50 to about 100 mg/kg. In certain embodiments, the compound is administered at a dose of about 0.1, 0.15, 0.2, 0.25, 0.3, 0.35, 0.4, 0.45, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, 20, 25, 30, 35, 40, 45, 50, 60, 70, 80, 90, or 100 mg/kg. Doses may be administered, e.g., 1, 2, 3, 4, 5, 6, 7, 8, 9, 10, 11, 12, 13, 14, or 15 or more times per day or per week. For example, a compound may be administered once, twice, or three times per day. In some embodiments, the compound is administered before (e.g., about 1, 2, 3, 4, 5, or 6 hours before) or with a meal. Non-limiting examples of methods for converting doses from animals such as mice to human equivalent doses are known in the art. See, e.g., U.S. Food and Drug Administration Center for Drug Evaluation and Research (CDER) (2005) Guidance For Industry: Estimating the Maximum Safe Starting Dose in Initial Clinical Trials for Therapeutics in Adult Healthy Volunteers (available from www.fda.gov/downloads/drugs/guidances/ucm078932.pdf). For example, a mouse dose in mg/kg may be converted to a human equivalent dose (assuming a 60 kg human) based on body surface area by multiplying the mouse dose by 0.08.

Some compounds may have limited solubility in water and therefore may require a surfactant or other appropriate co-solvent in the composition. Such co-solvents include: Polysorbate 20, 60 and 80; Pluronic F-68, F-84 and P-103; cyclodextrin; polyoxyl 35 castor oil; or other agents known to those skilled in the art. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, combinations of the foregoing, and other agents known to those skilled in the art. Such agents are typically employed at a level between about 0.01% and about 2% by weight. Determination of acceptable amounts of any of the above adjuvants is readily ascertained by one skilled in the art.

The compositions may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g., emphysema, asthma, ARDS including oxygen toxicity, pneumonia, chronic obstructive pulmonary disease (COPD), emphysema, cystic fibrosis, bronchopulmonary dysplasia, chronic sinusitis, pulmonary fibrosis), kind of concurrent treatment, complications from the disease being treated or other health-related problems. The disease may be a primary cause for a weight gain disease and/or disorder. The disease may be a caused by a primary weight gain disorder and/or disorder. Other therapeutic regimens or agents can be used in conjunction with the methods and compounds disclosed herein. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present disclosure should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. In embodiments, the dosage range is 0.001% to 10% w/v. In another embodiment, the dosage range is 0.1% to 5% w/v.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The ratio between toxicity and therapeutic effect for a particular compound is its therapeutic index and can be expressed as the ratio between LD50 (the amount of compound lethal in 50% of the population) and ED50 (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the ED50 with little or no toxicity. The dosage may vary within this range depending upon the dosage form employed and the route of administration utilized. See, e.g. Fingl et al., In: The Pharmacological Basis of Therapeutics, Ch. 1, p. 1, 1975. The exact formulation, route of administration and dosage can be chosen by the individual physician in view of the patient's condition and the particular method in which the compound is used.

V. Kit

In one aspect, provided herein is a kit comprising the compositions used for treating obesity as described herein, and instructions for use in treating obesity. In some embodiments, the kit may be used for an oral administration of the compositions of treating obesity, for example, such that the kit may further include an applicator for oral administration. In some embodiments, the kit may be used for intraperitoneal administration of the compositions of treating obesity.

EXAMPLES

The following examples illustrate certain specific embodiments of the invention and are not meant to limit the scope of the invention.

Embodiments herein are further illustrated by the following examples and detailed protocols. However, the examples are merely intended to illustrate embodiments and are not to be construed to limit the scope herein. The contents of all references and published patents and patent applications cited throughout this application are hereby incorporated by reference.

Chemistry

The following examples illustrate certain specific embodiments of the invention and are not meant to limit the scope of the invention.

Embodiments herein are further illustrated by the following examples and detailed protocols. However, the examples are merely intended to illustrate embodiments and are not to be construed to limit the scope herein. The contents of all references and published patents and patent applications cited throughout this application are hereby incorporated by reference.

Example 1

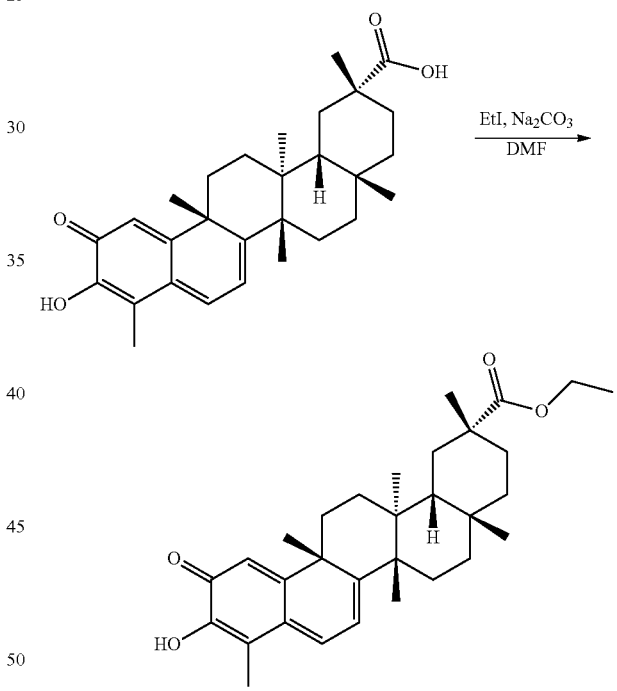

ERX1001

To a solution of celastrol (150 mg, 0.33 mmol) in DMF (3 mL) was added EtI, 104 mg, 0.054 mL, 0.67 mmol) and $Na_2CO_3$ (70.6 mg, 0.67 mmol). The reaction was stirred at room temperature overnight. Then the solution was diluted with $CH_2Cl_2$ (200 mL), washed with brine (100 mL), dried over $MgSO_4$ and concentrated in vacuo. The residue was purified by prep-TLC (petroleum ether/ethyl acetate=1:1) to afford product (70 mg, 0.146 mmol, Yield=44%) as red solid. $^1$HNMR δ(400 MHz, $CDCl_3$): 7.02 (1H, d, J=7.2 Hz), 6.96 (1H, s), 6.54 (1H, s), 6.35 (1H, d, J=7.2 Hz), 3.90-4.05 (2H, m), 2.44 (1H, d, J=15.5 Hz), 2.21 (3H, s), 2.13-2.25 (2H, m), 2.00-2.10 (1H, m), 1.77-1.93 (3H, m), 1.62-1.73

(3H, m), 1.47-1.55 (2H, m), 1.45 (3H, s), 1.32-1.42 (1H, m), 1.26 (3H, s), 1.21 (3H, t, J=7.2 Hz), 1.17 (3H, s), 1.10 (3H, s), 0.93-1.01 (1H, m), 0.56 (3H, s); $^{13}$CNMR δ(100 MHz, CDCl$_3$): 178.34, 178.19, 170.09, 164.71, 146.01, 134.12, 127.37, 119.55, 118.12, 117.12, 60.26, 45.04, 44.26, 42.93, 40.24, 39.40, 38.22, 36.35, 34.76, 33.51, 32.76, 31.59, 30.69, 30.55, 29.78, 29.60, 28.66, 21.63, 18.44, 14.02, 10.26; LC-MS (Mobile Phase: A: water (0.01% TFA) B: ACN (0.01% TFA); Gradient: 5%-95% B in 1.2 min; Flow Rate: 2.2 ml/min; Column: Poroshell 120 EC-C18, 4.6*30 mm, 2.7 um): rt=2.20 min, m/z=479.3 [M+H]$^+$, purity=100% (214, 254 nm).

Example 2

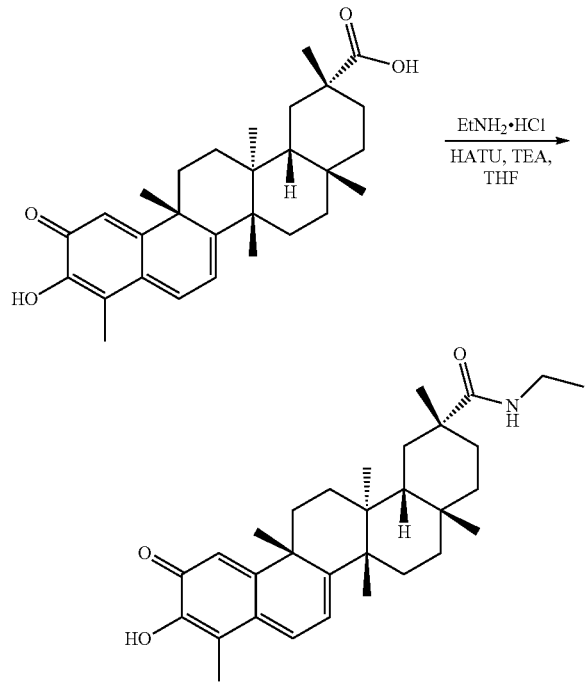

ERX1002

To a solution of celastrol (150 mg, 0.333 mmol) in THF (3 mL) was added EtNH$_2$·HCl (40 mg, 0.50 mmol), HATU (190 mg, 0.5 mmol) followed by NEt$_3$ (101 mg, 0.14 ml, 1 mmol). The reaction was stirred at room temperature overnight. Then the solution was diluted with CH$_2$Cl$_2$ (200 mL), washed with brine (100 mL), dried over MgSO$_4$ and concentrated in vacuo. The residue was purified by prep-TLC (petroleum ether/ethyl acetate=1:1) to afford product (23.5 mg, 0.0492 mmol, Yield=15%) as red solid. $^1$HNMR δ(400 MHz, CDCl$_3$): 7.01 (1H, dd, J=7.2, 0.9 Hz), 6.98 (1H, s), 6.53 (1H, d, J=0.9 Hz), 6.34 (1H, d, J=7.2 Hz), 5.62 (1H, t, J=5.0 Hz), 3.13-3.20 (2H, m), 2.46 (1H, d, J=15.8 Hz), 2.21 (3H, s), 2.10-2.17 (1H, m), 1.98-2.09 (1H, m), 1.82-1.97 (4H, m), 1.47-1.74 (7H, m), 1.44 (3H, s), 1.26 (3H, s), 1.15 (3H, s), 1.13 (3H, s), 1.06 (3H, t, J=7.2 Hz), 0.98-1.05 (1H, m), 0.65 (3H, s); LC-MS (Mobile Phase: A: water (0.01% TFA); B: ACN (0.01% TFA); Gradient: 5%-95% B in 1.7 min; Flow Rate: 2.2 ml/min; Column: SunFire C18, 4.6*50 mm, 3.5 um): rt=2.33 min, m/z=478.3 [M+H]$^+$, purity=100% (214, 254 nm).

Example 3

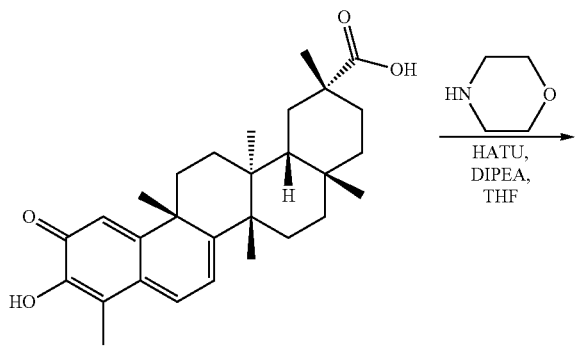

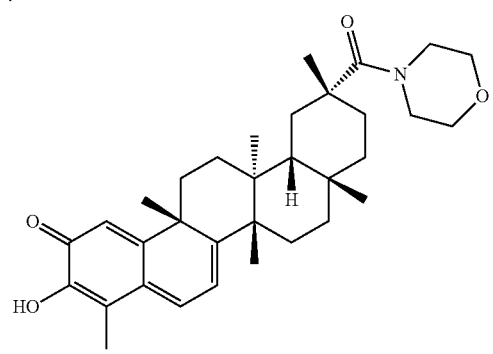

ERX1003

To a solution of celastrol (200 mg, 0.44 mmol) in THF (5 mL) was added morpholine (78 mg, 0.88 mmol), HATU (254 mg, 0.66 mmol) followed by DIPEA (114 mg, 0.16 ml, 0.88 mmol). The reaction was stirred at room temperature overnight. Then the solution was diluted with CH$_2$Cl$_2$ (200 mL), washed with brine (100 mL), dried over MgSO$_4$ and concentrated in vacuo. The residue was purified by prep-TLC (petroleum ether/ethyl acetate=1:1) to afford product (74 mg, 0.142 mmol, Yield=32%) as red solid. $^1$HNMR δ(400 MHz, CDCl$_3$): 7.02 (1H, dd, J=7.2, 1.0 Hz), 6.97 (1H, s), 6.54 (1H, d, J=1.0 Hz), 6.36 (1H, d, J=7.2 Hz), 3.50-3.80 (8H, m), 2.28-2.36 (2H, m), 2.22 (3H, s), 2.16-2.23 (1H, m), 2.03-2.13 (1H, m), 1.49-1.93 (8H, m), 1.46 (3H, s), 1.34-1.40 (1H, m), 1.25-1.33 (1H, m), 1.30 (3H, s), 1.28 (3H, s), 1.15 (3H, s), 0.96-1.02 (1H, m), 0.61 (3H, s); LC-MS (Mobile Phase: A: water (0.01% TFA); B: ACN (0.01% TFA); Gradient: 5%-95% B in 1.4 min; Flow Rate: 2.3 ml/min; Column: SunFire C18, 4.6*50 mm, 3.5 um): rt=2.36 min, m/z=520.3 [M+H]$^+$, purity=100% (214, 254 nm).

Example 4

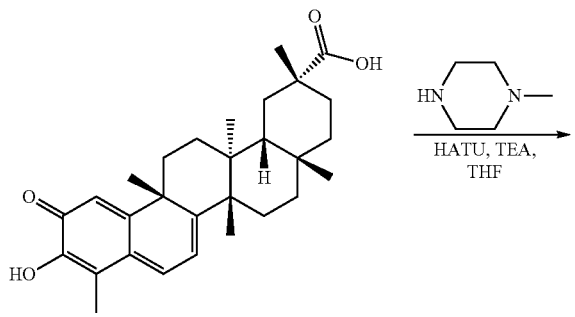

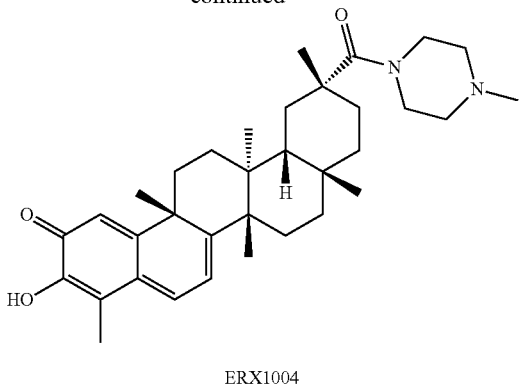

ERX1004

To a solution of celastrol (150 mg, 0.333 mmol) in THF (3 mL) was added 1-methylpiperazine (50 mg, 0.055 mL, 0.50 mmol), HATU (190 mg, 0.5 mmol) followed by $NEt_3$ (67.4 mg, 0.093 mmol, 0.666 mmol). The reaction was stirred at room temperature overnight. Then the solution was diluted with $CH_2Cl_2$ (200 mL), washed with brine (100 mL), dried over $MgSO_4$ and concentrated in vacuo. The residue was purified by prep-TLC ($CH_2C_2$/MeOH=10:1) to afford product (25.2 mg, 0.0473 mmol, Yield=14.2%) as red solid. $^1$HNMR: δ(400 MHz, $CDCl_3$): 7.02 (1H, dd, J=7.2, 1.0 Hz), 6.98 (1H, br), 6.51 (1H, d, J=1.0 Hz), 6.35 (1H, d, J=7.2 Hz), 3.60-3.80 (2H, m), 2.31-2.45 (5H, m), 2.30 (3H, s), 2.21 (3H, s), 2.04-2.19 (2H, m), 1.65-1.92 (8H, m), 1.49-1.62 (3H, m), 1.45 (3H, s), 1.33-1.39 (1H, m), 1.29 (3H, s), 1.28 (3H, s), 1.24-1.30 (1H, m), 1.14 (3H, s), 0.95-1.01 (1H, m), 0.61 (3H, s); LC-MS (Mobile Phase: A: water (0.01% TFA); B: ACN (0.01% TFA); Gradient: 5%-95% B in 1.7 min; Flow Rate: 2.2 ml/min; Column: SunFire C18, 4.6*50 mm, 3.5 um): rt=1.88 min, m/z=533.3 [M+H]$^+$, purity=100% (214, 254 nm).

Example 5

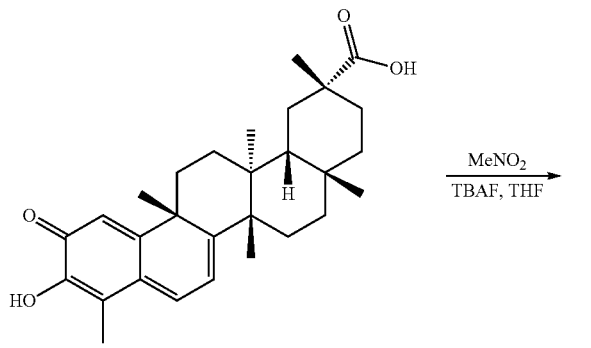

ERX1005

To a solution of celastrol (200 mg, 0.44 mmol) and $MeNO_2$ (54 mg, 0.88 mmol) in THF (3 mL) was added 1M TBAF in THF solution (0.22 mL, 0.22 mmol). The reaction was stirred at room temperature overnight. The reaction was quenched by addition of $H_2O$ (50 mL). Then the solution was extracted with $Et_2O$ (2×50 mL). The combined organic layers were washed with brine (100 mL), dried over $MgSO_4$ and concentrated in vacuo. The residue was purified by prep-TLC (petroleum ether/EtOAc=1:1) to afford product (139.6 mg, 0.273 mmol, Yield=62%) as pale yellow solid. $^1$HNMR: δ(400 MHz, $CDCl_3$): 6.77 (1H, s), 5.69 (1H, d, J=5.9 Hz), 4.54 (1H, dd, J=11.3, 4.0 Hz), 4.24-4.31 (1H, m), 4.11 (1H, t, J=11.3 Hz), 2.38 (1H, d, J=15.5 Hz), 2.28 (3H, s), 1.48-2.14 (9H, m), 1.45 (3H, s), 1.29-1.39 (4H, m), 1.20 (3H, s), 1.13 (3H, s), 1.05 (3H, s), 0.84-0.92 (1H, m), 0.57 (3H, s); LC-MS (Gradient: 5%-95% B in 1.2 min; Flow Rate: 2.2 ml/min; Column: Poroshell 120 EC-C18, 4.6*30 mm, 2.7 um): rt=1.86 min, m/z=451.2 [M–$CH_2NO_2$]$^+$, purity=100% (214, 254 nm).

Example 6

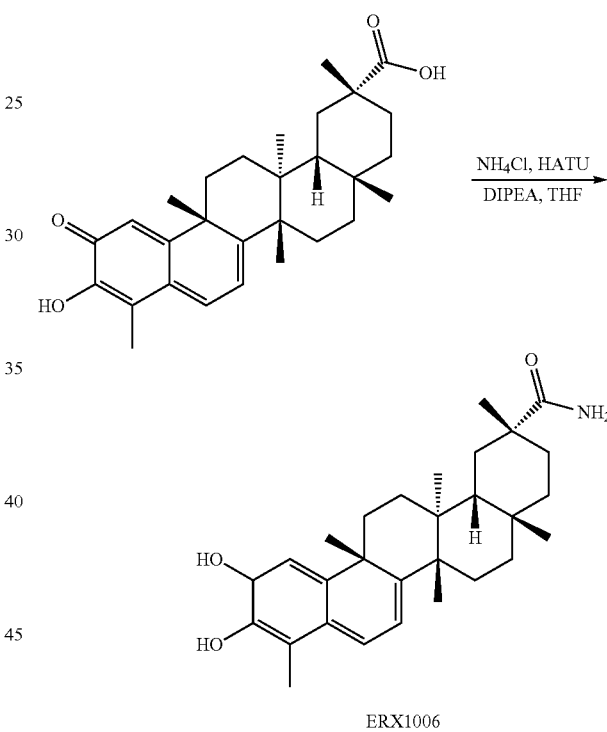

ERX1006

To a solution of celastrol (225 mg, 0.5 mmol) in DMF (10 mL) was added $NH_4Cl$ (80 mg, 1.5 mmol), HATU (209 mg, 0.55 mmol) followed by DIPEA (129 mg, 0.18 mL, 1.0 mmol). The reaction was stirred at room temperature overnight. Then the solution was diluted with $CH_2Cl_2$ (200 mL), washed with brine (100 mL), dried over $MgSO_4$ and concentrated in vacuo. The residue was purified by prep-TLC (petroleum ether/EtOAc=1:1) to afford product (200 mg, 0.445 mmol, Yield=89%) as red solid. $^1$HNMR: δ (400 MHz, $CDCl_3$): 7.01 (1H, s), 7.00 (1H, d, J=7.0 Hz), 6.51 (1H, s), 6.33 (1H, dd, J=7.0, 2.4 Hz), 5.34-5.74 (2H, br), 2.42 (1H, d, J=15.1 Hz), 2.22 (3H, s), 2.00-2.16 (2H, m), 1.82-1.98 (4H, m), 1.46-1.72 (7H, m), 1.44 (3H, s), 1.26 (3H, s), 1.20 (3H, s), 1.12 (3H, s), 0.98-1.05 (1H, m), 0.72-0.73 (3H, s); LC-MS (Mobile Phase: A: water (0.01% TFA); B: ACN (0.01% TFA); Gradient: 5%-95% B in 1.2 min; Flow Rate: 2.2 ml/min; Column: Poroshell 120 EC-C18, 4.6*30 mm, 2.7 um): rt=1.81 min, m/z=450.4 [M+H]$^+$, purity=100% (214, 254 nm).

Example 7

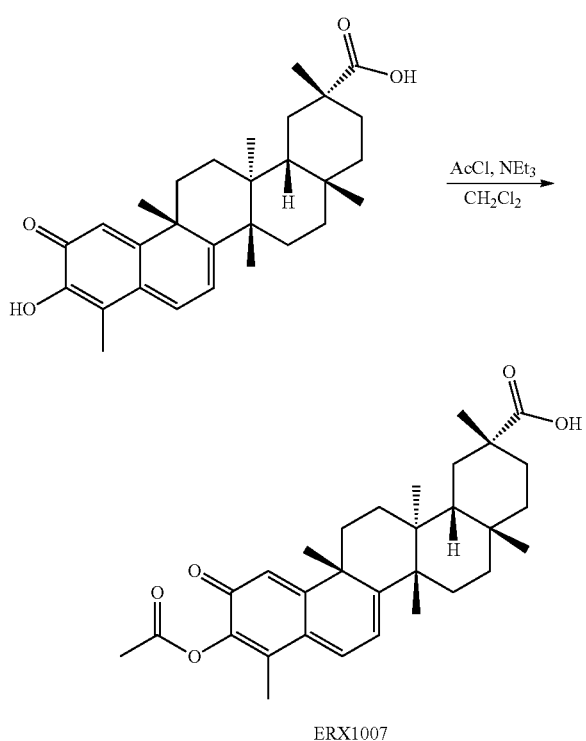

ERX1007

To a solution of celastrol (100 mg, 0.222 mmol) in CH₂Cl₂ (4 mL) was added NEt₃ (45 mg, 0.062 mL, 0.444 mmol) followed by AcCl (20.9 mg, 0.019 mmol, 0.266 mmol). The reaction was stirred at 0° C. for 1 hour. Then the solution was diluted with CH₂Cl₂ (100 mL), washed with brine (100 mL), dried over MgSO₄ and concentrated in vacuo. The residue was purified by prep-TLC (petroleum ether/ethyl acetate=1:1, then CH₂Cl₂/ethyl acetate=1:1) to afford product (17.3 mg, 0.0351 mmol, Yield=15.8%) as yellow solid. ¹HNMR: δ(400 MHz, CDCl₃): 7.07 (1H, d, J=7.0 Hz), 6.60 (1H, s), 6.30 (1H, d, J=7.0 Hz), 2.24 (1H, d, J=15.5 Hz), 2.35 (3H, s), 2.15 (3H, s), 2.10-2.18 (2H, m), 1.95-2.10 (2H, m), 1.78-1.90 (3H, m), 1.46-1.72 (4H, m), 1.45 (3H, s), 1.28-1.40 (2H, m), 1.25 (3H, s), 1.18 (3H, s), 1.08 (3H, s), 0.91-0.97 (1H, m), 0.66 (3H, s); LC-MS (Mobile Phase: A: H2O (0.01% TFA); B: MeCN (0.01% TFA); Gradient: 5%-95% B in 1.2 min; Flow Rate: 2 ml/min; Column: SunFire C18 50*4.6 mm, 3.5 um): rt=2.19 min, m/z=493.2 [M+H]⁺, purity=100% (214, 254 nm).

Example 8

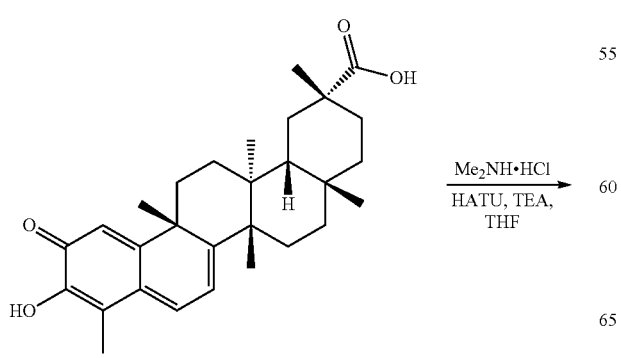

ERX1008

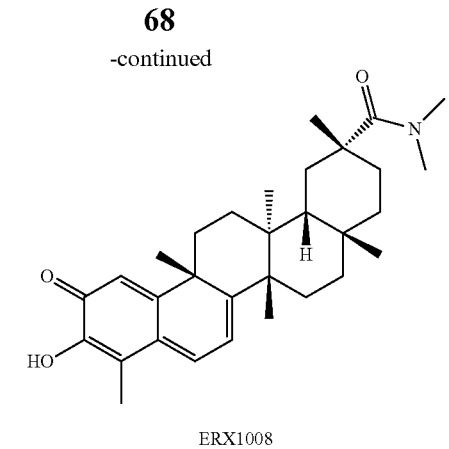

To a solution of celastrol (200 mg, 0.444 mmol) in THF (5 mL) was added Me₂NH.HCl (72.4 mg, 0.888 mmol), HATU (338 mg, 0.888 mmol) followed by NEt₃ (134.8 mg, 0.186 mmol, 1.332 mmol). The reaction was stirred at room temperature overnight. Then the solution was diluted with CH₂Cl₂ (200 mL), washed with brine (100 mL), dried over MgSO₄ and concentrated in vacuo. The residue was purified by prep-TLC (petroleum ether/EtOAc=1:1) to afford product (101.4 mg, 0.212 mmol, Yield=48%) as red solid. ¹HNMR: δ(400 MHz, CDCl₃): 7.02 (1H, dd, J=7.2, 1.2 Hz), 6.96 (1H, s), 6.53 (1H, d, J=1.2 Hz), 6.36 (1H, d, J=7.2 Hz), 3.00-3.25 (3H, br), 2.70-3.00 (3H, br), 2.32-2.46 (2H, m), 2.22 (3H, s), 2.06-2.20 (2H, m), 1.48-1.93 (9H, m), 1.46 (3H, s), 1.30-1.36 (1H, m), 1.29 (3H, s), 1.28 (3H, s), 1.14 (3H, s), 0.95-1.01 (1H, m), 0.54 (3H, s); LC-MS (Mobile Phase: A: water (0.01% TFA); B: ACN (0.01% TFA); Gradient: 5%-95% B in 1.2 min; Flow Rate: 2.2 ml/min; Column: Poroshell 120 EC-C18, 4.6*30 mm, 2.7 um): rt=1.96 min, m/z=478.4 [M+H]⁺, purity=100% (214, 254 nm).

Example 9

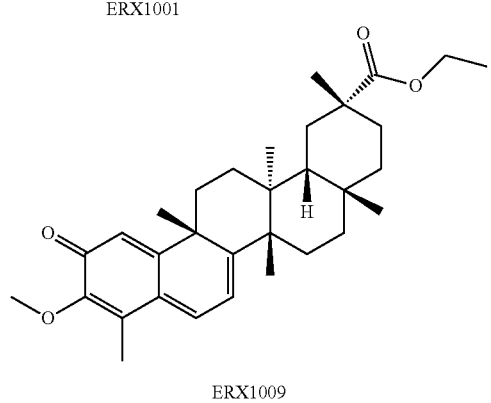

ERX1001

ERX1009

To a solution of celastrol ethyl ester ERX1001 (200 mg, 0.418 mmol) in acetone (4 mL) was added $K_2CO_3$ (115 mg, 0.836 mmol) followed by MeI (1 mL). The reaction was heated at 40° C. overnight. Then the solution was diluted with $CH_2Cl_2$ (200 mL), washed with brine (100 mL), dried over $MgSO_4$ and concentrated in vacuo. The residue was purified by prep-TLC (petroleum ether/EtOAc=2:1) to afford product (120 mg, 0.244 mmol, Yield=58%) as red solid. $^1$HNMR δ (400 MHz, $CDCl_3$): 6.98 (1H, d, J=7.2, 1.2 Hz), 6.43 (1H, d, J=1.2 Hz), 6.30 (1H, d, J=7.2 Hz), 3.90-4.06 (2H, m), 3.85 (3H, s), 2.44 (1H, d, J=15.8 Hz), 2.22 (3H, s), 2.00-2.22 (3H, m), 1.77-1.92 (3H, m), 1.48-1.72 (6H, m), 1.45 (3H, s), 1.32-1.42 (1H, m), 1.26 (3H, s), 1.21 (3H, t, J=7.0 Hz), 1.17 (3H, s), 1.10 (3H, s), 0.93-1.00 (1H, m), 0.58 (3H, s); LC-MS (Mobile Phase: A: water (0.01% TFA); B: ACN (0.01% TFA); Gradient: 5%-95% B in 1.4 min; Flow Rate: 2.3 ml/min; Column: SunFire C18, 4.6*50 mm, 3.5 um): rt=2.78 min, m/z=493.3 $[M+H]^+$, purity=100% (214, 254 nm).

Example 10 temperature overnight. The reaction was quenched by addition of $H_2O$ (5 mL) and acidified to pH 6-7 by 0.1 M HCl. Then the solution was diluted with EtOAc (200 mL), filtered to remove solid. The filtrate was washed with brine (100 mL), dried over $MgSO_4$ and concentrated in vacuo to afford crude intermediate. The crude intermediate was dissolved in MeOH (10 mL) and oxidized with a O2 balloon with heating at 40° C. overnight. The solution was concentrated in vacuo and the residue was purified by prep-TLC (petroleum ether/EtOAc=2:1) to afford product (58.5 mg, 0.134 mmol, Yield=41% (2 steps)) as red solid. $^1$HNMR: δ(400 MHz, $CDCl_3$): 7.03 (1H, dd, J=7.1, 1.2 Hz), 6.97 (1H, s), 6.53 (1H, d, J=1.2 Hz), 6.38 (1H, d, J=7.1 Hz), 3.43 (1H, dd, J=10.5, 5.5 Hz), 3.22 (1H, dd, J=10.5, 4.3 Hz), 2.21 (3H, s), 2.09-2.16 (1H, m), 2.01 (1H, s), 1.54-1.94 (9H, m), 1.45 (3H, s), 1.38 (3H, s), 1.24-1.50 (4H, m), 1.19 (3H, s), 1.00 (3H, s), 0.94-1.00 (1H, m), 0.80 (3H, s); LC-MS (Mobile Phase: A: water (0.01% TFA), B: ACN (0.01% TFA); Gradient: 5%-95% B in 1.7 min; Flow Rate: 2.2 ml/min; Column: SunFire C18, 4.6*50 mm, 3.5 um): rt=2.48 min, m/z=437.3 $[M+H]^+$, purity=100% (214, 254 nm).

Example 11

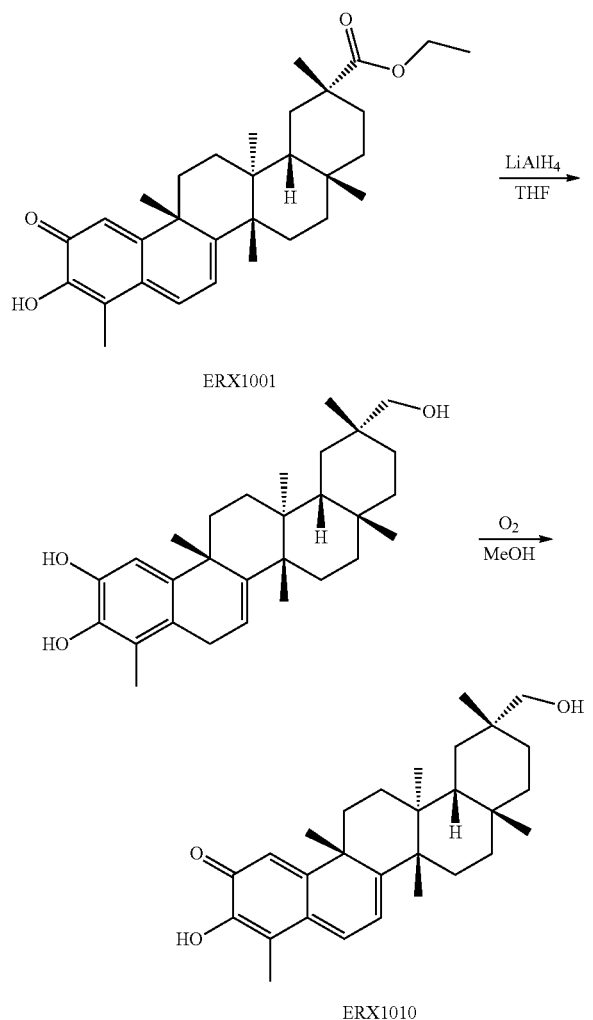

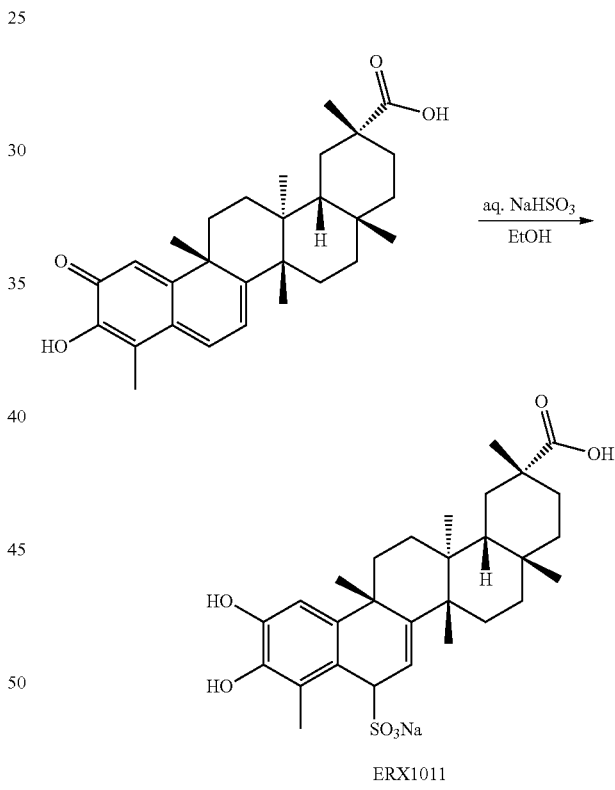

To a solution of celastrol ethyl ester ERX1001 (160 mg, 0.33 mmol) in THF (20 mL) was added $LiAlH_4$ (50.8 mg, 1.33 mmol) in portions. The reaction was stirred at room To a solution of celastrol (500 mg, 1.11 mmol) in EtOH (10 mL) was added $NaHSO_3$ (127 mg, 1.22 mmol) in 5 mL $H_2O$ solution. The reaction was stirred at room temperature for 3 hours. The solution became approximately colorless and transparent. The solution was concentrated to dryness in vacuo at 40° C. to obtain a white powder. Enough EtOH was added to dissolve the crude product. The solution was filtered and filtrate was concentrated in vacuo (<40° C.) to about 10 mL. The solution was kept at refrigerator overnight. Solid was filtered and dissolved in water. After lyophilization, pure product (114.7 mg, 0.207 mmol, yield=18.6%) was obtained as white solid. $^1$HNMR: δ(400

MHz, d6-DMSO): 12.10 (1H, br), 8.84 (1H, br), 7.69 (1H, br), 6.56 (1H, br), 5.78 (1H, d, J=6.3 Hz), 4.44 (1H, d, J=6.3 Hz), 2.30-2.38 (1H, m), 2.20 (3H, s), 1.75-2.07 (4H, m), 1.61 (3H, s), 1.20-1.60 (9H, m), 1.17 (3H, s), 1.08 (3H, s), 1.05 (3H, s), 0.80-0.88 (1H, m), 0.60 (3H, s); LC-MS (Mobile Phase: A: water (10 mM Ammonium hydrogen carbonate); B: CAN; Gradient: 5%-95% B in 1.5 min; Flow Rate: 2.0 ml/min; Column: XBridge C18, 4.6*50 mm, 3.5 um): rt=1.48 min, m/z=530.8 [M−Na]⁻ (negative ion), purity=95.47% (214 nm).

Example 12

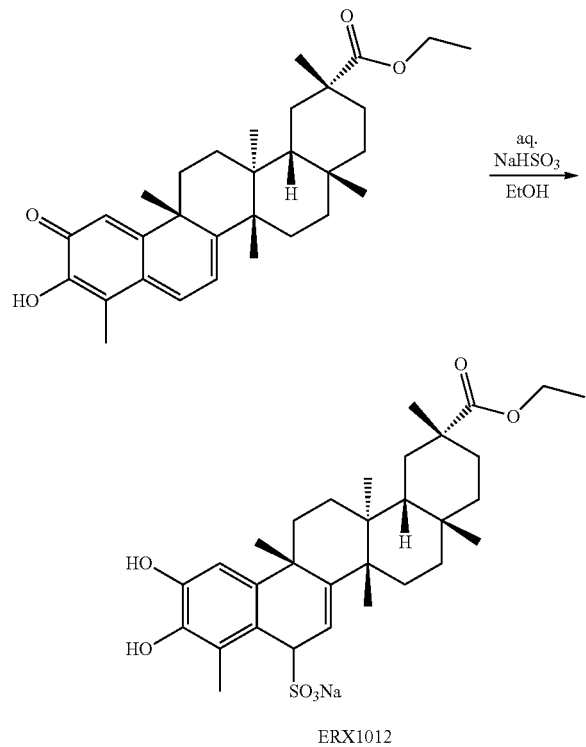

ERX1012

To a solution of celastrol ethyl ester (500 mg, 1.045 mmol) in EtOH (10 mL) was added NaHSO3 (119.6 mg, 1.149 mmol) in 5 mL H$_2$O solution. The reaction was stirred at room temperature overnight. The solution became pale yellow. The solution was concentrated to dryness in vacuo under 40° C. The residue was washed with CH$_2$Cl$_2$ (4×10 mL), dissolved in enough water, lyophilized overnight to afford product (487.6 mg, 0.837 mmol, Yield=80%) as pale yellow solid. The product could be oxidized gradually in air. ¹HNMR: δ(400 MHz, d6-DMSO): 8.78 (1H, s), 7.62 (1H, s), 6.57 (1H, s), 5.80 (1H, d, J=5.9 Hz), 4.46 (1H, d, J=5.9 Hz), 3.80-3.94 (2H, m), 2.34 (1H, d, J=15.5 Hz), 2.20 (3H, s), 1.76-2.10 (4H, m), 1.62 (3H, s), 1.27-1.65 (9H, m), 1.18 (3H, s), 1.10 (3H, s), 1.08 (3H, t, J=7.2 Hz), 1.06 (3H, s), 0.84-0.92 (1H, m), 0.45 (3H, s); LC-MS (Mobile Phase: A: water (10 mM Ammonium hydrogen carbonate); B: ACN; Gradient: 5%-95% B in 1.5 min; Flow Rate: 2.0 ml/min; Column: XBridge; C18, 4.6*50 mm, 3.5 um): rt=1.83 min, m/z=558.8 [M−Na]⁻ (negative ion), purity=95.93% (214 nm).

Example 13

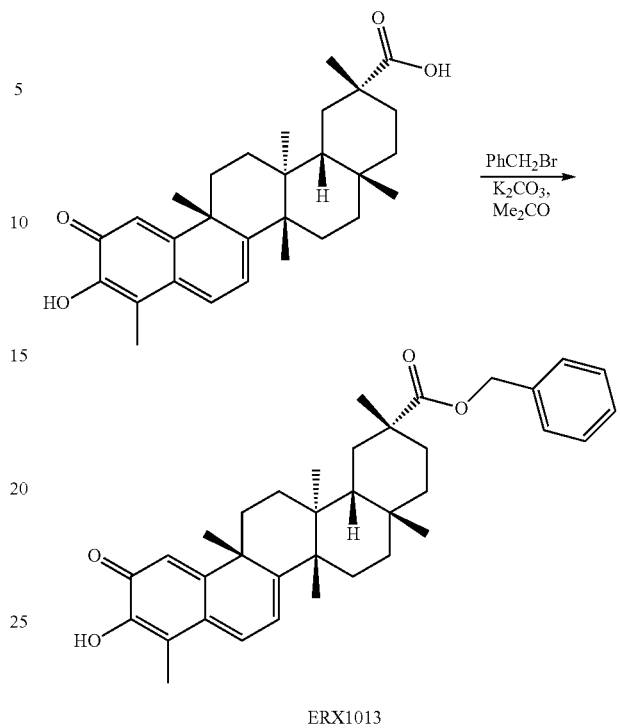

ERX1013

To a solution of celastrol (200 mg, 0.444 mmol) in acetone (5 mL) was added K$_2$CO$_3$ (184 mg, 1.332 mmol) followed by PhCH$_2$Br (83.5 mg, 0.058 mL, 0.488 mmol). The reaction was stirred at room temperature overnight. Then the solution was diluted with CH$_2$Cl$_2$ (200 mL), washed with brine (100 mL), dried over MgSO$_4$ and concentrated in vacuo. The residue was purified by prep-TLC (petroleum ether/ethyl acetate=3:1) to afford crude product. But it was not pure enough. Then the crude product was further washed with petroleum ether with heating at 60° C. twice to afford product (40.6 mg, 0.0751 mmol, Yield=17%) as yellow solid. ¹HNMR: δ(400 MHz, CDCl$_3$): 7.27-7.36 (5H, m), 7.01 (1H, d, J=6.9 Hz), 6.98 (1H, s), 6.48 (1H, s), 6.33 (1H, d, J=6.9 Hz), 5.01 (1H, AB, J=12.3 Hz), 4.94 (1H, AB, J=12.3 Hz), 2.44 (1H, d, J=15.7 Hz), 2.20-2.28 (1H, m), 2.22 (3H, s), 1.82-2.12 (3H, m), 1.46-1.74 (8H, m), 1.42 (3H, s), 1.35-1.44 (1H, m), 1.24 (3H, s), 1.21 (3H, s), 1.09 (3H, s), 0.95-1.01 (1H, m), 0.51 (3H, s); LC-MS: (Mobile Phase: A: water (0.01% TFA); B: ACN (0.01% TFA); Gradient: 5%-95% B in 1.4 min; Flow Rate: 2.3 ml/min; Column: SunFire C18, 4.6*50 mm, 3.5 um): rt=2.91 min, m/z=541.3 [M+H]⁺, purity=97.41% (214 nm), 100% (254 nm).

Example 14

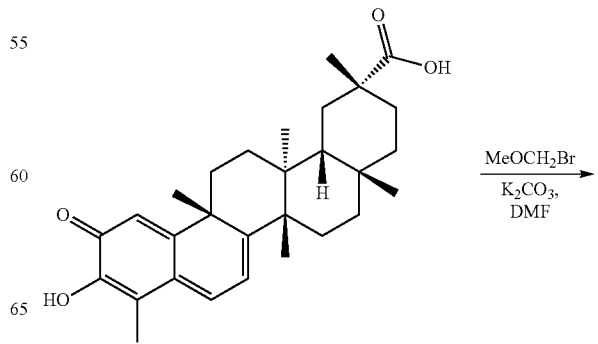

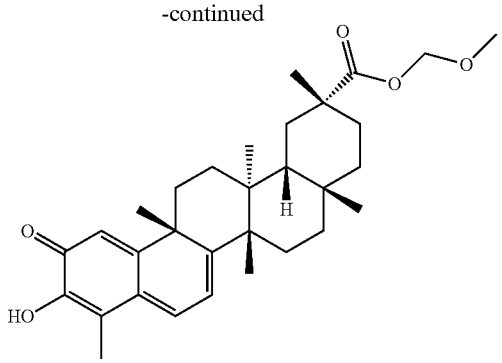

ERX1014

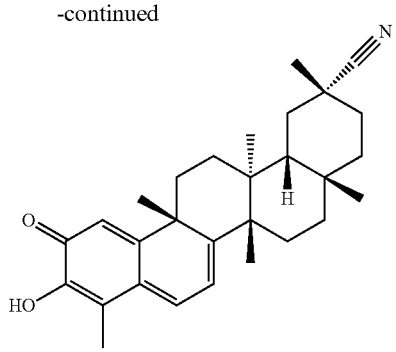

ERX1015

To a solution of celastrol (200 mg, 0.444 mmol) in DMF (2 mL) was added K$_2$CO$_3$ (123 mg, 0.888 mmol) followed by MeOCH$_2$Br (61 mg, 0.04 mL, 0.488 mmol). The reaction was stirred at room temperature overnight. Then the solution was diluted with CH$_2$Cl$_2$ (200 mL), washed with brine (100 mL), dried over MgSO$_4$ and concentrated in vacuo. The residue was purified by prep-TLC (petroleum ether/ethyl acetate=5:2) to afford product (10.0 mg, 0.0202 mmol, Yield=4.6%) as yellow solid. $^1$HNMR: δ(400 MHz, CDCl$_3$): 7.02 (1H, d, J=7.0 Hz), 6.97 (1H, s), 6.52 (1H, s), 6.35 (1H, d, J=7.0 Hz), 5.20 (1H, AB, J=5.9 Hz), 5.07 (1H, AB, J=5.9 Hz), 3.44 (3H, s), 2.45 (1H, d, J=15.6 Hz), 2.21 (3H, s), 1.30-2.26 (13H, m), 1.45 (3H, s), 1.27 (3H, s), 1.23 (3H, s), 1.11 (3H, s), 0.96-1.02 (1H, m), 0.60 (3H, s); LC-MS (Mobile Phase: A: water (10 mM Ammonium hydrogen carbonate); B: ACN; Gradient: 5%-95% B in 1.5 min; Flow Rate: 2.0 ml/min; Column: XBridge C18, 4.6*50 mm, 3.5 um; rt=2.75 min, m/z=463.3 [M-OMe]$^+$, purity=100% (214, 254 nm).

Example 15

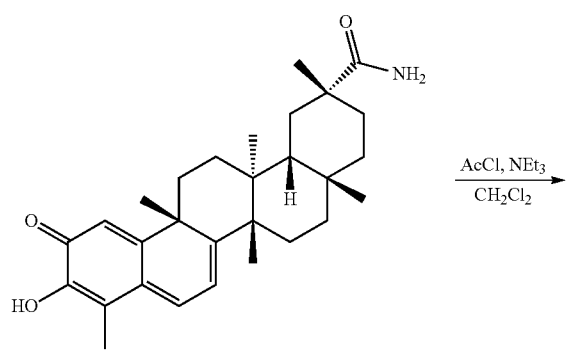

ERX1006

To a solution of ERX1006 (1.0 g, 2.22 mmol) in CH$_2$Cl$_2$ (10 mL) was added NEt$_3$ (449 mg, 0.62 mL, 4.44 mmol) followed by AcCl (261 mg, 0.24 mL, 3.33 mmol). The reaction was stirred at room temperature for 1 hour. The reaction was quenched by addition of H$_2$O (5 mL). Then the solution was diluted with CH$_2$Cl$_2$ (200 mL), washed with brine (100 mL), dried over MgSO$_4$ and concentrated in vacuo. The residue was purified by silica gel chromatography (petroleum ether/ethyl acetate=5:1) to afford intermediate (910 mg, 1.92 mmol, Yield=90%) as yellow solid.

To a solution of intermediate (590 mg, 1.2 mmol) in CH$_2$Cl$_2$ (20 mL) was added ClCO$_2$CCl$_3$ (475 mg, 2.4 mmol) followed by NEt3 (242 mg, 0.33 mL, 2.4 mmol) dropwise. The reaction was stirred at room temperature overnight. The reaction was quenched by addition of H$_2$O (5 mL). Then the solution was diluted with CH$_2$Cl$_2$ (200 mL), washed with brine (100 mL), dried over MgSO$_4$ and concentrated in vacuo. The residue was purified by silica gel chromatography (petroleum ether/ethyl acetate=2:1) and then reverse phase prep-HPLC to afford intermediate (120 mg, 0.278 mmol, Yield=23%) as red solid.

To a solution of ERX1006 (650 mg, 1.446 mmol) in CH$_2$Cl$_2$ (20 mL) was added (MeO)$_2$P(O)Cl (1044 mg, 0.78 mL, 7.23 mmol) followed by NEt$_3$ (732 mg, 0.726 mL, 7.23 mmol). The reaction was stirred at room temperature overnight. The reaction was quenched by addition of H$_2$O (5 mL). Then the solution was diluted with CH$_2$Cl$_2$ (200 mL), washed with brine (100 mL), dried over MgSO$_4$ and concentrated in vacuo. The residue was purified by prep-TLC (CH$_2$Cl$_2$/MeOH=30:1) to afford product (321 mg, 0.744 mmol, Yield=51%) as red solid. $^1$HNMR: δ(400 MHz, CDCl$_3$): 7.02 (1H, dd, J=7.1, 1.4 Hz), 6.97 (1H, s), 6.53 (1H, d, J=1.3 Hz), 6.37 (1H, d, J=7.5 Hz), 2.22 (3H, s), 1.55-2.20 (14H, m), 1.47 (3H, s), 1.44 (3H, s), 1.29 (3H, s), 1.09-1.15 (1H, m), 1.09 (3H, s), 1.03 (3H, s); LC-MS (Mobile Phase: A: water (0.01% TFA); B: ACN (0.01% TFA); Gradient: 5%-95% B in 1.4 min; Flow Rate: 2.3 ml/min; Column: SunFire C18, 4.6*50 mm, 3.5 um): rt=2.38 min, m/z=432.3 [M+H]$^+$, purity=100% (214,254 nm).

Example 16

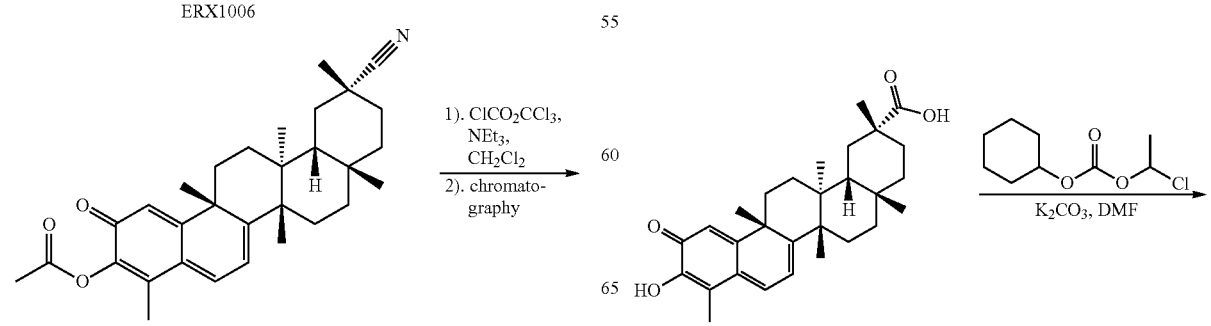

75

-continued

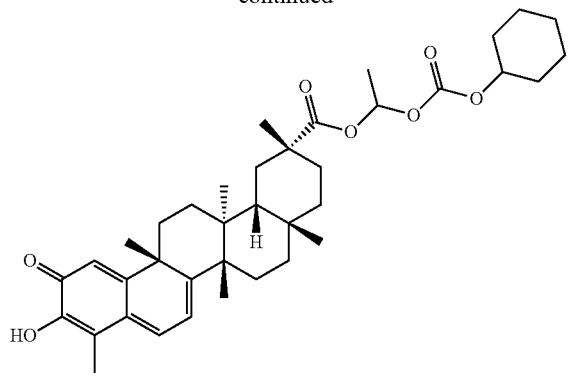

ERX1016, 2 isomers
P1 (less polar) and P2 (more polar)

To a solution of celastrol (300 mg, 0.666 mmol) in DMF (4 mL) was added $K_2CO_3$ (184 mg, 1.332 mmol) followed by carbonic acid 1-chloroethyl cyclohexyl ester (151 mg, 0.134 mL, 0.732 mmol). The reaction was stirred at room temperature overnight. Then the solution was diluted with $CH_2Cl_2$ (200 mL), washed with brine (100 mL), dried over $MgSO_4$ and concentrated in vacuo. The residue was purified by prep-TLC (petroleum ether/ethyl acetate=5:2) twice to afford isomer1 (less polar, 29.7 mg, 0.0478 mmol, Yield=7.2%) and isomer 2 (more polar, 20.0 mg, 0.0322 mmol, Yield=4.8%) as yellow solid. Isomer 1: $^1$HNMR: δ(400 MHz, $CDCl_3$): 7.02 (1H, dd, J=7.3, 1.1 Hz), 6.98 (1H, s), 6.74 (1H, q, J=5.5 Hz), 6.55 (1H, d, J=1.1 Hz), 6.35 (1H, d, J=7.3 Hz), 4.45-4.53 (1H, m), 2.41 (1H, d, J=16.1 Hz), 2.20 (3H, s), 1.00-2.20 (23H, m), 1.46 (3H, s), 1.45 (3H, d, J=5.5 Hz), 1.27 (3H, s), 1.20 (3H, s), 1.09 (3H, s), 0.93-1.00 (1H, m), 0.61 (3H, s); LC-MS: SP-0012508-089-1-01262-LCMSA043 Mobile Phase: A: water (10 mM Ammonium hydrogen carbonate); B: ACN; Gradient: 5%-95% B in 1.5 min; Flow Rate: 2.0 ml/min; Column: XBridge C18, 4.6*50 mm, 3.5 um): rt=3.11 min, m/z=477.4 $[M-C6H11OCO2]^+$, purity=100% (214,254 nm). Isomer 2: $^1$HNMR: δ(400 MHz, $CDCl_3$): 7.02 (1H, dd, J=7.1, 1.1 Hz), 6.97 (1H, s), 6.67 (1H, q, J=5.4 Hz), 6.52 (1H, d, J=1.1 Hz), 6.35 (1H, d, J=7.1 Hz), 4.52-4.58 (1H, m), 2.41 (1H, d, J=15.9 Hz), 2.21 (3H, s), 1.05-2.25 (23H, m), 1.46 (3H, d, J=5.4 Hz), 1.45 (3H, s), 1.26 (3H, s), 1.19 (3H, s), 1.10 (3H, s), 0.94-1.01 (1H, m), 0.60 (3H, s); LC-MS (Mobile Phase: A: water (10 mM Ammonium hydrogen carbonate); B: ACN; Gradient: 5%-95% B in 1.5 min; Flow Rate: 2.0 ml/min; Column: XBridge C18, 4.6*50 mm, 3.5 um): rt=3.12 min, m/z=477.3 $[M-C_6H_{11}OCO_2]^+$, purity=94.91% (254 nm).

Example 17

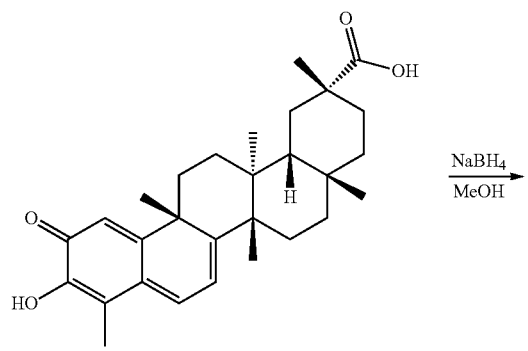

76

-continued

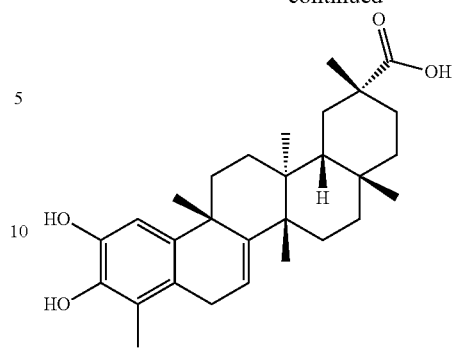

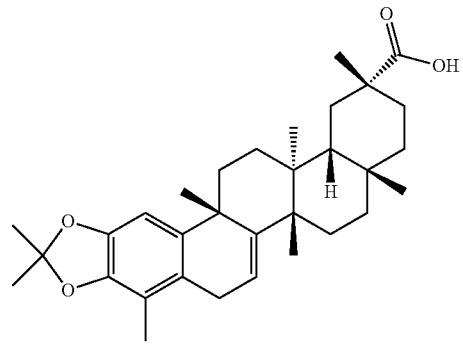

ERX1017

To a solution of celastrol (1.8 g, 4.0 mmol) in MeOH (20 mL) was added $NaBH_4$ (1.52 g, 40 mmol) in portions at 0° C. The reaction was stirred at room temperature for 30 minutes. The solution was turned form reddish to colorless. The reaction was quenched by 0.1 M HCl and neutralized to pH=7. Then the mixture was extracted with $CH_2Cl_2$ (2×100 mL) and the combined organic layers were washed with brine (100 mL), dried over $MgSO_4$ and concentrated in vacuo to afford crude intermediate (500 mg, 1.104 mmol, Yd=28%) as white solid.

To a solution of crude intermediate (300 mg, 0.66 mmol) in $CH_2Cl_2$ (20 mL) was added $(MeO)_2CMe_2$ (690 mg, 6.6 mmol) followed by TsOH (12 mg, 0.066 mmol). The reaction was stirred at room temperature overnight. The solution was diluted with $CH_2Cl_2$ (200 mL), washed with brine (100 mL), dried over $Mg_2SO_4$ and concentrated in vacuo. The residue was purified by silica gel chromatography (petroleum ether/ethyl acetate=10:1) to afford product (230 mg, 0.467 mmol, Yield=71%) as white solid. $^1$HNMR: δ(400 MHz, $CDCl_3$): 6.64 (1H, s), 5.73 (1H, dd, J=6.0, 1.5 Hz), 3.27 (1H, dd, J=20.8, 6.3 Hz), 2.98 (1H, d, J=20.8 Hz), 2.41 (1H, d, J=15.7 Hz), 2.10 (3H, s), 1.95-2.15 (4H, m), 1.69 (3H, s), 1.64 (3H, s), 1.24-1.85 (9H, m), 1.30 (3H, s), 1.20 (3H, s), 1.17 (3H, s), 1.05 (3H, s), 0.84-0.91 (1H, m), 0.68 (3H, s); LC-MS (Mobile Phase: A: water (0.01% TFA); B: ACN (0.01% TFA); Gradient: 5%-95% B in 1.2 min; Flow Rate: 2.2 ml/min; Column: Poroshell 120 EC-C18, 4.6*30 mm, 2.7 um): rt=2.34 min, m/z=493 $[M+H]^+$, purity=100% (214, 254 nm).

Example 18

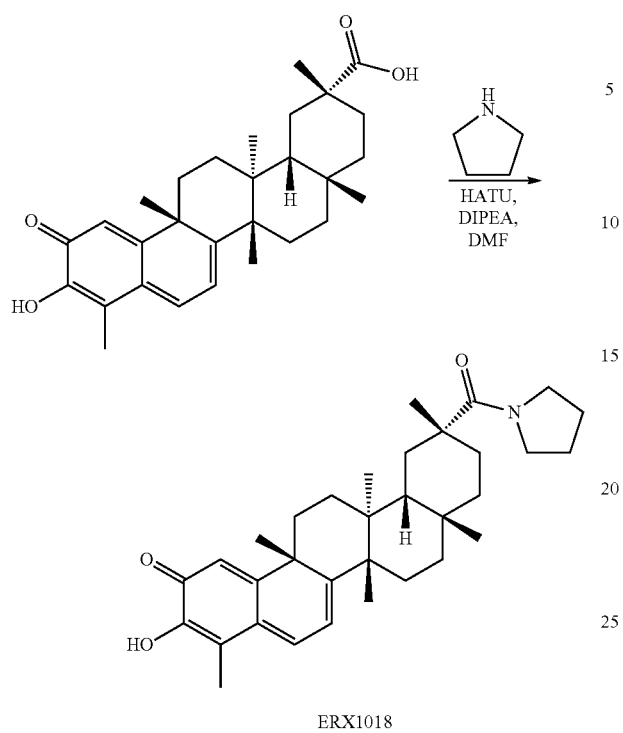

To a solution of celastrol (200 mg, 0.444 mmol) in DMF (10 mL) was added pyrrolidine (63 mg, 0.074 mL, 0.888 mmol), HATU (185 mg, 0.48 mmol) followed by DIPEA (115 mg, 0.16 mL, 0.88 mmol). The reaction was stirred at room temperature for 1 hour. Then the solution was diluted with CH$_2$Cl$_2$ (200 mL), washed with H$_2$O (2×100 mL) followed by brine (100 mL), dried over MgSO$_4$ and concentrated in vacuo. The residue was purified by prep-TLC (petroleum ether/ethyl acetate=1:1) to afford product (140 mg, 0.278 mmol, Yield=63%) as red solid. $^1$HNMR δ(400 MHz, CDCl$_3$): 7.03 (1H, dd, J=7.2, 1.0 Hz), 6.96 (1H, s), 6.53 (1H, d, J=1.0 Hz), 6.35 (1H, d, J=7.2 Hz), 3.56-3.70 (2H, m), 3.39-3.50 (1H, m), 3.19-3.29 (1H, m), 2.34-2.44 (2H, m), 2.22 (3H, s), 2.09-2.20 (2H, m), 1.47-1.97 (12H, m), 1.46 (3H, s), 1.23-1.33 (2H, m), 1.27 (3H, s), 1.22 (3H, s), 1.13 (3H, s), 0.94-1.10 (1H, m), 0.55 (3H, s); LC-MS: Mobile Phase: A: water (0.01% TFA): B: ACN (0.01% TFA); Gradient: 5%-95% B in 1.2 min; Flow Rate: 2.2 ml/min; Column: Poroshell 120 EC-C18, 4.6*30 mm, 2.7 um): rt=2.01 min, m/z=504.4 [M+H]$^+$, purity=100% (214, 254 nm).

Example 19

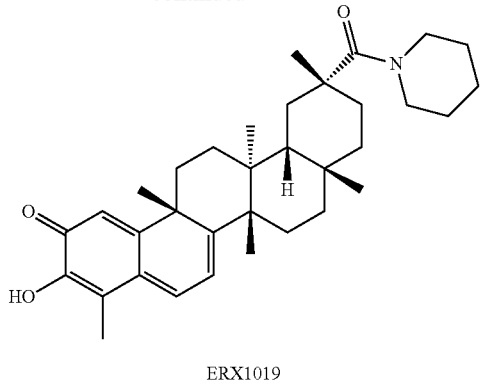

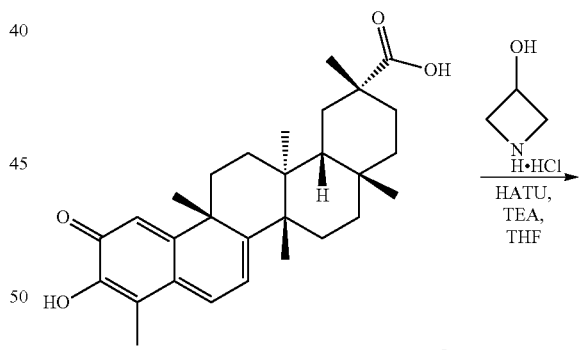

To a solution of celastrol (200 mg, 0.444 mmol) in DMF (10 mL) was added piperidine (76 mg, 0.088 mL, 0.888 mmol), HATU (185 mg, 0.48 mmol) followed by DIPEA (115 mg, 0.16 mL, 0.88 mmol). The reaction was stirred at room temperature overnight. Then the solution was diluted with CH$_2$Cl$_2$ (200 mL), washed with water (2×100 mL) followed by brine (100 mL), dried over MgSO$_4$ and concentrated in vacuo. The residue was purified by prep-TLC (petroleum ether/ethyl acetate=1:1) to afford product (95 mg, 0.188 mmol, Yield=42%) as yellow solid. $^1$HNMR: δ(400 MHz, CDCl$_3$): 7.04 (1H, d, J=7.2 Hz), 6.97 (1H, s), 6.54 (1H, s), 6.36 (1H, d, J=7.2 Hz), 2.90-4.10 (4H, br), 2.28-2.42 (2H, m), 2.22 (3H, s), 2.05-2.21 (2H, m), 1.24-1.92 (16H, m), 1.46 (3H, s), 1.29 (3H, s), 1.27 (3H, s), 1.14 (3H, s), 0.94-1.01 (1H, m), 0.60 (3H, s); LC-MS (Mobile Phase: A: water (0.01% TFA); B: ACN (0.01% TFA); Gradient: 5%-95% B in 1.4 min; Flow Rate: 2.3 ml/min; Column: SunFire C18, 4.6*50 mm, 3.5 um): rt=2.63 min, m/z=518.5 [M+H]$^+$, purity=100% (214, 254 nm).

Example 20

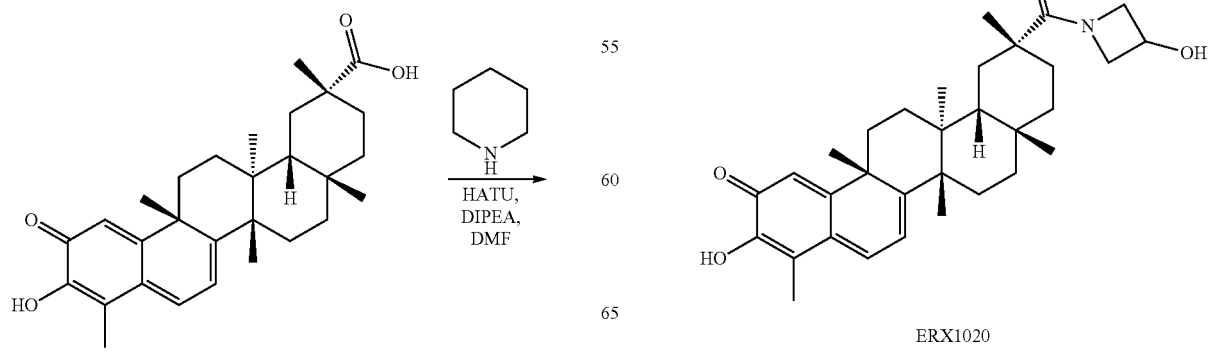

To a solution of celastrol (200 mg, 0.444 mmol) in THF (5 mL) was added 3-hydroxyazetidine hydrochloride (97 mg, 0.888 mmol), HATU (338 mg, 0.888 mmol) followed by NEt$_3$ (180 mg, 0.25 mL, 1.776 mmol). The reaction was stirred at room temperature overnight. Then the solution was diluted with CH$_2$Cl$_2$ (200 mL), washed with brine (100 mL), dried over MgSO$_4$ and concentrated in vacuo. The residue was purified by prep-TLC (petroleum ether/ethyl acetate=1:4) and reverse phase prep-HPLC to afford product (80.5 mg, 0.159 mmol, Yield=36%) as red solid. $^1$HNMR: δ(400 MHz, CDCl$_3$): 7.05 (1H, d, J=7.2 Hz), 6.93 (1H, s), 6.54 (1H, s), 6.36 (1H, d, J=7.2 Hz), 4.50-4.60 (2H, m), 3.55-4.30 (4H, m), 2.23 (3H, s), 1.82-2.28 (6H, m), 1.46-1.74 (6H, m), 1.43 (3H, s), 1.20-1.34 (2H, m), 1.25 (3H, s), 1.14 (3H, s), 1.11 (3H, s), 0.94-1.01 (1H, m), 0.64&0.60 (3H, s); LC-MS (Mobile Phase: A: water (10 mM Ammonium hydrogen carbonate); B: ACN; Gradient: 5%-95% B in 1.5 min; Flow Rate: 2.0 ml/min; Column: XBridge C18, 4.6*50 mm, 3.5 um): rt=2.34 min, m/z=556.4 [M+H]$^+$, purity=100% (214, 254 nm).

Example 21

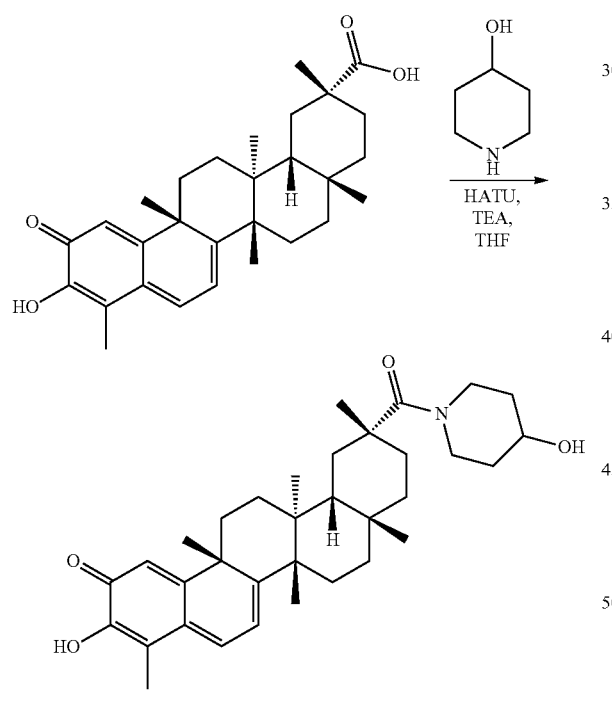

ERX1021

To a solution of celastrol (300 mg, 0.666 mmol) in THF (7.5 mL) was added 4-hydroxypiperidine (135 mg, 1.33 mmol), HATU (507 mg, 1.33 mmol) followed by NEt$_3$ (202 mg, 0.28 mL, 2.0 mmol). The reaction was stirred at room temperature overnight. Then the solution was diluted with CH$_2$Cl$_2$ (300 mL), washed with brine (100 mL), dried over MgSO$_4$ and concentrated in vacuo. The residue was purified by prep-TLC (petroleum ether/ethyl acetate=1:3) and reverse phase prep-HPLC to afford product (34.8 mg, 0.0652 mmol, Yield=9.8%) as yellow solid. $^1$HNMR: δ(400 MHz, CDCl$_3$): 7.03 (1H, d, J=7.1 Hz), 6.96 (1H, s), 6.53 (1H, s), 6.36 (1H, d, J=7.1 Hz), 4.0-4.4 (1H, br), 3.94 (1H, s), 3.0-3.9 (2H, br), 2.00-2.40 (3H, m), 2.22 (3H, s), 1.20-1.95 (17H, m), 1.46 (3H, s), 1.29 (3H, s), 1.28 (3H, s), 1.15 (3H, s), 0.95-1.02 (2H, m), 0.58 (3H, s); LC-MS (Mobile Phase: A: water (10 mM Ammonium hydrogen carbonate); B: ACN; Gradient: 5%-95% B in 1.5 min; Flow Rate: 2.0 ml/min; Column: XBridge C18, 4.6*50 mm, 3.5 um): rt=2.41 min, m/z=534.3 [M+H]$^+$, purity=96.7% (214 nm), 100% (254 nm).

Example 22

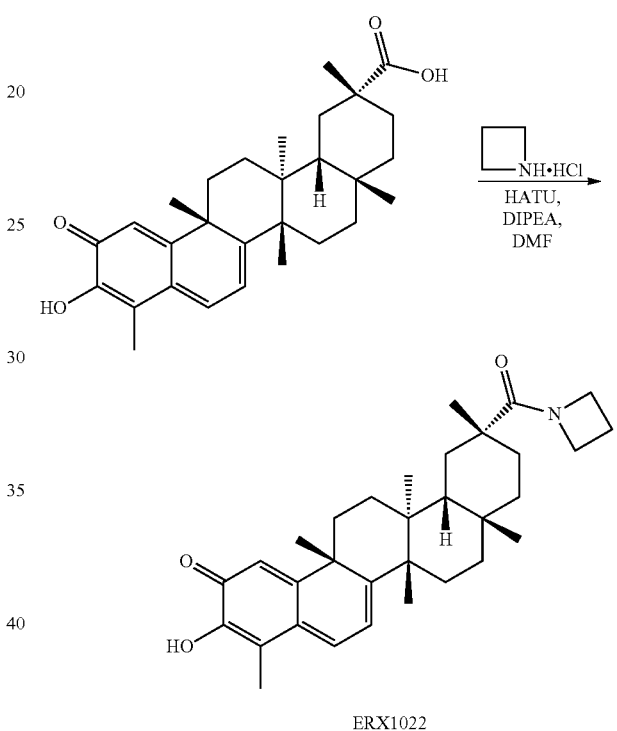

ERX1022

To a solution of celastrol (150 mg, 0.33 mmol) in DMF (10 mL) was added azetidine hydrochloride (62 mg, 0.67 mmol), HATU (139 mg, 0.36 mmol) followed by DIPEA (86 mg, 0.12 mL, 0.67 mmol). The reaction was stirred at room temperature overnight. Then the solution was diluted with CH$_2$Cl$_2$ (200 mL), washed with brine (100 mL), dried over MgSO$_4$ and concentrated in vacuo. The residue was purified by prep-TLC (petroleum ether/ethyl acetate=1:4) and reverse phase prep-HPLC to afford product (96 mg, 0.196 mmol, Yield=52%) as yellow solid. $^1$HNMR: δ(400 MHz, CDCl$_3$): 7.04 (1H, d, J=7.1 Hz), 6.97 (1H, s), 6.56 (1H, s), 6.36 (1H, d, J=7.1 Hz), 4.35-4.45 (2H, m), 3.75-3.95 (2H, m), 2.22 (3H, s), 1.50-2.30 (14H, m), 1.47 (3H, s), 1.28 (3H, s), 1.24-1.34 (2H, m), 1.15 (3H, s), 1.10 (3H, s), 0.93-1.00 (1H, m), 0.66 (3H, s); LC-MS (Mobile Phase: A: water (0.01% TFA); B: ACN (0.01% TFA); Gradient: 5%-95% B in 1.4 min; Flow Rate: 2.3 ml/min; Column: SunFire C18, 4.6*50 mm, 3.5 um): rt=2.38 min, m/z=490.4 [M+H]$^+$, purity=100% (214, 254 nm).

Example 23

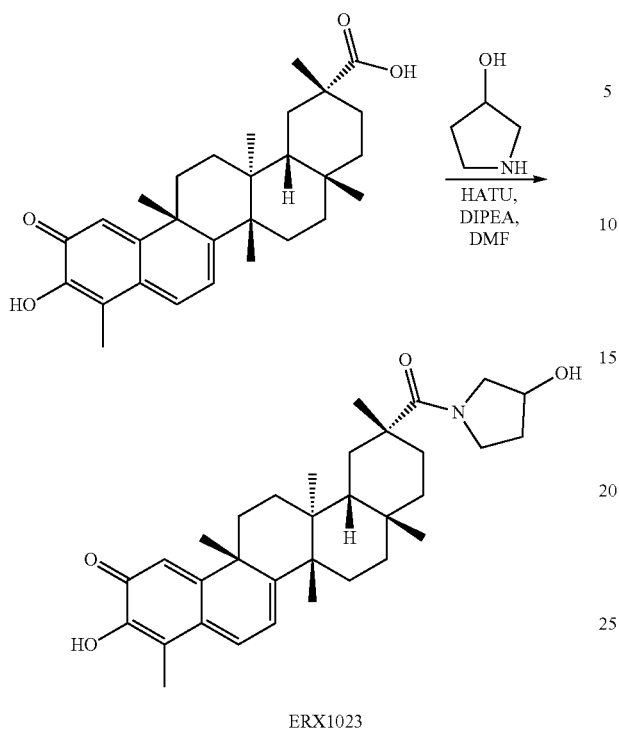

ERX1023

To a solution of celastrol (300 mg, 0.666 mmol) in DMF (10 mL) was added 3-hydroxypyrrolidine (116 mg, 1.33 mmol), HATU (279 mg, 0.73 mmol) followed by DIPEA (172 mg, 0.24 mL, 1.33 mmol). The reaction was stirred at room temperature overnight. Then the solution was diluted with CH$_2$Cl$_2$ (300 mL), washed with brine (100 mL), dried over MgSO$_4$ and concentrated in vacuo. The residue was purified by prep-TLC (petroleum ether/ethyl acetate=1:5) to afford product (110 mg, 0.212 mmol, Yield=32%) as yellow solid. $^1$HNMR: δ(400 MHz, CDCl$_3$): 7.04 (1H, d, J=7.0 Hz), 6.95 (1H, s), 6.51&6.46 (1H, s), 6.35 (1H, d, J=7.0 Hz), 4.33-4.55 (1H, m), 3.15-3.95 (1H, m), 2.50-3.05 (1H, m), 2.20 (3H, s), 1.20-2.50 (16H, m), 1.27 (3H, s), 1.25 (3H, s), 1.20 (3H, s), 1.13 (3H, s), 0.93-1.01 (1H, m), 0.61&0.59&0.53 (3H, s); LC-MS (Mobile Phase: A: water (0.01% TFA); B: ACN (0.01% TFA); Gradient: 5%-95% B in 1.4 min; Flow Rate: 2.3 ml/min; Column: SunFire C18, 4.6*50 mm, 3.5 um): rt=2.23 min, m/z=520.3 [M+H]$^+$, purity=100% (214,254 nm).

Example 24

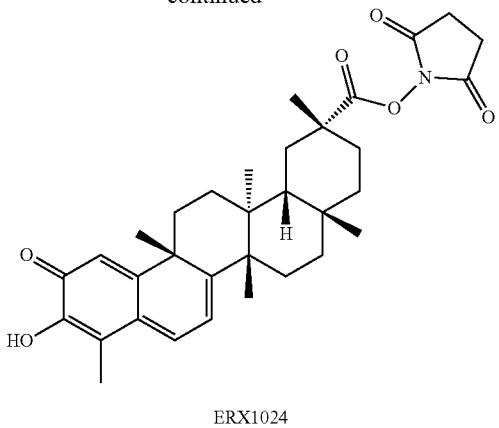

ERX1024

To a solution of celastrol (200 mg, 0.444 mmol) in DMF (15 mL) was added N-hydroxysuccinimide (153 mg, 1.33 mmol), HATU (185 mg, 0.48 mmol) followed by DIPEA (115 mg, 0.16 mL, 0.89 mmol). The reaction was stirred at room temperature overnight. Then the solution was diluted with CH$_2$Cl$_2$ (300 mL), washed with brine (100 mL), dried over MgSO$_4$ and concentrated in vacuo. The residue was purified by prep-TLC (CH$_2$Cl$_2$/MeOH=40:1) to afford product (80 mg, 0.146 mmol, Yield=33%) as yellow solid. $^1$HNMR: δ(400 MHz, CDCl$_3$): 7.01 (1H, dd, J=7.2, 1.0 Hz), 6.98 (1H, s), 6.57 (1H, d, J=1.0 Hz), 6.35 (1H, d, J=7.2 Hz), 2.70-2.90 (4H, m), 2.57 (1H, d, J=15.9 Hz), 2.28-2.35 (1H, m), 2.21 (3H, s), 1.48-2.20 (11H, m), 1.46 (6H, s), 1.25-1.30 (1H, m), 1.28 (3H, s), 1.12 (3H, s), 0.99-1.06 (1H, m), 0.71 (3H, s); LC-MS (Mobile Phase: A: water (0.01% TFA); B: ACN (0.01% TFA); Gradient: 5%-95% B in 1.2 min; Flow Rate: 2.2 ml/min; Column: Poroshell 120 EC-C18, 4.6*30 mm, 2.7 um): rt=1.97 min, m/z=548.3 [M+H]$^+$, purity=100% (214 nm), 97.26% (254 nm).

Example 25

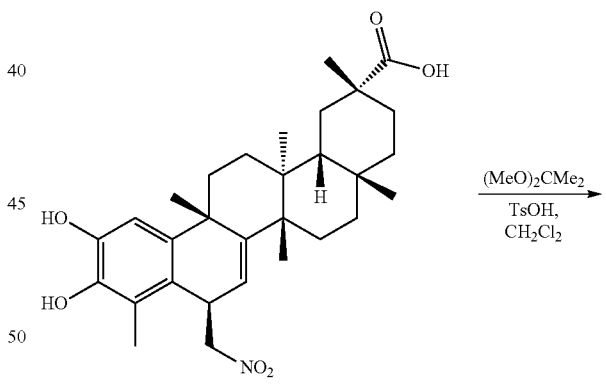

ERX1005

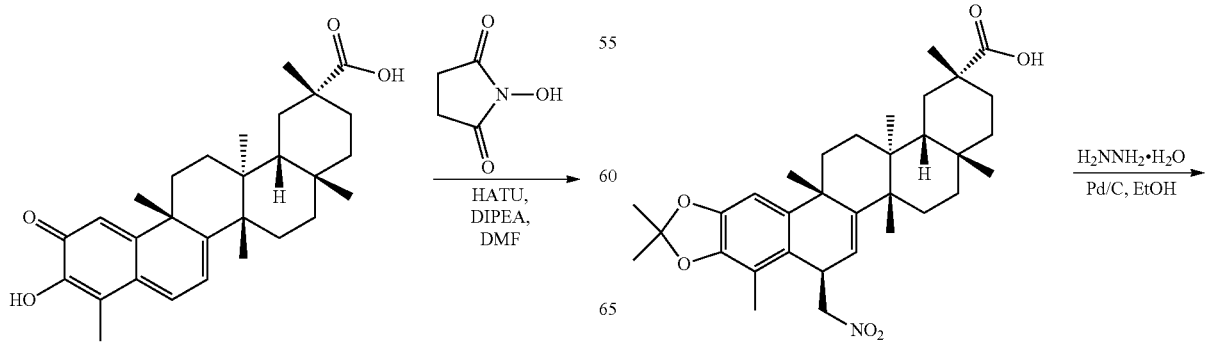

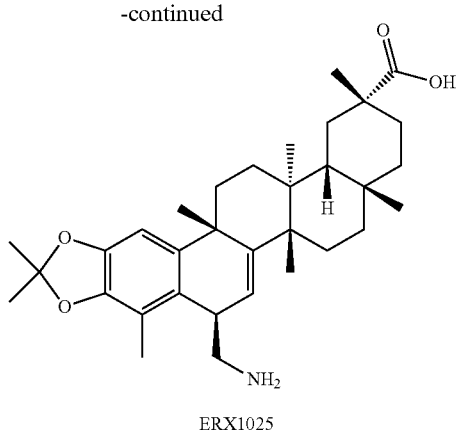

ERX1025

To a solution of ERX1005 (500 mg, 0.97 mmol) in CH$_2$Cl$_2$ (10 mL) was added (MeO)$_2$CMe$_2$ (1.01 g, 9.7 mmol) followed by p-TsOH.H$_2$O (18 mg, 0.1 mmol). The reaction was stirred at room temperature overnight. The solution was diluted with CH$_2$Cl$_2$ (200 mL), washed with sat. NaHCO$_3$ (100 mL) followed by brine (100 mL), dried over MgSO$_4$ and concentrated in vacuo. The residue was purified by silica gel chromatography (petroleum ether/EtOAc=10:1) to afford intermediate (350 mg, 0.635 mmol, Yield=65%) as white solid.

To a solution of intermediate (300 mg, 0.54 mmol) in EtOH (20 mL) was added Pd/C (50 mg) followed by H$_2$NNH$_2$.H$_2$O (270 mg, 5.4 mmol). The reaction was stirred at 75° C. overnight. The reaction solution was filtered and concentrated in vacuo. The residue was diluted with CH$_2$Cl$_2$ (200 mL), washed with water (2×100 mL) followed by brine (100 mL), dried over MgSO$_4$ and concentrated in vacuo. The residue was purified by silica gel chromatography (CH$_2$Cl$_2$/MeOH=30:1) to afford product (160 mg, 0.29 mmol, Yield=57%) as white solid. $^1$HNMR δ(400 MHz, d4-MeOD): 6.63 (1H, s), 5.90 (1H, d, J=5.9 Hz), 3.53-3.60 (1H, m), 3.01 (1H, dd, J=12.0, 3.4 Hz), 2.43-2.55 (2H, m), 2.02-2.26 (3H, m), 2.06 (3H, s), 1.79-1.95 (3H, m), 1.54-1.76 (6H, m), 1.67 (3H, s), 1.61 (3H, s), 1.47 (3H, s), 1.43-1.51 (1H, m), 1.30-1.40 (2H, m), 1.29 (3H, s), 1.12 (3H, s), 1.10 (3H, s), 0.85-0.92 (1H, m), 0.82 (3H, s); LC-MS (Mobile Phase: A: water (0.01% TFA); B: ACN (0.01% TFA); Gradient: 5%-95% B in 1.7 min; Flow Rate: 2.2 ml/min; Column: SunFire C18, 4.6*50 mm, 3.5 um): rt=1.98 min, m/z=522.3 [M+H]$^+$, purity=100% (214, 254 nm).

Example 26

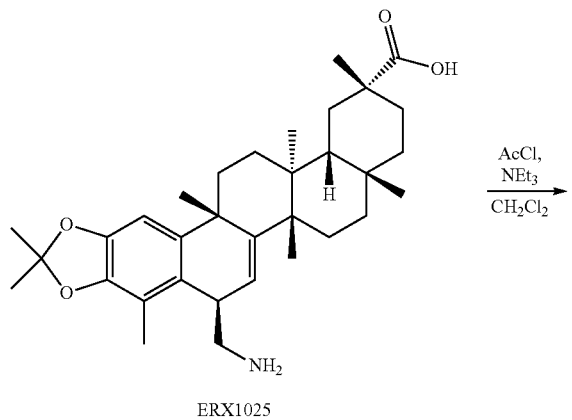

ERX1025

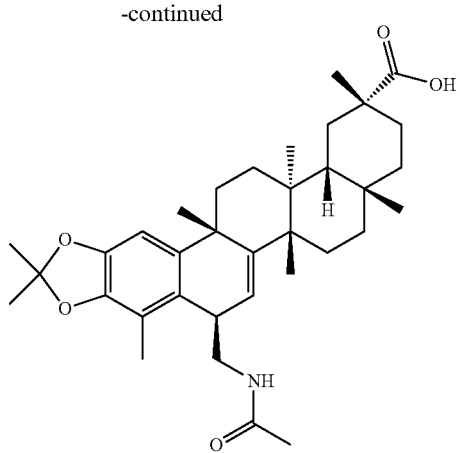

ERX1026

To a solution of ERX1025 (90 mg, 0.17 mmol) in CH$_2$C$_2$ (10 mL) was added NEt3 (34 mg, 0.34 mmol) followed by AcCl (20 mg, 0.26 mmol). The reaction was stirred at room temperature for 30 minutes. The solution was diluted with CH$_2$Cl$_2$ (100 mL), washed with sat. NaHCO$_3$ (50 mL) followed by brine (50 mL), dried over MgSO$_4$ and concentrated in vacuo. The residue was purified by prep-TLC (petroleum ether/EtOAc=10:1) to afford product (60 mg, 0.106 mmol, Yield=63%) as white solid. $^1$HNMR: δ(400 MHz, CDCl$_3$): 6.64 (1H, s), 6.24 (1H, t, J=5.6 Hz), 5.67 (1H, d, J=6.5 Hz), 3.68-3.75 (1H, m), 3.45-3.53 (1H, m), 3.05-3.14 (1H, m), 2.39 (1H, d, J=16.0 Hz), 2.27 (3H, s), 1.98-2.12 (2H, m), 2.05 (3H, s), 1.68 (3H, s), 1.66 (3H, s), 1.47 (3H, s), 1.04-1.82 (12H, m), 1.16 (6H, s), 1.01 (3H, s), 0.72-0.80 (1H, m), 0.45 (3H, s); LC-MS (Mobile Phase: A: water (10 mM Ammonium hydrogen carbonate); B: ACN; Gradient: 5%-95% B in 1.5 min; Flow Rate: 2.0 ml/min; Column: XBridge C18, 4.6*50 mm, 3.5 um): rt=2.17 min, m/z=564.4 [M+H]$^+$, purity=100% (214, 254 nm).

Example 27

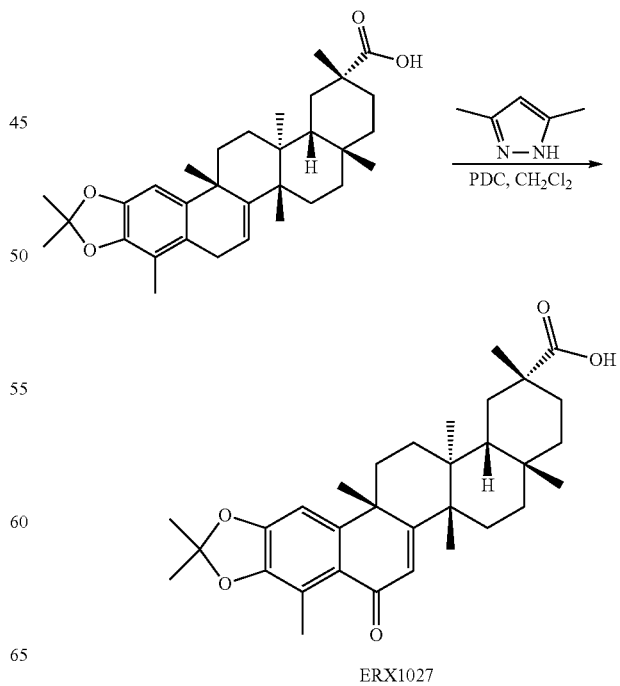

ERX1027

To a solution of SM (860 mg, 1.746 mmol) in $CH_2Cl_2$ (20 mL) was added 3,5-dimethylpyrazole (336 mg, 3.492 mmol) followed by PDC (647 mg, 1.746 mmol). The reaction was stirred at room temperature overnight. The solution was filtered through celite and concentrated in vacuo. The residue was purified by silica gel chromatography (petroleum ether/ethyl acetate=4:1) to afford product (410 mg, 0.809 mmol, Yield=46%) as white solid. $^1$HNMR: δ(400 MHz, $CDCl_3$): 6.72 (1H, s), 6.24 (1H, s), 2.55 (3H, s), 2.41 (1H, d, J=15.6 Hz), 1.25-2.20 (13H, m), 1.70 (3H, s), 1.67 (3H, s), 1.52 (3H, s), 1.28 (3H, s), 1.16 (3H, s), 1.09 (3H, s), 0.91-0.99 (1H, m), 0.66 (3H, s); LC-MS (Mobile Phase: A: H2O (0.01% TFA); B: MeCN (0.01% TFA); Gradient: 5%-95% B in 1.2 min; Flow Rate: 2 ml/min; Column: SunFire C18 50*4.6 mm, 3.5 um): rt=2.39 min, m/z=507.3 [M+H]$^+$, purity=99.28% (214 nm), 100% (254 nm).

Example 28

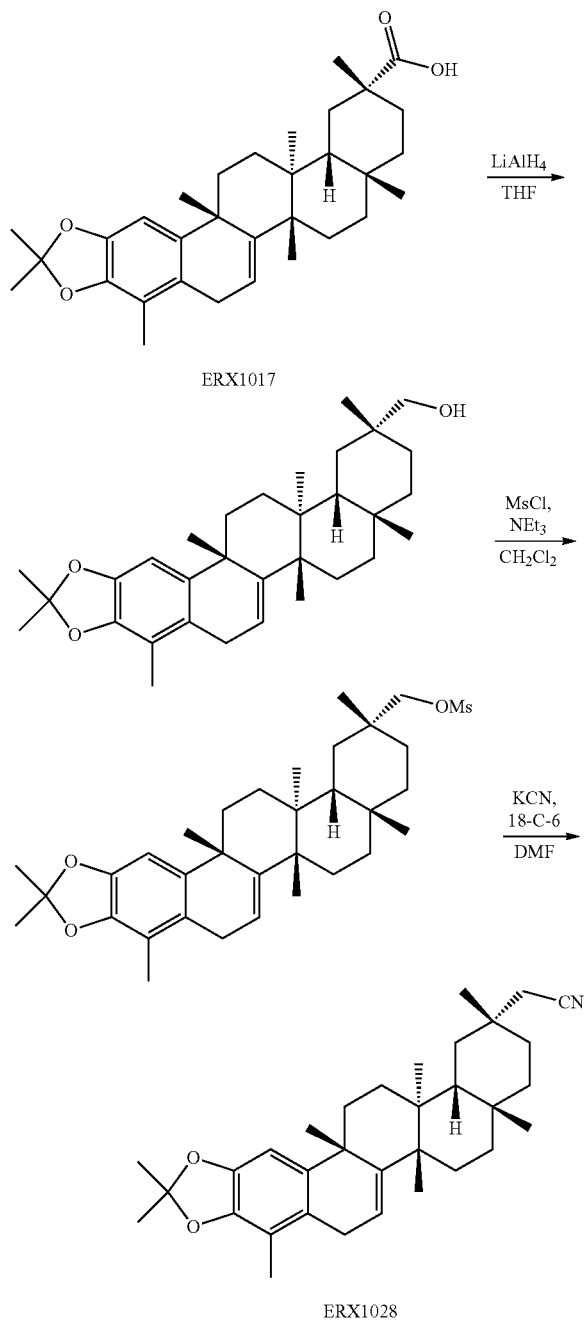

To a solution of ERX1017 (300 mg, 0.61 mmol) in THF (10 mL) was added $LiAlH_4$ (70 mg, 1.83 mmol) in portions. The reaction was stirred at room temperature for 1 hour. The reaction was quenched by addition of water (5 mL). The solution was diluted with EtOAc (200 mL), filtered. The filtrate was separated and the organic layer was washed with brine (100 mL), dried over $MgSO_4$ and concentrated in vacuo. The residue was purified by silica gel chromatography (petroleum ether/EtOAc=10:1) to afford intermediate (180 mg, 0.376 mmol, Yield=62%) as white solid.

To a solution of intermediate (150 mg, 0.31 mmol) in $CH_2C_2$ (10 mL) was added $NEt_3$ (63 mg, 0.62 mmol) followed by MsCl (71 mg, 0.62 mmol). The reaction was stirred at room temperature overnight. The solution was diluted with $CH_2Cl_2$ (200 mL), washed with brine (100 mL), dried over $MgSO_4$ and concentrated in vacuo. The residue was purified by silica gel chromatography (petroleum ether/EtOAc=10:1) to afford intermediate (160 mg, 0.287 mmol, Yield=93%) as white solid.

To a solution of intermediate (170 mg, 0.305 mmol) in DMF (5 mL) was added KCN (99 mg, 1.528 mmol) and 18-Crown-6 (403 mg, 1.528). The reaction was heated at 120° C. in a microwave reactor for 6 hours. The solution was diluted with EtOAc (200 mL), washed with water (2×100 mL) followed by brine (100 mL), dried over $MgSO_4$ and concentrated in vacuo. The residue was purified by prep-HPLC to afford product (110 mg, 0.226 mmol, Yield=74%) as white solid. $^1$HNMR: δ(400 MHz, $CDCl_3$): 6.65 (1H, s), 5.80 (1H, d, J=4.7 Hz), 3.30 (1H, dd, J=20.8, 6.3 Hz), 3.01 (1H, d, J=20.1 Hz), 2.46 (1H, AB, J=16.5 Hz), 2.19 (1H, AB, J=16.5 Hz), 2.11 (3H, s), 2.00-2.07 (2H, m), 1.50-1.85 (9H, m), 1.68 (3H, s), 1.64 (3H, s), 1.25-1.38 (3H, m), 1.31 (3H, s), 1.29 (3H, s), 1.16 (3H, s), 1.14 (3H, s), 0.97-1.03 (1H, m), 0.87 (3H, s); LC-MS (Mobile Phase: A: water (0.01% TFA); B: ACN (0.01% TFA); Gradient: 5%-95% B in 1.2 min; Flow Rate: 2.2 ml/min; Column: Poroshell 120 EC-C18, 4.6*30 mm, 2.7 um): rt=2.35 min, no MS peaks integrated, purity=100% (214, 254 nm).

Example 29

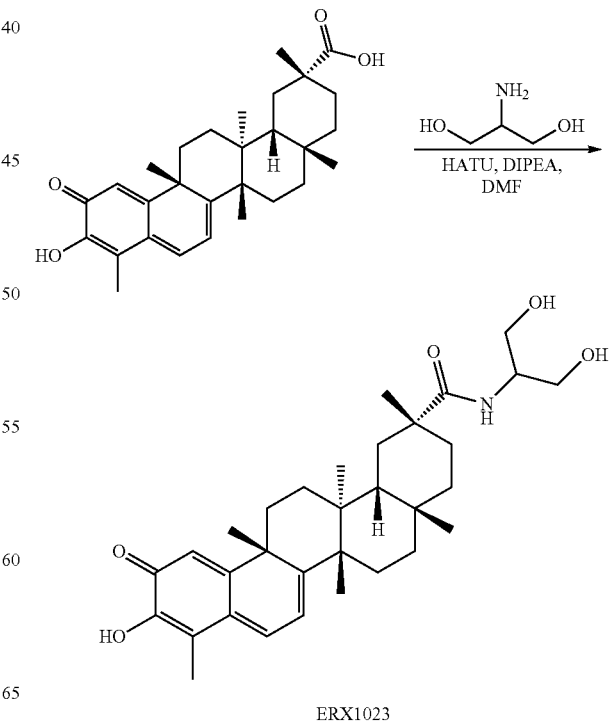

To a solution of celastrol (150 mg, 0.33 mmol) in DMF (10 mL) was added 2-amino-1,3-propanediol (91 mg, 1.0 mmol), HATU (139 mg, 0.36 mmol) followed by DIPEA (129 mg, 0.17 mL, 1.0 mmol). The reaction was stirred at room temperature overnight. Then the solution was diluted with CH$_2$Cl$_2$ (200 mL), washed with water (2×100 mL), brine (100 mL), dried over MgSO$_4$ and concentrated in vacuo. The residue was purified by prep-TLC (CH$_2$Cl$_2$/MeOH=8:1) to afford product (60 mg, 0.115 mmol, Yield=35%) as red solid. $^1$HNMR δ(400 MHz, CDCl$_3$): 7.03 (1H, d, J=7.1 Hz), 7.00 (1H, s), 6.61 (1H, d, J=3.0 Hz), 6.53 (1H, s), 6.35 (1H, d, J=7.1 Hz), 3.45-3.90 (5H, m), 3.00-3.45 (2H, m), 2.43 (1H, d, J=15.7 Hz), 2.21 (3H, s), 1.47-2.18 (12H, m), 1.43 (3H, s), 1.26 (3H, s), 1.24-1.28 (1H, m), 1.18 (3H, s), 1.12 (3H, s), 0.95-1.05 (1H, m), 0.66 (3H, s); LC-MS (Mobile Phase: A: water (0.01% TFA) B: ACN (0.01% TFA); Gradient: 5%-95% B in 1.4 min; Flow Rate: 2.3 ml/min; Column: SunFire C18, 4.6*50 mm, 3.5 um): rt=2.08 min, m/z=524.3 [M+H]$^+$, purity=95.73% (214 nm).

Example 30

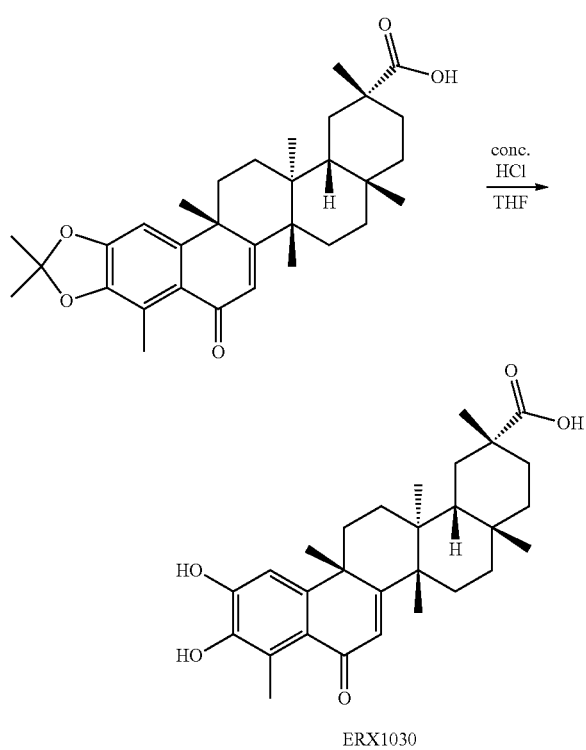

ERX1030

To a solution of SM (90 mg, 0.178 mmol) in THF (5 mL) was added conc. HCl (1 mL). The reaction was stirred at 70° C. for 2 days. Then most THF solvent was removed in vacuo. The residue was diluted with CH$_2$Cl$_2$ (200 mL), separated aqueous layer, dried over MgSO$_4$ and concentrated in vacuo. The residue was purified by prep-TLC (CH$_2$Cl$_2$/MeOH=10:1) to afford product (4.4 mg, 0.00943 mmol, Yield=5.3%) as pale yellow solid. $^1$HNMR δ(400 MHz, CD$_3$OD): 6.86 (1H, s), 6.18 (1H, s), 4.62 (2H, br), 2.55 (3H, s), 1.40-2.50 (14H, m), 1.54 (3H, s), 1.35 (3H, s), 1.18 (3H, s), 1.13 (3H, s), 0.93-1.00 (1H, m), 0.76 (3H, s); LC-MS (Mobile Phase: A: H2O (0.01% TFA); B: MeCN (0.01% TFA); Gradient: 5%-95% B in 1.2 min; Flow Rate: 2 ml/min; Column: SunFire C18 50*4.6 mm, 3.5 um): rt=2.05 min, m/z=467 [M+H]$^+$, purity=97.30% 9214 nm), 97.25% (254 nm).

Example 31

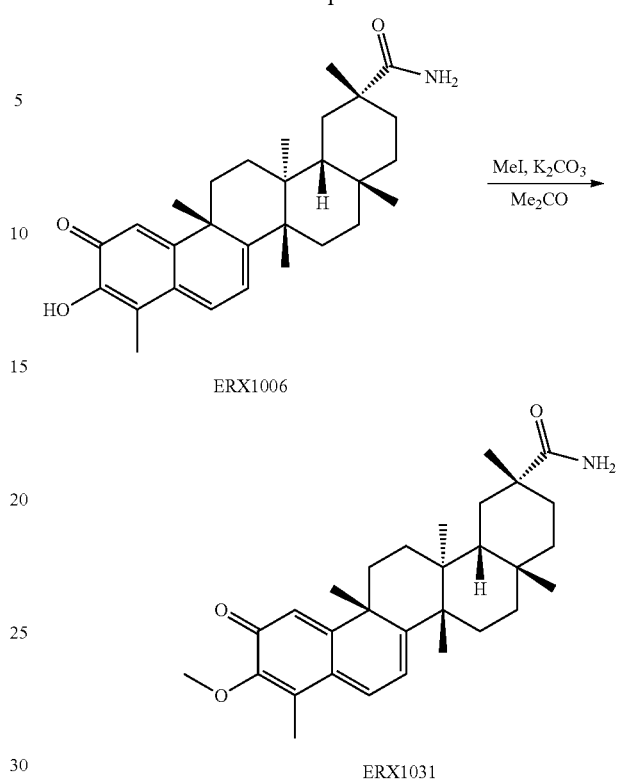

To a solution of ERX1006 (60 mg, 0.133 mmol) in acetone (2 mL) was added K$_2$CO$_3$ (37 mg, 0.267 mmol) followed by MeI (1 mL). The reaction was stirred at 40° C. for overnight. The mixture was diluted with CH$_2$Cl$_2$ (300 mL), washed with brine (100 mL), dried over MgSO$_4$ and concentrated in vacuo. The residue was purified by prep-TLC (petroleum ether/ethyl acetate=1:2) to afford product (38.4 mg, 0.0826 mmol, Yield=62%) as yellow solid.
$^1$HNMR δ(400 MHz, CDCl3): 6.96 (1H, dd, J=7.0, 1.0 Hz), 6.40 (1H, d, J=1.0 Hz), 6.27 (1H, d, J=7.0 Hz), 5.72 (1H, br), 5.55 (1H, br), 3.84 (3H, s), 2.40 (1H, d, J=15.7 Hz), 2.22 (3H, s), 1.45-2.13 (13H, m), 1.44 (3H, s), 1.25 (3H, s), 1.20 (3H, s), 1.11 (3H, s), 0.97-1.04 (1H, m), 0.73 (3H, s); LC-MS (Mobile Phase: A: water (0.01% TFA); B: ACN (0.01% TFA); Gradient: 5%-95% B in 1.4 min; Flow Rate: 2.3 ml/min; Column: SunFire C18, 4.6*50 mm, 3.5 um): rt=2.16 min, m/z=464.3 [M+H]$^+$, purity=100% (214, 254 nm).

Example 32

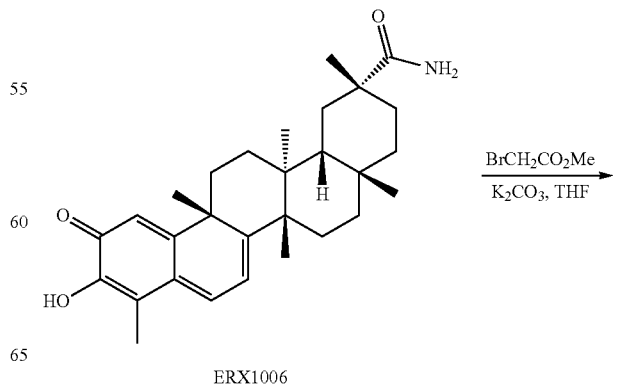

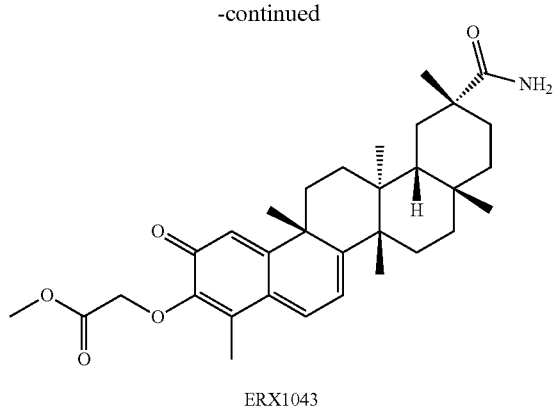

ERX1043

To a solution of ERX1006 (100 mg, 0.22 mmol) in THF (15 mL) was added K$_2$CO$_3$ (46 mg, 0.33 mmol) followed by BrCH$_2$CO$_2$Me (51 mg, 0.032 mL, 0.33 mmol). The reaction was stirred at 50° C. overnight. The mixture was diluted with CH$_2$C$_2$ (200 mL), washed with brine (100 mL), dried over MgSO$_4$ and concentrated in vacuo. The residue was purified by prep-TLC (petroleum ether/EtOAc=1:1) to afford product (40 mg, 0.077 mmol, Yield=35%) as yellow solid. $^1$HNMR δ(400 MHz, CDCl3): 7.01 (1H, d, J=7.1 Hz), 6.36 (1H, s), 6.29 (1H, d, J=7.1 Hz), 5.70 (1H, br), 5.39 (1H, br), 4.85 (2H, s), 3.77 (3H, s), 2.40 (1H, d, J=15.4 Hz), 2.31 (3H, s), 1.80-2.12 (7H, m), 1.46-1.72 (6H, m), 1.43 (3H, s), 1.26 (3H, s), 1.20 (3H, s), 1.11 (3H, s), 0.88-1.05 (1H, m), 0.74 (3H, s); LC-MS (Mobile Phase: A: water (0.01% TFA); B: ACN (0.01% TFA); Gradient: 5%-95% B in 1.4 min; Flow Rate: 2.3 ml/min; Column: SunFire C18, 4.6*50 mm, 3.5 um): rt=2.16 min, m/z=522.3 [M+H]$^+$, purity=100% (214, 254 nm).

Example 33

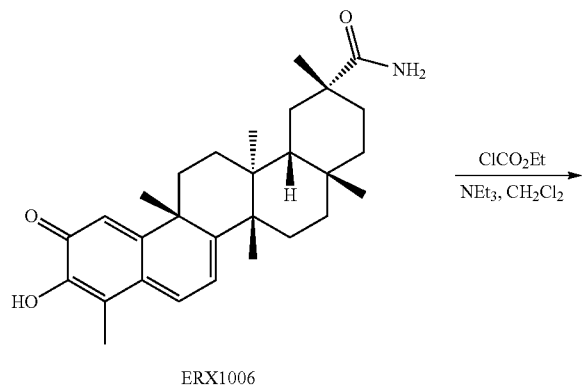

To a solution of ERX1006 (300 mg, 0.667 mmol) in CH$_2$Cl$_2$ (5 mL) was added Et$_3$N (135 mg, 0.19 mL, 1.334 mmol) followed by ClCO$_2$Et (145 mg, 0.13 mL, 1.334 mmol) dropwise at 0° C. The reaction was stirred at room temperature overnight. The mixture was diluted with CH$_2$Cl$_2$ (300 mL), washed with brine (200 mL), dried over MgSO$_4$ and concentrated in vacuo. The residue was purified by prep-TLC (CH$_2$Cl$_2$/MeOH=10:1) to afford product (150.6 mg, 0.289 mmol, Yield=43%) as yellow solid. $^1$HNMR δ(500 MHz, CDCl3): 7.06 (1H, dd, J=7.0, 1.0 Hz), 6.47 (1H, d, J=1.0 Hz), 6.33 (1H, d, J=7.0 Hz), 5.67 (1H, br), 5.26 (1H, br), 4.32 (2H, q, J=7.2 Hz), 2.39 (1H, d, J=15.6 Hz), 2.21 (3H, s), 1.49-2.04 (13H, m), 1.46 (3H, s), 1.39 (1H, t, J=7.2 Hz), 1.27 (3H, s), 1.21 (3H, s), 1.12 (3H, s), 0.99-1.05 (1H, m), 0.76 (3H, s); LC-MS (Mobile Phase: A: water (0.01% TFA); B: ACN (0.01% TFA); Gradient: 5%-95% B in 1.4 min; Flow Rate: 2.3 ml/min; Column: SunFire C18, 4.6*50 mm, 3.5 um): rt=2.15 min, m/z=522.3 [M+H]$^+$, purity=100% (214, 254 nm).

Example 34

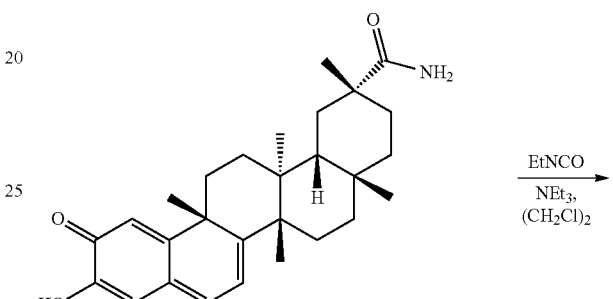

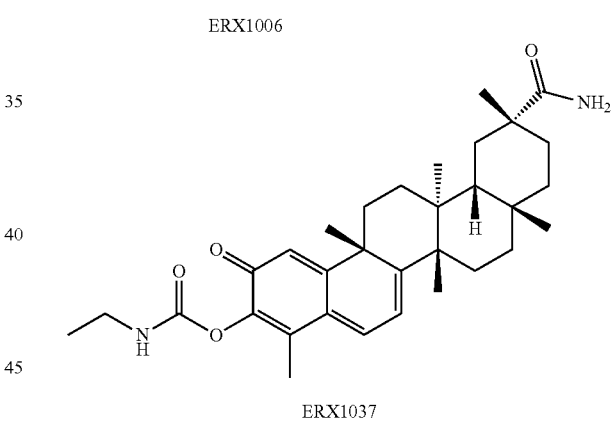

ERX1037

To a solution of ERX1006 (300 mg, 0.667 mmol) in (CH$_2$Cl)$_2$ (10 mL) was added Et$_3$N (202 mg, 0.28 mL, 2.0 mmol) followed by EtNCO (142 mg, 0.158 mL, 2.0 mmol). The reaction was stirred at 55° C. overnight. The mixture was diluted with CH$_2$Cl$_2$ (300 mL), washed with brine (200 mL), dried over MgSO$_4$ and concentrated in vacuo. The residue was purified by prep-TLC (CH$_2$Cl$_2$/MeOH=20:1) to remove unreacted SM. Then the crude product was heated at 80° C. with 20 mL ethyl acetate. Solid was filtered and further purified by prep-TLC (ethyl acetate/CH$_2$Cl$_2$=3:1) to afford product (74.7 mg, 0.143 mmol, Yield=22%) as yellow solid. $^1$HNMR: δ(400 MHz, CDCl3): 7.03 (1H, d, J=7.2 Hz), 6.45 (1H, s), 6.31 (1H, d, J=7.2 Hz), 5.70 (1H, br), 5.38 (1H, br), 5.26 (1H, t, J=5.0 Hz), 3.26-3.45 (2H, m), 2.38 (1H, d, J=15.7 Hz), 2.18 (3H, s), 1.47-2.15 (13H, m), 1.45 (3H, s), 1.26 (3H, s), 1.22 (3H, t, J=7.2 Hz), 1.20 (3H, s), 1.12 (3H, s), 0.98-1.05 (1H, m), 0.75 (3H, s); LC-MS (Mobile Phase: A: water (0.01% TFA); B: ACN (0.01% TFA); Gradient: 5%-95% B in 1.4 min; Flow Rate: 2.3 ml/min; Column: SunFire C18, 4.6*50 mm, 3.5 um; rt=2.06 min, m/z=521.4 [M+H]$^+$, purity=100% (214,254 nm).

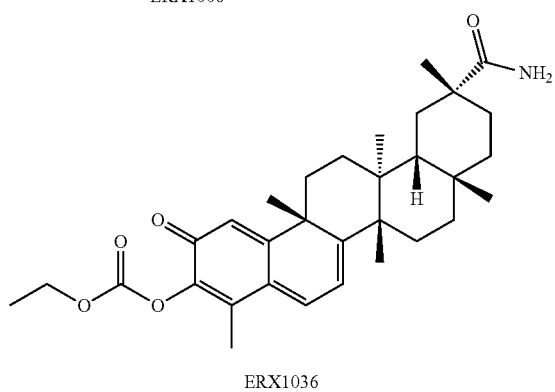

ERX1036

Example 35

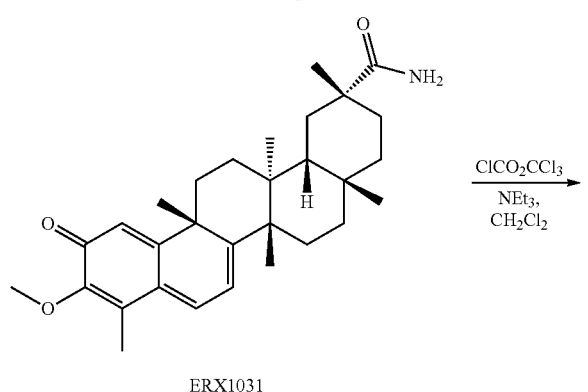

ERX1031

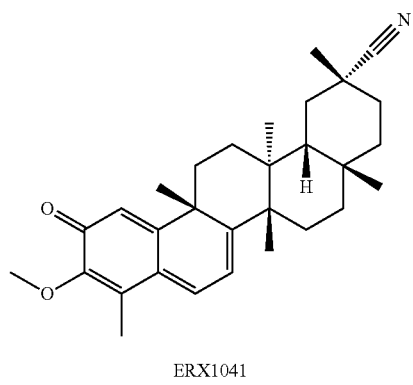

ERX1041

To a solution of SM (160 mg, 0.345 mmol) in CH$_2$Cl$_2$ (5 mL) was added ClCO$_2$CCl$_3$ (341 mg, 0.21 mL, 1.725 mmol) followed by NEt$_3$ (175 mg, 0.24 mL, 1.725 mmol) dropwise at 0° C. The reaction was stirred at room temperature overnight. The mixture was diluted with CH$_2$Cl$_2$ (300 mL), washed with brine (200 mL), dried over MgSO$_4$ and concentrated in vacuo. The residue was purified by prep-TLC (CH$_2$Cl$_2$/MeOH=30:1) to afford product (71 mg, 0.159 mmol, Yield=46%) as yellow solid. $^1$HNMR δ(400 MHz, CDCl3): 6.97 (1H, d, J=6.9 Hz), 6.42 (1H, s), 6.32 (1H, d, J=6.9 Hz), 3.85 (3H, s), 2.22 (3H, s), 2.09-2.18 (3H, m), 1.89-2.01 (3H, m), 1.53-1.81 (8H, m), 1.47 (3H, s), 1.44 (3H, s), 1.29 (3H, s), 1.08-1.15 (1H, m), 1.09 (3H, s), 1.05 (3H, s); LC-MS (Mobile Phase: A: water (0.01% TFA); B: ACN (0.01% TFA); Gradient: 5%-95% B in 1.4 min; Flow Rate: 2.3 ml/min; Column: SunFire C18, 4.6*50 mm, 3.5 um): rt=2.33 min, m/z=446.3 [M+H]$^+$, purity=100% (214, 254 nm).

Example 36

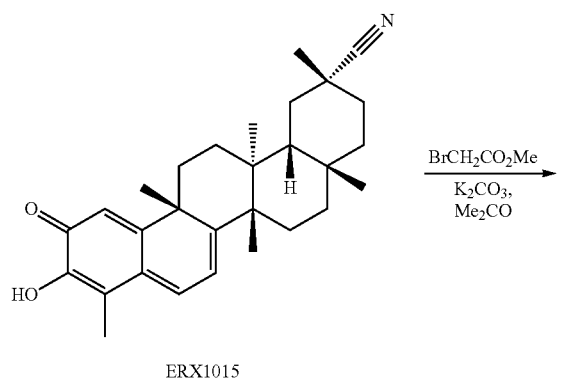

ERX1015

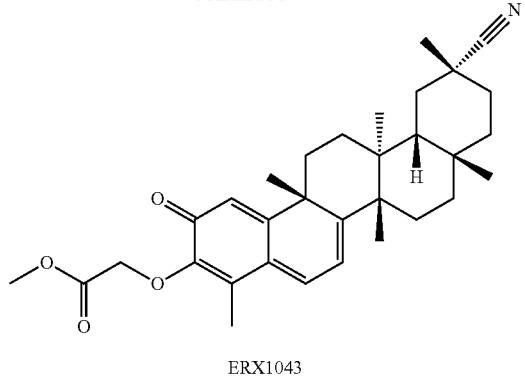

ERX1043

To a solution of SM (100 mg, 0.232 mmol) in acetone (2 mL) was added K$_2$CO$_3$ (64 mg, 0.463 mmol) followed by BrCH$_2$CO$_2$Me (71 mg, 0.044 mL, 0.463 mmol). The reaction was stirred at 55° C. overnight. The mixture was diluted with CH$_2$Cl$_2$ (200 mL), washed with brine (100 mL), dried over MgSO$_4$ and concentrated in vacuo. The residue was purified by prep-TLC (CH$_2$Cl$_2$/EtOAc=10:1) to afford crude product. The crude product was further washed with Et$_2$O (2×2 mL) to afford pure product (55 mg, 0.109 mmol, Yield=47%) as yellow solid. $^1$HNMR δ(400 MHz, CDCl3): 7.03 (1H, dd, J=7.0, 1.0 Hz), 6.38 (1H, d, J=1.0 Hz), 6.33 (1H, d, J=7.0 Hz), 4.85 (1H, AB, J=16.5 Hz), 4.84 (1H, AB, J=16.5 Hz), 3.77 (3H, s), 2.32 (3H, s), 2.08-2.18 (3H, m), 1.89-2.00 (3H, m), 1.52-1.81 (8H, m), 1.46 (3H, s), 1.44 (3H, s), 1.29 (3H, s), 1.08-1.15 (1H, m), 1.09 (3H, s), 1.04 (3H, s); LC-MS (Mobile Phase: A: water (0.1% TFA); B: ACN (0.1% TFA); Gradient: 5%-95% B in 1.2 min; Flow Rate: 2.2 ml/min; Column: Poroshell 120 EC-C18, 4.6*30 mm, 2.7 um): rt=1.94 min, m/z=504.3 [M+H]$^+$, purity=100% (214,254 nm).

Example 37

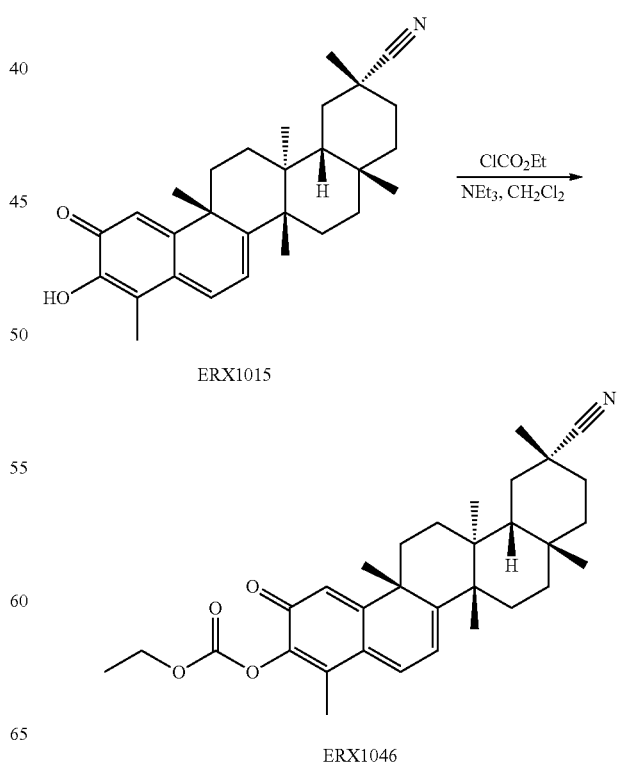

ERX1015

ERX1046

To a solution of ERX1015 (120 mg, 0.278 mmol) in CH$_2$Cl$_2$ (5 mL) was added Et$_3$N (84 mg, 0.12 mL, 0.834 mmol) followed by ClCO$_2$Et (91 mg, 0.834 mL, 0.834 mmol) dropwise at 0° C. The reaction was stirred at room temperature overnight. The mixture was diluted with CH$_2$Cl$_2$ (300 mL), washed with brine (200 mL), dried over MgSO$_4$ and concentrated in vacuo. The residue was purified by prep-TLC (CH$_2$Cl$_2$/MeOH=50:1) to afford product (97.3 mg, 0.193 mmol, Yield=69%) as yellow solid. $^1$HNMR: δ(400 MHz, CDCl3): 7.08 (1H, d, J=7.2 Hz), 6.49 (1H, s), 6.36 (1H, d, J=7.2 Hz), 4.32 (2H, q, J=7.2 Hz), 2.22 (3H, s), 2.09-2.20 (3H, m), 1.89-2.03 (3H, m), 1.51-1.81 (8H, m), 1.49 (3H, s), 1.44 (3H, s), 1.39 (3H, t, J=7.2 Hz), 1.30 (3H, s), 1.07-1.15 (1H, m), 1.09 (3H, s), 1.05 (3H, s); LC-MS (Mobile Phase: A: water (0.01% TFA); B: ACN (0.01% TFA); Gradient: 5%-95% B in 1.2 min; Flow Rate: 2.2 ml/min; Column: Poroshell 120 EC-C18, 4.6*30 mm, 2.7 um): rt=1.92 min, m/z=504.4 [M+H]$^+$, purity=98.02% (214 nm), 97.42% (254 nm).

Example 38

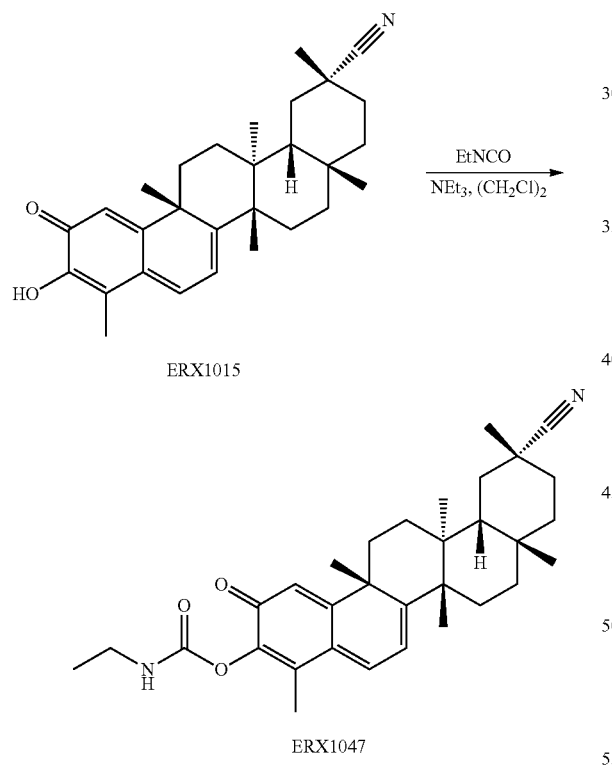

ERX1015

ERX1047

To a solution of ERX1015 (100 mg, 0.232 mmol) in (CH$_2$Cl)$_2$ (5 mL) was added Et$_3$N (117 mg, 0.16 mL, 1.158 mmol) followed by EtNCO (82 mg, 0.0917 mL, 1.158 mmol). The reaction was stirred at 50° C. overnight. The mixture was diluted with CH$_2$Cl$_2$ (300 mL), washed with brine (200 mL), dried over MgSO$_4$ and concentrated in vacuo. The residue was purified by prep-TLC (CH$_2$Cl$_2$/MeOH=20:1) to afford product (59.6 mg, 0.119 mmol, Yield=51%) as yellow solid. $^1$HNMR δ(400 MHz, CDCl3): 7.04 (1H, d, J=7.0 Hz), 6.47 (1H, s), 6.34 (1H, d, J=7.0 Hz), 5.17&4.71 (1H, br), 3.19-3.36 (2H, m), 2.19 (3H, s), 2.09-2.17 (3H, m), 1.89-2.02 (4H, m), 1.54-1.81 (8H, m), 1.48 (3H, s), 1.44 (3H, s), 1.29 (3H, s), 1.20-1.27 (3H, m), 1.23&1.14 (3H, t, J=7.2 Hz), 1.09 (3H, s), 1.05 (3H, s); LC-MS (Mobile Phase: A: water (0.01% TFA); B: ACN (0.01% TFA); Gradient: 5%-95% B in 1.2 min; Flow Rate: 2.2 ml/min; Column: Poroshell 120 EC-C18, 4.6*30 mm, 2.7 um): rt=1.83 min, m/z=503.4 [M+H]$^+$, purity=95.00% (214 nm), 98.55% (254 nm).

Example 39

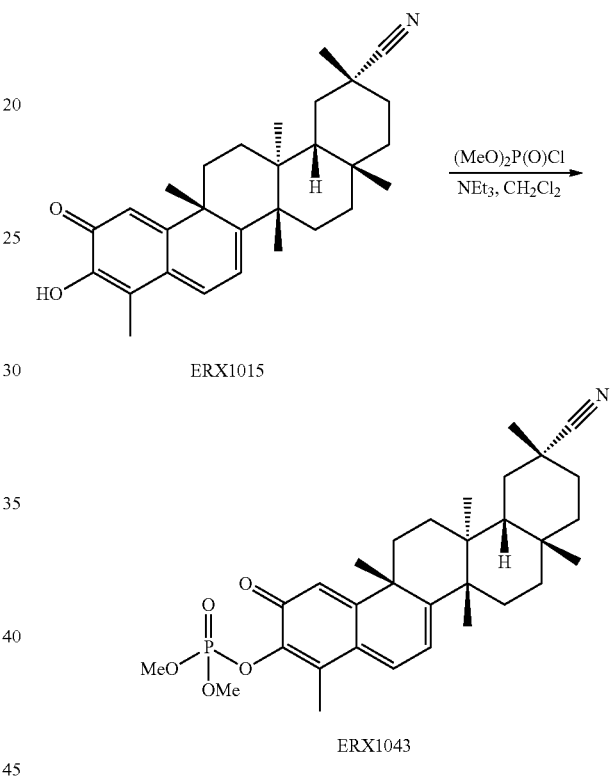

ERX1015

ERX1043

To a solution of ERX1015 (100 mg, 0.23 mmol) in CH$_2$Cl$_2$ (10 mL) was added NEt$_3$ (47 mg, 0.065 mL, 0.46 mmol) followed by (MeO)$_2$P(O)Cl (70 mg, 0.052 mL, 0.46 mmol). The reaction was stirred at room temperature overnight. The mixture was diluted with CH$_2$Cl$_2$ (200 mL), washed with brine (100 mL), dried over MgSO$_4$ and concentrated in vacuo. The residue was purified by prep-TLC (petroleum ether/EtOAc=2:1) to afford product (28 mg, 0.0519 mmol, Yield=23%) as yellow solid. $^1$HNMR δ(500 MHz, CDCl3): 7.06 (1H, d, J=7.0 Hz), 6.47 (1H, s), 6.35 (1H, d, J=7.0 Hz), 4.00 (3H, d, J=11.4 Hz), 3.96 (3H, d, J=11.2 Hz), 2.30 (3H, d, J=1.5 Hz), 2.10-2.18 (3H, m), 1.90-2.00 (3H, m), 1.54-1.80 (8H, m), 1.47 (3H, s), 1.44 (3H, s), 1.29 (3H, s), 1.09-1.14 (1H, m), 1.09 (3H, s), 1.05 (3H, s); LC-MS (Mobile Phase: A: water (0.1% TFA); B: ACN (0.1% TFA); Gradient: 5%-95% B in 1.2 min; Flow Rate: 2.2 ml/min; Column: Poroshell 120 EC-C18, 4.6*30 mm, 2.7 um): rt=1.82 min, m/z=540.3 [M+H]$^+$, purity=94.11% (254 nm).

Example 40

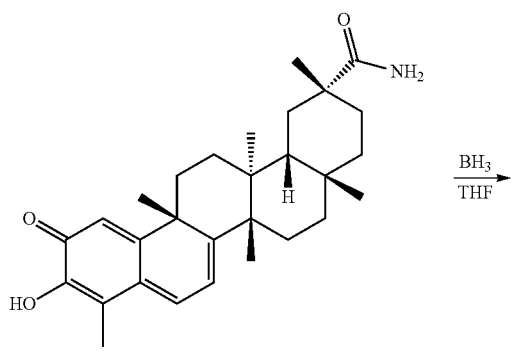

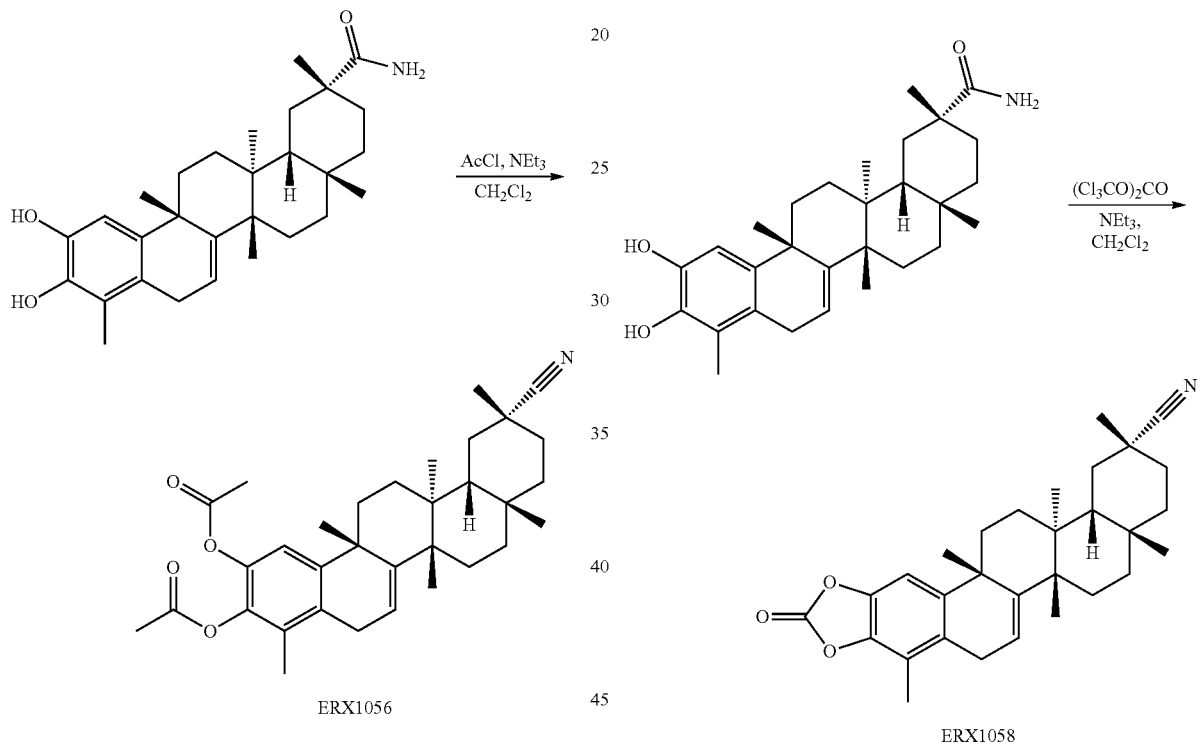

To a solution of ERX1006 (250 mg, 0.56 mmol) in THF (15 mL) was added 1M BH$_3$.THF (1.67 mL, 1.67 mmol). The reaction was stirred at room temperature for 1 hour. The reaction was quenched by addition of water (5 mL). Most solvent was removed in vacuo and the solution was acidified by 0.1 M HCl to pH 5-6. The mixture was diluted with CH$_2$Cl$_2$ (200 mL), filtered. The filtrate was washed with brine (100 mL), dried over MgSO$_4$ and concentrated in vacuo to afford crude product (250 mg, 0.554 mmol, Yd=100%) as white solid. The crude was used in the next step without further purification.

To a solution of intermediate (250 mg, 0.56 mmol) in CH$_2$Cl$_2$ (15 mL) was added NEt$_3$ (224 mg, 0.31 mL, 2.21 mmol) followed by AcCl (174 mg, 2.21 mmol). The reaction was stirred at room temperature overnight. The reaction was quenched by addition of water (5 mL). The mixture was diluted with CH$_2$Cl$_2$ (200 mL), washed with sat Na$_2$CO$_3$ (2×100 mL) followed by brine (100 mL), dried over MgSO$_4$ and concentrated in vacuo. The residue was purified by prep-TLC (petroleum ether/EtOAc=10:1) to afford product (40 mg, 0.0773 mmol, Yd=14%) as white solid. $^1$HNMR δ(400 MHz, CDCl3): 7.00 (1H, s), 5.78 (1H, d, J=6.0 Hz), 3.35 (1H, dd, J=21.0, 6.0 Hz), 3.07 (1H, d, J=21.0 Hz), 2.31 (3H, s), 2.27 (3H, s), 2.03-2.20 (4H, m), 2.07 (3H, s), 1.85-1.97 (2H, m), 1.48-1.72 (8H, m), 1.43 (3H, s), 1.36 (3H, s), 1.24 (3H, s), 1.02-1.10 (1H, m), 1.07 (3H, s), 1.06 (3H, s); LC-MS (Mobile Phase: A: water (0.01% TFA); B: ACN (0.01% TFA); Gradient: 5%-95% B in 1.2 min; Flow Rate: 2.2 ml/min; Column: Poroshell 120 EC-C18, 4.6*30 mm, 2.7 um): rt=2.06 min, m/z=518.3 [M+H]$^+$, purity=97.21% (214 nm).

Example 41

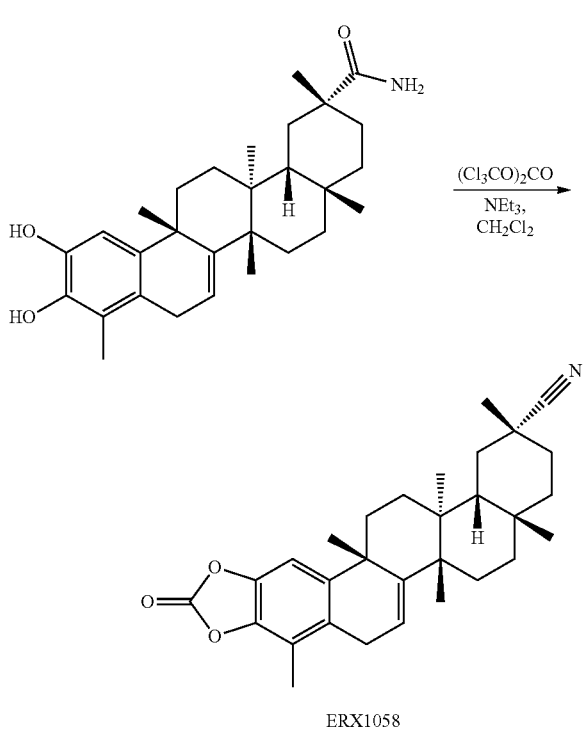

To a solution of intermediate (300 mg, 0.66 mmol) in CH$_2$Cl$_2$ (10 mL) was added NEt$_3$ (134 mg, 0.18 mL, 1.32 mmol) followed by (Cl$_3$CO)$_2$CO (395 mg, 1.32 mmol). The reaction was stirred at room temperature overnight. The reaction was quenched by addition of water (5 mL). The mixture was diluted with CH$_2$Cl$_2$ (200 mL), washed with sat Na$_2$CO$_3$ (2×100 mL) followed by brine (100 mL), dried over MgSO$_4$ and concentrated in vacuo. The residue was purified by prep-TLC (petroleum ether/EtOAc=10:1) to afford product (70 mg, 0.152 mmol, Yd=18%) as white solid. $^1$HNMR δ(500 MHz, CDCl3): 7.11 (1H, s), 5.83 (1H, d, J=6.4 Hz), 3.41 (1H, dd, J=21.0, 6.4 Hz), 3.09 (1H, d, J=21.0 Hz), 2.28 (3H, s), 2.09-2.18 (4H, m), 1.87-1.96 (2H, m), 1.49-1.72 (8H, m), 1.44 (3H, s), 1.34 (3H, s), 1.25 (3H, s), 1.06-1.11 (1H, m), 1.07 (3H, s), 1.06 (3H, s); LC-MS (Mobile Phase: A: water (0.1% TFA); B: ACN (0.1% TFA); Gradient: 5%-95% B in 1.2 min; Flow Rate: 2.2 ml/min; Column: Poroshell 120 EC-C18, 4.6*30 mm, 2.7 um): rt=2.23 min, m/z=460.3 [M+H]$^+$, purity=97.77% (214 nm).

Example 42

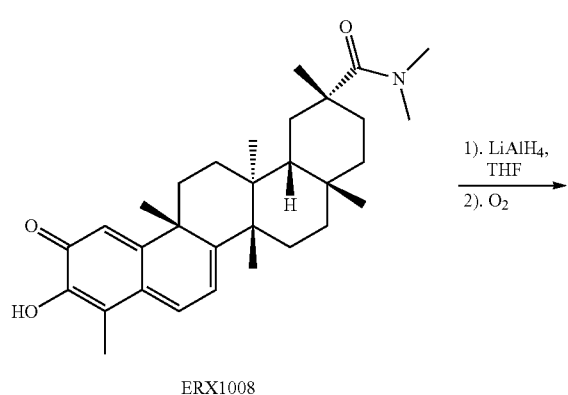

ERX1008

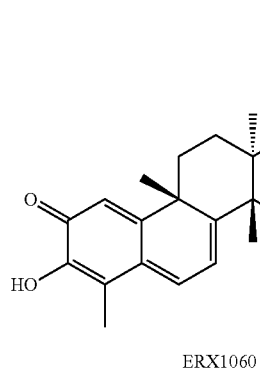

ERX1060

To a solution of ERX1008 (477 mg, 1.0 mmol) in anhydrous THF (40 mL) was added LiAlH4 (2.38 g, 75 mmol). The mixture was refluxed overnight. The reaction was quenched by sat. NH$_4$Cl solution. The mixture was heated at 50° C. for 2 hours and filtered through a thin layer of silica gel. The solid was washed with THF (3×50 mL). The combined filtrate was concentrated in vacuo. The residue was purified by prep-TLC (CH$_2$Cl$_2$: MeOH=10:1) to afford product (23.9 mg, 0.0515 mmol, Yd=5%) as red solid. $^1$HNMR δ(500 MHz, CDCl3): 7.03 (1H, d, J=7.1 Hz), 6.96 (1H, s), 6.52 (1H, s), 6.39 (1H, d, J=7.1 Hz), 2.34 (6H, br), 2.22 (3H, s), 1.95-2.25 (4H, m), 1.35-1.88 (12H, m), 1.44 (3H, s), 1.42 (3H, s), 1.24 (3H, s), 1.09 (3H, s), 0.97-1.03 (1H, m), 0.79 (3H, s); LC-MS (Mobile Phase: A: water (0.01% TFA) B: ACN (0.01% TFA); Gradient: 5%-95% B in 1.4 min; Flow Rate: 2.3 ml/min; Column: SunFire C18, 4.6*50 mm, 3.5 um): rt=1.83 min, m/z=480.4 [M+H]$^+$, purity=98.20% (214 nm), 99.51% (254 nm).

Example 43

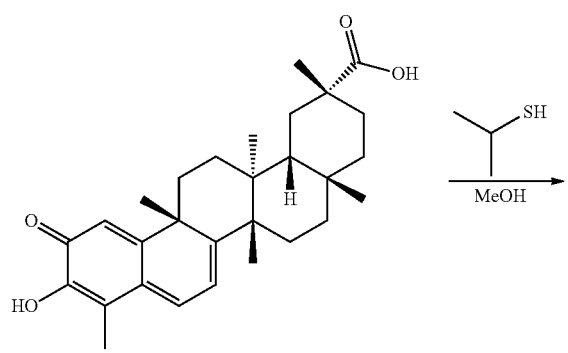

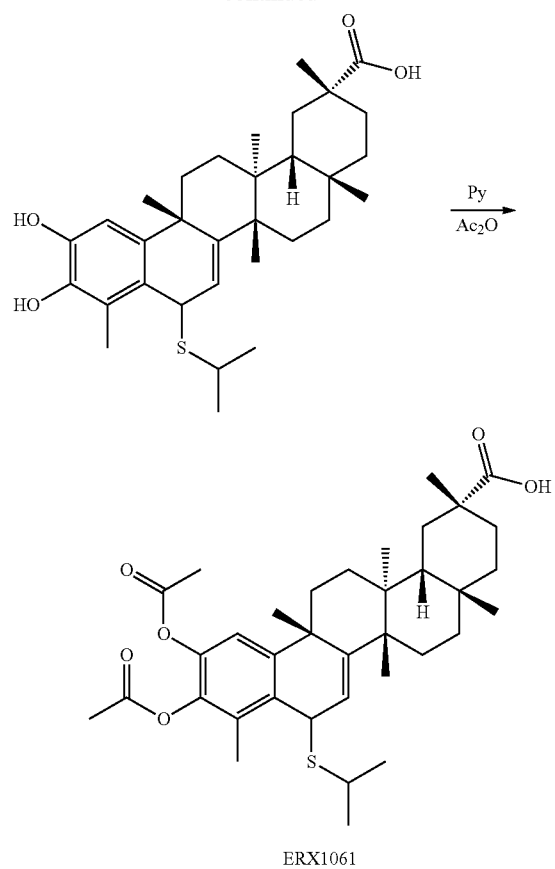

ERX1061

To a solution of celastrol (100 mg, 0.222 mmol) in MeOH (3 mL) was added i-C$_3$H7SH (84.5 mg, 0.10 mL, 1.11 mmol). The reaction was stirred at room temperature for 3 hours. The solution was turned from red to pale reddish-yellow. Then the solution was concentrated in vacuo to afford crude mixture which was used in the next step without further purification.

To a crude mixture (117 mg, 0.222 mmol, theoretical amount) in Ac$_2$O (4 mL) was added pyridine (0.5 mL). The reaction was stirred at room temperature overnight. Then the mixture was diluted with EtOAc (200 mL), washed with water (2×100 mL), brine (100 mL), dried over MgSO$_4$ and concentrated in vacuo. The residue was purified by silica gel chromatography (petroleum ether/EtOAc=5:2) to afford product (85.2 mg, 0.139 mmol, overall yield=63%) as white solid. $^1$HNMR δ (400 MHz, CDCl3): 7.01 (1H, s), 5.97 (1H, d, J=6.2 Hz), 4.57 (1H, d, J=6.2 Hz), 3.11-3.22 (1H, m), 2.39 (1H, d, J=15.8 Hz), 2.30 (3H, s), 2.27 (3H, s), 2.26 (3H, s), 1.25-2.15 (13H, m), 1.58 (3H, s), 1.39 (1H, d, J=6.5 Hz), 1.27 (1H, d, J=6.5 Hz), 1.25 (3H, s), 1.16 (3H, s), 1.07 (3H, s), 0.89-0.96 (1H, m), 0.67 (3H, s); LC-MS (Mobile Phase: A: water (0.01% TFA) B: ACN (0.01% TFA); Gradient: 5%-95% B in 1.7 min; Flow Rate: 2.2 ml/min, Column: SunFire C18, 4.6*50 mm, 3.5 um): rt=2.68 min, m/z=535.2 [M−C$_3$H7S]$^+$, purity=100% (214,254 nm).

Example 44

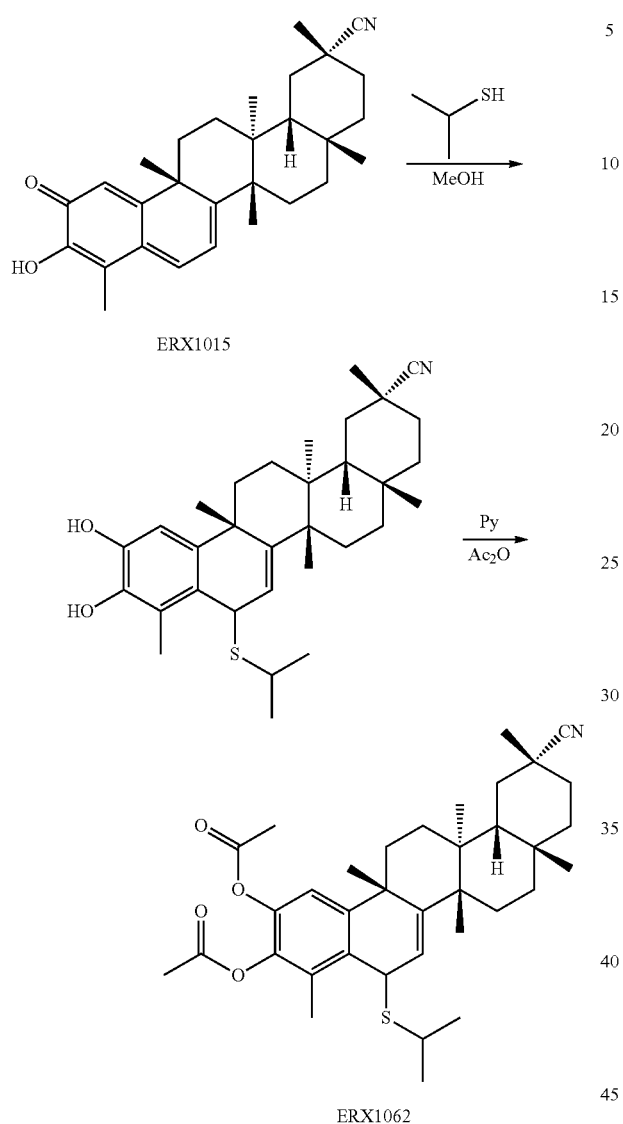

To a solution of celastrol (50 mg, 0.111 mmol) in MeOH (10 mL) was added i-C₃H7SH (44 mg, 0.58 mmol). The reaction was stirred at room temperature for 1 hour. The solution was turned from red to almost colorless. Then the solution was concentrated in vacuo to afford crude mixture which was used in the next step without further purification.

To a crude mixture (56.3 mg, 0.111 mmol, theoretical amount) in Ac$_2$O (3 mL) was added pyridine (91 mg, 1.2 mmol). The reaction was stirred at room temperature overnight. Then the mixture was diluted with EtOAc (200 mL), washed with water (2×100 mL), brine (100 mL), dried over MgSO$_4$ and concentrated in vacuo. The residue was purified by silica gel chromatography (petroleum ether/EtOAc=4:1) to afford product (35 mg, 0.059 mmol, overall yield=49%) as white solid. $^1$HNMR δ(500 MHz, CDCl3): 7.02 (1H, s), 6.01 (1H, d, J=6.2 Hz), 4.59 (1H, d, J=6.2 Hz), 3.13-3.22 (1H, m), 2.30 (3H, s), 2.28 (3H, s), 2.26 (3H, s), 1.88-2.18 (6H, m), 1.50-1.74 (8H, m), 1.64 (3H, s), 1.43 (3H, s), 1.40 (3H, d, J=6.7 Hz), 1.29 (3H, d, J=6.7 Hz), 1.27 (3H, s), 1.06-1.11 (1H, m), 1.07 (3H, s), 1.04 (3H, s); LC-MS (Mobile Phase: A: water (0.1% TFA) B: ACN (0.1% TFA); Gradient: 5%-95% B in 1.2 min; Flow Rate: 2.2 ml/min Column: Poroshell 120 EC-C18, 4.6*30 mm, 2.7 um): rt=2.11 min, m/z=516.3 [M−C$_3$H7S]$^+$, purity=100% (214, 254 nm).

Example 45

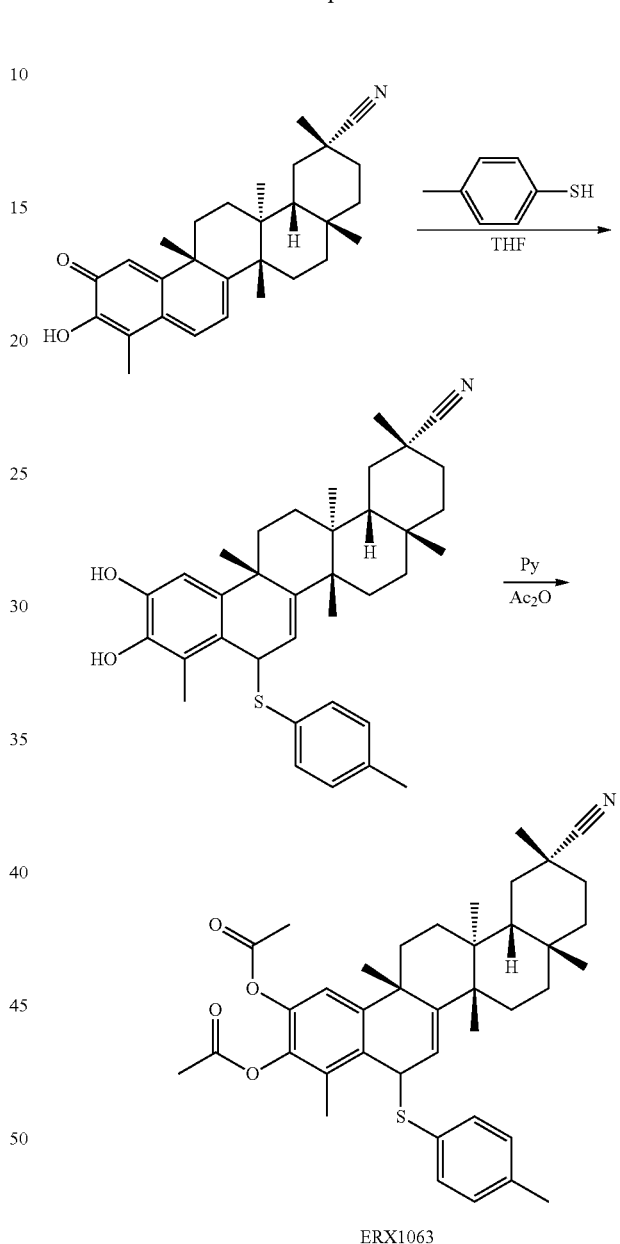

To a solution of SM (50 mg, 0.116 mmol) in THF (3 mL) was added 4-methylbenzenethiol (144 mg, 1.16 mmol). The reaction was stirred at room temperature for 3 hours. The solution was turned from deep reddish to pale reddish. Then the solution was concentrated in vacuo to afford crude mixture which was used in the next step without further purification.

To a crude mixture (64.5 mg, 0.116 mmol, theoretical amount) in Ac$_2$O (2 mL) was added pyridine (0.25 mL). The reaction was stirred at room temperature overnight. Then the mixture was diluted with EtOAc (200 mL), washed with water (2×100 mL), brine (100 mL), dried over MgSO$_4$ and concentrated in vacuo. The residue was purified by silica gel chromatography (petroleum ether/EtOAc=5:2) to afford product (62.4 mg, 0.0975 mmol, overall yield=84%) as white solid. $^1$HNMR δ(400 MHz, CDCl3): 7.36 (1H, d, J=8.0 Hz), 7.12 (1H, d, J=8.0 Hz), 7.03 (1H, s), 5.77 (1H, d, J=6.1 Hz), 4.79 (1H, d, J=6.1 Hz), 2.35 (3H, s), 2.32 (3H, s), 2.28 (3H, s), 1.84-2.15 (6H, m), 1.35-1.68 (8H, m), 1.51 (3H, s), 1.42 (3H, s), 1.26 (3H, s), 1.02-1.08 (1H, m), 1.06 (3H, s), 1.00 (3H, s); LC-MS (Mobile Phase: A: water (0.1% TFA) B: ACN (0.1% TFA); Gradient: 5%-95% B in 1.2 min; Flow Rate: 2.2 ml/min; Column: Poroshell 120 EC-C18, 4.6*30 mm, 2.7 um): rt=2.17 min, m/z=516.3 [M–C$_7$H7S]$^+$, purity=98.54% (214 nm), 96.35% (254 nm).

Example 46

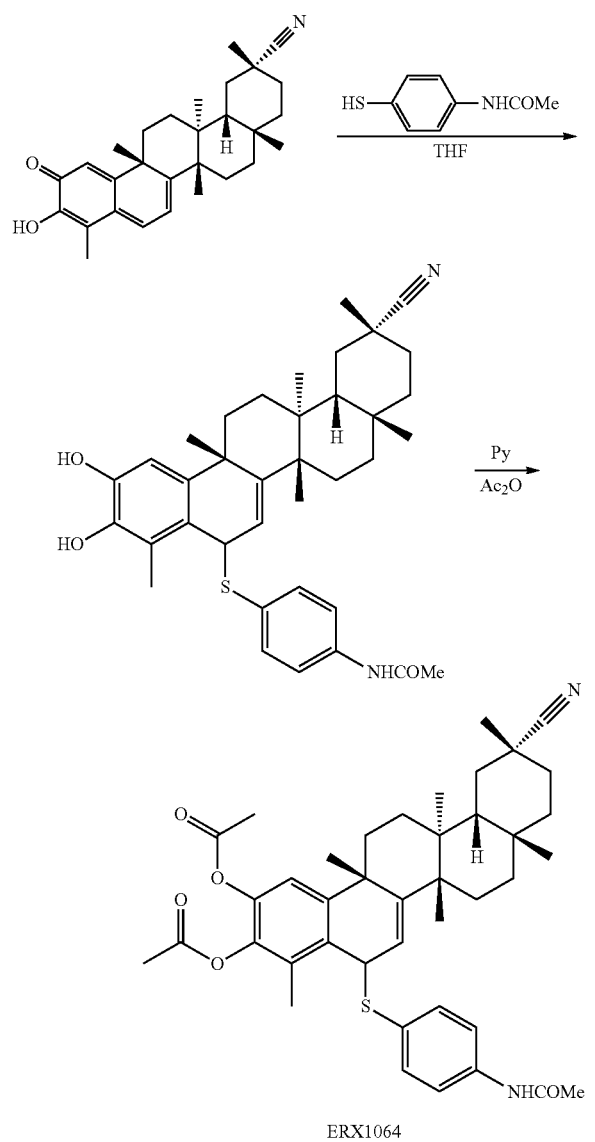

To a solution of SM (50 mg, 0.116 mmol) in THF (2 mL) was added 4-acetamidothiophenol (58 mg, 0.348 mmol). The reaction was stirred at room temperature for 1 hour. The solution was turned from deep reddish to pale reddish. Then the solution was concentrated in vacuo to afford crude mixture which was used in the next step without further purification.

To a crude mixture (69.4 mg, 0.116 mmol, theoretical amount) in Ac$_2$O (2 mL) was added pyridine (0.5 mL). The reaction was stirred at room temperature overnight. Then the mixture was diluted with EtOAc (200 mL), washed with water (2×100 mL), brine (100 mL), dried over MgSO$_4$ and concentrated in vacuo. The residue was purified by prep-TLC (petroleum ether/EtOAc=1:1) to afford product (45.1 mg, 0.066 mmol, overall yield=57%) as white solid. $^1$HNMR δ(400 MHz, CDCl3): 7.47 (1H, d, J=8.6 Hz), 7.40 (1H, d, J=8.6 Hz), 7.20 (1H, s), 7.03 (1H, s), 5.76 (1H, d, J=6.2 Hz), 4.80 (1H, d, J=6.2 Hz), 2.33 (3H, s), 2.31 (3H, s), 2.28 (3H, s), 2.19 (3H, s), 1.82-2.14 (7H, m), 1.30-1.66 (7H, m), 1.49 (3H, s), 1.42 (3H, s), 1.26 (3H, s), 1.02-1.09 (1H, m), 1.06 (3H, s), 1.00 (3H, s); LC-MS (Mobile Phase: A: water (0.01% TFA) B: ACN (0.01% TFA); Gradient: 5%-95% B in 1.4 min; Flow Rate: 2.3 ml/min; Column: SunFire C18, 4.6*50 mm, 3.5 um): rt=2.26 min, m/z=684.4 [M+H]$^+$, purity=100% (214, 254 nm).

Example 47

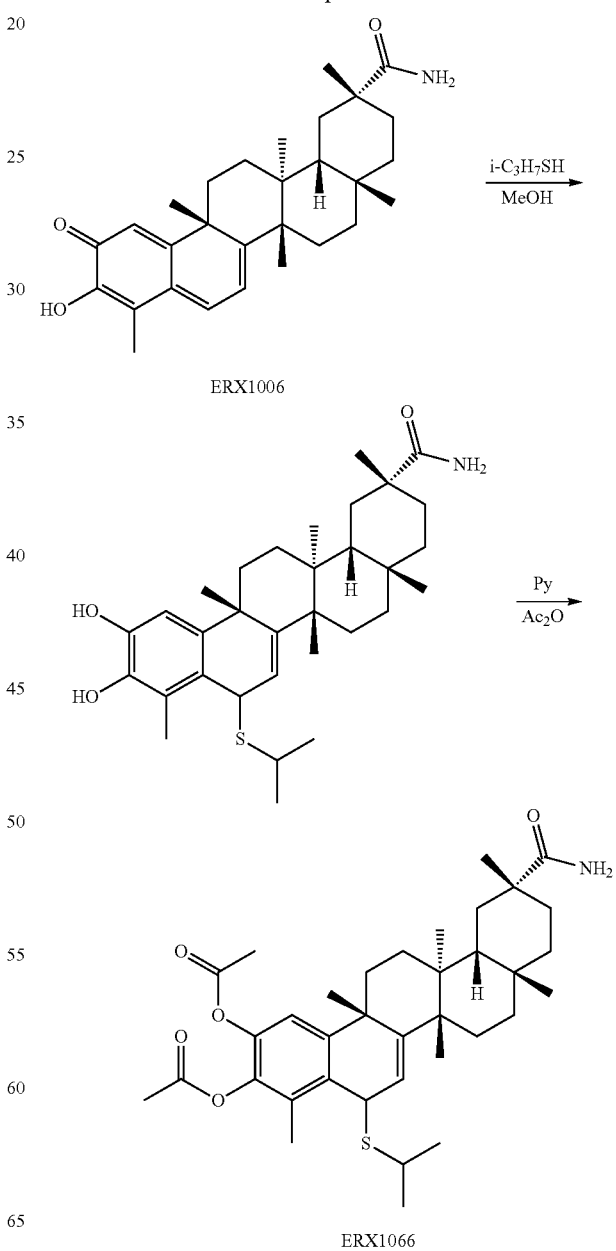

To a solution of ERX1006 (90 mg, 0.2 mmol) in MeOH (3 mL) was added i-C$_3$H$_7$SH (23 mg, 0.3 mmol). The reaction was stirred at room temperature for 2 hours. The solution was turned from red to pale yellow. Then the solution was concentrated in vacuo to afford crude mixture.

To a crude mixture prepared above in Ac$_2$O (4 mL) was added pyridine (0.5 mL). The reaction was stirred at room temperature overnight. Then the mixture was diluted with EtOAc (200 mL), washed with water (2×100 mL), brine (100 mL), dried over MgSO$_4$ and concentrated in vacuo. The residue was purified by prep-HPLC (petroleum ether/acetone=1:1) to afford product (46.6 mg, 0.0764 mmol, overall yield=38%) as white solid. $^1$HNMR δ(400 MHz, CDCl3): 7.00 (1H, s), 5.97 (1H, d, J=6.3 Hz), 5.63 (1H, br), 5.24 (1H, br), 4.57 (1H, d, J=6.3 Hz), 3.12-3.22 (1H, m), 2.40 (1H, d, J=15.3 Hz), 2.30 (3H, s), 2.27 (3H, s), 2.26 (3H, s), 1.42-2.10 (13H, m), 1.57 (3H, s), 1.40 (3H, d, J=6.7 Hz), 1.28 (3H, d, J=6.7 Hz), 1.26 (3H, s), 1.19 (3H, s), 1.11 (3H, s), 0.95-1.02 (1H, m), 0.74 (3H, s); LC-MS (Mobile Phase: A: water (0.01% TFA) B: ACN (0.01% TFA); Gradient: 5%-95% B in 1.7 min; Flow Rate: 2.2 ml/min; Column: SunFire C18, 4.6*50 mm, 3.5 um): rt=2.50 min, m/z=610.3 [M+H]$^+$, purity=96.87% (214 nm).

Example 48

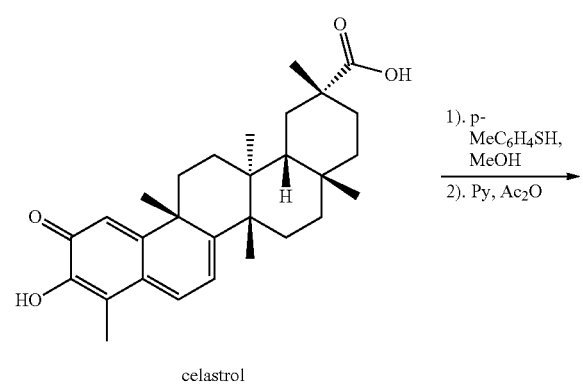

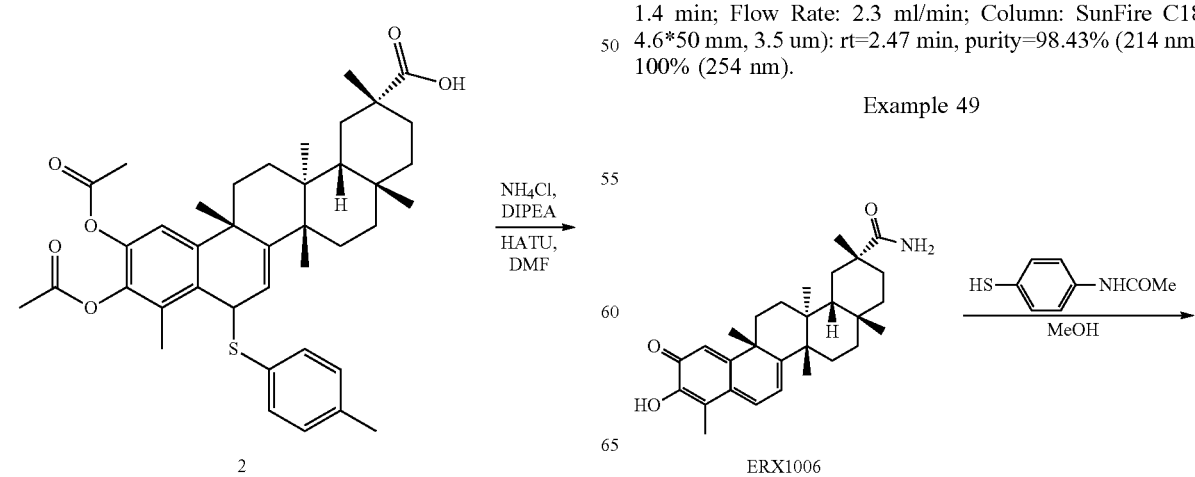

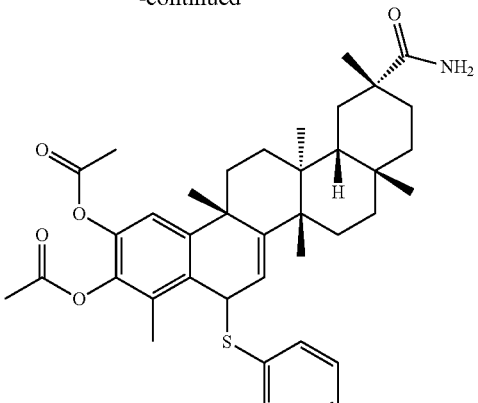

ERX1067

To a solution of celastrol (200 mg, 0.44 mmol) in MeOH (6 mL) was added p-MeC$_6$H$_4$SH (82 mg, 0.66 mmol). The reaction was stirred at room temperature for 1 hour. The solution was turned from red to pale yellow. Then the solution was concentrated in vacuo to afford crude mixture To a crude mixture prepared above in Ac$_2$O (8 mL) was added pyridine (1 mL). The reaction was stirred at room temperature overnight. Then the mixture was diluted with EtOAc (200 mL), washed with water (2×100 mL), brine (100 mL), dried over MgSO$_4$ and concentrated in vacuo. The residue was purified by silica gel chromatography (petroleum ether/ethyl acetate=1:1) to afford product (30 mg, 0.0457 mmol, Yield=10%) as white solid.

To a solution of compound 2 (100 mg, 0.15 mmol) in DMF (10 mL) was added NH$_4$Cl (18 mg, 0.34 mmol), HATU (65 mg, 0.17 mmol) followed by DIPEA (39 mg, 0.3 mmol). The reaction was stirred at room temperature overnight. Then the solution was diluted with EtOAc (200 mL), washed with brine (100 mL), dried over MgSO$_4$ and concentrated in vacuo. The residue was purified by prep-TLC (EtOAc) to afford product (30 mg, 0.0456 mmol, Yield=30%) as white solid. $^1$HNMR δ(500 MHz, CDCl3): 7.35 (1H, d, J=7.7 Hz), 7.12 (1H, d, J=7.7 Hz), 7.02 (1H, s), 5.73 (1H, d, J=6.1 Hz), 5.61 (1H, br), 5.15 (1H, br), 4.76 (1H, d, J=6.1 Hz), 2.38 (1H, d, J=15.2 Hz), 2.35 (3H, s), 2.32 (3H, s), 2.31 (3H, s), 2.28 (3H, s), 1.30-2.06 (13H, m), 1.48 (3H, s), 1.24 (3H, s), 1.18 (3H, s), 1.09 (3H, s), 0.94-0.99 (1H, m), 0.70 (3H, s); LC-MS (Mobile Phase: A: water (0.01% TFA) B: ACN (0.01% TFA); Gradient: 5%-95% B in 1.4 min; Flow Rate: 2.3 ml/min; Column: SunFire C18, 4.6*50 mm, 3.5 um): rt=2.47 min, purity=98.43% (214 nm), 100% (254 nm).

Example 49

105
-continued

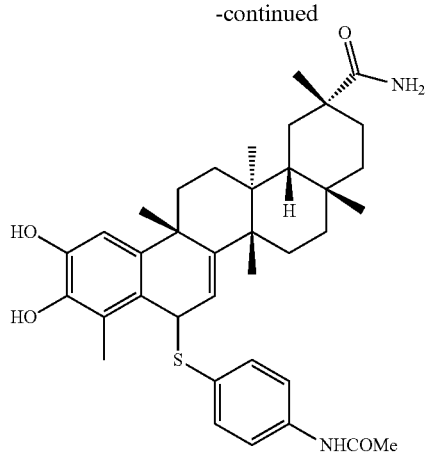

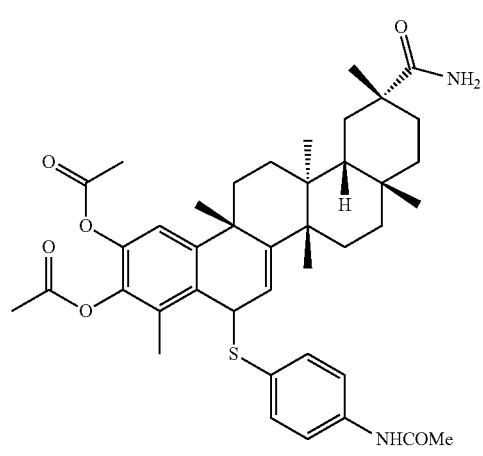

ERX1066

To a solution of ERX1006 (500 mg, 11.0 mmol) in MeOH (15 mL) was added 4-acetamidothiophenol (250 mg, 16.0 mmol). The reaction was stirred at room temperature for 1 hour. The solution was turned from deep reddish to pale reddish. Then the solution was concentrated in vacuo to afford crude mixture.

To a crude mixture prepared above in Ac$_2$O (20 mL) was added pyridine (2.5 mL). The reaction was stirred at room temperature overnight. Then the mixture was diluted with EtOAc (200 mL), washed with water (2×100 mL), brine (100 mL), dried over MgSO$_4$ and concentrated in vacuo. The residue was purified by prep-TLC (EtOAc) to afford product (250 mg, 0.357 mmol, Yield=51%) as white solid. $^1$HNMR δ(500 MHz, CDCl3): 7.45 (1H, d, J=8.5 Hz), 7.39 (1H, d, J=8.5 Hz), 7.30 (1H, s), 7.01 (1H, s), 5.71 (1H, d, J=6.3 Hz), 5.63 (1H, br), 5.21 (1H, br), 4.76 (1H, d, J=6.3 Hz), 2.39 (1H, d, J=16.1 Hz), 2.32 (3H, s), 2.30 (3H, s), 2.28 (3H, s), 2.18 (3H, s), 1.30-2.06 (13H, m), 1.48 (3H, s), 1.23 (3H, s), 1.18 (3H, s), 1.09 (3H, s), 0.92-0.99 (1H, m), 0.69 (3H, s); LC-MS (Mobile Phase: A: water (0.01% TFA) B: ACN (0.01% TFA); Gradient: 5%-95% B in 1.4 min; Flow Rate: 2.3 ml/min; Column: SunFire C18, 4.6*50 mm, 3.5 um): rt=2.13 min, m/z=701.3 [M+H]$^+$, purity=99.36% (214 nm), 97.26% (254 nm).

106
Example 50

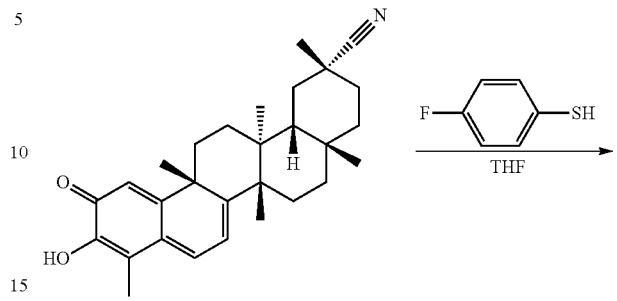

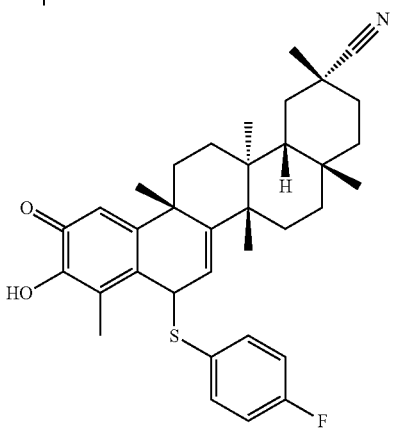

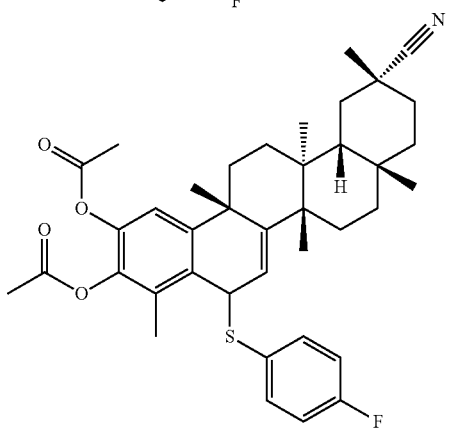

ERX1071

To a solution of SM (50 mg, 0.116 mmol) in THF (3 mL) was added 4-fluorobenzenethiol (74 mg, 0.579 mmol). The reaction was stirred at room temperature for 1 hour. The solution was turned from deep reddish to pale reddish. Then the solution was concentrated in vacuo to afford crude mixture which was used in the next step without further purification.

To a crude mixture (74.7 mg, 0.116 mmol, theoretical amount) in Ac$_2$O (2 mL) was added pyridine (0.5 mL). The reaction was stirred at room temperature overnight. Then the mixture was diluted with EtOAc (200 mL), washed with water (2×100 mL), brine (100 mL), dried over MgSO$_4$ and concentrated in vacuo. The residue was purified by prep-TLC (petroleum ether/EtOAc=3:1) to afford product (18.2 mg, 0.0283 mmol, Yield=24%) as white solid.

$^1$HNMR δ(400 MHz, CDCl3): 7.38-7.43 (2H, m), 6.98-7.04 (3H, m), 5.72 (1H, d, J=6.0 Hz), 4.81 (1H, d, J=6.0 Hz), 2.33 (3H, s), 2.31 (3H, s), 2.28 (3H, s), 1.84-2.14 (6H, m), 1.32-1.66 (8H, m), 1.44 (3H, s), 1.42 (3H, s), 1.25 (3H, s), 1.02-1.10 (1H, m), 1.06 (3H, s), 1.00 (3H, s); LC-MS (Mobile Phase: A: water (0.1% TFA) B: ACN (0.1% TFA); Gradient: 5%-95% B in 1.2 min; Flow Rate: 2.2 ml/min; Column: Poroshell 120 EC-C18, 4.6*30 mm, 2.7 um): rt=2.10 min, m/z=516.3 [M−FC6H4S]$^+$, purity=97.87% (214 nm), 99.10% (254 nm).

Example 51

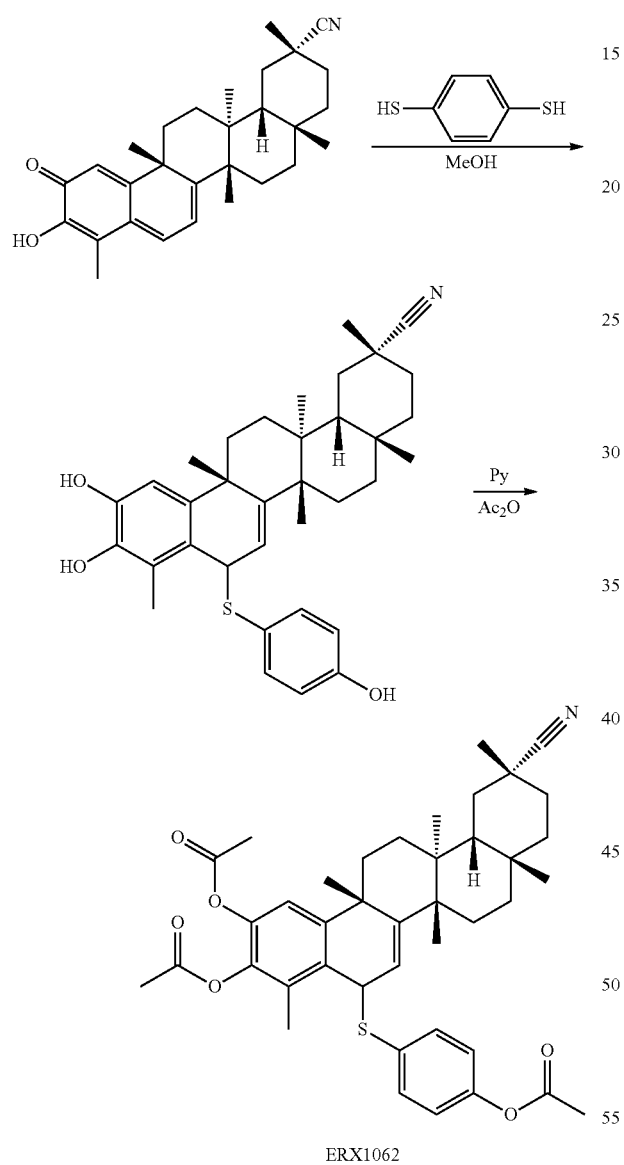

ERX1062

To a solution of celastrol (50 mg, 0.116 mmol) in MeOH (5 mL) was added 4-hydroxybenzenethiol (44 mg, 0.348 mmol). The reaction was stirred at room temperature for 1 hour. The solution was turned from red to almost colorless. Then the solution was concentrated in vacuo to afford crude mixture which was used in the next step without further purification.

To a crude mixture (61.9 mg, 0.116 mmol, theoretical amount) in Ac$_2$O (3 mL) was added pyridine (0.3 mL). The reaction was stirred at room temperature overnight. Then the mixture was diluted with EtOAc (200 mL), washed with water (2×100 mL), brine (100 mL), dried over MgSO$_4$ and concentrated in vacuo. The residue was purified by silica gel chromatography (petroleum ether/EtOAc=3:1) to afford product (20 mg, 0.0292 mmol, Yield=18%) as white solid. $^1$HNMR δ(400 MHz, CDCl3): 7.43 (2H, d, J=8.4 Hz), 7.04 (2H, d, J=8.4 Hz), 7.03 (1H, s), 5.79 (1H, d, J=6.3 Hz), 4.85 (1H, d, J=6.3 Hz), 2.32 (3H, s), 2.30 (6H, s), 2.28 (3H, s), 1.82-2.14 (6H, m), 1.32-1.66 (9H, m), 1.47 (3H, s), 1.42 (3H, s), 1.25 (3H, s), 1.02-1.10 (1H, m), 1.06 (3H, s), 1.00 (3H, s); LC-MS (Mobile Phase: A: water (0.1% TFA) B: ACN (0.1% TFA); Gradient: 5%-95% B in 1.2 min; Flow Rate: 2.2 ml/min; Column: Poroshell 120 EC-C18, 4.6*30 mm, 2.7 um): rt=2.01 min, m/z=516.3 [M−MeCO$_2$C$_6$H$_4$S]$^+$, purity=100% (214 nm), 99.7% (254 nm).

Example 52

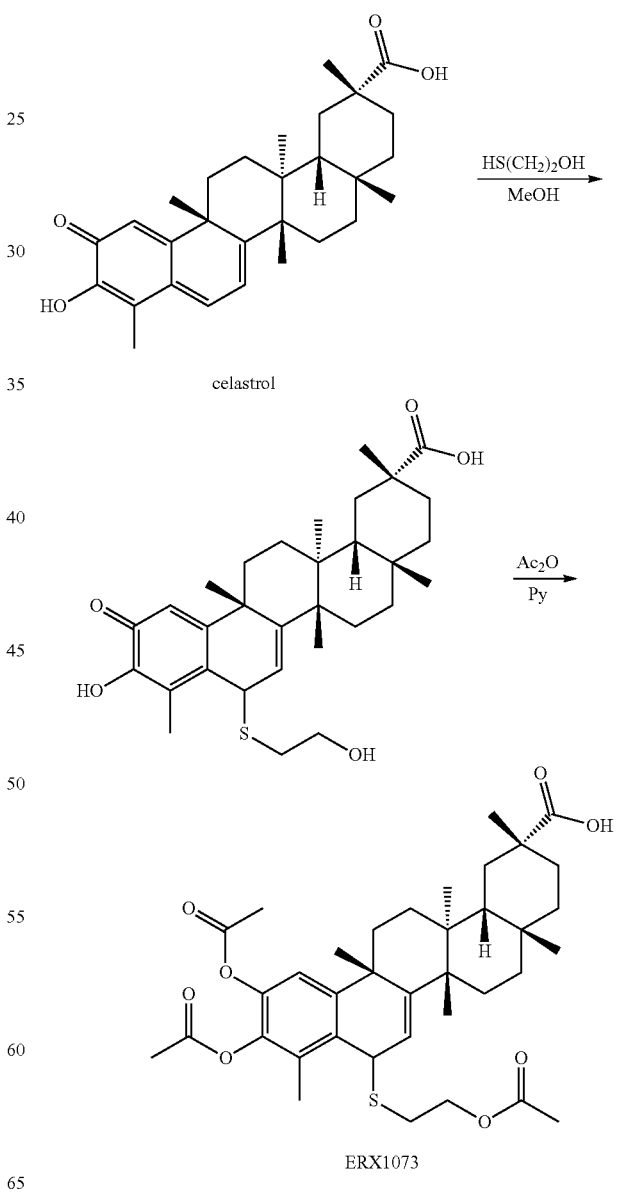

ERX1073

To a solution of celastrol (200 mg, 0.44 mmol) in MeOH (6 mL) was added HSCH$_2$CH$_2$OH (53 mg, 0.67 mmol). The reaction was stirred at room temperature for 1 hour. The solution was turned from red to pale yellow. Then the solution was concentrated in vacuo to afford crude mixture.

To a crude mixture prepared above in Ac$_2$O (8 mL) was added pyridine (1 mL). The reaction was stirred at room temperature overnight. Then the mixture was diluted with EtOAc (200 mL), washed with water (2×100 mL), brine (100 mL), dried over MgSO$_4$ and concentrated in vacuo. The residue was purified by prep-TLC (EtOAc) to afford product (20 mg, 0.0305 mmol, Yield=7%) as white solid. $^1$HNMR δ(500 MHz, CDCl3): 7.02 (1H, s), 5.98 (1H, d, J=6.0 Hz), 4.63 (1H, d, J=6.0 Hz), 4.20-4.34 (2H, m), 2.96-3.01 (1H, m), 2.74-2.83 (1H, m), 2.38 (1H, d, J=15.5 Hz), 2.30 (3H, s), 2.27 (3H, s), 2.07 (3H, s), 1.30-2.14 (11H, m), 1.58 (3H, s), 1.25 (3H, s), 1.12 (3H, s), 1.07 (3H, s), 0.82-0.94 (3H, m), 0.65 (3H, s); LC-MS: rt=2.33 min, m/z=535.3 [M−MeCO$_2$CH$_2$CH$_2$S]$^+$, purity=95.75% (214 nm).

Example 53

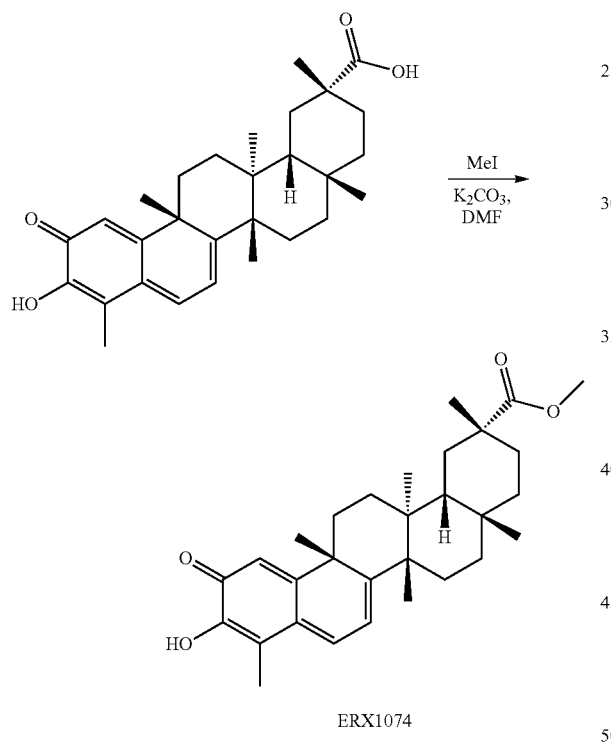

ERX1074

To a solution of celastrol (300 mg, 0.666 mmol) in DMF (3 mL) was added K$_2$CO$_3$ (184 mg, 1.332 mmol) followed by CH$_3$I (141 mg, 0.061 ml, 0.732 mmol). The reaction was stirred at room temperature for 2 hours. A lot of solid appeared. The mixture was diluted with H$_2$O (30 mL), filtered. The solid was dissolved with CH$_2$Cl$_2$ (300 mL), washed with H$_2$O (2×100 mL) followed by brine (100 mL), dried over MgSO$_4$ and concentrated in vacuo. The residue was purified by prep-TLC (petroleum ether/ethyl acetate=3: 1) to afford product (87.6 mg, 0.189 mmol, Yield=28%) as reddish-yellow solid. $^1$HNMR δ(400 MHz, CDCl$_3$): 7.02 (1H, dd, J=7.0, 1.2 Hz), 6.96 (1H, s), 6.53 (1H, d, J=1.2 Hz), 6.35 (1H, d, J=7.0 Hz), 3.55 (3H, s), 2.42 (1H, d, J=15.6 Hz), 2.18 (3H, s), 2.00-2.20 (3H, m), 1.30-1.93 (10H, m), 1.45 (3H, s), 1.26 (3H, s), 1.18 (3H, s), 1.10 (3H, s), 0.94-1.01 (1H, m), 0.53 (3H, s); LC-MS (Mobile Phase: A: water (10 mM Ammonium hydrogen carbonate) B: ACN; Gradient: 5%-95% B in 1.5 min; Flow Rate: 2.0 ml/min; Column: XBridge C18, 4.6*50 mm, 3.5 um): rt=2.77 min, m/z=465.4 [M+H]$^+$, purity=97.25% (214 nm), 99.77% (254 nm).

Example 54

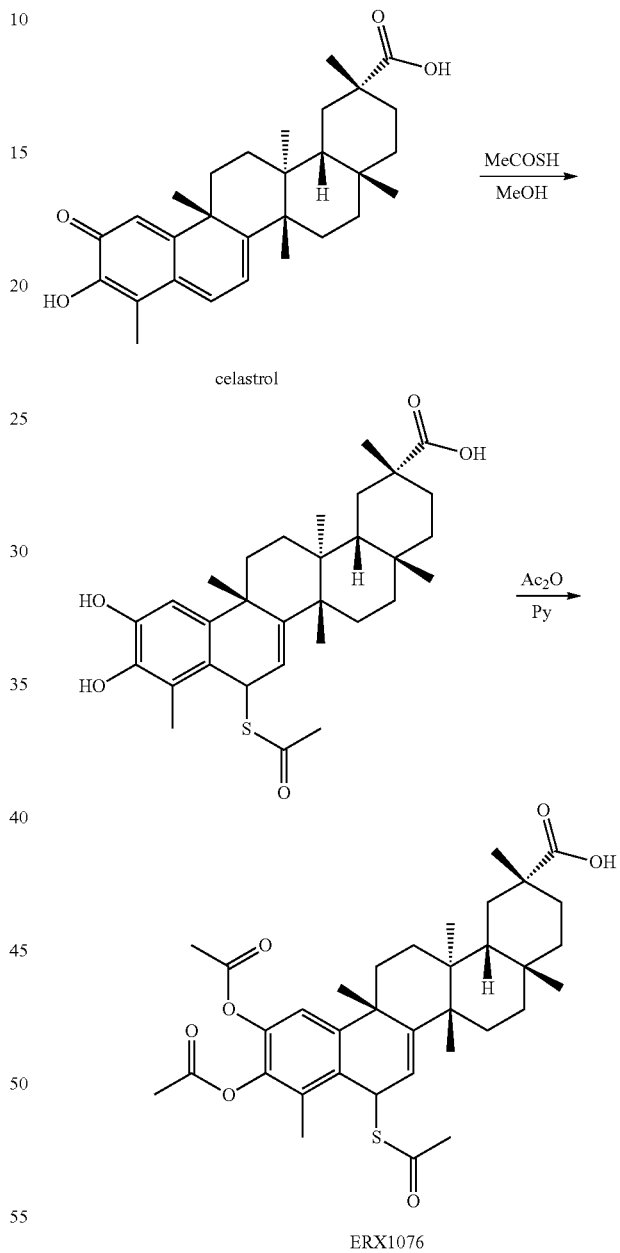

To a solution of celastrol (200 mg, 0.44 mmol) in MeOH (20 mL) was added MeCOSH (51 mg, 0.67 mmol). The reaction was stirred at room temperature for 0.5 hour. The solution was turned from red to pale yellow. Then the solution was concentrated in vacuo to afford crude mixture.

To a crude mixture prepared above in Ac$_2$O (8 mL) was added pyridine (1 mL). The reaction was stirred at room temperature overnight. Then the mixture was diluted with EtOAc (200 mL), washed with water (2×100 mL), brine (100 mL), dried over MgSO$_4$ and concentrated in vacuo. The residue was purified by prep-TLC (EtOAc) to afford product (131 mg, 0.214 mmol, Yield=49%) as white solid. $^1$HNMR δ(500 MHz, CDCl3): 7.02 (1H, s), 5.94&5.95 (1H, d, J=6.4 Hz), 5.36&5.37 (1H, d, J=6.4 Hz), 2.39 (1H, d, J=15.4 Hz), 2.34 (3H, s), 2.303&2.307 (3H, s), 2.269&2.273 (3H, s), 2.074&2.077 (3H, s), 1.30-2.20 (13H, m), 1.438&1.451 (3H, s), 1.215&1.253 (3H, s), 1.169&1.201 (3H, s), 1.062&1.083 (3H, s), 0.90-1.00 (1H, m), 0.666&0.702 (1H, s); LC-MS (Mobile Phase: A: water (0.01% TFA) B: ACN (0.01% TFA) Gradient: 5%-95% B in 1.7 min; Flow Rate: 2.2 ml/min; Column: SunFire C18, 4.6*50 mm, 3.5 um): rt=2.49 & 2.52 min, two peaks.

Example 55

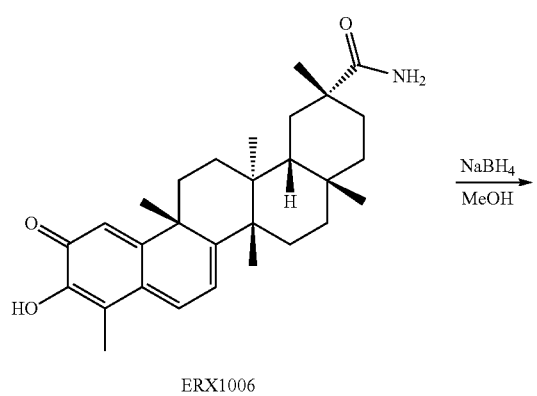

To a solution of ERX1006 (200 mg, 0.445 mmol) in MeOH (10 mL) was added NaBH$_4$ (168 mg, 4.445 mmol) in portions. The solution was turned form reddish to colorless. The reaction was stirred at room temperature for 1 hour. Then the reaction was quenched by 0.1 M HCl and acidified to pH 5-6 by 0.1 M HCl. The mixture was diluted with CH$_2$Cl$_2$ (300 mL), filtered, separated. The organic layer was washed with brine (100 mL), dried over MgSO$_4$ and concentrated in vacuo to afford crude intermediate which was used in the next step without further purification.

To a crude mixture (201 mg, 0.445 mmol, theoretical amount) in CH$_2$Cl$_2$ (10 mL) was added NEt$_3$ (180 mg, 0.25 mL, 1.78 mmol) followed by EtCO$_2$Cl (193 mg, 0.17 mmol, 1.78 mmol). The reaction was stirred at room temperature for 1 hour. Then the mixture was diluted with EtOAc (200 mL), washed with water (100 mL), brine (100 mL), dried over MgSO$_4$ and concentrated in vacuo. The residue was purified by silica gel chromatography (petroleum ether/EtOAc=2:3) to afford product (89.3 mg, 0.150 mmol, Yield=34%) as white solid. $^1$HNMR δ(400 MHz, CDCl3): 7.09 (1H, s), 5.75 (1H, d, J=6.1 Hz), 5.65 (1H, br), 5.21 (1H, br), 4.31 (2H, q, J=7.1 Hz), 4.31 (2H, q, J=7.1 Hz), 3.33 (1H, dd, J=20.9, 6.1 Hz), 3.06 (1H, d, J=20.9 Hz), 2.41 (1H, d, J=15.6 Hz), 2.12 (3H, s), 1.40-2.12 (13H, m), 1.38 (3H, t, J=7.1 Hz), 1.38 (3H, t, J=7.1 Hz), 1.33 (3H, s), 1.22 (3H, s), 1.19 (3H, s), 1.10 (3H, s), 0.94-1.10 (1H, m), 0.77 (3H, s); LC-MS (Mobile Phase: A: water (0.01% TFA) B: ACN (0.01% TFA); Gradient: 5%-95% B in 1.4 min; Flow Rate: 2.3 ml/min; Column: SunFire C18, 4.6*50 mm, 3.5 um): rt=2.39 min, m/z=596.3 [M+H]$^+$, purity=97.29% (214 nm).

Example 56

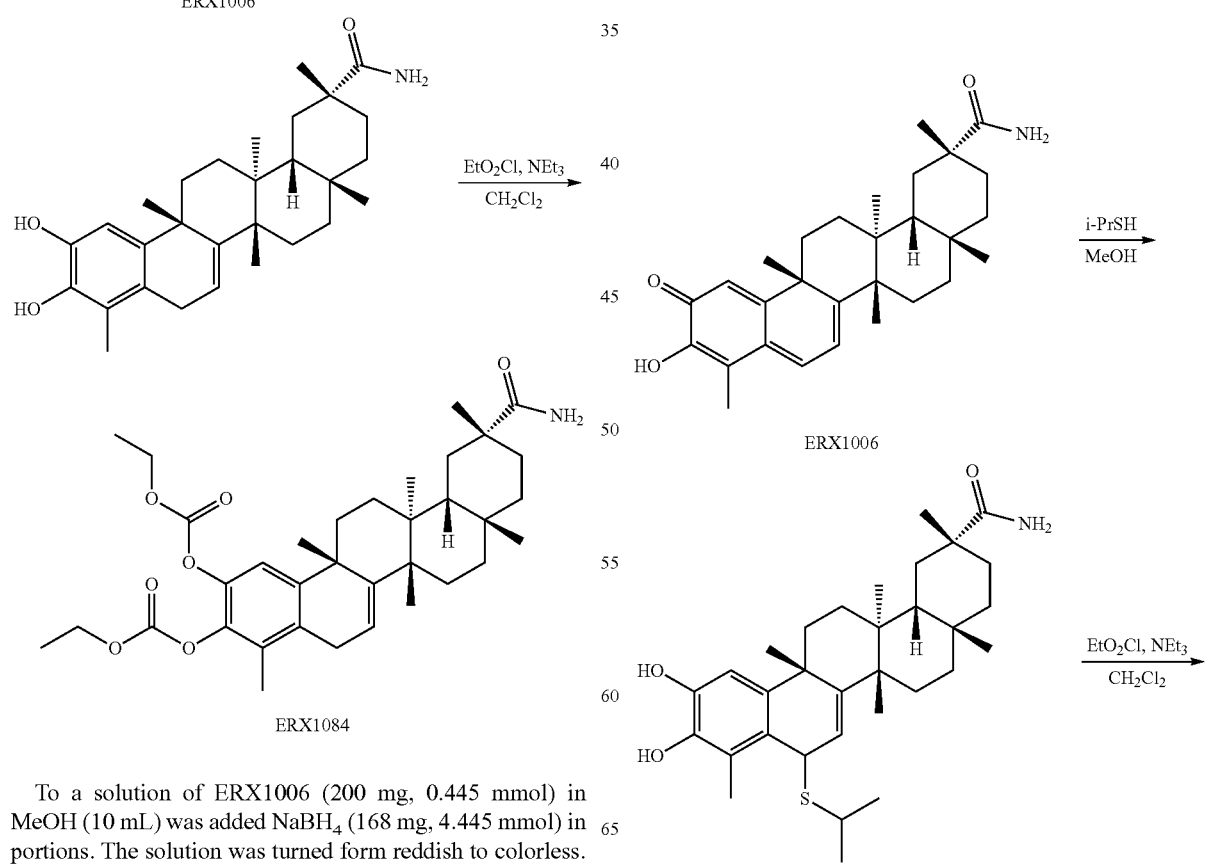

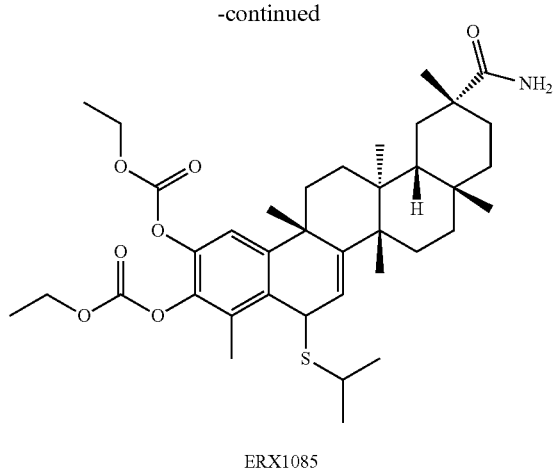

ERX1085

To a solution of ERX1006 (200 mg, 0.445 mmol) in MeOH (10 mL) was added i-PrSH (101.7 mg, 0.124 mL, 1.335 mmol). The solution was turned form reddish to pale yellow. The reaction was stirred at room temperature for 0.5 hour. The solution was diluted with $CH_2Cl_2$ (200 mL), washed with $H_2O$ (100 mL), brine (100 mL), dried over $MgSO_4$ and concentrated in vacuo to afford crude intermediate which was used in the next step without further purification.

To a crude mixture (234 mg, 0.445 mmol, theoretical amount) in $CH_2Cl_2$ (10 mL) was added $NEt_3$ (225 mg, 0.31 mL, 2.225 mmol) followed by $EtCO_2Cl$ (241 mg, 0.21 mL, 2.225 mmol). The reaction was stirred at room temperature for 1 hour. Then the mixture was diluted with EtOAc (200 mL), washed with water (100 mL), brine (100 mL), dried over $MgSO_4$ and concentrated in vacuo. The residue was purified by silica gel chromatography (petroleum ether/EtOAc=2:3) to afford product (145.6 mg, 0.217 mmol, Yield=49%) as white solid. $^1$HNMR δ(400 MHz, CDCl3): 7.11 (1H, s), 5.97 (1H, d, J=6.3 Hz), 5.64 (1H, br), 5.18 (1H, br), 4.58 (1H, d, J=6.3 Hz), 3.32 (2H, q, J=7.2 Hz), 3.31 (2H, q, J=7.2 Hz), 3.14-3.23 (1H, m), 2.40 (1H, d, J=15.0 Hz), 2.34 (3H, s), 1.42-2.12 (13H, m), 1.56 (3H, s), 1.38 (6H, t, J=7.2 Hz), 1.37 (3H, d, J=6.9 Hz), 1.28 (3H, d, J=6.9 Hz), 1.26 (3H, s), 1.19 (3H, s), 1.11 (3H, s), 0.96-1.03 (1H, m), 0.74 (3H, s); LC-MS (Mobile Phase: A: water (10 mM Ammonium hydrogen carbonate) B: ACN; Gradient: 5%-95% B in 1.5 min; Flow Rate: 2.0 ml/min; Column: XBridge C18, 4.6*50 mm, 3.5 um): rt=2.69 min, m/z=594.2 [M−C3H7S]$^+$, purity=100% (214,254 nm).

Example 57

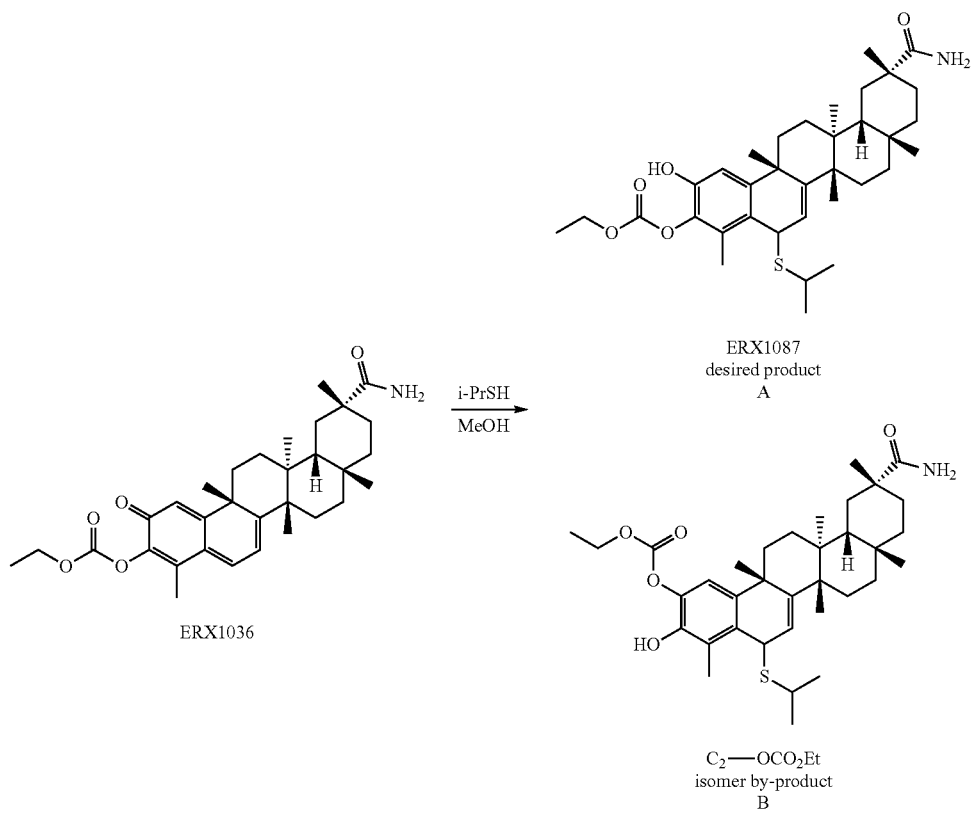

To a solution of ERX1036 (329 mg, 0.631 mmol) in MeOH (6 mL) was added i-PrSH (144 mg, 0.176 mL, 1.892 mmol). The reaction was stirred at room temperature for 1 hour. Then the mixture was diluted with EtOAc (300 mL), washed with water (2×100 mL), brine (100 mL), dried over MgSO$_4$ and concentrated in vacuo. The residue was purified by prep-TLC twice (petroleum ether/EtOAc=1:3) to afford unseparated 3:1 mixture of A and B (181.8 mg, 0.304 mmol, Yield=48%) as yellow solid.

$^1$HNMR: C3-OCO$_2$Et isomer:

δ(400 MHz, CDCl3): 6.87 (1H, s), 5.97 (1H, d, J=6.2 Hz), 5.70 (1H, br), 5.70 (1H, s), 5.26 (1H, br), 4.56 (1H, d, J=6.2 Hz), 4.32 (2H, q, J=7.2 Hz), 3.11-3.22 (1H, m), 2.43 (1H, d, J=15.1 Hz), 2.30 (3H, s), 1.42-2.10 (13H, m), 1.57 (3H, s), 1.39 (3H, t, J=7.2 Hz), 1.39 (3H, d, J=7.0 Hz), 1.27 (3H, d, J=7.0 Hz), 1.26 (3H, s), 1.19 (3H, s), 1.11 (3H, s), 0.95-1.03 (1H, m), 0.74 (3H, s).

C2-OCO$_2$Et isomer:

δ(400 MHz, CDCl3): 7.04 (1H, s), 5.97 (1H, d, J=6.2 Hz), 5.70 (1H, br), 5.38 (1H, s), 5.26 (1H, br), 4.60 (1H, d, J=6.2 Hz), 4.34 (2H, q, J=7.2 Hz), 3.11-3.22 (1H, m), 2.43 (1H, d, J=15.1 Hz), 2.41 (3H, s), 1.42-2.10 (13H, m), 1.57 (3H, s), 1.39 (3H, t, J=7.2 Hz), 1.39 (3H, d, J=7.0 Hz), 1.27 (3H, d, J=7.0 Hz), 1.26 (3H, s), 1.19 (3H, s), 1.11 (3H, s), 0.95-1.03 (1H, m), 0.73 (3H, s). LC-MS (Mobile Phase: A: water (10 mM Ammonium hydrogen carbonate) B: ACN; Gradient: 5%-95% B in 1.5 min; Flow Rate: 2.0 ml/min; Column: XBridge C18, 4.6*50 mm, 3.5 um): rt=2.58 min, m/z=522.3 [M−C3H7S]$^+$, purity=97.47% (214 nm).

Example 58

To a solution of ERX1090 (277 mg, 0.517 mmol) in MeOH (6 mL) was added i-PrSH (118 mg, 0.144 mL, 1.551 mmol). The reaction was stirred at room temperature for 1 hour. Then the mixture was diluted with EtOAc (300 mL), washed with water (2×100 mL), brine (100 mL), dried over MgSO$_4$ and concentrated in vacuo. The residue was purified by prep-TLC twice (petroleum ether/EtOAc=1:3) to afford unseparated 3:1 mixture of A and B (180.4 mg, 0.295 mmol, Yield=57%) as yellow solid.

$^1$HNMR: C3-OCO$_2$Pr-i isomer:

δ(400 MHz, CDCl3): 6.87 (1H, s), 5.97 (1H, d, J=6.4 Hz), 5.73 (1H, s), 5.69 (1H, br), 5.29 (1H, br), 4.94-5.02 (1H, m), 4.56 (1H, d, J=6.4 Hz), 3.10-3.22 (1H, m), 2.42 (1H, d, J=15.6 Hz), 2.30 (3H, s), 1.42-2.10 (13H, m), 1.56 (3H, s), 1.39 (3H, d, J=6.8 Hz), 1.37 (6H, d, J=6.8 Hz), 1.27 (3H, d, J=6.8 Hz), 1.25 (3H, s), 1.19 (3H, s), 1.11 (3H, s), 0.94-1.02 (1H, m), 0.74 (3H, s).

C2-OCO$_2$Pr-i isomer:

δ(400 MHz, CDCl3): 7.04 (1H, s), 5.97 (1H, d, J=6.4 Hz), 5.69 (1H, br), 5.42 (1H, s), 5.29 (1H, br), 4.94-5.02 (1H, m), 4.60 (1H, d, J=6.4 Hz), 3.10-3.22 (1H, m), 2.42 (1H, d, J=15.6 Hz), 2.37 (3H, s), 1.42-2.10 (13H, m), 1.56 (3H, s), 1.39 (3H, d, J=6.8 Hz), 1.37 (6H, d, J=6.8 Hz), 1.27 (3H, d, J=6.8 Hz), 1.25 (3H, s), 1.19 (3H, s), 1.11 (3H, s), 0.94-1.02 (1H, m), 0.74 (3H, s). LC-MS (Phase: A: water (10 mM Ammonium hydrogen carbonate) B: ACN; Gradient: 5%-95% B in 1.5 min; Flow Rate: 2.0 ml/min; Column: XBridge C18, 4.6*50 mm, 3.5 um; rt=2.62 min, m/z=536.4 [M−C3H7S]$^+$, purity=95.39% (214 nm).

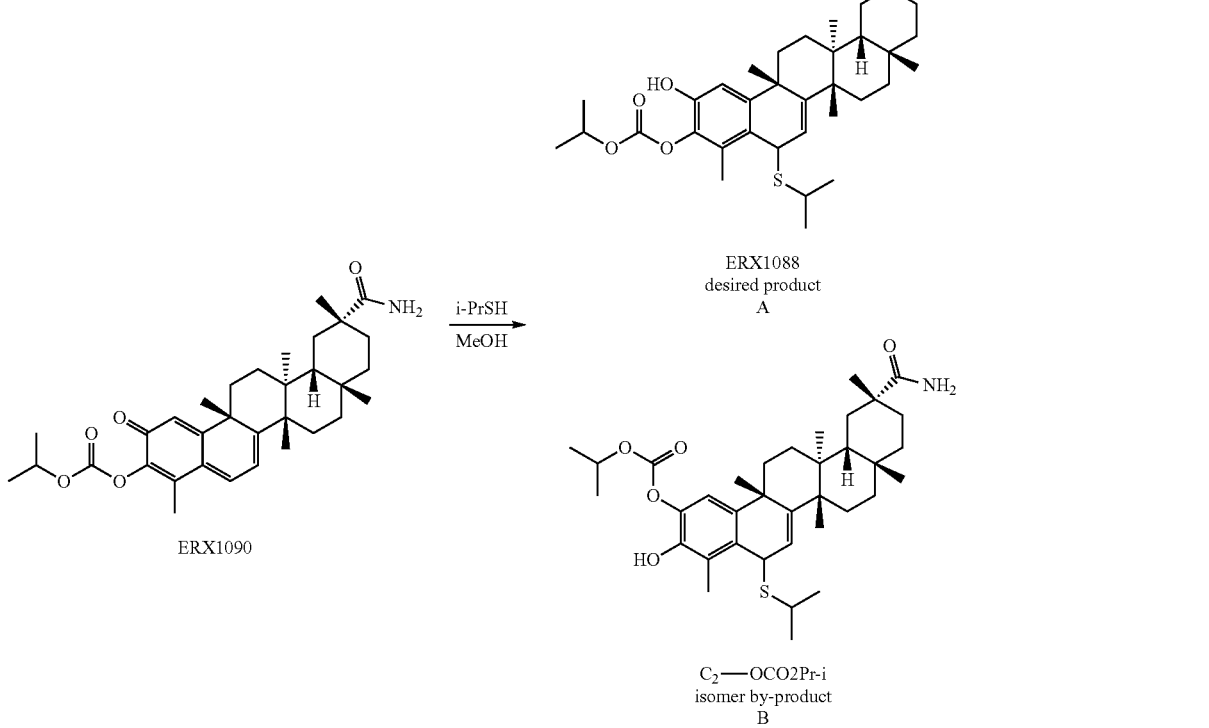

ERX1090 → i-PrSH / MeOH →

ERX1088
desired product
A

C2—OCO2Pr-i
isomer by-product
B

Example 59

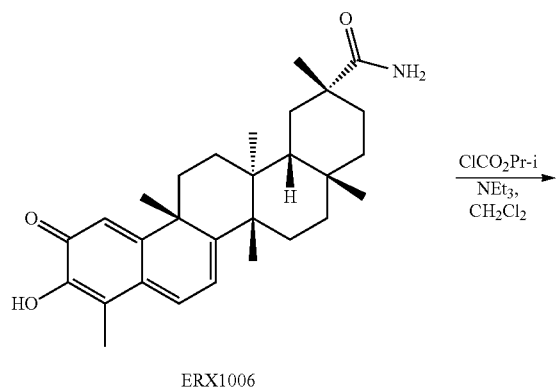

ERX1006

ERX1090

To a solution of ERX1006 (300 mg, 0.667 mmol) in CH$_2$Cl$_2$ (6 mL) was added Et$_3$N (135 mg, 0.19 mL, 1.334 mmol) followed by 1M ClCO$_2$Pr-i in PhMe solution (163 mg, 1.33 mL, 1.334 mmol) dropwise at 0° C. The reaction was stirred at room temperature overnight. The mixture was diluted with CH$_2$Cl$_2$ (300 mL), washed with brine (200 mL), dried over MgSO$_4$ and concentrated in vacuo. The residue was purified by prep-TLC (petroleum ether/ethyl acetate=1:3) to afford product (302.6 mg, 0.565 mmol, Yield=85%) as yellow solid. $^1$HNMR δ(500 MHz, CDCl3): 7.06 (1H, dd, J=7.4, 1.3 Hz), 6.47 (1H, d, J=1.3 Hz), 6.32 (1H, d, J=7.4 Hz), 5.67 (1H, br), 5.23 (1H, br), 4.93-5.01 (1H, m), 2.39 (1H, d, J=15.4 Hz), 2.21 (3H, s), 1.82-2.14 (7H, m), 1.48-1.73 (6H, m), 1.46 (3H, s), 1.39 (3H, d, J=6.0 Hz), 1.39 (3H, d, J=6.4 Hz), 1.27 (3H, s), 1.21 (3H, s), 0.99-1.05 (1H, m), 0.76 (3H, s); LC-MS (Mobile Phase: A: water (0.01% TFA) B: ACN (0.01% TFA); Gradient: 5%-95% B in 1.4 min; Flow Rate: 2.3 ml/min Column: Hypersil GOLD, 4.6*50 mm, 3 um): rt=2.11 min, m/z=536.3 [M+H]$^+$, purity=97.63% (214 nm), 100% (254 nm).

Example 60

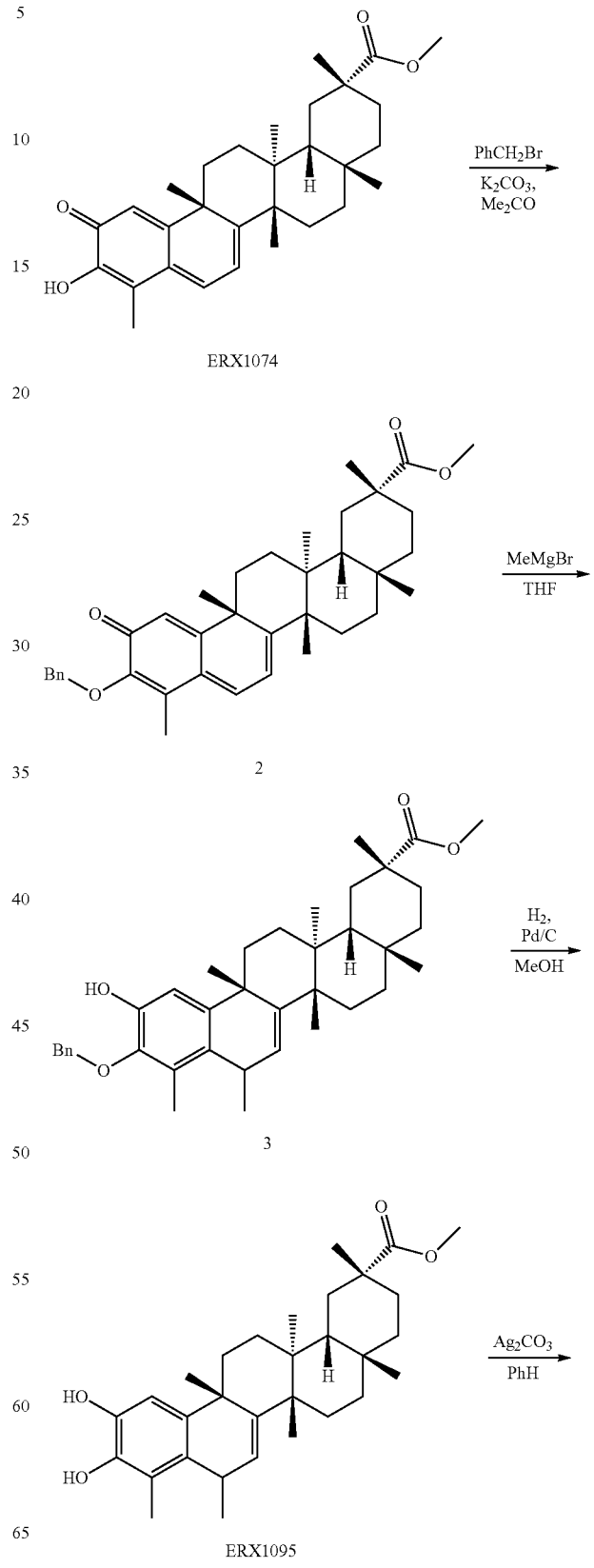

-continued

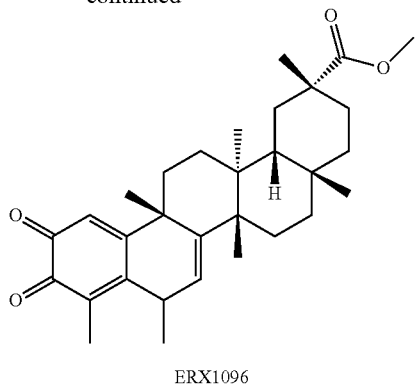

ERX1096

To a solution of ERX1074 (2.05 g, 4.412 mmol) in Me$_2$CO (30 mL) was added K$_2$CO$_3$ (3.05 g, 22.06 mmol) followed by PhCH$_2$Br (3.77 g, 2.62 mL, 22.06 mmol). The reaction was heated at 50° C. overnight. Most acetone was removed in vacuo. The residue was dissolved in EtOAc (300 mL), washed with H$_2$O (200 mL), brine (200 mL), dried over MgSO$_4$ and concentrated in vacuo. The residue was purified by silica gel chromatography (petroleum ether/ethyl acetate=3:1) to afford product 2 (2.45 g, 4.416 mmol, Yd=100%) as yellow solid.

To a solution of 2 (2.5 g, 4.51 mmol) in anhydrous THF (100 mL) was added 3 M MeMgBr in THF solution (7.5 mL, 22.5 mmol) at 0° C. dropwise. The reaction was stirred at 0° C. for 1 hour. The reaction was quenched by addition of H$_2$O (50 mL) and extracted with CH$_2$Cl$_2$ (3×50 mL). The combined organic extracts were washed with brine (50 mL), dried over MgSO$_4$ and concentrated in vacuo. The residue was purified by silica gel chromatography (petroleum ether/ethyl acetate=2:1) to afford crude product (2.0 g, 3.53 mmol, Yd=78%) as white solid.

The solution was hydrogenated with a balloon of hydrogen. The solution was filtered with celite. The filtrated was concentrated in vacuo. The residue was purified by prep-TLC (petroleum ether/EtOAc=2:1) to afford product ERX1095 (1.5 g, 3.26 mmol, Yd=89%) as white solid.

To a solution of ERX1095 (130 mg, 0.27 mmol) in benzene (5 mL) was added Ag$_2$CO$_3$ (148 mg, 0.54 mmol). The reaction was heated at rt overnight. The solution was filtered and concentrated in vacuo. The residue was purified by prep-TLC (petroleum ether/EtOAc=2:1) to afford final product (80 mg, 0.167 mmol, Yd=62%) as red solid.

ERX1095 data:
$^1$HNMR δ(500 MHz, CDCl$_3$): 6.78 (1H, s), 5.77 (1H, d, J=6.2 Hz), 5.15 (1H, s), 5.07 (1H, s), 3.52 (3H, s), 3.44-3.50 (1H, m), 2.42 (1H, d, J=15.7 Hz), 2.22 (3H, s), 2.14-2.20 (1H, m), 2.01-2.11 (2H, m), 1.80-1.89 (2H, m), 1.30-1.70 (8H, m), 1.47 (3H, s), 1.21 (3H, s), 1.16 (3H, s), 1.16 (3H, d, J=6.8 Hz), 1.08 (3H, s), 0.91-0.97 (1H, m), 0.55 (3H, s); LC-MS: rt=2.19 min, m/z=481 [M+H]$^+$, purity=97.35% (214 nm).

ERX1096 data:
$^1$HNMR δ(500 MHz, CDCl$_3$): 6.28 (1H, s), 5.70 (1H, d, J=6.0 Hz), 3.58 (3H, s), 3.39-3.46 (1H, m), 2.39 (1H, d, J=15.7 Hz), 2.15-2.24 (1H, m), 2.02-2.10 (1H, m), 2.00 (3H, s), 1.78-1.92 (3H, m), 1.59 (3H, s), 1.24-1.74 (8H, m), 1.28 (3H, d, J=7.3 Hz), 1.18 (3H, s), 1.17 (3H, s), 1.08 (3H, s), 0.93-0.98 (1H, m), 0.60 (3H, s); $^{13}$CNMR δ(125 MHz, CDCl$_3$): 181.32, 180.57, 178.83, 167.19, 149.49, 146.44, 132.47, 122.64, 122.32, 51.58, 44.25, 43.88, 40.39, 38.68, 37.18, 36.59, 36.00, 34.77, 34.71, 32.75, 32.54, 31.57, 30.61, 30.48, 29.90, 28.77, 22.77, 20.50, 18.13, 11.35. LC-MS: rt=2.21 min, m/z=479 [M+H]$^+$, purity=100% (214 nm).

Example 61

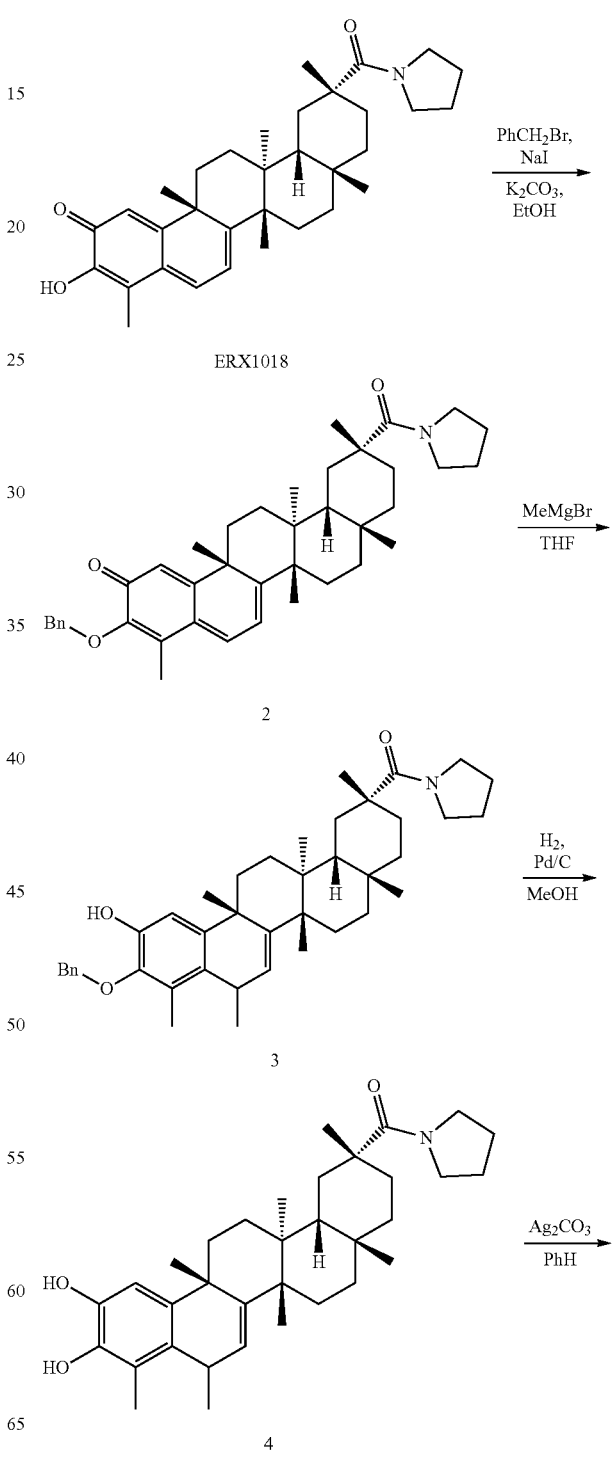

-continued

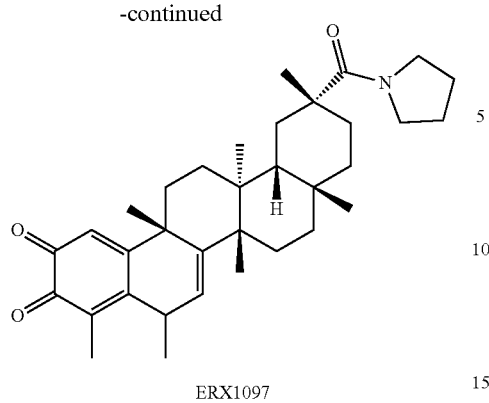

ERX1097

To a solution of ERX1018 (503 mg, 1.0 mmol) in EtOH (50 mL) was added K$_2$CO$_3$ (276 mg, 2.0 mmol), NaI (6 mg, 0.04 mmol) followed by PhCH$_2$Br (187 mg, 1.1 mmol). The reaction was heated at 80° C. overnight. Most EtOH was removed in vacuo. The residue was dissolved in CH$_2$Cl$_2$ (200 mL), washed with H$_2$O (2×100 mL), brine (100 mL), dried over MgSO$_4$ and concentrated in vacuo. The residue was purified by silica gel chromatography (petroleum ether/ethyl acetate=1:1) to afford product 2 (255 mg, 0.43 mmol, Yd=43%) as yellow solid.

To a solution of 2 (100 mg, 0.17 mmol) in anhydrous THF (10 mL) was added 3 M MeMgBr in THF solution (0.57 mL, 1.7 mmol) at 0° C. dropwise. The reaction was stirred at 0° C. for 1 hour. The reaction was quenched by addition of H$_2$O (50 mL) and extracted with CH$_2$Cl$_2$ (3×50 mL). The combined organic extracts were washed with brine (50 mL), dried over MgSO$_4$ and concentrated in vacuo to afford crude product (50 mg, 0.0824 mmol, Yd=48%) as white solid.

To a solution of crude 3 (50 mg, 0.0824 mmol) in MeOH (10 mL) was added 10% Pd/C (5 mg). The solution was hydrogenated with a balloon of hydrogen. The solution was filtered with celite. The filtrated was concentrated in vacuo and the residue was purified by silica gel chromatography (petroleum ether/ethyl acetate=1:1) to afford product 4 (20 mg, 0.0385 mmol, Yd=47%) as white solid.

To a solution of 4 (40 mg, 0.0771 mmol) in benzene (10 mL) was added Ag$_2$CO$_3$ (43 mg, 0.154 mmol). The reaction was heated at 60° C. for 1 hour. The reaction quenched by H$_2$O (50 mL) and extracted with CH$_2$Cl$_2$ (3×50 mL). The combined organic extracts were washed with brine (50 mL), dried over MgSO$_4$ and concentrated in vacuo. The residue was purified by prep-TLC (CH$_2$Cl$_2$: MeOH=10:1) to afford final product (33 mg, 0.0637 mmol, Yd=83%) as red solid. $^1$HNMR δ(500 MHz, CDCl$_3$): 6.27 (1H, s), 5.70 (1H, d, J=6.4 Hz), 3.58-3.68 (2H, m), 3.40-3.51 (2H, m), 3.25-3.33 (1H, m), 2.34-2.41 (2H, m), 2.09-2.18 (1H, m), 2.00 (3H, s), 1.42-1.96 (15H, m), 1.59 (3H, s), 1.26 (3H, d, J=7.1 Hz), 1.22 (3H, s), 1.19 (3H, s), 1.11 (3H, s), 0.93-0.99 (1H, m), 0.62 (3H, s); LC-MS: rt=2.57 min, m/z=518 [M+H]$^+$, purity=97.84% (214 nm).

Example 62

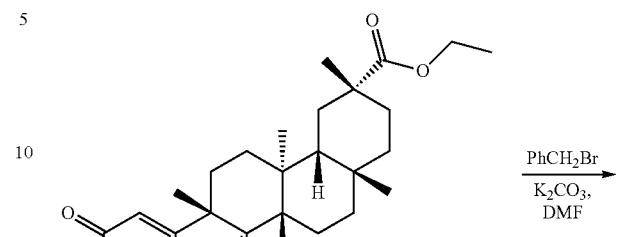

ERX1001

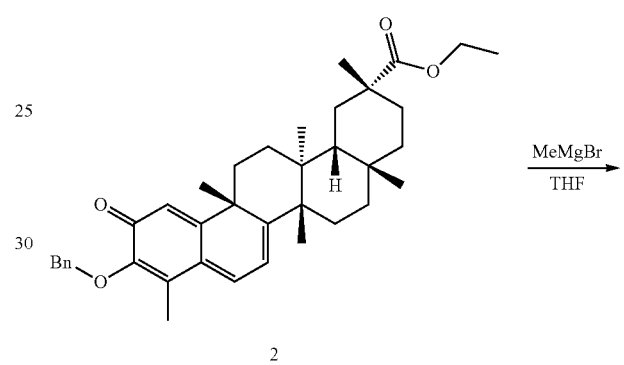

2

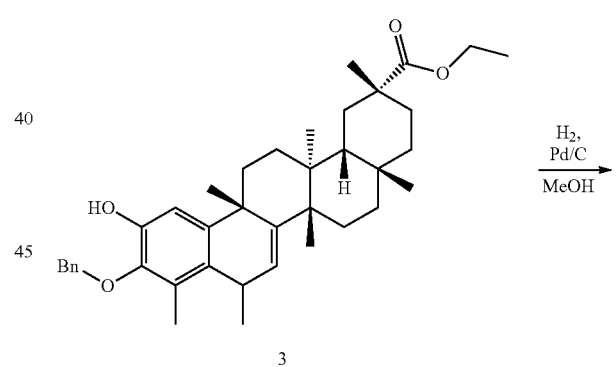

3

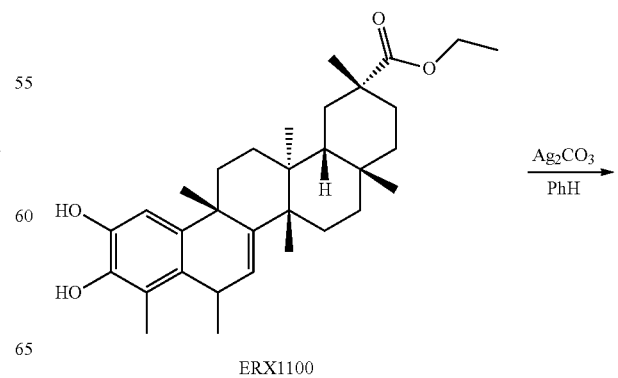

ERX1100

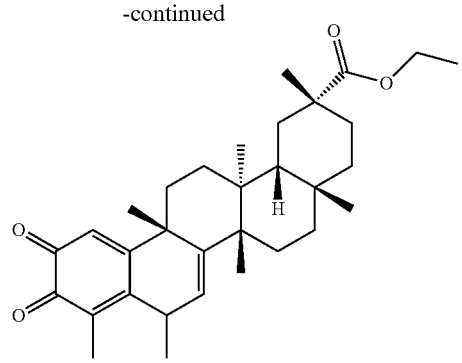

ERX1099

To a solution of ERX1001 (478 mg, 1.0 mmol) in DMF (10 mL) was added K$_2$CO$_3$ (276 g, 2.0 mmol) followed by PhCH$_2$Br (187 mg, 1.1 mmol). The reaction was heated at 80° C. for 2 hours. The reaction was quenched by ice-H$_2$O (50 mL) and filtered. The solid was dissolved in CH$_2$Cl$_2$ (200 mL), washed with H$_2$O (100 mL), brine (100 mL), dried over MgSO$_4$ and concentrated in vacuo. The residue was purified by silica gel chromatography (petroleum ether/ethyl acetate=3:1) to afford product 2 (300 mg, 0.528 mmol, Yd=53%) as yellow solid.

To a solution of 2 (568 g, 1.0 mmol) in anhydrous THF (20 mL) was added 3 M MeMgBr in THF solution (2.33 mL, 7.0 mmol) at 0° C. dropwise. The reaction was stirred at 0° C. for 1 hour. The reaction was quenched by addition of H$_2$O (50 mL) and extracted with CH$_2$Cl$_2$ (3×50 mL). The combined organic extracts were washed with brine (50 mL), dried over MgSO$_4$ and concentrated in vacuo. The residue was purified by silica gel chromatography (petroleum ether/ethyl acetate=2:1) to afford crude product (400 mg, 0.685 mmol, Yd=69%) as white solid.

To a solution of crude 3 (584 mg, 1.0 mmol) in MeOH (10 mL) was added 10% Pd/C (58 mg). The solution was hydrogenated with a balloon of hydrogen. The solution was filtered with celite. The filtrated was concentrated in vacuo. The residue was purified by prep-TLC (petroleum ether/EtOAc=3:1) to afford product ERX1100 (450 mg, 0.911 mmol, Yd=91%) as white solid.

To a solution of ERX1100 (494 mg, 1.0 mmol) in benzene (20 mL) was added Ag$_2$CO$_3$ (548 mg, 2.0 mmol). The reaction was heated at 60° C. overnight. The solution was filtered and concentrated in vacuo. The residue was purified by prep-TLC (petroleum ether/EtOAc=3:1) to afford final product (200 mg, 0.813 mmol, Yd=81%) as red solid.

ERX1100 data:
$^1$HNMR: δ(500 MHz, d6-DMSO): 8.85 (1H, s), 7.86 (1H, s), 6.60 (1H, s), 5.73 (1H, d, J=6.2 Hz), 3.82-3.94 (2H, m), 3.32-3.40 (1H, m), 2.34 (1H, d, J=15.2 Hz), 2.06 (3H, s), 1.91-2.09 (3H, m), 1.20-1.85 (10H, m), 1.39 (3H, s), 1.17 (3H, s), 1.11 (3H, t, J=7.2 Hz), 1.11 (3H, s), 1.06 (3H, d, J=6.7 Hz), 1.06 (3H, s), 0.85-0.91 (1H, m), 0.49 (3H, s); LC-MS: rt=2.85 min, m/z=495 [M+H]$^+$, purity=100% (214 nm).

ERX1099 data:
$^1$HNMR δ(500 MHz, CDCl$_3$): 6.28 (1H, s), 5.70 (1H, d, J=5.6 Hz), 3.93-4.08 (2H, m), 3.39-3.46 (1H, m), 2.41 (1H, d, J=15.6 Hz), 2.18-2.23 (1H, m), 2.01-2.09 (1H, m), 2.00 (3H, s), 1.15-1.92 (11H, m), 1.59 (3H, s), 1.27 (3H, d, J=7.2 Hz), 1.22 (3H, t, J=7.3 Hz), 1.18 (3H, s), 1.17 (3H, s), 1.08 (3H, s), 0.92-0.98 (1H, m), 0.63 (3H, s); LC-MS: rt=2.81 min, m/z=493 [M+H]$^+$, purity=100% (214,254 nm).

Example 63

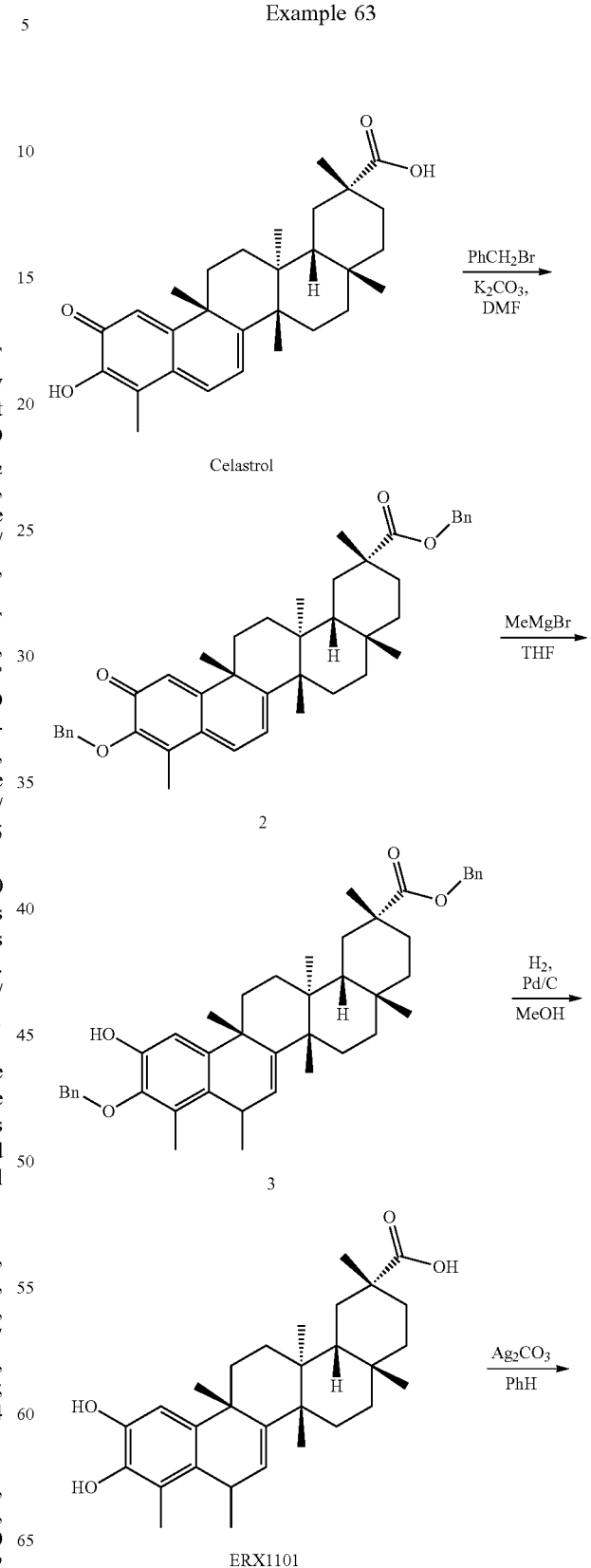

125
-continued

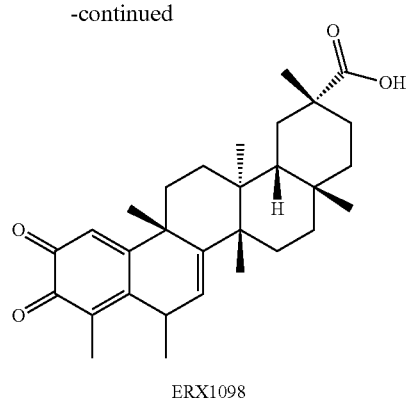

ERX1098

To a solution of Celastrol (450 mg, 1.0 mmol) in DMF (10 mL) was added $K_2CO_3$ (276 mg, 2.0 mmol) followed by $PhCH_2Br$ (374 mg, 2.2 mmol). The reaction was heated at 80° C. for 2 hours. The reaction was quenched by ice-water (50 mL). The mixture was filtered. The solid was dissolved in $CH_2Cl_2$ (200 mL), washed with $H_2O$ (100 mL), brine (100 mL), dried over $MgSO_4$ and concentrated in vacuo. The residue was purified by silica gel chromatography (petroleum ether/ethyl acetate=3:1) to afford product 2 (400 mg, 0.635 mmol, Yd=64%) as yellow solid.

To a solution of 2 (630 mg, 1.0 mmol) in anhydrous THF (20 mL) was added 3 M MeMgBr in THF solution (3.3 mL, 10 mmol) at 0° C. dropwise. The reaction was stirred at 0° C. for 1 hour. The reaction was quenched by addition of $H_2O$ (50 mL) and extracted with $CH_2Cl_2$ (2×100 mL). The combined organic extracts were washed with brine (100 mL), dried over $MgSO_4$ and concentrated in vacuo. The residue was purified by silica gel chromatography (petroleum ether/ethyl acetate=2:1) to afford crude product (500 mg, 0.774 mmol, Yd=77%) as white solid.

To a solution of compound 3 (64.6 mg, 0.1 mmol) in MeOH (10 mL) was added 10% Pd/C (6 mg). The solution was hydrogenated with a balloon of hydrogen. The solution was filtered with celite. The filtrated was concentrated in vacuo. The residue was purified by prep-TLC (petroleum ether/EtOAc=1:1) to afford product ERX1101 (30 mg, 0.0644 mmol, Yd=64%) as white solid.

To a solution of ERX1101 (47 mg, 0.1 mmol) in benzene (10 mL) was added $Ag_2CO_3$ (55 mg, 0.2 mmol). The reaction was heated at 60° C. overnight. The solution was filtered and concentrated in vacuo. The residue was purified by prep-TLC (petroleum ether/EtOAc=1:1) to afford final product ERX1098 (40 mg, 0.0862 mmol, Yd=86%) as red solid.

ERX1101 data:
$^1$HNMR δ(500 MHz, d6-DMSO): 11.9-12.2 (1H, br), 8.80-9.10 (1H, br), 7.80-8.10 (1H, br), 6.60 (1H, s), 5.72 (1H, d, J=5.6 Hz), 2.35 (1H, d, J=15.3 Hz), 2.05 (3H, s), 1.94-2.05 (3H, m), 1.20-1.85 (1H, m), 1.38 (3H, s), 1.17 (3H, s), 1.08 (3H, s), 1.07 (3H, s), 1.04 (3H, s), 0.80-0.88 (1H, m), 0.65 (3H, s); LC-MS: rt=2.03 min, m/z=467.3 $[M+H]^+$, purity=100% (214 nm).

ERX1098 data:
$^1$HNMR (400 MHz, $CDCl_3$): 6.27 (1H, s), 6.65 (1H, d, J=6.5 Hz), 3.36-3.45 (1H, m), 2.38 (1H, d, J=13.9 Hz), 2.07-2.16 (1H, m), 2.00 (3H, s), 1.93-2.03 (1H, m), 1.32-1.90 (13H, m), 1.58 (3H, s), 1.29 (3H, d, J=7.3 Hz), 1.17 (3H, s), 1.16 (3H, s), 1.05 (3H, s), 0.86-0.94 (1H, m), 0.69 (3H, s); LC-MS: rt=2.04 min, m/z=467 $[M+H]^+$, purity=100% (214 nm).

126
Example 64

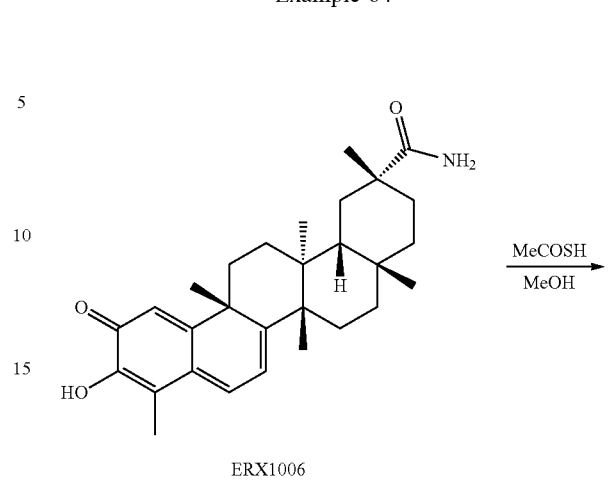

ERX1006

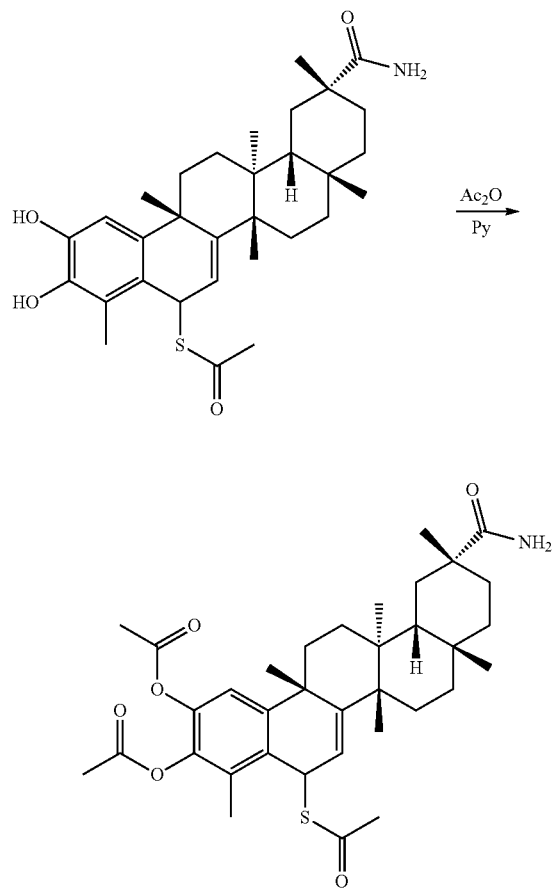

ERX1102

To a solution of ERX1006 (200 mg, 0.44 mmol) in MeOH (6 mL) was added MeCOSH (51 mg, 0.67 mmol). The reaction was stirred at room temperature for 1 hour. The solution was turned from red to pale yellow. Then the solution was concentrated in vacuo to afford crude mixture.

To a crude mixture prepared above in $Ac_2O$ (8 mL) was added pyridine (1 mL). The reaction was stirred at room temperature overnight. Then the mixture was diluted with EtOAc (200 mL), washed with water (2×100 mL), brine (100 mL), dried over MgSO₄ and concentrated in vacuo. The residue was purified by prep-TLC (EtOAc) to afford product (100 mg, 0.164 mmol, Yield=37%) as white solid. ¹HNMR δ(500 MHz, CDCl3): 7.02 (1H, s), 5.94 (1H, d, J=6.4 Hz), 5.68 (1H, br), 5.45 (1H, br), 5.36 (1H, d, J=6.4 Hz), 2.43 (1H, d, J=15.9 Hz), 2.34 (3H, s), 2.31 (3H, s), 2.28 (3H, s), 2.07 (3H, s), 1.45-2.06 (13H, m), 1.43 (3H, s), 1.21 (3H, s), 1.19 (3H, s), 1.09 (3H, s), 0.96-1.02 (1H, m), 0.73 (3H, s); LC-MS: rt=1.90 min, m/z=610 [M+H]⁺, purity=97.73% (214 nm).

Example 65

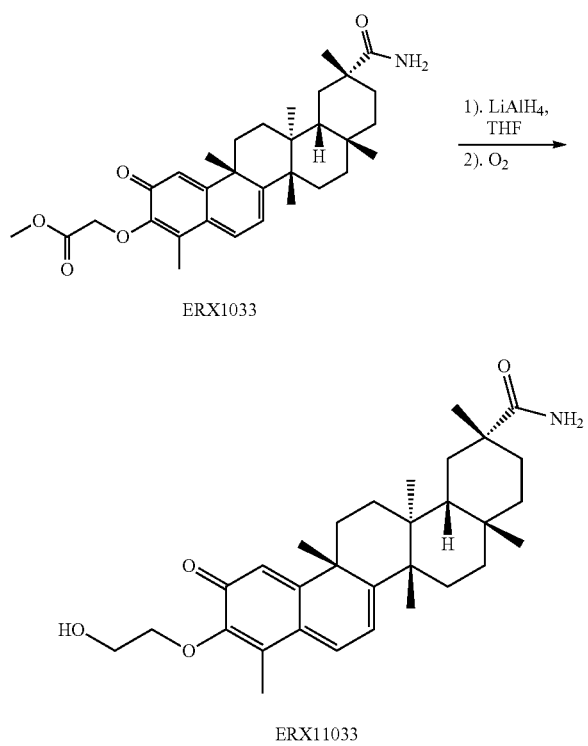

ERX1033

ERX11033

To a solution of ERX1033 (200 mg, 0.58 mmol) in THF (5.0 mL) was added LiAlH₄ (28 mg, 0.76 mmol). The reaction was stirred at 0° C. for 0.5 hour. The reaction was quenched by sat. NH₄Cl solution. The solution was heated at 50° C. in air for 2 hours. The mixture was diluted with CH₂Cl₂ (200 mL), washed with brine (100 mL), dried over MgSO₄ and concentrated in vacuo. The residue was purified by prep-TLC (CH₂Cl₂/MeOH=10:1) to afford product (6 mg, 0.0122 mmol, Yield=3%) as red solid. ¹HNMR δ(400 MHz, CDCl3): 7.06 (1H, dd, J=7.1, 0.9 Hz), 6.47 (1H, d, J=0.9 Hz), 6.34 (1H, d, J=7.1 Hz), 5.68 (1H, br), 5.24 (1H, br), 5.09 (1H, t, J=5.2 Hz), 3.98-4.10 (2H, m), 3.78-3.86 (2H, m), 2.39 (1H, d, J=15.8 Hz), 2.26 (3H, s), 1.47-2.20 (13H, m), 1.45 (3H, s), 1.27 (3H, s), 1.21 (3H, s), 1.12 (3H, s), 0.99-1.06 (1H, m), 0.76 (3H, s); LC-MS: rt=2.05 min, m/z=494.3 [M+H]⁺, purity=93.7% (214 nm), 100% (254 nm).

Example 66

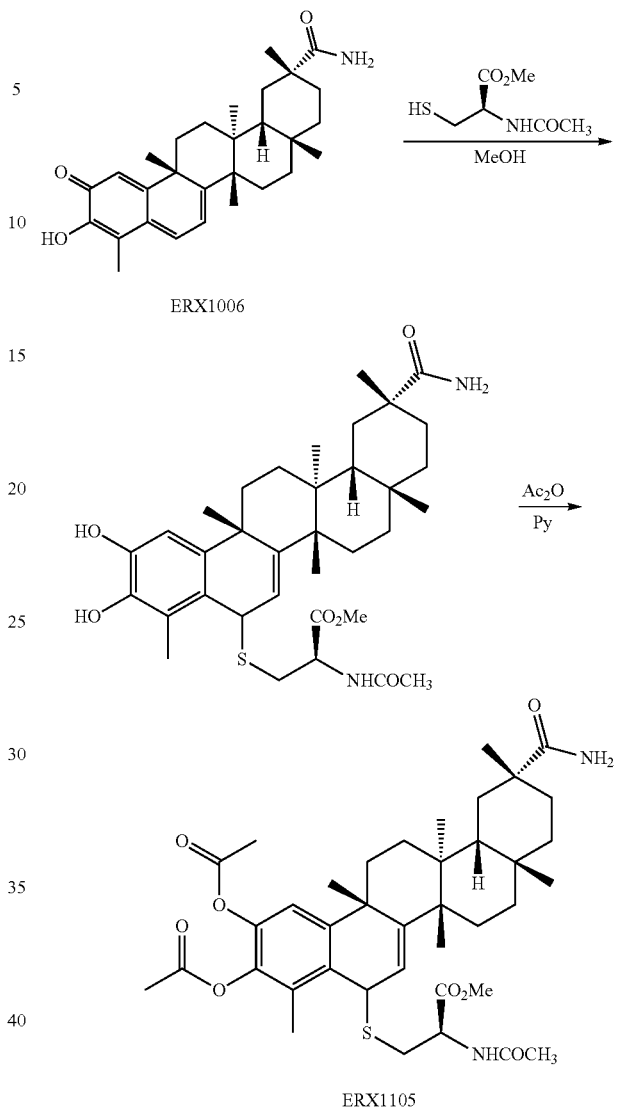

ERX1006

ERX1105

To a solution of ERX1006 (200 mg, 0.444 mmol) in MeOH (20 mL) was added N-acetyl-L-cysteine ethyl ester (157 mg, 0.888 mmol). The reaction was stirred at room temperature for 1 hour. The solution was turned from red to pale yellow. Then the solution was concentrated in vacuo to afford crude mixture.

To a crude mixture prepared above in pyridine (2 mL) was added Ac₂O (1 mL). The reaction was stirred at room temperature overnight. Then the mixture was poured into H₂O (100 mL), filtered. The solid was dissolved in EtOAc (200 mL), washed with water (100 mL), brine (100 mL), dried over MgSO₄ and concentrated in vacuo. The residue was purified by prep-TLC (EtOAc) to afford product (184.2 mg, 0.259 mmol, overall yield=58%) as white solid. ¹HNMR δ(400 MHz, CDCl3): 7.01 (1H, s), 6.26 (1H, d, J=7.5 Hz), 5.94 (1H, d, J=6.3 Hz), 5.65 (1H, br), 5.19 (1H, br), 4.88 (1H, q, J=6.0 Hz), 4.63 (1H, d, J=6.3 Hz), 3.74 (3H, s), 3.31 (1H, dd, J=13.5, 4.8 Hz), 2.93 (1H, dd, J=13.5, 5.9 Hz), 2.42 (1H, d, J=15.2 Hz), 2.31 (3H, s), 2.27 (3H, s), 2.25 (3H, s), 2.06 (3H, s), 1.45-2.10 (13H, m), 1.56 (3H, s), 1.26 (3H, s), 1.19 (3H, s), 1.11 (3H, s), 0.97-1.04 (1H, m), 0.73 (3H, s); LC-MS: rt=2.00 min, m/z=534.4 [M−SCH₂CH(CO₂Me)NHCOMe]⁺, purity=100% (214, 254 nm).

Example 67

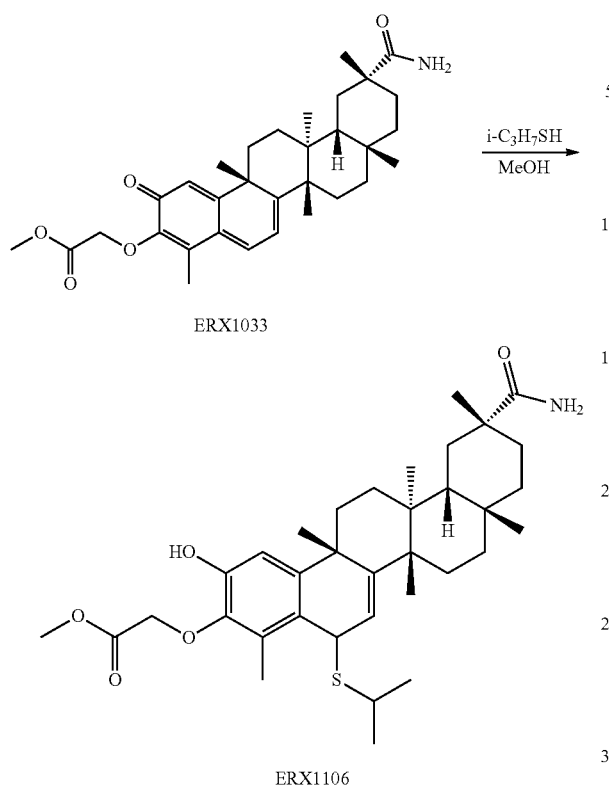

To a solution of ERX1033 (52 mg, 0.1 mmol) in MeOH (5.0 mL) was added i-C₃H7SH (11.4 mg, 0.15 mmol). The reaction was stirred at r.t. for 2.0 hours. The solution was concentrated in vacuo. The residue was purified by prep-TLC (CH₂Cl₂/MeOH=10:1) to afford product (16 mg, 0.0268 mmol, Yield=27%) as yellow solid. ¹HNMR δ(500 MHz, d4-MeOD): 6.73 (1H, s), 6.06 (1H, d, J=6.2 Hz), 4.61 (1H, d, J=6.2 Hz), 3.80 (3H, s), 3.14-3.22 (1H, m), 2.47 (1H, d, J=15.7 Hz), 2.39 (3H, s), 2.04-2.15 (3H, m), 1.79-1.95 (3H, m), 1.45-1.71 (8H, m), 1.54 (3H, s), 1.40 (3H, d, J=6.6 Hz), 1.27 (3H, s), 1.25 (3H, d, J=6.4 Hz), 1.16 (3H, s), 1.12 (3H, s), 0.92-0.98 (1H, m), 0.77 (3H, s); LC-MS: rt=2.02 min, m/z=522.2 [M−C3H7S]⁺, purity=94.01% (214 nm), 86.66% (254 nm).

Example 68

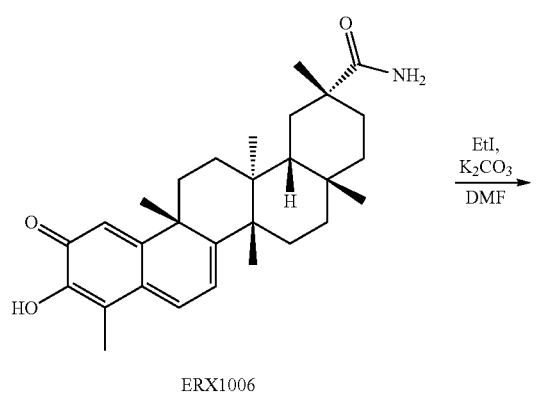

-continued

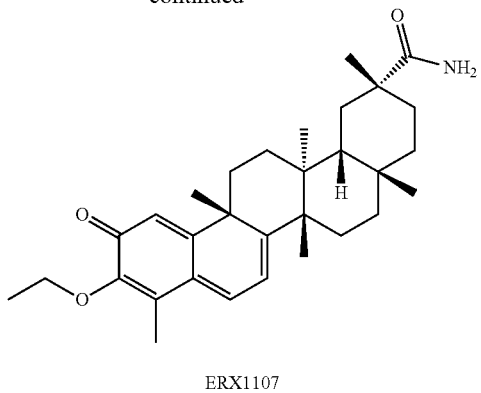

To a solution of ERX1006 (45 mg, 0.1 mmol) in DMF (5 mL) was added K₂CO₃ (28 mg, 0.2 mmol) followed by EtI (156 mg, 1.0 mmol). The reaction was stirred at 40° C. for 4 hours. The reaction was quenched by ice-water (50 mL) and filtered. The solid was dissolved with CH₂Cl₂ (200 mL), washed with brine (100 mL), dried over MgSO₄ and concentrated in vacuo. The residue was purified by prep-TLC (ethyl acetate) to afford product (25 mg, 0.0523 mmol, Yield=52%) as yellow solid. ¹HNMR δ(500 MHz, CDCl3): 6.94 (1H, dd, J=7.1, 1.2 Hz), 6.39 (1H, d, J=1.2 Hz), 6.28 (1H, d, J=7.1 Hz), 5.66 (1H, br), 5.20 (1H, br), 4.10 (2H, q, J=7.1 Hz), 2.39 (1H, d, J=16.1 Hz), 2.22 (3H, s), 1.45-2.15 (13H, m), 1.44 (3H, s), 1.34 (3H, t, J=7.0 Hz), 1.26 (3H, s), 1.20 (3H, s), 1.12 (3H, s), 0.99-1.05 (1H, m), 0.76 (3H, s); LC-MS: rt=1.83 min, m/z=478.3 [M+H]⁺, purity=100% (214, 254 nm).

Example 69

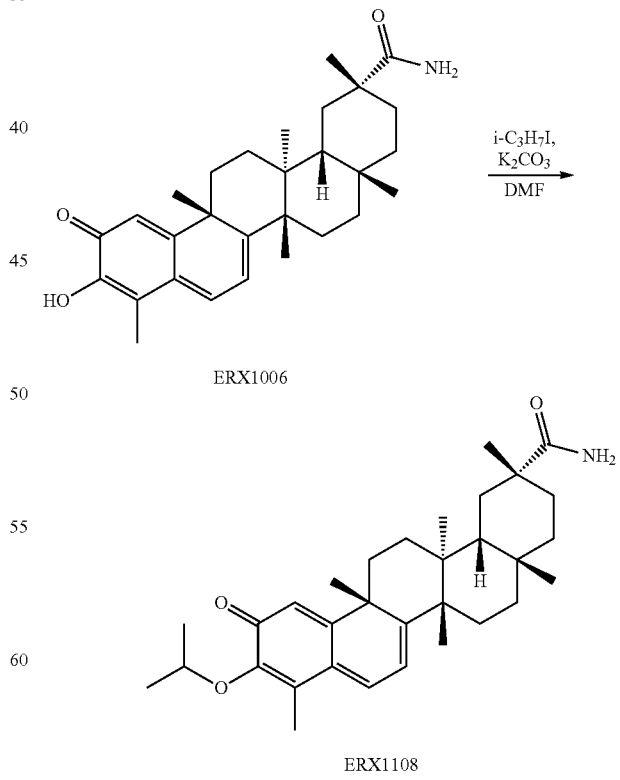

To a solution of ERX1006 (45 mg, 0.1 mmol) in DMF (5 mL) was added K₂CO₃ (28 mg, 0.2 mmol) followed by i-C₃H7I (170 mg, 1.0 mmol). The reaction was stirred at 40° C. for 4 hours. The reaction was quenched by ice-water (50 mL) and filtered. The solid was dissolved with CH₂Cl₂ (200 mL), washed with brine (100 mL), dried over MgSO₄ and concentrated in vacuo. The residue was purified by prep-TLC (ethyl acetate) to afford product (20 mg, 0.0407 mmol, Yield=41%) as yellow solid. ¹HNMR δ(500 MHz, CDCl3): 6.92 (1H, dd, J=7.1, 1.2 Hz), 6.36 (1H, d, J=1.3 Hz), 6.27 (1H, d, J=7.1 Hz), 5.68 (1H, br), 5.25 (1H, br), 4.69-4.75 (1H, m), 2.39 (1H, d, J=15.9 Hz), 2.20 (3H, s), 1.47-2.13 (13H, m), 1.44 (3H, s), 1.28 (3H, d, J=6.0 Hz), 1.26 (3H, d, J=6.0 Hz), 1.26 (3H, s), 1.20 (3H, s), 1.12 (3H, s), 0.99-1.04 (1H, m), 0.77 (3H, s); LC-MS: rt=1.90 min, m/z=492.4 [M+H]⁺, purity=100% (214, 254 nm).

Example 70

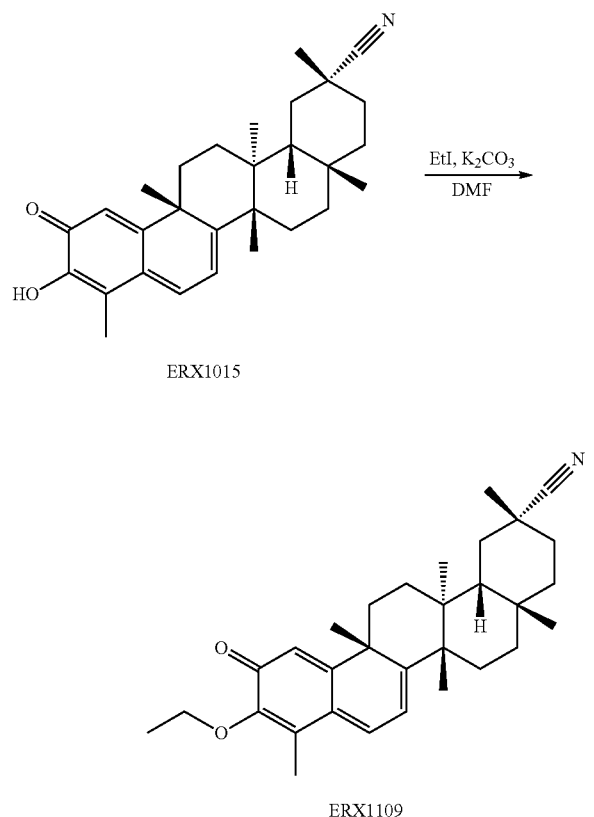

To a solution of ERX1015 (80 mg, 0.174 mmol) in EtI (1 mL) and DMF (2 mL) was added K₂CO₃ (72 mg, 0.522 mmol). The reaction was stirred at 50° C. overnight. The solution was diluted with CH₂Cl₂ (300 mL), washed with sat. LiCl.H₂O (2×100 mL), H₂O (100 mL), brine (100 mL), dried over MgSO₄ and concentrated in vacuo. The residue was purified by prep-TLC (petroleum ether/ethyl acetate=2:1) to afford product (33.5 mg, 0.0729 mmol, Yield=42%) as yellow solid. ¹HNMR: δ(400 MHz, CDCl3): 6.96 (1H, dd, J=7.1, 1.1 Hz), 6.41 (1H, d, J=1.2 Hz), 6.31 (1H, d, J=7.2 Hz), 4.06-4.16 (2H, m), 2.22 (3H, s), 1.54-2.18 (14, m), 1.47 (3H, s), 1.44 (3H, s), 1.35 (3H, t, J=7.1 Hz), 1.29 (3H, s), 1.08-1.15 (1H, m), 1.09 (3H, s), 1.05 (3H, s); LC-MS: rt=1.98 min, m/z=460.2 [M+H]⁺, purity=100% (214, 254 nm).

Example 71

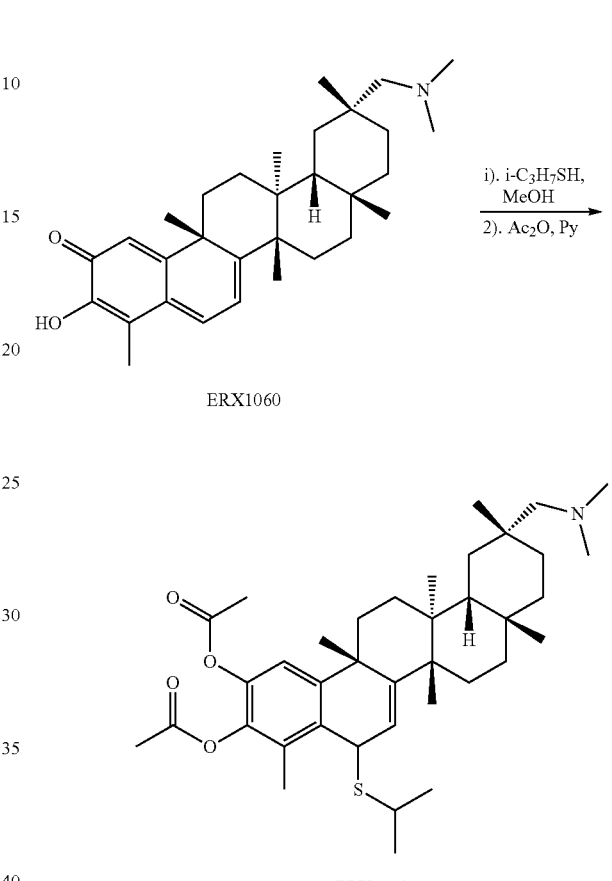

To a solution of ERX1060 (30 mg, 0.0647 mmol) in MeOH (1 mL) was added i-C₃H7SH (7.6 mg, 0.1 mmol). The reaction was stirred at room temperature for 1 hour. The solution was turned from reddish to pale red-yellow. Then the solution was concentrated in vacuo to afford crude mixture which was used in the next step without further purification.

To a crude mixture prepared above in Ac₂O (4 mL) was added pyridine (0.5 mL). The reaction was stirred at room temperature overnight. Then the mixture was diluted with CH₂Cl₂ (100 mL), washed with water (2×50 mL), brine (50 mL), dried over MgSO₄ and concentrated in vacuo. The residue was purified by silica gel chromatography (CH₂Cl₂/MeOH=10:1) to afford product (5 mg, 0.00801 mmol, overall yield=12%) as pale yellow solid. ¹HNMR: δ(500 MHz, CDCl3): 7.02 (1H, s), 6.01 (1H, d, J=6.0 Hz), 4.59 (1H, d, J=6.1 Hz), 3.16-3.23 (1H, m), 2.20-2.50 (6H, br), 2.31 (3H, s), 2.29 (3H, s), 2.27 (3H, s), 1.20-2.05 (16H, m), 1.57 (3H, s), 1.42 (3H, s), 1.41 (3H, d, J=7.0 Hz), 1.31 (3H, d, J=7.0 Hz), 1.22 (3H, s), 1.10 (3H, br), 0.95-1.01 (1H, m), 0.77 (3H, s); LC-MS: rt=1.76 min, m/z=624.3 [M+H]⁺, purity=95.93% (214 nm), 95.26% (254 nm).

Example 72

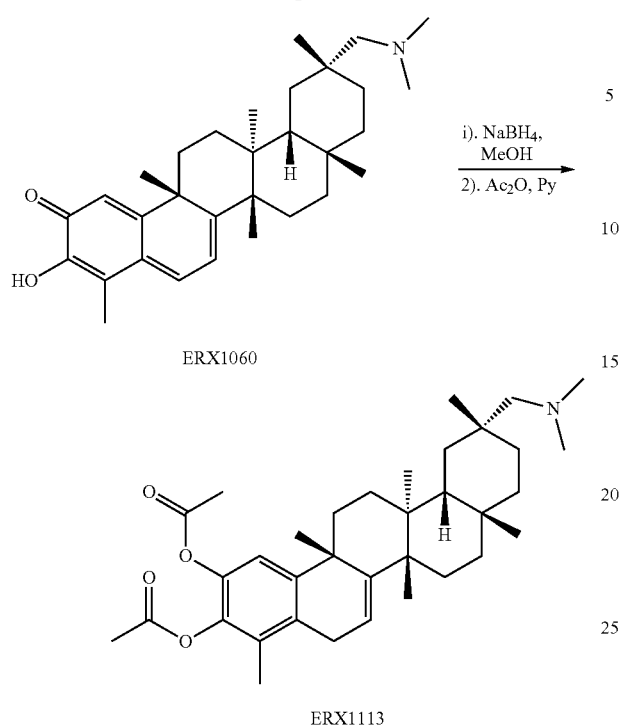

ERX1060 i). NaBH₄, MeOH
2). Ac₂O, Py

ERX1113

To a solution of ERX1060 (70 mg, 0.15 mmol) in MeOH (1 mL) was added NaBH₄ (5.7 mg, 0.15 mmol). The reaction was stirred at room temperature for 1 hour. The solution was turned from reddish to pale yellow. Then the solution was concentrated in vacuo to afford crude mixture which was used in the next step without further purification.

To a crude mixture prepared above in Ac₂O (0.5 mL) was added pyridine (0.5 mL). The reaction was stirred at room temperature overnight. Then the mixture was diluted with CH₂Cl₂ (100 mL), washed with water (2×50 mL), brine (50 mL), dried over MgSO₄ and concentrated in vacuo. The residue was purified by silica gel chromatography (CH₂Cl₂/MeOH=10:1) to afford product (10 mg, 0.0182 mmol, Yield=12%) as pale yellow solid. ¹HNMR: δ(500 MHz, CDCl3): 7.00 (1H, s), 5.80 (1H, dd, J=6.4, 1.9 Hz), 3.36 (1H, dd, J=20.5, 6.4 Hz), 3.09 (1H, d, J=20.5 Hz), 2.30-2.50 (6H, br), 2.32 (3H, s), 2.20 (3H, s), 2.08 (3H, s), 1.33-2.07 (16H, m), 1.39 (3H, s), 1.31 (3H, s), 1.22 (3H, s), 1.11 (3H, br), 0.95-1.01 (1H, m), 0.80 (3H, s); LC-MS: rt=1.66 min, m/z=550.4 [M+H]⁺, purity=94.27% (214 nm).

Example 73

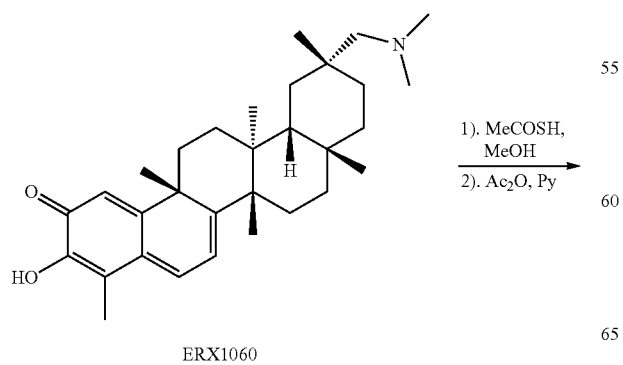

ERX1060

1). MeCOSH, MeOH
2). Ac₂O, Py

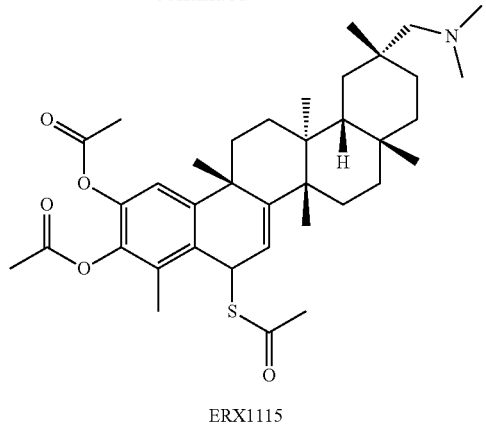

ERX1115

To a solution of ERX1060 (20 mg, 0.0431 mmol) in MeOH (1 mL) was added i-C₃H7SH (5 mg, 0.0647 mmol). The reaction was stirred at room temperature for 1 hour. The solution was turned from reddish to pale red-yellow. Then the solution was concentrated in vacuo to afford crude mixture which was used in the next step without further purification.

To a crude mixture prepared above in Ac₂O (0.5 mL) was added pyridine (0.5 mL). The reaction was stirred at room temperature overnight. Then the mixture was diluted with CH₂Cl₂ (100 mL), washed with water (2×50 mL), brine (50 mL), dried over MgSO₄ and concentrated in vacuo. The residue was purified by silica gel chromatography (CH₂Cl₂/MeOH=10:1) to afford product (10 mg, 0.016 mmol, overall yield=37%) as pale yellow solid. ¹HNMR: δ(500 MHz, CDCl3): 7.03 (1H, s), 5.95 (1H, d, J=6.4 Hz), 5.39 (1H, d, J=6.4 Hz), 2.26-2.50 (6H, br), 2.36 (3H, s), 2.31 (3H, s), 2.28 (3H, s), 2.08 (3H, s), 1.25-2.06 (16H, m), 1.42 (3H, s), 1.37 (3H, s), 1.21 (3H, s), 1.11 (3H, br), 0.94-1.00 (1H, m), 0.77 (3H, s); LC-MS: rt=1.65 min, m/z=624.3 [M+H]⁺, purity=92.90% (214 nm), 97.84% (254 nm).

Example 74

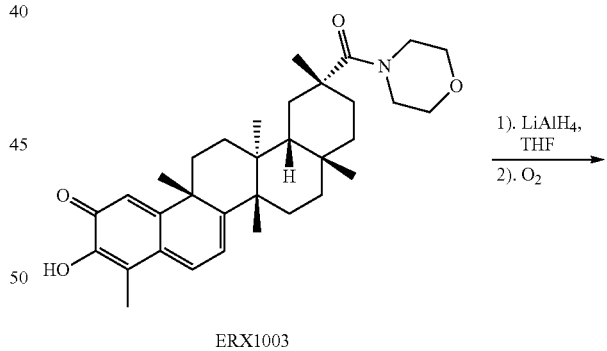

ERX1003

1). LiAlH₄, THF
2). O₂

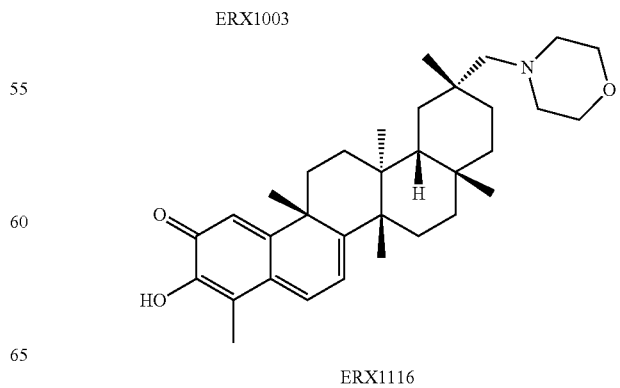

ERX1116

To a solution of ERX1003 (90 mg, 0.174 mmol) in anhydrous THF (15 mL) was added LiAlH4 (494 mg, 13 mmol). The mixture was refluxed overnight. The reaction was quenched by sat. NH4Cl solution. The mixture was heated at 50° C. for 2 hours and filtered through a thin layer of silica gel. The solid was washed with THF (3×50 mL). The combined filtrate was concentrated in vacuo. The residue was purified by prep-TLC (CH2Cl2: MeOH=10:1) to afford product (10 mg, 0.0198 mmol, Yd=11%) as red solid. $^1$HNMR: δ(500 MHz, CDCl3): 7.03 (1H, dd, J=7.3, 1.2 Hz), 6.97 (1H, s), 6.53 (1H, d, J=1.0 Hz), 6.39 (1H, d, J=6.9 Hz), 3.66 (1H, t, J=4.4 Hz), 2.46-2.53 (4H, m), 2.22 (3H, s), 2.06-2.20 (2H, m), 2.00-2.04 (1H, m), 1.30-1.91 (13H, m), 1.44 (3H, s), 1.40 (3H, s), 1.22 (3H, s), 1.01 (3H, s), 0.94-0.99 (1H, m), 0.79 (3H, s); LC-MS: rt=1.60 min, m/z=506.3 [M+H]$^+$, purity=100% (214,254 nm).

Example 75

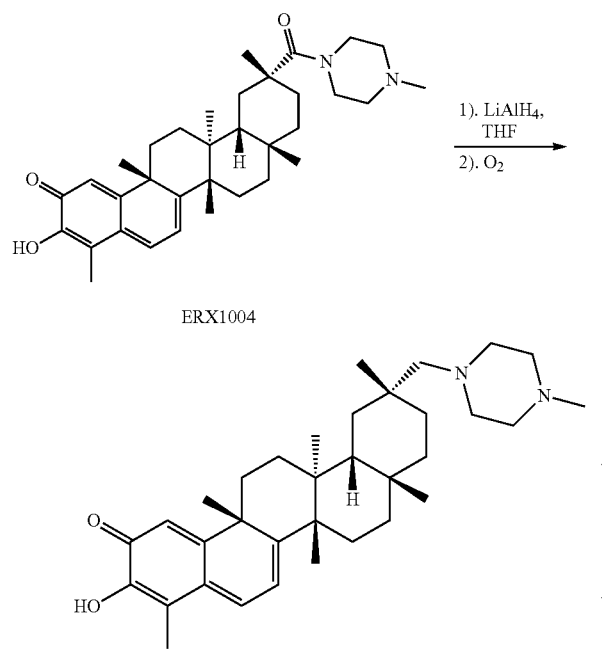

To a solution of ERX1004 (150 mg, 0.282 mmol) in anhydrous THF (10 mL) was added LiAlH4 (54 mg, 1.5 mmol). The mixture was refluxed overnight. The reaction was quenched by sat. NH4Cl solution. The mixture was heated at 50° C. for 2 hours and filtered through a thin layer of silica gel. The solid was washed with THF (3×50 mL). The combined filtrate was concentrated in vacuo. The residue was purified by prep-TLC (CH2Cl2: MeOH=10:1) to afford product (10 mg, 0.0193 mmol, Yd=7%) as red solid. $^1$HNMR: δ(500 MHz, CDCl3): 7.03 (1H, dd, J=7.4, 1.4 Hz), 6.96 (1H, s), 6.53 (1H, d, J=1.0 Hz), 6.39 (1H, d, J=6.9 Hz), 2.42-2.70 (8H, m), 2.37 (3H, s), 2.22 (3H, s), 1.23-2.23 (16H, m), 1.44 (3H, s), 1.40 (3H, s), 1.21 (3H, s), 1.01 (3H, s), 0.93-0.99 (1H, m), 0.78 (3H, s); LC-MS: rt=1.69 min, m/z=519.3 [M+H]$^+$, purity=100% (214 nm), 97.88% (254 nm).

Example 76

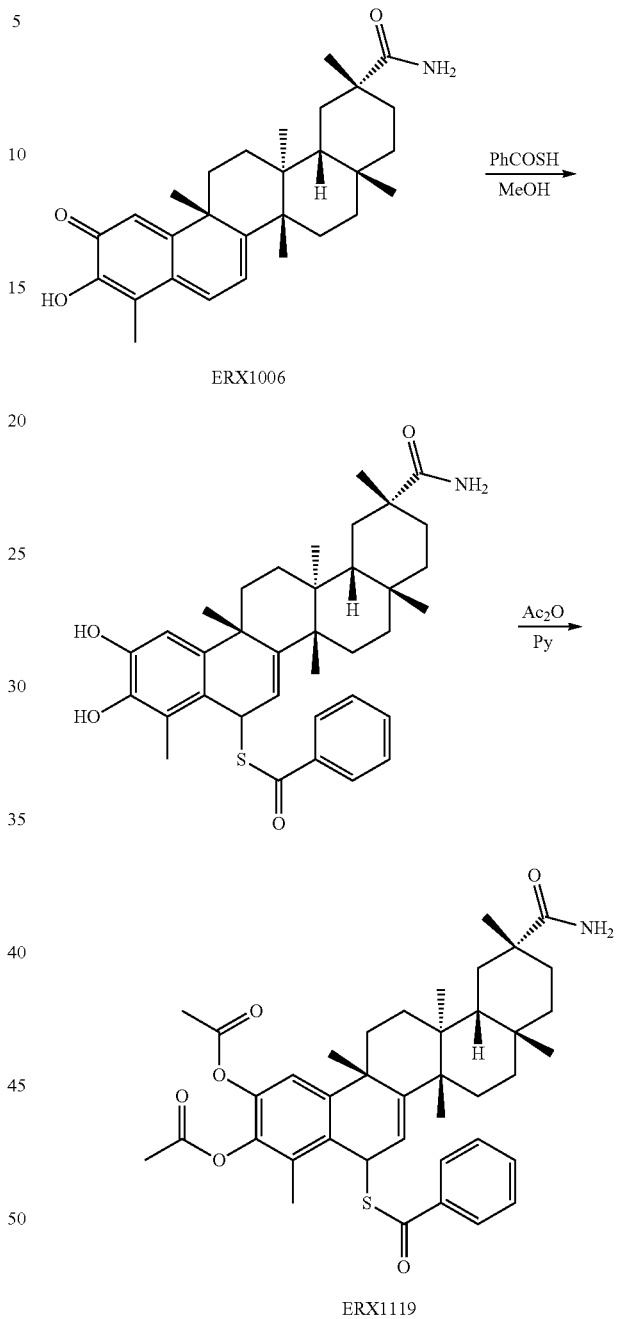

To a solution of ERX1006 (100 mg, 0.222 mmol) in MeOH (10 mL) was added PhCOSH (46 mg, 0.333 mmol). The reaction was stirred at room temperature for 1 hour. The solution was turned from red to pale yellow. Then the solution was concentrated in vacuo to afford crude mixture.

To a crude mixture prepared above in Ac2O (4 mL) was added pyridine (0.5 mL). The reaction was stirred at room temperature overnight. Then the mixture was diluted with CH2Cl2 (200 mL), washed with water (2×100 mL), brine (100 mL), dried over MgSO4 and concentrated in vacuo. The residue was purified by prep-TLC (CH2Cl2/MeOH=10:1) to afford product (50 mg, 0.0744 mmol, Yield=34%) as white solid. ¹HNMR: δ(500 MHz, CDCl3): 7.95 (2H, t, J=7.4 Hz), 7.56 (1H, t, J=7.4 Hz), 7.44 (2H, t, J=7.4 Hz), 7.06 (1H, s), 6.06 (1H, d, J=6.5 Hz), 5.68 (1H, br), 5.60 (1H, d, J=6.5 Hz), 5.24 (1H, br), 2.44 (1H, d, J=14.9 Hz), 2.30 (3H, s), 2.28 (3H, s), 2.12 (3H, s), 1.40-2.10 (13H, m), 1.51 (3H, s), 1.20 (3H, s), 1.19 (3H, s), 1.09 (3H, s), 0.96-1.02 (1H, m), 0.76 (3H, s); LC-MS: rt=2.01 min, no mass peaks intergrated, purity=99.59% (254 nm).

Example 77

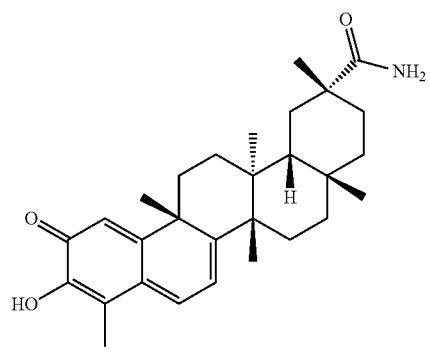

ERX1006

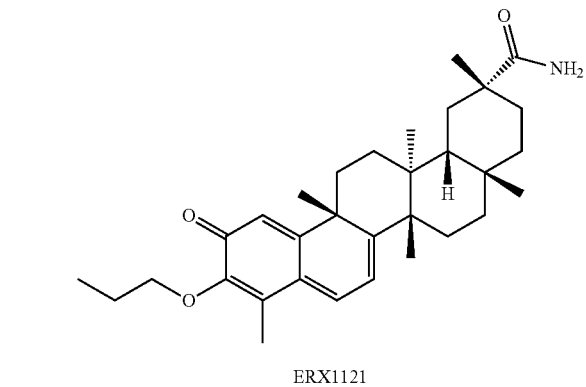

ERX1121

To a solution of ERX1006 (200 mg, 0.445 mmol) in DMF (5 mL) was added K₂CO₃ (123 mg, 0.890 mmol) followed by CH₃CH₂CH₂I (756 mg, 0.43 mL, 4.45 mmol). The reaction was stirred at 50° C. overnight. The mixture was diluted with EtOAc (200 mL), washed with sat. LiCl.H₂O solution (3×100 mL), brine (100 mL), dried over MgSO₄ and concentrated in vacuo. The residue was purified by prep-TLC (petroleum ether/ethyl acetate=1:3, two times) to afford product (101 mg, 0.205 mmol, Yield=46%) as yellow solid. ¹HNMR (400 MHz, CDCl3): 6.94 (1H, dd, J=7.0, 1.4 Hz), 6.38 (1H, d, J=1.4 Hz), 6.28 (1H, d, J=7.0 Hz), 5.70 (1H, br), 5.35 (1H, br), 4.00 (1H, t, J=6.8 Hz), 2.39 (1H, d, J=15.5 Hz), 2.22 (3H, s), 1.45-2.15 (15H, m), 1.44 (3H, s), 1.26 (3H, s), 1.20 (3H, s), 1.12 (3H, s), 1.00 (3H, t, J=7.6 Hz), 0.98-1.05 (1H, m), 0.75 (3H, s); LC-MS: rt=1.89 min, m/z=492.4 [M+H]⁺, purity=100% (214 nm), 97.59% (254 nm).

Example 78

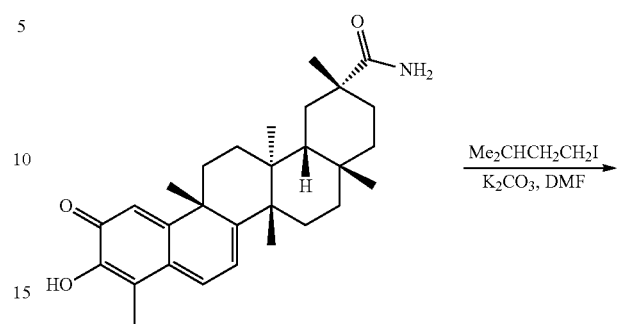

ERX1006

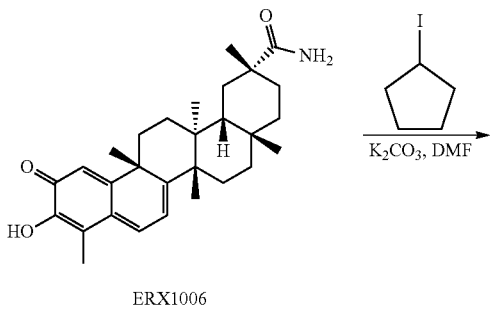

ERX1122

To a solution of ERX1006 (200 mg, 0.445 mmol) in DMF (5 mL) was added K₂CO₃ (123 mg, 0.890 mmol) followed by Me₂CHCH₂CH₂I (881 mg, 0.59 mL, 4.45 mmol). The reaction was stirred at 50° C. overnight. The mixture was diluted with CH₂Cl₂ (200 mL), washed with sat. LiCl.H₂O solution (2×100 mL), brine (100 mL), dried over MgSO₄ and concentrated in vacuo. The residue was purified by prep-TLC (petroleum ether/ethyl acetate=1:3) to afford product (88.8 mg, 0.171 mmol, Yield=38%) as yellow solid. ¹HNMR δ(400 MHz, CDCl3): 6.94 (1H, d, J=7.1 Hz), 6.38 (1H, s), 6.28 (1H, d, J=7.1 Hz), 5.69 (1H, br), 5.30 (1H, br), 4.06 (1H, t, J=6.9 Hz), 2.39 (1H, d, J=15.7 Hz), 2.21 (3H, s), 1.45-2.14 (16H, m), 1.44 (3H, s), 1.26 (3H, s), 1.20 (3H, s), 1.12 (3H, s), 0.98-1.05 (1H, m), 0.94 (6H, d, J=6.4 Hz), 0.76 (3H, s); LC-MS: rt=2.00 min, m/z=520.4 [M+H]⁺, purity=98.46% (214 nm), 98.77% (254 nm).

Example 79

-continued

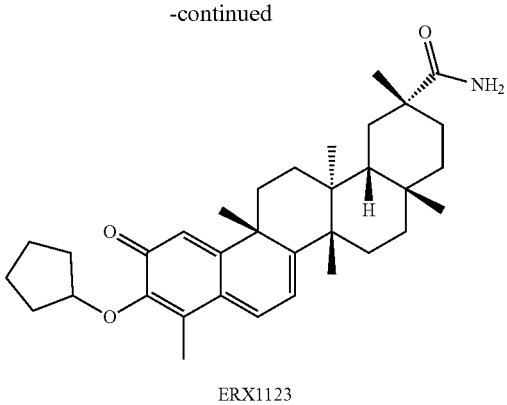

ERX1123

To a solution of ERX1006 (100 mg, 0.222 mmol) in DMF (10 mL) was added K$_2$CO$_3$ (61 mg, 0.44 mmol) followed by iodocyclopentane (217 mg, 1.11 mmol). The reaction was stirred at 40° C. overnight. The mixture was diluted with CH$_2$Cl$_2$ (100 mL), washed with sat. LiCl.H$_2$O solution (2×50 mL), brine (50 mL), dried over MgSO$_4$ and concentrated in vacuo. The residue was purified by prep-TLC (ethyl acetate) to afford product (56 mg, 0.108 mmol, Yield=50%) as yellow solid. $^1$HNMR δ(500 MHz, CDCl3): 6.91 (1H, dd, J=7.0, 1.1 Hz), 6.36 (1H, d, J=1.1 Hz), 6.27 (1H, d, J=7.0 Hz), 5.70 (1H, br), 5.36 (1H, br), 5.15-5.19 (1H, m), 2.39 (1H, d, J=15.6 Hz), 2.18 (3H, s), 1.46-2.12 (21H, m), 1.44 (3H, s), 1.26 (3H, s), 1.20 (3H, s), 1.11 (3H, s), 0.98-1.04 (1H, m), 0.76 (3H, s); LC-MS: rt=1.44 min, m/z=518.4 [M+H]$^+$, purity=97.22% (214 nm), 99.30% (254 nm).

Example 80

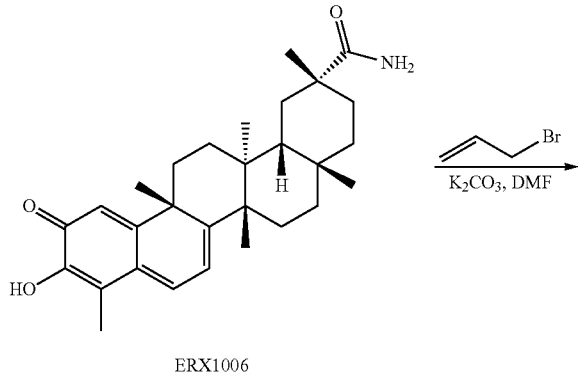

ERX1006

ERX1124

To a solution of ERX1006 (180 mg, 0.4 mmol) in DMF (10 mL) was added K$_2$CO$_3$ (110 mg, 0.8 mmol) followed by allyl bromide (242 mg, 2.0 mmol). The reaction was stirred at 40° C. overnight. The mixture was diluted with CH$_2$Cl$_2$ (100 mL), washed with sat. LiCl.H$_2$O solution (2×50 mL), brine (50 mL), dried over MgSO$_4$ and concentrated in vacuo. The residue was purified by prep-TLC (ethyl acetate) to afford product (98 mg, 0.2 mmol, Yield=50%) as yellow solid. $^1$HNMR δ(500 MHz, CDCl3): 6.95 (1H, dd, J=7.0, 1.0 Hz), 6.39 (1H, d, J=1.0 Hz), 6.28 (1H, d, J=7.0 Hz), 6.02-6.12 (1H, m), 5.68 (1H, br), 5.34 (1H, dd, J=17.2, 1.4 Hz), 5.20 (1H, d, J=10.4 Hz), 4.60 (1H, d, J=5.1 Hz), 2.39 (1H, d, J=16.1 Hz), 2.21 (3H, s), 1.45-2.12 (13H, m), 1.44 (3H, s), 1.26 (3H, s), 1.20 (3H, s), 1.12 (3H, s), 0.98-1.05 (1H, m), 0.76 (3H, s); LC-MS: rt=1.84 min, m/z=490.2 [M+H]$^+$, purity=100% (214, 254 nm).

Example 81

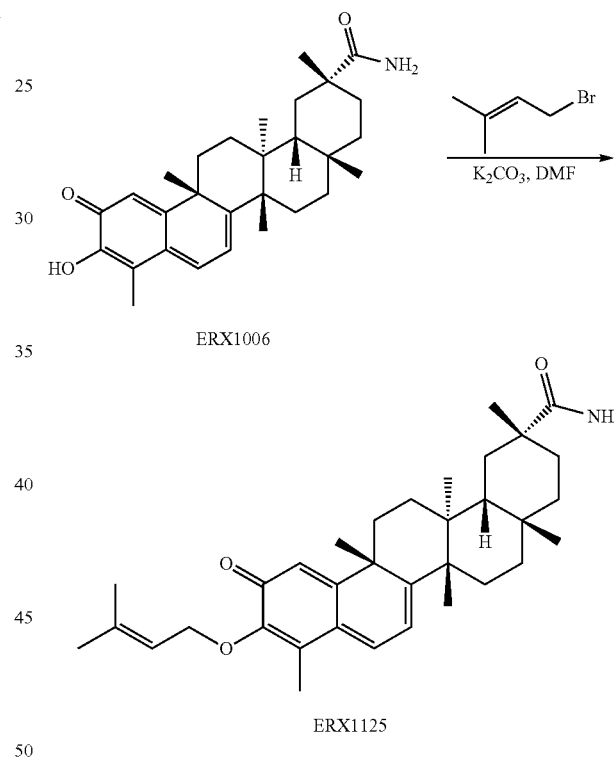

ERX1006

ERX1125

To a solution of ERX1006 (100 mg, 0.22 mmol) in DMF (10 mL) was added K$_2$CO$_3$ (61 mg, 0.44 mmol) followed by 3,3-dimethylallyl bromide (217 mg, 1.11 mmol). The reaction was stirred at 40° C. overnight. The mixture was diluted with CH$_2$Cl$_2$ (100 mL), washed with sat. LiCl.H$_2$O solution (2×50 mL), brine (50 mL), dried over MgSO$_4$ and concentrated in vacuo. The residue was purified by prep-TLC (ethyl acetate) to afford product (56 mg, 0.11 mmol, Yield=50%) as yellow solid. $^1$HNMR δ(500 MHz, CDCl3): 6.94 (1H, dd, J=7.0, 1.1 Hz), 6.38 (1H, d, J=1.1 Hz), 6.27 (1H, d, J=7.0 Hz), 5.72 (1H, br), 5.52 (1H, tt, J=7.2, 1.3 Hz), 5.46 (1H, br), 4.54-4.63 (2H, m), 2.40 (1H, d, J=15.7 Hz), 2.20 (3H, s), 1.45-2.12 (13H, m), 1.75 (3H, s), 1.69 (3H, s), 1.43 (3H, s), 1.25 (3H, s), 1.20 (3H, s), 1.11 (3H, s), 0.98-1.04 (1H, m), 0.75 (3H, s); LC-MS: rt=2.43 min, m/z=518.3 [M+H]$^+$, purity=100% (214, 254 nm).

Example 82

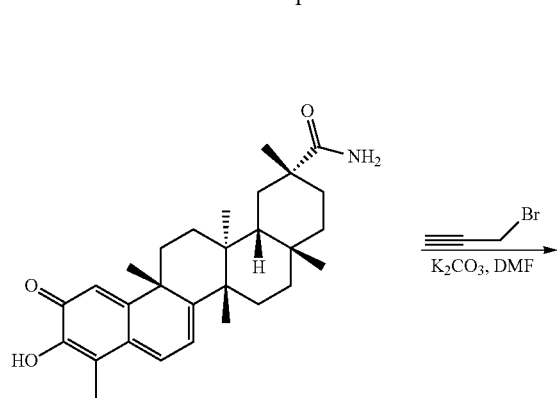

ERX1006

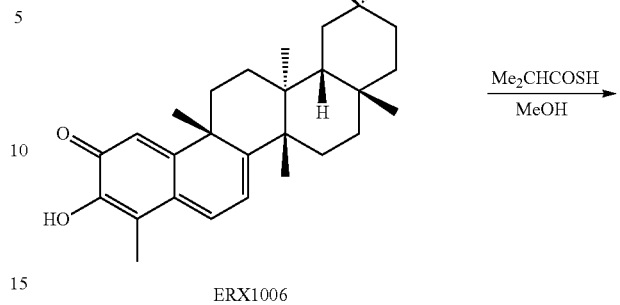

ERX1126

To a solution of ERX1006 (200 mg, 0.44 mmol) in DMF (10 mL) was added K₂CO₃ (121 mg, 0.88 mmol) followed by propargyl bromide (263 mg, 2.23 mmol). The reaction was stirred at 40° C. overnight. The mixture was diluted with CH₂Cl₂ (100 mL), washed with sat. LiCl.H₂O solution (2×50 mL), brine (50 mL), dried over MgSO₄ and concentrated in vacuo. The residue was purified by prep-TLC (ethyl acetate) to afford product (100 mg, 0.205 mmol, Yield=47%) as yellow solid. ¹HNMR δ(500 MHz, CDCl3): 7.00 (1H, dd, J=7.0, 1.0 Hz), 6.39 (1H, d, J=1.0 Hz), 6.30 (1H, d, J=7.5 Hz), 5.68 (1H, br), 5.34 (1H, br), 4.88 (1H, ABxd, J=15.9, 2.4 Hz), 4.85 (1H, ABxd, J=15.9, 2.4 Hz), 2.42 (1H, t, J=2.3 Hz), 2.40 (1H, d, J=16.0 Hz), 2.28 (3H, s), 1.46-2.13 (13H, m), 1.45 (3H, s), 1.26 (3H, s), 1.20 (3H, s), 1.12 (3H, s), 0.99-1.05 (1H, m), 0.76 (3H, s); LC-MS: rt=1.78 min, m/z=488.3 [M+H]⁺, purity=100% (214 nm), 93.38% (254 nm).

Example 83

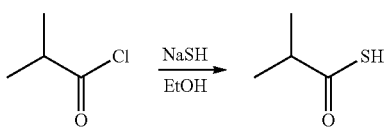

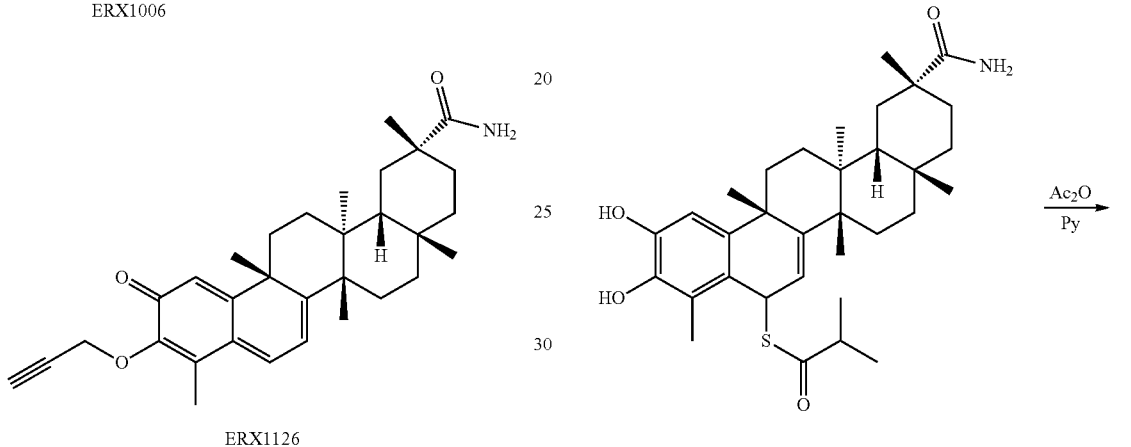

ERX1006

ERX1127

To a solution of NaSH (2.0 g, 35.7 mmol) in EtOH (20 mL) was added Me₂CHCOCl (4.0 g, 37.6 mmol) dropwise. The solution was stirred at rt for 1 hour. The solution was concentrated in vacuo and used in the next step without further purification.

To a solution of ERX1006 (50 mg, 0.11 mmol) in MeOH (5 mL) was added Me₂CHCOSH (23 mg, 0.22 mmol) in EtOH (2 mL). The reaction was stirred at room temperature for 1 hour. The solution was turned from red to pale yellow. Then the solution was concentrated in vacuo to afford crude mixture (45 mg, 0.081 mmol, Yd=74%).

To a crude mixture (45 mg, 0.081 mmol) prepared above in Ac₂O (1 mL) was added pyridine (1 mL). The reaction was stirred at room temperature overnight. Then the mixture was diluted with CH$_2$Cl$_2$ (50 mL), washed with water (2×30 mL), brine (30 mL), dried over MgSO$_4$ and concentrated in vacuo. The residue was purified by prep-TLC (petroleum ether/ethyl acetate=1:1) to afford product (10 mg, 0.0157 mmol, Yield=20%) as white solid. 1HNMR δ(500 MHz, CDCl3): 7.01 (1H, s), 5.92 (1H, d, J=6.5 Hz), 5.67 (1 h, br), 5.34 (1H, d, J=6.5 Hz), 5.24 (1H, br), 2.68-2.77 (1H, m), 2.30 (3H, s), 2.27 (3H, s), 2.06 (3H, s), 1.30-2.08 (13H, m), 1.44 (3H, s), 1.20 (3H, s), 1.20 (3H, d, J=6.7 Hz), 1.19 (3H, s), 1.19 (3H, d, J=5.5 Hz), 1.09 (3H, s), 0.95-1.01 (1H, m), 0.74 (3H, s); LC-MS: rt=1.99 min, m/z=638.3 [M+H]$^+$, purity=96.8% (214 nm), 97.11% (254 nm).

Example 84

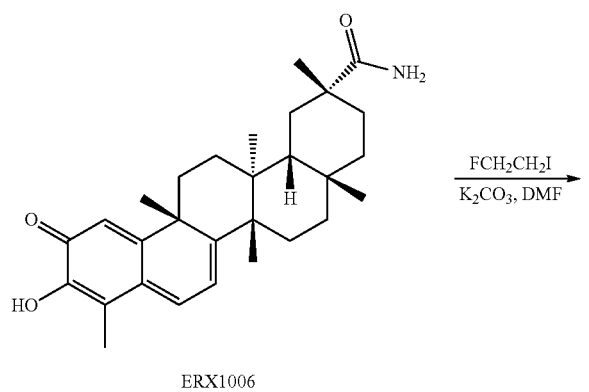

ERX1006

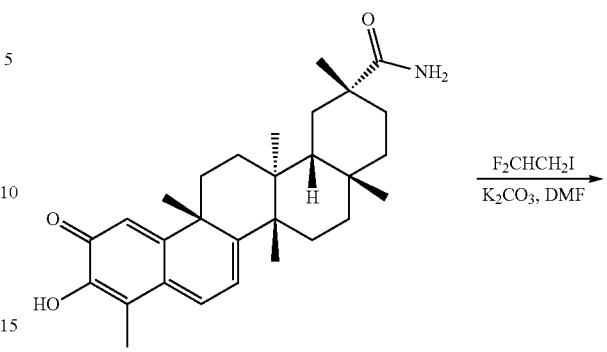

ERX1128

To a solution of ERX1006 (200 mg, 0.445 mmol) in DMF (5 mL) was added K$_2$CO$_3$ (123 mg, 0.890 mmol) followed by FCH$_2$CH$_2$I (774 mg, 0.36 mL, 4.45 mmol). The reaction was stirred at 50° C. for 1 day. The mixture was diluted with EtOAc (200 mL), washed with sat. LiCl.H$_2$O solution (3×100 mL), brine (100 mL), dried over MgSO$_4$ and concentrated in vacuo. The residue was purified by prep-TLC (ethyl acetate) to afford product (79.4 mg, 0.160 mmol, Yield=36%) as yellow solid. $^1$HNMR δ(400 MHz, CDCl3): 7.00 (1H, dd, J=7.0, 1.2 Hz), 6.39 (1H, d, J=1.0 Hz), 6.30 (1H, d, J=7.2 Hz), 5.69 (1H, br), 5.31 (1H, br), 4.66 (2H, d×t, J=47.8, 4.0 Hz), 4.37 (2H, d×t, J=31.0, 4.0 Hz), 2.40 (1H, t, J=16.1 Hz), 2.25 (3H, s), 1.46-2.14 (13H, m), 1.44 (3H, s), 1.26 (3H, s), 1.20 (3H, s), 1.12 (3H, s), 0.98-1.05 (1H, m), 0.75 (3H, s); LC-MS: rt=1.77 min, m/z=496.4 [M+H]$^+$, purity=98.76% (214 nm), 98.72% (254 nm).

Example 85

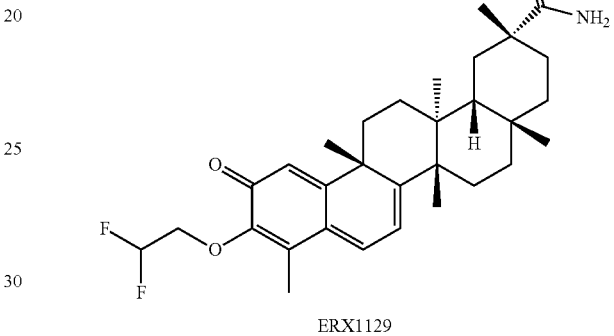

ERX1006

ERX1129

To a solution of ERX1006 (200 mg, 0.445 mmol) in DMF (5 mL) was added K$_2$CO$_3$ (123 mg, 0.890 mmol) followed by F$_2$CHCH$_2$I (854 mg, 0.39 mL, 4.45 mmol). The reaction was stirred at 50° C. for 1 day. The mixture was diluted with EtOAc (200 mL), washed with sat. LiCl.H$_2$O solution (3×100 mL), brine (100 mL), dried over MgSO$_4$ and concentrated in vacuo. The residue was purified by prep-TLC (ethyl acetate) to afford product (72.2 mg, 0.141 mmol, Yield=32%) as yellow solid. $^1$HNMR δ(400 MHz, CDCl3): 7.02 (1H, dd, J=7.0, 1.3 Hz), 6.40 (1H, d, J=1.3 Hz), 6.32 (1H, d, J=7.3 Hz), 6.10 (1H, tt, J=55.5, 4.1 Hz), 5.68 (1H, br), 5.28 (1H, br), 4.31 (1H, td, J=14.0, 4.0 Hz), 2.41 (1H, d, J=15.7 Hz), 2.24 (3H, s), 1.46-2.15 (13H, m), 1.45 (3H, s), 1.27 (3H, s), 1.21 (3H, s), 1.13 (3H, s), 0.99-1.06 (1H, m), 0.76 (3H, s); LC-MS: rt=2.19 min, m/z=514.4 [M+H]$^+$, purity=100% (214,254 nm).

Example 86

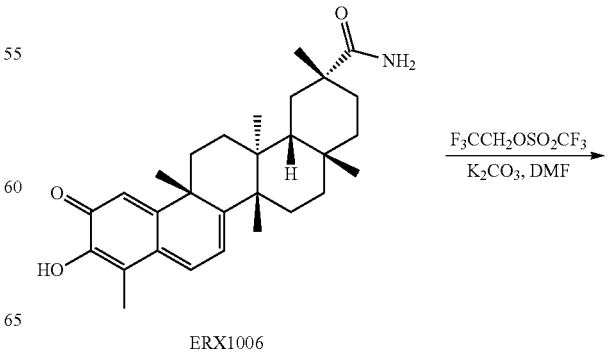

ERX1006

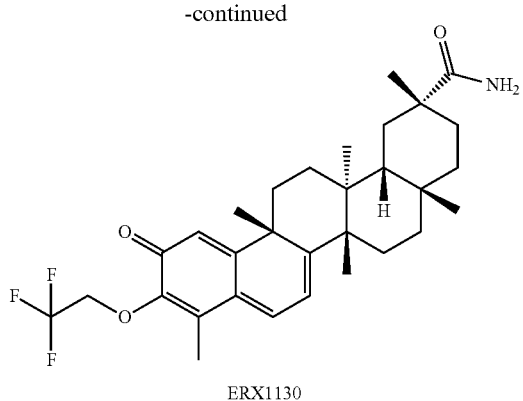

ERX1130

To a solution of ERX1006 (50 mg, 0.11 mmol) in DMF (5 mL) was added $K_2CO_3$ (45 mg, 0.33 mmol) followed by $F_3CCH_2OSO_2CF_3$ (30 mg, 0.13 mmol). The reaction was stirred at r.t. overnight. The mixture was diluted with $CH_2Cl_2$ (100 mL), washed with sat. $LiCl·H_2O$ solution (3×50 mL), brine (50 mL), dried over $MgSO_4$ and concentrated in vacuo. The residue was purified by prep-TLC (ethyl acetate) to afford product (30 mg, 0.0564 mmol, Yield=51%) as yellow solid. $^1$HNMR δ(500 MHz, CDCl3): 7.04 (1H, dd, J=7.5, 1.2 Hz), 6.40 (1H, d, J=1.2 Hz), 6.31 (1H, d, J=7.5 Hz), 5.68 (1H, br), 5.32 (1H, br), 4.57 (1H, q, J=8.8 Hz), 2.40 (1H, d, J=15.9 Hz), 2.24 (3H, s), 1.47-2.14 (13H, m), 1.44 (3H, s), 1.27 (3H, s), 1.20 (3H, s), 1.12 (3H, s), 0.99-1.05 (1H, m), 0.75 (3H, s); LC-MS: rt=1.27 min, m/z=532.4 [M+H]$^+$, purity=100% (214,254 nm).

Example 87

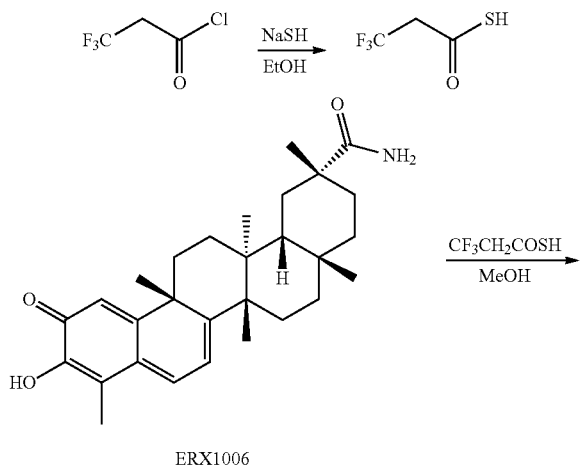

ERX1131

To a solution of NaSH (56 mg, 1.0 mmol) in EtOH (5 mL) was added $CF_3CH_2COCl$ (161 mg, 1.1 mmol) dropwise at 0° C. The solution was stirred at rt for 1 hour. The solution was concentrated in vacuo and used in the next step without further purification.

To a solution of ERX1006 (50 mg, 0.11 mmol) in MeOH (5 mL) was added $Me_2CHCOSH$ (80 mg, 0.55 mmol) in EtOH (2 mL). The reaction was stirred at room temperature for 1 hour. The solution was turned from red to pale yellow. Then the solution was concentrated in vacuo to afford crude mixture (50 mg, 0.0842 mmol, Yd=77%).

To a crude mixture (50 mg, 0.0842 mmol) prepared above in $Ac_2O$ (1 mL) was added pyridine (1 mL). The reaction was stirred at room temperature overnight. Then the mixture was diluted with $CH_2Cl_2$ (50 mL), washed with water (2×30 mL), brine (30 mL), dried over $MgSO_4$ and concentrated in vacuo. The residue was purified by prep-TLC (PE:EA=1:1) to afford product (11 mg, 0.0162 mmol, overall yield=20%) as white solid. $^1$HNMR δ(500 MHz, CDCl3): 7.04 (1H, s), 5.96 (1H, d, J=6.4 Hz), 5.68 (1H, br), 5.49 (1H, d, J=6.4 Hz), 5.31 (1H, br), 3.35 (2H, q, J=10.0 Hz), 2.43 (1H, d, J=15.3 Hz), 2.31 (3H, s), 2.28 (3H, s), 2.07 (3H, s), 1.44-2.05 (13H, m), 1.43 (3H, s), 1.20 (3H, s), 1.18 (3H, s), 1.09 (3H, s), 0.95-1.01 (1H, m), 0.73 (3H, s); LC-MS: rt=1.88 min, m/z=678.2 [M+H]$^+$, purity=100% (214,254 nm).

Example 88

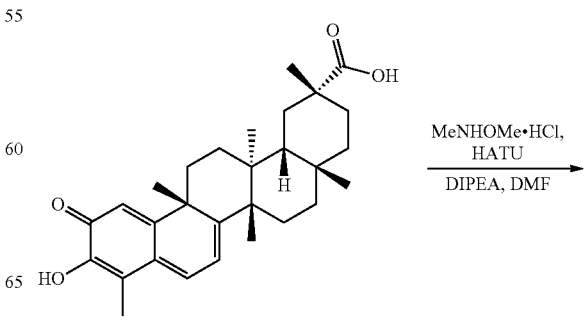

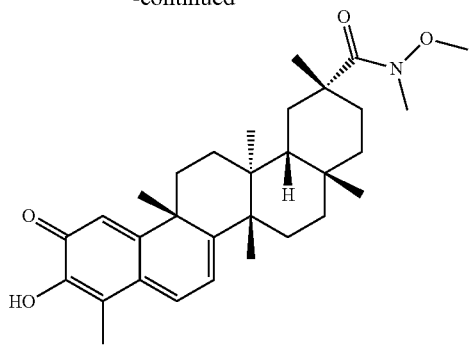

ERX1006

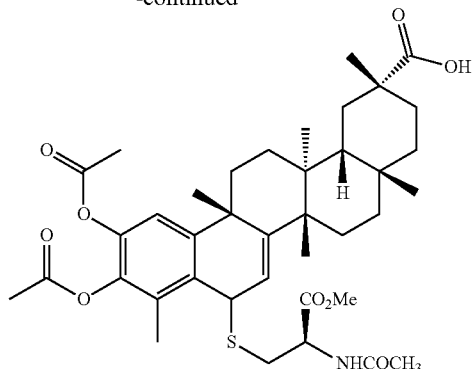

ERX1133

To a solution of celastrol (200 mg, 0.44 mmol) in DMF (5 mL) was added MeNHOMe.HCl (131 mg, 1.33 mmol), HATU (186 mg, 0.49 mmol) followed by DIPEA (115 mg, 0.89 mmol). The reaction was stirred at room temperature overnight. Then the solution was diluted with $CH_2Cl_2$ (200 mL), washed with brine (100 mL), dried over $MgSO_4$ and concentrated in vacuo. The residue was purified by prep-TLC (petroleum ether/EtOAc=1:1) to afford product (150 mg, 0.304 mmol, Yield=69%) as red solid. $^1$HNMR δ(500 MHz, $CDCl_3$): 7.03 (1H, dd, J=7.2, 1.1 Hz), 6.96 (1H, s), 6.54 (1H, d, J=1.1 Hz), 6.35 (1H, d, J=7.2 Hz), 3.71 (3H, s), 3.05 (3H, s), 2.81 (1H, d, J=16.2 Hz), 2.22 (3H, s), 2.04-2.32 (3H, m), 1.24-1.90 (10H, m), 1.46 (3H, s), 1.26 (3H, s), 1.22 (3H, s), 1.12 (3H, s), 0.94-1.00 (1H, m), 0.50 (3H, s); LC-MS: rt=2.56 min, m/z=494.2 [M+H]$^+$, purity=96.78% (214 nm), 91.29% (254 nm).

Example 89

To a solution of Celastrol (500 mg, 1.11 mmol) in MeOH (20 mL) was added N-acetyl-L-cysteine ethyl ester (393 mg, 2.22 mmol). The reaction was stirred at room temperature for 1 hour. The solution was turned from red to pale yellow. Then the solution was concentrated in vacuo to afford crude mixture.

To a crude mixture prepared above in pyridine (5 mL) was added $Ac_2O$ (3 mL). The reaction was stirred at room temperature overnight. Then the mixture was poured into $H_2O$ (100 mL), filtered. The solid was dissolved in $CH_2Cl_2$ (200 mL), washed with water (100 mL), brine (100 mL), dried over $MgSO_4$ and concentrated in vacuo. The residue was purified by prep-TLC (EtOAc) to afford product (408 mg, 0.573 mmol, overall yield=52%) as white solid. $^1$HNMR δ(400 MHz, CDCl3): 7.02 (1H, s), 6.29 (1H, d, J=6.8 Hz), 5.93 (1H, d, J=6.1 Hz), 4.89 (1H, q, J=5.8 Hz), 4.61 (1H, d, J=6.0 Hz), 3.73 (3H, s), 3.29 (1H, dd, J=13.6, 4.9 Hz), 2.92 (1H, dd, J=13.6, 6.0 Hz), 2.39 (1H, d, J=15.9 Hz), 2.31 (3H, s), 2.27 (3H, s), 2.23 (3H, s), 2.05 (3H, s), 1.30-2.16 (13H, m), 1.56 (3H, s), 1.25 (3H, s), 1.15 (3H, s), 1.07 (3H, s), 0.89-0.97 (1H, m), 0.66 (3H, s); LC-MS: rt=1.78 min, m/z=535.2 [M−SCH$_2$CH(CO$_2$Me)NHCOMe]$^+$, purity=97.44% (214 nm), 100% (254 nm).

Example 90

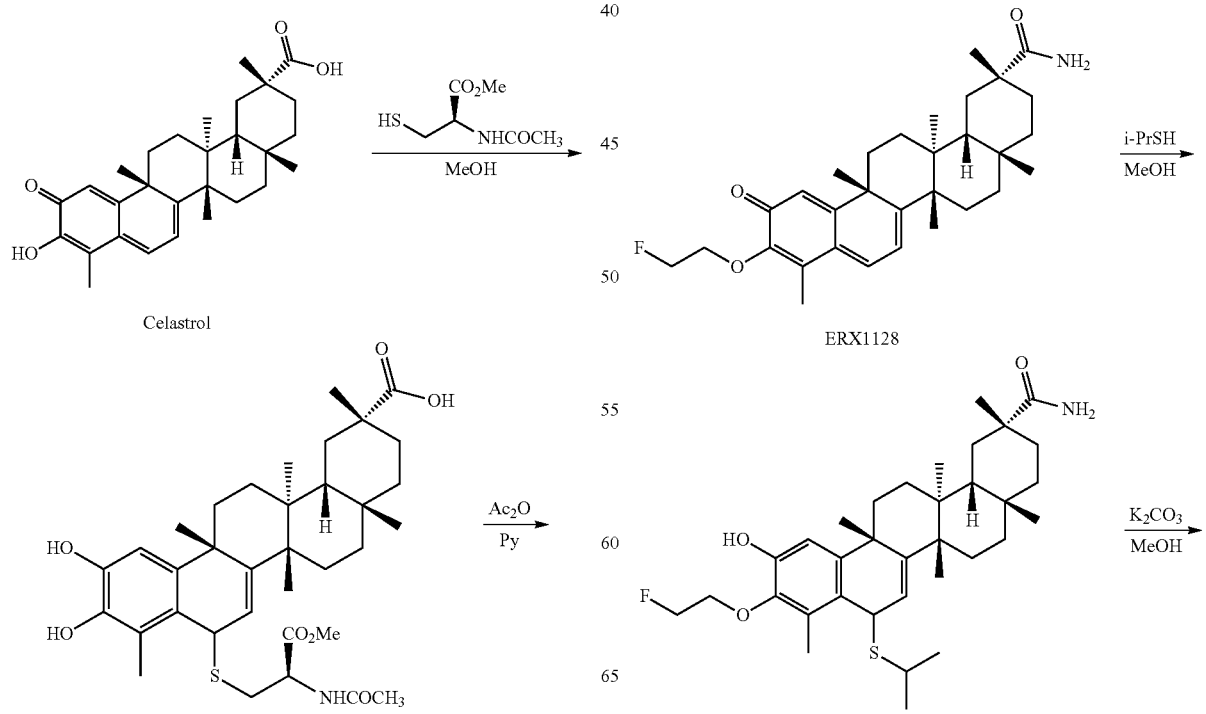

-continued

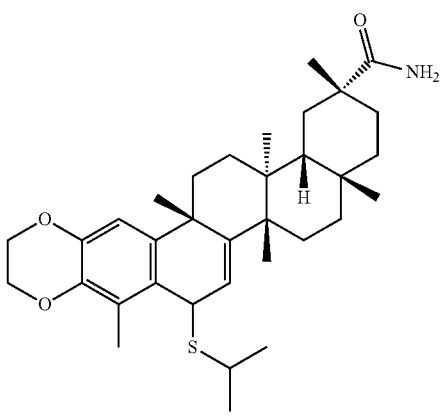

ERX1134

To a solution of ERX1128 (125 mg, 0.252 mmol) in MeOH (10 mL) was added i-PrSH (77 mg, 1.01 mmol). The reaction was stirred at room temperature for 1 hour. Then the solution was concentrated in vacuo. The residue was purified by prep-TLC (petroleum ether/ethyl acetate=1:3) to afford product. The crude product was partly oxidized in air to starting material.

To a solution of crude mixture prepared above in MeOH (10 mL) was added $K_2CO_3$ (70 mg, 0.504 mmol). The reaction was stirred at room temperature overnight. Most MeOH was removed in vacuo. Then the mixture was dissolved in $CH_2Cl_2$ (200 mL), washed with water (100 mL), brine (100 mL), dried over $MgSO_4$ and concentrated in vacuo. The residue was purified by prep-TLC (petroleum ether: ethyl acetate=1:2) to afford product (29.4 mg, 0.0533 mmol, two steps overall yield=21%) as white solid. $^1$HNMR δ(400 MHz, CDCl3): 6.72 (1H, s), 5.98 (1H, d, J=6.3 Hz), 5.63 (1H, br), 5.16 (1H, br), 4.60 (1H, d, J=6.3 Hz), 4.19-4.28 (4H, m), 3.13-3.23 (1H, m), 2.39 (1H, d, J=15.2 Hz), 2.29 (3H, s), 1.43-2.10 (13H, m), 1.56 (3H, s), 1.40 (3H, d, J=6.8 Hz), 1.28 (3H, d, J=6.8 Hz), 1.25 (3H, s), 1.19 (3H, s), 1.11 (3H, s), 0.96-1.02 (1H, m), 0.74 (3H, s); LC-MS: rt=2.18 min, m/z=552.3 [M+H]$^+$, purity=99.56% (214 nm), 100% (254 nm).

Example 91

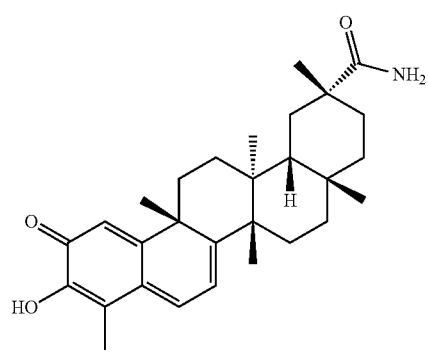

ERX1006

-continued

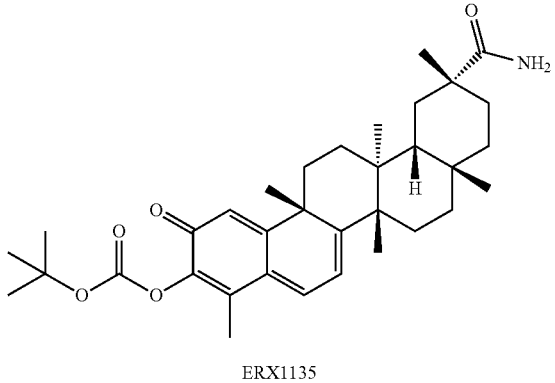

ERX1135

To a solution of ERX1006 (50 mg, 0.11 mmol) in $CH_2Cl_2$ (10 mL) was added $Mg(ClO_4)_2$ (7.4 mg, 0.03 mmol) followed by $Boc_2O$ (84 mg, 0.39 mmol). The reaction was stirred at 40° C. overnight. The mixture was diluted with $CH_2Cl_2$ (100 mL), washed with water (3×50 mL), brine (50 mL), dried over $MgSO_4$ and concentrated in vacuo. The residue was purified by prep-TLC (ethyl acetate) to afford product (20 mg, 0.0364 mmol, Yield=33%) as yellow solid. $^1$HNMR δ(500 MHz, CDCl3): 7.04 (1H, d, J=7.2 Hz), 6.46 (1H, s), 6.31 (1H, d, J=7.2 Hz), 5.66 (1H, br), 5.22 (1H, br), 2.39 (1H, d, J=15.3 Hz), 2.20 (3H, s), 1.47-2.15 (13H, m), 1.54 (9H, s), 1.45 (3H, s), 1.27 (3H, s), 1.21 (3H, s), 1.12 (3H, s), 0.99-1.05 (1H, m), 0.76 (3H, s); LC-MS: rt=2.30 min, m/z=550.2 [M+H]$^+$, purity=100% (214,254 nm).

Example 92

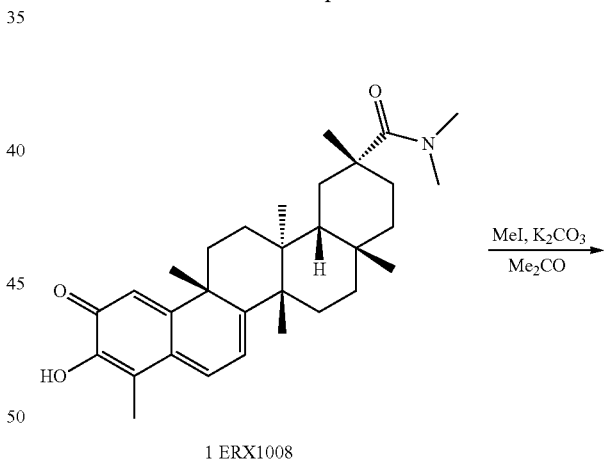

1 ERX1008

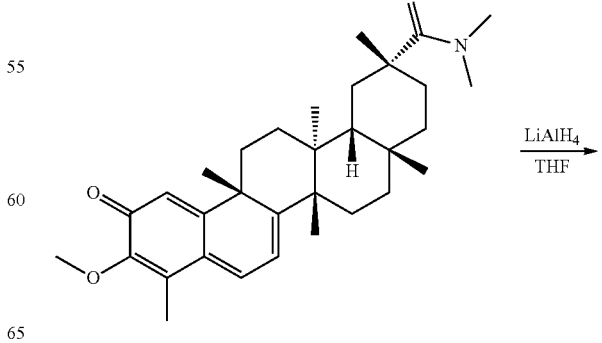

2

151
-continued

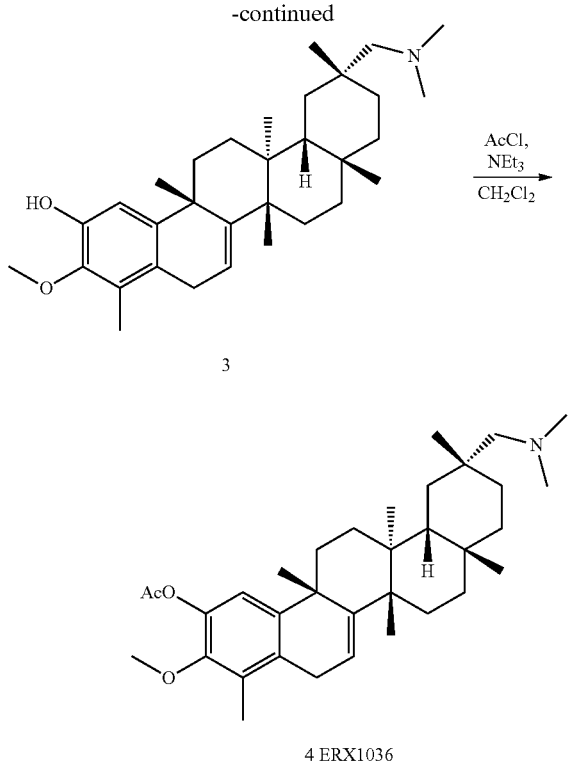

Example 93

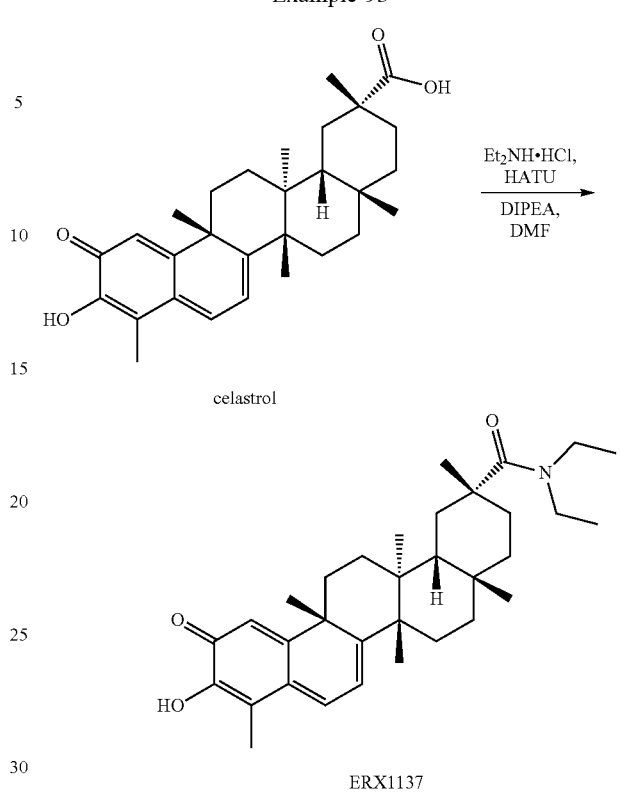

To a solution of ERX1008 (800 mg, 1.68 mmol) in acetone (5 mL) was added K₂CO₃ (462 mg, 3.35 mmol) followed by MeI (1.2 g, 8.4 mmol). The reaction was heated at 40° C. overnight. The mixture was filtered, concentrated in vacuo. The residue was purified by silica gel chromatography (eluant: petroleum ether/ethyl acetate=1:1) to afford product 2 (530 mg, 1.078 mmol, yield=64%) as yellow solid.

To a solution of 2 (530 mg, 1.08 mmol) in THF (10 mL) was added 1.0 M LiAlH₄ in THF solution (5.4 mL, 5.4 mmol). The reaction was refluxed overnight. The reaction was quenched by sat. NH₄Cl solution, filtered and concentrated in vacuo. The residue was purified by silica gel chromatography (eluant: petroleum ether/ethyl acetate=1:1) to afford product 3 (400 mg, 0.834 mmol, yield=77%) as white solid.

To a solution of 3 (400 mg, 0.84 mmol) in CH₂Cl₂ (10 mL) was AcCl (651 mg, 8.4 mmol) and NEt3 (840 mg, 8.4 mmol). Then the mixture was stirred at r.t. for 2 hours. Water was added to quench the reaction. The mixture was extracted with CH₂Cl₂ (3×20 mL). The combined layers were washed with brine (50 mL), dried over Na₂SO₄ and concentrated in vacuo. The residue was purified by prep-TLC (petroleum ether/ethyl acetate=1:1) to afford product 4 (190 mg, 0.364 mmol, yield=43%) as white solid. ¹HNMR δ(400 MHz, CDCl₃): 6.89 (1H, s), 5.81 (1H, dd, J=6.3, 2.1 Hz), 3.72 (3H, s), 3.35 (1H, dd, J=20.9, 6.3 Hz), 3.06 (1H, dd, J=20.9, 2.1 Hz), 2.87 (6H, br), 2.33 (3H, s), 2.20 (3H, s), 1.24-2.05 (19H, m), 1.39 (3H, s), 1.29 (3H, s), 1.23 (3H, s), 1.02-1.08 (1H, m), 0.79 (3H, s); LCMS: rt=1.73 min, m/z=522.3 [M+H]⁺, purity=100% (214,254 nm).

To a solution of celastrol (450 mg, 1.0 mmol) in DMF (10 mL) was added Et₂NH.HCl (241 mg, 2.2 mmol), HATU (418 mg, 1.1 mmol) followed by DIPEA (645 mg, 5.0 mmol). The reaction was stirred at room temperature overnight. Then the solution was diluted with CH₂Cl2 (200 mL), washed with sat. LiCl.H₂O solution (2×200 mL), brine (200 mL), dried over MgSO₄ and concentrated in vacuo. The residue was purified by prep-TLC (petroleum ether/ethyl acetate=1:1) to afford product (101 mg, 0.20 mmol, Yield=20%) as red solid. ¹HNMR δ(400 MHz, CDCl₃): 7.03 (1H, dd, J=7.0, 1.1 Hz), 6.95 (1H, br), 6.52 (1H, d, J=1.1 Hz), 6.36 (1H, d, J=7.1 Hz), 3.62-3.80 (1H, m), 3.10-3.42 (3H, m), 2.22 (3H, s), 1.98-2.40 (5H, m), 0.95-1.90 (16H, m), 1.45 (3H, s), 1.30 (3H, s), 1.26 (3H, s), 1.15 (3H, s), 0.63 (3H, s); LC-MS: rt=1.98 min, m/z=506.3 [M+H]⁺, purity=98.77% (214 nm), 100% (254 nm).

Example 94

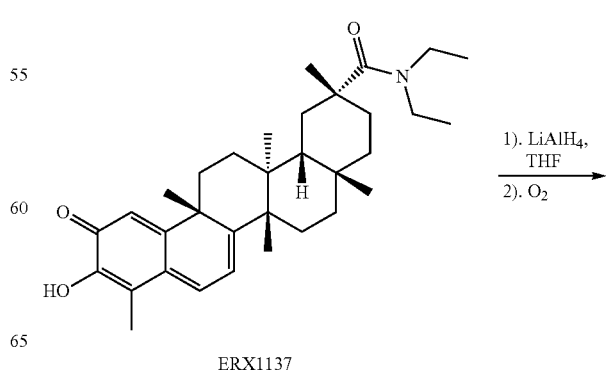

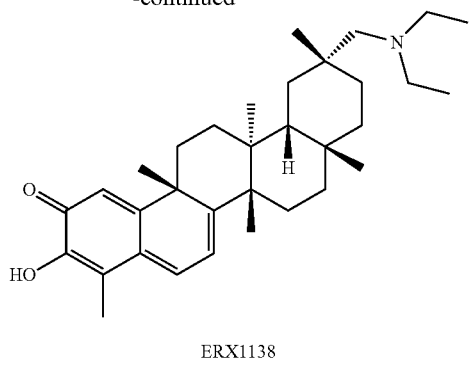

ERX1138

To a solution of ERX1137 (100 mg, 0.198 mmol) in THF (20 mL) was added LiAlH₄ (38 mg, 1.0 mmol). The reaction was refluxed overnight. The reaction was quenched by sat. NH₄Cl solution. The mixture was heated at 60° C. for 3 hours. The color was turned to brown. Then the solution was diluted with CH₂Cl₂ (200 mL), filtered. The filtrate was concentrated in vacuo. The residue was purified by prep-TLC (CH₂Cl₂/MeOH=5:1) to afford product (30 mg, 0.061 mmol, Yield=31%) as black solid. ¹HNMR: δ(400 MHz, CDCl₃): 7.04 (1H, d, J=7.0 Hz), 6.98 (1H, s), 6.54 (1H, s), 6.41 (1H, d, J=7.0 Hz), 2.90-3.20 (2H, m), 2.48-2.62 (3H, m), 2.24 (3H, s), 1.30-2.20 (15H, m), 1.46 (3H, s), 1.45 (3H, s), 1.27 (3H, s), 1.26 (3H, s), 0.92-1.04 (7H, m), 0.81 (3H, s); LC-MS: rt=1.34 min, m/z=492.3 [M+H]⁺, purity=95.35% (214 nm), 100% (254 nm).

Example 95

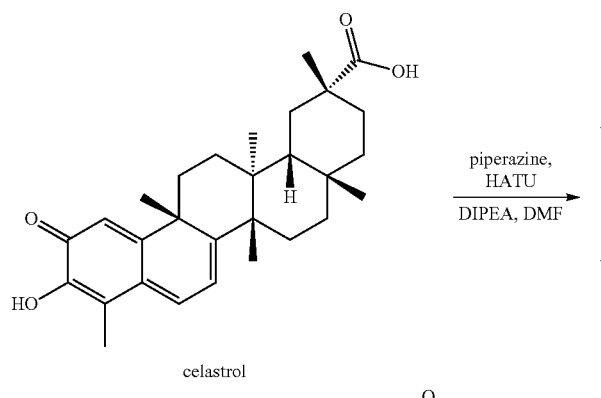

celastrol

ERX1139

To a solution of celastrol (100 mg, 0.222 mmol) in DMF (5 mL) was added HATU (101 mg, 0.266 mmol) followed by DIPEA (57 mg, 0.076 mL, 0.444 mmol). The solution was stirred at rt for 1 hour. Then piperazine (23 mg, 0.266 mmol) was added. The reaction was stirred at room temperature overnight. Then the solution was diluted with CH₂Cl₂ (200 mL), washed with sat. LiCl.H₂O solution (2×200 mL), brine (200 mL), dried over MgSO₄ and concentrated in vacuo. The residue was purified by prep-TLC (CH₂Cl₂/MeOH=10:1) to afford product (35 mg, 0.0675 mmol, Yield=30%) as red solid. ¹HNMR δ(400 MHz, CDCl₃): 7.02 (1H, d, J=7.2 Hz), 6.54 (1H, s), 6.35 (1H, d, J=7.2 Hz), 3.55-3.75 (2H, m), 2.80-2.90 (3H, m), 2.28-2.39 (2H, m), 2.21 (3H, s), 1.25-2.25 (17H, m), 1.46 (3H, s), 1.29 (3H, s), 1.28 (3H, s), 1.14 (3H, s), 0.95-1.02 (1H, m), 0.62 (3H, s); LC-MS: rt=1.21 min, m/z=519.3 [M+H]⁺, purity=95.17% (214 nm), 96.74% (254 nm).

Example 96

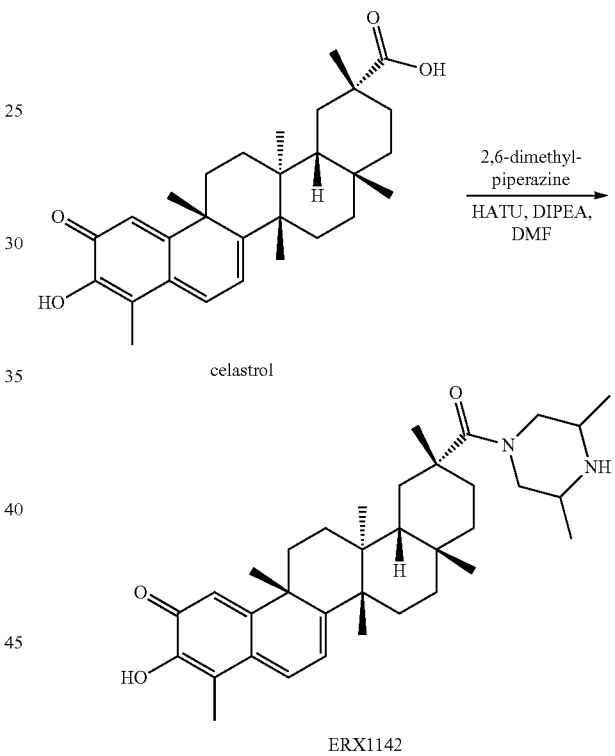

celastrol

ERX1142

To a solution of celastrol (100 mg, 0.22 mmol) in DMF (5 mL) was added 2,6-dimethylpiperazine (30 mg, 0.26 mmol), HATU (91 mg, 0.24 mmol) followed by DIPEA (57 mg, 0.44 mmol). The reaction was stirred at room temperature overnight. Then the solution was diluted with CH₂Cl₂ (100 mL), washed with sat. LiCl.H₂O solution (2×50 mL), brine (50 mL), dried over MgSO₄ and concentrated in vacuo. The residue was purified by prep-TLC (CH₂C12/MeOH=10:1) to afford product (60 mg, 0.11 mmol, Yield=50%) as red solid. ¹HNMR δ(400 MHz, CDCl₃): 7.03 (1H, d, J=7.1 Hz), 6.97 (1H, br), 6.55 (1H, s), 6.36 (1H, d, J=7.1 Hz), 4.00-4.60 (2H, m), 2.60-2.90 (2H, m), 2.28-2.40 (2H, m), 2.22 (3H, s), 1.30-2.20 (15H, m), 1.46 (3H, s), 1.29 (3H, s), 1.27 (3H, s), 1.14 (3H, s), 1.12 (6H, br), 0.94-1.02 (1H, m), 0.59 (3H, br); LC-MS: rt=1.38 min, m/z=547.3 [M+H]⁺, purity=100% (214, 254 nm).

Example 97

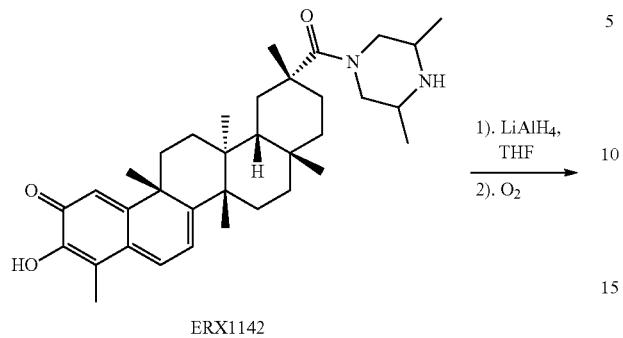

ERX1142

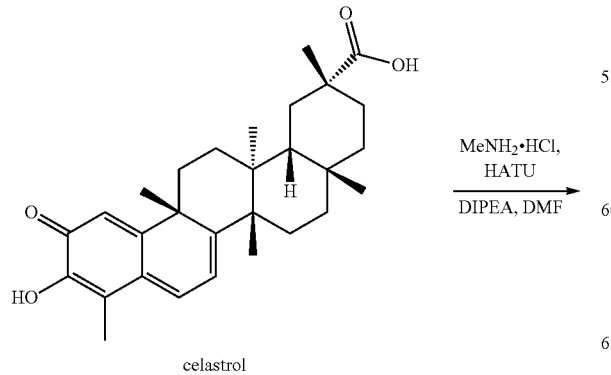

ERX1143

To a solution of ERX1142 (88 mg, 0.16 mmol) in THF (10 mL) was added LiAlH₄ (30 mg, 0.8 mmol). The reaction was refluxed overnight. The reaction was quenched by sat. NH₄Cl solution. The mixture was heated at 60° C. for 3 hours. The color was turned to brown. Then the solution was diluted with CH$_2$Cl$_2$ (200 mL), filtered. The filtrate was concentrated in vacuo. The residue was purified by prep-TLC (CH$_2$Cl$_2$/MeOH=5:1) to afford product (20 mg, 0.0375 mmol, Yield=23%) as red solid. $^1$HNMR δ(400 MHz, CDCl$_3$): 7.03 (1H, d, J=7.1 Hz), 6.53 (1H, s), 6.39 (1H, d, J=7.1 Hz), 2.94-3.06 (2H, m), 2.65-2.74 (2H, m), 2.22 (3H, s), 0.92-2.20 (21H, m), 1.44 (3H, s), 1.40 (3H, s), 1.21 (3H, s), 1.10 (6H, br), 1.00 (3H, s), 0.78 (3H, s); LC-MS: rt=1.25 min, m/z=533.3 [M+H]$^+$, purity=97.84% (214 nm), 96.36% (254 nm).

Example 98

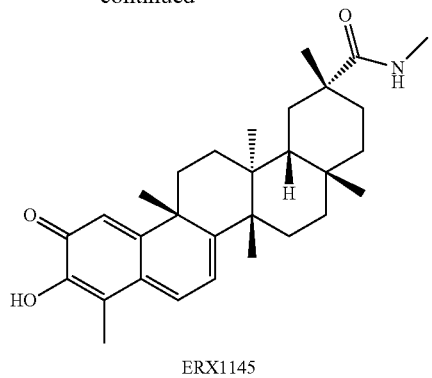

ERX1145

To a solution of celastrol (500 mg, 1.11 mmol) in DMF (10 mL) was added MeNH$_2$.HCl (220 mg, 3.3 mmol), HATU (464 mg, 1.2 mmol) followed by DIPEA (287 mg, 2.2 mmol). The reaction was stirred at room temperature overnight. Then the solution was diluted with CH$_2$Cl$_2$ (200 mL), washed with sat. LiCl.H$_2$O solution (2×200 mL), brine (200 mL), dried over MgSO$_4$ and concentrated in vacuo. The residue was purified by prep-TLC (petroleum ether/ethyl acetate=1:1) to afford product (420 mg, 0.906 mmol, Yield=82%) as red solid. $^1$HNMR δ(400 MHz, CDCl$_3$): 7.00 (1H, dd, J=7.2, 1.2 Hz), 6.97 (1H, br), 6.53 (1H, d, J=1.2 Hz), 6.33 (1H, d, J=7.2 Hz), 5.72 (1H, q, J=4.7 Hz), 2.67 (3H, d, J=4.7 Hz), 2.46 (1H, d, J=15.4 Hz), 2.21 (3H, s), 1.47-2.17 (13H, m), 1.44 (3H, s), 1.26 (3H, s), 1.15 (3H, s), 1.12 (3H, s), 0.99-1.06 (1H, m), 0.62 (3H, s); LC-MS: rt=1.66 min, m/z=464.2 [M+H]$^+$, purity=99.0% (214 nm), 100% (254 nm).

Example 99

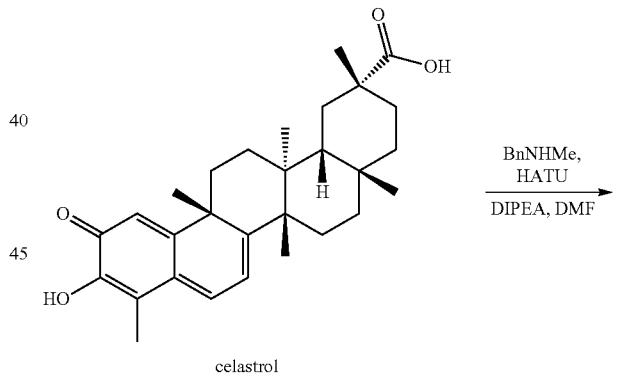

celastrol

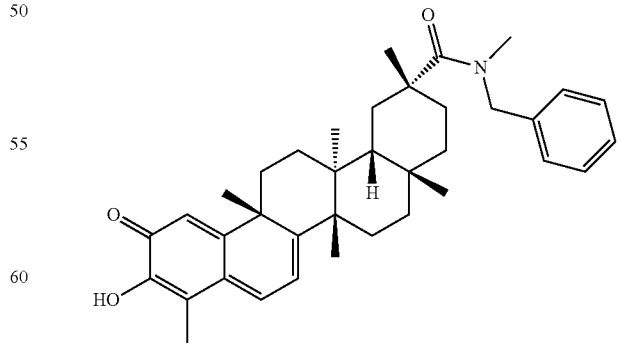

ERX1150

To a solution of celastrol (450 mg, 1.0 mmol) in DMF (10 mL) was added BnNHMe (363 mg, 3.0 mmol), HATU (420 mg, 1.1 mmol) followed by DIPEA (260 mg, 2.0 mmol). The reaction was stirred at room temperature overnight. Then the solution was diluted with CH$_2$Cl$_2$ (200 mL), washed with sat. LiCl.H$_2$O solution (2×200 mL), brine (200 mL), dried over MgSO$_4$ and concentrated in vacuo. The residue was purified by prep-TLC (petroleum ether/ethyl acetate=1:1) to afford product (370 mg, 0.669 mmol, Yield=67%) as red solid. $^1$HNMR δ(400 MHz, CDCl$_3$): 7.15-7.30 (5H, m), 7.03 (1H, dd, J=7.2, 1.1 Hz), 6.98 (1H, s), 6.53 (1H, s), 6.36 (1H, d, J=7.2 Hz), 4.85 (1H, br), 4.00 (1H, br), 3.08 (3H, br), 2.35-2.48 (2H, m), 2.23 (3H, s), 2.06-2.18 (2H, m), 1.32-1.89 (10H, m), 1.46 (3H, s), 1.31 (3H, s), 1.29 (3H, s), 1.15 (3H, s), 0.97-1.04 (1H, m), 0.55 (3H, s); LC-MS: rt=2.04 min, m/z=554.2 [M+H]$^+$, purity=100% (214, 254 nm).

Example 100

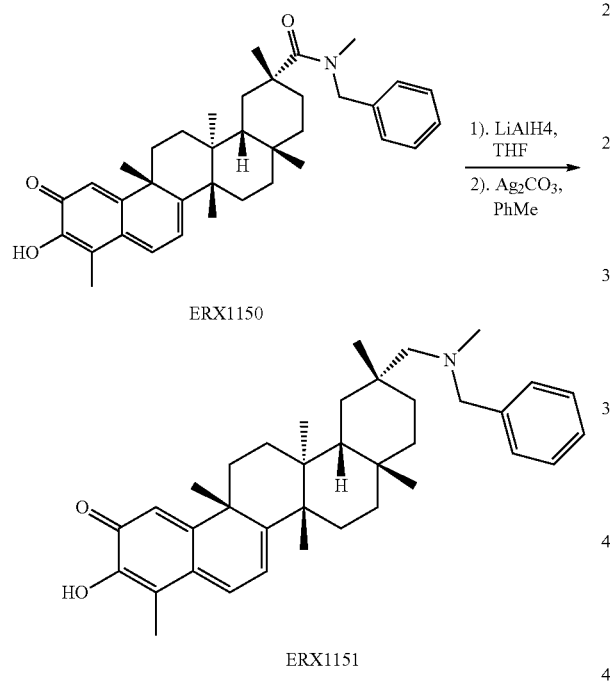

ERX1150

ERX1151

To a solution of ERX1150 (100 mg, 0.18 mmol) in THF (5 mL) was added LiAlH$_4$ (34 mg, 0.9 mmol). The reaction was refluxed overnight. The reaction was quenched by sat. NH$_4$Cl solution. Then the solution was diluted with CH$_2$Cl$_2$ (100 mL), filtered. The filtrate was separated and the organic layer was dried over Na$_2$SO$_4$ and concentrated in vacuo. The residue was dissolved in PhMe (5 mL) and Ag$_2$CO$_3$ (61 mg, 0.22 mmol) was added. The mixture was stirred at r.t. overnight, filtered and concentrated in vacuo. The residue was purified by prep-TLC (petroleum ether/ethyl acetate=1:1) to afford product (15 mg, 0.0278 mmol, Yield=25%) as red solid. $^1$HNMR δ(400 MHz, CDCl$_3$): 7.19-7.36 (5H, m), 7.03 (1H, dd, J=7.1, 0.9 Hz), 6.96 (1H, s), 6.53 (1H, d, J=0.9 Hz), 6.38 (1H, d, J=7.1 Hz), 3.56 (1H, AB, J=13.8 Hz), 3.55 (1H, AB, J=13.8 Hz), 2.37 (1H, AB, J=13.5 Hz), 2.23 (3H, s), 2.22 (3H, s), 2.17 (1H, AB, J=13.5 Hz), 2.07-2.13 (1H, m), 1.17-1.90 (15H, m), 1.44 (3H, s), 1.41 (3H, s), 1.23 (3H, s), 1.06 (3H, s), 0.91-0.97 (1H, m), 0.75 (3H, s); LC-MS: rt=1.48 min, m/z=540.4 [M+H]$^+$, purity=100% (214, 254 nm).

Example 101

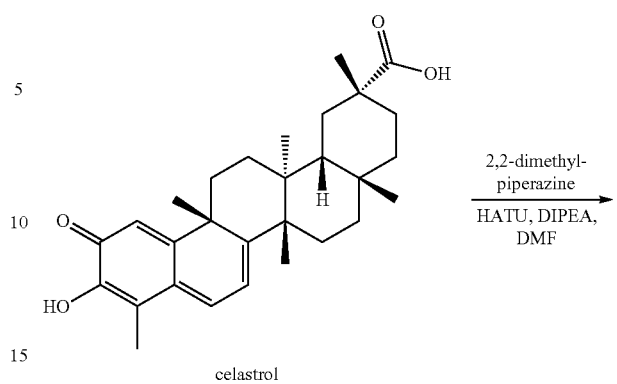

celastrol

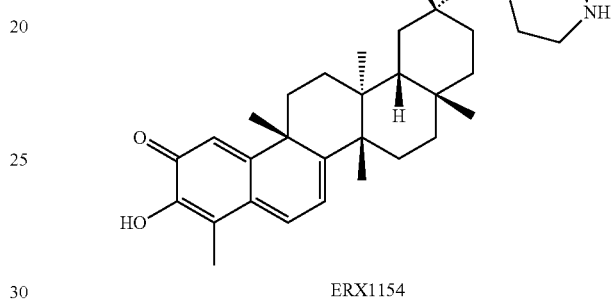

ERX1154

To a solution of celastrol (200 mg, 0.44 mmol) in DMF (10 mL) was added 2,2-dimethylpiperazine (62 mg, 0.54 mmol), HATU (184 mg, 0.48 mmol) followed by DIPEA (114 mg, 0.88 mmol). The reaction was stirred at room temperature overnight. Then the solution was diluted with CH$_2$Cl$_2$ (200 mL), washed with sat. LiCl.H$_2$O solution (2×100 mL), brine (100 mL), dried over MgSO$_4$ and concentrated in vacuo. The residue was purified by prep-TLC (CH$_2$C2/MeOH=10:1) to afford product (100 mg, 0.183 mmol, Yield=42%) as red solid. $^1$HNMR δ(400 MHz, CDCl$_3$): 7.02 (1H, d, J=7.0 Hz), 6.54 (1H, s), 6.35 (1H, d, J=7.0 Hz), 3.35-4.20 (2H, br), 2.95-3.10 (2H, m), 2.27-2.38 (2H, m), 2.21 (3H, s), 1.35-2.20 (16H, m), 1.45 (3H, s), 1.32 (3H, s), 1.30 (3H, s), 1.19 (3H, s), 1.18 (3H, s), 1.15 (3H, s), 0.95-1.02 (1H, m), 0.55 (3H, s); LC-MS: rt=1.39 min, m/z=547.3 [M+H]$^+$, purity=97.82% (214 nm), 98.76%, (254 nm).

Example 102

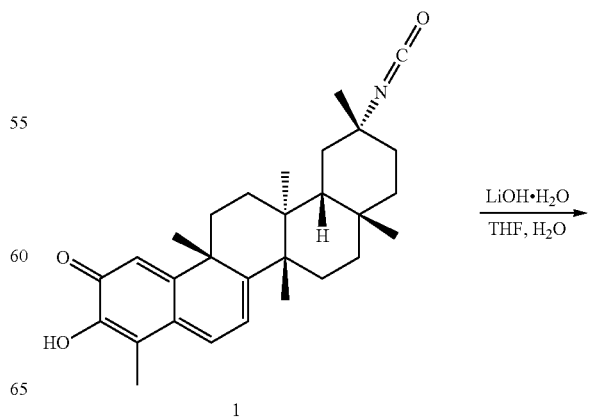

1

-continued

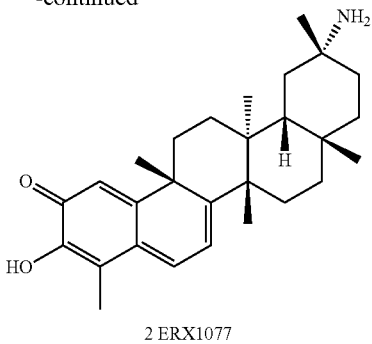

2 ERX1077

To a solution of 1 (240 mg, 0.54 mmol) in THF (10 mL) and H₂O (1 mL) was added LiOH.H₂O (113 mg, 2.68 mmol). The reaction was heated at 50° C. for 4 hours. Most THF was removed in vacuo. The residue was extracted with CH₂Cl₂ (100×3 mL). The combined extracts were washed with brine (100 mL), dried over MgSO₄ and concentrated in vacuo. The residue was purified by prep-TLC (CH₂Cl₂: MeOH=5:1) to afford product (120 mg, 0.284 mmol, Yield=53%) as brown solid. ¹HNMR δ(400 MHz, CDCl₃): 7.03 (1H, dd, J=7.2, 1.3 Hz), 6.53 (1H, d, J=1.3 Hz), 6.37 (1H, d, J=7.2 Hz), 2.22 (3H, s), 2.12-2.18 (1H, m), 1.50-2.05 (16H, m), 1.46 (3H, s), 1.30 (3H, s), 1.14 (3H, s), 1.10 (3H, s), 0.94-1.01 (1H, m), 0.96 (3H, s); LC-MS: rt=1.43 min, m/z=422.3 [M+H]⁺, purity=100% (214, 254 nm).

Example 103

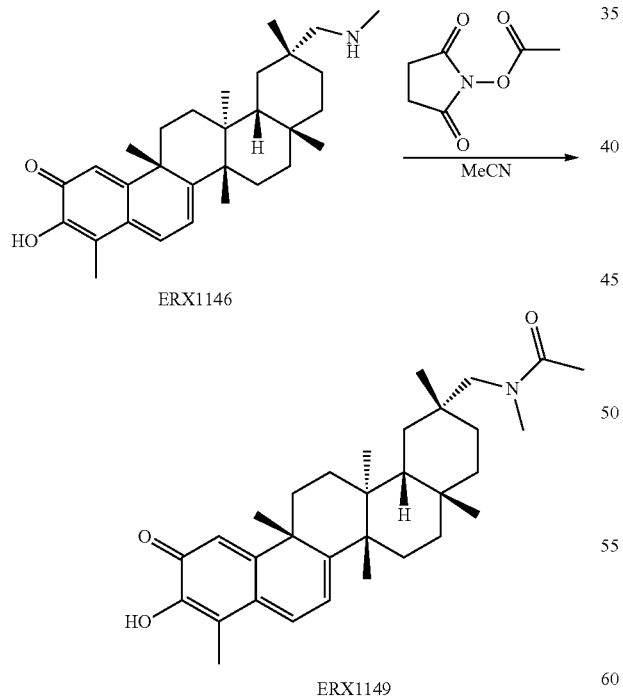

To a solution of ERX1146 (80 mg, 0.18 mmol) in MeCN (5 mL) was added acetic acid N-hydroxysuccinimide ester (112 mg, 0.72 mmol). The reaction was stirred at room temperature overnight. The solution was filtered and concentrated in vacuo. The residue was purified by prep-TLC (petroleum ether:EtOAc=1:1) to afford product (32 mg, 0.065 mmol, Yield=36%) as red solid.

¹HNMR (two atropisomers mixture) i) Major isomer δ(400 MHz, d6-DMSO): 8.71 (1H, s), 7.10 (1H, d, J=7.1 Hz), 6.40 (1H, d, J=7.1 Hz), 6.37 (1H, s), 3.61 (1H, AB, J=13.2 Hz), 3.00 (3H, s), 2.79 (1H, AB, J=13.2 Hz), 2.11-2.17 (1H, s), 2.10 (3H, s), 1.98 (3H, s), 1.20-1.85 (13H, m), 1.38 (3H, s), 1.35 (3H, s), 1.17 (3H, s), 0.95 (3H, s), 0.84-0.92 (1H, m), 0.74 (3H, s); ii) Minor isomer δ(400 MHz, d6-DMSO): 8.71 (1H, s), 7.10 (1H, d, J=7.1 Hz), 6.40 (1H, d, J=7.1 Hz), 6.37 (1H, s), 3.30 (1H, AB, J=14.8 Hz), 3.08 (1H, AB, J=14.8 Hz), 2.85 (3H, s), 2.11-2.17 (1H, s), 2.10 (3H, s), 1.99 (3H, s), 1.20-1.85 (13H, m), 1.38 (3H, s), 1.35 (3H, s), 1.22 (3H, s), 1.00 (3H, s), 0.84-0.92 (1H, m), 0.74 (3H, s). LC-MS: rt=1.88 min, m/z=492.3 [M+H]⁺, purity=100% (214, 254 nm).

Example 104

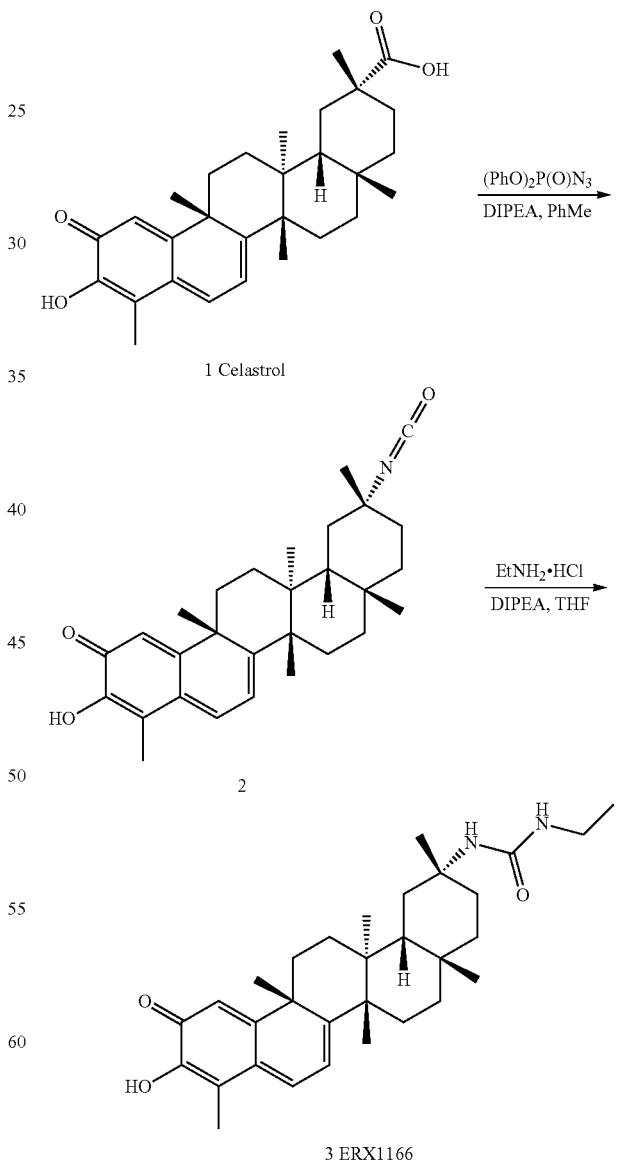

To a solution of celastrol (500 mg, 1.11 mmol) in PhMe (25 mL) was added DIPEA (430 mg, 0.57 mL, 3.33 mmol)

followed by (PhO)$_2$P(O)N$_3$ (458 mg, 0.36 mL, 1.66 mmol). The reaction was heated at 100° C. overnight. The solution was diluted with CH$_2$Cl$_2$ (200 mL), washed with H$_2$O (200 mL), brine (200 mL), dried over MgSO$_4$ and concentrated in vacuo. The residue was purified by prep-TLC (petroleum ether:ethyl acetate=3:1) to afford crude product (342 mg, 0.764 mmol, Yield=69%) as red solid.

To a solution of crude 2 (342 mg, 0.764 mmol) in THF (20 mL) was added EtNH$_2$.HCl (312 mg, 3.82 mmol) and DIPEA (494 mg, 0.65 mL, 3.82 mmol). The reaction was heated at 50° C. for 3 hours. Most THF was removed in vacuo. The residue was dissolved in CH$_2$Cl$_2$ (200 mL), washed with H$_2$O (200 mL), brine (200 mL), dried over MgSO$_4$ and concentrated in vacuo. The residue was purified by prep-TLC (CH$_2$Cl$_2$: MeOH=10:1) to afford product (233.6 mg, 0.474 mmol, Yield=62%) as red solid. $^1$HNMR δ(400 MHz, CDCl$_3$): 7.02 (1H, dd, J=7.1, 1.1 Hz), 6.98 (1H, s), 6.53 (1H, d, J=1.0 Hz), 6.36 (1H, d, J=7.3 Hz), 3.96 (1H, t, J=5.5 Hz), 3.85 (1H, s), 2.95-3.15 (2H, m), 2.89 (1H, d, J=13.8 Hz), 2.21 (3H, s), 1.45-2.20 (13H, m), 1.44 (3H, s), 1.40 (3H, s), 1.27 (3H, s), 1.12 (3H, s), 1.03 (3H, t, J=7.1 Hz), 0.94-1.01 (1H, m), 0.77 (3H, s). LC-MS: rt=1.79 min, m/z=493.3 [M+H]$^+$, purity=100% (214,254 nm).

2.74 (1H, d, J=14.8 Hz), 2.22 (3H, s), 2.11-2.18 (1H, m), 1.20-2.05 (12H, m), 1.45 (3H, s), 1.37 (3H, s), 1.27 (3H, s), 1.14 (3H, t, J=7.0 Hz), 1.12 (3H, s), 0.95-1.01 (1H, m), 0.75 (3H, s). LC-MS: rt=1.99 min, m/z=494.3 [M+H]$^+$, purity=100% (214,254 nm).

Example 106

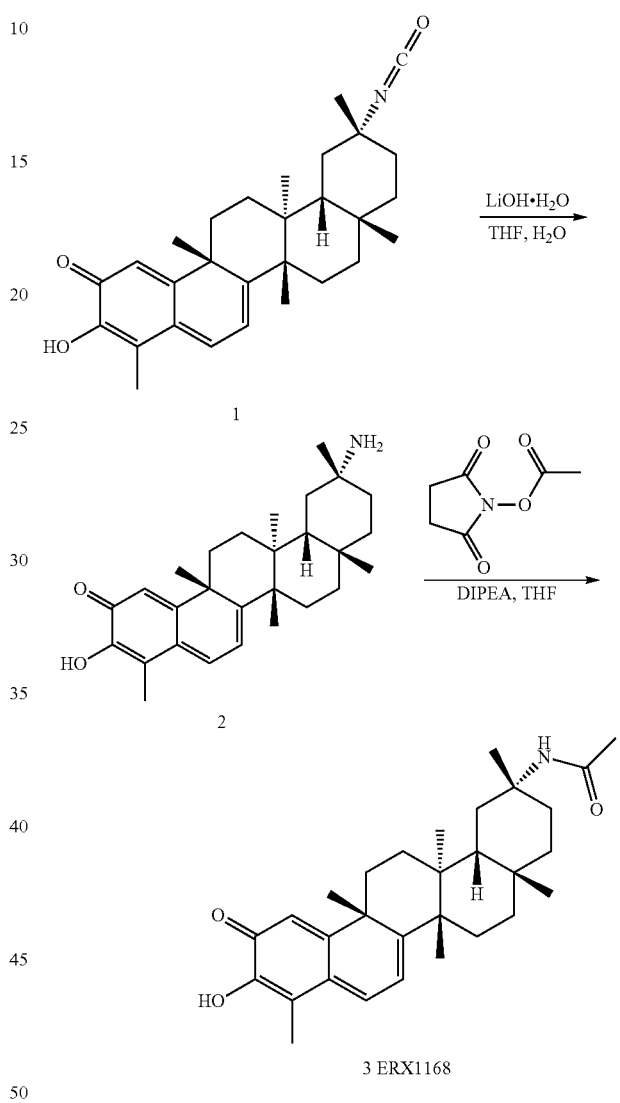

Example 105

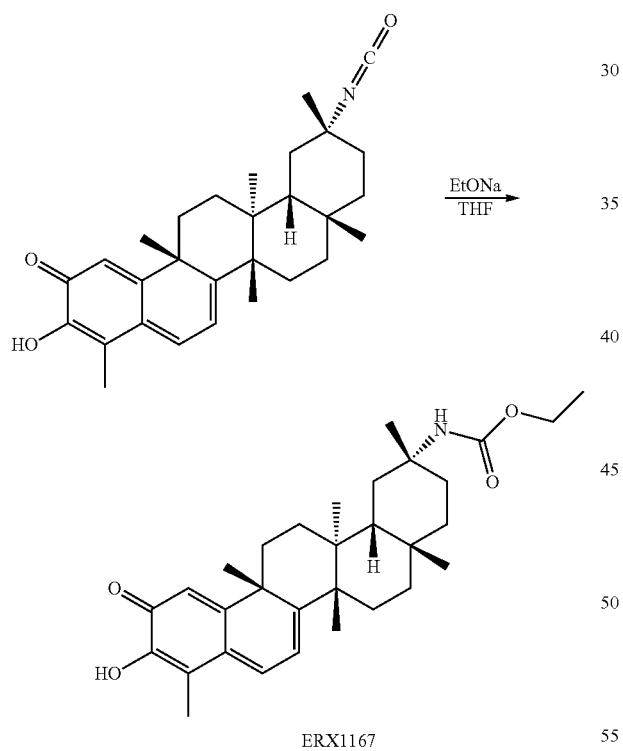

To a solution of isocyanate (50 mg, 0.112 mmol) in THF (2 mL) was added EtONa (38 mg, 0.559 mmol). The reaction was heated at room temperature for 1 hour. The reaction was quenched by NH$_4$Cl (10 mL). The mixture was diluted in CH$_2$Cl$_2$ (100 mL), washed with H$_2$O (100 mL), brine (100 mL), dried over MgSO$_4$ and concentrated in vacuo. The residue was purified by prep-TLC (CH$_2$Cl$_2$: MeOH=20:1) to afford product (11.8 mg, 0.0239 mmol, Yield=21%) as red solid. $^1$HNMR δ (400 MHz, CDCl$_3$): 7.03 (1H, dd, J=7.2, 0.9 Hz), 6.98 (1H, s), 6.54 (1H, d, J=0.9 Hz), 6.37 (1H, d, J=7.2 Hz), 4.39 (1H, s), 3.90-4.07 (2H, m), To a solution of isocyanate 1 (478 mg, 1.068 mmol) in THF (20 mL) and H$_2$O (2 mL) was added LiOH.H$_2$O (220 mg, 5.24 mmol). The reaction was heated at 50° C. for 4 hour. Most THF was removed in vacuo. The residue was diluted in CH$_2$Cl$_2$ (100 mL), washed with 0.1 M HCl (100 mL). All solution was filtered. The organic layer was washed with H$_2$O (100 mL), brine (100 mL), dried over MgSO$_4$ and concentrated in vacuo. The residue and the solid obtained by filtration were dissolved in 200 mL CH$_2$Cl2: MeOH=10:1 solution, concentrated in vacuo. The residue was purified by prep-TLC (CH$_2$Cl$_2$: MeOH=5:1) to afford intermediate (50 mg, 0.119 mmol, Yield=11%) as brown solid.

To a solution of intermediate 2 (50 mg, 0.119 mmol) in THF (3 mL) was added acetic acid N-hydroxy succinimide ester (93 mg, 0.594 mmol) and DIPEA (77 mg, 0.10 mL, 0.594 mmol). The reaction was stirred at room temperature overnight. Most THF was removed in vacuo. The residue was diluted in CH$_2$Cl$_2$ (100 mL), washed with H$_2$O (100 mL), brine (100 mL), dried over MgSO$_4$ and concentrated in vacuo. The residue was purified by prep-TLC (petroleum ether/ethyl acetate=1:3) to afford product (17.5 mg, 0.0377 mmol, Yield=32%) as red solid. $^1$HNMR δ(400 MHz, CDCl$_3$): 7.01 (1H, dd, J=7.2, 1.2 Hz), 6.98 (1H, s), 6.54 (1H, d, J=1.2 Hz), 6.36 (1H, d, J=7.2 Hz), 5.04 (1H, s), 2.82 (1H, d, J=13.9 Hz), 2.21 (3H, s), 2.12-2.18 (1H, m), 1.60-2.05 (12H, m), 1.81 (3H, s), 1.45 (3H, s), 1.42 (3H, s), 1.28 (3H, s), 1.12 (3H, s), 0.97-1.03 (1H, m), 0.77 (3H, s). LC-MS: rt=1.81 min, m/z=464.3 [M+H]$^+$, purity=100% (214,254 nm).

Example 107

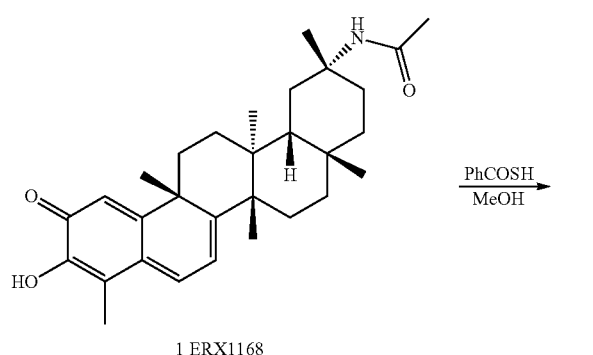

To a solution of ERX1168 (116 mg, 0.258 mmol) in MeOH (5 mL) was added PhCOSH (71 mg, 0.06 mL, 0.516 mmol). The mixture immediately turned from reddish to light yellow. The reaction was stirred at r.t. for 10 minutes. The solution was concentrated in vacuo. The crude intermediate 2 was used in the next step without further purification To a solution of intermediate 2 (155 mg, 0.258 mmol, theoretical amount) in pyridine (3 mL) was added Ac$_2$O (1 mL). The reaction was stirred at room temperature overnight. Then the solution was diluted with CH$_2$Cl$_2$ (100 mL), washed with sat. CuSO$_4$.5H$_2$O (2×100 mL), H$_2$O (100 mL), brine (100 mL), dried over MgSO$_4$ and concentrated in vacuo. The residue was purified by prep-TLC (petroleum ether/ethyl acetate=2:3) followed by re-crystallization from MeCN (5 mL) to afford product (59.9 mg, 0.0873 mmol, Yield=34%) as white solid. $^1$HNMR δ(400 MHz, CDCl$_3$): 7.93-7.97 (2H, m), 7.54-7.60 (1H, m), 7.41-7.48 (2H, m), 7.07 (1H, s), 6.07 (1H, d, J=6.4 Hz), 5.60 (1H, d, J=6.4 Hz), 5.08 (1H, s), 2.77-2.86 (1H, m), 2.30 (3H, s), 2.30 (3H, s), 2.12 (3H, s), 1.81 (3H, s), 1.43-2.10 (13H, m), 1.51 (13H, s), 1.41 (3H, s), 1.20 (3H, s), 1.08 (3H, s), 0.93-1.00 (1H, m), 0.79 (3H, s). LC-MS: rt=2.42 min, m/z=686.4 [M+H]$^+$, purity=97.26% (214 nm), 100% (254 nm).

Example 108

To a solution of ERX1077 (220 mg, 0.52 mmol) in CH$_2$Cl$_2$ (10 mL) was added NEt3 (105 mg, 1.04 mmol) followed by Ms$_2$O (109 mg, 0.63 mmol). The reaction was stirred at room temperature overnight. The reaction was quenched by H$_2$O (20 mL). The solution was extracted with CH$_2$Cl$_2$ (3×20 mL). The combined extracts were washed with brine (50 mL), dried over MgSO$_4$ and concentrated in vacuo. The residue was purified by prep-TLC (hexanes: EtOAc=1:3) to afford product (22 mg, 0.044 mmol, Yield=8.4%) as red solid. $^1$HNMR δ(400 MHz, CDCl$_3$): 7.08 (1H, s), 7.02 (1H, d, J=6.2 Hz), 6.51 (1H, s), 6.37 (1H, d, J=6.2 Hz), 4.42 (1H, s), 2.96 (3H, s), 2.21 (3H, s), 2.14-2.23 (2H, m), 1.45-2.05 (12H, m), 1.49 (3H, s), 1.46 (3H, s), 1.29 (3H, s), 1.12 (3H, s), 1.00-1.06 (1H, m), 1.00 (3H, s). LC-MS: rt=1.52 min, m/z=500.3 [M+H]$^+$, purity=100% (214,254 nm).

Example 109

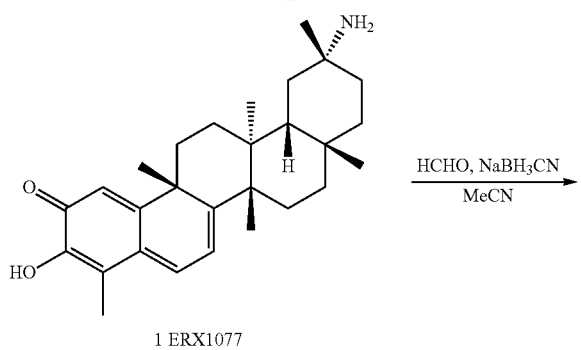

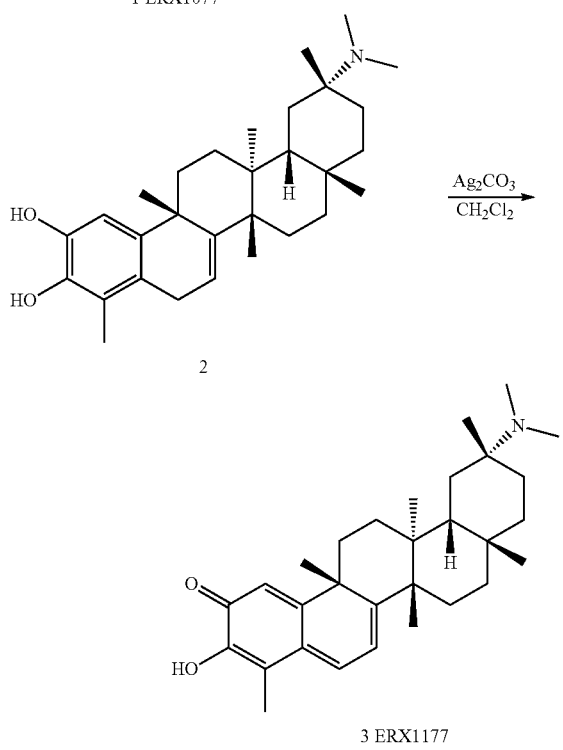

To a solution of ERX1077 (880 mg, 2.087 mmol) in MeCN (20 mL) was added 37% HCHO solution (7.0 mL) followed by NaBH$_3$CN (656 mg, 10.44 mmol) in portions. The reaction was stirred at room temperature overnight. The solution was diluted with CH$_2$Cl$_2$ (200 mL), washed with 0.1 M HCl (320 mL), H$_2$O (3×100 mL), brine (100 mL), dried over MgSO$_4$ and concentrated in vacuo to afford crude intermediate 2 (653 mg, 1.446 mmol, Yield=69%) as white solid.

$^1$HNMR: T242-T242-H1-20160216-SP-0012627-016-CDCL3

$\delta$ (400 MHz, CDCl$_3$): 6.83 (1H, s), 5.77 (1H, d, J=4.5 Hz), 3.29 (1H, dd, J=20.7, 6.2 Hz), 3.01 (1H, dd, J=20.3 Hz), 2.63 (6H, s), 2.15 (3H11, s), 2.01 (3H, s), 1.25-2.00 (17H, m), 1.38 (3H, s), 1.23 (3H, s), 1.19 (3H, s), 0.67 (3H, s).

To a solution of crude intermediate 2 (600 mg, 1.328 mmol) in CH$_2$Cl$_2$ (50 mL) was added Ag$_2$CO$_3$ (733 mg, 2.657 mmol). The reaction was stirred at room temperature overnight. The solution was filtered and concentrated in vacuo. The residue was purified by prep-TLC (CH$_2$Cl$_2$: MeOH=5:1) to afford product (86 mg, 0.191 mmol, Yield=14%) as red solid. $^1$HNMR $\delta$ (400 MHz, CDCl$_3$): 7.02 (1H, dd, J=7.1, 1.3 Hz), 6.95 (1H, s), 6.51 (1H, d, J=7.2 Hz), 6.40 (1H, d, J=1.2 Hz), 2.67 (6H, s), 2.22 (3H, s), 1.47-2.13 (15H, m), 1.46 (3H, s), 1.43 (3H, s), 1.27 (6H, s), 0.85 (3H, s). LC-MS: rt=1.27 min, m/z=450.3 [M+H]$^+$, purity=100% (214,254 nm).

Biological Study: I.P. Administration

The following test compounds were studied to determine any anti-obesity effect when administered to rodents. First, test compounds were formulated in 50, 100, 200, 400, 500, 1000 and 2000 µg/kg doses and administered once daily in a dose volume of 2 mL/kg i.p. for multiple days. Test compounds were compared to administration of vehicle to mice. The experiment consisted of two phases: a pre-dosing phase and a dosing phase. Weight of the animals in each testing group was measured daily. Fluid samples were taken as well. Tables 2-5 summarize the study parameters. Table 6 shows the results of the compounds tested, their dosing and anti-obesity effects.

TABLE 2

Study Parameters

| | |
|---|---|
| Dosing Duration | Acclimation dosing - all 75 animals on Day 11 through Day 14 of the predose phase (approximately 100 µl for each animal) |
| | Test Compound dosing: Daily for 10 days (~15:00) |
| Frequency of Preparation | Daily |
| Verification Vial Section | Groups 2-12: Prep 1 day's worth one day prior to dosing phase (P14) to confirm that the compound is going into solution, this prep will not be dosed but will be used to confirm that the compound will be viable for dosing on Day 1. |
| Test Compound Storage Conditions | ≤−60° C., Protect from light |
| Test Dosing Mix Instructions | For test articles (Groups 2-12): Stock solution: 1:1 solution (v/v) of solutol in DMAC to dissolve test compound; stock solution to be stored frozen at −60° C. and thawed only once before use. Dosing Solution: dilute stock solution into the appropriate amount of saline (Final vehicle: 10% solutol, 10% DMAC, 80% saline) on the day of dosing. |
| Vehicle | Groups 1-12 and acclimation dosing: Stock: 1:1 solution (v/v) of Solutol:DMAC Dosing Solution: 0.9% Saline Final Vehicle: 10% Solutol, 10% DMAC, 80% saline |

TABLE 2-continued

Study Parameters

| | |
|---|---|
| Dose Preparation Storage Conditions | Refrigerated and protected from light |
| Dose Volume Adjustment | Calculate doses based on most recent body weight |
| Covance ACUA Protocol | 04811-B |
| Species and Strain | Mouse - C57BL/6 Diet Induced Obese (DIO) |
| Sex | Male |
| Source | Taconic |
| Vendor Nomenclature | C57BL/6NTac (DIO) |
| Approximate Age | 20-21 weeks at study start |
| Quantity to Order | 75 |
| Quantity Enrolled on Study | 60 |
| Supplier/Food Type | TD95217 |
| Feeding Details | Feed ad libitum, see fasting details during live phase parameters. Provide enough food for the entire study on Day 1 of the dosing phase. |
| Dietary Enrichment | Animals will not receive specialty food enrichment. |
| Water | Greenfield- city water Gel cups will not be placed in with these animals; animals will be observed and if they do not take to the automatic watering then they will be placed on water bottles. |
| Housing | Individually house in shoe box caging with wood chip bedding and nestlets. |
| Acclimation | House in vivarium at least 1 week prior to vehicle dosing |
| Environmental Conditions | Photoperiod: Lights on 05:00-17:00 12 hours light, 12 hours dark (maybe interrupted for study-related activities) Temperature: 68-79° F. Relative humidity: 30%-70% |

TABLE 3

Predose Phase

| | |
|---|---|
| Acclimation Dosing | Days 11 through 14 of the predose phase (approximately at 15:00). Note: Dose all 75 animals with vehicle intraperineal (approximately 100 uL) off-line, ⅓ cc syringes will be used for intraperitoneal dosing |
| Clinical Signs | Twice Daily (morning and afternoon) for mortality |
| Randomization | On Day 14 of the predose phase; animals will be randomized based on body weight. The BRAT system will be utilized. |
| Body Weight | Predose body weights collected daily Days 11 through 14 of the predose phase on all animals. |
| Food Consumption | Collected daily Days 11 through 14 of the predose phase If consumption value is not 0-6 grams per 24 hour period, reweigh once and document. |
| Blood Glucose Level | Day 14 of the predose phase (all animals) Approximately 08:00: Fast mice into clean shoebox cages. Approximately 14:00: All animals will be tail clip bled at each time point. Place a drop of blood from each animal onto two different Accu Chek Aviva glucometers to assess glucose values. Record all glucometer readings. |

TABLE 4

Dosing Phase

| | |
|---|---|
| Clinical Signs | Twice Daily (moring and afternoon) for mortality Record overt changes |

TABLE 4-continued

| Dosing Phase | |
| --- | --- |
| Compound Dosing | Daily at approximately 15:00 each day<br>(Note: ⅓ cc syringes will be used for intraperitoneal dosing)<br>Dose volume calculated on most recent body weight. Animals will be dosed in numerical order. |
| Body Weights<br>Food Consumption | Daily<br>Daily (approximately 30 minutes before start of dark photoperiod)<br>If consumption value is not 0-6 grams per 24 hour period, reweigh once and document. |
| Blood Glucose Level | Day 11 of the dosing phase<br>Approximately 08:00: Fast mice into clean shoebox cages.<br>Approximately 14:00: Animals will be tail clip bled at each time point. Place a drop of blood from each animal onto two different Accu Chek Aviva glucometers to assess glucose values. Record all glucometer readings. |

TABLE 5

Fluid Sample Collection

| Specimen Number | Collection Type | Phase Day | Time Point | Tube Prep and Processing | Collection Method | Sample Volume | Anti-coagulant and/or tube type | Pre-process Storage | Centrifuge to Obtain |
| --- | --- | --- | --- | --- | --- | --- | --- | --- | --- |
| 1 | Whole Blood | P14, 11 | After 6 hr fast | NA | Tail clip | 5 μL | Glucometer (in duplicate) | NA | NA |

Abbreviations:
P = Predose

Animals were euthanized by carbon dioxide (or anesthesia) followed by decapitation, bilateral thoracotomy, exsanguination, or vital organ removal to ensure death following last blood collection or at scheduled termination. Cervical dislocation was acceptable for animals not requiring exams or gavage checks.

Any animal that did not survive to study termination was discarded without further evaluation.

Descriptive statistics (n, mean, standard error of the mean, standard deviation) were completed. Additionally, one way analysis of variance followed by Dunnett's post-hoc test was performed on body weight (cumulative body weight change), glucose (glucose percent change), and food consumption (cumulative food consumption). Area under the curve (for body weight, cumulative body weight change, daily body weight change, and food consumption) was computed for treatment groups. An appropriate comparison test, such as one-way analysis of variance and Dunnett's, was performed on the group means for the area under the curve computations.

All procedures in this protocol were in compliance with the U.S. Department of Agriculture's (USDA) Animal Welfare Act (9 CFR Parts 1, 2, and 3); the Guide for the Care and Use of Laboratory Animals (Institute for Laboratory Animal Research, The National Academies Press, Washington, D.C.); and the National Institutes of Health, Office of Laboratory Animal Welfare (for NIH funded studies). Whenever possible, procedures in this study were designed to avoid or minimize discomfort, distress, and pain to animals.

This non-clinical laboratory study was not intended to be conducted in full accordance with the United States Food and Drug Administration (FDA) Good Laboratory Practice (GLP) regulations, 21 CFR Part 58, but was conducted in accordance with Covance standard operating procedures.

This study complied with all applicable sections of the Guide for the Care and Use of Laboratory Animals. Whenever possible, procedures used in this study were designed to avoid or minimize discomfort, distress, and pain to animals. All procedures were described in this study protocol or in written laboratory procedures. These procedures were based on the most current available technologies concerning proper laboratory animal use and management.

TABLE 6-A
*In vivo* activity of compounds (I.P. administration).
| Compound | Structure | dose (μg/kg) | activity<br>+++ > celastrol @100 μg/kg<br>++ = celastrol @100 μg/kg<br>+ < celastrol @100 μg/kg<br>− active<br>*too active - study terminated | Oral bioavailability |
|---|---|---|---|---|
| ERX1000 | 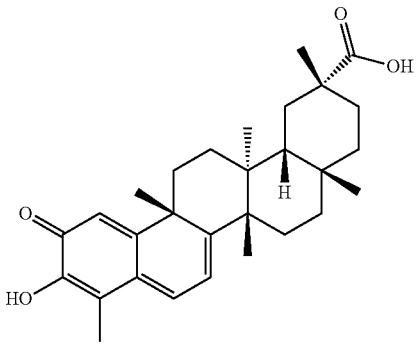 | 100 | ++ | |
| ERX1001 | 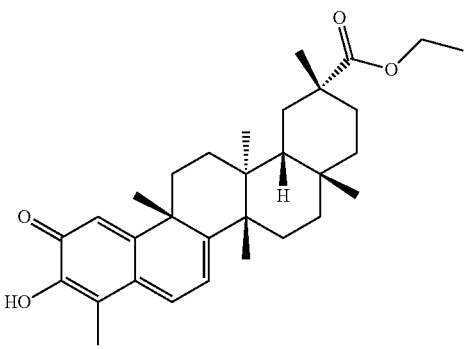  ERX1001 | 200 | ++ | − |
| ERX1001 | 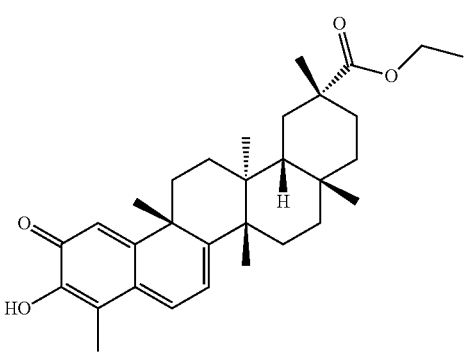  ERX1001 | 100 | ++ | |

TABLE 6-A-continued

*In vivo* activity of compounds (I.P. administration).

| Compound | Structure | dose (µg/kg) | activity +++ > celastrol @100 µg/kg ++ = celastrol @100 µg/kg + < celastrol @100 µg/kg − active *too active - study terminated | Oral bioavailability |
|---|---|---|---|---|
| ERX1002 | ERX1002 | 100 | ++ | |
| ERX1003 | ERX1003 | 100 | ++ | − |
| ERX1004 | ERX1004 | 100 | − | |

TABLE 6-A-continued

*In vivo* activity of compounds (I.P. administration).

| Compound | Structure | dose (µg/kg) | activity +++ > celastrol @100 µg/kg ++ = celastrol @100 µg/kg + < celastrol @100 µg/kg – active *too active - study terminated | Oral bioavailability |
|---|---|---|---|---|
| ERX1005 | ERX1005 | 100 | – | |
| ERX1006 | ERX1006 | 100 | +++ | ++ |
| ERX1007 | ERX1007 | 100 | ++ | |

TABLE 6-A-continued

*In vivo* activity of compounds (I.P. administration).

| Compound | Structure | dose (μg/kg) | activity<br>+++ > celastrol @100 μg/kg<br>++ = celastrol @100 μg/kg<br>+ < celastrol @100 μg/kg<br>− active<br>*too active - study terminated | Oral bioavailability |
|---|---|---|---|---|
| ERX1008 | ERX1008 | 100 | ++ | |
| ERX1009 | ERX1009 | 400 | ++ | |
| ERX1009 | ERX1009 | 1,000 | * | |

TABLE 6-A-continued

*In vivo* activity of compounds (I.P. administration).

| Compound | Structure | dose (μg/kg) | activity<br>+++ > celastrol @100 μg/kg<br>++ = celastrol @100 μg/kg<br>+ < celastrol @100 μg/kg<br>− active<br>*too active - study terminated | Oral bioavailability |
|---|---|---|---|---|
| ERX1009 | ERX1009 | 100 | − | |
| ERX1010 | ERX1010 | 100 | +++ | − |
| ERX1011 | ERX1011 | 100 | − | |

TABLE 6-A-continued

*In vivo* activity of compounds (I.P. administration).

| Compound | Structure | dose (µg/kg) | activity<br>+++ > celastrol @100 µg/kg<br>++ = celastrol @100 µg/kg<br>+ < celastrol @100 µg/kg<br>− active<br>*too active - study terminated | Oral bioavailability |
|---|---|---|---|---|
| ERX1012 | ERX1012 | 100 | − | |
| ERX1013 | ERX1013 | 100 | − | |
| ERX1014 | ERX1014 | 200 | ++ | |

TABLE 6-A-continued

*In vivo* activity of compounds (I.P. administration).

| Compound | Structure | dose (μg/kg) | activity<br>+++ > celastrol @100 μg/kg<br>++ = celastrol @100 μg/kg<br>+ < celastrol @100 μg/kg<br>− active<br>*too active - study terminated | Oral bioavailability |
|---|---|---|---|---|
| ERX1014 | ERX1014 | 100 | − | |
| ERX1015 | ERX1015 | 100 | ++ | − |
| ERX1016-P1 | 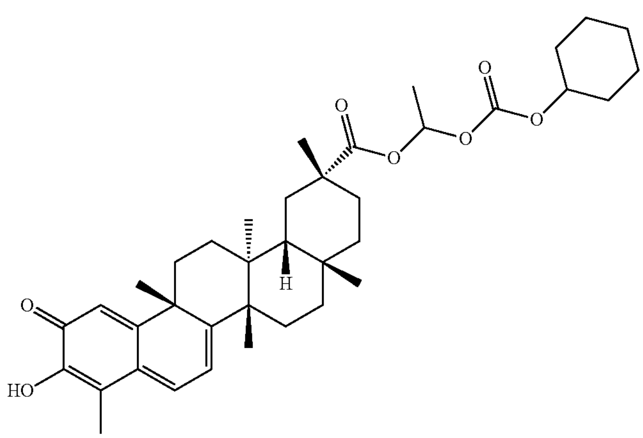 | 100 | − | |

TABLE 6-A-continued
*In vivo* activity of compounds (I.P. administration).
| Compound | Structure | dose (μg/kg) | activity +++ > celastrol @100 μg/kg ++ = celastrol @100 μg/kg + < celastrol @100 μg/kg − active *too active - study terminated | Oral bioavailability |
|---|---|---|---|---|
| ERX1016-P2 | 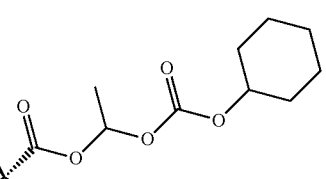 | 100 | − | |
| ERX1017 | 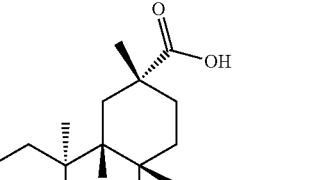
ERX1017 | 100 | − | |
| ERX1018 | 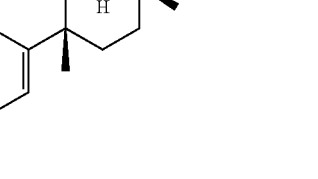
ERX1018 | 400 | ++ | |

TABLE 6-A-continued

*In vivo* activity of compounds (I.P. administration).

| Compound | Structure | dose (μg/kg) | activity +++ > celastrol @100 μg/kg ++ = celastrol @100 μg/kg + < celastrol @100 μg/kg − active *too active − study terminated | Oral bioavailability |
|---|---|---|---|---|
| ERX1018 | ERX1018 | 100 | + | |
| ERX1019 | ERX1019 | 100 | + | |
| ERX1020 | ERX1020 | 100 | ++ | + |

TABLE 6-A-continued

*In vivo* activity of compounds (I.P. administration).

| Compound | Structure | dose (μg/kg) | activity +++ > celastrol @100 μg/kg ++ = celastrol @100 μg/kg + < celastrol @100 μg/kg − active *too active - study terminated | Oral bioavailability |
|---|---|---|---|---|
| ERX1021 | ERX1021 | 100 | ++ | |
| ERX1022 | ERX1022 | 100 | ++ | |
| ERX1023 | ERX1023 | 100 | ++ | |

TABLE 6-A-continued

*In vivo* activity of compounds (I.P. administration).

| Compound | Structure | dose (µg/kg) | activity +++ > celastrol @100 µg/kg ++ = celastrol @100 µg/kg + < celastrol @100 µg/kg − active *too active - study terminated | Oral bioavailability |
|---|---|---|---|---|
| ERX1024 | ERX1024 | 100 | − | |
| ERX1025 | ERX1025 | 100 | − | |
| ERX1026 | ERX1026 | 100 | − | |

TABLE 6-A-continued

*In vivo* activity of compounds (I.P. administration).

| Compound | Structure | dose (µg/kg) | activity +++ > celastrol @100 µg/kg ++ = celastrol @100 µg/kg + < celastrol @100 µg/kg − active *too active - study terminated | Oral bioavailability |
|---|---|---|---|---|
| ERX1027 | ERX1027 | 100 | − | |
| ERX1028 | ERX1028 | 100 | − | |
| ERX1029 | ERX1029 | 100 | +++ | − |

TABLE 6-A-continued

*In vivo* activity of compounds (I.P. administration).

| Compound | Structure | dose (μg/kg) | activity<br>+++ > celastrol @100 μg/kg<br>++ = celastrol @100 μg/kg<br>+ < celastrol @100 μg/kg<br>− active<br>*too active - study terminated | Oral bioavailability |
|---|---|---|---|---|
| ERX1030 | ERX1030 | 100 | − | − |
| ERX1031 | ERX1031 | 400 | ++ | |
| ERX1031 | ERX1031 | 100 | − | |

TABLE 6-A-continued

*In vivo* activity of compounds (I.P. administration).

| Compound | Structure | dose (μg/kg) | activity<br>+++ > celastrol @100 μg/kg<br>++ = celastrol @100 μg/kg<br>+ < celastrol @100 μg/kg<br>− active<br>*too active - study terminated | Oral bioavailability |
|---|---|---|---|---|
| ERX1033 | | 500 | − | |
| ERX1033 | | 100 | − | |
| ERX1036 | 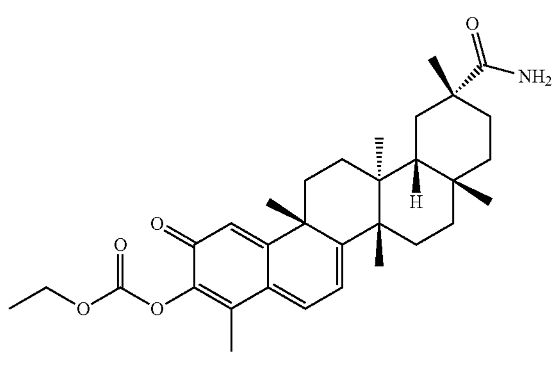 | 100 | ++ | + |

ERX1036

TABLE 6-A-continued

*In vivo* activity of compounds (I.P. administration).

| Compound | Structure | dose (µg/kg) | activity +++ > celastrol @100 µg/kg ++ = celastrol @100 µg/kg + < celastrol @100 µg/kg − active *too active - study terminated | Oral bioavailability |
|---|---|---|---|---|
| ERX1037 | ERX1037 | 200 | ++ | − |
| ERX1037 | ERX1037 | 100 | + | |
| ERX1041 | ERX1041 | 100 | − | |

TABLE 6-A-continued

*In vivo* activity of compounds (I.P. administration).

| Compound | Structure | dose (μg/kg) | activity<br>+++ > celastrol @100 μg/kg<br>++ = celastrol @100 μg/kg<br>+ < celastrol @100 μg/kg<br>− active<br>*too active - study terminated | Oral bioavailability |
|---|---|---|---|---|
| ERX1043 | ERX1043 | 500 | − | |
| ERX1043 | ERX1043 | 100 | − | |
| ERX1046 | ERX1046 | 100 | | |

TABLE 6-A-continued

*In vivo* activity of compounds (I.P. administration).

| Compound | Structure | dose (μg/kg) | activity +++ > celastrol @100 μg/kg ++ = celastrol @100 μg/kg + < celastrol @100 μg/kg − active *too active - study terminated | Oral bioavailability |
|---|---|---|---|---|
| ERX1047 | ERX1047 | 400 | ++ | |
| ERX1047 | ERX1047 | 100 | − | |
| ERX1050 | 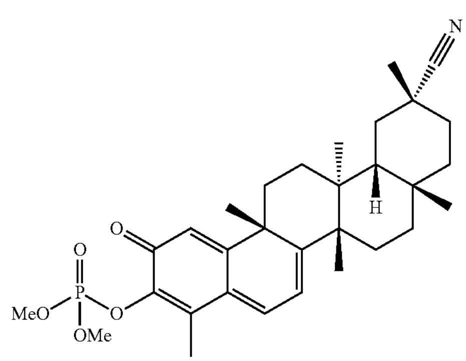 | 400 | − | |

TABLE 6-A-continued

*In vivo* activity of compounds (I.P. administration).

| Compound | Structure | dose (μg/kg) | activity<br>+++ > celastrol @100 μg/kg<br>++ = celastrol @100 μg/kg<br>+ < celastrol @100 μg/kg<br>− active<br>*too active - study terminated | Oral bioavailability |
|---|---|---|---|---|
| ERX1050 | (structure shown) | 100 | − | |
| ERX1056 | ERX1056 (structure shown) | 100 | − | |
| ERX1058 | ERX1058 (structure shown) | 100 | − | |

TABLE 6-A-continued

*In vivo* activity of compounds (I.P. administration).

| Compound | Structure | dose (μg/kg) | activity<br>+++ > celastrol @100 μg/kg<br>++ = celastrol @100 μg/kg<br>+ < celastrol @100 μg/kg<br>− active<br>*too active - study terminated | Oral bioavailability |
|---|---|---|---|---|
| ERX1060 | ERX1060 | 100 | ++ | ++ |
| ERX1061 | ERX1061 | 100 | − | |
| ERX1062 | ERX1062 | 100 | − | |

TABLE 6-A-continued
*In vivo* activity of compounds (I.P. administration).
| Compound | Structure | dose (µg/kg) | activity<br>+++ > celastrol @100 µg/kg<br>++ = celastrol @100 µg/kg<br>+ < celastrol @100 µg/kg<br>− active<br>*too active - study terminated | Oral bioavailability |
|---|---|---|---|---|
| ERX1063 | 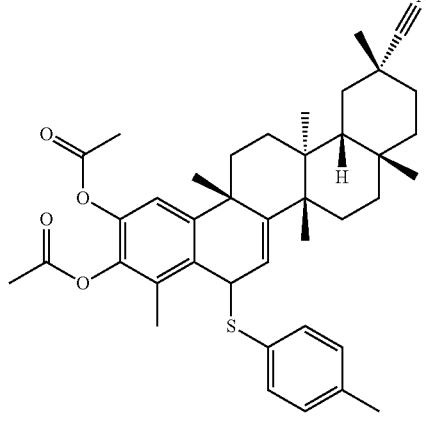<br>ERX1063 | 400 | ++ | |
| ERX1063 | 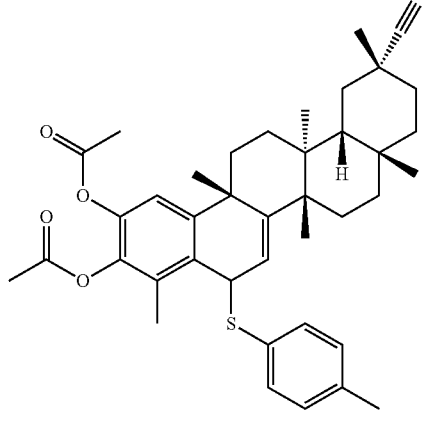<br>ERX1063 | 100 | − | |

TABLE 6-A-continued

*In vivo* activity of compounds (I.P. administration).

| Compound | Structure | dose (μg/kg) | activity +++ > celastrol @100 μg/kg ++ = celastrol @100 μg/kg + < celastrol @100 μg/kg − active *too active - study terminated | Oral bioavailability |
|---|---|---|---|---|
| ERX1064 | ERX1064 | 400 | +++ | |
| ERX1064 | ERX1064 | 100 | − | |

TABLE 6-A-continued

*In vivo* activity of compounds (I.P. administration).

| Compound | Structure | dose (μg/kg) | activity +++ > celastrol @100 μg/kg ++ = celastrol @100 μg/kg + < celastrol @100 μg/kg − active *too active - study terminated | Oral bioavailability |
|---|---|---|---|---|
| ERX1066 | ERX1066 | 400 | +++ | ++ |
| ERX1066 | ERX1066 | 200 | ++ | ++ |
| ERX1066 | ERX1066 | 100 | + | ++ |

TABLE 6-A-continued

*In vivo* activity of compounds (I.P. administration).

| Compound | Structure | dose (µg/kg) | activity<br>+++ > celastrol @100 µg/kg<br>++ = celastrol @100 µg/kg<br>+ < celastrol @100 µg/kg<br>− active<br>*too active - study terminated | Oral bioavailability |
|---|---|---|---|---|
| ERX1067 | ERX1067 | 100 | ++ | |
| ERX1068 | ERX1068 | 100 | ++ | |

TABLE 6-A-continued

*In vivo* activity of compounds (I.P. administration).

| Compound | Structure | dose (μg/kg) | activity<br>+++ > celastrol @100 μg/kg<br>++ = celastrol @100 μg/kg<br>+ < celastrol @100 μg/kg<br>− active<br>*too active - study terminated | Oral bioavailability |
|---|---|---|---|---|
| ERX1071 | ERX1071 | 100 | − | |
| ERX1072 | | 400 | +++ | |
| ERX1072 | | 200 | ++ | |

TABLE 6-A-continued

*In vivo* activity of compounds (I.P. administration).

| Compound | Structure | dose (μg/kg) | activity +++ > celastrol @100 μg/kg ++ = celastrol @100 μg/kg + < celastrol @100 μg/kg − active *too active - study terminated | Oral bioavailability |
|---|---|---|---|---|
| ERX1072 | 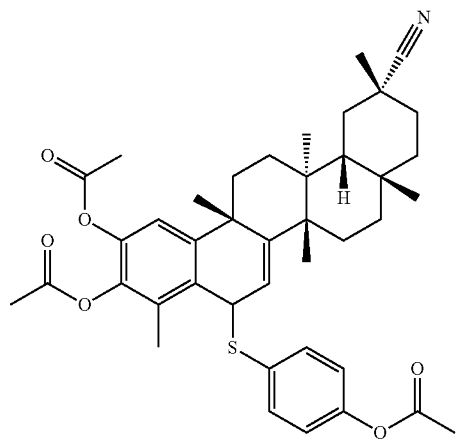 | 100 | + | |
| ERX1073 | 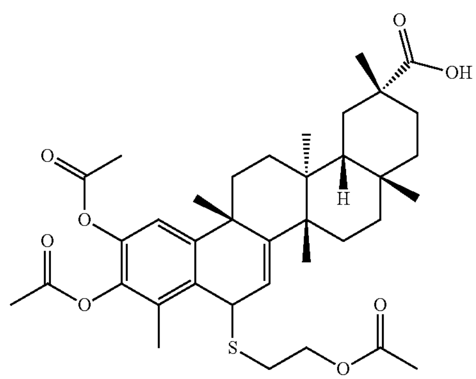 | 100 | − | |
| ERX1076 | 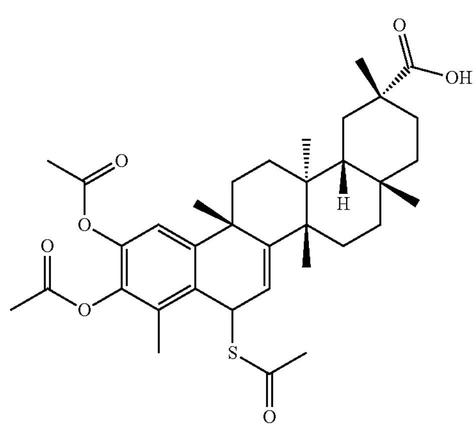 | 1,000 | ++ | + |

TABLE 6-A-continued

*In vivo* activity of compounds (I.P. administration).

| Compound | Structure | dose (μg/kg) | activity +++ > celastrol @100 μg/kg ++ = celastrol @100 μg/kg + < celastrol @100 μg/kg − active *too active - study terminated | Oral bioavailability |
|---|---|---|---|---|
| ERX1076 | ERX1076 | 400 | + | + |
| ERX1076 | ERX1076 | 100 | − | + |
| ERX1077 | 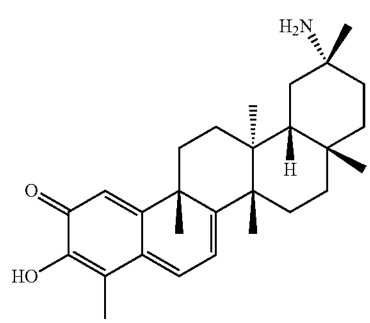 | 100 | ++ | |

TABLE 6-A-continued

*In vivo* activity of compounds (I.P. administration).

| Compound | Structure | dose (μg/kg) | activity<br>+++ > celastrol @100 μg/kg<br>++ = celastrol @100 μg/kg<br>+ < celastrol @100 μg/kg<br>− active<br>*too active - study terminated | Oral bioavailability |
|---|---|---|---|---|
| ERX1084 | ERX1084 | 400 | − | |
| ERX1084 | ERX1084 | 100 | − | |
| ERX1085 | ERX1085 | 200 | − | ++ |

TABLE 6-A-continued

*In vivo* activity of compounds (I.P. administration).

| Compound | Structure | dose (μg/kg) | activity +++ > celastrol @100 μg/kg ++ = celastrol @100 μg/kg + < celastrol @100 μg/kg − active *too active - study terminated | Oral bioavailability |
|---|---|---|---|---|
| ERX1085 | ERX1085 | 100 | − | ++ |
| ERX1085 | ERX1085 | 400 | ++ | |
| ERX1087 | ERX1087 | 400 | ++ | |

TABLE 6-A-continued

*In vivo* activity of compounds (I.P. administration).

| Compound | Structure | dose (μg/kg) | activity<br>+++ > celastrol @100 μg/kg<br>++ = celastrol @100 μg/kg<br>+ < celastrol @100 μg/kg<br>− active<br>*too active - study terminated | Oral bioavailability |
|---|---|---|---|---|
| ERX1088 | ERX1088 | 400 | ++ | |
| ERX1090 | ERX1090 | 200 | − | |
| ERX1090 | ERX1090 | 100 | − | |

TABLE 6-A-continued
*In vivo* activity of compounds (I.P. administration).
| Compound | Structure | dose (μg/kg) | activity<br>+++ > celastrol @100 μg/kg<br>++ = celastrol @100 μg/kg<br>+ < celastrol @100 μg/kg<br>− active<br>*too active -<br>study terminated | Oral bioavailability |
|---|---|---|---|---|
| ERX1090 | 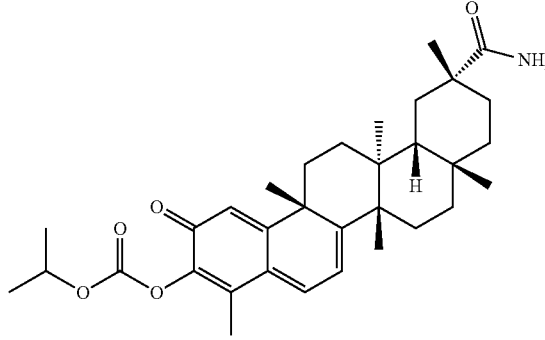<br>ERX1090 | 400 | ++ | |
| ERX1095 | 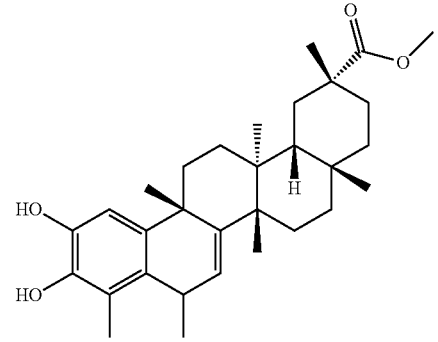<br>ERX1095 | 2,000 | − | |
| ERX1096 | 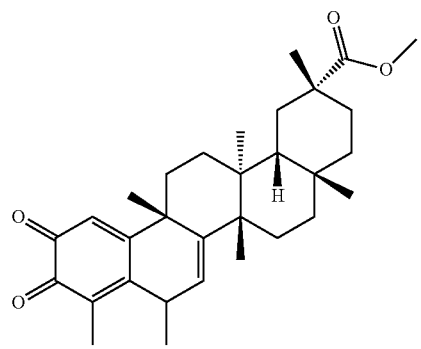<br>ERX1096 | 2,000 | − | |

TABLE 6-A-continued

*In vivo* activity of compounds (I.P. administration).

| Compound | Structure | dose (μg/kg) | activity<br>+++ > celastrol @100 μg/kg<br>++ = celastrol @100 μg/kg<br>+ < celastrol @100 μg/kg<br>− active<br>*too active - study terminated | Oral bioavailability |
|---|---|---|---|---|
| ERX1096 | ERX1096 | 500 | − | |
| ERX1097 | ERX1097 | 1,500 | − | |
| ERX1098 | ERX1098 | 2,000 | − | |

TABLE 6-A-continued

*In vivo* activity of compounds (I.P. administration).

| Compound | Structure | dose (µg/kg) | activity<br>+++ > celastrol @100 µg/kg<br>++ = celastrol @100 µg/kg<br>+ < celastrol @100 µg/kg<br>− active<br>*too active - study terminated | Oral bioavailability |
|---|---|---|---|---|
| ERX1098 | ERX1098 | 500 | − | |
| ERX1101 | ERX1101 | 2,000 | − | |
| ERX1102 | ERX1102 | 50 | + | |

TABLE 6-A-continued

*In vivo* activity of compounds (I.P. administration).

| Compound | Structure | dose (μg/kg) | activity<br>+++ > celastrol @100 μg/kg<br>++ = celastrol @100 μg/kg<br>+ < celastrol @100 μg/kg<br>− active<br>*too active − study terminated | Oral bioavailability |
|---|---|---|---|---|
| ERX1102 | ERX1102 | 200 | +++ | |
| ERX1102 | ERX1102 | 100 | ++ | |

TABLE 6-A-continued

*In vivo* activity of compounds (I.P. administration).

| Compound | Structure | dose (µg/kg) | activity<br>+++ > celastrol @100 µg/kg<br>++ = celastrol @100 µg/kg<br>+ < celastrol @100 µg/kg<br>− active<br>*too active - study terminated | Oral bioavailability |
|---|---|---|---|---|
| ERX1102 | ERX1102 | 400 | ++ | |
| ERX1103 | ERX1103 | 1,000 | ++ | |
| ERX1103 | ERX1103 | 400 | − | |

TABLE 6-A-continued

*In vivo* activity of compounds (I.P. administration).

| Compound | Structure | dose (µg/kg) | activity<br>+++ > celastrol @100 µg/kg<br>++ = celastrol @100 µg/kg<br>+ < celastrol @100 µg/kg<br>− active<br>*too active - study terminated | Oral bioavailability |
|---|---|---|---|---|
| ERX1105 | ERX1105 | 400 | +++ | |
| ERX1106 | ERX1106 | 2,000 | − | |
| ERX1107 | ERX1107 | 50 | − | |

TABLE 6-A-continued

*In vivo* activity of compounds (I.P. administration).

| Compound | Structure | dose (μg/kg) | activity +++ > celastrol @100 μg/kg ++ = celastrol @100 μg/kg + < celastrol @100 μg/kg − active *too active - study terminated | Oral bioavailability |
|---|---|---|---|---|
| ERX1107 | ERX1107 | 100 | + | |
| ERX1107 | ERX1107 | 1,000 | * | |
| ERX1107 | ERX1107 | 400 | * | |

TABLE 6-A-continued

*In vivo* activity of compounds (I.P. administration).

| Compound | Structure | dose (μg/kg) | activity<br>+++ > celastrol @100 μg/kg<br>++ = celastrol @100 μg/kg<br>+ < celastrol @100 μg/kg<br>− active<br>*too active - study terminated | Oral bioavailability |
|---|---|---|---|---|
| ERX1108 | ERX1108 | 100 | − | |
| ERX1108 | ERX1108 | 1,000 | * | |
| ERX1109 | ERX1109 | 100 | − | |

TABLE 6-A-continued

*In vivo* activity of compounds (I.P. administration).

| Compound | Structure | dose (μg/kg) | activity +++ > celastrol @100 μg/kg ++ = celastrol @100 μg/kg + < celastrol @100 μg/kg − active *too active - study terminated | Oral bioavailability |
|---|---|---|---|---|
| ERX1109 | ERX1109 | 1,000 | +++ | |
| ERX1112 | ERX1112 | 200 | − | |
| ERX1113 | ERX1113 | 400 | − | |

TABLE 6-A-continued

*In vivo* activity of compounds (I.P. administration).

| Compound | Structure | dose (μg/kg) | activity<br>+++ > celastrol @100 μg/kg<br>++ = celastrol @100 μg/kg<br>+ < celastrol @100 μg/kg<br>− active<br>*too active - study terminated | Oral bioavailability |
|---|---|---|---|---|
| ERX1115 | ERX1115 | 200 | + | |
| ERX1116 | ERX1116 | 400 | ++ | |
| ERX1116 | ERX1116 | 100 | − | |

TABLE 6-A-continued

*In vivo* activity of compounds (I.P. administration).

| Compound | Structure | dose (μg/kg) | activity +++ > celastrol @100 μg/kg ++ = celastrol @100 μg/kg + < celastrol @100 μg/kg − active *too active - study terminated | Oral bioavailability |
|---|---|---|---|---|
| ERX1117 | ERX1117 | 400 | +++ | |
| ERX1119 | ERX1119 | 200 | +++ | |
| ERX1121 | ERX1121 | 200 | ++ | |

TABLE 6-A-continued

*In vivo* activity of compounds (I.P. administration).

| Compound | Structure | dose (µg/kg) | activity +++ > celastrol @100 µg/kg ++ = celastrol @100 µg/kg + < celastrol @100 µg/kg − active *too active - study terminated | Oral bioavailability |
|---|---|---|---|---|
| ERX1123 | ERX1123 | 200 | ++ | |
| ERX1124 | ERX1124 | 200 | ++ | |
| ERX1125 | ERX1125 | 200 | − | |

TABLE 6-A-continued

*In vivo* activity of compounds (I.P. administration).

| Compound | Structure | dose (µg/kg) | activity<br>+++ > celastrol @100 µg/kg<br>++ = celastrol @100 µg/kg<br>+ < celastrol @100 µg/kg<br>− active<br>*too active - study terminated | Oral bioavailability |
|---|---|---|---|---|
| ERX1126 | ERX1126 | 200 | ++ | |
| ERX1127 | ERX1127 | 200 | ++ | |
| ERX1129 | ERX1129 | 200 | ++ | |

TABLE 6-A-continued
*In vivo* activity of compounds (I.P. administration).
| Compound | Structure | dose (μg/kg) | activity +++ > celastrol @100 μg/kg ++ = celastrol @100 μg/kg + < celastrol @100 μg/kg − active *too active - study terminated | Oral bioavailability |
|---|---|---|---|---|
| ERX1131 | 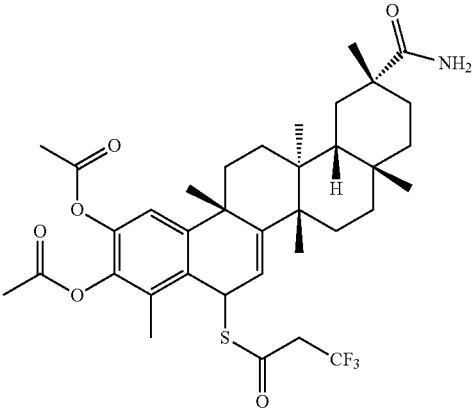<br>ERX1131 | 200 | ++ | |
| ERX1132 | 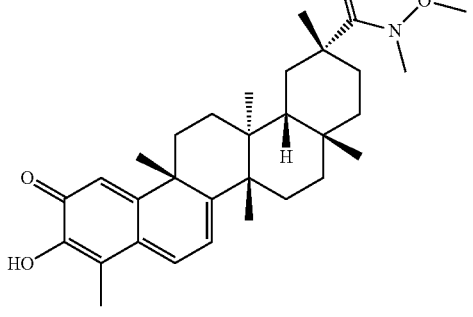 | 200 | ++ | |
| ERX1136 | 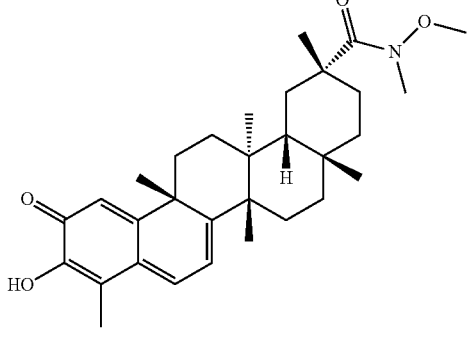 | 400 | − | |

TABLE 6-A-continued

*In vivo* activity of compounds (I.P. administration).

| Compound | Structure | dose (μg/kg) | activity<br>+++ > celastrol @100 μg/kg<br>++ = celastrol @100 μg/kg<br>+ < celastrol @100 μg/kg<br>− active<br>*too active - study terminated | Oral bioavailability |
|---|---|---|---|---|
| ERX1138 | ERX1138 | 400 | ++ | |
| ERX1139 | ERX1139 | 400 | ++ | |
| ERX1140 | ERX1140 | 400 | ++ | |

TABLE 6-A-continued

*In vivo* activity of compounds (I.P. administration).

| Compound | Structure | dose (μg/kg) | activity +++ > celastrol @100 μg/kg ++ = celastrol @100 μg/kg + < celastrol @100 μg/kg − active *too active - study terminated | Oral bioavailability |
|---|---|---|---|---|
| ERX1142 | ERX1142 | 400 | ++ | |
| ERX1143 | ERX1143 | 400 | − | |
| ERX1145 | ERX1145 | 400 | +++ | |

TABLE 6-A-continued

*In vivo* activity of compounds (I.P. administration).

| Compound | Structure | dose (μg/kg) | activity<br>+++ > celastrol @100 μg/kg<br>++ = celastrol @100 μg/kg<br>+ < celastrol @100 μg/kg<br>− active<br>*too active - study terminated | Oral bioavailability |
|---|---|---|---|---|
| ERX1146 | 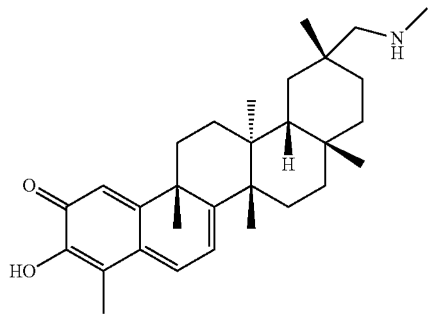 | 400 | +++ | |
| ERX1147 | 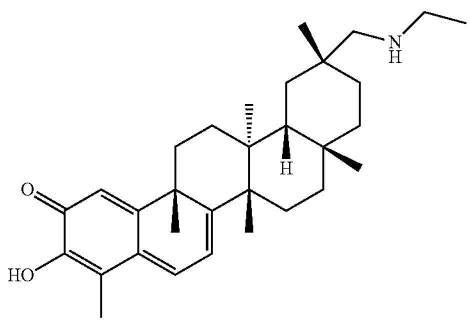 | 400 | +++ | |
| ERX1149 | 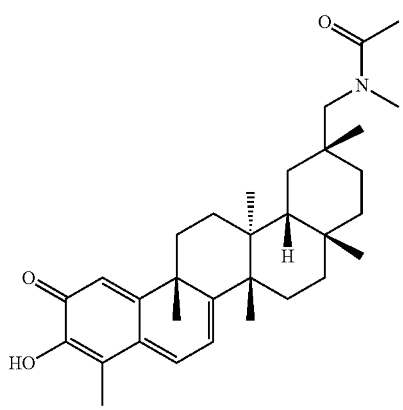 | 100 | +++ | |
| ERX1155 | 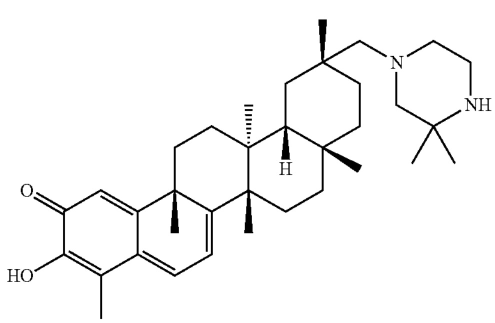 | 400 | ++ | |

TABLE 6-A-continued

*In vivo* activity of compounds (I.P. administration).

| Compound | Structure | dose (μg/kg) | activity<br>+++ > celastrol @100 μg/kg<br>++ = celastrol @100 μg/kg<br>+ < celastrol @100 μg/kg<br>− active<br>*too active - study terminated | Oral bioavailability |
|---|---|---|---|---|
| ERX1166 | 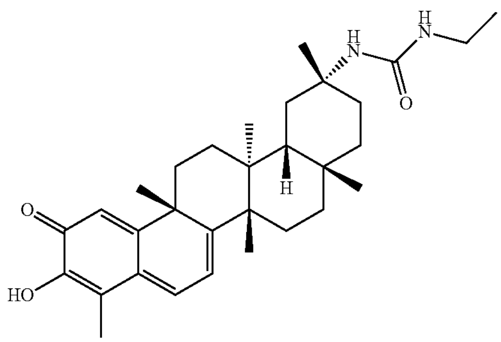 | 400 | +++ | |
| ERX1167 | 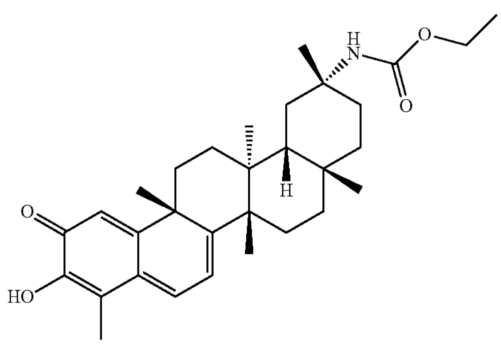 | 400 | +++ | |
| ERX1168 | | 100 | ++ | |
| ERX1168 | | 400 | +++ | |

TABLE 6-A-continued

*In vivo* activity of compounds (I.P. administration).

| Compound | Structure | dose (μg/kg) | activity<br>+++ > celastrol @100 μg/kg<br>++ = celastrol @100 μg/kg<br>+ < celastrol @100 μg/kg<br>− active<br>*too active - study terminated | Oral bioavailability |
|---|---|---|---|---|
| ERX1173 | 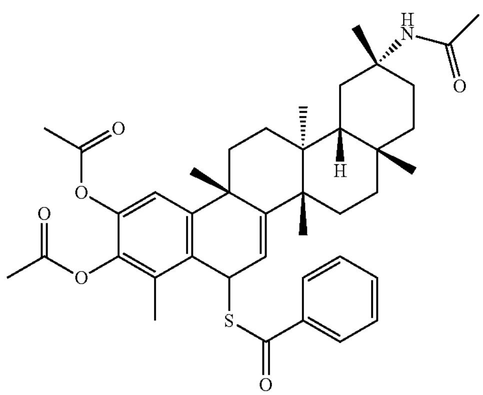 | 100 | ++ | |
| ERX1175 | 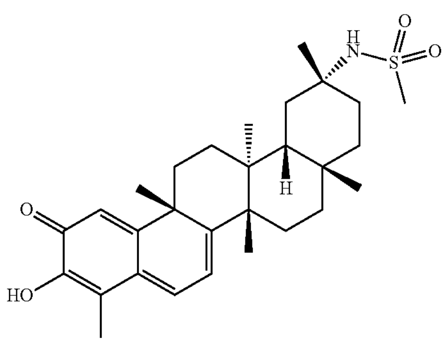 | 400 | +++ | |
| ERX1177 | 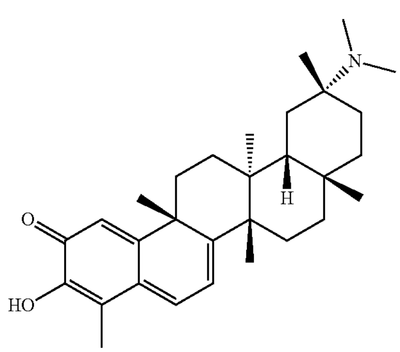 | 400 | ++ | |

TABLE 6-A-continued

In vivo activity of compounds (I.P. administration).

| Compound | Structure | dose (μg/kg) | activity +++ > celastrol @100 μg/kg ++ = celastrol @100 μg/kg + < celastrol @100 μg/kg − active *too active - study terminated | Oral bioavailability |
|---|---|---|---|---|
| Pristimerin | 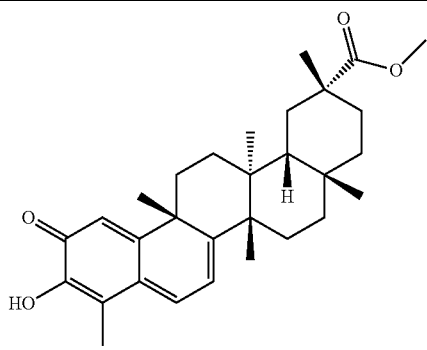<br>ERX1074 | 100 | +++ | |

TABLE 6-B

Summary of compound solubility.

| | | Solubility (μM) | |
|---|---|---|---|
| Test article | Test system | Mean | RSD |
| Propranolol | PBS (pH 7.4) | 97.45 | 0.01 |
| Ketoconazole | PBS (pH 7.4) | 35.70 | 0.01 |
| Tamoxifen | PBS (pH 7.4) | 0.82 | 0.05 |
| ERX1077 | PBS (pH 7.4) | 16.70 | 0.02 |
| ERX1107 | PBS (pH 7.4) | 11.40 | 0.07 |
| ERX1115 | PBS (pH 7.4) | 0.56 | 0.24 |
| ERX1117 | PBS (pH 7.4) | 0.91 | 0.03 |
| ERX1116 | PBS (pH 7.4) | 0.47 | 0.37 |
| ERX1121 | PBS (pH 7.4) | 1.55 | 0.02 |
| ERX1169 | PBS (pH 7.4) | 0.12 | 0.26 |
| ERX1124 | PBS (pH 7.4) | 1.04 | 0.01 |
| ERX1066 | PBS (pH 7.4) | 0.63 | 0.04 |
| ERX1076 | PBS (pH 7.4) | 6.44 | 0.02 |
| ERX1170 | PBS (pH 7.4) | 13.40 | 0.08 |
| ERX1171 | PBS (pH 7.4) | 3.18 | 0.01 |
| ERX1174 | PBS (pH 7.4) | 3.90 | 0.03 |
| ERX1175 | PBS (pH 7.4) | 4.03 | 0.03 |
| ERX1177 | PBS (pH 7.4) | 49.50 | 0.00 |
| ERX1187 | PBS (pH 7.4) | 91.95 | 0.00 |
| ERX1074 (Pristimerin) | PBS (pH 7.4) | 4.19 | 0.07 |
| ERX1188 | PBS (pH 7.4) | 3.30 | 0.05 |
| ERX1037 | PBS (pH 7.4) | 23.50 | 0.02 |
| ERX1047 | PBS (pH 7.4) | 1.13 | 0.09 |
| ERX1060 | PBS (pH 7.4) | 1.11 | 0.03 |
| ERX1006 | PBS (pH 7.4) | 1.15 | 0.02 |
| ERX1015 | PBS (pH 7.4) | 0.79 | 0.06 |
| ERX1020 | PBS (pH 7.4) | 0.54 | 0.45 |
| ERX1029 | PBS (pH 7.4) | 1.61 | 0.11 |
| ERX1031 | PBS (pH 7.4) | 8.56 | 0.03 |
| ERX1000 (Celastrol) | PBS (pH 7.4) | 3.89 | 0.01 |
| ERX1008 | PBS (pH 7.4) | 0.08 | 0.04 |

TABLE 6-B-continued

Summary of compound solubility.

| | | Solubility (μM) | |
|---|---|---|---|
| Test article | Test system | Mean | RSD |
| ERX1010 | PBS (pH 7.4) | 0.64 | 0.05 |
| ERX1007 | PBS (pH 7.4) | 48.75 | 0.02 |

N/A: Not Acquired
Test concentration 100 μM (1% of DMSO)
Test systems PBS (pH 7.4)
Incubation condition shaken (1000 rpm) for 1 h at room temperature
Sample size Duplicates (n = 2)
Bioanalytical method LC-MS/MS Comments:

As summarized in Table 6-B, solubility values less than 10 μM suggested these compounds showed low solubility; solubility values between 10 μM and 80 μM suggested these compounds showed moderate solubility; solubility values higher than 80 μM suggested these compounds showed high solubility.

TABLE 6-C

Summary of compound solubility.

| | | Solubility (μM) | |
|---|---|---|---|
| Test article | Test system | Mean | RSD |
| Propranolol | PBS (pH 7.4) | >100(107.50) | 0.03 |
| Ketoconazole | PBS (pH 7.4) | 35.20 | 0.06 |
| Tamoxifen | PBS (pH 7.4) | 1.49 | 0.16 |
| ERX1168 | PBS (pH 7.4) | 5.05 | 0.06 |
| ERX1172 | PBS (pH 7.4) | 0.90 | 0.27 |
| ERX1173 | PBS (pH 7.4) | 1.74 | 0.01 |

Test concentration: 100 µM (1% of DMSO)
Test systems: PBS (pH 7.4)
Incubation condition: shaken (1000 rpm) for 1 h at room temperature
Sample size: Duplicates (n=2)
Bioanalytical method: LC-MS/MS
Comments:
As summarized in Table 6-C, solubility values less than 10 µM suggested these compounds showed low solubility; solubility values between 10 µM and 80 µM suggested these compounds showed moderate solubility; solubility values higher than 80 µM suggested these compounds showed high solubility.

TABLE 6-D

Summary of compound solubility

| Test article | Test system | Solubility (µM) | RSD |
|---|---|---|---|
| Propranolol | PBS (pH 7.4) | 97.45 | 0.009432928 |
| Ketoconazole | PBS (pH 7.4) | 35.7 | 0.007922765 |
| Tamoxifen | PBS (pH 7.4) | 0.8155 | 0.047689605 |
| ERX1077 | PBS (pH 7.4) | 16.7 | 0.016936689 |
| ERX1107 | PBS (pH 7.4) | 11.4 | 0.074432293 |
| ERX1115 | PBS (pH 7.4) | 0.5575 | 0.244792123 |
| ERX1117 | PBS (pH 7.4) | 0.914 | 0.030945592 |
| ERX1116 | PBS (pH 7.4) | 0.4705 | 0.368206507 |
| ERX1121 | PBS (pH 7.4) | 1.55 | 0.018247917 |
| ERX1169 | PBS (pH 7.4) | 0.1235 | 0.257650244 |
| ERX1124 | PBS (pH 7.4) | 1.035 | 0.00683195 |
| ERX1066 | PBS (pH 7.4) | 0.6275 | 0.043947672 |
| ERX1076 | PBS (pH 7.4) | 6.435 | 0.023075746 |
| ERX1170 | PBS (pH 7.4) | 13.4 | 0.08443066 |
| ERX1171 | PBS (pH 7.4) | 3.175 | 0.01113554 |
| ERX1174 | PBS (pH 7.4) | 3.895 | 0.03086217 |
| ERX1175 | PBS (pH 7.4) | 4.03 | 0.028073718 |
| ERX1177 | PBS (pH 7.4) | 49.5 | 0.002856997 |
| ERX1187 | PBS (pH 7.4) | 91.95 | 0.003845061 |
| ERX1074 (Pristimerin) | PBS (pH 7.4) | 4.19 | 0.067504227 |
| ERX1188 | PBS (pH 7.4) | 3.3 | 0.051425948 |
| ERX1037 | PBS (pH 7.4) | 23.5 | 0.02407172 |
| ERX1047 | PBS (pH 7.4) | 1.13 | 0.08760615 |
| ERX1060 | PBS (pH 7.4) | 1.11 | 0.025481325 |
| ERX1006 | PBS (pH 7.4) | 1.145 | 0.018526815 |
| ERX1015 | PBS (pH 7.4) | 0.7915 | 0.058069413 |
| ERX1020 | PBS (pH 7.4) | 0.5405 | 0.451344754 |
| ERX1029 | PBS (pH 7.4) | 1.605 | 0.110141243 |
| ERX1031 | PBS (pH 7.4) | 8.56 | 0.026433898 |
| ERX1000 (Celastrol) | PBS (pH 7.4) | 3.89 | 0.010906531 |
| ERX1008 | PBS (pH 7.4) | 0.0841 | 0.040358056 |
| ERX1010 | PBS (pH 7.4) | 0.644 | 0.052703611 |
| ERX1007 | PBS (pH 7.4) | 48.75 | 0.01595523 |

Biological Study: Oral (P.O.) Administration
1. Summary
The purpose of this study was to assess test articles in the Diet Induced Obese (DIO) mouse.
Male C57BL/6 DIO mice were assigned to 12 groups, and doses of 2 mg/kg Celastrol (ERX1000-4), ERX1006, ERX1007, ERX1037, ERX1060, ERX1077, ERX1107, ERX1149, ERX1168, ERX1177, and Pristimerin were administered to Groups 2 through 12, respectively. Animals were dosed via oral gavage once daily for 10 days at a volume of 2 mL/kg. The vehicle control article was 1% methyl cellulose (400 cps) in citric acid and phosphate buffer.
Parameters assessed included mortality, clinical observations, body weights and food consumption and blood glucose evaluations.

All animals survived to the scheduled termination. Statistically significant changes in body weight, food consumption, and percent change of glucose value were noted for animals administered ERX1000-4 and ERX1168. Statistically significant changes in body weight were noted for animals administered ERX1006.

2. Methods
2.1 Test System and Study Design
2.1.1 Animal Specifications and Acclimation
Male C57BL/6 Diet Induced Obese (DIO) mice were received from Taconic. Animals were acclimated to housing conditions for at least 1 week prior to vehicle acclimation dosing. Animals were acclimated to oral gavage dosing with vehicle once daily for Days 11 through 14 of the predose phase.
At initiation of dosing, animals were 21 to 22 weeks old, and their body weights ranged from 29.8 to 40.1 g.
2.1.2 Environmental Conditions, Diet, and Water
2.1.2.1 Housing
Animals were individually housed in shoe box caging with wood chip bedding and nestlets.
2.1.2.2 Water
Water was provided ad libitum.
2.1.2.3 Diet
Animals were offered TD95217ad libitum, unless fasted for study procedures.
2.1.2.4 Environment
Environmental controls were set to maintain the following animal room conditions: a temperature range of 68 to 79° F., a relative humidity range of 30 to 70%, and a 12-hour light/12-hour dark cycle. Any variations to these conditions are maintained in the raw data and had no effect on the outcome of the study.
2.1.2.5 Dietary Enrichment
Animals were not given specialty food enrichment.
2.1.3 Animal Identification and Assignment to the Study
Animals were identified using indelible ink on tail and a cage card.
Animals were assigned to the study using a computerized procedure designed to achieve body weight balance with respect to group assignment.
2.1.4 Study Design:

TABLE 7

| Group | Test Article | Dose (mg/kg) | Animal Numbers |
|---|---|---|---|
| 1 | Vehicle | 0 | 1-5 |
| 2 | ERX1000-4 | 2 | 6-10 |
| 3 | ERX1006 | 2 | 11-15 |
| 4 | ERX1007 | 2 | 16-20 |
| 5 | ERX1037 | 2 | 21-25 |
| 6 | ERX1060 | 2 | 26-30 |
| 7 | ERX1077 | 2 | 31-35 |
| 8 | ERX1107 | 2 | 36-40 |
| 9 | ERX1149 | 2 | 41-45 |
| 10 | ERX1168 | 2 | 46-50 |
| 11 | ERX1177 | 2 | 51-55 |
| 12 | Pristimerin | 2 | 56-60 |

2.2 Test Article and Vehicle
2.2.1 Test Article

| Test Article | Storage |
|---|---|
| ERX1000-4 | Store at ≤ −60° C., Protected from light |
| ERX1006 | Store at ≤ −60° C., Protected from light |
| ERX1007 | Store at ≤ −60° C., Protected from light |
| ERX1037 | Store at ≤ −60° C., Protected from light |
| ERX1060 | Store at ≤ −60° C., Protected from light |
| ERX1077 | Store at ≤ −60° C., Protected from light |
| ERX1107 | Store at ≤ −60° C., Protected from light |
| ERX1149 | Store at ≤ −60° C., Protected from light |
| ERX1168 | Store at ≤ −60° C., Protected from light |
| ERX1177 | Store at ≤ −60° C., Protected from light |
| Pristimerin | Store at ≤ −60° C., Protected from light |

2.2.2 Vehicle

The vehicle was 1% methyl cellulose (400 cps) in citric acid and phosphate buffer.

2.2.3 Test Article Formulation

Test article formulations were prepared twice according to the mixing procedure. Dose concentrations were based on the test article as supplied.

Dose formulations were stored refrigerated and protected from light.

2.3 Inlife Procedures 2.3.1 Dose Administration

Dose formulations were administered by oral gavage once daily for 10 days at a dose volume of 2 mL/kg. Doses were based on the most recently recorded scheduled body weight.

2.3.2 Body Weights

Body weights were recorded daily on Days 11 through 14 of the predose phase. Body weights were collected for all animals daily during the dosing phase prior to dosing.

2.3.3 Food Consumption

A quantitative assessment of food consumption was recorded daily on Days 11 through 14 of the predose phase and daily prior to dosing during the dosing phase.

2.3.4 Blood Glucose Level

Blood for blood glucose was collected from all animals via tail clip on Day 14 of the predose phase, and Day 11 of the dosing phase after 6 hours of fasting. A drop of blood from each animal was placed onto two different Accu-Chek® Aviva glucometers to assess glucose values. A third value was taken, if necessary.

2.4 Terminal Procedures

All animals were anesthetized via carbon dioxide, sacrificed, and discarded without further evaluation on Day 11.

2.5 Data Evaluation and Statistical Analysis

Descriptive statistics (n, mean, standard error of the mean, standard deviation) were completed. Additionally, one-way analysis of variance followed by Dunnett's post-hoc test were performed on body weight (cumulative body weight change), glucose (glucose percent change), and food consumption (cumulative food consumption). Area under the curve (for body weight, cumulative body weight change, daily body weight change, and food consumption) was computed for treatment groups. An appropriate comparison test, such as one-way analysis of variance and Dunnett's, was performed on the group means for the area under the curve computations. Any additional statistical analysis and interpretation of the results were the responsibility of the sponsor.

3. Results 3.1 Inlife Evaluations 3.1.1 Animal Fate

Animal fate data are presented in Tables 11-1 to 11-12.

All animals survived to the scheduled termination.

3.1.2 Clinical Observations

No changes in clinical condition were noted for any treated groups.

3.1.3 Body Weights

Body weight data are summarized in Tables 9-1 to 9-12 and FIG. 1-5; individual data are presented in Tables 12-1 to 12-36 and FIGS. 10-12 (Daily Body Weight, Daily Body Weight Change, and Cumulative Body Weight Change).

ERX1000-4 had a statistically significant decreases in area under the curve (AUC) for daily and cumulative body weight change, and cumulative body weight change, compared with controls.

ERX1168 had a statistically significant decreases in area under the curve (AUC) for daily and cumulative body weight change, and cumulative body weight change, compared with controls.

ERX1008 had a statistically significant decreases in cumulative body weight change, compared with controls.

3.1.4 Food Consumption

Figure 6:
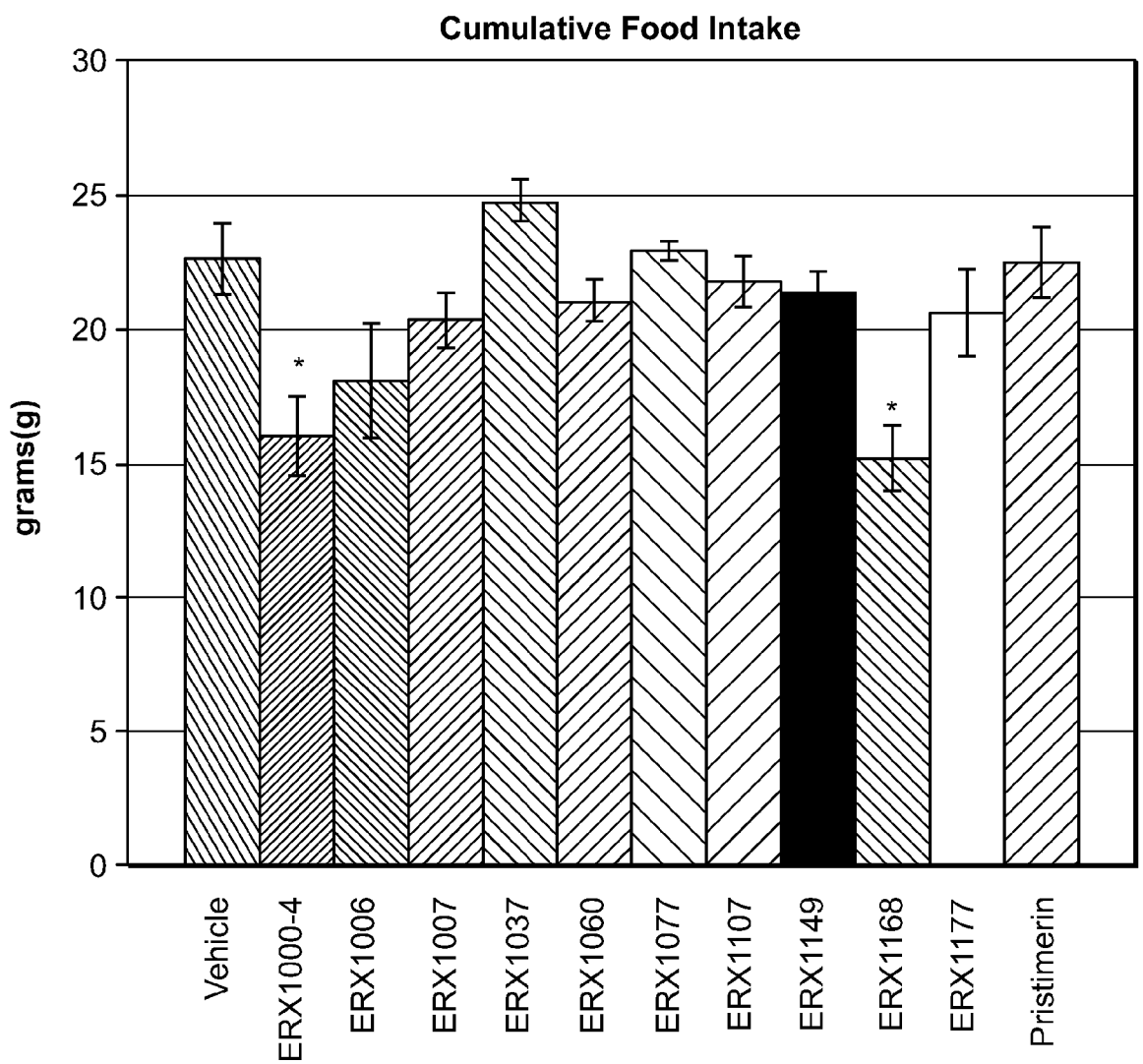
FIG. 6 is a graph of cumulative food intake of the diet induced obese (DIO) mice during treatments by oral administration of the compounds at a dose of 2,000 μg/kg as listed in Table 13 for 11 days.
Figure 7:
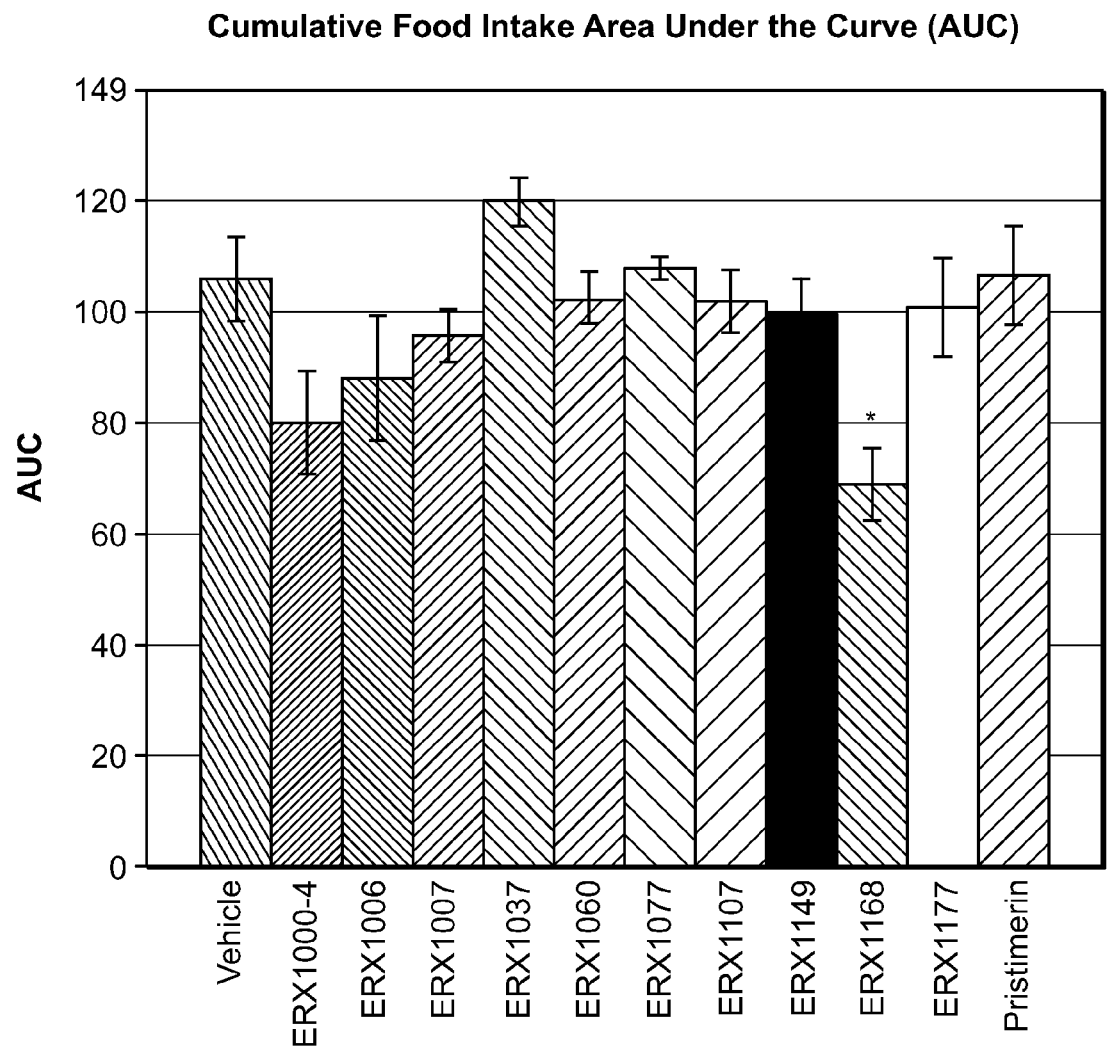
FIG. 7 is a graph of cumulative body weight change area under the curve (AUC) of the diet induced obese (DIO) mice during treatments by oral administration of the compounds at a dose of 2,000 μg/kg as listed in Table 13 for 11 days.

Food consumption data are summarized in Tables 10-1 to 10-6 and FIGS. 6-7; individual data are presented in FIGS. 13-14.

ERX1000-4 had a statistically significant decreases in cumulative food intake, compared with controls.

ERX1168 had a statistically significant decreases in area under the curve (AUC) for cumulative food intake and cumulative food intake, compared with controls.

3.1.5 Blood Glucose Level

Figure 8:
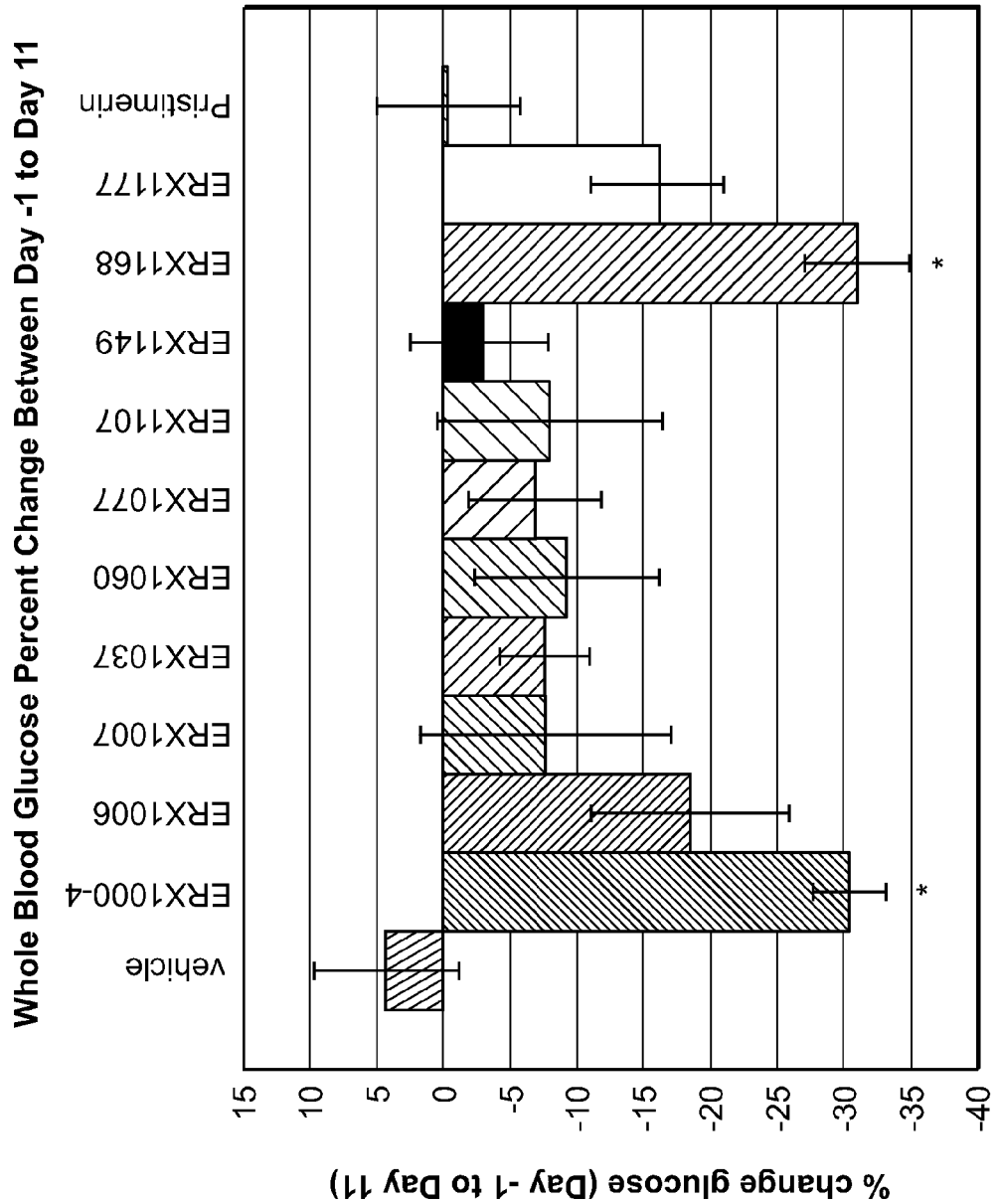
FIG. 8 is a graph of whole blood glucose percent change between day 1-day 11 of the diet induced obese (DIO) mice during treatments by oral administration of the compounds at a dose of 2,000 μg/kg as listed in Table 13 for 11 days.
Figure 9:
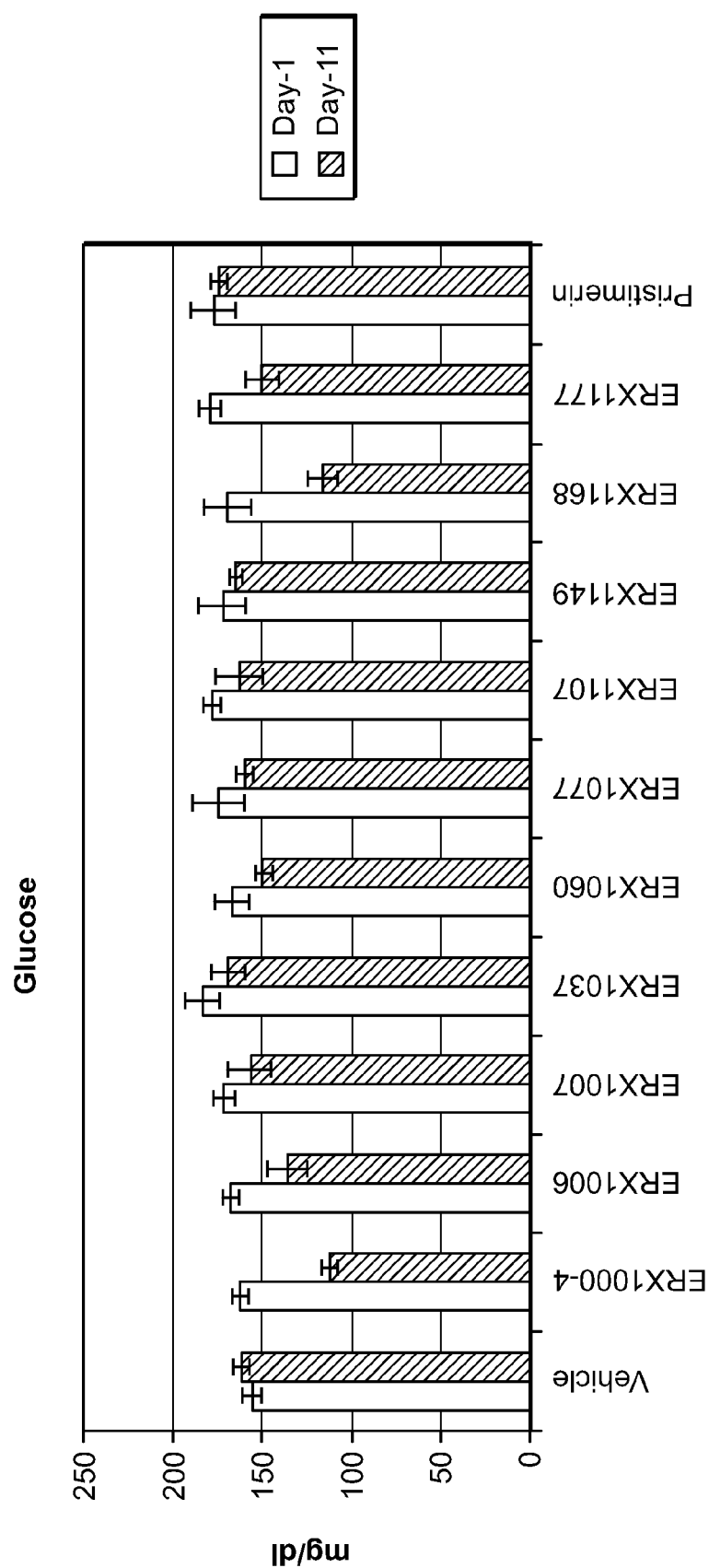
FIG. 9 is a graph of glucose values between day 1-day 11 of the diet induced obese (DIO) mice during treatments by oral administration of the compounds at a dose of 2,000 μg/kg as listed in Table 13 for 11 days.

Blood glucose data are summarized in FIGS. 8-9; individual data are presented in FIGS. 15-17.

ERX1000-4 had a statistically significant decreases in glucose value percent change, compared with controls.

ERX1168 had a statistically significant decreases in glucose value percent change, compared with controls.

4. Associated Study Information 4.1 Study Deviations 4.1.1 Protocol Deviations

TABLE 8

| Procedure | Protocol Deviations |
|---|---|
| | Test System and Study Design |
| Dose Administration | On Day 6, food consumption, body weights, and dosing occurred from 15:53 to 16:24. |

These study deviations neither affected the overall interpretation of study findings nor compromised the integrity of the study.

5. Summary of Results
TABLE 9
Summary of in vivo activity of compounds (P.O. administration).
| Compound | Structure | dose (μg/kg) | activity<br>+++ > celastrol @2000 μg/kg<br>++ = celastrol @2000 μg/kg<br>+ < celastrol @2000 μg/kg<br>−Inactive |
|---|---|---|---|
| ERX1000-4 (Celastrol) | 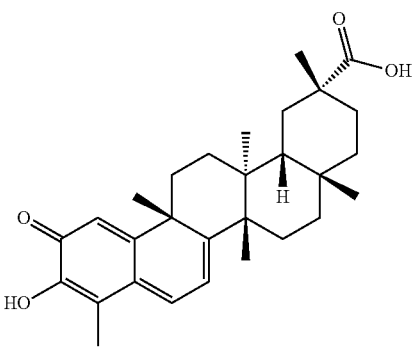 | 2000 | ++ |
| ERX1006 | 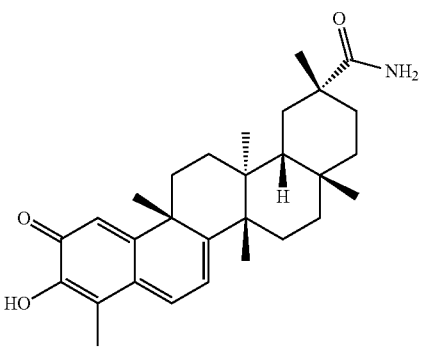 ERX1006 | 2000 | ++ |
| ERX1007 | 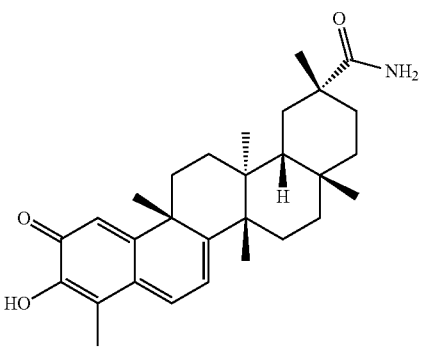 ERX1007 | 2000 | + |

TABLE 9-continued

Summary of in vivo activity of compounds (P.O. administration).

| Compound | Structure | dose (µg/kg) | activity<br>+++ > celastrol @2000 µg/kg<br>++ = celastrol @2000 µg/kg<br>+ < celastrol @2000 µg/kg<br>−Inactive |
|---|---|---|---|
| ERX1037 | ERX1037 | 2000 | − |
| ERX1060 | ERX1060 | 2000 | − |
| ERX1077 | 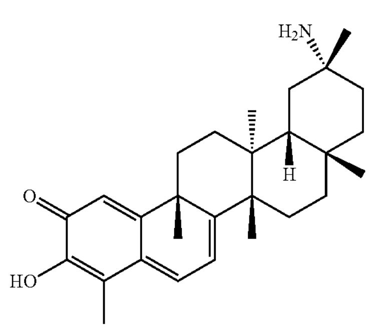 | 2000 | − |

TABLE 9-continued

Summary of in vivo activity of compounds (P.O. administration).

| Compound | Structure | dose (µg/kg) | activity +++ > celastrol @2000 µg/kg ++ = celastrol @2000 µg/kg + < celastrol @2000 µg/kg −Inactive |
|---|---|---|---|
| ERX1107 | ERX1107 | 2000 | + |
| ERX1149 | 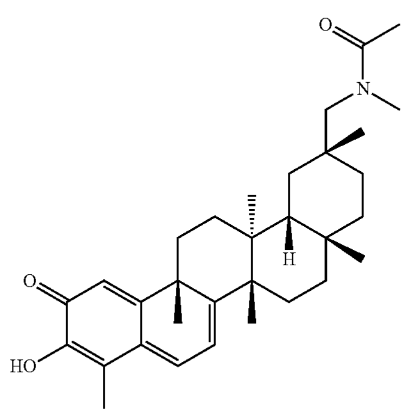 | 2000 | + |
| ERX1168 | 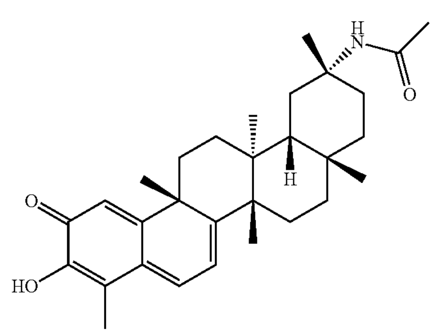 | 2000 | +++ |

TABLE 9-continued

Summary of in vivo activity of compounds (P.O. administration).

| Compound | Structure | dose (μg/kg) | activity +++ > celastrol @2000 μg/kg ++ = celastrol @2000 μg/kg + < celastrol @2000 μg/kg −Inactive |
|---|---|---|---|
| ERX1177 | 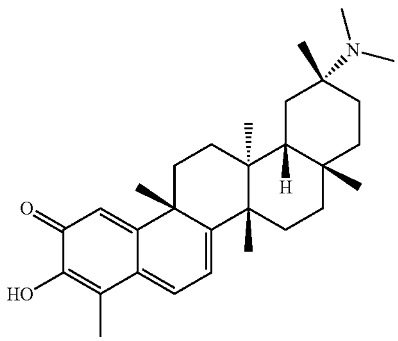 | 2000 | + |
| Pristimerin | ERX1074 | 2000 | − |

5.1 Summary of Body Weight

TABLE 9-1

| Test Article | (dosage) | 1 | 2 | 3 | 4 | 5 | 6 | 7 | 8 | 9 | 10 | 11 | 12 |
|---|---|---|---|---|---|---|---|---|---|---|---|---|---|
| Vehicle | mg/kg | 0 | — | — | — | — | — | — | — | — | — | — | — |
| ERX1000 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | — | 2 | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| Group/ | | Data Presented in "g" Phase DSNG Day | | | | | |
|---|---|---|---|---|---|---|---|
| Sex | | 1 | 2 | 3 | 4 | 5 | 6 |
| 1/M | Mean | 34.3 | 34.5 | 33.9 | 33.4 | 33.8 | 33.5 |
| | SD | 2.33 | 2.48 | 2.29 | 3.01 | 2.58 | 2.68 |
| | N | 5 | 5 | 5 | 5 | 5 | 5 |

TABLE 9-1-continued

| | | | | | | | |
|---|---|---|---|---|---|---|---|
| 2/M | Mean | 34.2 | 34.0 | 33.1 | 32.5 | 32.1 | 31.4 |
| | SD | 2.27 | 2.09 | 2.08 | 2.59 | 2.79 | 2.43 |
| | N | 5 | 5 | 5 | 5 | 5 | 5 |
| | %-Diff | 0% | −1% | −2% | −3% | −5% | −6% |

TABLE 9-2

| Test Article | (dosage) | 1 | 2 | 3 | 4 | 5 | 6 | 7 | 8 | 9 | 10 | 11 | 12 |
|---|---|---|---|---|---|---|---|---|---|---|---|---|---|
| Vehicle | mg/kg | 0 | — | — | — | — | — | — | — | — | — | — | — |
| ERX1000 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| Group/ | | Data Presented in "g" Phase DSNG Day | | | | | |
|---|---|---|---|---|---|---|---|
| Sex | | 1 | 2 | 3 | 4 | 5 | 6 |
| 3/M | Mean | 34.1 | 33.9 | 33.4 | 32.8 | 32.6 | 32.5 |
| | SD | 1.49 | 1.91 | 1.83 | 2.25 | 2.11 | 1.90 |
| | N | 5 | 5 | 5 | 5 | 5 | 5 |
| | %-Diff | −1% | −2% | −1% | −2% | −4% | −3% |
| 4/M | Mean | 34.5 | 34.1 | 33.3 | 33.3 | 33.1 | 32.4 |
| | SD | 2.02 | 2.50 | 2.25 | 2.03 | 2.13 | 2.39 |
| | N | 5 | 5 | 5 | 5 | 5 | 5 |
| | %-Diff | 1% | −1% | −2% | 0% | −2% | −3% |

TABLE 9-3

| Test Article | (dosage) | 1 | 2 | 3 | 4 | 5 | 6 | 7 | 8 | 9 | 10 | 11 | 12 |
|---|---|---|---|---|---|---|---|---|---|---|---|---|---|
| Vehicle | mg/kg | 0 | — | — | — | — | — | — | — | — | — | — | — |
| ERX1000 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| Group/ | | Data Presented in "g" Phase DSNG Day | | | | | |
|---|---|---|---|---|---|---|---|
| Sex | | 1 | 2 | 3 | 4 | 5 | 6 |
| 5/M | Mean | 35.0 | 34.8 | 34.6 | 34.2 | 34.3 | 34.5 |
| | SD | 2.73 | 2.56 | 2.77 | 2.92 | 2.83 | 2.81 |
| | N | 5 | 5 | 5 | 5 | 5 | 5 |
| | %-Diff | 2% | 1% | 2% | 2% | 1% | 3% |
| 6/M | Mean | 34.6 | 34.1 | 34.4 | 34.1 | 34.2 | 34.4 |
| | SD | 2.81 | 3.05 | 2.54 | 2.63 | 2.48 | 2.75 |
| | N | 5 | 5 | 5 | 5 | 5 | 5 |
| | %-Diff | 1% | −1% | 1% | 2% | 1% | 3% |

TABLE 9-4

| Test Article | (dosage) | 1 | 2 | 3 | 4 | 5 | 6 | 7 | 8 | 9 | 10 | 11 | 12 |
|---|---|---|---|---|---|---|---|---|---|---|---|---|---|
| Vehicle | mg/kg | 0 | — | — | — | — | — | — | — | — | — | — | — |
| ERX1000 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| Group/Sex | | Data Presented in "g" Phase DSNG Day | | | | | |
|---|---|---|---|---|---|---|---|
| | | 1 | 2 | 3 | 4 | 5 | 6 |
| 7/M | Mean | 34.4 | 34.1 | 34.0 | 33.7 | 33.7 | 34.0 |
| | SD | 2.57 | 2.72 | 2.44 | 2.59 | 2.60 | 2.62 |
| | N | 5 | 5 | 5 | 5 | 5 | 5 |
| | %-Diff | 0% | −1% | 0% | 1% | 0% | 1% |
| 8/M | Mean | 34.2 | 34.3 | 33.4 | 33.2 | 33.1 | 32.7 |
| | SD | 2.02 | 2.31 | 1.97 | 2.05 | 2.29 | 2.25 |
| | N | 5 | 5 | 5 | 5 | 5 | 5 |
| | %-Diff | 0% | −1% | −1% | −1% | −2% | −2% |

TABLE 9-5

| Test Article | (dosage) | 1 | 2 | 3 | 4 | 5 | 6 | 7 | 8 | 9 | 10 | 11 | 12 |
|---|---|---|---|---|---|---|---|---|---|---|---|---|---|
| Vehicle | mg/kg | 0 | — | — | — | — | — | — | — | — | — | — | — |
| ERX1000 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| Group/Sex | | Data Presented in "g" Phase DSNG Day | | | | | |
|---|---|---|---|---|---|---|---|
| | | 1 | 2 | 3 | 4 | 5 | 6 |
| 9/M | Mean | 34.9 | 34.5 | 34.1 | 34.0 | 33.5 | 33.1 |
| | SD | 3.10 | 3.26 | 3.44 | 3.63 | 3.63 | 3.74 |
| | N | 5 | 5 | 5 | 5 | 5 | 5 |
| | %-Diff | 2% | 0% | 1% | 2% | −1% | −1% |
| 10/M | Mean | 34.5 | 34.0 | 32.2 | 31.9 | 31.1 | 29.5 |
| | SD | 3.57 | 4.26 | 3.58 | 3.78 | 3.46 | 3.13 |
| | N | 5 | 5 | 5 | 5 | 5 | 5 |
| | %-Diff | 1% | −1% | −5% | −4% | −8% | −12% |

TABLE 9-6

| Test Article | (dosage) | 1 | 2 | 3 | 4 | 5 | 6 | 7 | 8 | 9 | 10 | 11 | 12 |
|---|---|---|---|---|---|---|---|---|---|---|---|---|---|
| Vehicle | mg/kg | 0 | — | — | — | — | — | — | — | — | — | — | — |
| ERX1000 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |

TABLE 9-6-continued

| Test Article | (dosage) | 1 | 2 | 3 | 4 | 5 | 6 | 7 | 8 | 9 | 10 | 11 | 12 |
|---|---|---|---|---|---|---|---|---|---|---|---|---|---|
| ERX1107 | mg/kg | — | — | — | — | — | — | 2 | — | — | — | — | — |
| ERX1149 | mg/kg | — | — | — | — | — | — | — | 2 | — | — | — | — |
| ERX1168 | mg/kg | — | — | — | — | — | — | — | — | 2 | — | — | — |
| ERX1177 | mg/kg | — | — | — | — | — | — | — | — | — | 2 | — | — |
| Pristimerin | mg/kg | — | — | — | — | — | — | — | — | — | — | 2 | — |

| | | Data Presented in "g" Phase DSNG Day | | | | | |
|---|---|---|---|---|---|---|---|
| Group/Sex | | 1 | 2 | 3 | 4 | 5 | 6 |
| 11/M | Mean | 34.9 | 34.4 | 34.2 | 33.7 | 33.8 | 33.5 |
| | SD | 3.30 | 2.61 | 2.64 | 2.83 | 2.86 | 3.08 |
| | N | 5 | 5 | 5 | 5 | 5 | 5 |
| | %-Diff | 2% | 0% | 1% | 1% | 0% | 0% |
| 12/M | Mean | 34.2 | 34.0 | 33.7 | 33.3 | 33.3 | 33.4 |
| | SD | 3.84 | 3.53 | 4.22 | 4.45 | 4.63 | 4.87 |
| | N | 5 | 5 | 5 | 5 | 5 | 5 |
| | %-Diff | 0% | −1% | −1% | 0% | −1% | 0% |

TABLE 9-7

| Test Article | (dosage) | 1 | 2 | 3 | 4 | 5 | 6 | 7 | 8 | 9 | 10 | 11 | 12 |
|---|---|---|---|---|---|---|---|---|---|---|---|---|---|
| Vehicle | mg/kg | 0 | — | — | — | — | — | — | — | — | — | — | — |
| ERX1000 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| | | Data Presented in "g" Phase DSNG Day | | | | |
|---|---|---|---|---|---|---|
| Group/Sex | | 7 | 8 | 9 | 10 | 11 |
| 1/M | Mean | 33.5 | 33.8 | 33.2 | 33.5 | 34.1 |
| | SD | 2.51 | 2.64 | 3.05 | 3.15 | 2.77 |
| | N | 5 | 5 | 5 | 5 | 5 |
| 2/M | Mean | 30.6 | 30.4 | 30.3 | 30.0 | 29.1 |
| | SD | 2.50 | 2.36 | 2.41 | 2.57 | 2.41 |
| | N | 5 | 5 | 5 | 5 | 5 |
| | %-Diff | −9% | −10% | −9% | −10% | −15% |

TABLE 9-8

| Test Article | (dosage) | 1 | 2 | 3 | 4 | 5 | 6 | 7 | 8 | 9 | 10 | 11 | 12 |
|---|---|---|---|---|---|---|---|---|---|---|---|---|---|
| Vehicle | mg/kg | 0 | — | — | — | — | — | — | — | — | — | — | — |
| ERX1000 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

TABLE 9-8-continued

| Group/ | | Data Presented in "g" Phase DSNG Day | | | | |
|---|---|---|---|---|---|---|
| Sex | | 7 | 8 | 9 | 10 | 11 |
| 3/M | Mean | 32.0 | 31.7 | 31.4 | 31.2 | 30.9 |
| | SD | 2.04 | 2.18 | 2.05 | 2.39 | 2.34 |
| | N | 5 | 5 | 5 | 5 | 5 |
| | %-Diff | −4% | −6% | −5% | −7% | −9% |
| 4/M | Mean | 32.4 | 32.7 | 32.3 | 32.1 | 32.3 |
| | SD | 2.21 | 2.35 | 2.56 | 2.83 | 2.98 |
| | N | 5 | 5 | 5 | 5 | 5 |
| | %-Diff | −3% | −3% | −3% | −4% | −5% |

TABLE 9-9

| Test Article | (dosage) | 1 | 2 | 3 | 4 | 5 | 6 | 7 | 8 | 9 | 10 | 11 | 12 |
|---|---|---|---|---|---|---|---|---|---|---|---|---|---|
| Vehicle | mg/kg | 0 | — | — | — | — | — | — | — | — | — | — | — |
| ERX1000 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| Group/ | | Data Presented in "g" Phase DSNG Day | | | | |
|---|---|---|---|---|---|---|
| Sex | | 7 | 8 | 9 | 10 | 11 |
| 5/M | Mean | 35.0 | 34.8 | 34.3 | 34.8 | 34.9 |
| | SD | 2.66 | 3.05 | 3.45 | 3.43 | 3.43 |
| | N | 5 | 5 | 5 | 5 | 5 |
| | %-Diff | 4% | 3% | 3% | 4% | 2% |
| 6/M | Mean | 33.8 | 33.3 | 33.1 | 33.5 | 34.4 |
| | SD | 2.90 | 2.73 | 3.29 | 3.26 | 3.28 |
| | N | 5 | 5 | 5 | 5 | 5 |
| | %-Diff | 1% | −1% | 0% | 0% | 1% |

TABLE 9-10

| Test Article | (dosage) | 1 | 2 | 3 | 4 | 5 | 6 | 7 | 8 | 9 | 10 | 11 | 12 |
|---|---|---|---|---|---|---|---|---|---|---|---|---|---|
| Vehicle | mg/kg | 0 | — | — | — | — | — | — | — | — | — | — | — |
| ERX1000 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| Group/ | | Data Presented in "g" Phase DSNG Day | | | | |
|---|---|---|---|---|---|---|
| Sex | | 7 | 8 | 9 | 10 | 11 |
| 7/M | Mean | 33.3 | 33.7 | 33.5 | 33.8 | 33.9 |
| | SD | 2.52 | 2.29 | 2.13 | 2.42 | 2.71 |

TABLE 9-10-continued

|     |       |      |      |      |      |      |
|-----|-------|------|------|------|------|------|
|     | N     | 5    | 5    | 5    | 5    | 5    |
|     | %-Diff| −1%  | 0%   | 1%   | 1%   | −1%  |
| 8/M | Mean  | 32.4 | 32.3 | 32.2 | 32.4 | 32.7 |
|     | SD    | 2.53 | 2.38 | 2.35 | 2.85 | 2.40 |
|     | N     | 5    | 5    | 5    | 5    | 5    |
|     | %-Diff| −3%  | −4%  | −3%  | −3%  | −4%  |

TABLE 9-11

| Test Article | (dosage) | 1 | 2 | 3 | 4 | 5 | 6 | 7 | 8 | 9 | 10 | 11 | 12 |
|---|---|---|---|---|---|---|---|---|---|---|---|---|---|
| Vehicle | mg/kg | 0 | — | — | — | — | — | — | — | — | — | — | — |
| ERX1000 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| | | Data Presented in "g" Phase DSNG Day | | | | |
|---|---|---|---|---|---|---|
| Group/Sex | | 7 | 8 | 9 | 10 | 11 |
| 9/M | Mean | 32.8 | 33.3 | 33.1 | 33.5 | 33.6 |
|     | SD   | 3.90 | 3.69 | 3.81 | 3.28 | 4.01 |
|     | N    | 5    | 5    | 5    | 5    | 5    |
|     | %-Diff | −2% | −1% | 0%  | 0%  | −1% |
| 10/M | Mean | 29.2 | 29.1 | 30.0 | 29.2 | 29.2 |
|      | SD   | 2.26 | 2.24 | 2.50 | 3.56 | 3.34 |
|      | N    | 5    | 5    | 5    | 5    | 5    |
|      | %-Diff | −13% | −14% | −10% | −13% | −14% |

TABLE 9-12

| Test Article | (dosage) | 1 | 2 | 3 | 4 | 5 | 6 | 7 | 8 | 9 | 10 | 11 | 12 |
|---|---|---|---|---|---|---|---|---|---|---|---|---|---|
| Vehicle | mg/kg | 0 | — | — | — | — | — | — | — | — | — | — | — |
| ERX1000 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| | | Data Presented in "g" Phase DSNG Day | | | | |
|---|---|---|---|---|---|---|
| Group/Sex | | 7 | 8 | 9 | 10 | 11 |
| 11/M | Mean | 33.4 | 33.1 | 33.0 | 33.1 | 33.0 |
|      | SD   | 3.08 | 3.08 | 3.29 | 3.17 | 3.49 |
|      | N    | 5    | 5    | 5    | 5    | 5    |
|      | %-Diff | 0% | −2% | −1% | −1% | −3% |
| 12/M | Mean | 33.5 | 33.1 | 32.9 | 33.2 | 33.9 |
|      | SD   | 4.77 | 4.91 | 5.05 | 4.81 | 5.01 |
|      | N    | 5    | 5    | 5    | 5    | 5    |
|      | %-Diff | 0% | −2% | −1% | −1% | −1% |

TABLE 10-1

| Test Article | (dosage) | 1 | 2 | 3 | 4 | 5 | 6 | 7 | 8 | 9 | 10 | 11 | 12 |
|---|---|---|---|---|---|---|---|---|---|---|---|---|---|
| Vehicle | mg/kg | 0 | — | — | — | — | — | — | — | — | — | — | — |
| ERX1000 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| Group/ Sex | | Data Presented in "g/animal/day" Interval X to X Phase PRED Day | | |
|---|---|---|---|---|
| | | 11-12 | 12-13 | 13-14 |
| 1/M | Mean | 3.5 | 1.9 | 1.6 |
| | SD | 0.74 | 0.38 | 0.67 |
| | N | 5 | 5 | 5 |
| 2/M | Mean | 3.0 | 2.0 | 1.9 |
| | SD | 1.68 | 1.25 | 0.55 |
| | N | 5 | 5 | 5 |
| | %-Diff | −15% | 9% | 16% |

TABLE 10-2

| Test Article | (dosage) | 1 | 2 | 3 | 4 | 5 | 6 | 7 | 8 | 9 | 10 | 11 | 12 |
|---|---|---|---|---|---|---|---|---|---|---|---|---|---|
| Vehicle | mg/kg | 0 | — | — | — | — | — | — | — | — | — | — | — |
| ERX1000 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| Group/ Sex | | Data Presented in "g/animal/day" Interval X to X Phase PRED Day | | |
|---|---|---|---|---|
| | | 11-12 | 12-13 | 13-14 |
| 3/M | Mean | 3.8 | 2.7 | 1.8 |
| | SD | 0.36 | 0.61 | 0.46 |
| | N | 5 | 5 | 5 |
| | %-Diff | 9% | 45% | 10% |
| 4/M | Mean | 2.8 | 2.4 | 1.9 |
| | SD | 0.92 | 0.80 | 0.50 |
| | N | 5 | 5 | 5 |
| | %-Diff | −19% | 30% | 17% |

TABLE 10-3

| Test Article | (dosage) | 1 | 2 | 3 | 4 | 5 | 6 | 7 | 8 | 9 | 10 | 11 | 12 |
|---|---|---|---|---|---|---|---|---|---|---|---|---|---|
| Vehicle | mg/kg | 0 | — | — | — | — | — | — | — | — | — | — | — |
| ERX1000 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |

TABLE 10-3-continued

| | | 1 | 2 | 3 | 4 | 5 | 6 | 7 | 8 | 9 | 10 | 11 | 12 |
|---|---|---|---|---|---|---|---|---|---|---|---|---|---|
| ERX1149 | mg/kg | — | — | — | — | — | — | — | 2 | — | — | — | — |
| ERX1168 | mg/kg | — | — | — | — | — | — | — | — | 2 | — | — | — |
| ERX1177 | mg/kg | — | — | — | — | — | — | — | — | — | 2 | — | — |
| Pristimerin | mg/kg | — | — | — | — | — | — | — | — | — | — | — | 2 |

| Group/ Sex | | Data Presented in "g/animal/day" Interval X to X Phase PRED Day | | |
|---|---|---|---|---|
| | | 11-12 | 12-13 | 13-14 |
| 5/M | Mean | 4.1 | 2.9 | 2.2 |
| | SD | 2.19 | 0.81 | 0.38 |
| | N | 5 | 5 | 5 |
| | %-Diff | 18% | 53% | 33% |
| 6/M | Mean | 2.6 | 1.5 | 1.2 |
| | SD | 0.81 | 1.24 | 0.52 |
| | N | 5 | 5 | 5 |
| | %-Diff | −25% | −19% | −26% |

TABLE 10-4

| Test Article | (dosage) | 1 | 2 | 3 | 4 | 5 | 6 | 7 | 8 | 9 | 10 | 11 | 12 |
|---|---|---|---|---|---|---|---|---|---|---|---|---|---|
| Vehicle | mg/kg | 0 | — | — | — | — | — | — | — | — | — | — | — |
| ERX1000 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| Group/ Sex | | Data Presented in "g/animal/day" Interval X to X Phase PRED Day | | |
|---|---|---|---|---|
| | | 11-12 | 12-13 | 13-14 |
| 7/M | Mean | 2.9 | 2.5 | 2.2 |
| | SD | 0.27 | 0.66 | 0.63 |
| | N | 5 | 5 | 5 |
| | %-Diff | −17% | 32% | 38% |
| 8/M | Mean | 3.5 | 2.9 | 2.0 |
| | SD | 1.99 | 1.28 | 0.35 |
| | N | 5 | 5 | 5 |
| | %-Diff | 1% | 52% | 23% |

TABLE 10-5

| Test Article | (dosage) | 1 | 2 | 3 | 4 | 5 | 6 | 7 | 8 | 9 | 10 | 11 | 12 |
|---|---|---|---|---|---|---|---|---|---|---|---|---|---|
| Vehicle | mg/kg | 0 | — | — | — | — | — | — | — | — | — | — | — |
| ERX1000 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

TABLE 10-5-continued

| Group/ | | Data Presented in "g/animal/day" Interval X to X Phase PRED Day | | |
|---|---|---|---|---|
| Sex | | 11-12 | 12-13 | 13-14 |
| 9/M | Mean | 3.3 | 2.3 | 1.9 |
| | SD | 0.62 | 0.30 | 0.54 |
| | N | 5 | 5 | 5 |
| | %-Diff | −5% | 21% | 16% |
| 10/M | Mean | 2.5 | 2.5 | 2.4 |
| | SD | 1.88 | 1.05 | 0.97 |
| | N | 5 | 5 | 5 |
| | %-Diff | −30% | 31% | 47% |

TABLE 10-6

| Test Article | (dosage) | 1 | 2 | 3 | 4 | 5 | 6 | 7 | 8 | 9 | 10 | 11 | 12 |
|---|---|---|---|---|---|---|---|---|---|---|---|---|---|
| Vehicle | mg/kg | 0 | — | — | — | — | — | — | — | — | — | — | — |
| ERX1000 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| Group/ | | Data Presented in "g/animal/day" Interval X to X Phase PRED Day | | |
|---|---|---|---|---|
| Sex | | 11-12 | 12-13 | 13-14 |
| 11/M | Mean | 3.9 | 2.4 | 1.8 |
| | SD | 0.82 | 0.70 | 0.43 |
| | N | 5 | 5 | 5 |
| | %-Diff | 10% | 27% | 11% |
| 12/M | Mean | 2.6 | 2.5 | 2.3 |
| | SD | 0.67 | 0.11 | 0.48 |
| | N | 5 | 5 | 5 |
| | %-Diff | −25% | 32% | 40% |

TABLE 11-1

Individual Animal Fate

| Test Article | (dosage) | 1 | 2 | 3 | 4 | 5 | 6 | 7 | 8 | 9 | 10 | 11 | 12 |
|---|---|---|---|---|---|---|---|---|---|---|---|---|---|
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| Group/ Sex | Animal Number | Phase of Fate | Phase Week | Phase Day | Fate Status | Terminal Body Weight (g) |
|---|---|---|---|---|---|---|
| 1/M | 1 | Dosing | 2 | 11 | Scheduled Sacrifice and Discard | — |

TABLE 11-1-continued

| | | Individual Animal Fate | | | | |
|---|---|---|---|---|---|---|
| | 2 | Dosing | 2 | 11 | Scheduled Sacrifice and Discard | — |
| | 3 | Dosing | 2 | 11 | Scheduled Sacrifice and Discard | — |
| | 4 | Dosing | 2 | 11 | Scheduled Sacrifice and Discard | — |
| | 5 | Dosing | 2 | 11 | Scheduled Sacrifice and Discard | — |

TABLE 11-2

| | | Individual Animal Fate | | | | | | | | | | |
|---|---|---|---|---|---|---|---|---|---|---|---|---|
| Test Article | (dosage) | 1 | 2 | 3 | 4 | 5 | 6 | 7 | 8 | 9 | 10 | 11 | 12 |
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| Group/Sex | Animal Number | Phase of Fate | Phase Week | Phase Day | Fate Status | Terminal Body Weight (g) |
|---|---|---|---|---|---|---|
| 2/M | 10 | Dosing | 2 | 11 | Scheduled Sacrifice and Discard | — |
| | 6 | Dosing | 2 | 11 | Scheduled Sacrifice and Discard | — |
| | 7 | Dosing | 2 | 11 | Scheduled Sacrifice and Discard | — |
| | 8 | Dosing | 2 | 11 | Scheduled Sacrifice and Discard | — |
| | 9 | Dosing | 2 | 11 | Scheduled Sacrifice and Discard | — |

TABLE 11-3

| | | Individual Animal Fate | | | | | | | | | | |
|---|---|---|---|---|---|---|---|---|---|---|---|---|
| Test Article | (dosage) | 1 | 2 | 3 | 4 | 5 | 6 | 7 | 8 | 9 | 10 | 11 | 12 |
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| Group/Sex | Animal Number | Phase of Fate | Phase Week | Phase Day | Fate Status | Terminal Body Weight (g) |
|---|---|---|---|---|---|---|
| 3/M | 11 | Dosing | 2 | 11 | Scheduled Sacrifice and Discard | — |
| | 12 | Dosing | 2 | 11 | Scheduled Sacrifice and Discard | — |
| | 13 | Dosing | 2 | 11 | Scheduled Sacrifice and Discard | — |

TABLE 11-3-continued

| | | Individual Animal Fate | | | | |
|---|---|---|---|---|---|---|
| | 14 | Dosing | 2 | 11 | Scheduled Sacrifice and Discard | — |
| | 15 | Dosing | 2 | 11 | Scheduled Sacrifice and Discard | — |

TABLE 11-4

| Individual Animal Fate | | | | | | | | | | | | | |
|---|---|---|---|---|---|---|---|---|---|---|---|---|---|
| Test Article | (dosage) | 1 | 2 | 3 | 4 | 5 | 6 | 7 | 8 | 9 | 10 | 11 | 12 |
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| Group/Sex | Animal Number | Phase of Fate | Phase Week | Phase Day | Fate Status | Terminal Body Weight (g) |
|---|---|---|---|---|---|---|
| 4/M | 16 | Dosing | 2 | 11 | Scheduled Sacrifice and Discard | — |
| | 17 | Dosing | 2 | 11 | Scheduled Sacrifice and Discard | — |
| | 18 | Dosing | 2 | 11 | Scheduled Sacrifice and Discard | — |
| | 19 | Dosing | 2 | 11 | Scheduled Sacrifice and Discard | — |
| | 20 | Dosing | 2 | 11 | Scheduled Sacrifice and Discard | — |

TABLE 11-5

| Individual Animal Fate | | | | | | | | | | | | | |
|---|---|---|---|---|---|---|---|---|---|---|---|---|---|
| Test Article | (dosage) | 1 | 2 | 3 | 4 | 5 | 6 | 7 | 8 | 9 | 10 | 11 | 12 |
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| Group/Sex | Animal Number | Phase of Fate | Phase Week | Phase Day | Fate Status | Terminal Body Weight (g) |
|---|---|---|---|---|---|---|
| 5/M | 21 | Dosing | 2 | 11 | Scheduled Sacrifice and Discard | — |
| | 22 | Dosing | 2 | 11 | Scheduled Sacrifice and Discard | — |
| | 23 | Dosing | 2 | 11 | Scheduled Sacrifice and Discard | — |
| | 24 | Dosing | 2 | 11 | Scheduled Sacrifice and Discard | — |
| | 25 | Dosing | 2 | 11 | Scheduled Sacrifice and Discard | — |

TABLE 11-6

| | | \multicolumn{12}{c}{Individual Animal Fate} |
|---|---|---|---|---|---|---|---|---|---|---|---|---|---|
| Test Article | (dosage) | 1 | 2 | 3 | 4 | 5 | 6 | 7 | 8 | 9 | 10 | 11 | 12 |
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| Group/Sex | Animal Number | Phase of Fate | Phase Week | Phase Day | Fate Status | Terminal Body Weight (g) |
|---|---|---|---|---|---|---|
| 6/M | 26 | Dosing | 2 | 11 | Scheduled Sacrifice and Discard | — |
| | 27 | Dosing | 2 | 11 | Scheduled Sacrifice and Discard | — |
| | 28 | Dosing | 2 | 11 | Scheduled Sacrifice and Discard | — |
| | 29 | Dosing | 2 | 11 | Scheduled Sacrifice and Discard | — |
| | 30 | Dosing | 2 | 11 | Scheduled Sacrifice and Discard | — |

TABLE 11-7

| | | \multicolumn{12}{c}{Individual Animal Fate} |
|---|---|---|---|---|---|---|---|---|---|---|---|---|---|
| Test Article | (dosage) | 1 | 2 | 3 | 4 | 5 | 6 | 7 | 8 | 9 | 10 | 11 | 12 |
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| Group/Sex | Animal Number | Date | Phase of Fate | Phase Week | Phase Day | Fate Status | Terminal Body Weight (g) |
|---|---|---|---|---|---|---|---|
| 7/M | 31 | | Dosing | 2 | 11 | Scheduled Sacrifice and Discard | — |
| | 32 | | Dosing | 2 | 11 | Scheduled Sacrifice and Discard | — |
| | 33 | | Dosing | 2 | 11 | Scheduled Sacrifice and Discard | — |
| | 34 | | Dosing | 2 | 11 | Scheduled Sacrifice and Discard | — |
| | 35 | | Dosing | 2 | 11 | Scheduled Sacrifice and Discard | — |

TABLE 11-8

| | | \multicolumn{12}{c}{Individual Animal Fate} |
|---|---|---|---|---|---|---|---|---|---|---|---|---|---|
| Test Article | (dosage) | 1 | 2 | 3 | 4 | 5 | 6 | 7 | 8 | 9 | 10 | 11 | 12 |
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |

TABLE 11-8-continued

| | | 1 | 2 | 3 | 4 | 5 | 6 | 7 | 8 | 9 | 10 | 11 | 12 |
|---|---|---|---|---|---|---|---|---|---|---|---|---|---|
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| Group/Sex | Animal Number | Phase of Fate | Phase Week | Phase Day | Fate Status | Terminal Body Weight (g) |
|---|---|---|---|---|---|---|
| 8/M | 36 | Dosing | 2 | 11 | Scheduled Sacrifice and Discard | — |
| | 37 | Dosing | 2 | 11 | Scheduled Sacrifice and Discard | — |
| | 38 | Dosing | 2 | 11 | Scheduled Sacrifice and Discard | — |
| | 39 | Dosing | 2 | 11 | Scheduled Sacrifice and Discard | — |
| | 40 | Dosing | 2 | 11 | Scheduled Sacrifice and Discard | — |

TABLE 11-9

8351983
Individual Animal Fate

| Test Article | (dosage) | 1 | 2 | 3 | 4 | 5 | 6 | 7 | 8 | 9 | 10 | 11 | 12 |
|---|---|---|---|---|---|---|---|---|---|---|---|---|---|
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| Group/Sex | Animal Number | Date | Phase of Fate | Phase Week | Phase Day | Fate Status | Terminal Body Weight (g) |
|---|---|---|---|---|---|---|---|
| 9/M | 41 | | Dosing | 2 | 11 | Scheduled Sacrifice and Discard | — |
| | 42 | | Dosing | 2 | 11 | Scheduled Sacrifice and Discard | — |
| | 43 | | Dosing | 2 | 11 | Scheduled Sacrifice and Discard | — |
| | 44 | | Dosing | 2 | 11 | Scheduled Sacrifice and Discard | — |
| | 45 | | Dosing | 2 | 11 | Scheduled Sacrifice and Discard | — |

TABLE 11-10

Individual Animal Fate

| Test Article | (dosage) | 1 | 2 | 3 | 4 | 5 | 6 | 7 | 8 | 9 | 10 | 11 | 12 |
|---|---|---|---|---|---|---|---|---|---|---|---|---|---|
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |

TABLE 11-10-continued

| Test Article | (dosage) | 1 | 2 | 3 | 4 | 5 | 6 | 7 | 8 | 9 | 10 | 11 | 12 |
|---|---|---|---|---|---|---|---|---|---|---|---|---|---|
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| Group/Sex | Animal Number | Date | Phase of Fate | Phase Week | Phase Day | Fate Status | Terminal Body Weight (g) |
|---|---|---|---|---|---|---|---|
| 10/M | 46 | | Dosing | 2 | 11 | Scheduled Sacrifice and Discard | — |
| | 47 | | Dosing | 2 | 11 | Scheduled Sacrifice and Discard | — |
| | 48 | | Dosing | 2 | 11 | Scheduled Sacrifice and Discard | — |
| | 49 | | Dosing | 2 | 11 | Scheduled Sacrifice and Discard | — |
| | 50 | | Dosing | 2 | 11 | Scheduled Sacrifice and Discard | — |

TABLE 11-11

Individual Animal Fate

| Test Article | (dosage) | 1 | 2 | 3 | 4 | 5 | 6 | 7 | 8 | 9 | 10 | 11 | 12 |
|---|---|---|---|---|---|---|---|---|---|---|---|---|---|
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| Group/Sex | Animal Number | Date | Phase of Fate | Phase Week | Phase Day | Fate Status | Terminal Body Weight (g) |
|---|---|---|---|---|---|---|---|
| 11/M | 51 | | Dosing | 2 | 11 | Scheduled Sacrifice and Discard | — |
| | 52 | | Dosing | 2 | 11 | Scheduled Sacrifice and Discard | — |
| | 53 | | Dosing | 2 | 11 | Scheduled Sacrifice and Discard | — |
| | 54 | | Dosing | 2 | 11 | Scheduled Sacrifice and Discard | — |
| | 55 | | Dosing | 2 | 11 | Scheduled Sacrifice and Discard | — |

TABLE 11-12

Individual Animal Fate

| Test Article | (dosage) | 1 | 2 | 3 | 4 | 5 | 6 | 7 | 8 | 9 | 10 | 11 | 12 |
|---|---|---|---|---|---|---|---|---|---|---|---|---|---|
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

TABLE 11-12-continued

| Group/Sex | Animal Number | Phase of Fate | Phase Week | Phase Day | Fate Status | Terminal Body Weight (g) |
|---|---|---|---|---|---|---|
| 12/M | 56 | Dosing | 2 | 11 | Scheduled Sacrifice and Discard | — |
|  | 57 | Dosing | 2 | 11 | Scheduled Sacrifice and Discard | — |
|  | 58 | Dosing | 2 | 11 | Scheduled Sacrifice and Discard | — |
|  | 59 | Dosing | 2 | 11 | Scheduled Sacrifice and Discard | — |
|  | 60 | 2Dosing | 2 | 11 | Scheduled Sacrifice and Discard | — |

TABLE 12-1

Individual Body Weight

| Test Article | (dosage) | 1 | 2 | 3 | 4 | 5 | 6 | 7 | 8 | 9 | 10 | 11 | 12 |
|---|---|---|---|---|---|---|---|---|---|---|---|---|---|
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| Group/Sex | Animal Number | Phase Day | Data Presented in "g" |||||| 
|---|---|---|---|---|---|---|---|---|
|  |  |  | PRED 11 | PRED 12 | PRED 13 | PRED 14 | DSNG 1 | DSNG 2 |
| 1/M | 1 | | 34.9 | 34.1 | 33.5 | 34.4 | 33.0 | 32.1 |
|  | 2 | | 35.3 | 36.2 | 35.2 | 35.5 | 35.2 | 34.8 |
|  | 3 | | 38.7 | 37.6 | 37.0 | 37.1 | 34.4 | 35.7 |
|  | 4 | | 40.1 | 38.1 | 37.9 | 38.0 | 37.5 | 37.9 |
|  | 5 | | 34.3 | 34.1 | 33.2 | 33.0 | 31.3 | 32.1 |

TABLE 12-2

Individual Body Weight

| Test Article | (dosage) | 1 | 2 | 3 | 4 | 5 | 6 | 7 | 8 | 9 | 10 | 11 | 12 |
|---|---|---|---|---|---|---|---|---|---|---|---|---|---|
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| Group/Sex | Animal Number | Phase Day | Data Presented in "g" |||||| 
|---|---|---|---|---|---|---|---|---|
|  |  |  | PRED 11 | PRED 12 | PRED 13 | PRED 14 | DSNG 1 | DSNG 2 |
| 10/M | 46 | | 35.6 | 35.2 | 35.0 | 35.1 | 33.1 | 32.5 |
|  | 47 | | 39.3 | 40.3 | 40.0 | 41.2 | 39.5 | 40.4 |
|  | 48 | | 37.3 | 37.2 | 37.2 | 37.5 | 36.9 | 36.2 |
|  | 49 | | 35.3 | 33.1 | 32.5 | 33.3 | 31.9 | 31.2 |
|  | 50 | | 33.0 | 31.0 | 30.6 | 32.1 | 31.1 | 29.9 |

TABLE 12-3

| | | \multicolumn{12}{c}{Individual Body Weight} |
|---|---|---|---|---|---|---|---|---|---|---|---|---|---|
| Test Article | (dosage) | 1 | 2 | 3 | 4 | 5 | 6 | 7 | 8 | 9 | 10 | 11 | 12 |
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| Group/ Sex | Animal Number | Phase Day | \multicolumn{6}{c}{Data Presented in "g"} | | | | | |
|---|---|---|---|---|---|---|---|---|
| | | | PRED 11 | PRED 12 | PRED 13 | PRED 14 | DSNG 1 | DSNG 2 |
| 11/M | 51 | | 33.8 | 32.5 | 31.8 | 31.7 | 32.0 | 32.2 |
| | 52 | | 33.3 | 33.7 | 32.6 | 33.1 | 32.1 | 31.9 |
| | 53 | | 37.1 | 36.7 | 35.6 | 36.4 | 35.5 | 34.5 |
| | 54 | | 41.9 | 41.6 | 42.2 | 41.7 | 40.1 | 38.4 |
| | 55 | | 35.5 | 36.2 | 36.1 | 36.2 | 35.0 | 34.9 |

TABLE 12-4

| | | \multicolumn{12}{c}{Individual Body Weight} |
|---|---|---|---|---|---|---|---|---|---|---|---|---|---|
| Test Article | (dosage) | 1 | 2 | 3 | 4 | 5 | 6 | 7 | 8 | 9 | 10 | 11 | 12 |
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| Group/ Sex | Animal Number | Phase Day | \multicolumn{6}{c}{Data Presented in "g"} | | | | | |
|---|---|---|---|---|---|---|---|---|
| | | | PRED 11 | PRED 12 | PRED 13 | PRED 14 | DSNG 1 | DSNG 2 |
| 12/M | 56 | | 42.4 | 41.2 | 41.3 | 41.9 | 40.0 | 39.4 |
| | 57 | | 35.2 | 34.5 | 33.4 | 35.0 | 33.3 | 33.1 |
| | 58 | | 31.7 | 31.0 | 31.4 | 31.6 | 29.8 | 30.2 |
| | 59 | | 38.2 | 37.5 | 37.3 | 37.6 | 35.5 | 35.4 |
| | 60 | | 33.9 | 32.5 | 32.9 | 33.1 | 32.3 | 32.1 |

TABLE 12-5

| | | \multicolumn{12}{c}{Individual Body Weight} |
|---|---|---|---|---|---|---|---|---|---|---|---|---|---|
| Test Article | (dosage) | 1 | 2 | 3 | 4 | 5 | 6 | 7 | 8 | 9 | 10 | 11 | 12 |
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

TABLE 12-5-continued

| Group/Sex | Animal Number | Phase Day | PRED 11 | PRED 12 | PRED 13 | PRED 14 | DSNG 1 | DSNG 2 |
|---|---|---|---|---|---|---|---|---|
| | | | Data Presented in "g" | | | | | |
| 2/M | 10 | | 35.9 | 35.2 | 35.1 | 35.5 | 34.6 | 34.4 |
| | 6 | | 35.1 | 33.5 | 32.5 | 32.9 | 30.8 | 30.8 |
| | 7 | | 37.3 | 37.4 | 37.7 | 37.9 | 37.0 | 36.4 |
| | 8 | | 34.5 | 35.5 | 34.0 | 34.6 | 33.5 | 33.5 |
| | 9 | | 37.5 | 37.3 | 36.0 | 37.2 | 34.9 | 35.0 |

TABLE 12-6

Individual Body Weight

| Test Article | (dosage) | 1 | 2 | 3 | 4 | 5 | 6 | 7 | 8 | 9 | 10 | 11 | 12 |
|---|---|---|---|---|---|---|---|---|---|---|---|---|---|
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| Group/Sex | Animal Number | Phase Day | PRED 11 | PRED 12 | PRED 13 | PRED 14 | DSNG 1 | DSNG 2 |
|---|---|---|---|---|---|---|---|---|
| | | | Data Presented in "g" | | | | | |
| 3/M | 11 | | 37.6 | 38.0 | 37.4 | 38.5 | 35.7 | 35.0 |
| | 12 | | 34.5 | 35.2 | 35.4 | 35.4 | 35.0 | 35.6 |
| | 13 | | 32.2 | 32.7 | 32.5 | 32.7 | 32.7 | 31.8 |
| | 14 | | 35.2 | 34.8 | 34.1 | 34.3 | 32.4 | 31.8 |
| | 15 | | 36.7 | 36.8 | 36.3 | 36.9 | 34.9 | 35.2 |

TABLE 12-7

Individual Body Weight

| Test Article | (dosage) | 1 | 2 | 3 | 4 | 5 | 6 | 7 | 8 | 9 | 10 | 11 | 12 |
|---|---|---|---|---|---|---|---|---|---|---|---|---|---|
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| Group/Sex | Animal Number | Phase Day | PRED 11 | PRED 12 | PRED 13 | PRED 14 | DSNG 1 | DSNG 2 |
|---|---|---|---|---|---|---|---|---|
| | | | Data Presented in "g" | | | | | |
| 4/M | 16 | | 36.8 | 35.2 | 34.1 | 34.2 | 33.8 | 33.2 |
| | 17 | | 39.8 | 38.9 | 38.7 | 38.6 | 36.3 | 36.4 |
| | 18 | | 35.7 | 35.7 | 35.3 | 35.2 | 34.7 | 34.2 |
| | 19 | | 32.5 | 31.7 | 32.3 | 32.7 | 31.4 | 30.3 |
| | 20 | | 37.6 | 36.9 | 36.5 | 37.3 | 36.2 | 36.2 |

TABLE 12-8

| Test Article | (dosage) | 1 | 2 | 3 | 4 | 5 | 6 | 7 | 8 | 9 | 10 | 11 | 12 |
|---|---|---|---|---|---|---|---|---|---|---|---|---|---|
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| Group/Sex | Animal Number | Phase Day | Data Presented in "g" | | | | | |
|---|---|---|---|---|---|---|---|---|
| | | | PRED 11 | PRED 12 | PRED 13 | PRED 14 | DSNG 1 | DSNG 2 |
| 5/M | 21 | | 36.0 | 36.7 | 35.4 | 35.7 | 35.1 | 36.4 |
| | 22 | | 38.7 | 38.8 | 38.8 | 39.2 | 39.1 | 38.4 |
| | 23 | | 31.8 | 33.1 | 33.4 | 32.7 | 32.0 | 32.4 |
| | 24 | | 37.3 | 36.2 | 36.9 | 36.7 | 35.7 | 34.1 |
| | 25 | | 36.1 | 33.6 | 33.4 | 34.0 | 33.1 | 32.7 |

TABLE 12-9

| Test Article | (dosage) | 1 | 2 | 3 | 4 | 5 | 6 | 7 | 8 | 9 | 10 | 11 | 12 |
|---|---|---|---|---|---|---|---|---|---|---|---|---|---|
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| Group/Sex | Animal Number | Phase Day | Data Presented in "g" | | | | | |
|---|---|---|---|---|---|---|---|---|
| | | | PRED 11 | PRED 12 | PRED 13 | PRED 14 | DSNG 1 | DSNG 2 |
| 6/M | 26 | | 36.2 | 34.5 | 33.2 | 33.7 | 32.9 | 33.2 |
| | 27 | | 38.2 | 36.6 | 34.7 | 35.1 | 34.3 | 34.1 |
| | 28 | | 35.9 | 34.9 | 33.5 | 32.7 | 31.3 | 29.8 |
| | 29 | | 40.9 | 41.2 | 39.8 | 40.6 | 38.7 | 38.2 |
| | 30 | | 38.9 | 39.0 | 37.1 | 37.4 | 35.6 | 35.2 |

TABLE 12-10

| Test Article | (dosage) | 1 | 2 | 3 | 4 | 5 | 6 | 7 | 8 | 9 | 10 | 11 | 12 |
|---|---|---|---|---|---|---|---|---|---|---|---|---|---|
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

TABLE 12-10-continued

| Group/ Sex | Animal Number | Phase Day | Data Presented in "g" | | | | | |
|---|---|---|---|---|---|---|---|---|
| | | | PRED 11 | PRED 12 | PRED 13 | PRED 14 | DSNG 1 | DSNG 2 |
| 7/M | 31 | | 32.6 | 33.2 | 31.6 | 32.7 | 31.5 | 31.2 |
| | 32 | | 34.8 | 34.0 | 33.1 | 33.6 | 32.8 | 32.5 |
| | 33 | | 36.1 | 35.8 | 35.6 | 35.7 | 34.5 | 34.1 |
| | 34 | | 40.2 | 40.4 | 39.7 | 40.6 | 38.3 | 38.4 |
| | 35 | | 38.0 | 37.0 | 36.9 | 36.6 | 34.9 | 34.4 |

TABLE 12-11

Individual Body Weight

| Test Article | (dosage) | 1 | 2 | 3 | 4 | 5 | 6 | 7 | 8 | 9 | 10 | 11 | 12 |
|---|---|---|---|---|---|---|---|---|---|---|---|---|---|
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| Group/ Sex | Animal Number | Phase Day | Data Presented in "g" | | | | | |
|---|---|---|---|---|---|---|---|---|
| | | | PRED 11 | PRED 12 | PRED 13 | PRED 14 | DSNG 1 | DSNG 2 |
| 8/M | 36 | | 34.1 | 35.1 | 34.9 | 35.1 | 33.6 | 33.5 |
| | 37 | | 36.6 | 37.5 | 38.0 | 37.5 | 35.8 | 36.5 |
| | 38 | | 37.7 | 37.9 | 37.6 | 37.7 | 36.3 | 36.5 |
| | 39 | | 36.2 | 33.2 | 31.9 | 32.5 | 31.2 | 31.0 |
| | 40 | | 34.1 | 34.6 | 33.8 | 34.6 | 34.1 | 33.9 |

TABLE 12-12

Individual Body Weight

| Test Article | (dosage) | 1 | 2 | 3 | 4 | 5 | 6 | 7 | 8 | 9 | 10 | 11 | 12 |
|---|---|---|---|---|---|---|---|---|---|---|---|---|---|
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| Group/ Sex | Animal Number | Phase Day | Data Presented in "g" | | | | | |
|---|---|---|---|---|---|---|---|---|
| | | | PRED 11 | PRED 12 | PRED 13 | PRED 14 | DSNG 1 | DSNG 2 |
| 9/M | 41 | | 33.3 | 33.3 | 33.1 | 33.5 | 33.3 | 32.2 |
| | 42 | | 38.3 | 37.3 | 36.8 | 36.1 | 35.8 | 34.8 |
| | 43 | | 41.4 | 41.5 | 41.4 | 41.0 | 39.7 | 39.9 |
| | 44 | | 33.7 | 33.4 | 32.3 | 32.5 | 31.5 | 31.7 |
| | 45 | | 35.6 | 36.3 | 35.2 | 36.5 | 34.3 | 34.1 |

TABLE 12-13

| | | | | | | | | | | | | | |
|---|---|---|---|---|---|---|---|---|---|---|---|---|---|
| | | colspan="13" | Individual Body Weight | | | | | | | | | | |
| Test Article | (dosage) | 1 | 2 | 3 | 4 | 5 | 6 | 7 | 8 | 9 | 10 | 11 | 12 |
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| Group/ Sex | Animal Number | Phase Day | Data Presented in "g" | | | | | |
|---|---|---|---|---|---|---|---|---|
| | | | DSNG 3 | DSNG 4 | DSNG 5 | DSNG 6 | DSNG 7 | DSNG 8 |
| 1/M | 1 | | 32.1 | 31.5 | 31.0 | 30.3 | 30.9 | 30.6 |
| | 2 | | 34.3 | 34.0 | 34.5 | 34.8 | 35.0 | 35.6 |
| | 3 | | 35.6 | 36.0 | 36.1 | 35.3 | 35.4 | 36.2 |
| | 4 | | 36.5 | 36.2 | 36.3 | 36.1 | 35.7 | 35.2 |
| | 5 | | 31.1 | 29.2 | 31.2 | 30.9 | 30.7 | 31.2 |

TABLE 12-14

| | | | | | | | | | | | | | |
|---|---|---|---|---|---|---|---|---|---|---|---|---|---|
| | | colspan="13" | Individual Body Weight | | | | | | | | | | |
| Test Article | (dosage) | 1 | 2 | 3 | 4 | 5 | 6 | 7 | 8 | 9 | 10 | 11 | 12 |
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| Group/ Sex | Animal Number | Phase Day | Data Presented in "g" | | | | | |
|---|---|---|---|---|---|---|---|---|
| | | | DSNG 3 | DSNG 4 | DSNG 5 | DSNG 6 | DSNG 7 | DSNG 8 |
| 10/M | 46 | | 30.7 | 30.0 | 29.2 | 28.4 | 28.9 | 28.7 |
| | 47 | | 37.3 | 37.5 | 36.1 | 33.9 | 32.3 | 32.7 |
| | 48 | | 34.4 | 34.2 | 33.2 | 31.6 | 30.7 | 29.5 |
| | 49 | | 30.5 | 29.1 | 28.8 | 27.0 | 27.0 | 27.7 |
| | 50 | | 28.3 | 28.9 | 28.0 | 26.7 | 27.3 | 26.9 |

TABLE 12-15

| | | | | | | | | | | | | | |
|---|---|---|---|---|---|---|---|---|---|---|---|---|---|
| | | colspan="13" | Individual Body Weight | | | | | | | | | | |
| Test Article | (dosage) | 1 | 2 | 3 | 4 | 5 | 6 | 7 | 8 | 9 | 10 | 11 | 12 |
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

TABLE 12-15-continued

| Group/Sex | Animal Number | Phase Day | Data Presented in "g" | | | | | |
|---|---|---|---|---|---|---|---|---|
| | | | DSNG 3 | DSNG 4 | DSNG 5 | DSNG 6 | DSNG 7 | DSNG 8 |
| 11/M | 51 | | 31.8 | 31.2 | 31.3 | 31.4 | 31.4 | 31.0 |
| | 52 | | 31.8 | 30.8 | 30.9 | 30.1 | 29.9 | 29.8 |
| | 53 | | 34.6 | 34.8 | 34.2 | 33.7 | 33.7 | 33.4 |
| | 54 | | 38.2 | 37.7 | 38.0 | 38.1 | 38.0 | 37.8 |
| | 55 | | 34.6 | 34.2 | 34.4 | 34.4 | 34.1 | 33.7 |

TABLE 12-16

| Individual Body Weight | | | | | | | | | | | | | |
|---|---|---|---|---|---|---|---|---|---|---|---|---|---|
| Test Article | (dosage) | 1 | 2 | 3 | 4 | 5 | 6 | 7 | 8 | 9 | 10 | 11 | 12 |
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| Group/Sex | Animal Number | Phase Day | Data Presented in "g" | | | | | |
|---|---|---|---|---|---|---|---|---|
| | | | DSNG 3 | DSNG 4 | DSNG 5 | DSNG 6 | DSNG 7 | DSNG 8 |
| 12/M | 56 | | 40.1 | 40.3 | 40.3 | 40.9 | 40.7 | 40.3 |
| | 57 | | 32.6 | 32.4 | 32.3 | 32.2 | 31.6 | 31.2 |
| | 58 | | 29.2 | 29.0 | 28.6 | 28.7 | 29.1 | 28.2 |
| | 59 | | 35.3 | 34.7 | 35.1 | 35.1 | 35.8 | 35.8 |
| | 60 | | 31.2 | 30.3 | 30.1 | 29.9 | 30.2 | 30.0 |

TABLE 12-17

| Individual Body Weight | | | | | | | | | | | | | |
|---|---|---|---|---|---|---|---|---|---|---|---|---|---|
| Test Article | (dosage) | 1 | 2 | 3 | 4 | 5 | 6 | 7 | 8 | 9 | 10 | 11 | 12 |
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| Group/Sex | Animal Number | Phase Day | Data Presented in "g" | | | | | |
|---|---|---|---|---|---|---|---|---|
| | | | DSNG 3 | DSNG 4 | DSNG 5 | DSNG 6 | DSNG 7 | DSNG 8 |
| 2/M | 10 | | 33.3 | 32.7 | 31.1 | 30.6 | 29.8 | 30.2 |
| | 6 | | 30.3 | 29.2 | 30.1 | 29.6 | 28.4 | 27.8 |
| | 7 | | 36.0 | 36.3 | 37.0 | 35.4 | 34.6 | 34.2 |
| | 8 | | 32.2 | 31.4 | 30.7 | 29.5 | 28.9 | 29.4 |
| | 9 | | 33.5 | 33.1 | 31.7 | 31.8 | 31.4 | 30.3 |

TABLE 12-18

| | | \multicolumn{12}{c}{Individual Body Weight} |
|---|---|---|---|---|---|---|---|---|---|---|---|---|---|
| Test Article | (dosage) | 1 | 2 | 3 | 4 | 5 | 6 | 7 | 8 | 9 | 10 | 11 | 12 |
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| Group/ | Animal | Phase | \multicolumn{6}{c}{Data Presented in "g"} |
|---|---|---|---|---|---|---|---|---|
| Sex | Number | Day | DSNG 3 | DSNG 4 | DSNG 5 | DSNG 6 | DSNG 7 | DSNG 8 |
| 3/M | 11 | | 33.4 | 31.9 | 32.1 | 31.5 | 30.4 | 29.2 |
| | 12 | | 35.1 | 35.7 | 35.6 | 34.8 | 34.3 | 34.2 |
| | 13 | | 32.1 | 32.0 | 31.7 | 31.8 | 31.1 | 31.5 |
| | 14 | | 31.2 | 30.0 | 30.0 | 30.3 | 30.0 | 30.1 |
| | 15 | | 35.4 | 34.4 | 33.6 | 34.2 | 34.0 | 33.7 |

TABLE 12-19

| | | \multicolumn{12}{c}{Individual Body Weight} |
|---|---|---|---|---|---|---|---|---|---|---|---|---|---|
| Test Article | (dosage) | 1 | 2 | 3 | 4 | 5 | 6 | 7 | 8 | 9 | 10 | 11 | 12 |
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| Group/ | Animal | Phase | \multicolumn{6}{c}{Data Presented in "g"} |
|---|---|---|---|---|---|---|---|---|
| Sex | Number | Day | DSNG 3 | DSNG 4 | DSNG 5 | DSNG 6 | DSNG 7 | DSNG 8 |
| 4/M | 16 | | 32.4 | 32.9 | 32.1 | 31.9 | 32.0 | 31.8 |
| | 17 | | 35.7 | 35.1 | 35.4 | 34.8 | 34.7 | 34.8 |
| | 18 | | 33.1 | 32.8 | 32.4 | 31.7 | 31.6 | 32.0 |
| | 19 | | 30.2 | 30.4 | 30.4 | 29.0 | 29.4 | 29.6 |
| | 20 | | 35.3 | 35.4 | 35.1 | 34.6 | 34.5 | 35.3 |

TABLE 12-20

| | | \multicolumn{12}{c}{Individual Body Weight} |
|---|---|---|---|---|---|---|---|---|---|---|---|---|---|
| Test Article | (dosage) | 1 | 2 | 3 | 4 | 5 | 6 | 7 | 8 | 9 | 10 | 11 | 12 |
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

TABLE 12-20-continued

| Group/ Sex | Animal Number | Phase Day | Data Presented in "g" | | | | | |
|---|---|---|---|---|---|---|---|---|
| | | | DSNG 3 | DSNG 4 | DSNG 5 | DSNG 6 | DSNG 7 | DSNG 8 |
| 5/M | 21 | | 35.5 | 34.6 | 34.9 | 35.8 | 36.1 | 36.2 |
| | 22 | | 39.0 | 38.9 | 38.6 | 38.6 | 38.8 | 39.0 |
| | 23 | | 32.4 | 31.3 | 31.5 | 31.7 | 32.7 | 31.3 |
| | 24 | | 33.3 | 33.5 | 34.7 | 34.4 | 35.1 | 34.9 |
| | 25 | | 32.6 | 32.5 | 32.0 | 32.2 | 32.3 | 32.5 |

TABLE 12-21

| | | Individual Body Weight | | | | | | | | | | | |
|---|---|---|---|---|---|---|---|---|---|---|---|---|---|
| Test Article | (dosage) | 1 | 2 | 3 | 4 | 5 | 6 | 7 | 8 | 9 | 10 | 11 | 12 |
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| Group/ Sex | Animal Number | Phase Day | Data Presented in "g" | | | | | |
|---|---|---|---|---|---|---|---|---|
| | | | DSNG 3 | DSNG 4 | DSNG 5 | DSNG 6 | DSNG 7 | DSNG 8 |
| 6/M | 26 | | 32.7 | 33.4 | 33.3 | 33.6 | 32.2 | 32.0 |
| | 27 | | 34.6 | 33.1 | 33.5 | 32.5 | 32.2 | 31.9 |
| | 28 | | 31.3 | 30.9 | 31.2 | 31.5 | 30.7 | 30.2 |
| | 29 | | 37.8 | 38.0 | 37.8 | 38.1 | 37.3 | 36.5 |
| | 30 | | 35.7 | 35.0 | 35.4 | 36.4 | 36.4 | 35.8 |

TABLE 12-22

| | | Individual Body Weight | | | | | | | | | | | |
|---|---|---|---|---|---|---|---|---|---|---|---|---|---|
| Test Article | (dosage) | 1 | 2 | 3 | 4 | 5 | 6 | 7 | 8 | 9 | 10 | 11 | 12 |
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| Group/Sex | Animal Number | Phase Day | Data Presented in "g" | | | | | |
|---|---|---|---|---|---|---|---|---|
| | | | DSNG 3 | DSNG 4 | DSNG 5 | DSNG 6 | DSNG 7 | DSNG 8 |
| 7/M | 31 | | 31.3 | 31.3 | 31.1 | 31.9 | 31.1 | 32.0 |
| | 32 | | 32.4 | 31.5 | 31.7 | 32.3 | 31.3 | 32.1 |
| | 33 | | 34.3 | 33.6 | 33.4 | 33.1 | 33.0 | 33.1 |
| | 34 | | 37.7 | 37.6 | 37.6 | 38.4 | 37.3 | 37.6 |
| | 35 | | 34.4 | 34.7 | 34.7 | 34.1 | 34.0 | 33.7 |

TABLE 12-23

| | | | | | | | | | | | | | |
|---|---|---|---|---|---|---|---|---|---|---|---|---|---|
| | | Individual Body Weight | | | | | | | | | | | |
| Test Article | (dosage) | 1 | 2 | 3 | 4 | 5 | 6 | 7 | 8 | 9 | 10 | 11 | 12 |
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| | Animal | Phase | Data Presented in "g" | | | | | |
|---|---|---|---|---|---|---|---|---|
| Group/Sex | Number | Day | DSNG 3 | DSNG 4 | DSNG 5 | DSNG 6 | DSNG 7 | DSNG 8 |
| 8/M | 36 | | 31.9 | 32.0 | 32.0 | 31.4 | 31.2 | 30.8 |
| | 37 | | 35.6 | 35.4 | 35.2 | 34.7 | 34.6 | 34.9 |
| | 38 | | 35.0 | 34.5 | 34.7 | 34.7 | 34.7 | 33.9 |
| | 39 | | 31.0 | 30.3 | 29.6 | 29.5 | 28.7 | 29.0 |
| | 40 | | 33.7 | 33.9 | 33.9 | 33.3 | 33.0 | 32.8 |

TABLE 12-24

| | | | | | | | | | | | | | |
|---|---|---|---|---|---|---|---|---|---|---|---|---|---|
| | | Individual Body Weight | | | | | | | | | | | |
| Test Article | (dosage) | 1 | 2 | 3 | 4 | 5 | 6 | 7 | 8 | 9 | 10 | 11 | 12 |
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| | Animal | Phase | Data Presented in "g" | | | | | |
|---|---|---|---|---|---|---|---|---|
| Group/Sex | Number | Day | DSNG 3 | DSNG 4 | DSNG 5 | DSNG 6 | DSNG 7 | DSNG 8 |
| 9/M | 41 | | 31.2 | 31.0 | 30.8 | 30.6 | 30.3 | 30.5 |
| | 42 | | 35.0 | 35.5 | 35.1 | 34.3 | 34.4 | 34.5 |
| | 43 | | 39.5 | 39.6 | 39.0 | 38.9 | 38.8 | 38.9 |
| | 44 | | 31.1 | 31.1 | 30.1 | 29.4 | 29.0 | 29.6 |
| | 45 | | 33.8 | 32.7 | 32.5 | 32.2 | 31.5 | 32.8 |

TABLE 12-25

| | | | | | | | | | | | | | |
|---|---|---|---|---|---|---|---|---|---|---|---|---|---|
| | | Individual Body Weight | | | | | | | | | | | |
| Test Article | (dosage) | 1 | 2 | 3 | 4 | 5 | 6 | 7 | 8 | 9 | 10 | 11 | 12 |
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

TABLE 12-25-continued

| Group/Sex | Animal Number | Phase Day | Data Presented in "g" | | |
|---|---|---|---|---|---|
| | | | DSNG 9 | DSNG 10 | DSNG 11 |
| 1/M | 1 | | 29.8 | 29.7 | 30.7 |
| | 2 | | 35.4 | 35.8 | 35.5 |
| | 3 | | 35.6 | 35.8 | 36.7 |
| | 4 | | 35.4 | 35.9 | 36.0 |
| | 5 | | 30.0 | 30.5 | 31.5 |

TABLE 12-26

| Individual Body Weight | | | | | | | | | | | | | |
|---|---|---|---|---|---|---|---|---|---|---|---|---|---|
| Test Article | (dosage) | 1 | 2 | 3 | 4 | 5 | 6 | 7 | 8 | 9 | 10 | 11 | 12 |
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| Group/Sex | Animal Number | Phase Day | Data Presented in "g" | | |
|---|---|---|---|---|---|
| | | | DSNG 9 | DSNG 10 | DSNG 11 |
| 10/M | 46 | | 29.5 | 28.3 | 28.9 |
| | 47 | | 34.1 | 34.6 | 34.0 |
| | 48 | | 30.4 | 30.7 | 30.9 |
| | 49 | | 27.8 | 27.2 | 26.0 |
| | 50 | | 28.3 | 25.4 | 26.3 |

TABLE 12-27

| Individual Body Weight | | | | | | | | | | | | | |
|---|---|---|---|---|---|---|---|---|---|---|---|---|---|
| Test Article | (dosage) | 1 | 2 | 3 | 4 | 5 | 6 | 7 | 8 | 9 | 10 | 11 | 12 |
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| Group/Sex | Animal Number | Phase Day | Data Presented in "g" | | |
|---|---|---|---|---|---|
| | | | DSNG 9 | DSNG 10 | DSNG 11 |
| 11/M | 51 | | 31.0 | 31.2 | 31.3 |
| | 52 | | 29.4 | 29.5 | 28.8 |
| | 53 | | 33.3 | 33.8 | 34.0 |
| | 54 | | 38.1 | 37.9 | 38.2 |
| | 55 | | 33.4 | 33.0 | 32.6 |

TABLE 12-28

Individual Body Weight

| Test Article | (dosage) | 1 | 2 | 3 | 4 | 5 | 6 | 7 | 8 | 9 | 10 | 11 | 12 |
|---|---|---|---|---|---|---|---|---|---|---|---|---|---|
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| Group/Sex | Animal Number | Phase Day | Data Presented in "g" | | |
|---|---|---|---|---|---|
| | | | DSNG 9 | DSNG 10 | DSNG 11 |
| 12/M | 56 | | 40.6 | 40.2 | 41.4 |
| | 57 | | 31.4 | 31.3 | 32.3 |
| | 58 | | 28.2 | 28.6 | 29.6 |
| | 59 | | 35.2 | 35.9 | 36.4 |
| | 60 | | 29.3 | 29.8 | 29.8 |

TABLE 12-29

Individual Body Weight

| Test Article | (dosage) | 1 | 2 | 3 | 4 | 5 | 6 | 7 | 8 | 9 | 10 | 11 | 12 |
|---|---|---|---|---|---|---|---|---|---|---|---|---|---|
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| Group/Sex | Animal Number | Phase Day | Data Presented in "g" | | |
|---|---|---|---|---|---|
| | | | DSNG 9 | DSNG 10 | DSNG 11 |
| 2/M | 10 | | 30.8 | 30.1 | 28.7 |
| | 6 | | 27.4 | 27.5 | 26.9 |
| | 7 | | 33.9 | 33.7 | 32.9 |
| | 8 | | 29.0 | 27.7 | 27.3 |
| | 9 | | 30.4 | 31.1 | 29.8 |

TABLE 12-30

Individual Body Weight

| Test Article | (dosage) | 1 | 2 | 3 | 4 | 5 | 6 | 7 | 8 | 9 | 10 | 11 | 12 |
|---|---|---|---|---|---|---|---|---|---|---|---|---|---|
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

TABLE 12-30-continued

| | Animal | Phase | Data Presented in "g" | | |
|---|---|---|---|---|---|
| Group/Sex | Number | Day | DSNG 9 | DSNG 10 | DSNG 11 |
| 3/M | 11 | | 28.9 | 28.2 | 27.6 |
| | 12 | | 33.7 | 34.4 | 33.9 |
| | 13 | | 31.2 | 31.9 | 31.4 |
| | 14 | | 30.1 | 29.6 | 29.8 |
| | 15 | | 33.3 | 31.9 | 31.6 |

TABLE 12-31

Individual Body Weight

| Test Article | (dosage) | 1 | 2 | 3 | 4 | 5 | 6 | 7 | 8 | 9 | 10 | 11 | 12 |
|---|---|---|---|---|---|---|---|---|---|---|---|---|---|
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| | Animal | Phase | Data Presented in "g" | | |
|---|---|---|---|---|---|
| Group/Sex | Number | Day | DSNG 9 | DSNG 10 | DSNG 11 |
| 4/M | 16 | | 31.2 | 30.9 | 30.8 |
| | 17 | | 34.6 | 34.7 | 35.3 |
| | 18 | | 31.3 | 30.7 | 31.3 |
| | 19 | | 29.1 | 28.9 | 28.7 |
| | 20 | | 35.2 | 35.5 | 35.5 |

TABLE 12-32

Individual Body Weight

| Test Article | (dosage) | 1 | 2 | 3 | 4 | 5 | 6 | 7 | 8 | 9 | 10 | 11 | 12 |
|---|---|---|---|---|---|---|---|---|---|---|---|---|---|
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| | Animal | Phase | Data Presented in "g" | | |
|---|---|---|---|---|---|
| Group/Sex | Number | Day | DSNG 9 | DSNG 10 | DSNG 11 |
| 5/M | 21 | | 36.2 | 36.1 | 36.5 |
| | 22 | | 39.0 | 39.6 | 39.7 |
| | 23 | | 31.0 | 30.8 | 31.2 |
| | 24 | | 34.5 | 35.2 | 35.0 |
| | 25 | | 31.0 | 32.3 | 32.1 |

TABLE 12-33

| | | \multicolumn{12}{c}{Individual Body Weight} |
|---|---|---|---|---|---|---|---|---|---|---|---|---|---|
| Test Article | (dosage) | 1 | 2 | 3 | 4 | 5 | 6 | 7 | 8 | 9 | 10 | 11 | 12 |
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| | Animal | Phase | \multicolumn{3}{c}{Data Presented in "g"} |
|---|---|---|---|---|---|
| Group/Sex | Number | Day | DSNG 9 | DSNG 10 | DSNG 11 |
| 6/M | 26 | | 31.1 | 30.6 | 31.5 |
| | 27 | | 31.6 | 32.4 | 32.7 |
| | 28 | | 29.8 | 30.8 | 32.0 |
| | 29 | | 37.5 | 38.0 | 38.9 |
| | 30 | | 35.7 | 35.8 | 36.8 |

TABLE 12-34

| | | \multicolumn{12}{c}{Individual Body Weight} |
|---|---|---|---|---|---|---|---|---|---|---|---|---|---|
| Test Article | (dosage) | 1 | 2 | 3 | 4 | 5 | 6 | 7 | 8 | 9 | 10 | 11 | 12 |
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

| | Animal | Phase | \multicolumn{3}{c}{Data Presented in "g"} |
|---|---|---|---|---|---|
| Group/Sex | Number | Day | DSNG 9 | DSNG 10 | DSNG 11 |
| 7/M | 31 | | 32.1 | 31.9 | 31.9 |
| | 32 | | 31.5 | 31.7 | 31.3 |
| | 33 | | 33.4 | 33.4 | 33.3 |
| | 34 | | 37.0 | 37.7 | 38.1 |
| | 35 | | 33.4 | 34.1 | 34.7 |

TABLE 12-35

| | | \multicolumn{12}{c}{Individual Body Weight} |
|---|---|---|---|---|---|---|---|---|---|---|---|---|---|
| Test Article | (dosage) | 1 | 2 | 3 | 4 | 5 | 6 | 7 | 8 | 9 | 10 | 11 | 12 |
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

TABLE 12-35-continued

|  |  |  | Data Presented in "g" | | |
|---|---|---|---|---|---|
| Group/Sex | Animal Number | Phase Day | DSNG 9 | DSNG 10 | DSNG 11 |
| B/M | 36 |  | 30.0 | 30.0 | 30.1 |
|  | 37 |  | 34.6 | 35.2 | 35.4 |
|  | 38 |  | 34.3 | 34.5 | 34.7 |
|  | 39 |  | 29.6 | 28.8 | 30.5 |
|  | 40 |  | 32.7 | 33.6 | 33.0 |

TABLE 12-36

Individual Body Weight

| Test Article | (dosage) | 1 | 2 | 3 | 4 | 5 | 6 | 7 | 8 | 9 | 10 | 11 | 12 |
|---|---|---|---|---|---|---|---|---|---|---|---|---|---|
| Vehicle | mg/kg | 0 | — | — | — | — | — | — | — | — | — | — | — |
| ERX1000-4 | mg/kg | — | 2 | — | — | — | — | — | — | — | — | — | — |
| ERX1006 | mg/kg | — | — | 2 | — | — | — | — | — | — | — | — | — |
| ERX1007 | mg/kg | — | — | — | 2 | — | — | — | — | — | — | — | — |
| ERX1037 | mg/kg | — | — | — | — | 2 | — | — | — | — | — | — | — |
| ERX1060 | mg/kg | — | — | — | — | — | 2 | — | — | — | — | — | — |
| ERX1077 | mg/kg | — | — | — | — | — | — | 2 | — | — | — | — | — |
| ERX1107 | mg/kg | — | — | — | — | — | — | — | 2 | — | — | — | — |
| ERX1149 | mg/kg | — | — | — | — | — | — | — | — | 2 | — | — | — |
| ERX1168 | mg/kg | — | — | — | — | — | — | — | — | — | 2 | — | — |
| ERX1177 | mg/kg | — | — | — | — | — | — | — | — | — | — | 2 | — |
| Pristimerin | mg/kg | — | — | — | — | — | — | — | — | — | — | — | 2 |

|  |  |  | Data Presented in "g" | | |
|---|---|---|---|---|---|
| Group/Sex | Animal Number | Phase Day | DSNG 9 | DSNG 10 | DSNG 11 |
| 9/M | 41 |  | 31.1 | 31.8 | 30.7 |
|  | 42 |  | 34.4 | 34.3 | 36.1 |
|  | 43 |  | 38.9 | 38.6 | 39.1 |
|  | 44 |  | 28.9 | 29.9 | 29.3 |
|  | 45 |  | 32.0 | 32.8 | 32.6 |

6. Protocol
6.1 Test Articles and Sturdy Design

TABLE 13

Study Design

| Group | Test Article | Dose (mg/kg) | Animal Numbers |
|---|---|---|---|
| 1 | Vehicle | 0 | 1-5 |
| 2 | ERX1000 | 2 | 6-10 |
| 3 | ERX1006 | 2 | 11-15 |
| 4 | ERX1007 | 2 | 16-20 |
| 5 | ERX1037 | 2 | 21-25 |
| 6 | ERX1060 | 2 | 26-30 |
| 7 | ERX1077 | 2 | 31-35 |
| 8 | ERX1107 | 2 | 36-40 |
| 9 | ERX1149 | 2 | 41-45 |
| 10 | ERX1168 | 2 | 46-50 |
| 11 | ERX1177 | 2 | 51-55 |
| 12 | Pristimerin | 2 | 56-60 |

Vehicle contained 1% methyl cellulose (400 cps) in citric acid/phosphoate buffer 6.2. Dose Formulation Detail

TABLE 14

| Acclimation Dosing | All 75 animals will be dosed with 0.9% saline (approximately 0.1 mL per animal) daily on Days 11 through 14 of the predose phase. 0.9% saline will be dispensed as a batch. |
|---|---|
| Dose Administration | Daily (Days 1 to 10) |
| Dose Volume | 2 mL/kg |
| Dose Route | Oral Gasage |
| Frequency of Preparation | Preparations will be made twice during the study (each for 3 days) and apportioned into daily aliquots. Preparations may be made up to 24 hours in advance. |
| Vehicle Mix Instructions | Components: Citric Acid Monohydrate (4.204 mg/ml), Sodium Phosphate Dibasic Heptahydrate (4.124 mg/ml), Purified Water, Methylcellulose (400 cps) (1%) Heat purified water to approximately 75° C.. Dissolve citric acid and sodium phosphate dibasic heptahydrate in purified water. Add methylcellulose. Stir to mix. Allow to cool. QS to final volume with cold purified water, mix. Measure and record pH. pH should be 4 × 0.2. If pH is not in the appropriate range, adjust as necessary using HCl or NaOH. |
| Vehicle Storage Conditions | Store refrigerated for no more than 7 days. |
| Test Article Storage Conditions | Store at ≤ −60° C., Protect from light |
| Verification Vial Section | Verification vial will not be performed. |

TABLE 14-continued

| | |
|---|---|
| Dose Preparation Mix Instructions | Groups 2 through 12: Weigh appropriate amount of test article into a formulation container. Add a small quantity of vehicle and mix with a spatula to create a smooth paste. Add any remaining vehicle to achieve final volume. Mix with homogenizer as needed to form a homogeneous suspension or solution. Portion batch preparation into daily aliquots. |
| Dose Preparation Storage Conditions | Refrigerated and protected from light. |
| Disposition of Dose Preparation | Following the completion of inlife testing, any remaining dosing material will be disposed. |
| Test Article Return Shipment | Covance to keep remaining test article for possible use on future studies. |

6.3 Test Animal and Husbandary Details

TABLE 15

| | |
|---|---|
| Covance ACUA Protocol | 04811-B |
| Species and Strain | Mouse, C57BL/6 Diet Induced Obese (DIO) |
| Sex | Male |
| Source | Taconic |
| Vendor Nomenclature | C57BL/6NTac (DIO) |
| Apporixmate Age | 21 to 22 weeks at study start |
| Quantity to Order | 75 |
| Quantity Enrolled on Study | 60 |
| Supplier/Food Type | TD95217 |
| Feeding Details | Feed ad libitum, see fasting details in Inlife Parameters. Provide enough food for the entire study on Day 1 of the dosing phase |
| Dietary Enrichment | Animals will not receive specialty food enrichment. |
| Water | Greenfield city water Gel cups will not be placed in with these animals; animals will be observed and if they do not take to the automatic watering then they will be placed on water bottles. |
| Housing | Individually house in shoe box caging with wood chip bedding and nestlets. |
| Acclimation | Animals will be allowed to acclimate to housing conditions at least 1 week prior to vehicle acclimation dosing. |
| Environmental Conditions | Photoperiod: Lights on 05:00-17:00 12 hours light. 12 hours dark (may be interrupted for study-related activities) Temperature: 68 to 79° F. Relative humidity: 30 to 70%. |

6.4 Inlife Parameters

6.4.1 Predose Phase

TABLE 16

| | |
|---|---|
| Accimation Dosing | Days 11 through 14 (at approximately 15:00). |
| Clinical Observations | Check for dead or moribund animals daily. Record abnormal changes. |

TABLE 16-continued

| | |
|---|---|
| Randomization | On Day 14 animals will be manually excluded and randomized based on body weight. |
| Body Weight | Body weights will be collected daily on Days 11 through 14 on all animals at approximately 15:00. |
| Food Consumption | Food consumption will be collected daily on Days 11 through 14 of the predose phase at approximately 15:00. If consumption value is not 0 to 6 grams per 24 hour period, reweigh once and document. |
| Glucose Measurements | Day 14 Approximately 08:00: Fast mice into clean shoebox cages. Approximately 14:00: Approximately 5 μL of blood will be collected via tail clip and blood glucose will be measured using Aviva glucometers. Glucometers measurements will be performed in duplicate. If the values differ by more than 20 mg/dL (calculated glucometer value) then a triplicate value will be recorded. Animals will have food returned following the last scheduled glucometer collection. |

Note:
Dose all 75 animals off-line for acclimation dosing.

6.4.2. Dosing Phase

TABLE 17

| | |
|---|---|
| Clinical Observations | Check for dead or moribund animals daily. Record abnormal observations. |
| Test Article Dosing | Daily at 15:00 (+/− 30 minutes) Dose volume calculated on most recent body weight. Animals will be dosed in numerical order. |
| Body Weights | Daily at 15:00 (+/−30 minutes) prior to dosing |
| Food Consumption | Daily at 15:00 (+/− 30 minutes) prior to dosing If consumption value is not 0 to 6 grams per 24 hour period, reweigh once and document. |
| Glucose Measurements | Day 11 Approximately 08:00: Fast mice into clean shoebox cages. Approximately 14.00: Approximately 5 μL of blood will be collected via tail clip and blood glucose will be measured using Aviva glucometers. Glucometers measurements will be performed in duplicate. If the values differ by more than 20 mg/dL (calculated glucometer value) then a triplicate value will be recorded. |

What is claimed is:

1. A compound of Formula (I):

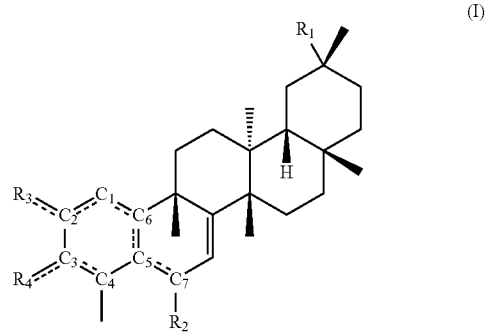

wherein the dotted lines between $C_1$ and $C_2$, $C_2$ and $R_3$, $C_3$ and $R_4$, $C_5$ and $C_6$, $C_5$ and $C_7$, $C_1$ and $C_6$, and $C_3$ and $C_4$ indicate that a single or double bond may be present, as valence permits;

$R_1$ is alkylsulfate, alkylsulfonate, alkylphosphate, —$CH_2OSO_3R_5$, —$CH_2OSO_2R_5$, —$CH_2OPO_3R_5R_5$, —$CH_2OPO_3HR_5$, —$CH_2OPO_3H_2$, —$C(=NR_5)NR_5R_5$, —$NR_5C(=NR_5)NR_5R_5$, —$CONH_2$, —$CH_2CONR_5R_5$, —$SR_5$, —$SO_3R_5$, —$SO_2R_5$, —$CH_2COSR_5$, —$CH_2NR_5COSR_5$, —$CH=NR_5$, —$CH=NOR_5$, —H, —$NH_2$, —$NHR_5$, —$NR_5R_5$, —OH, —$OR_5$, phosphate, —$OPO_3R_5R_5$, —$OPO_3HR_5$, —$OPO_3H_2$, —NCO, —NCS, —$N_3$, —$C\equiv CR_5$, —$(CH=CH)R_5$, —SH, —$SR_5$, —$SO_2H$, —$SO_3H$, —$SO_2NR_5R_5$, —$SO_3R_5$, —$NHCOR_5$, —, $NHCNR_5NR_5R_5$, —$NHCOSR_5$, secondary amide, tertiary amide, —$NR_5COR_5$, —$NR_5C(=NH)NR_5R_5$, —$NR_5COSR_5$, —$NHC(=NR_5)R_5$, —$NR_5C(=NR_5)R_5$, —$NHSO_2(NH_2)$, —$NHSO_2R_5$, —$NR_5SO_2R_5$, —$NR_5SO_2NR_5R_5$, —$OCOR_5$, —$OCONR_5R_5$, —$O(C=O)OR_5$, —$SCOR_5$, —$O(C=NH)NR_5R_5$, —$OCSNHR_5$, —$OS(=O_2)R_5$, —$OS(=O_2)NR_5R_5$, —$SCONR_5R_5$, —$CH_2$-aryl, —$CH_2$-heteroaryl, or

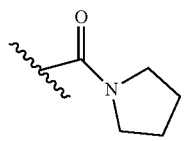 [SMILES: *C(=O)N1CCCC1]

$R_2$ is —H, —$CH_3$, —$SCH(CH_3)_2$, —$SC(=O)CH_3$, —$SC(=O)R_5$, —$SCH_2CH_2OCOCH_3$, —$SR_5$, —$SOR_5$, —$SOOR_5$, —$SCONR_5R_5$,

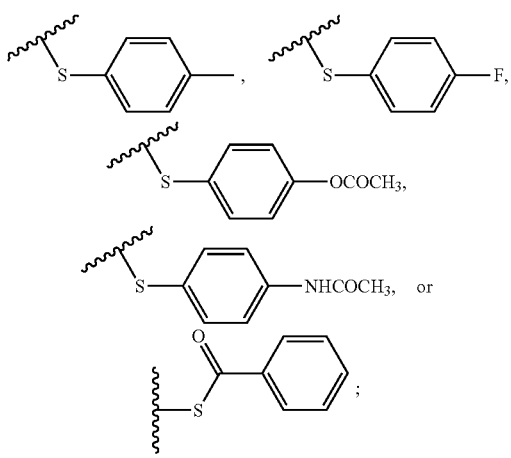

$R_3$ is —$OCOCH_3$, —$OCOOCH_2CH_3$, —$OR_7$, —$R_7$, or —$NR_5R_5$ when a double bond is present between $C_1$ and $C_2$, $C_3$ and $C_4$, and $C_5$ and $C_6$;

$R_4$ is —$OCOCH_3$, —$OCOOCH_2CH_3$, —$OR_7$, —$R_7$, or —$NR_5R_5$ when a double bond is present between $C_1$ and $C_2$, $C_3$ and $C_4$, and $C_5$ and $C_6$;

$R_3$ is O when $R_4$ is O and a double bond is present between $C_2$ and $R_3$ and $C_3$ and $R_4$;

$R_4$ is —$OCH_3$, —$OP(=O)(OCH_3)_2$, —OH, —$OCOOCH_2CH_3$, —$OCONHCH_2CH_3$, —$OCOOCH(CH_3)_2$, —$OR_7$, —$R_7$, or —$NR_5R_5$ when $R_3$ is O and a double bond is present between $C_2$ and $R_3$; $R_3$ and $R_4$ may also be combined to form a heterocylic or carbocyclic ring;

$R_5$ is independently selected for each occurrence hydrogen, an alkyl, cycloalkyl, alkoxy, heterocycloalkyl, alkylaryl, alkenyl, alkynyl, aryl, amine, or heteroaryl, optionally substituted with substituents individually selected from alkyl, alkoxy, cycloalkyl, ether, amine optionally substituted with one or more alkyl, halogen, hydroxyl, ether, cyano, nitrile, $CF_3$, ester, amide, cycloalkyl amide, sugar, heteroarylamide optionally substituted with alkyl and/or alkoxy, urea, carbamate, thioether, sulfate, sulfonyl, sulfonic acid carboxylic acid, and aryl or two $R_5$ groups taken together to form a cycloalkyl, heterocycloalkyl, aryl or hetearyl group, optionally substituted with substituents individually selected from alkyl, cycloalkyl, alkoxy, heterocyloalkyl, alkylaryl, alkenyl, alkynyl, aryl, heteroaryl, amine, halogen, hydroxyl, ether, nitrile, cyano, nitro, $CF_3$, ester amide, urea, carbamate, thioether, or carboxylic acid group; and $R_7$ is hydrogen, an alkyl, cycloalkyl, heterocycloalkyl, alkylaryl, alkenyl, alkynyl, aryl, or heteroaryl, optionally substituted with substituents individually selected from alkyl, cycloalkyl, ether, amine, halogen, hydroxyl, ether, nitrile, cyano, nitrile, $CF_3$, ester, amide, urea, carbamate, thioether, or carboxylic acid, or a pharmaceutically acceptable salt or prodrug thereof.

2. The compound of claim 1, wherein $R_1$ is —$NR_5C(=NR_5)NR_5R_5$, —$SR_5$, —$SO_3R_5$, —$SO_2R_5$, —$NH_2$, —$NHR_5$, —$NR_5R_5$, —OH, —$OR_5$, —NCO, —NCS, —$N_3$, —SH, —$SR_5$, —$SO_2H$, —$SO_3H$, —$SO_2NR_5R_5$, —$SO_3R_5$, —$NHCOR_5$, —$NHCNR_5NR_5R_5$, —$NHCOSR_5$, —$NR_5COR_5$, —$NR_5C(=NH)NR_5R_5$, —$NR_5COSR_5$, —$NHC(=NR_5)R_5$, —$NR_5C(=NR_5)R_5$, —$NHSO_2(NH_2)$, —$NHSO_2R_5$, —$NR_5SO_2R_5$, —$NR_5SO_2NR_5R_5$, —$OCOR_5$, —$OCONR_5R_5$, —$O(C=O)OR_5$, —$SCOR_5$, —$O(C=NH)NR_5R_5$, —$OCSNHR_5$, —$OS(=O_2)R_5$, —$OS(=O_2)NR_5R_5$, or —$SCONR_5R_5$.

3. The compound of claim 1, wherein $R_1$ is $NH(CO)R_5$.

4. The compound of claim 3, wherein $R_5$ is alkyl, cycloalkyl, or aryl.

5. The compound of claim 3, wherein $R_5$ is $CH_3$.

6. The compound of claim 3, wherein $R_2$ is H; and $R_4$ is —OH, —$OR_7$, or —$R_7$ when $R_3$ is O and a double bond is present between $C_2$ and $R_3$.

7. The compound of claim 2, wherein the compound is selected from the group consisting of:

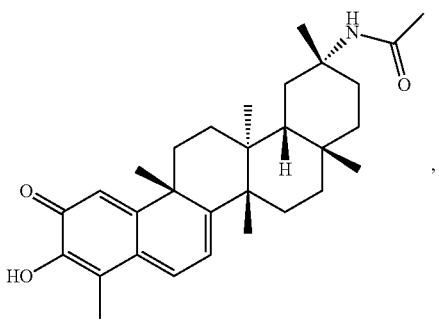

341
-continued

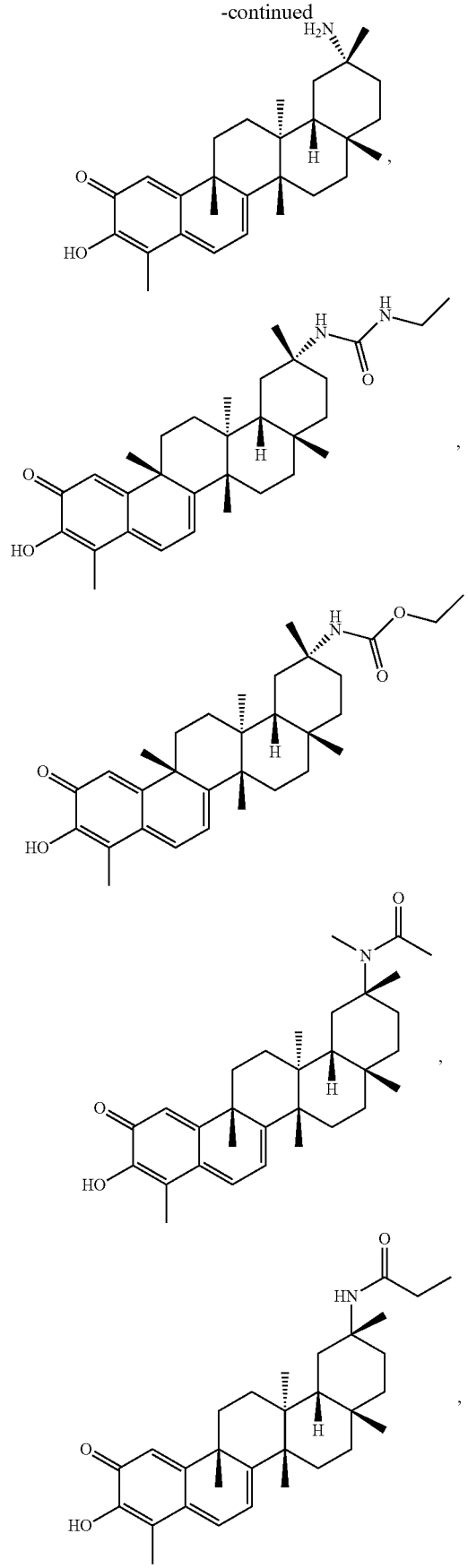

342
-continued

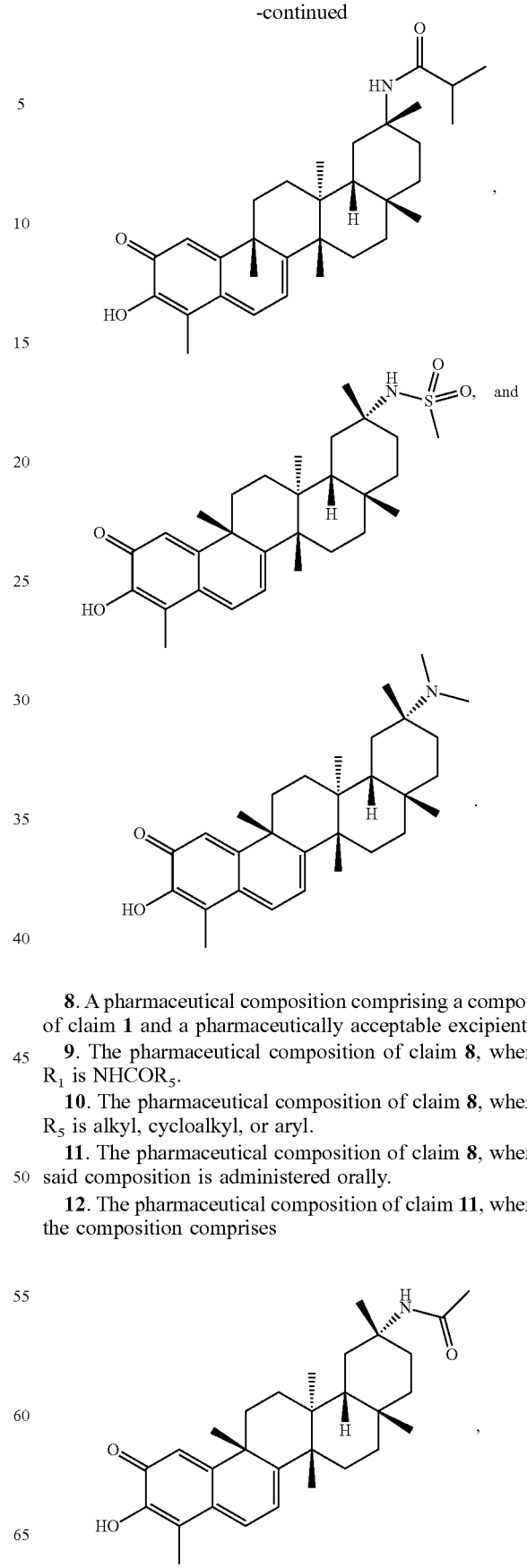

8. A pharmaceutical composition comprising a compound of claim 1 and a pharmaceutically acceptable excipient.

9. The pharmaceutical composition of claim 8, wherein $R_1$ is $NHCOR_5$.

10. The pharmaceutical composition of claim 8, wherein $R_5$ is alkyl, cycloalkyl, or aryl.

11. The pharmaceutical composition of claim 8, wherein said composition is administered orally.

12. The pharmaceutical composition of claim 11, wherein the composition comprises

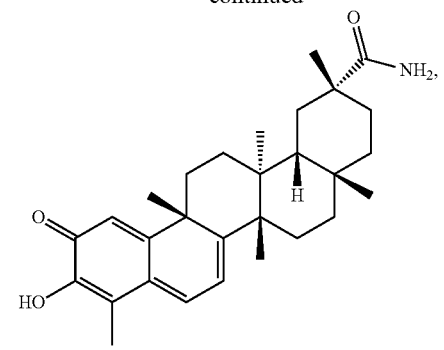
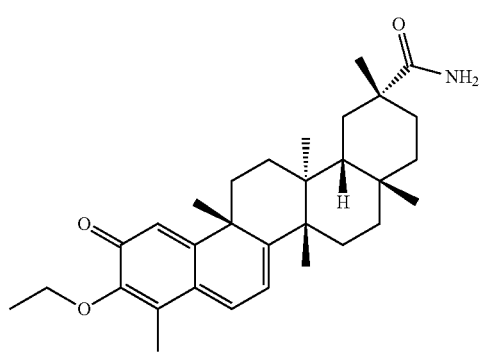
or
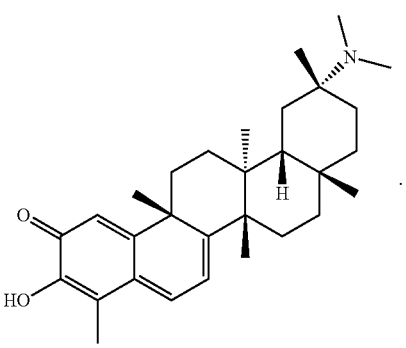
13. The pharmaceutical composition of claim 8, wherein said composition is administered intraperitoneally.
14. The pharmaceutical composition of claim 13, wherein the composition comprises at least compounds selected from the group consisting of:
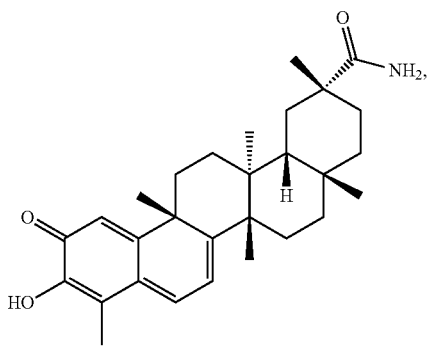
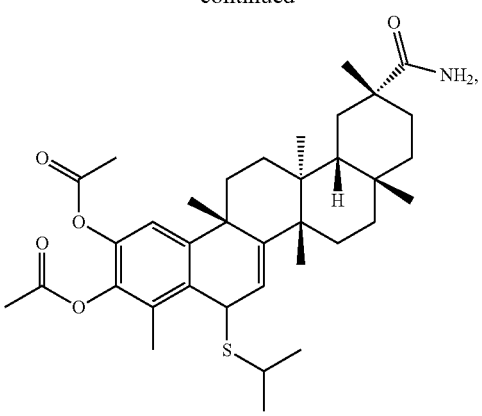
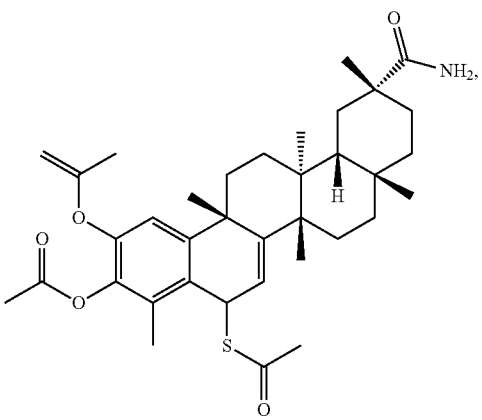
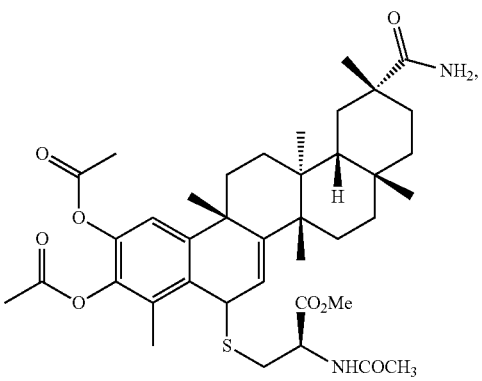
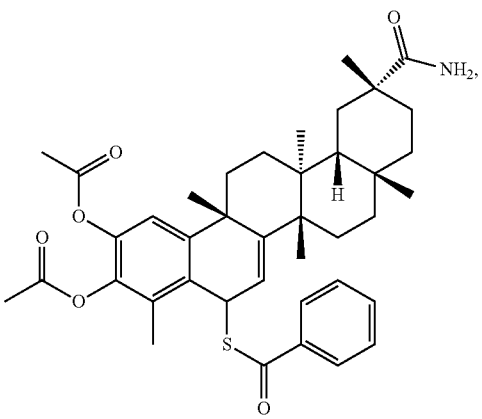

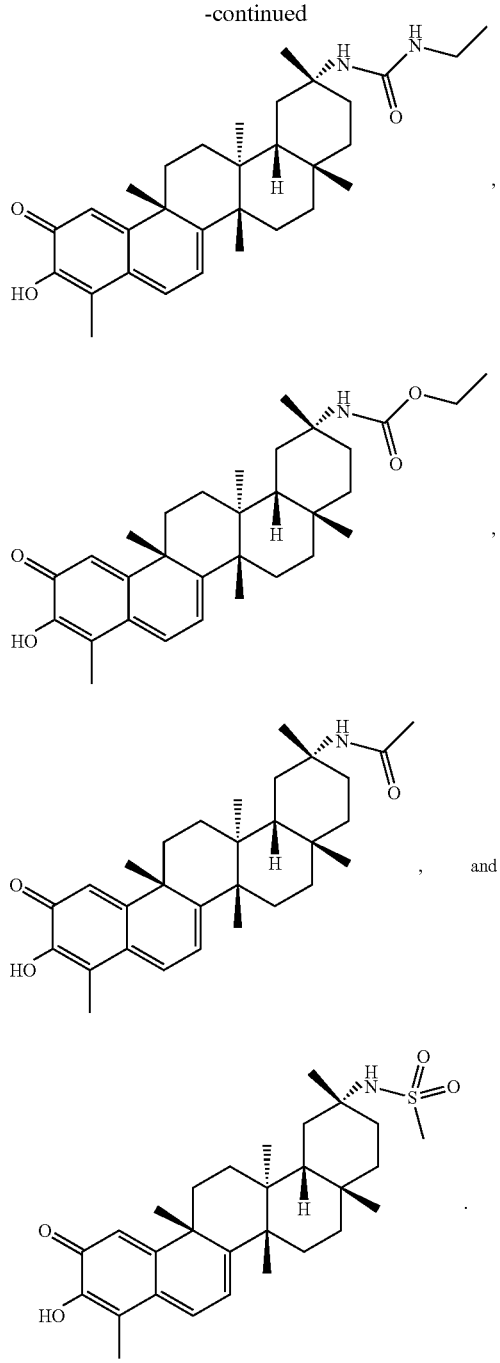

holic steatohepatitis, hyperlipidemia, hypertension, diabetes, lipodystrophy, fatty liver, Bardet-Biedl Syndrome, Cohen Syndrome, cardiovascular disease, arthritis, stroke, metabolic syndrome and MOMO Syndrome.

19. The method of claim 16, wherein the compound or the composition is administered in combination with another therapy.

20. The method of claim 16, wherein administering comprises oral administration, intravenous administration, topical administration, parenteral administration, intraperitoneal administration, intramuscular administration, intrathecal administration, intralesional administration, intracranial administration, intranasal administration, intraocular administration, intracardiac administration, intravitreal administration, intraosseous administration, intracerebral administration, intraarterial administration, intraarticular administration, intradermal administration, transdermal administration, transmucosal administration, sublingual administration, enteral administration, sublabial administration, insufflation administration, suppository administration, inhaled administration, or subcutaneous administration.

21. The method of claim 16, wherein the composition is administered in a form selected from the group comprising pills, capsules, tablets, granules, powders, salts, crystals, liquid, serums, syrups, suspensions, gels, creams, pastes, films, patches, and vapors.

22. The method of claim 16, wherein is the subject is a mammal.

23. The method of claim 22, wherein the subject is a human.

24. The method of claim 23, wherein the subject is a human with a body mass index (BMI) greater than 30 kg/m$^2$.

25. The method of claim 16, wherein the compound or the composition is administered orally.

26. The method of claim 16, wherein the compound or the composition is administered orally at a dose of about 0.1 to about 0.5 mg/kg, about 0.1 to about 1 mg/kg, about 0.1 to about 5 mg/kg, about 0.1 to about 10 mg/kg.

27. A composition comprising a compound of Formula (II):

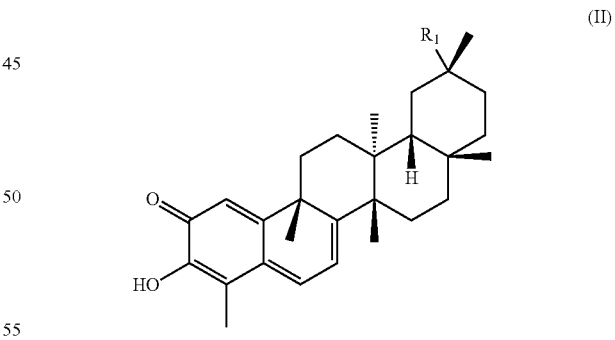

(II)

15. The pharmaceutical composition of claim 8, wherein said composition has a higher oral bioavailability than Celastrol.

16. A method of treating obesity in a subject in need thereof comprising administering to the subject an effective amount of a compound of claim 1.

17. A method of treating an obesity-related disease or disorder comprising administering to a subject suffering from or at risk of suffering from an obesity-related disease or disorder a composition of claim 8.

18. The method of claim 17, wherein the obesity-related disease or disorder is selected from the group comprising obesity, pre-obesity, morbid obesity, Prader-Willi Syndrome, Hypothalamic Injury Associated Obesity, Non-alcowherein $R_1$ is $OR_a$ or $NR_aR_b$, each $R_a$ and $R_b$ is independently hydrogen, $R_5$, C(=NR$_5$)NR$_5$R$_5$, —CO, —CS, —COR$_5$, —CNR$_5$NR$_5$R$_5$, —COSR$_5$, —C(=NH)NR$_5$R$_5$, —C(=NR$_5$)R$_5$, —SO$_2$(NH$_2$), —SO$_2$R$_5$, —SO$_2$R$_5$, —SO$_2$NR$_5$R$_5$, —CONR$_5$R$_5$, —(C=O)OR$_5$, —(C=NH)NR$_5$R$_5$, —CSNHR$_5$, —S(=O$_2$)R$_5$, or —S(=O$_2$)NR$_5$R$_5$, and $R_5$ is independently selected for each occurrence hydrogen, an alkyl, cycloalkyl, alkoxy, heterocycloalkyl, alkylaryl, alkenyl, alkynyl, aryl, amine, or heteroaryl, optionally substituted with substituents individually selected from alkyl, alkoxy, cycloalkyl, ether, amine optionally substituted with one or more alkyl, halogen, hydroxyl, ether, cyano, nitrile, $CF_3$, ester, amide, cycloalkyl amide, sugar, heteroarylamide optionally substituted with alkyl and/or alkoxy, urea, carbamate, thioether, sulfate, sulfonyl, sulfonic acid carboxylic acid, and aryl or two $R_5$ groups taken together to form a cycloalkyl, heterocycloalkyl, aryl or heteraryl group, optionally substituted with substituents individually selected from alkyl, cycloalkyl, alkoxy, heterocycloalkyl, alkylaryl, alkenyl, alkynyl, aryl, heteroaryl, amine, halogen, hydroxyl, ether, nitrile, cyano, nitro, $CF_3$, ester amide, urea, carbamate, thioether, or carboxylic acid group; and a pharmaceutically acceptable salt or prodrug thereof.

28. The composition of claim 27, wherein $R_1$ is $NR_aR_b$.

29. The composition of claim 27, wherein $R_1$ is $NHCOR_5$.

30. The composition of claim 29, $R_5$ is alkyl, cycloalkyl, or aryl.

31. The composition of claim 27 comprising at least one compound selected from the group consisting of:

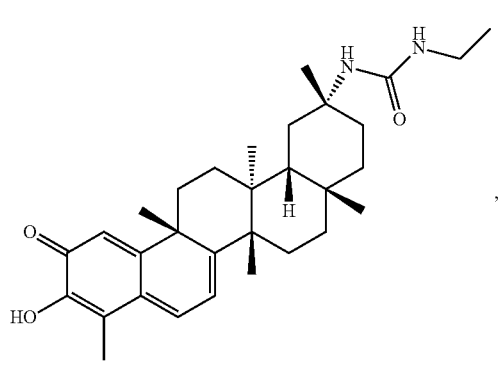

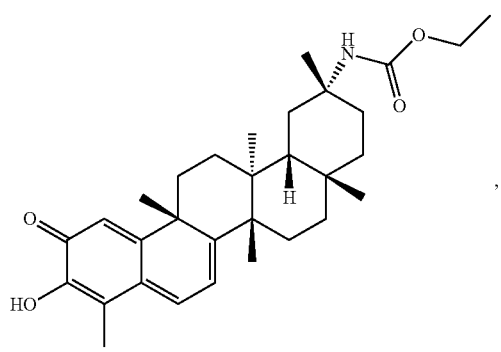

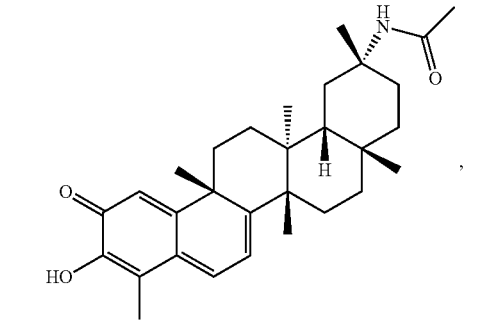

-continued

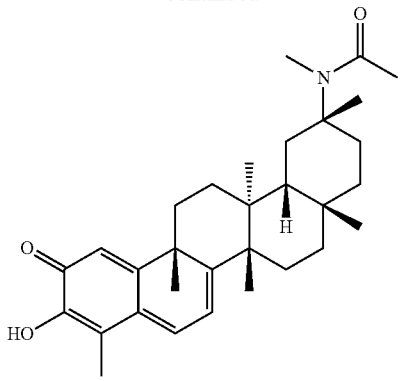

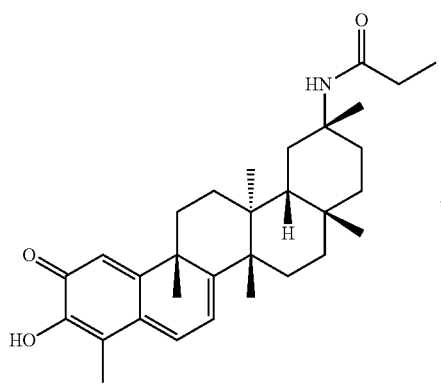

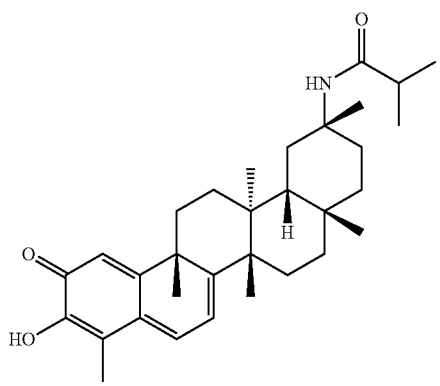

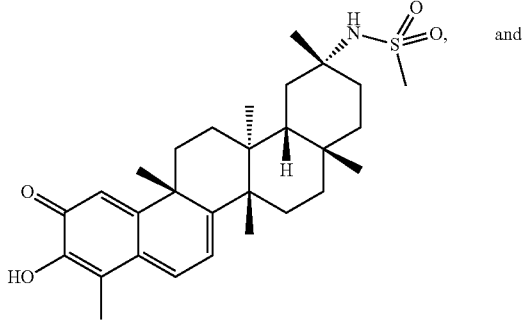

and

-continued

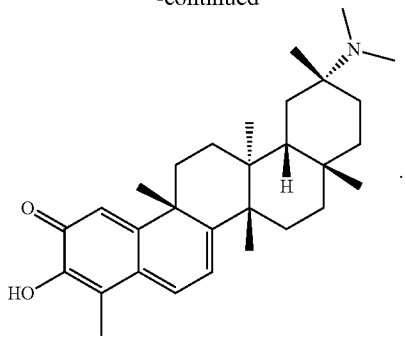

32. A method of treating an obesity-related disease or disorder comprising administering to a subject suffering from or at risk of suffering from an obesity-related disease or disorder a composition of claim 27.

33. The method of claim 32, wherein the obesity-related disease or disorder is selected from the group comprising obesity, pre-obesity, morbid obesity, Prader-Willi Syndrome, Hypothalamic Injury Associated Obesity, Non-alcoholic steatohepatitis, hyperlipidemia, hypertension, diabetes, lipodystrophy, fatty liver, Bardet-Biedl Syndrome, Cohen Syndrome, cardiovascular disease, arthritis, stroke, metabolic syndrome and MOMO Syndrome.

34. The method of claim 32, wherein the composition is administered in combination with another therapy.

35. The method of claim 32, wherein administering comprises oral administration, intravenous administration, topical administration, parenteral administration, intraperitoneal administration, intramuscular administration, intrathecal administration, intralesional administration, intracranial administration, intranasal administration, intraocular administration, intracardiac administration, intravitreal administration, intraosseous administration, intracerebral administration, intraarterial administration, intraarticular administration, intradermal administration, transdermal administration, transmucosal administration, sublingual administration, enteral administration, sublabial administration, insufflation administration, suppository administration, inhaled administration, or subcutaneous administration.

36. The method of claim 32, wherein the composition is administered in a form selected from the group comprising pills, capsules, tablets, granules, powders, salts, crystals, liquid, serums, syrups, suspensions, gels, creams, pastes, films, patches, and vapors.

37. The method of claim 32, wherein is the subject is a mammal.

38. The method of claim 37, wherein the subject is a human.

39. The method of claim 38, wherein the subject is a human with a body mass index (BMI) greater than 30 kg/m$^2$.

40. The method of claim 32, wherein the composition is administered orally.

41. The method of claim 32, wherein the composition is administered orally at a dose of about 0.1 to about 0.5 mg/kg, about 0.1 to about 1 mg/kg, about 0.1 to about 5 mg/kg, or about 0.1 to about 10 mg/kg.

42. A kit comprising a compound of claim 1.

43. The kit of claim 42 further comprising an oral applicator.

44. The kit of claim 42 further comprising an intraperitoneal applicator.

45. A kit comprising a composition of claim 27.

46. The kit of claim 45 further comprising an oral applicator.

47. The kit of claim 45 further comprising an intraperitoneal applicator.

48. The compound of claim 1, wherein the compound is

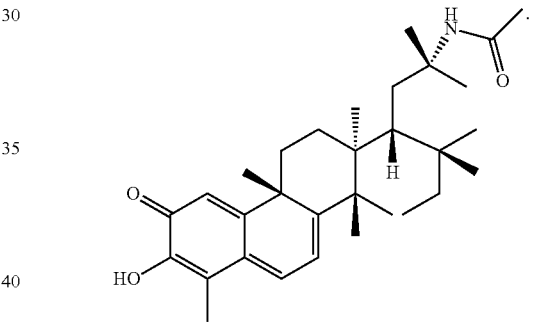

* * * * *